United States Patent
Jadhav et al.

(10) Patent No.: US 8,748,426 B2
(45) Date of Patent: Jun. 10, 2014

(54) INHIBITORS OF DIACYLGLYCEROL ACYL TRANSFERASE

(75) Inventors: Ravindra Dnyandev Jadhav, Mumbai (IN); Rajiv Sharma, Mumbai (IN)

(73) Assignee: Piramal Enterprises Limited, Mumbai (IN)

( * ) Notice: Subject to any disclaimer, the term of this patent is extended or adjusted under 35 U.S.C. 154(b) by 0 days.

(21) Appl. No.: 13/519,910

(22) PCT Filed: Dec. 30, 2010

(86) PCT No.: PCT/IB2010/056141
§ 371 (c)(1),
(2), (4) Date: Jun. 29, 2012

(87) PCT Pub. No.: WO2011/080718
PCT Pub. Date: Jul. 7, 2011

(65) Prior Publication Data
US 2012/0289505 A1  Nov. 15, 2012

Related U.S. Application Data

(60) Provisional application No. 61/291,575, filed on Dec. 31, 2009.

(51) Int. Cl.
*A61K 31/4035* (2006.01)
*C07D 257/12* (2006.01)
*C07D 251/12* (2006.01)
*C07D 403/04* (2006.01)
*C07D 401/04* (2006.01)

(52) U.S. Cl.
USPC ............... 514/241; 514/252.06; 514/254.08; 514/256; 514/339; 544/179; 544/180; 544/238; 544/333; 544/405; 546/277.1; 548/466

(58) Field of Classification Search
USPC ............................................................ 548/466
See application file for complete search history.

(56) References Cited

U.S. PATENT DOCUMENTS

2007/0213342 A1  9/2007 Chapdelaine et al.

FOREIGN PATENT DOCUMENTS

| WO | 2007/016538 A2 | 2/2007 |
| WO | 2009/040410 A1 | 4/2009 |
| WO | 2009/126861 A2 | 10/2009 |

OTHER PUBLICATIONS

Zhang, et al. Document No. 138:14016, CAPLUS, retrieved on Jul. 3, 2013.*
Diabetes Guide [online], [retrieved from the internet on Jun. 17, 2008][URL;http://diabetes.webmd.com/guide/diabetes-overview].*
Expert Opin. Ther. Targets, 2009, 13, 2, 195-207.
Nature Genetics, 2000, 25, 87-90.
Expert Opin. Ther. Targets, 2006, 10, 5, 749-757.
The Practice of Medicinal Chemistry, Edited by Camille G. Wermuth, Second Edition, 2003, 189-21.
Graham. L. Patrick, An introduction to Medicinal Chemistry, Second Edition, Oxford University Press pp. 239-248, 2001.
European Journal of Pharmacology, 2004, 501, 137-142.
International Journal of Obesity, 2001, 25, 1459-1464.
Arteriosclerosis, Thrombosis, and Vascular Biology, 1997, 17, 2532-2539.
King, Andrew J., et al. Diacylglycerol Acyltransferase 1 Inhibition Lowers Serum Triglycerides in the Zucker Fatty Rat and the Hyperlipidemic Hamster. Journal of Pharmacology and Experimental Therapeutics, vol. 300, No. 2, pp. 526-531 (1990).
Chen, Hubert C. Enhancing energy and glucose Metabolism by disrupting triglyceride synthesis: Lessons from mice lacking DGAT1. Nutrition & Metabolism, vol. 3, No. 10 (2006).
Chen, Hubert C. Inhibition of Triglyceride Synthesis as a Treatment Strategy for Obesity: Lessons From DGAT1-Deficient Mice. Arteriosclerosis, Thrombosis, and Vascular. Biology, vol. 25, pp. 482-486 (2005).
Villanueva, Claudio J., et al. A specific Role for Dgat1 in Hepatic Steatosis Due to Exogenous Fatty Acids. Hepatology, vol. 50, No. 2, pp. 434-442 (Aug. 2009).
Sato. Takashi, et al. A Citrus Polymethoxy Flavonoid, Nobeiletin Inhibits Sebum Production and Sebocyte Proliferation, and Augments Sebum Excretion in Hamsters. Journal of Investigative Dermatology, vol. 127. pp. 2740-2748 (2007).
de Melo, Celio L., et al. Betulinic Acid, a Natural Pentacyclic Triterpenoid, Prevents Abdominal Fat Accumulation in Mice Fed a High-Fat Diet. Journal of Agricultural Food Chemistry (2009). doi:10.1021/jf900768w.

* cited by examiner

*Primary Examiner* — Shawquia Young
(74) *Attorney, Agent, or Firm* — Ladas & Parry LLP

(57) ABSTRACT

The present invention relates to heterocyclic compounds in all their stereoisomeric and tautomeric forms; and their pharmaceutically acceptable salts, pharmaceutically acceptable solvates and pharmaceutically acceptable polymorphs. The invention also relates to processes for the manufacture of the heterocyclic compounds and to pharmaceutical compositions containing them. The compounds and their pharmaceutical compositions are useful in the prevention and treatment of diseases or disorders mediated by diacylglycerol acyltransferase (DGAT), particularly DGAT1. The present invention further provides a method of treatment of such diseases or disorders by administering a therapeutically effective amount of the compounds or their pharmaceutical compositions, to a mammal in need thereof.

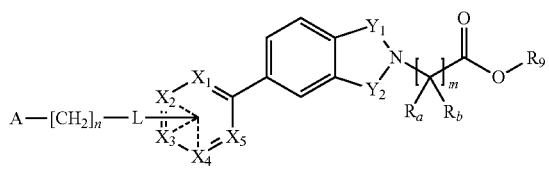

30 Claims, No Drawings

INHIBITORS OF DIACYLGLYCEROL ACYL TRANSFERASE

RELATED APPLICATION INFORMATION

This application is a 371 of International Application PCT/IB2010/056141 filed 30 Dec. 2010 entitled "INHIBITORS OF DIACYLGLYCEROL ACYL TRANSFERASE", which was published in the English language on Jul. 7, 2011, with International Publication Number WO WO201180718 A1, and which claims priority from U.S. Provisional Patent Application 61/291,575 filed 31 Dec. 2009, the content of which is incorporated herein by reference.

FIELD OF THE INVENTION

The present invention relates to heterocyclic compounds, to processes for their preparation, pharmaceutical compositions containing them, and their use in the prevention and treatment of diseases or disorders mediated by diacylglycerol acyl transferase (DGAT), particularly DGAT1.

BACKGROUND OF THE INVENTION

Obesity is a disease of energy imbalance, when energy input is more than output. Excess energy is stored in the form of triglycerides (TGs) in the adipose tissue. Increased adipose cell size causes hypertrophic obesity and increased cell number causes hyperplastic obesity characteristic of a more severe condition. The key causes of obesity are the increased consumption of energy-rich but nutrient-poor diets (like saturated fats and sugars) and reduced physical activity. 65% of the US population is overweight, where body mass index (BMI) is greater than 25 and approximately 25% of them are obese, having BMI>30. The prevalence of obesity has increased dramatically over the last decade. Obesity leads to increased risk of chronic diseases such as type 2 diabetes, insulin resistance, hypertension, stroke, cardiovascular diseases, respiratory problems, gallbladder disease, osteoarthritis, sleep apnea and certain cancers (Expert Opin. Ther. Targets, 2009, 13, 2, 195-207). The increasing evidence that severe obesity has a genetic basis, resulting in maintaining and defending an elevated weight, may explain why long-term weight loss is very difficult to achieve. This has strengthened the argument that severe obesity should be treated with pharmacological agents along with conventional diet and exercise regimes.

Diacylglycerol acyltransferase (DGAT) is an enzyme that catalyses the biosynthesis of triglyceride at the final step of the process, converting diacylglycerol (DAG) and fatty acyl-coenzyme A (CoA) into triglyceride. The enzymatic activity is present in all cell types because of the necessity of producing triglyceride for cellular needs. The amount of triglyceride synthesized varies from cell to cell, with the adipocytes, hepatocytes and intestinal enterocytes producing much more triglyceride, for storage or incorporation into lipoproteins, than other cell types. Because of its critical role in the biosynthesis of triglyceride, a neutral lipid that is the densest form of energy storage in animals, alteration of the expression and/or activity of DGAT in any of the tissues or organs would be expected to perturb the systemic energy metabolism. Diacyl glycerolacyltransferase 1 (DGAT1) is one of two known DGAT enzymes that catalyze the final step in triglyceride synthesis. Although most tissues generate triacylglycerols, DGAT1 is known to be highly expressed in the intestine and adipose with lower levels in the liver and muscle. Inhibition of DGAT1 in each of these tissues (intestine, adipose, liver and muscle) would inhibit triacylglycerol synthesis and may reverse the pathophysiology of excessive lipid accumulation in human metabolic disease.

Inhibitors of varying structural types of DGAT1 have been reported to be potential agents for the treatment for obesity and other disorders. The particular interest in DGAT1 inhibition stems from the reported phenotype of DGAT1 deficient (Dgat1−/−) mice. These animals are viable, resistant to weight gain when fed a high-fat diet, and show increased insulin and leptin sensitivity (Nature Genetics, 2000, 25, 87-90). Resistance to weight gain results from increased energy expenditure rather than decreased food intake (the animals are in fact hyperphagic) and is associated with loss of adipose rather than lean tissue mass. Most aspects of this phenotype can be reproduced in rodents by treatment with a potent and selective small molecule inhibitor of DGAT1.

XP620 (BMS) has been reported to be a selective DGAT1 inhibitor, which is able to block DGAT1 mediated retinyl-ester formation in Caco-2 cells. The potency against DGAT1 was in the order of 100 nM with no activity against DGAT2. Other small-molecule inhibitors reported are aryl alkyl acids from Bayer, phosphonic acid diesters from Otsuka, substituted ureas from Sankyo, pyrrolo[1,2-b]pyridazine derivatives from Tularik (now Amgen) and oxadiazoles from Astra-Zeneca (Expert Opin. Ther. Targets, 2006, 10, 5, 749-757). The PCT publication, WO2007016538 discloses biphenyl amino acid derivatives, and pharmaceutical salts and esters, thereof that have utility in the inhibition of DGAT1 and in the treatment of obesity and related diseases. The PCT publication, WO2009040410 discloses oxadiazolyl substituted benzimidazole and indole derivatives useful for treating conditions or disorders associated with DGAT1 activity in animals, particularly humans. However to date, there is an unmet medical need for effective and safe pharmacotherapy for obesity thus leaving a significant challenge to pharmaceutical industry.

SUMMARY OF THE INVENTION

The present invention relates to heterocyclic compounds, processes for their preparation and their use in the prevention and treatment of diseases or disorders mediated by diacylglycerol acyltransferase (DGAT), particularly DGAT1.

According to one aspect of the present invention, there are provided heterocyclic compounds of formula 1 (as provided herein below), as well as stereoisomers, tautomeric forms, pharmaceutically acceptable salts, solvates, polymorphs, prodrugs, N-oxides and carboxylic acid isosteres thereof.

According to another aspect of the present invention, there are provided processes for producing heterocyclic compounds of formula 1.

According to yet another aspect, there is provided the use of heterocyclic compounds of formula 1 in the prevention and treatment of diseases or disorders mediated by diacylglycerol acyltransferase (DGAT), particularly DGAT1.

According to a further aspect of the present invention, there are provided pharmaceutical compositions including heterocyclic compounds of formula 1 as active ingredient.

According to a still further aspect of the present invention, there is provided a method for the treatment of diseases or disorders mediated by diacylglycerol acyltransferase (DGAT), particularly DGAT1, the method including administering to a mammal in need thereof a therapeutically effective amount of a compound of formula 1.

According to another aspect of the present invention, there are provided methods for the manufacture of medicaments including compounds of formula 1, which are useful for the prevention or treatment of diseases or disorders mediated by diacylglycerol acyltransferase (DGAT), particularly DGAT1.

DETAILED DESCRIPTION OF THE INVENTION

The present invention provides compounds of formula 1:

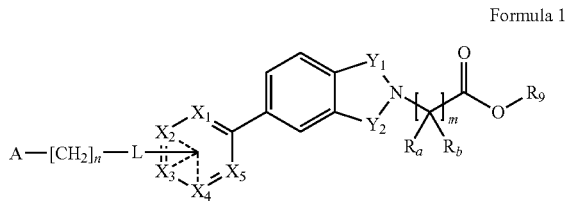

Formula 1 in all their stereoisomeric and tautomeric forms, their pharmaceutically acceptable salts, solvates, polymorphs, prodrugs, N-oxides and carboxylic acid isosteres;
wherein,
A is selected from unsubstituted or substituted $(C_1-C_{12})$-alkyl, unsubstituted or substituted $(C_3-C_{12})$-cycloalkyl, unsubstituted or substituted aryl and unsubstituted or substituted heterocyclyl; wherein the aryl group may be fused with an unsubstituted or substituted 5 or 6-membered cycloalkyl ring optionally containing heteroatoms selected from O, N or S;
n is 0 or 1;
L is selected from NHC(O)NH, NHC(S)NH, *NHSO$_2$, *CONH and *SO$_2$NH; wherein * indicates the point of attachment to A-[CH$_2$]$_n$—;
$X_1$, $X_2$, $X_3$, $X_4$ and $X_5$ are independently selected from N, N-oxide, C, CH and CR; wherein R is selected from halogen, hydroxy, $(C_1-C_{12})$-alkoxy, cyano, $(C_1-C_{12})$-alkyl, $CF_3$, $OCF_3$, $(C_2-C_{12})$-alkenyl, $(C_2-C_{12})$-alkynyl, $(C_3-C_{12})$-cycloalkyl, aryl, aryloxy, heterocyclyl, O-heterocyclyl, C(O)R$_p$, C(O)OR$_p$, NR$_p$R$_q$, SR$_p$, S(O)R$_p$, SO$_2$R$_p$ and C(O)NR$_p$R$_q$;
R$_p$ and R$_q$ are independently selected from hydrogen, unsubstituted or substituted $(C_1-C_{12})$-alkyl, unsubstituted or substituted aryl, unsubstituted or substituted aralkyl and unsubstituted or substituted heterocyclyl, or R$_p$ and R$_q$ can optionally form a 3-7 membered ring;
$Y_1$ and $Y_2$ are independently selected from C=O and CH$_2$;
m is an integer selected from 1 to 4; wherein,
when m is 1, R$_a$ and R$_b$ may be selected from R$_1$ and R$_2$;
when m is 2, R$_a$ and R$_b$ may be selected from R$_1$, R$_2$, R$_3$ and R$_4$;
when m is 3, R$_a$ and R$_b$ may be selected from R$_1$, R$_2$, R$_3$, R$_4$, R$_5$ and R$_6$;
when m is 4, R$_a$ and R$_b$ may be selected from R$_1$, R$_2$, R$_3$, R$_4$, R$_5$, R$_6$, R$_7$ and R$_8$;
R$_1$, R$_2$, R$_3$, R$_4$, R$_5$, R$_6$, R$_7$ and R$_8$ are independently selected from hydrogen, unsubstituted or substituted $(C_1-C_{12})$-alkyl, unsubstituted or substituted aryl, unsubstituted or substituted aralkyl and unsubstituted or substituted heterocyclyl;
or any two of R$_1$, R$_2$, R$_3$, R$_4$, R$_5$, R$_6$, R$_7$ and R$_8$ can form a $(C_3-C_{12})$cycloalkyl ring;
R$_9$ is selected from hydrogen, unsubstituted or substituted $(C_1-C_{12})$-alkyl, unsubstituted or substituted aryl, unsubstituted or substituted aralkyl and unsubstituted or substituted heterocyclyl;
wherein,
$(C_1-C_{12})$-alkyl is unsubstituted or substituted with one or more groups selected from halogen, hydroxy, unsubstituted or substituted $(C_1-C_{12})$-alkoxy, cyano, nitro, unsubstituted or substituted $(C_3-C_{12})$-cycloalkyl, unsubstituted or substituted aryl, C(O)R$_p$, C(O)OR$_p$, NR$_p$R$_q$, SR$_p$, S(O)R$_p$ and SO$_2$R$_p$;
$(C_3-C_{12})$-cycloalkyl is unsubstituted or substituted with one or more groups selected from halogen, hydroxy, unsubstituted or substituted $(C_1-C_{12})$-alkoxy cyano, nitro, unsubstituted or substituted aryl, unsubstituted or substituted heterocyclyl, C(O)R$_p$, C(O)OR$_p$, NR$_p$R$_q$, SR$_p$, S(O)R$_p$ and SO$_2$R$_p$;
aryl is unsubstituted or substituted with one or more groups selected from halogen, hydroxy, unsubstituted or substituted $(C_1-C_{12})$-alkoxy, cyano, nitro, unsubstituted or substituted $(C_1-C_{12})$-alkyl, $CF_3$, $OCF_3$, $(C_2-C_{12})$-alkenyl, $(C_2-C_{12})$-alkynyl, unsubstituted or substituted $(C_3-C_{12})$-cycloalkyl, unsubstituted or substituted aryl, unsubstituted or substituted aryloxy, unsubstituted or substituted heterocyclyl, unsubstituted or substituted O-heterocyclyl, C(O)R$_p$, C(O)OR$_p$, NR$_p$R$_q$, SR$_p$, S(O)R$_p$ and SO$_2$R$_p$, or aryl may be fused with an unsubstituted or substituted 5 or 6-membered cycloalkyl ring optionally containing heteroatoms selected from O, N and S;
heterocyclyl is unsubstituted or substituted with one or more groups selected from halogen, hydroxy, unsubstituted or substituted $(C_1-C_{12})$-alkoxy, cyano, nitro, unsubstituted or substituted $(C_1-C_{12})$-alkyl, $CF_3$, $OCF_3$, $(C_2-C_{12})$-alkenyl, $(C_2-C_{12})$-alkynyl, unsubstituted or substituted $(C_3-C_{12})$-cycloalkyl, unsubstituted or substituted aryl, unsubstituted or substituted aryloxy, unsubstituted or substituted heterocyclyl, unsubstituted or substituted O-heterocyclyl, C(O)R$_p$, C(O)OR$_p$, NR$_p$R$_q$, SR$_p$, S(O)R$_p$ and SO$_2$R$_p$; and
R$_p$ and R$_q$ are independently selected from hydrogen, unsubstituted or substituted $(C_1-C_{12})$-alkyl, unsubstituted or substituted aryl, unsubstituted or substituted aralkyl and unsubstituted or substituted heterocyclyl, or R$_p$ and R$_q$ can optionally form a 3-7 membered ring.

Definitions

As used herein, the term "alkyl" whether used alone or as part of a substituent group, refers to the radical of saturated aliphatic groups, including straight or branched-chain alkyl groups. An alkyl group can have a straight chain or branched chain containing 1 to 12 carbon atoms. Alkyl groups include methyl, ethyl, n-propyl, isopropyl, n-butyl, t-butyl, iso-butyl, sec-butyl, neo-pentyl, n-pentyl, n-heptyl, n-octyl, n-nonyl and n-decyl groups.

A substituted alkyl refers to an alkyl group substituted with one or more groups selected from halogen, hydroxy, cyano, nitro, unsubstituted or substituted $(C_1-C_{12})$-alkoxy, unsubstituted or substituted cycloalkyl, unsubstituted or substituted aryl, unsubstituted or substituted heterocyclyl, C(O)R$_p$, C(O)OR$_p$, SR$_p$, S(O)R$_p$, SO$_2$R$_p$, NR$_p$R$_q$ and C(O)NR$_p$R$_q$; wherein R$_p$ and R$_q$ are independently selected from hydrogen, unsubstituted or substituted $(C_1-C_{12})$alkyl, unsubstituted or substituted aryl, unsubstituted or substituted aralkyl and unsubstituted or substituted heterocyclyl, or R$_p$ and R$_q$ can optionally form a 3-7 membered ring;
Examples of substituted alkyls include benzyl, hydroxymethyl, hydroxyethyl, 2-hydroxyethyl, N-morpholinomethyl, N-indolomethyl, piperidinylmethyl, trifluoromethyl and aminoethyl.

As used herein, the term "alkenyl" whether used alone or as part of a substituent group, refers to a straight or branched chain hydrocarbon radical containing the indicated number of carbon atoms and at least one carbon-carbon double bond (two adjacent sp$^2$ carbon atoms). For example, $(C_2-C_{12})$-alkenyl refers to an alkenyl group having 2 to 12 carbon atoms. Depending on the placement of double bond and substituents if any, the geometry of the double bond may be entgegen (E), or zusammen (Z), cis or trans. Examples of alkenyl include, but are not limited to, vinyl, allyl and 2-propenyl.

A substituted alkenyl refers to an alkenyl group substituted with one or more groups selected from halogen, hydroxy, cyano, nitro, unsubstituted or substituted $(C_1-C_{12})$-alkoxy, unsubstituted or substituted aryl, unsubstituted or substituted heterocyclyl, $C(O)R_p$, $C(O)OR_p$, $SR_p$, $S(O)R_p$, $SO_2R_p$, $NR_pR_q$ and $C(O)NR_pR_q$; wherein $R_p$ and $R_q$ are independently selected from hydrogen, unsubstituted or substituted $(C_1-C_{12})$alkyl, unsubstituted or substituted aryl, unsubstituted or substituted aralkyl and unsubstituted or substituted heterocyclyl, or $R_p$ and $R_q$ can optionally form a 3-7 membered ring.

As used herein, the term "alkynyl" whether used alone or as part of a substituent group, refers to a straight or branched chain hydrocarbon radical containing the indicated number of carbon atoms and at least one carbon-carbon triple bond (two adjacent sp carbon atoms). For example, $(C_2-C_{12})$-alkynyl refers to an alkynyl group having 2-12 carbon atoms. Examples of alkynyl include, but are not limited to, ethynyl, 1-propynyl, 3-propynyl and 3-butynyl.

A substituted alkynyl refers to an alkynyl group substituted with one or more groups selected from halogen, hydroxy, cyano, nitro, unsubstituted or substituted $(C_1-C_{12})$-alkoxy, unsubstituted or substituted aryl, unsubstituted or substituted heterocyclyl, $C(O)R_p$, $C(O)OR_p$, $SR_p$, $S(O)R_p$, $SO_2R_p$, $NR_pR_q$ and $C(O)NR_pR_q$; wherein $R_p$ and $R_q$ are independently selected from hydrogen, unsubstituted or substituted $(C_1-C_{12})$alkyl, unsubstituted or substituted aryl, unsubstituted or substituted aralkyl and unsubstituted or substituted heterocyclyl, or $R_p$ and $R_q$ can optionally form a 3-7 membered ring.

As used herein, the term "alkoxyl" or "alkoxy" refers to a $(C_1-C_{12})$-alkyl having an oxygen radical attached thereto. Representative alkoxy groups include methoxy, ethoxy, propoxy, isopropoxy, isobutoxy and tert-butoxy.

A substituted alkoxy refers to an alkoxy group in which the alkyl is substituted with one or more groups selected from halogen, hydroxy, cyano, nitro, unsubstituted or substituted aryl, unsubstituted or substituted heterocyclyl, $C(O)R_p$, $C(O)OR_p$, $SR_p$, $S(O)R_p$, $SO_2R_p$, $NR_pR_q$ and $C(O)NR_pR_q$; wherein $R_p$ and $R_q$ are independently selected from hydrogen, unsubstituted or substituted $(C_1-C_{12})$alkyl, unsubstituted or substituted aryl, unsubstituted or substituted aralkyl and unsubstituted or substituted heterocyclyl, or $R_p$ and $R_q$ can optionally form a 3-7 membered ring. Examples of substituted alkoxy are chloromethoxy, 2-cyanoethoxy, trifluoromethoxy and benzyloxy group. A benzyloxy group refers to a benzyl having an oxygen radical attached thereto.

The term "$(C_3-C_{12})$cycloalkyl" or "cycloalkyl" refers to monocyclic or polycyclic hydrocarbon groups of 3-12 carbon atoms, which may be optionally bridged such as adamantyl.

The term "$(C_3-C_7)$cycloalkyl" refers to monocyclic hydrocarbon groups of 3-7 carbon atoms.

A substituted $(C_3-C_{12})$cycloalkyl refers to a "$(C_3-C_{12})$cycloalkyl" substituted by one or more substituents such as halogen, hydroxy, unsubstituted or substituted $(C_1-C_{12})$-alkyl, $(C_1-C_{12})$-alkoxy cyano, nitro, unsubstituted or substituted aryl, unsubstituted or substituted heterocyclyl, $C(O)R_p$, $C(O)OR_p$, $SR_p$, $S(O)R_p$, $SO_2R_p$, $NR_pR_q$ and $C(O)NR_pR_q$; wherein $R_p$ and $R_q$ are independently selected from hydrogen, unsubstituted or substituted $(C_1-C_{12})$alkyl, unsubstituted or substituted aryl, unsubstituted or substituted aralkyl and unsubstituted or substituted heterocyclyl, or $R_p$ and $R_q$ can optionally form a 3-7 membered ring.

The term "aryl" as used herein refers to monocyclic or polycyclic hydrocarbon groups having 6 to 14 ring carbon atoms in which the carbocyclic ring(s) present have a conjugated pi electron system. Examples of $(C_6-C_{14})$-aryl residues are phenyl, naphthyl, fluorenyl or anthracenyl. Examples of $(C_6-C_{10})$-aryl residues are phenyl or naphthyl. Aryl groups can be unsubstituted or substituted by one or more, for example 1, 2, 3, 4 or 5, identical or different substituents selected from halogen, hydroxy, cyano, nitro, unsubstituted or substituted $(C_1-C_{12})$alkyl, unsubstituted or substituted $(C_2-C_{12})$-alkenyl, unsubstituted or substituted $(C_2-C_{12})$-alkynyl, unsubstituted or substituted $(C_1-C_{12})$-alkoxy, unsubstituted or substituted cycloalkyl, unsubstituted or substituted aryl, unsubstituted or substituted aryloxy, unsubstituted or substituted heterocyclyl, O-heterocyclyl, $CF_3$, $OCF_3$, $C(O)R_p$, $C(O)OR_p$, $SR_p$, $S(O)R_p$, $SO_2R_p$, $NR_pR_q$ and $C(O)NR_pR_q$; wherein $R_p$ and $R_q$ are independently selected from hydrogen, unsubstituted or substituted $(C_1-C_{12})$alkyl, unsubstituted or substituted aryl, unsubstituted or substituted aralkyl and unsubstituted or substituted heterocyclyl, or $R_p$ and $R_q$ can optionally form a 3-7 membered ring.

In monosubstituted phenyl residues the substituent can be located in the 2-position, the 3-position, the 4-position or the 5-position. If the phenyl carries two substituents, they can be located in 2,3-position, 2,4-position, 2,5-position, 2,6-position, 3,4-position or 3,5-position. Examples of monosubstituted phenyl groups are biphenyl, 4-phenoxyphenyl, 3-trifluoromethylphenyl, 4-chlorophenyl and 4-cyanophenyl. Examples of disubstituted phenyl groups are 3,5-difluorophenyl, 3-chloro-5-phenoxy phenyl and 3,4-dimethoxyphenyl.

As used herein, the term "aryloxy" refers to an aryl group having an oxygen radical attached thereto. The aryl of aryloxy group as used herein may also be defined as given herein above and may be unsubstituted or substituted. Representative aryloxy groups include phenyloxy, 4-chlorophenoxy, 3,4-dimethoxy phenoxy, etc.

The term "aralkyl" refers to an aryl group bonded directly through an alkyl group, such as benzyl. The aryl of the aralkyl group may be unsubstituted or substituted as explained in the definition of substituted aryl herein above.

The term "heteroatom" as used herein includes nitrogen, oxygen and sulfur. Any heteroatom with unsatisfied valency is assumed to have a hydrogen atom to satisfy the valency.

Heterocyclyl includes saturated heterocyclic ring systems, which do not contain any double bonds within the rings, as well as unsaturated heterocyclic ring systems, which contain one or more, for example, 3 double bonds within a ring, provided that the resulting mono, bi or tricyclic ring system is stable. The heterocyclyl group may, for example, have 1 or 2 oxygen atoms and/or 1 or 2 sulfur atoms and/or 1 to 3 nitrogen atoms in the ring. Examples of heterocyclyls include pyrrolyl, pyrrolidinyl, pyrazolyl, imidazolyl, pyrazinyl, piperazinyl, oxazolyl, isoxazolyl, thiazolyl, furyl, thienyl, pyridyl, pyrimidyl, piperidyl, benzothiazolyl, purinyl, benzimidazolyl, benzooxazolyl, indolyl, isoindolyl, isoquinolyl, morpholinyl, quinoxalinyl, and quinolyl. Aromatic heterocyclyl groups may also be referred to by the customary term "heteroaryl" for which all the definitions and explanations relating to heterocyclyl apply.

A substituted heterocyclyl refers to a heterocyclyl substituted with one or more groups selected from halogen, hydroxy, cyano, nitro, unsubstituted or substituted $(C_1-C_{12})$-alkyl, $CF_3$, $(C_2-C_{12})$-alkenyl, $(C_2-C_{12})$-alkynyl, unsubstituted or substituted $(C_1-C_{12})$-alkoxy, $OCF_3$, unsubstituted or substituted cycloalkyl, unsubstituted or substituted aryl, unsubstituted or substituted aryloxy, heterocyclyl, —O-heterocyclyl, $C(O)R_p$, $C(O)OR_p$, $SR_p$, $S(O)R_p$, $SO_2R_p$, $NR_pR_q$ and $C(O)NR_pR_q$; wherein $R_p$ and $R_q$ are independently selected from hydrogen, unsubstituted or substituted $(C_1-C_{12})$alkyl, unsubstituted or substituted aryl, unsubstituted or substituted aralkyl and unsubstituted or substituted heterocyclyl, $R_p$ and $R_q$ can optionally form a 3-7 membered ring.

The substituents may be present on either the ring carbon or the ring nitrogen atoms. The substituents can be present at one or more positions provided that a stable molecule results.

The term "halogen" refers to a fluorine, chlorine, bromine, or iodine atom.

The term "solvate" describes a complex wherein the compound is coordinated with a proportional amount of a solvent molecule. Specific solvates, wherein the solvent is water, are referred to as hydrates.

The term "tautomer" refers to the coexistence of two (or more) compounds that differ from each other only in the position of one (or more) mobile atoms and in electron distribution, for example, keto-enol tautomers.

Carboxylic acid isosteres refer to groups or molecules that have physical and chemical similarities to a carboxylic acid group, producing similar biological effects as those produced by a carboxylic acid group. Examples of carboxylic acid isosteres include groups selected from hydroxamic, acylcyanamide, phosphonate, sulfonate, sulfonamide, tetrazole, hydroxylisoxazole and oxadiazolone (The Practice of Medicinal Chemistry, Edited by Camille G. Wermuth, Second Edition, 2003, 189-214).

The term "N-oxide" as used herein refers to the oxide of the nitrogen atom of a nitrogen-containing heteroaryl or heterocycle. N-oxide can be formed in presence of an oxidizing agent for example peroxide such as m-chloro-perbenzoic acid or hydrogen peroxide. N-oxide is also known as amine-N-oxide, and is a chemical compound that contains N→O bond.

It will be understood that "substitution" or "substituted with" includes the implicit proviso that such substitution is in accordance with permitted valence of the substituted atom and the substituent, as well as represents a stable compound, which does not readily undergo undesired transformation such as by rearrangement, cyclization, or elimination.

As used herein, the term "compound of formula 1" includes all the stereoisomeric and tautomeric forms and mixtures thereof in all ratios, and their pharmaceutically acceptable salts, solvates, polymorphs, prodrugs, carboxylic acid isosteres and N-oxides.

Embodiments of the Invention

In an embodiment, the present invention provides compounds of formula 1, wherein A is an unsubstituted aryl or an aryl substituted with one or more groups selected from halogen, hydroxy, unsubstituted or substituted $(C_1-C_{12})$-alkoxy, cyano, nitro, unsubstituted or substituted $(C_1-C_{12})$-alkyl, $CF_3$, $OCF_3$, $(C_2-C_{12})$-alkenyl, $(C_2-C_{12})$-alkynyl, unsubstituted or substituted cycloalkyl, unsubstituted or substituted aryl, unsubstituted or substituted aryloxy, unsubstituted or substituted heterocyclyl, unsubstituted or substituted O-heterocyclyl, $C(O)R_p$, $C(O)OR_p$, $NR_pR_q$, $SR_p$ and $S(O)R_p$ and $SO_2R_p$, where $R_p$ and $R_q$ are as defined in formula 1.

In an embodiment, the present invention provides compounds of formula 1, wherein A is an unsubstituted aryl or an aryl substituted with one or more groups selected from halogen, hydroxy, unsubstituted or substituted $(C_1-C_{12})$-alkoxy, cyano, unsubstituted or substituted $(C_1-C_{12})$-alkyl, $CF_3$, $OCF_3$, unsubstituted or substituted cycloalkyl, unsubstituted or substituted aryl, unsubstituted or substituted aryloxy and unsubstituted or substituted heterocyclyl.

In another embodiment, the present invention provides compounds of formula 1, wherein the aryl group of A may be fused with an unsubstituted or substituted 5 or 6-membered cycloalkyl ring optionally containing heteroatoms selected from O, N or S.

In a further embodiment, the present invention provides compounds of formula 1, wherein A is an unsubstituted heterocyclyl or a heterocyclyl substituted with one or more groups selected from halogen, hydroxy, unsubstituted or substituted $(C_1-C_{12})$-alkoxy, $CF_3$, $OCF_3$, cyano, nitro, unsubstituted or substituted $(C_1-C_{12})$-alkyl, $(C_2-C_{12})$-alkenyl, $(C_2-C_{12})$-alkynyl, unsubstituted or substituted cycloalkyl, unsubstituted or substituted aryl, unsubstituted or substituted aryloxy, unsubstituted or substituted heterocyclyl, unsubstituted or substituted O-heterocyclyl, $C(O)R_p$, $C(O)OR_p$, $NR_pR_q$, $SR_p$, $S(O)R_p$ and $SO_2R_p$, where $R_p$ and $R_q$ are as defined in formula 1.

In a further embodiment, the present invention provides compounds of formula 1, wherein A is an unsubstituted heterocyclyl or a heterocyclyl substituted with one or more groups selected from halogen, hydroxy, unsubstituted or substituted $(C_1-C_{12})$-alkoxy, $CF_3$, $OCF_3$, cyano, unsubstituted or substituted $(C_1-C_{12})$-alkyl, unsubstituted or substituted cycloalkyl, unsubstituted or substituted aryl, unsubstituted or substituted aryloxy and unsubstituted or substituted heterocyclyl.

In a still further embodiment, the present invention provides compounds of formula 1, wherein A is an unsubstituted $(C_1-C_{12})$-alkyl or $(C_1-C_{12})$-alkyl substituted with one or more groups selected from halogen, hydroxy, unsubstituted or substituted $(C_1-C_{12})$-alkoxy, cyano, nitro, unsubstituted or substituted cycloalkyl, unsubstituted or substituted aryl, $C(O)R_p$, $C(O)OR_p$, $NR_pR_q$, $SR_p$, $S(O)R_p$ and $SO_2R_p$, where $R_p$ and $R_q$ are as defined in formula 1.

In a still further embodiment, the present invention provides compounds of formula 1, wherein A is an unsubstituted $(C_1-C_{12})$-alkyl or $(C_1-C_{12})$-alkyl substituted with one or more groups selected from halogen, hydroxy, unsubstituted or substituted $(C_1-C_{12})$-alkoxy, cyano, unsubstituted or substituted cycloalkyl and unsubstituted or substituted aryl.

In another embodiment, the present invention provides compounds of formula 1, wherein A is an unsubstituted $(C_3-C_{12})$-cycloalkyl or $(C_3-C_{12})$-cycloalkyl substituted with one or more groups selected from halogen, hydroxy, unsubstituted or substituted $(C_1-C_{12})$-alkyl, unsubstituted or substituted $(C_1-C_{12})$-alkoxy, cyano, nitro, unsubstituted or substituted aryl, unsubstituted or substituted heterocyclyl, $C(O)R_p$, $C(O)OR_p$, $NR_pR_q$, $SR_p$, $S(O)R_p$ and $SO_2R_p$, where $R_p$ and $R_q$ are as defined in formula 1.

In another embodiment, the present invention provides compounds of formula 1, wherein A is an unsubstituted $(C_3-C_{12})$-cycloalkyl or $(C_3-C_{12})$-cycloalkyl substituted with one or more groups selected from halogen, hydroxy, unsubstituted or substituted $(C_1-C_{12})$-alkyl, unsubstituted or substituted $(C_1-C_{12})$-alkoxy, cyano, unsubstituted or substituted aryl and unsubstituted or substituted heterocyclyl.

In an embodiment, the present invention provides compounds of formula 1, wherein n is 0.

In another embodiment, the present invention provides compounds of formula 1, wherein n is 1.

In an embodiment, the present invention provides compounds of formula 1, wherein L is *CONH.

In another embodiment, the present invention provides compounds of formula 1, wherein L is NHC(O)NH.

In yet another embodiment, the present invention provides compounds of formula 1, wherein L is NHC(S)NH.

In a still further embodiment, the present invention provides compounds of formula 1, wherein L is *SO$_2$NH.

In an embodiment, the present invention provides compounds of formula 1, wherein $X_3$ is C, to which A-(CH$_2$)$_n$-L- is attached; and $X_1$, $X_2$, $X_4$ and $X_5$ are independently selected from CH and CR; wherein R is selected from halogen, hydroxy, unsubstituted or substituted $(C_1-C_{12})$-alkoxy, cyano, unsubstituted or substituted $(C_1-C_{12})$-alkyl, $CF_3$, $OCF_3$, $(C_2-C_{12})$-alkenyl, $(C_2-C_{12})$-alkynyl, unsubstituted or substituted cycloalkyl, unsubstituted or substituted aryl, unsubstituted or substituted aryloxy, unsubstituted or substituted heterocyclyl, unsubstituted or substituted O-heterocyclyl, $C(O)R_p$, $C(O)OR_p$, $NR_pR_q$, $SR_p$, $S(O)R_p$ and $SO_2R_p$, where $R_p$ and $R_q$ are as defined in formula 1.

In an embodiment, the present invention provides compounds of formula 1, wherein $X_3$ is C, to which A-$(CH_2)_n$-L- is attached; and $X_1$, $X_2$, $X_4$ and $X_5$ are independently selected from CH and CR; wherein R is selected from halogen, hydroxy, unsubstituted or substituted $(C_1-C_{12})$-alkoxy, cyano, unsubstituted or substituted $(C_1-C_{12})$-alkyl, $CF_3$, $OCF_3$, unsubstituted or substituted cycloalkyl, unsubstituted or substituted aryl, unsubstituted or substituted aryloxy and unsubstituted or substituted heterocyclyl.

In another embodiment, the present invention provides compounds of formula 1, wherein $X_3$ is C, to which A-$(CH_2)_n$-L- is attached; $X_4$ is N; and $X_1$, $X_2$ and $X_5$ are independently selected from CH and CR; wherein R is selected from halogen, hydroxy, unsubstituted or substituted $(C_1-C_{12})$-alkoxy, cyano, unsubstituted or substituted $(C_1-C_{12})$-alkyl, $CF_3$, $OCF_3$, $(C_2-C_{12})$-alkenyl, $(C_2-C_{12})$-alkynyl, unsubstituted or substituted cycloalkyl, unsubstituted or substituted aryl, unsubstituted or substituted aryloxy, unsubstituted or substituted heterocyclyl, unsubstituted or substituted O-heterocyclyl, $C(O)R_p$, $C(O)OR_p$, $NR_pR_q$, $SR_p$, $S(O)R_p$ and $SO_2R_p$, where $R_p$ and $R_q$ are as defined in formula 1

In another embodiment, the present invention provides compounds of formula 1, wherein $X_3$ is C, to which A-$(CH_2)_n$-L- is attached; $X_4$ is N; and $X_1$, $X_2$ and $X_5$ are independently selected from CH and CR; wherein R is selected from halogen, hydroxy, unsubstituted or substituted $(C_1-C_{12})$-alkoxy, cyano, unsubstituted or substituted $(C_1-C_{12})$-alkyl, $CF_3$, $OCF_3$, unsubstituted or substituted cycloalkyl, unsubstituted or substituted aryl, unsubstituted or substituted aryloxy and unsubstituted or substituted heterocyclyl In yet another embodiment, the present invention provides compounds of formula 1, wherein $X_3$ is C, to which A-$(CH_2)_n$-L- is attached; $X_4$ and $X_5$ are N, and $X_1$ and $X_2$ are independently selected from CH and CR; wherein R is selected from halogen, hydroxy, unsubstituted or substituted $(C_1-C_{12})$-alkoxy, cyano, unsubstituted or substituted $(C_1-C_{12})$-alkyl, $CF_3$, $OCF_3$, $(C_2-C_{12})$-alkenyl, $(C_2-C_{12})$-alkynyl, unsubstituted or substituted cycloalkyl, unsubstituted or substituted aryl, unsubstituted or substituted aryloxy, unsubstituted or substituted heterocyclyl, unsubstituted or substituted O-heterocyclyl, $C(O)R_1$, $C(O)OR_p$, $NR_pR_q$, $SR_p$, $S(O)R_p$ and $SO_2R_p$, where $R_p$ and $R_q$ are as defined in formula 1.

In yet another embodiment, the present invention provides compounds of formula 1, wherein $X_3$ is C, to which A-$(CH_2)_n$-L- is attached; $X_4$ and $X_5$ are N, and $X_1$ and $X_2$ are independently selected from CH and CR; wherein R is selected from halogen, hydroxy, unsubstituted or substituted $(C_1-C_{12})$-alkoxy, cyano, unsubstituted or substituted $(C_1-C_{12})$-alkyl, $CF_3$, $OCF_3$, unsubstituted or substituted cycloalkyl, unsubstituted or substituted aryl, unsubstituted or substituted aryloxy, unsubstituted or substituted heterocyclyl.

In a further embodiment, the present invention provides compounds of formula 1, wherein $X_3$ is C, to which A-$(CH_2)_n$-L- is attached; $X_1$ and $X_4$ are N, and $X_2$ and $X_5$ are independently selected from CH and CR; wherein R is selected from halogen, hydroxy, $(C_1-C_{12})$-alkoxy, cyano, unsubstituted or substituted $(C_1-C_{12})$-alkyl, $CF_3$, $OCF_3$, $(C_2-C_{12})$-alkenyl, $(C_2-C_{12})$-alkynyl, unsubstituted or substituted cycloalkyl, unsubstituted or substituted aryl, unsubstituted or substituted aryloxy, unsubstituted or substituted heterocyclyl, unsubstituted or substituted O-heterocyclyl, $C(O)R_p$, $C(O)OR_p$, $NR_pR_q$, $SR_p$, $S(O)R_p$ and $SO_2R_p$, where $R_p$ and $R_q$ are as defined in formula 1.

In a further embodiment, the present invention provides compounds of formula 1, wherein $X_3$ is C, to which A-$(CH_2)_n$-L- is attached; $X_1$ and $X_4$ are N, and $X_2$ and $X_5$ are independently selected from CH and CR; wherein R is selected from halogen, hydroxy, $(C_1-C_{12})$-alkoxy, cyano, unsubstituted or substituted $(C_1-C_{12})$-alkyl, $CF_3$, unsubstituted or substituted cycloalkyl, unsubstituted or substituted aryl, unsubstituted or substituted aryloxy and unsubstituted or substituted heterocyclyl.

In an embodiment, the present invention provides compounds of formula 1, wherein $Y_1$ is $CH_2$ and $Y_2$ is C=O.

In another embodiment, the present invention provides compounds of formula 1, wherein $Y_1$ is C=O and $Y_2$ is $CH_2$.

In a further embodiment, the present invention provides compounds of formula 1, wherein $Y_1$ is C=O and $Y_2$ is C=O.

In a still further embodiment, the present invention provides compounds of formula 1, wherein $Y_1$ is $CH_2$ and $Y_2$ is $CH_2$.

In another embodiment, the present invention provides compounds of formula 1, wherein m is 1 and $R_a$ and $R_b$ are selected from $R_1$ and $R_2$, wherein $R_1$ and $R_2$ are independently selected from hydrogen, unsubstituted or substituted $(C_1-C_{12})$-alkyl, unsubstituted or substituted aryl, unsubstituted or substituted aralkyl and unsubstituted or substituted heterocyclyl.

In another embodiment, the present invention provides compounds of formula 1, wherein m is 2, and $R_a$ and $R_b$ are selected from $R_1$, $R_2$, $R_3$ and $R_4$, wherein $R_1$, $R_2$, $R_3$ and $R_4$ are independently selected from hydrogen, unsubstituted or substituted $(C_1-C_{12})$-alkyl, unsubstituted or substituted aryl, unsubstituted or substituted aralkyl and unsubstituted or substituted heterocyclyl.

In another embodiment, the present invention provides compounds of formula 1, wherein m is 3, and $R_a$ and $R_b$ are selected from $R_1$, $R_2$, $R_3$, $R_4$, $R_5$ and $R_6$, wherein $R_1$, $R_2$, $R_3$, $R_4$, $R_5$, $R_6$, $R_7$ and $R_8$ are independently selected from hydrogen, unsubstituted or substituted $(C_1-C_{12})$-alkyl, unsubstituted or substituted aryl, unsubstituted or substituted aralkyl and unsubstituted or substituted heterocyclyl.

In another embodiment, the present invention provides compounds of formula 1, wherein m is 4, and $R_a$ and $R_b$ are selected from $R_1$, $R_2$, $R_3$, $R_4$, $R_5$, $R_6$, $R_7$ and $R_8$, wherein $R_1$, $R_2$, $R_3$, $R_4$, $R_5$, $R_6$, $R_7$ and $R_8$ are independently selected from hydrogen, unsubstituted or substituted $(C_1-C_{12})$-alkyl, unsubstituted or substituted aryl, unsubstituted or substituted aralkyl and unsubstituted or substituted heterocyclyl.

In an embodiment, the present invention provides compounds of formula 1, wherein m is 1 and $R_1$ and $R_2$ form a $(C_3-C_{12})$cycloalkyl ring.

In an embodiment, the present invention provides compounds of formula 1, wherein m is 1 and $R_1$ and $R_2$ form a $(C_3-C_7)$cycloalkyl ring.

In an embodiment, the present invention provides compounds of formula 1, wherein m is 1 and $R_1$ and $R_2$ form an adamantyl ring.

In another embodiment, the present invention provides compounds of formula 1, wherein m is 2 and any two of $R_1$, $R_2$, $R_3$ and $R_4$ form a $(C_3-C_{12})$cycloalkyl ring and the remaining substituents are hydrogen.

In another embodiment, the present invention provides compounds of formula 1, wherein m is 2 and any two of $R_1$, $R_2$, $R_3$ and $R_4$ form a $(C_3$-$C_7)$cycloalkyl ring and the remaining substituents are hydrogen.

In another embodiment, the present invention provides compounds of formula 1, wherein m is 2 and any two of $R_1$, $R_2$, $R_3$ and $R_4$ form an adamantyl ring and the remaining substituents are hydrogen.

In another embodiment, the present invention provides compounds of formula 1, wherein m is 3 and any two of $R_1$, $R_2$, $R_3$, $R_4$, $R_5$ and $R_6$ form a $(C_3$-$C_{12})$cycloalkyl ring and the remaining substituents are hydrogen.

In another embodiment, the present invention provides compounds of formula 1, wherein m is 3 and any two of $R_1$, $R_2$, $R_3$, $R_4$, $R_5$ and $R_6$ form a $(C_3$-$C_7)$cycloalkyl ring and the remaining substituents are hydrogen.

In another embodiment, the present invention provides compounds of formula 1, wherein m is 3 and any two of $R_1$, $R_2$, $R_3$, $R_4$, $R_5$ and $R_6$ form an adamantyl ring and the remaining substituents are hydrogen.

In another embodiment, the present invention provides compounds of formula 1, wherein m is 4 and any two of $R_1$, $R_2$, $R_3$, $R_4$, $R_5$, $R_6$, $R_7$ and $R_8$ form a $(C_3$-$C_{12})$cycloalkyl ring and the remaining substituents are hydrogen.

In another embodiment, the present invention provides compounds of formula 1, wherein m is 4 and any two of $R_1$, $R_2$, $R_3$, $R_4$, $R_5$, $R_6$, $R_7$ and $R_8$ form a $(C_3$-$C_7)$cycloalkyl ring and the remaining substituents are hydrogen.

In another embodiment, the present invention provides compounds of formula 1, wherein m is 4 and any two of $R_1$, $R_2$, $R_3$, $R_4$, $R_5$, $R_6$, $R_7$ and $R_8$ form an adamantyl ring and the remaining substituents are hydrogen.

In an embodiment, the present invention provides compounds of formula 1, wherein, $R_9$ is selected from hydrogen, unsubstituted or substituted $(C_1$-$C_{12})$-alkyl, unsubstituted or substituted aryl, unsubstituted or substituted aralkyl and unsubstituted or substituted heterocyclyl.

In another embodiment, the present invention provides compounds of formula 1, wherein $R_9$ is unsubstituted or substituted $(C_1$-$C_{12})$-alkyl, wherein $(C_1$-$C_{12})$-alkyl is unsubstituted or substituted with one or more groups selected from halogen, hydroxy, $(C_1$-$C_{12})$-alkoxy, cyano and aryl.

In another embodiment, the present invention provides compounds of formula 1, wherein $R_9$ is hydrogen.

In an embodiment, the compounds of formula 1 encompass compounds of formula 1a:

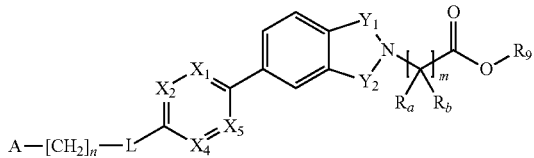

Formula 1a in all their stereoisomeric and tautomeric forms, their pharmaceutically acceptable salts, solvates, polymorphs, prodrugs, N-oxides and carboxylic acid isosteres;
wherein,
A is selected from unsubstituted or substituted $(C_1$-$C_{12})$-alkyl, unsubstituted or substituted $(C_3$-$C_{12})$-cycloalkyl, unsubstituted or substituted aryl and unsubstituted or substituted heterocyclyl; wherein the aryl group may be fused with an unsubstituted or substituted 5 or 6-membered cycloalkyl ring optionally containing heteroatoms selected from O, N or S;

n is 0 or 1;

L is selected from NHC(O)NH, NHC(S)NH, *$NHSO_2$, *CONH and *$SO_2$NH; wherein * indicates the point of attachment to A-$[CH_2]_n$—;

$X_1$, $X_2$, $X_4$ and $X_5$ are independently selected from N, N-oxide, CH and CR; wherein R is selected from halogen, hydroxy, $(C_1$-$C_{12})$-alkoxy, cyano, $(C_1$-$C_{12})$-alkyl, $CF_3$, $OCF_3$, $(C_2$-$C_{12})$-alkenyl, $(C_2$-$C_{12})$-alkynyl, $(C_3$-$C_{12})$-cycloalkyl, aryl, aryloxy, heterocyclyl, O-heterocyclyl, $C(O)R_p$, $C(O)OR_p$, $NR_pR_q$, $SR_p$, $S(O)R_p$, $SO_2R_p$ and $C(O)NR_pR_q$; $R_p$ and $R_q$ are independently selected from hydrogen, unsubstituted or substituted $(C_1$-$C_{12})$-alkyl, unsubstituted or substituted aryl, unsubstituted or substituted aralkyl and unsubstituted or substituted heterocyclyl, or $R_p$ and $R_q$ can optionally form a 3-7 membered ring;

$Y_1$ and $Y_2$ are independently selected from C=O and $CH_2$;
m is an integer selected from 1 to 4; wherein,
when m is 1, $R_a$ and $R_b$ may be selected from $R_1$ and $R_2$;
when m is 2, $R_a$ and $R_b$ may be selected from $R_1$, $R_2$, $R_3$ and $R_4$;
when m is 3, $R_a$ and $R_b$ may be selected from $R_1$, $R_2$, $R_3$, $R_4$, $R_5$ and $R_6$;
when m is 4, $R_a$ and $R_b$ may be selected from $R_1$, $R_2$, $R_3$, $R_4$, $R_5$, $R_6$, $R_7$ and $R_8$;

$R_1$, $R_2$, $R_3$, $R_4$, $R_5$, $R_6$, $R_7$ and $R_8$ are independently selected from hydrogen, unsubstituted or substituted $(C_1$-$C_{12})$-alkyl, unsubstituted or substituted aryl, unsubstituted or substituted aralkyl and unsubstituted or substituted heterocyclyl;
or any two of $R_1$, $R_2$, $R_3$, $R_4$, $R_5$, $R_6$, $R_7$ and $R_8$ can form a $(C_3$-$C_{12})$cycloalkyl ring;

$R_9$ is selected from hydrogen, unsubstituted or substituted $(C_1$-$C_{12})$-alkyl, unsubstituted or substituted aryl, unsubstituted or substituted aralkyl and unsubstituted or substituted heterocyclyl;
wherein,
$(C_1$-$C_{12})$-alkyl is unsubstituted or substituted with one or more groups selected from halogen, hydroxy, unsubstituted or substituted $(C_1$-$C_{12})$-alkoxy, cyano, nitro, unsubstituted or substituted $(C_3$-$C_{12})$-cycloalkyl, unsubstituted or substituted aryl, $C(O)R_p$, $C(O)OR_p$, $NR_pR_q$, $SR_p$, $S(O)R_p$ and $SO_2R_p$;
$(C_3$-$C_{12})$-cycloalkyl is unsubstituted or substituted with one or more groups selected from halogen, hydroxy, unsubstituted or substituted $(C_1$-$C_{12})$-alkoxy cyano, nitro, unsubstituted or substituted aryl, unsubstituted or substituted heterocyclyl, $C(O)R_p$, $C(O)OR_p$, $NR_pR_q$, $SR_p$, $S(O)R_p$ and $SO_2R_p$;
aryl is unsubstituted or substituted with one or more groups selected from halogen, hydroxy, unsubstituted or substituted $(C_1$-$C_{12})$-alkoxy, cyano, nitro, unsubstituted or substituted $(C_1$-$C_{12})$-alkyl, $CF_3$, $OCF_3$, $(C_2$-$C_{12})$-alkenyl, $(C_2$-$C_{12})$-alkynyl, unsubstituted or substituted $(C_3$-$C_{12})$-cycloalkyl, unsubstituted or substituted aryl, unsubstituted or substituted aryloxy, unsubstituted or substituted heterocyclyl, unsubstituted or substituted O-heterocyclyl, $C(O)R_p$, $C(O)OR_p$, $NR_pR_q$, $SR_p$, $S(O)R_p$ and $SO_2R_p$, or aryl may be fused with an unsubstituted or substituted 5 or 6-membered cycloalkyl ring optionally containing heteroatoms selected from O, N and S;
heterocyclyl is unsubstituted or substituted with one or more groups selected from halogen, hydroxy, unsubstituted or substituted $(C_1$-$C_{12})$-alkoxy, cyano, nitro, unsubstituted or substituted $(C_1$-$C_{12})$-alkyl, $CF_3$, $OCF_3$, $(C_2$-$C_{12})$-alkenyl, $(C_2$-$C_{12})$-alkynyl, unsubstituted or substituted $(C_3$-$C_{12})$-cycloalkyl, unsubstituted or substituted aryl, unsubstituted or substituted aryloxy, unsubstituted or substituted heterocyclyl, unsubstituted or substituted O-heterocyclyl, C(O)$R_p$, C(O)O$R_p$, $NR_pR_q$, $SR_p$, S(O)$R_p$ and $SO_2R_p$; and $R_p$ and $R_q$ are independently selected from hydrogen, unsubstituted or substituted ($C_1$-$C_{12}$)-alkyl, unsubstituted or substituted aryl, unsubstituted or substituted aralkyl and unsubstituted or substituted heterocyclyl, or $R_p$ and $R_q$ can optionally form a 3-7 membered ring.

In an embodiment, the compounds of formula 1 encompass compounds of formula 1a, in all their stereoisomeric and tautomeric forms, their pharmaceutically acceptable salts, solvates, polymorphs, prodrugs, N-oxides and carboxylic acid isosteres;

wherein,

A is selected from unsubstituted or substituted ($C_1$-$C_{12}$)-alkyl, unsubstituted or substituted ($C_3$-$C_{12}$)-cycloalkyl, unsubstituted or substituted aryl and unsubstituted or substituted heterocyclyl; wherein the aryl group may be fused with an unsubstituted or substituted 5 or 6-membered cycloalkyl ring optionally containing heteroatoms selected from O, N or S;

n is 0 or 1;

L is selected from NHC(O)NH, NHC(S)NH, *$NHSO_2$, *CONH and *$SO_2NH$; wherein * indicates the point of attachment to A-[$CH_2$]$_n$—;

$X_1$, $X_2$, $X_4$ and $X_5$ are independently selected from N, N-oxide, CH and CR; wherein R is selected from halogen, hydroxy, ($C_1$-$C_{12}$)-alkoxy, cyano, ($C_1$-$C_{12}$)-alkyl, $CF_3$, $OCF_3$, ($C_3$-$C_{12}$)-cycloalkyl, aryl, aryloxy, heterocyclyl;

$Y_1$ and $Y_2$ are independently selected from C=O and $CH_2$;

m is an integer selected from 1 to 4; wherein, when m is 1, $R_a$ and $R_b$ may be selected from $R_1$ and $R_2$;

when m is 2, $R_a$ and $R_b$ may be selected from $R_1$, $R_2$, $R_3$ and $R_4$, when m is 3, $R_a$ and $R_b$ may be selected from $R_1$, $R_2$, $R_3$, $R_4$, $R_5$ and $R_6$;

when m is 4, $R_a$ and $R_b$ may be selected from $R_1$, $R_2$, $R_3$, $R_4$, $R_5$, $R_6$, $R_7$ and $R_8$;

$R_1$, $R_2$, $R_3$, $R_4$, $R_5$, $R_6$, $R_7$ and $R_8$ are independently selected from hydrogen, unsubstituted or substituted ($C_1$-$C_{12}$)-alkyl, unsubstituted or substituted aryl, unsubstituted or substituted aralkyl and unsubstituted or substituted heterocyclyl;

or any two of $R_1$, $R_2$, $R_3$, $R_4$, $R_5$, $R_6$, $R_7$ and $R_8$ can form a ($C_3$-$C_{12}$)cycloalkyl ring;

$R_9$ is selected from hydrogen and unsubstituted or substituted ($C_1$-$C_{12}$)-alkyl;

wherein, ($C_1$-$C_{12}$)-alkyl is unsubstituted or substituted with one or more groups selected from halogen, hydroxy, unsubstituted or substituted ($C_1$-$C_{12}$)-alkoxy, cyano, nitro, unsubstituted or substituted ($C_3$-$C_{12}$)-cycloalkyl and unsubstituted or substituted aryl, ($C_3$-$C_{12}$)-cycloalkyl is unsubstituted or substituted with one or more groups selected from halogen, hydroxy, unsubstituted or substituted ($C_1$-$C_{12}$)-alkoxy cyano, unsubstituted or substituted aryl and unsubstituted or substituted heterocyclyl; aryl is unsubstituted or substituted with one or more groups selected from halogen, hydroxy, unsubstituted or substituted ($C_1$-$C_{12}$)-alkoxy, cyano, unsubstituted or substituted ($C_1$-$C_{12}$)-alkyl, $CF_3$, $OCF_3$, unsubstituted or substituted ($C_3$-$C_{12}$)-cycloalkyl, unsubstituted or substituted aryl, unsubstituted or substituted aryloxy and unsubstituted or substituted heterocyclyl, or aryl may be fused with an unsubstituted or substituted 5 or 6-membered cycloalkyl ring optionally containing heteroatoms selected from O, N and S; and heterocyclyl is unsubstituted or substituted with one or more groups selected from halogen, hydroxy, unsubstituted or substituted ($C_1$-$C_{12}$)-alkoxy, cyano, unsubstituted or substituted ($C_1$-$C_{12}$)-alkyl, $CF_3$, $OCF_3$, unsubstituted or substituted ($C_3$-$C_{12}$)-cycloalkyl, unsubstituted or substituted aryl, unsubstituted or substituted aryloxy and unsubstituted or substituted heterocyclyl.

In an embodiment, the compounds of formula 1 encompass compounds of formula 1a, in all their stereoisomeric and tautomeric forms, their pharmaceutically acceptable salts, solvates, polymorphs, prodrugs, N-oxides and carboxylic acid isosteres;

wherein,

A is selected from unsubstituted or substituted ($C_1$-$C_{12}$)-alkyl, unsubstituted or substituted ($C_3$-$C_{12}$)-cycloalkyl, unsubstituted or substituted aryl and unsubstituted or substituted heterocyclyl; wherein aryl group may be fused with an unsubstituted or substituted 5 or 6-membered cycloalkyl ring optionally containing heteroatoms selected from O, N or S;

n is 0 or 1;

L is *C(O)NH wherein * indicates the point of attachment to A-[$CH_2$]$_n$—;

$X_2$ is selected from CH and CR; $X_1$, $X_4$ and $X_5$ are independently selected from CH, CR and N; wherein R is selected from halogen, hydroxy, ($C_1$-$C_{12}$)-alkoxy, cyano, ($C_1$-$C_{12}$)-alkyl, $CF_3$, $OCF_3$ and cycloalkyl;

$Y_1$ and $Y_2$ are independently selected from C=O and $CH_2$;

m is an integer selected from 1 to 4; wherein, when m=1, $R_a$ and $R_b$ may be selected from $R_1$ and $R_2$;

when m=2, $R_a$ and $R_b$ may be selected from $R_1$, $R_2$, $R_3$ and $R_4$;

when m=3, $R_a$ and $R_b$ may be selected from $R_1$, $R_2$, $R_3$, $R_4$, $R_5$ and $R_6$;

when m=4, $R_a$ and $R_b$ may be selected from $R_1$, $R_2$, $R_3$, $R_4$, $R_5$, $R_6$, $R_7$ and $R_8$;

$R_1$, $R_2$, $R_3$, $R_4$, $R_5$, $R_6$, $R_7$ and $R_8$ are independently selected from hydrogen, unsubstituted or substituted ($C_1$-$C_{12}$)-alkyl, unsubstituted or substituted aryl; and unsubstituted or substituted aralkyl; or any two of $R_1$, $R_2$, $R_3$, $R_4$, $R_5$, $R_6$, $R_7$ and $R_8$ form a ($C_3$-$C_{12}$)cycloalkyl ring; and $R_9$ is selected from hydrogen and unsubstituted ($C_1$-$C_6$)-alkyl;

wherein, ($C_1$-$C_{12}$)-alkyl is unsubstituted or substituted with one or more groups selected from halogen, hydroxy, unsubstituted or substituted ($C_1$-$C_{12}$)-alkoxy, cyano, nitro, unsubstituted or substituted ($C_3$-$C_{12}$)-cycloalkyl and unsubstituted or substituted aryl, ($C_3$-$C_{12}$)-cycloalkyl is unsubstituted or substituted with one or more groups selected from halogen, hydroxy, unsubstituted or substituted ($C_1$-$C_{12}$)-alkoxy cyano, unsubstituted or substituted aryl and unsubstituted or substituted heterocyclyl;

aryl is unsubstituted or substituted with one or more groups selected from halogen, hydroxy, unsubstituted or substituted ($C_1$-$C_{12}$)-alkoxy, cyano, unsubstituted or substituted ($C_1$-$C_{12}$)-alkyl, $CF_3$, $OCF_3$, unsubstituted or substituted ($C_3$-$C_{12}$)-cycloalkyl, unsubstituted or substituted aryl, unsubstituted or substituted aryloxy and unsubstituted or substituted heterocyclyl, or aryl may be fused with an unsubstituted or substituted 5 or 6-membered cycloalkyl ring optionally containing heteroatoms selected from O, N and S; and heterocyclyl is unsubstituted or substituted with one or more groups selected from halogen, hydroxy, unsubstituted or substituted ($C_1$-$C_{12}$)-alkoxy, cyano, unsubstituted or substituted ($C_1$-$C_{12}$)-alkyl, $CF_3$, $OCF_3$, unsubstituted or substituted ($C_3$-$C_{12}$)-cycloalkyl, unsubstituted or substituted aryl, unsubstituted or substituted aryloxy and unsubstituted or substituted heterocyclyl.

In an embodiment, the compounds of formula 1 encompass compounds of formula 1a, in all their stereoisomeric and tautomeric forms, their pharmaceutically acceptable salts, solvates, polymorphs, prodrugs, N-oxides and carboxylic acid isosteres;

wherein,

A is selected from unsubstituted or substituted aryl and unsubstituted or substituted heterocyclyl;

n is 0;

L is *C(O)NH wherein * indicates the point of attachment to A-[CH$_2$]$_n$—;

$X_1$, $X_2$, $X_4$ and $X_5$ are independently selected from CH and CR; wherein R is selected from halogen, hydroxy, ($C_1$-$C_{12}$)-alkoxy, cyano, ($C_1$-$C_{12}$)-alkyl, $CF_3$ and $OCF_3$;

$Y_1$ is $CH_2$ and $Y_2$ is C=O;

m is 1; wherein $R_a$ and $R_b$ may be selected from $R_1$ and $R_2$; $R_1$ and $R_2$ are independently selected from hydrogen and unsubstituted or substituted ($C_1$-$C_{12}$)-alkyl; and $R_9$ is selected from hydrogen and unsubstituted ($C_1$-$C_6$)-alkyl;

wherein, aryl is unsubstituted or substituted with one or more groups selected from halogen, hydroxy, unsubstituted or substituted ($C_1$-$C_{12}$)-alkoxy, unsubstituted or substituted ($C_1$-$C_{12}$)-alkyl, $CF_3$, $OCF_3$, unsubstituted or substituted aryl, unsubstituted or substituted aryloxy and unsubstituted or substituted heterocyclyl, or aryl may be fused with an unsubstituted or substituted 5 or 6-membered cycloalkyl ring optionally containing heteroatoms selected from O, N and S; and heterocyclyl is unsubstituted or substituted with one or more groups selected from halogen, hydroxy, unsubstituted or substituted ($C_1$-$C_{12}$)-alkoxy, unsubstituted or substituted ($C_1$-$C_{12}$)-alkyl, $CF_3$, $OCF_3$, unsubstituted or substituted aryl, unsubstituted or substituted aryloxy and unsubstituted or substituted heterocyclyl.

In an embodiment, the compounds of formula 1 encompass compounds of formula 1a, in all their stereoisomeric and tautomeric forms, their pharmaceutically acceptable salts, solvates, polymorphs, prodrugs, N-oxides and carboxylic acid isosteres;

wherein,

A is selected from unsubstituted or substituted ($C_1$-$C_{12}$)-alkyl, unsubstituted or substituted aryl and unsubstituted or substituted heterocyclyl; wherein aryl group may be fused with an unsubstituted or substituted 5 or 6-membered cycloalkyl ring optionally containing heteroatoms selected from O, N or S;

n is 0 or 1;

L is selected from NHC(O)NH and NHC(S)NH;

$X_2$ is selected from CH and CR; $X_1$, $X_4$ and $X_5$ are independently selected from CH, CR and N; wherein R is selected from halogen, hydroxy, ($C_1$-$C_{12}$)-alkoxy, cyano, ($C_1$-$C_{12}$)-alkyl, $CF_3$, $OCF_3$ and cycloalkyl;

$Y_1$ and $Y_2$ are independently selected from C=O and $CH_2$;

m is an integer selected from 1 to 4; wherein, when m is 1, $R_a$ and $R_b$ may be selected from $R_1$ and $R_2$;

when m is 2, $R_a$ and $R_b$ may be selected from $R_1$, $R_2$, $R_3$ and $R_4$;

when m is 3, $R_a$ and $R_b$ may be selected from $R_1$, $R_2$, $R_3$, $R_4$, $R_5$ and $R_6$;

when m is 4, $R_a$ and $R_b$ may be selected from $R_1$, $R_2$, $R_3$, $R_4$, $R_5$, $R_6$, $R_7$ and $R_8$; $R_1$, $R_2$, $R_3$, $R_4$, $R_5$, $R_6$, $R_7$ and $R_8$ are independently selected from hydrogen, unsubstituted or substituted ($C_1$-$C_{12}$)-alkyl, unsubstituted or substituted aryl; and unsubstituted or substituted aralkyl; or any two of $R_1$, $R_2$, $R_3$, $R_4$, $R_5$, $R_6$, $R_7$ and $R_8$ form a ($C_3$-$C_{12}$) cycloalkyl ring; and $R_9$ is selected from hydrogen and unsubstituted ($C_1$-$C_6$)-alkyl;

wherein, ($C_1$-$C_{12}$)-alkyl is unsubstituted or substituted with one or more groups selected from halogen, hydroxy, unsubstituted or substituted ($C_1$-$C_{12}$)-alkoxy, cyano, unsubstituted or substituted ($C_3$-$C_{12}$)-cycloalkyl and unsubstituted or substituted aryl, ($C_3$-$C_{12}$)-cycloalkyl is unsubstituted or substituted with one or more groups selected from halogen, hydroxy, unsubstituted or substituted ($C_1$-$C_{12}$)-alkoxy cyano, unsubstituted or substituted aryl and unsubstituted or substituted heterocyclyl;

aryl is unsubstituted or substituted with one or more groups selected from halogen, hydroxy, unsubstituted or substituted ($C_1$-$C_{12}$)-alkoxy, cyano, unsubstituted or substituted ($C_1$-$C_{12}$)-alkyl, $CF_3$, $OCF_3$, unsubstituted or substituted ($C_3$-$C_{12}$)-cycloalkyl, unsubstituted or substituted aryl, unsubstituted or substituted aryloxy and unsubstituted or substituted heterocyclyl, or aryl may be fused with an unsubstituted or substituted 5 or 6-membered cycloalkyl ring optionally containing heteroatoms selected from O, N and S; and heterocyclyl is unsubstituted or substituted with one or more groups selected from halogen, hydroxy, unsubstituted or substituted ($C_1$-$C_{12}$)-alkoxy, cyano, unsubstituted or substituted ($C_1$-$C_{12}$)-alkyl, $CF_3$, $OCF_3$, unsubstituted or substituted ($C_3$-$C_{12}$)-cycloalkyl, unsubstituted or substituted aryl, unsubstituted or substituted aryloxy and unsubstituted or substituted heterocyclyl.

In an embodiment, the compounds of formula 1 encompass compounds of formula 1a, in all their stereoisomeric and tautomeric forms, their pharmaceutically acceptable salts, solvates, polymorphs, prodrugs, N-oxides and carboxylic acid isosteres;

wherein,

A is selected from unsubstituted or substituted ($C_1$-$C_{12}$)-alkyl, unsubstituted or substituted aryl and unsubstituted or substituted heterocyclyl; wherein aryl group may be fused with an unsubstituted or substituted 5 or 6-membered cycloalkyl ring optionally containing heteroatoms selected from O, N or S;

n is 0 or 1;

L is *SO$_2$NH wherein * indicates the point of attachment to A-[CH$_2$]$_n$—;

$X_2$ is selected from CH and CR; $X_1$, $X_4$ and $X_5$ are independently selected from CH, CR and N; wherein R is selected from halogen, hydroxy, ($C_1$-$C_{12}$)-alkoxy, cyano, ($C_1$-$C_{12}$)-alkyl, $CF_3$, $OCF_3$ and cycloalkyl;

$Y_1$ and $Y_2$ are independently selected from C=O and $CH_2$;

m is an integer selected from 1 to 4; wherein, when m is 1, $R_a$ and $R_b$ may be selected from $R_1$ and $R_2$;

when m is 2, $R_a$ and $R_b$ may be selected from $R_1$, $R_2$, $R_3$ and $R_4$;

when m is 3, $R_a$ and $R_b$ may be selected from $R_1$, $R_2$, $R_3$, $R_4$, $R_5$ and $R_6$;

when m is 4, $R_a$ and $R_b$ may be selected from $R_1$, $R_2$, $R_3$, $R_4$, $R_5$, $R_6$, $R_7$ and $R_8$; $R_1$, $R_2$, $R_3$, $R_4$, $R_5$, $R_6$, $R_7$ and $R_8$ are independently selected from hydrogen, unsubstituted or substituted ($C_1$-$C_{12}$)-alkyl, unsubstituted or substituted aryl; and unsubstituted or substituted aralkyl; or any two of $R_1$, $R_2$, $R_3$, $R_4$, $R_5$, $R_6$, $R_7$ and $R_8$ form a ($C_3$-$C_{12}$) cycloalkyl ring; and $R_9$ is selected from hydrogen and unsubstituted ($C_1$-$C_6$)-alkyl.

wherein, (C$_1$-C$_{12}$)-alkyl is unsubstituted or substituted with one or more groups selected from halogen, hydroxy, unsubstituted or substituted (C$_1$-C$_{12}$)-alkoxy, cyano, unsubstituted or substituted (C$_3$-C$_{12}$)-cycloalkyl and unsubstituted or substituted aryl, (C$_3$-C$_{12}$)-cycloalkyl is unsubstituted or substituted with one or more groups selected from halogen, hydroxy, unsubstituted or substituted (C$_1$-C$_{12}$)-alkoxy cyano, unsubstituted or substituted aryl and unsubstituted or substituted heterocyclyl;

aryl is unsubstituted or substituted with one or more groups selected from halogen, hydroxy, unsubstituted or substituted (C$_1$-C$_{12}$)-alkoxy, cyano, unsubstituted or substituted (C$_1$-C$_{12}$)-alkyl, CF$_3$, OCF$_3$, unsubstituted or substituted (C$_3$-C$_{12}$)-cycloalkyl, unsubstituted or substituted aryl, unsubstituted or substituted aryloxy and unsubstituted or substituted heterocyclyl, or aryl may be fused with an unsubstituted or substituted 5 or 6-membered cycloalkyl ring optionally containing heteroatoms selected from O, N and S; and heterocyclyl is unsubstituted or substituted with one or more groups selected from halogen, hydroxy, unsubstituted or substituted (C$_1$-C$_{12}$)-alkoxy, cyano, unsubstituted or substituted (C$_1$-C$_{12}$)-alkyl, CF$_3$, OCF$_3$, unsubstituted or substituted (C$_3$-C$_{12}$)-cycloalkyl, unsubstituted or substituted aryl, unsubstituted or substituted aryloxy and unsubstituted or substituted heterocyclyl.

In an embodiment, the compounds of formula 1 encompass compounds of formula 1b:

Formula 1b wherein,

A is selected from unsubstituted or substituted (C$_1$-C$_{12}$)-alkyl, unsubstituted or substituted (C$_3$-C$_{12}$)-cycloalkyl, unsubstituted or substituted aryl and unsubstituted or substituted heterocyclyl; wherein the aryl group may be fused with an unsubstituted or substituted 5 or 6-membered cycloalkyl ring optionally containing heteroatoms selected from O, N or S;

n is 0 or 1;

L is selected from NHC(O)NH, NHC(S)NH, *NHSO$_2$, *CONH and *SO$_2$NH; wherein * indicates the point of attachment to A-[CH$_2$]$_n$—;

X$_1$, X$_2$, X$_4$ and X$_5$ are independently selected from N, N-oxide, CH and CR; wherein R is selected from halogen, hydroxy, (C$_1$-C$_{12}$)-alkoxy, cyano, (C$_1$-C$_{12}$)-alkyl, CF$_3$, OCF$_3$, (C$_2$-C$_{12}$)-alkenyl, (C$_2$-C$_{12}$)-alkynyl, (C$_3$-C$_{12}$)-cycloalkyl, aryl, aryloxy, heterocyclyl, O-heterocyclyl, C(O)R$_p$, C(O)OR$_p$, NR$_p$R$_q$, SR$_p$, S(O)R$_p$, SO$_2$R$_p$ and C(O)NR$_p$R$_q$;

R$_p$ and R$_q$ are independently selected from hydrogen, unsubstituted or substituted (C$_1$-C$_{12}$)-alkyl, unsubstituted or substituted aryl, unsubstituted or substituted aralkyl and unsubstituted or substituted heterocyclyl, or R$_p$ and R$_q$ can optionally form a 3-7 membered ring;

Y$_1$ and Y$_2$ are independently selected from C=O and CH$_2$;

R$_9$ is selected from hydrogen, unsubstituted or substituted (C$_1$-C$_{12}$)-alkyl, unsubstituted or substituted aryl, unsubstituted or substituted aralkyl and unsubstituted or substituted heterocyclyl; and Y is a cycloalkyl ring selected from:

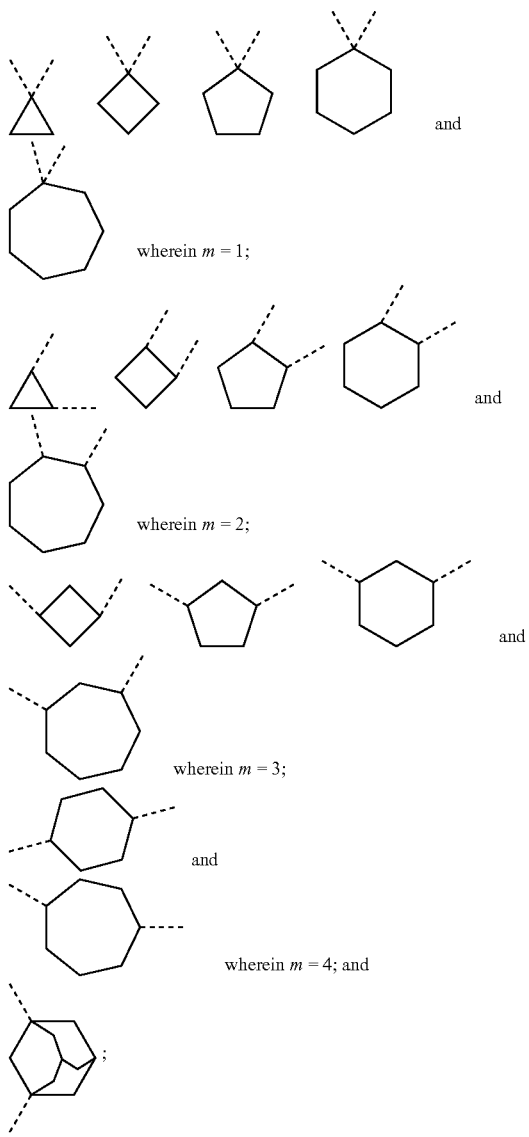

wherein m = 1;

wherein m = 2;

wherein m = 3;

and wherein m = 4; and

;

wherein, (C$_1$-C$_{12}$)-alkyl is unsubstituted or substituted with one or more groups selected from halogen, hydroxy, unsubstituted or substituted (C$_1$-C$_{12}$)-alkoxy, cyano, unsubstituted or substituted (C$_3$-C$_{12}$)-cycloalkyl, unsubstituted or substituted aryl;

(C$_3$-C$_{12}$)-cycloalkyl is unsubstituted or substituted with one or more groups selected from halogen, hydroxy, unsubstituted or substituted (C$_1$-C$_{12}$)-alkoxy cyano, unsubstituted or substituted aryl, unsubstituted or substituted heterocyclyl;

aryl is unsubstituted or substituted with one or more groups selected from halogen, hydroxy, unsubstituted or substituted (C$_1$-C$_{12}$)-alkoxy, cyano, unsubstituted or substituted (C$_1$-C$_{12}$)-alkyl, CF$_3$, OCF$_3$, unsubstituted or substituted (C$_3$-C$_{12}$)-cycloalkyl, unsubstituted or substituted aryl, unsubstituted or substituted aryloxy, unsubstituted or substituted heterocyclyl, or aryl may be fused with an unsubstituted or substituted 5 or 6-membered cycloalkyl ring optionally containing heteroatoms selected from O, N and S; and heterocyclyl is unsubstituted or substituted with one or more groups selected from halogen, hydroxy, unsubstituted or substituted ($C_1$-$C_{12}$)-alkoxy, cyano, unsubstituted or substituted ($C_1$-$C_{12}$)-alkyl, $CF_3$, $OCF_3$, unsubstituted or substituted ($C_3$-$C_{12}$)-cycloalkyl, unsubstituted or substituted aryl, unsubstituted or substituted aryloxy and unsubstituted or substituted heterocyclyl.

In an embodiment, the present invention provides compounds of formula 1 selected from:

(S)-Methyl 2-(6-(4-(3-(4-fluorophenyl)ureido)phenyl)-1-oxoisoindolin-2-yl)-3-methyl butanoate;
(S)-2-(6-(4-(3-(4-Fluorophenyl)ureido)phenyl)-1-oxoisoindolin-2-yl)-3-methyl butanoic acid,
(S)-Methyl 2-(6-(4-(3-(2,4-difluorophenyl)ureido)phenyl)-1-oxoisoindolin-2-yl)-3-methylbutanoate;
(S)-2-(6-(4-(3-(2,4-Difluorophenyl)ureido)phenyl)-1-oxoisoindolin-2-yl)-3-methylbutanoic acid;
(S)-Methyl 2-(6-(4-(3-(2-fluorophenyl)ureido)phenyl)-1-oxoisoindolin-2-yl)-3-methyl butanoate;
(S)-2-(6-(4-(3-(2-Fluorophenyl)ureido)phenyl)-1-oxoisoindolin-2-yl)-3-methyl butanoic acid;
(S)-Methyl 2-(6-(4-(3-(3-fluorophenyl)ureido)phenyl)-1-oxoisoindolin-2-yl)-3-methylbutanoate;
(S)-2-(6-(4-(3-(3-Fluorophenyl)ureido)phenyl)-1-oxoisoindolin-2-yl)-3-methyl butanoic acid;
(S)-Methyl 3-methyl-2-(1-oxo-6-(4-(3-phenylureido)phenyl)isoindolin-2-yl)butanoate;
(S)-3-Methyl-2-(1-oxo-6-(4-(3-phenylureido)phenyl)isoindolin-2-yl)butanoic acid;
(S)-Methyl 2-(6-(4-(3-benzylureido)phenyl)-1-oxoisoindolin-2-yl)-3-methyl butanoate;
(S)-2-(6-(4-(3-Benzylureido)phenyl)-1-oxoisoindolin-2-yl)-3-methylbutanoic acid;
(S)-Methyl 2-(6-(4-(3-(2,6-difluorophenyl)ureido)phenyl)-1-oxoisoindolin-2-yl)-3-methylbutanoate;
(S)-2-(6-(4-(3-(2,6-Difluorophenyl)ureido)phenyl)-1-oxoisoindolin-2-yl)-3-methylbutanoic acid;
(S)-Methyl 3-methyl-2-(1-oxo-6-(4-(3-m-tolylureido)phenyl)isoindolin-2-yl)butanoate;
(S)-3-Methyl-2-(1-oxo-6-(4-(3-m-tolylureido)phenyl)isoindolin-2-yl)butanoic acid;
(S)-Methyl 3-methyl-2-(1-oxo-6-(4-(3-p-tolylureido)phenyl)isoindolin-2-yl)butanoate;
(S)-3-Methyl-2-(1-oxo-6-(4-(3-p-tolylureido)phenyl)isoindolin-2-yl)butanoic acid;
(S)-Methyl 2-(6-(4-(3-(3-methoxyphenyl)ureido)phenyl)-1-oxoisoindolin-2-yl)-3-methylbutanoate;
(S)-2-(6-(4-(3-(3-Methoxyphenyl)ureido)phenyl)-1-oxoisoindolin-2-yl)-3-methyl butanoic acid;
(S)-Methyl-2-(6-(4-(3-(4-methoxyphenyl)ureido)phenyl)-1-oxoisoindolin-2-yl)-3-methylbutanoate;
(S)-2-(6-(4-(3-(4-Methoxyphenyl)ureido)phenyl)-1-oxoisoindolin-2-yl)-3-methylbutanoic acid;
(S)-Methyl-2-(6-(4-(3-(3,5-difluorophenyl)ureido)phenyl)-1-oxoisoindolin-2-yl)-3-methylbutanoate;
(S)-2-(6-(4-(3-(3,5-Difluorophenyl)ureido)phenyl)-1-oxoisoindolin-2-yl)-3-methylbutanoic acid;
(S)-Methyl 2-(6-(4-(3-(3,4-difluorophenyl)ureido)phenyl)-1-oxoisoindolin-2-yl)-3-methylbutanoate;
(S)-2-(6-(4-(3-(3,4-Difluorophenyl)ureido)phenyl)-1-oxoisoindolin-2-yl)-3-methylbutanoic acid;
(S)-Methyl 2-(6-(4-(3-cyclohexylureido)phenyl)-1-oxoisoindolin-2-yl)-3-methylbutanoate;
(S)-2-(6-(4-(3-Cyclohexylureido)phenyl)-1-oxoisoindolin-2-yl)-3-methylbutanoic acid;
(S)-Methyl 3-methyl-2-(1-oxo-6-(4-(3-(4-(trifluoromethyl)phenyl)ureido)phenyl)isoindolin-2-yl)butanoate;
(S)-3-Methyl-2-(1-oxo-6-(4-(3-(4-(trifluoromethyl)phenyl)ureido)phenyl)isoindolin-2-yl)butanoic acid;
(S)-Methyl 3-methyl-2-(1-oxo-6-(4-(3-(3-(trifluoromethyl)phenyl)ureido)phenyl)isoindolin-2-yl)butanoate;
(S)-3-Methyl-2-(1-oxo-6-(4-(3-(3-(trifluoromethyl)phenyl)ureido)phenyl)isoindolin-2-yl)butanoic acid;
(S)-Methyl 2-(6-(4-(3-(4-cyanophenyl)ureido)phenyl)-1-oxoisoindolin-2-yl)-3-methylbutanoate;
(S)-2-(6-(4-(3-(4-Cyanophenyl)ureido)phenyl)-1-oxoisoindolin-2-yl)-3-methyl butanoic acid;
(S)-Methyl 2-(6-(4-(3-(3-cyanophenyl)ureido)phenyl)-1-oxoisoindolin-2-yl)-3-methylbutanoate;
(S)-2-(6-(4-(3-(3-Cyanophenyl)ureido)phenyl)-1-oxoisoindolin-2-yl)-3-methyl butanoic acid;
(S)-Methyl 2-(6-(4-(3-(4-chloro-2-phenoxyphenyl)ureido)phenyl)-1-oxo isoindolin-2-yl)-3-methylbutanoate;
(S)-2-(6-(4-(3-(4-Chloro-2-phenoxyphenyl)ureido)phenyl)-1-oxoisoindolin-2-yl)-3-methylbutanoic acid;
(S)-Methyl 2-(6-(4-(3-(5-chloro-2-phenoxyphenyl)ureido)phenyl)-1-oxoisoindolin-2-yl)-3-methylbutanoate;
(S)-2-(6-(4-(3-(5-Chloro-2-phenoxyphenyl)ureido)phenyl)-1-oxoisoindolin-2-yl)-3-methylbutanoic acid;
(S)-Methyl 3-methyl-2-(1-oxo-6-(4-(3-(2-phenoxyphenyl)ureido)phenyl)isoindolin-2-yl)butanoate;
(S)-3-Methyl-2-(1-oxo-6-(4-(3-(2-phenoxyphenyl)ureido)phenyl)isoindolin-2-yl)butanoic acid;
(S)-Methyl 3-methyl-2-(1-oxo-6-(4-(3-(4-phenoxyphenyl)ureido)phenyl)isoindolin-2-yl)butanoate;
(S)-3-Methyl-2-(1-oxo-6-(4-(3-(4-phenoxyphenyl)ureido)phenyl)isoindolin-2-yl)butanoic acid;
(S)-Methyl 2-(6-(4-(3-(2-fluorophenyl)thioureido)phenyl)-1-oxoisoindolin-2-yl)-3-methylbutanoate;
(S)-2-(6-(4-(3-(2-Fluorophenyl)thioureido)phenyl)-1-oxoisoindolin-2-yl)-3-methylbutanoic acid;
(S)-Methyl 3-methyl-2-(1-oxo-6-(4-(3-p-tolylthioureido)phenyl)isoindolin-2-yl)butanoate;
(S)-3-Methyl-2-(1-oxo-6-(4-(3-p-tolylthioureido)phenyl)isoindolin-2-yl)butanoic acid;
(S)-Methyl 2-(6-(4-(3-(3-fluorophenyl)thioureido)phenyl)-1-oxoisoindolin-2-yl)-3-methylbutanoate;
(S)-2-(6-(4-(3-(3-Fluorophenyl)thioureido)phenyl)-1-oxoisoindolin-2-yl)-3-methylbutanoic acid;
(S)-Methyl 2-(6-(4-(3-(4-methoxyphenyl)thioureido)phenyl)-1-oxoisoindolin-2-yl)-3-methylbutanoate;
(S)-2-(6-(4-(3-(4-Methoxyphenyl)thioureido)phenyl)-1-oxoisoindolin-2-yl)-3-methylbutanoic acid;
(S)-Methyl 2-(6-(4-(3-(3-methoxyphenyl)thioureido)phenyl)-1-oxoisoindolin-2-yl)-3-methylbutanoate;
(S)-2-(6-(4-(3-(3-Methoxyphenyl)thioureido)phenyl)-1-oxoisoindolin-2-yl)-3-methylbutanoic acid;
(S)-Methyl 2-(6-(4-(3-(4-chlorophenyl)thioureido)phenyl)-1-oxoisoindolin-2-yl)-3-methylbutanoate;
(S)-2-(6-(4-(3-(4-Chlorophenyl)thioureido)phenyl)-1-oxoisoindolin-2-yl)-3-methyl butanoic acid;
(S)-Methyl 2-(6-(4-(3-(3-chlorophenyl)thioureido)phenyl)-1-oxoisoindolin-2-yl)-3-methylbutanoate;
(S)-2-(6-(4-(3-(3-Chlorophenyl)thioureido)phenyl)-1-oxoisoindolin-2-yl)-3-methyl butanoic acid;
(S)-Methyl 3-methyl-2-(1-oxo-6-(4-(3-(2-(trifluoromethyl)phenyl)thioureido)phenyl)isoindolin-2-yl)butanoate;
(S)-3-Methyl-2-(1-oxo-6-(4-(3-(2-trifluoromethyl)phenyl)thioureido)phenyl)isoindolin-2-yl)butanoic acid;
(S)-Methyl 2-(6-(4-(3-(4-cyanophenyl)thioureido)phenyl)-1-oxoisoindolin-2-yl)-3-methylbutanoate;
(S)-2-(6-(4-(3-(4-Cyanophenyl)thioureido)phenyl)-1-oxoisoindolin-2-yl)-3-methyl butanoic acid;
(S)-Methyl 2-(6-(4-(3-(4-cyanophenyl)thioureido)phenyl)-1-oxoisoindolin-2-yl)-3-methylbutanoate;

(S)-2-(6-(4-(3-(3-Cyanophenyl)thioureido)phenyl)-1-ox-oisoindolin-2-yl)-3-methyl butanoic acid;
(S)-Methyl 3-methyl-2-(1-oxo-6-(4-(3-o-tolylthioureido)phenyl)isoindolin-2-yl)butanoate;
(S)-3-Methyl-2-(1-oxo-6-(4-(3-o-tolylthioureido)phenyl)isoindolin-2-yl)butanoic acid;
(S)-Methyl 2-(6-(4-(3-(2-methoxyphenyl)thioureido)phenyl)-1-oxoisoindolin-2-yl)-3-methylbutanoate;
(S)-2-(6-(4-(3-(2-Methoxyphenyl)thioureido)phenyl)-1-oxoisoindolin-2-yl)-3-methylbutanoic acid;
(S)-Methyl 3-methyl-2-(1-oxo-6-(4-(3-(3-(trifluoromethyl)phenyl)thioureido)phenyl)isoindolin-2-yl)butanoate;
(S)-3-Methyl-2-(1-oxo-6-(4-(3-(3-(trifluoromethyl)phenyl)thioureido)phenyl)isoindolin-2-yl)butanoic acid;
(S)-Methyl 3-methyl-2-(1-oxo-6-(4-(phenylsulfonamido)phenyl)isoindolin-2-yl)butanoate;
(S)-3-Methyl-2-(1-oxo-6-(4-(phenylsulfonamido)phenyl)isoindolin-2-yl)butanoic acid;
(S)-Methyl 2-(6-(4-(4-cyanophenylsulfonamido)phenyl)-1-oxoisoindolin-2-yl)-3-methylbutanoate;
(S)-2-(6-(4-(4-Cyanophenylsulfonamido)phenyl)-1-oxoisoindolin-2-yl)-3-methyl butanoic acid;
(S)-Methyl 2-(6-(4-(3,4-difluorophenylsulfonamido)phenyl)-1-oxoisoindolin-2-yl)-3-methylbutanoate;
(S)-2-(6-(4-(3,4-Difluorophenylsulfonamido)phenyl)-1-oxoisoindolin-2-yl)-3-methylbutanoic acid;
(S)-Methyl 2-(6-(4-(2,4-difluorophenylsulfonamido)phenyl)-1-oxoisoindolin-2-yl)-3-methylbutanoate;
(S)-2-(6-(4-(2,4-Difluorophenylsulfonamido)phenyl)-1-oxoisoindolin-2-yl)-3-methylbutanoic acid;
(S)-Methyl 2-(6-(4-(3,4-dimethoxyphenylsulfonamido)phenyl)-1-oxoisoindolin-2-yl)-3-methylbutanoate;
(S)-2-(6-(4-(3,4-Dimethoxyphenylsulfonamido)phenyl)-1-oxoisoindolin-2-yl)-3-methylbutanoic acid;
(S)-Methyl 2-(6-(4-(3-chlorophenylsulfonamido)phenyl)-1-oxoisoindolin-2-yl)-3-methylbutanoate;
(S)-2-(6-(4-(3-Chlorophenylsulfonamido)phenyl)-1-oxoisoindolin-2-yl)-3-methylbutanoic acid;
(S)-Methyl 2-(6-(4-(4-methoxyphenylsulfonamido)phenyl)-1-oxoisoindolin-2-yl)-3-methylbutanoate;
(S)-2-(6-(4-(4-Methoxyphenylsulfonamido)phenyl)-1-oxoisoindolin-2-yl)-3-methylbutanoic acid;
(S)-Methyl 3-methyl-2-(1-oxo-6-(4-(4-(trifluoromethyl)phenylsulfonamido)phenyl)isoindolin-2-yl)butanoate;
(S)-3-Methyl-2-(1-oxo-6-(4-(4-(trifluoromethyl)phenylsulfonamido)phenyl)isoindolin-2-yl)butanoic acid;
(S)-Methyl 3-methyl-2-(1-oxo-6-(4-(phenylmethylsulfonamido)phenyl)isoindolin-2-yl)butanoate;
(S)-3-Methyl-2-(1-oxo-6-(4-(phenylmethylsulfonamido)phenyl)isoindolin-2-yl)butanoic acid;
(S)-Methyl 3-methyl-2-(6-(4-(1-methylethylsulfonamido)phenyl)-1-oxoisoindolin-2-yl)butanoate;
(S)-3-Methyl-2-(6-(4-(1-methylethylsulfonamido)phenyl)-1-oxoisoindolin-2-yl)butanoic acid;
(S)-Methyl 2-(6-(4-benzamidophenyl)-1-oxoisoindolin-2-yl)-3-methylbutanoate
(S)-2-(6-(4-Benzamidophenyl)-1-oxoisoindolin-2-yl)-3-methylbutanoic acid;
(S)-Methyl 2-(6-(4-(4-fluorobenzamido)phenyl)-1-oxoisoindolin-2-yl)-3-methylbutanoate;
(S)-2-(6-(4-(4-Fluorobenzamido)phenyl)-1-oxoisoindolin-2-yl)-3-methylbutanoic acid;
(S)-Methyl 3-methyl-2-(1-oxo-6-(4-(4-(trifluoromethyl)benzamido)phenyl)isoindolin-2-yl)butanoate;
(S)-3-Methyl-2-(1-oxo-6-(4-(4-(trifluoromethyl)benzamido)phenyl)isoindolin-2-yl)butanoic acid;
(S)-Methyl 2-(6-(4-(4-methoxybenzamido)phenyl)-1-oxoisoindolin-2-yl)-3-methylbutanoate;
(S)-2-(6-(4-(4-Methoxybenzamido)phenyl)-1-oxoisoindolin-2-yl)-3-methyl butanoic acid;
(S)-Methyl 2-(6-(4-(3-fluorobenzamido)phenyl)-1-oxoisoindolin-2-yl)-3-methyl butanoate;
(S)-2-(6-(4-(3-Fluorobenzamido)phenyl)-1-oxoisoindolin-2-yl)-3-methylbutanoic acid;
(S)-Methyl 2-(6-(4-(3-chlorobenzamido)phenyl)-1-oxoisoindolin-2-yl)-3-methylbutanoate;
(S)-2-(6-(4-(3-Chlorobenzamido)phenyl)-1-oxoisoindolin-2-yl)-3-methylbutanoic acid;
(S)-Methyl 2-(6-(4-(2,4-difluorobenzamido)phenyl)-1-oxoisoindolin-2-yl)-3-methylbutanoate;
(S)-2-(6-(4-(2,4-Difluorobenzamido)phenyl)-1-oxoisoindolin-2-yl)-3-methyl butanoic acid;
(S)-Methyl 3-methyl-2-(6-(4-(4-methylbenzamido)phenyl)-1-oxoisoindolin-2-yl)butanoate;
(S)-3-Methyl-2-(6-(4-(4-methylbenzamido)phenyl)-1-oxoisoindolin-2-yl)butanoic acid;
(S)-Methyl 2-(6-(4-(4-chlorobenzamido)phenyl)-1-oxoisoindolin-2-yl)-3-methylbutanoate;
(S)-2-(6-(4-(4-Chlorobenzamido)phenyl)-1-oxoisoindolin-2-yl)-3-methylbutanoic acid;
(S)-Methyl 2-(6-(4-(4-tert-butylbenzamido)phenyl)-1-oxoisoindolin-2-yl)-3-methylbutanoate;
(S)-2-(6-(4-(4-tert-Butylbenzamido)phenyl)-1-oxoisoindolin-2-yl)-3-methyl butanoic acid;
(S)-Methyl 2-(6-(4-(cyclohexanecarboxamido)phenyl)-1-oxoisoindolin-2-yl)-3-methylbutanoate;
(S)-2-(6-(4-(Cyclohexanecarboxamido)phenyl)-1-oxoisoindolin-2-yl)-3-methylbutanoic acid;
(S)-Methyl 2-(6-(4-biphenyl-4-ylcarboxamidophenyl)-1-oxoisoindolin-2-yl)-3-methylbutanoate;
(S)-2-(6-(4-Biphenyl-4-ylcarboxamidophenyl)-1-oxoisoindolin-2-yl)-3-methyl butanoic acid,
(S)-Methyl 2-(6-(4-(2-naphthamido)phenyl)-1-oxoisoindolin-2-yl)-3-methyl butanoate;
(S)-2-(6-(4-(2-Naphthamido)phenyl)-1-oxoisoindolin-2-yl)-3-methylbutanoic acid;
(S)-Methyl 3-methyl-2-(1-oxo-6-(4-(4-pentylbenzamido)phenyl)isoindolin-2-yl)butanoate;
(S)-3-Methyl-2-(1-oxo-6-(4-(4-pentylbenzamido)phenyl)isoindolin-2-yl)butanoic acid;
(S)-Methyl 2-(6-(4-(2-fluoro-6-(trifluoromethyl)benzamido)phenyl)-1-oxoisoindolin-2-yl)-3-methylbutanoate;
(S)-2-(6-(4-(2-Fluoro-6-(trifluoromethyl)benzamido)phenyl)-1-oxoisoindolin-2-yl)-3-methylbutanoic acid;
(S)-Methyl 2-(6-(4-(benzo[d][1,3]dioxole-5-carboxamido)phenyl)-1-oxo isoindolin-2-yl)-3-methylbutanoate;
(S)-2-(6-(4-(Benzo[d][1,3]dioxole-5-carboxamido)phenyl)-1-oxoisoindolin-2-yl)-3-methylbutanoic acid;
(S)-Methyl 2-(6-(4-(2,6-dichlorobenzamido)phenyl)-1-oxoisoindolin-2-yl)-3-methylbutanoate;
(S)-2-(6-(4-(2,6-Dichlorobenzamido)phenyl)-1-oxoisoindolin-2-yl)-3-methyl butanoic acid;
(S)-Methyl 2-(6-(4-(2-chlorobenzamido)phenyl)-1-oxoisoindolin-2-yl)-3-methyl butanoate;
(S)-2-(6-(4-(2-Chlorobenzamido)phenyl)-1-oxoisoindolin-2-yl)-3-methylbutanoic acid;
(S)-Methyl 2-(6-(4-(2,4-dichlorobenzamido)phenyl)-1-oxoisoindolin-2-yl)-3-methyl butanoate;
(S)-2-(6-(4-(2,4-Dichlorobenzamido)phenyl)-1-oxoisoindolin-2-yl)-3-methyl butanoic acid;
(S)-Methyl 2-(6-(4-(4-butoxybenzamido)phenyl)-1-oxoisoindolin-2-yl)-3-methyl butanoate;

(S)-2-(6-(4-(4-Butoxybenzamido)phenyl)-1-oxoisoindolin-2-yl)-3-methyl butanoic acid;
(S)-Methyl 2-(6-(4-(2,6-difluorobenzamido)phenyl)-1-oxoisoindolin-2-yl)-3-methylbutanoate;
(S)-2-(6-(4-(2,6-Difluorobenzamido)phenyl)-1-oxoisoindolin-2-yl)-3-methyl butanoic acid;
(S)-Methyl 2-(6-(4-(3,4-difluorobenzamido)phenyl)-1-oxoisoindolin-2-yl)-3-methylbutanoate;
(S)-2-(6-(4-(3,4-Difluorobenzamido)phenyl)-1-oxoisoindolin-2-yl)-3-methyl butanoic acid,
(S)-Methyl 2-(6-(4-(3,4-dimethoxybenzamido)phenyl)-1-oxoisoindolin-2-yl)-3-methylbutanoate;
(S)-2-(6-(4-(3,4-Dimethoxybenzamido)phenyl)-1-oxoisoindolin-2-yl)-3-methyl butanoic acid;
(S)-Methyl 3-methyl-2-(1-oxo-6-(4-(3,4,5-trimethoxybenzamido)phenyl)isoindolin-2-yl)butanoate;
(S)-3-Methyl-2-(1-oxo-6-(4-(3,4,5-trimethoxybenzamido)phenyl)isoindolin-2-yl)butanoic acid;
(S)-Methyl 2-(6-(4-(3,5-diethoxybenzamido)phenyl)-1-oxoisoindolin-2-yl)-3-methylbutanoate;
(S)-2-(6-(4-(3,5-Diethoxybenzamido)phenyl)-1-oxoisoindolin-2-yl)-3-methyl butanoic acid;
(S)-Methyl 3-methyl-2-(1-oxo-6-(4-(3-phenoxybenzamido)phenyl)isoindolin-2-yl)butanoate;
(S)-3-Methyl-2-(1-oxo-6-(4-(3-phenoxybenzamido)phenyl)isoindolin-2-yl)butanoic acid;
(S)-Methyl 3-methyl-2-(1-oxo-6-(4-(4-phenoxybenzamido)phenyl)isoindolin-2-yl)butanoate;
(S)-3-Methyl-2-(1-oxo-6-(4-(4-phenoxybenzamido)phenyl)isoindolin-2-yl)butanoic acid,
(S)-Methyl 3-methyl-2-(1-oxo-6-(4-(2-phenoxybenzamido)phenyl)isoindolin-2-yl)butanoate;
(S)-3-Methyl-2-(1-oxo-6-(4-(2-phenoxybenzamido)phenyl)isoindolin-2-yl)butanoic acid;
(S)-Methyl 3-methyl-2-(1-oxo-6-(4-(2,4,6-trimethylbenzamido)phenyl)isoindolin-2-yl)butanoate;
(S)-3-Methyl-2-(1-oxo-6-(4-(2,4,6-trimethylbenzamido)phenyl)isoindolin-2-yl)butanoic acid;
(S)-Methyl 2-(6-(4-(2,4-dimethoxybenzamido)phenyl)-1-oxoisoindolin-2-yl)-3-methylbutanoate;
(S)-2-(6-(4-(2,4-Dimethoxybenzamido)phenyl)-1-oxoisoindolin-2-yl)-3-methyl butanoic acid;
(S)-Methyl 3-methyl-2-(1-oxo-6-(4-(4-(trifluoromethoxy)benzamido)phenyl)isoindolin-2-yl)butanoate;
(S)-3-Methyl-2-(1-oxo-6-(4-(4-(trifluoromethoxy)benzamido)phenyl)isoindolin-2-yl)butanoic acid;
(S)-Methyl 2-(6-(4-(2-methoxybenzamido)phenyl)-1-oxoisoindolin-2-yl)-3-methylbutanoate;
(S)-2-(6-(4-(2-Methoxybenzamido)phenyl)-1-oxoisoindolin-2-yl)-3-methyl butanoic acid;
(S)-Methyl 2-(6-(4-(4-fluoro-3-methylbenzamido)phenyl)-1-oxoisoindolin-2-yl)-3-methylbutanoate;
(S)-2-(6-(4-(4-Fluoro-3-methylbenzamido)phenyl)-1-oxoisoindolin-2-yl)-3-methyl butanoic acid;
(S)-Methyl 2-(6-(4-(4-butylbenzamido)phenyl)-1-oxoisoindolin-2-yl)-3-methyl butanoate;
(S)-2-(6-(4-(4-Butylbenzamido)phenyl)-1-oxoisoindolin-2-yl)-3-methylbutanoic acid;
(S)-Methyl 2-(6-(4-(2,6-difluoro-3-methylbenzamido)phenyl)-1-oxoisoindolin-2-yl)-3-methylbutanoate;
(S)-2-(6-(4-(2,6-Difluoro-3-methylbenzamido)phenyl)-1-oxoisoindolin-2-yl)-3-methylbutanoic acid;
(S)-Methyl 2-(6-(4-(4-ethylbenzamido)phenyl)-1-oxoisoindolin-2-yl)-3-methyl butanoate;
(S)-2-(6-(4-(4-Ethylbenzamido)phenyl)-1-oxoisoindolin-2-yl)-3-methylbutanoic acid;
(S)-Methyl 3-methyl-2-(1-oxo-6-(4-(4-propylbenzamido)phenyl)isoindolin-2-yl)butanoate;
(S)-3-Methyl-2-(1-oxo-6-(4-(4-propylbenzamido)phenyl)isoindolin-2-yl)butanoic acid;
(S)-Methyl 3-methyl-2-(6-(4-(4-octylbenzamido)phenyl)-1-oxoisoindolin-2-yl)butanoate;
(S)-3-Methyl-2-(6-(4-(4-octylbenzamido)phenyl)-1-oxoisoindolin-2-yl)butanoic acid;
(S)-Methyl 2-(6-(4-(4-cyclohexylbenzamido)phenyl)-1-oxoisoindolin-2-yl)-3-methylbutanoate;
(S)-2-(6-(4-(4-Cyclohexylbenzamido)phenyl)-1-oxoisoindolin-2-yl)-3-methyl butanoic acid;
(S)-Methyl 3-methyl-2-(1-oxo-6-(4-(5,5,8,8-tetramethyl-5,6,7,8-tetrahydronaphthalene-2-carboxamido)phenyl)isoindolin-2-yl)butanoate;
(S)-3-Methyl-2-(1-oxo-6-(4-(5,5,8,8-tetramethyl-5,6,7,8-tetrahydro naphthalene-2-carboxamido)phenyl)isoindolin-2-yl)butanoic acid;
(S)-Methyl 2-(6-(4-(1-naphthamido)phenyl)-1-oxoisoindolin-2-yl)-3-methyl butanoate;
(S)-2-(6-(4-(1-Naphthamido)phenyl)-1-oxoisoindolin-2-yl)-3-methylbutanoic acid;
(S)-Methyl 2-(6-(4-(3,5-dimethoxybenzamido)phenyl)-1-oxoisoindolin-2-yl)-3-methylbutanoate;
(S)-2-(6-(4-(3,5-Dimethoxybenzamido)phenyl)-1-oxoisoindolin-2-yl)-3-methyl butanoic acid;
(S)-Methyl 2-(6-(4-(4-hexylbenzamido)phenyl)-1-oxoisoindolin-2-yl)-3-methyl butanoate;
(S)-2-(6-(4-(4-Hexylbenzamido)phenyl)-1-oxoisoindolin-2-yl)-3-methylbutanoic acid;
(S)-Methyl 2-(6-(4-(4-heptylbenzamido)phenyl)-1-oxoisoindolin-2-yl)-3-methyl butanoate;
(S)-2-(6-(4-(4-Heptylbenzamido)phenyl)-1-oxoisoindolin-2-yl)-3-methylbutanoic acid;
(S)-Methyl 3-methyl-2-(6-(4-(4-nonylbenzamido)phenyl)-1-oxoisoindolin-2-yl)butanoate;
(S)-3-Methyl-2-(6-(4-(4-nonylbenzamido)phenyl)-1-oxoisoindolin-2-yl)butanoic acid;
(S)-Methyl 2-(6-(4-(4-decylbenzamido)phenyl)-1-oxoisoindolin-2-yl)-3-methyl butanoate;
(S)-2-(6-(4-(4-Decylbenzamido)phenyl)-1-oxoisoindolin-2-yl)-3-methyl butanoic acid;
(S)-(Methyl 2-(6-(4-(adamentyl-2-carboxamido)phenyl)-1-oxoisoindolin-2-yl)-3-methylbutanoate;
(S)-2-(6-(4-(Adamantyl-2-carboxamido)phenyl)-1-oxoisoindolin-2-yl)-3-methylbutanoic acid;
(S)-Methyl 2-(6-(4-(2-fluoro-4-(trifluoromethyl)benzamido)phenyl)-1-oxoisoindolin-2-yl)-3-methylbutanoate;
(S)-2-(6-(4-(2-Fluoro-4-(trifluoromethyl)benzamido)phenyl)-1-oxoisoindolin-2-yl)-3-methylbutanoic acid;
(S)-Methyl 2-(6-(4-(2-fluoro-3-(trifluoromethyl)benzamido)phenyl)-1-oxoisoindolin-2-yl)-3-methylbutanoate;
(S)-2-(6-(4-(2-Fluoro-3-(trifluoromethyl)benzamido)phenyl)-1-oxoisoindolin-2-yl)-3-methylbutanoic acid;
(S)-Methyl 2-(6-(4-(3-fluoro-4-(trifluoromethyl)benzamido)phenyl)-1-oxoisoindolin-2-yl)-3-methylbutanoate;
(S)-2-(6-(4-(3-Fluoro-4-(trifluoromethyl)benzamido)phenyl)-1-oxoisoindolin-2-yl)-3-methylbutanoic acid;
(S)-Methyl 2-(6-(4-(4-fluoro-2-(trifluoromethyl)benzamido)phenyl)-1-oxoisoindolin-2-yl)-3-methylbutanoate;
(S)-2-(6-(4-(4-Fluoro-2-(trifluoromethyl)benzamido)phenyl)-1-oxoisoindolin-2-yl)-3-methylbutanoic acid;
(S)-Methyl 3-methyl-2-(1-oxo-6-(4-(2-(trifluoromethyl)benzamido)phenyl)iso indolin-2-yl)butanoate;
(S)-3-Methyl-2-(1-oxo-6-(4-(2-(trifluoromethyl)benzamido)phenyl)isoindolin-2-yl)butanoic acid;

(S)-Methyl 2-(6-(4-(2-ethoxybenzamido)phenyl)-1-oxoisoindolin-2-yl)-3-methyl butanoate;
(S)-2-(6-(4-(2-Ethoxybenzamido)phenyl)-1-oxoisoindolin-2-yl)-3-methylbutanoic acid;
(S)-Methyl 2-(6-(4-(4-cyanobenzamido)phenyl)-1-oxoisoindolin-2-yl)-3-methyl butanoate;
(S)-Methyl 2-(6-(4-(3-chloro-2-fluorobenzamido)phenyl)-1-oxoisoindolin-2-yl)-3-methylbutanoate;
(S)-Methyl 2-(6-(4-(4-fluoro-3-(trifluoromethyl)benzamido)phenyl)-1-oxoisoindolin-2-yl)-3-methylbutanoate;
(S)-Methyl 3-methyl-2-(6-(4-(nicotinamido)phenyl)-1-oxoisoindolin-2-yl)butanoate;
(S)-3-Methyl-2-(6-(4-(nicotinamido)phenyl)-1-oxoisoindolin-2-yl)butanoic acid;
(S)-Methyl 2-(6-(4-(2-chloronicotinamido)phenyl)-1-oxoisoindolin-2-yl)-3-methylbutanoate;
(S)-2-(6-(4-(2-Chloronicotinamido)phenyl)-1-oxoisoindolin-2-yl)-3-methyl butanoic acid;
(S)-Methyl 3-methyl-2-(1-oxo-5-(4-(6-(trifluoromethyl)nicotinamido)phenyl)iso indolin-2-yl)butanoate;
(S)-Methyl 2-(6-(4-(6-chloronicotinamido)phenyl)-1-oxoisoindolin-2-yl)-3-methyl butanoate;
(S)-Methyl 3-methyl-2-(6-(4-(6-morpholinonicotinamido)phenyl)-1-oxoisoindolin-2-yl)butanoate;
(S)-3-Methyl-2-(6-(4-(6-morpholinonicotinamido)phenyl)-1-oxoisoindolin-2-yl)butanoic acid;
(S)-Methyl 3-methyl-2-(1-oxo-6-(4-(6-(piperidin-1-yl)nicotinamido)phenyl)iso indolin-2-yl)butanoate;
(S)-3-Methyl-2-(1-oxo-6-(4-(6-(piperidin-1-yl)nicotinamido)phenyl)isoindolin-2-yl)butanoic acid;
(S)-Methyl 3-methyl-2-(1-oxo-6-(4-(6-(pyrrolidin-1-yl)nicotinamido)phenyl)iso indolin-2-yl)butanoate;
(S)-3-Methyl-2-(1-oxo-6-(4-(6-(pyrrolidin-1-yl)nicotinamido)phenyl)isoindolin-2-yl)butanoic acid;
(S)-Methyl 3-methyl-2-(6-(4-(6-(4-methylpiperazin-1-yl)nicotinamido)phenyl)-1-oxoisoindolin-2-yl)butanoate;
(S)-Methyl 2-(5-(4-(3-(4-fluorophenyl)ureido)phenyl)-1-oxoisoindolin-2-yl)-3-methylbutanoate;
(S)-2-(5-(4-(3-(4-Fluorophenyl)ureido)phenyl)-1-oxoisoindolin-2-yl)-3-methylbutanoic acid,
(S)-Methyl 2-(5-(4-(3-(2-fluorophenyl)ureido)phenyl)-1-oxoisoindolin-2-yl)-3-methylbutanoate;
(S)-2-(5-(4-(3-(2-Fluorophenyl)ureido)phenyl)-1-oxoisoindolin-2-yl)-3-methyl butanoic acid,
(S)-Methyl 2-(5-(4-(3-(3-fluorophenyl)ureido)phenyl)-1-oxoisoindolin-2-yl)-3-methylbutanoate;
(S)-2-(5-(4-(3-(3-Fluorophenyl)ureido)phenyl)-1-oxoisoindolin-2-yl)-3-methyl butanoic acid,
(S)-Methyl 3-methyl-2-(1-oxo-5-(4-(3-phenylureido)phenyl)isoindolin-2-yl)butanoate;
(S)-3-Methyl-2-(1-oxo-5-(4-(3-phenylureido)phenyl)isoindolin-2-yl)butanoic acid;
(S)-Methyl 2-(5-(4-(3-benzylureido)phenyl)-1-oxoisoindolin-2-yl)-3-methyl butanoate;
(S)-2-(5-(4-(3-Benzylureido)phenyl)-1-oxoisoindolin-2-yl)-3-methylbutanoic acid;
(S)-Methyl 2-(5-(4-(3-cyclohexylureido)phenyl)-1-oxoisoindolin-2-yl)-3-methyl butanoate;
(S)-2-(5-(4-(3-Cyclohexylureido)phenyl)-1-oxoisoindolin-2-yl)-3-methyl butanoic acid;
(S)-Methyl 2-(5-(4-(3-(2,4-difluorophenyl)ureido)phenyl)-1-oxoisoindolin-2-yl)-3-methylbutanoate;
(S)-2-(5-(4-(3-(2,4-Difluorophenyl)ureido)phenyl)-1-oxoisoindolin-2-yl)-3-methylbutanoic acid;
(S)-Methyl 2-(5-(4-(3-(3,4-difluorophenyl)ureido)phenyl)-1-oxoisoindolin-2-yl)-3-methylbutanoate;
(S)-2-(5-(4-(3-(3,4-Difluorophenyl)ureido)phenyl)-1-oxoisoindolin-2-yl)-3-methylbutanoic acid;
(S)-Methyl 3-methyl-2-(1-oxo-5-(4-(3-p-tolylureido)phenyl)isoindolin-2-yl)butanoate;
(S)-3-Methyl-2-(1-oxo-5-(4-(3-p-tolylureido)phenyl)isoindolin-2-yl)butanoic acid;
(S)-Methyl 3-methyl-2-(1-oxo-5-(4-(3-m-tolylureido)phenyl)isoindolin-2-yl)butanoate;
(S)-3-Methyl-2-(1-oxo-5-(4-(3-m-tolylureido)phenyl)isoindolin-2-yl)butanoic acid;
(S)-Methyl 3-methyl-2-(1-oxo-5-(4-(3-(4-(trifluoromethyl)phenyl)ureido)phenyl)isoindolin-2-yl)butanoate;
(S)-3-Methyl-2-(1-oxo-5-(4-(3-(4-(trifluoromethyl)phenyl)ureido)phenyl)isoindolin-2-yl)butanoic acid;
(S)-Methyl 3-methyl-2-(1-oxo-5-(4-(3-(3-(trifluoromethyl)phenyl)ureido)phenyl)isoindolin-2-yl)butanoate;
(S)-3-Methyl-2-(1-oxo-5-(4-(3-(3-(trifluoromethyl)phenyl)ureido)phenyl)isoindolin-2-yl)butanoic acid;
(S)-Methyl 2-(5-(4-(3-(4-methoxyphenyl)ureido)phenyl)-1-oxoisoindolin-2-yl)-3-methylbutanoate;
(S)-2-(5-(4-(3-(4-Methoxyphenyl)ureido)phenyl)-1-oxoisoindolin-2-yl)-3-methylbutanoic acid;
(S)-Methyl 2-(5-(4-(3-(3-methoxyphenyl)ureido)phenyl)-1-oxoisoindolin-2-yl)-3-methylbutanoate;
(S)-2-(5-(4-(3-(3-Methoxyphenyl)ureido)phenyl)-1-oxoisoindolin-2-yl)-3-methylbutanoic acid;
(S)-Methyl 2-(5-(4-(3-(4-cyanophenyl)ureido)phenyl)-1-oxoisoindolin-2-yl)-3-methylbutanoate;
(S)-2-(5-(4-(3-(4-Cyanophenyl)ureido)phenyl)-1-oxoisoindolin-2-yl)-3-methylbutanoic acid;
(S)-Methyl 2-(5-(4-(3-(3-cyanophenyl)ureido)phenyl)-1-oxoisoindolin-2-yl)-3-methylbutanoate;
(S)-2-(5-(4-(3-(3-Cyanophenyl)ureido)phenyl)-1-oxoisoindolin-2-yl)-3-methylbutanoic acid;
(S)-Methyl 2-(5-(4-(3-(2-fluorophenyl)thioureido)phenyl)-1-oxoisoindolin-2-yl)-3-methylbutanoate;
(S)-2-(5-(4-(3-(2-Fluorophenyl)thioureido)phenyl)-1-oxoisoindolin-2-yl)-3-methylbutanoic acid;
(S)-Methyl 2-(5-(4-(3-(3-fluorophenyl)thioureido)phenyl)-1-oxoisoindolin-2-yl)-3-methylbutanoate;
(S)-2-(5-(4-(3-(3-Fluorophenyl)thioureido)phenyl)-1-oxoisoindolin-2-yl)-3-methyl butanoic acid;
(S)-Methyl 2-(5-(4-(3-(4-methoxyphenyl)thioureido)phenyl)-1-oxoisoindolin-2-yl)-3-methylbutanoate;
(S)-2-(5-(4-(3-(4-Methoxyphenyl)thioureido)phenyl)-1-oxoisoindolin-2-yl)-3-methylbutanoic acid;
(S)-Methyl 2-(5-(4-(3-(3-methoxyphenyl)thioureido)phenyl)-1-oxoisoindolin-2-yl)-3-methylbutanoate;
(S)-2-(5-(4-(3-(3-Methoxyphenyl)thioureido)phenyl)-1-oxoisoindolin-2-yl)-3-methyl butanoic acid;
(S)-Methyl 2-(5-(4-(3-(4-chlorophenyl)thioureido)phenyl)-1-oxoisoindolin-2-yl)-3-methylbutanoate;
(S)-2-(5-(4-(3-(4-chlorophenyl)thioureido)phenyl)-1-oxoisoindolin-2-yl)-3-methylbutanoic acid;
(S)-Methyl 2-(5-(4-(3-(3-chlorophenyl)thioureido)phenyl)-1-oxoisoindolin-2-yl)-3-methylbutanoate;
(S)-2-(5-(4-(3-(3-Chlorophenyl)thioureido)phenyl)-1-oxoisoindolin-2-yl)-3-methylbutanoic acid;
(S)-Methyl 2-(5-(4-(3-(4-cyanophenyl)thioureido)phenyl)-1-oxoisoindolin-2-yl)-3-methylbutanoate;
(S)-2-(5-(4-(3-(4-Cyanophenyl)thioureido)phenyl)-1-oxoisoindolin-2-yl)-3-methyl butanoic acid;
(S)-Methyl 3-methyl-2-(1-oxo-5-(4-(3-(2-(trifluoromethyl)phenyl)thioureido)phenyl)isoindolin-2-yl)butanoate;
(S)-3-Methyl-2-(1-oxo-5-(4-(3-(2-(trifluoromethyl)phenyl)thioureido)phenyl)isoindolin-2-yl)butanoic acid;

(S)-Methyl 3-methyl-2-(1-oxo-5-(4-(3-o-tolylthioureido) phenyl)isoindolin-2-yl)butanoate;
(S)-3-Methyl-2-(1-oxo-5-(4-(3-o-tolylthioureido)phenyl) isoindolin-2-yl)butanoic acid;
(S)-Methyl 3-methyl-2-(1-oxo-5-(4-(3-p-tolylthioureido) phenyl)isoindolin-2-yl)butanoate;
(S)-3-Methyl-2-(1-oxo-5-(4-(3-p-tolylthioureido)phenyl) isoindolin-2-yl)butanoic acid;
(S)-Methyl 2-(5-(4-(3-(3-fluorophenyl)thioureido)phenyl)-1-oxoisoindolin-2-yl)-3-methylbutanoate,
(S)-2-(5-(4-(3-(3-Fluorophenyl)thioureido)phenyl)-1-oxoisoindolin-2-yl)-3-methyl butanoic acid;
(S)-Methyl 2-(5-(4-(3-(3-methoxyphenyl)thioureido)phenyl)-1-oxoisoindolin-2-yl)-3-methylbutanoate;
(S)-2-(5-(4-(3-(3-Methoxyphenyl)thioureido)phenyl)-1-oxoisoindolin-2-yl)-3-methylbutanoic acid;
(S)-Methyl 2-(5-(4-(3-(2-methoxyphenyl)thioureido)phenyl)-1-oxoisoindolin-2-yl)-3-methylbutanoate;
(S)-2-(5-(4-(3-(2-Methoxyphenyl)thioureido)phenyl)-1-oxoisoindolin-2-yl)-3-methylbutanoic acid;
(S)-Methyl 3-methyl-2-(1-oxo-5-(4-(3-(3-(trifluoromethyl) phenyl)thioureido)phenyl)isoindolin-2-yl)butanoate;
(S)-3-Methyl-2-(1-oxo-5-(4-(3-(3-(trifluoromethyl)phenyl) thioureido)phenyl)isoindolin-2-yl)butanoic acid;
(S)-Methyl 3-methyl-2-(1-oxo-6-(4-(phenylsulfonamido) phenyl)isoindolin-2-yl)butanoate;
(S)-3-Methyl-2-(1-oxo-6-(4-(phenylsulfonamido)phenyl) isoindolin-2-yl)butanoic acid;
(S)-Methyl 2-(5-(4-(4-cyanophenylsulfonamido)phenyl)-1-oxoisoindolin-2-yl)-3-methylbutanoate;
(S)-2-(5-(4-(4-Cyanophenylsulfonamido)phenyl)-1-oxoisoindolin-2-yl)-3-methyl butanoic acid;
(S)-Methyl 2-(5-(4-(3,4-difluorophenylsulfonamido)phenyl)-1-oxoisoindolin-2-yl)-3-methylbutanoate;
(S)-2-(5-(4-(3,4-Difluorophenylsulfonamido)phenyl)-1-oxoisoindolin-2-yl)-3-methylbutanoic acid;
(S)-Methyl 2-(5-(4-(2,4-difluorophenylsulfonamido)phenyl)-1-oxoisoindolin-2-yl)-3-methylbutanoate;
(S)-2-(5-(4-(2,4-Difluorophenylsulfonamido)phenyl)-1-oxoisoindolin-2-yl)-3-methylbutanoic acid;
(S)-Methyl 2-(5-(4-(3,4-dimethoxyphenylsulfonamido)phenyl)-1-oxoisoindolin-2-yl)-3-methylbutanoate;
(S)-2-(5-(4-(3,4-Dimethoxyphenylsulfonamido)phenyl)-1-oxoisoindolin-2-yl)-3-methylbutanoic acid;
(S)-Methyl 2-(5-(4-(4-chlorophenylsulfonamido)phenyl)-1-oxoisoindolin-2-yl)-3-methylbutanoate;
(S)-2-(5-(4-(3-Chlorophenylsulfonamido)phenyl)-1-oxoisoindolin-2-yl)-3-methyl butanoic acid;
(S)-Methyl 2-(5-(4-(4-methoxyphenylsulfonamido)phenyl)-1-oxoisoindolin-2-yl)-3-methylbutanoate;
(S)-2-(5-(4-(4-Methoxyphenylsulfonamido)phenyl)-1-oxoisoindolin-2-yl)-3-methylbutanoic acid;
(S)-Methyl 3-methyl-2-(1-oxo-5-(4-(4-(trifluoromethyl) phenylsulfonamido)phenyl)isoindolin-2-yl)butanoate;
(S)-3-Methyl-2-(1-oxo-5-(4-(4-(trifluoromethyl)phenylsulfonamido)phenyl)isoindolin-2-yl)butanoic acid;
(S)-Methyl 3-methyl-2-(1-oxo-5-(4-(phenylmethylsulfonamido)phenyl)isoindolin-2-yl)butanoate;
(S)-3-Methyl-2-(1-oxo-5-(4-(phenylmethylsulfonamido) phenyl)isoindolin-2-yl)butanoic acid;
(S)-Methyl 2-(5-(4-(cyclohexanesulfonamido)phenyl)-1-oxoisoindolin-2-yl)-3-methylbutanoate;
(S)-2-(5-(4-(Cyclohexanesulfonamido)phenyl)-1-oxoisoindolin-2-yl)-3-methylbutanoic acid;
(S)-Methyl 2-(5-(4-benzamidophenyl)-1-oxoisoindolin-2-yl)-3-methylbutanoate;
(S)-2-(5-(4-Benzamidophenyl)-1-oxoisoindolin-2-yl)-3-methylbutanoic acid;
(S)-Methyl 2-(5-(4-(4-fluorobenzamido)phenyl)-1-oxoisoindolin-2-yl)-3-methyl butanoate;
(S)-2-(5-(4-(4-Fluorobenzamido)phenyl)-1-oxoisoindolin-2-yl)-3-methylbutanoic acid;
(S)-Methyl 3-methyl-2-(1-oxo-5-(4-(4-(trifluoromethyl) benzamido)phenyl)isoindolin-2-yl)butanoate;
(S)-3-Methyl-2-(1-oxo-5-(4-(4-(trifluoromethyl)benzamido)phenyl)isoindolin-2-yl)butanoic acid;
(S)-Methyl 2-(5-(4-(4-methoxybenzamido)phenyl)-1-oxoisoindolin-2-yl)-3-methylbutanoate;
(S)-2-(5-(4-(4-Methoxybenzamido)phenyl)-1-oxoisoindolin-2-yl)-3-methyl butanoic acid;
(S)-Methyl 2-(5-(4-(3-fluorobenzamido)phenyl)-1-oxoisoindolin-2-yl)-3-methyl butanoate;
(S)-2-(5-(4-(3-Fluorobenzamido)phenyl)-1-oxoisoindolin-2-yl)-3-methylbutanoic acid;
(S)-Methyl 2-(5-(4-(3-chlorobenzamido)phenyl)-1-oxoisoindolin-2-yl)-3-methyl butanoate;
(S)-2-(5-(4-(3-Chlorobenzamido)phenyl)-1-oxoisoindolin-2-yl)-3-methylbutanoic acid;
(S)-Methyl 2-(5-(4-(2,4-difluorobenzamido)phenyl)-1-oxoisoindolin-2-yl)-3-methylbutanoate;
(S)-2-(5-(4-(2,4-Difluorobenzamido)phenyl)-1-oxoisoindolin-2-yl)-3-methylbutanoic acid,
(S)-Methyl 3-methyl-2-(5-(4-(4-methylbenzamido)phenyl)-1-oxoisoindolin-2-yl)butanoate;
(S)-3-Methyl-2-(5-(4-(4-methylbenzamido)phenyl)-1-oxoisoindolin-2-yl)butanoic acid;
(S)-Methyl 2-(5-(4-(4-chlorobenzamido)phenyl)-1-oxoisoindolin-2-yl)-3-methyl butanoate;
(S)-2-(5-(4-(4-Chlorobenzamido)phenyl)-1-oxoisoindolin-2-yl)-3-methylbutanoic acid;
(S)-Methyl 2-(5-(4-(4-tert-butylbenzamido)phenyl)-1-oxoisoindolin-2-yl)-3-methylbutanoate;
(S)-2-(5-(4-(4-tert-Butylbenzamido)phenyl)-1-oxoisoindolin-2-yl)-3-methyl butanoic acid,
(S)-Methyl 3-methyl-2-(1-oxo-5-(4-(4-pentylbenzamido) phenyl)isoindolin-2-yl)butanoate;
(S)-3-Methyl-2-(1-oxo-5-(4-(4-pentylbenzamido)phenyl) isoindolin-2-yl)butanoic acid;
(R)-Methyl-3-methyl-2-(1-oxo-6-(4-(3-(3-(trifluoromethyl) phenyl)ureido)phenyl)isoindolin-2-yl)butanoate;
(R)-3-Methyl-2-(1-oxo-6-(4-(3-(3-(trifluoromethyl)phenyl) ureido)phenyl)iso indolin-2-yl)butanoic acid;
Methyl 2-(1-oxo-6-(4-(3-(3-(trifluoromethyl)phenyl)ureido) phenyl)isoindolin-2-yl)acetate;
2-(1-Oxo-6-(4-(3-(3-(trifluoromethyl)phenyl)ureido)phenyl)isoindolin-2-yl)acetic acid;
(S)-Methyl 2-(1-oxo-6-(4-(3-(3-(trifluoromethyl)phenyl) ureido)phenyl)isoindolin-2-yl)propanoate;
(S)-2-(1-Oxo-6-(4-(3-(3-(trifluoromethyl)phenyl)ureido) phenyl)isoindolin-2-yl)propanoic acid;
Methyl 2-methyl-2-(1-oxo-6-(4-(3-(3-(trifluoromethyl)phenyl)ureido)phenyl)isoindolin-2-yl)propanoate;
2-Methyl-2-(1-oxo-6-(4-(3-(3-(trifluoromethyl)phenyl)ureido)phenyl)isoindolin-2-yl)propanoic acid;
Methyl 1-(1-oxo-6-(4-(3-(3-(trifluoromethyl)phenyl)ureido) phenyl)isoindolin-2-yl)cyclopentanecarboxylate;
1-(1-Oxo-6-(4-(3-(3-(trifluoromethyl)phenyl)ureido)phenyl)isoindolin-2-yl)cyclopentanecarboxylic acid;
(S)-Methyl 2-(1-oxo-6-(4-(3-(3-(trifluoromethyl)phenyl) ureido)phenyl)isoindolin-2-yl)-2-phenylacetate;
(S)-2-(1-Oxo-6-(4-(3-(3-(trifluoromethyl)phenyl)ureido) phenyl)isoindolin-2-yl)-2-phenylacetic acid;

Methyl 4-(1-oxo-6-(4-(3-(3-(trifluoromethyl)phenyl)ureido)phenyl)isoindolin-2-yl)butanoate;

4-(1-Oxo-6-(4-(3-(3-(trifluoromethyl)phenyl)ureido)phenyl)isoindolin-2-yl)butanoic acid;

(S)-Methyl 4-methyl-2-(1-oxo-6-(4-(3-(3-(trifluoromethyl)phenyl)ureido)phenyl)isoindolin-2-yl)pentanoate;

(S)-4-Methyl-2-(1-oxo-6-(4-(3-(3-(trifluoromethyl)phenyl)ureido)phenyl)iso indolin-2-yl)pentanoic acid;

(S)-Methyl 3-methoxy-2-(1-oxo-6-(4-(3-(3-(trifluoromethyl)phenyl)ureido)phenyl)isoindolin-2-yl)propanoate;

(S)-3-Methoxy-2-(1-oxo-6-(4-(3-(3-(trifluoromethyl)phenyl)ureido)phenyl)iso indolin-2-yl)propanoic acid;

(R)-Methyl 3-methyl-2-(1-oxo-5-(4-(3-(3-(trifluoromethyl)phenyl)ureido)phenyl)isoindolin-2-yl)butanoate;

(R)-3-Methyl-2-(1-oxo-5-(4-(3-(3-(trifluoromethyl)phenyl)ureido)phenyl)isoindolin-2-yl)butanoic acid;

Methyl 2-(1-oxo-5-(4-(3-(3-(trifluoromethyl)phenyl)ureido)phenyl)isoindolin-2-yl)acetate;

2-(1-Oxo-5-(4-(3-(3-(trifluoromethyl)phenyl)ureido)phenyl)isoindolin-2-yl)acetic acid;

(S)-Methyl 2-(1-oxo-5-(4-(3-(3-(trifluoromethyl)phenyl)ureido)phenyl)isoindolin-2-yl)propanoate;

(S)-2-(1-Oxo-5-(4-(3-(3-(trifluoromethyl)phenyl)ureido)phenyl)isoindolin-2-yl)propanoic acid;

Methyl 1-(1-oxo-5-(4-(3-(3-(trifluoromethyl)phenyl)ureido)phenyl)isoindolin-2-yl)cyclopentanecarboxylate;

1-(1-Oxo-5-(4-(3-(3-(trifluoromethyl)phenyl)ureido)phenyl)isoindolin-2-yl)cyclopentanecarboxylic acid;

(S)-Methyl 2-(1-oxo-5-(4-(3-(3-(trifluoromethyl)phenyl)ureido)phenyl)isoindolin-2-yl)-2-phenylacetate;

(S)-2-(1-Oxo-5-(4-(3-(3-(trifluoromethyl)phenyl)ureido)phenyl)isoindolin-2-yl)-2-phenylacetic acid;

Methyl 4-(1-oxo-5-(4-(3-(3-(trifluoromethyl)phenyl)ureido)phenyl)isoindolin-2-yl)butanoate;

4-(1-Oxo-5-(4-(3-(3-(trifluoromethyl)phenyl)ureido)phenyl)isoindolin-2-yl)butanoic acid, Ethyl 3-(1-oxo-5-(4-(3-(3-(trifluoromethyl)phenyl)ureido)phenyl)isoindolin-2-yl)propanoate;

3-(1-Oxo-5-(4-(3-(3-(trifluoromethyl)phenyl)ureido)phenyl)isoindolin-2-yl)propanoic acid, (S)-Methyl 2-(1-oxo-5-(4-(3-(3-(trifluoromethyl)phenyl)ureido)phenyl)isoindolin-2-yl)-3-phenylpropanoate;

(S)-2-(1-Oxo-5-(4-(3-(3-(trifluoromethyl)phenyl)ureido)phenyl)isoindolin-2-yl)-3-phenylpropanoic acid;

(S)-Methyl 3-methoxy-2-(1-oxo-5-(4-(3-(3-(trifluoromethyl)phenyl)ureido)phenyl)isoindolin-2-yl)propanoate;

(S)-3-Methoxy-2-(1-oxo-5-(4-(3-(3-(trifluoromethyl)phenyl)ureido)phenyl)isoindolin-2-yl)propanoic acid;

(S)-Methyl 4-methyl-2-(1-oxo-5-(4-(3-(3-(trifluoromethyl)phenyl)ureido)phenyl)isoindolin-2-yl)pentanoate;

(S)-4-Methyl-2-(1-oxo-5-(4-(3-(3-(trifluoromethyl)phenyl)ureido)phenyl)iso indolin-2-yl)pentanoic acid;

(S)-Methyl 2-(6-(5-(3-(2-chlorophenyl)ureido)pyridin-2-yl)-1-oxoisoindolin-2-yl)-3-methylbutanoate;

(S)-2-(6-(5-(3-(2-Chlorophenyl)ureido)pyridin-2-yl)-1-oxoisoindolin-2-yl)-3-methylbutanoic acid;

(S)-Methyl 2-(6-(5-(3-(4-chloro-2-phenoxyphenyl)ureido)pyridin-2-yl)-1-oxoisoindolin-2-yl)-3-methylbutanoate;

(S)-2-(6-(5-(3-(4-Chloro-2-phenoxyphenyl)ureido)pyridin-2-yl)-1-oxoisoindolin-2-yl)-3-methylbutanoic acid;

(S)-Methyl 2-(6-(5-(3-(3,4-dimethylphenyl)ureido)pyridin-2-yl)-1-oxoisoindolin-2-yl)-3-methylbutanoate;

(S)-2-(6-(5-(3-(3,4-Dimethylphenyl)ureido)pyridin-2-yl)-1-oxoisoindolin-2-yl)-3-methylbutanoic acid;

(S)-Methyl 2-(6-(5-(3-(3,4-difluorophenyl)ureido)pyridin-2-yl)-1-oxoisoindolin-2-yl)-3-methylbutanoate;

(S)-2-(6-(5-(3-(3,4-Difluorophenyl)ureido)pyridin-2-yl)-1-oxoisoindolin-2-yl)-3-methylbutanoic acid;

(S)-Methyl 2-(6-(5-(3-(2,3-dihydro-1H-inden-5-yl)ureido)pyridin-2-yl)-1-oxoisoindolin-2-yl)-3-methylbutanoate;

(S)-2-(6-(5-(3-(2,3-Dihydro-1H-inden-5-yl)ureido)pyridin-2-yl)-1-oxoisoindolin-2-yl)-3-methylbutanoic acid;

(S)-Methyl 2-(6-(5-(4-tert-butylbenzamido)pyridin-2-yl)-1-oxoisoindolin-2-yl)-3-methylbutanoate;

(S)-2-(6-(5-(4-tert-Butylbenzamido)pyridin-2-yl)-1-oxoisoindolin-2-yl)-3-methyl butanoic acid;

(S)-Methyl 3-methyl-2-(1-oxo-6-(5-(4-pentylbenzamido)pyridin-2-yl)isoindolin-2-yl)butanoate;

(S)-3-Methyl-2-(1-oxo-6-(5-(4-pentylbenzamido)pyridin-2-yl)isoindolin-2-yl)butanoic acid;

(S)-Methyl 2-(6-(5-biphenyl-4-ylcarboxamidopyridin-2-yl)-1-oxoisoindolin-2-yl)-3-methylbutanoate;

(S)-2-(6-(5-Biphenyl-4-ylcarboxamidopyridin-2-yl)-1-oxoisoindolin-2-yl)-3-methylbutanoic acid;

(S)-Methyl 2-(6-(5-(2-naphthamido)pyridin-2-yl)-1-oxoisoindolin-2-yl)-3-methyl butanoate;

(S)-2-(6-(5-(2-Naphthamido)pyridin-2-yl)-1-oxoisoindolin-2-yl)-3-methylbutanoic acid;

(S)-Methyl 2-(6-(5-(4-butoxybenzamido)pyridin-2-yl)-1-oxoisoindolin-2-yl)-3-methylbutanoate;

(S)-2-(6-(5-(4-Butoxybenzamido)pyridin-2-yl)-1-oxoisoindolin-2-yl)-3-methylbutanoic acid;

(S)-Methyl 2-(6-(4-(3-(2-chlorophenyl)ureido)-2-(trifluoromethyl)phenyl)-1-oxoisoindolin-2-yl)-3-methylbutanoate;

(S)-2-(6-(4-(3-(2-Chlorophenyl)ureido)-2-(trifluoromethyl)phenyl)-1-oxoisoindolin-2-yl)-3-methylbutanoic acid;

(S)-Methyl 2-(6-(4-(3-(3,4-difluorophenyl)ureido)-2-(trifluoromethyl)phenyl)-1-oxoisoindolin-2-yl)-3-methylbutanoate;

(S)-2-(6-(4-(3-(3,4-Difluorophenyl)ureido)-2-(trifluoromethyl)phenyl)-1-oxoisoindolin-2-yl)-3-methylbutanoic acid;

(S)-Methyl 2-(6-(4-(3-(2,3-dihydro-1H-inden-5-yl)ureido)-2-(trifluoromethyl)phenyl)-1-oxoisoindolin-2-yl)-3-methylbutanoate;

(S)-2-(6-(4-(3-(2,3-Dihydro-1H-inden-5-yl)ureido)-2-(trifluoromethyl)phenyl)-1-oxoisoindolin-2-yl)-3-methylbutanoic acid;

(S)-Methyl 2-(6-(4-(3-(3,4-dimethylphenyl)ureido)-2-(trifluoromethyl)phenyl)-1-oxoisoindolin-2-yl)-3-methylbutanoate;

(S)-2-(6-(4-(3-(3,4-Dimethylphenyl)ureido)-2-(trifluoromethyl)phenyl)-1-oxoisoindolin-2-yl)-3-methylbutanoic acid;

(S)-Methyl 2-(6-(4-(4-tert-butylbenzamido)-2-(trifluoromethyl)phenyl)-1-oxoisoindolin-2-yl)-3-methylbutanoate;

(S)-2-(6-(4-(4-tert-Butylbenzamido)-2-(trifluoromethyl)phenyl)-1-oxoisoindolin-2-yl)-3-methylbutanoic acid;

(S)-Methyl 2-(6-(4-biphenyl-4-ylcarboxamido-2-(trifluoromethyl)phenyl)-1-oxoisoindolin-2-yl)-3-methylbutanoate;

(S)-2-(6-(4-Biphenyl-4-ylcarboxamido-2-(trifluoromethyl)phenyl)-1-oxoisoindolin-2-yl)-3-methylbutanoic acid;

(S)-Methyl 2-(6-(4-(2-naphthamido)-2-(trifluoromethyl)phenyl)-1-oxoisoindolin-2-yl)-3-methylbutanoate;

(S)-2-(6-(4-(2-Naphthamido)-2-(trifluoromethyl)phenyl)-1-oxoisoindolin-2-yl)-3-methylbutanoic acid;

(S)-Methyl 3-methyl-2-(1-oxo-6-(4-(4-pentylbenzamido)-2-(trifluoromethyl)phenyl)isoindolin-2-yl)butanoate;

(S)-3-Methyl-2-(1-oxo-6-(4-(4-pentylbenzamido)-2-(trifluoromethyl)phenyl)isoindolin-2-yl)butanoic acid;

(S)-Methyl 2-(6-(4-(4-butoxybenzamido)-2-(trifluoromethyl)phenyl)-1-oxoisoindolin-2-yl)-3-methylbutanoate;
(S)-2-(6-(4-(4-Butoxybenzamido)-2-(trifluoromethyl)phenyl)-1-oxoisoindolin-2-yl)-3-methylbutanoic acid;
(S)-Methyl 2-(6-(4-(3-(3,4-dimethylphenyl)ureido)-3-fluorophenyl)-1-oxoisoindolin-2-yl)-3-methylbutanoate;
(S)-2-(6-(4-(3-(3,4-Dimethylphenyl)ureido)-3-fluorophenyl)-1-oxoisoindolin-2-yl)-3-methylbutanoic acid;
(S)-Methyl 2-(6-(4-(3-(2,3-dihydro-1H-inden-5-yl)ureido)-3-fluorophenyl)-1-oxoisoindolin-2-yl)-3-methylbutanoate;
(S)-2-(6-(4-(3-(2,3-Dihydro-1H-inden-5-yl)ureido)-3-fluorophenyl)-1-oxoisoindolin-2-yl)-3-methylbutanoic acid;
(S)-Methyl 2-(6-(4-(3-(3,4-difluorophenyl)ureido)-3-fluorophenyl)-1-oxoisoindolin-2-yl)-3-methylbutanoate;
(S)-2-(6-(4-(3-(3,4-Difluorophenyl)ureido)-3-fluorophenyl)-1-oxoisoindolin-2-yl)-3-methylbutanoic acid;
(S)-Methyl 2-(6-(4-(3-(2-chlorophenyl)ureido)-3-fluorophenyl)-1-oxoisoindolin-2-yl)-3-methylbutanoate;
(S)-2-(6-(4-(3-(2-Chlorophenyl)ureido)-3-fluorophenyl)-1-oxoisoindolin-2-yl)-3-methylbutanoic acid;
(S)-Methyl 2-(6-(4-(4-tert-butylbenzamido)-3-fluorophenyl)-1-oxoisoindolin-2-yl)-3-methylbutanoate;
(S)-2-(6-(4-(4-tert-Butylbenzamido)-3-fluorophenyl)-1-oxoisoindolin-2-yl)-3-methylbutanoic acid;
(S)-Methyl 2-(6-(3-fluoro-4-(4-pentylbenzamido)phenyl)-1-oxoisoindolin-2-yl)-3-methylbutanoate;
(S)-2-(6-(3-Fluoro-4-(4-pentylbenzamido)phenyl)-1-oxoisoindolin-2-yl)-3-methylbutanoic acid;
(S)-Methyl 2-(6-(4-(biphenyl-4-ylcarboxamido-3-fluorophenyl)-1-oxoisoindolin-2-yl)-3-methylbutanoate;
(S)-2-(6-(4-(Biphenyl-4-ylcarboxamido-3-fluorophenyl)-1-oxoisoindolin-2-yl)-3-methylbutanoic acid;
(S)-Methyl 2-(6-(4-(2-naphthamido)-3-fluorophenyl)-1-oxoisoindolin-2-yl)-3-methylbutanoate;
(S)-2-(6-(4-(2-Naphthamido)-3-fluorophenyl)-1-oxoisoindolin-2-yl)-3-methyl butanoic acid;
(S)-Methyl 2-(6-(4-(4-butoxybenzamido)-3-fluorophenyl)-1-oxoisoindolin-2-yl)-3-methylbutanoate;
(S)-2-(6-(4-(4-Butoxybenzamido)-3-fluorophenyl)-1-oxoisoindolin-2-yl)-3-methyl butanoic acid;
(S)-Methyl 2-(6-(4-(4-tert-butylbenzamido)-2-methoxyphenyl)-1-oxoisoindolin-2-yl)-3-methylbutanoate;
(S)-2-(6-(4-(4-tert-Butylbenzamido)-2-methoxyphenyl)-1-oxoisoindolin-2-yl)-3-methylbutanoic acid;
(S)-Methyl 2-(6-(4-biphenyl-4-ylcarboxamido-2-methoxyphenyl)-1-oxoisoindolin-2-yl)-3-methylbutanoate;
(S)-2-(6-(4-Biphenyl-4-ylcarboxamido-2-methoxyphenyl)-1-oxoisoindolin-2-yl)-3-methylbutanoic acid;
(S)-Methyl 2-(6-(4-(4-butoxybenzamido)-2-methoxyphenyl)-1-oxoisoindolin-2-yl)-3-methylbutanoate;
(S)-2-(6-(4-(4-Butoxybenzamido)-2-methoxyphenyl)-1-oxoisoindolin-2-yl)-3-methylbutanoic acid;
(S)-Methyl 2-(6-(2-methoxy-4-(4-pentylbenzamido)phenyl)-1-oxoisoindolin-2-yl)-3-methylbutanoate;
(S)-2-(6-(2-Methoxy-4-(4-pentylbenzamido)phenyl)-1-oxoisoindolin-2-yl)-3-methylbutanoic acid;
(S)-Methyl 2-(6-(2-methoxy-4-(4-(trifluoromethoxy)benzamido)phenyl)-1-oxo isoindolin-2-yl)-3-methylbutanoate;
(S)-2-(6-(2-Methoxy-4-(4-(trifluoromethoxy)benzamido)phenyl)-1-oxoisoindolin-2-yl)-3-methylbutanoic acid;
(S)-Methyl 2-(6-(4-(4-tert-butylbenzamido)-2-methylphenyl)-1-oxoisoindolin-2-yl)-3-methylbutanoate;
(S)-2-(6-(4-(4-tert-Butylbenzamido)-2-methylphenyl)-1-oxoisoindolin-2-yl)-3-methylbutanoic acid;
(S)-Methyl 2-(6-(4-biphenyl-4-ylcarboxamido-2-methylphenyl)-1-oxoisoindolin-2-yl)-3-methylbutanoate;
(S)-2-(6-(4-Biphenyl-4-ylcarboxamido-2-methylphenyl)-1-oxoisoindolin-2-yl)-3-methylbutanoic acid;
(S)-Methyl 2-(6-(4-(4-butoxybenzamido)-2-methylphenyl)-1-oxoisoindolin-2-yl)-3-methylbutanoate;
(S)-2-(6-(4-(4-Butoxybenzamido)-2-methylphenyl)-1-oxoisoindolin-2-yl)-3-methylbutanoic acid;
(S)-Methyl 3-methyl-2-(6-(2-methyl-4-(4-pentylbenzamido)phenyl)-1-oxoisoindolin-2-yl)butanoate;
(S)-3-Methyl-2-(6-(2-methyl-4-(4-pentylbenzamido)phenyl)-1-oxoisoindolin-2-yl)butanoic acid;
(S)-Methyl 3-methyl-2-(6-(2-methyl-4-(4-(trifluoromethoxy)benzamido)phenyl)-1-oxoisoindolin-2-yl)butanoate;
(S)-3-Methyl-2-(6-(2-methyl-4-(4-(trifluoromethoxy)benzamido)phenyl)-1-oxoisoindolin-2-yl)butanoic acid;
(S)-Methyl 2-(6-(4-(4-tert-butylbenzamido)-2-chlorophenyl)-1-oxoisoindolin-2-yl)-3-methylbutanoate;
(S)-2-(6-(4-(4-tert-Butylbenzamido)-2-chlorophenyl)-1-oxoisoindolin-2-yl)-3-methylbutanoic acid;
(S)-Methyl 2-(6-(4-biphenyl-4-ylcarboxamido-2-chlorophenyl)-1-oxoisoindolin-2-yl)-3-methylbutanoate;
(S)-2-(6-(4-Biphenyl-4-ylcarboxamido-2-chlorophenyl)-1-oxoisoindolin-2-yl)-3-methylbutanoic acid;
(S)-Methyl 2-(6-(4-(4-butoxybenzamido)-2-chlorophenyl)-1-oxoisoindolin-2-yl)-3-methylbutanoate;
(S)-2-(6-(4-(4-Butoxybenzamido)-2-chlorophenyl)-1-oxoisoindolin-2-yl)-3-methylbutanoic acid;
(S)-Methyl 2-(6-(2-chloro-4-(4-pentylbenzamido)phenyl)-1-oxoisoindolin-2-yl)-3-methylbutanoate;
(S)-2-(6-(2-Chloro-4-(4-pentylbenzamido)phenyl)-1-oxoisoindolin-2-yl)-3-methylbutanoic acid;
(S)-Methyl 2-(6-(2-chloro-4-(4-(trifluoromethoxy)benzamido)phenyl)-1-oxo isoindolin-2-yl)-3-methylbutanoate;
(S)-2-(6-(2-Chloro-4-(4-(trifluoromethoxy)benzamido)phenyl)-1-oxoisoindolin-2-yl)-3-methylbutanoic acid;
(S)-Methyl 2-(6-(6-(4-tert-butylbenzamido)pyridin-3-yl)-1-oxoisoindolin-2-yl)-3-methylbutanoate;
(S)-2-(6-(6-(4-tert-Butylbenzamido)pyridin-3-yl)-1-oxoisoindolin-2-yl)-3-methylbutanoic acid;
(S)-Methyl 2-(6-(6-biphenyl-4-ylcarboxamidopyridin-3-yl)-1-oxoisoindolin-2-yl)-3-methylbutanoate;
(S)-Methyl 3-methyl-2-(1-oxo-6-(6-(4-pentylbenzamido)pyridin-3-yl)iso indolin-2-yl)butanoate;
(S)-Methyl 3-methyl-2-(1-oxo-6-(6-(4-(trifluoromethoxy)benzamido)pyridin-3-yl)isoindolin-2-yl)butanoate;
(S)-Methyl 2-(6-(6-(4-tert-butylbenzamido)pyridazin-3-yl)-1-oxoisoindolin-2-yl)-3-methylbutanoate;
(S)-2-(6-(6-(4-tert-Butylbenzamido)pyridazin-3-yl)-1-oxoisoindolin-2-yl)-3-methylbutanoic acid;
(S)-Methyl 3-methyl-2-(1-oxo-6-(6-(4-pentylbenzamido)pyridazin-3-yl)iso indolin-2-yl)butanoate;
(S)-3-Methyl-2-(1-oxo-6-(6-(4-pentylbenzamido)pyridazin-3-yl)isoindolin-2-yl)butanoic acid;
(S)-Methyl 3-methyl-2-(1-oxo-6-(6-(4-(trifluoromethoxy)benzamido)pyridazin-3-yl)isoindolin-2-yl)butanoate;
(S)-3-Methyl-2-(1-oxo-6-(6-(4-(trifluoromethoxy)benzamido)pyridazin-3-yl)isoindolin-2-yl)butanoic acid;
(S)-Methyl 2-(6-(5-(4-tert-butylbenzamido)pyrazin-2-yl)-1-oxoisoindolin-2-yl)-3-methylbutanoate;
(S)-2-(6-(5-(4-tert-Butylbenzamido)pyrazin-2-yl)-1-oxoisoindolin-2-yl)-3-methylbutanoic acid;
(S)-Methyl 2-(6-(5-biphenyl-4-ylcarboxamidopyrazin-2-yl)-1-oxoisoindolin-2-yl)-3-methylbutanoate;
(S)-2-(6-(5-Biphenyl-4-ylcarboxamidopyrazin-2-yl)-1-oxoisoindolin-2-yl)-3-methylbutanoic acid;
(S)-Methyl 2-(6-(5-(4-butoxybenzamido)pyrazin-2-yl)-1-oxoisoindolin-2-yl)-3-methylbutanoate;

(S)-2-(6-(5-(4-Butoxybenzamido)pyrazin-2-yl)-1-oxoisoindolin-2-yl)-3-methylbutanoic acid;
(S)-Methyl 3-methyl-2-(1-oxo-6-(5-(4-pentylbenzamido)pyrazin-2-yl)isoindolin-2-yl)butanoate;
(S)-3-Methyl-2-(1-oxo-6-(5-(4-pentylbenzamido)pyrazin-2-yl)isoindolin-2-yl)butanoic acid;
(S)-Methyl 3-methyl-2-(1-oxo-6-(5-(4-(trifluoromethoxy)benzamido)pyrazin-2-yl)isoindolin-2-yl)butanoate;
(S)-3-Methyl-2-(1-oxo-6-(5-(4-(trifluoromethoxy)benzamido)pyrazin-2-yl)isoindolin-2-yl)butanoic acid;
Methyl 2-(6-(4-([1,1'-biphenyl]-4-ylcarboxamido)phenyl)-1-oxoisoindolin-2-yl)-2-methylpropanoate;
2-(6-(4-([1,1'-Biphenyl]-4-ylcarboxamido)phenyl)-1-oxoisoindolin-2-yl)-2-methyl propanoic acid;
Methyl 2-(6-(4-(4-(tert-butyl)benzamido)phenyl)-1-oxoisoindolin-2-yl)-2-methyl propanoate;
2-(6-(4-(4-(tert-Butyl)benzamido)phenyl)-1-oxoisoindolin-2-yl)-2-methyl propanoic acid;
Methyl 2-(6-(4-(4-chlorobenzamido)phenyl)-1-oxoisoindolin-2-yl)-2-methyl propanoate;
2-(6-(4-(4-Chlorobenzamido)phenyl)-1-oxoisoindolin-2-yl)-2-methylpropanoic acid;
Methyl 2-methyl-2-(1-oxo-6-(4-(4-(trifluoromethoxy)benzamido)phenyl)iso indolin-2-yl)propanoate
2-Methyl-2-(1-oxo-6-(4-(4-(trifluoromethoxy)benzamido)phenyl)isoindolin-2-yl)propanoic acid;
Methyl 2-methyl-2-(1-oxo-6-(4-(4-pentylbenzamido)phenyl)isoindolin-2-yl)propanoate;
2-Methyl-2-(1-oxo-6-(4-(4-pentylbenzamido)phenyl)isoindolin-2-yl)propanoic acid;
Methyl 1-(6-(4-([1,1'-biphenyl]-4-ylcarboxamido)phenyl)-1-oxoisoindolin-2-yl)cyclopentanecarboxylate;
1-(6-(4-([1,1'-Biphenyl]-4-ylcarboxamido)phenyl)-1-oxoisoindolin-2-yl)cyclopentane carboxylic acid;
Methyl 1-(6-(4-(4-(tert-butyl)benzamido)phenyl)-1-oxoisoindolin-2-yl)cyclopentanecarboxylate;
1-(6-(4-(4-(tert-Butyl)benzamido)phenyl)-1-oxoisoindolin-2-yl)cyclopentane carboxylic acid;
Methyl 1-(6-(4-(4-chlorobenzamido)phenyl)-1-oxoisoindolin-2-yl)cyclopentane carboxylate;
1-(6-(4-(4-Chlorobenzamido)phenyl)-1-oxoisoindolin-2-yl)cyclopentane carboxylic acid;
Methyl 1-(1-oxo-6-(4-(4-(trifluoromethoxy)benzamido)phenyl)isoindolin-2-yl)cyclopentanecarboxylate;
1-(1-Oxo-6-(4-(4-(trifluoromethoxy)benzamido)phenyl)isoindolin-2-yl)cyclopentane carboxylic acid;
Methyl 1-(1-oxo-6-(4-(4-pentylbenzamido)phenyl)isoindolin-2-yl)cyclopentane carboxylate;
1-(1-Oxo-6-(4-(4-pentylbenzamido)phenyl)isoindolin-2-yl)cyclopentane carboxylic acid;
(R)-Methyl 2-(6-(4-([1,1'-biphenyl]-4-ylcarboxamido)phenyl)-1-oxoisoindolin-2-yl)-3-methylbutanoate;
(R)-2-(6-(4-([1,1'-Biphenyl]-4-ylcarboxamido)phenyl)-1-oxoisoindolin-2-yl)-3-methylbutanoic acid;
Methyl 3-(6-(4-([1,1'-biphenyl]-4-ylcarboxamido)phenyl)-1-oxoisoindolin-2-yl)cyclohexanecarboxylate;
3-(6-(4-([1,1'-Biphenyl]-4-ylcarboxamido)phenyl)-1-oxoisoindolin-2-yl)cyclo hexane carboxylic acid;
Methyl 3-(6-(4-(3-chlorobenzamido)phenyl)-1-oxoisoindolin-2-yl)cyclohexane carboxylate;
3-(6-(4-(3-Chlorobenzamido)phenyl)-1-oxoisoindolin-2-yl)cyclohexane carboxylic acid;
Methyl 3-(6-(4-(4-chlorobenzamido)phenyl)-1-oxoisoindolin-2-yl)cyclohexane carboxylate;
3-(6-(4-(4-Chlorobenzamido)phenyl)-1-oxoisoindolin-2-yl)cyclohexane carboxylic acid;
Methyl 3-(1-oxo-6-(4-(4-(trifluoromethyl)benzamido)phenyl)isoindolin-2-yl)cyclohexanecarboxylate;
3-(1-Oxo-6-(4-(4-(trifluoromethyl)benzamido)phenyl)isoindolin-2-yl)cyclohexanecarboxylic acid;
Methyl 3-(6-(4-(5-methyl-2-phenyloxazole-4-carboxamido)phenyl)-1-oxo isoindolin-2-yl)cyclohexanecarboxylate;
3-(6-(4-(5-Methyl-2-phenyloxazole-4-carboxamido)phenyl)-1-oxoisoindolin-2-yl)cyclohexanecarboxylic acid;
(1r,4r)-Methyl 4-(6-(4-([1,1'-biphenyl]-4-ylcarboxamido)phenyl)-1-oxoisoindolin-2-yl)cyclohexanecarboxylate;
(1r,4r)-4-(6-(4-([1,1'-Biphenyl]-4-ylcarboxamido)phenyl)-1-oxoisoindolin-2-yl)cyclohexanecarboxylic acid;
(1r,4r)-Methyl 4-(6-(4-(3-chlorobenzamido)phenyl)-1-oxoisoindolin-2-yl)cyclo hexanecarboxylate;
(1r,4r)-4-(6-(4-(3-Chlorobenzamido)phenyl)-1-oxoisoindolin-2-yl)cyclohexane carboxylic acid;
(1r,4r)-Methyl 4-(6-(4-(4-chlorobenzamido)phenyl)-1-oxoisoindolin-2-yl)cyclohexanecarboxylate;
(1r,4r)-4-(6-(4-(4-Chlorobenzamido)phenyl)-1-oxoisoindolin-2-yl)cyclohexane carboxylic acid;
(1r,4r)-Methyl 4-(1-oxo-6-(4-(4-(trifluoromethyl)benzamido)phenyl)isoindolin-2-yl)cyclohexanecarboxylate;
(1r,4r)-4-(1-Oxo-6-(4-(4-(trifluoromethyl)benzamido)phenyl)isoindolin-2-yl)cyclohexanecarboxylic acid;
(1r,3s,5R,7S)-Methyl 3-(6-(4-(3-chlorobenzamido)phenyl)-1-oxoisoindolin-2-yl)adamantane-1-carboxylate;
(1r,3s,5R,7S)-3-(6-(4-(3-Chlorobenzamido)phenyl)-1-oxoisoindolin-2-yl)adamantane-1-carboxylic acid;
(1r,3s,5R,7S)-Methyl 3-(6-(4-(4-chlorobenzamido)phenyl)-1-oxoisoindolin-2-yl)adamantane-1-carboxylate;
(1r,3s,5R,7S)-3-(6-(4-(4-Chlorobenzamido)phenyl)-1-oxoisoindolin-2-yl)adamantane-1-carboxylic acid;
(1r,3s,5R,7S)-Methyl 3-(1-oxo-6-(4-(4-(trifluoromethyl)benzamido)phenyl)isoindolin-2-yl)adamantane-1-carboxylate;
(1r,3s,5R,7S)-3-(1-Oxo-6-(4-(4-(trifluoromethyl)benzamido)phenyl)isoindolin-2-yl)adamantane-1-carboxylic acid;
(1r,3s,5R,7S)-3-(6-(4-(4-Methylbenzamido)phenyl)-1-oxoisoindolin-2-yl)adamantane-1-carboxylic acid;
Methyl 1-(6-(4-([1,1'-biphenyl]-4-ylcarboxamido)phenyl)-1-oxoisoindolin-2-yl)cyclobutanecarboxylate;
1-(6-(4-([1,1'-Biphenyl]-4-ylcarboxamido)phenyl)-1-oxoisoindolin-2-yl)cyclo butanecarboxylic acid;
Methyl 1-(6-(4-(4-chlorobenzamido)phenyl)-1-oxoisoindolin-2-yl)cyclobutane carboxylate;
1-(6-(4-(4-Chlorobenzamido)phenyl)-1-oxoisoindolin-2-yl)cyclobutane carboxylic acid;
Methyl 1-(1-Oxo-6-(4-(4-(trifluoromethyl)benzamido)phenyl)isoindolin-2-yl)cyclobutanecarboxylate;
1-(1-Oxo-6-(4-(4-(trifluoromethyl)benzamido)phenyl)isoindolin-2-yl)cyclo butanecarboxylic acid;
Methyl 1-(6-(4-(4-methylbenzamido)phenyl)-1-oxoisoindolin-2-yl)cyclobutane carboxylate;
1-(6-(4-(4-Methylbenzamido)phenyl)-1-oxoisoindolin-2-yl)cyclobutane carboxylic acid;
Methyl 1-(6-(4-biphenyl-4-ylcarboxamidophenyl)-1-oxoisoindolin-2-yl)cyclo propanecarboxylate;
1-(6-(4-([1,1'-Biphenyl]-4-ylcarboxamido)phenyl)-1-oxoisoindolin-2-yl)cyclopropanecarboxylic acid;
Methyl 1-(6-(4-(4-chlorobenzamido)phenyl)-1-oxoisoindolin-2-yl)cyclopropane carboxylate;
1-(6-(4-(4-Chlorobenzamido)phenyl)-1-oxoisoindolin-2-yl)cyclopropane carboxylic acid;
Methyl 1-(1-oxo-6-(4-(4-(trifluoromethyl)benzamido)phenyl)isoindolin-2-yl)cyclopropane carboxylate;

1-(1-Oxo-6-(4-(4-(trifluoromethyl)benzamido)phenyl) isoindolin-2-yl)cyclopropane carboxylic acid;

(1S,2R)-Methyl 2-(6-(4-([1,1'-biphenyl]-4-ylcarboxamido) phenyl)-1-oxo isoindolin-2-yl)cyclopentanecarboxylate;

(1S,2R)-2-(6-(4-([1,1'-Biphenyl]-4-ylcarboxamido)phenyl)-1-oxoisoindolin-2-yl)cyclopentanecarboxylic acid;

(1S,2R)-Methyl 2-(6-(4-(4-chlorobenzamido)phenyl)-1-oxoisoindolin-2-yl)cyclopentanecarboxylate;

(1S,2R)-2-(6-(4-(4-Chlorobenzamido)phenyl)-1-oxoisoindolin-2-yl)cyclopentane carboxylic acid;

(1S,2R)-Methyl 2-(1-oxo-6-(4-(4-(trifluoromethyl)benzamido)phenyl)isoindolin-2-yl)cyclopentanecarboxylate;

(1S,2R)-2-(1-Oxo-6-(4-(4-(trifluoromethyl)benzamido)phenyl)isoindolin-2-yl)cyclopentanebcarboxylic acid;

(S)-Methyl 2-(6-(4-([1,1'-biphenyl]-4-ylcarboxamido)-2-fluorophenyl)-1-oxo isoindolin-2-yl)-3-methylbutanoate;

(S)-2-(6-(4-([1,1'-Biphenyl]-4-ylcarboxamido)-2-fluorophenyl)-1-oxoisoindolin-2-yl)-3-methylbutanoic acid;

(S)-Methyl 2-(6-(4-(4-(tert-butyl)benzamido)-2-fluorophenyl)-1-oxoisoindolin-2-yl)-3-methylbutanoate;

(S)-2-(6-(4-(4-(tert-Butyl)benzamido)-2-fluorophenyl)-1-oxoisoindolin-2-yl)-3-methylbutanoic acid;

(S)-Methyl 2-(6-(4-(4-chlorobenzamido)-2-fluorophenyl)-1-oxoisoindolin-2-yl)-3-methylbutanoate;

(S)-2-(6-(4-(4-Chlorobenzamido)-2-fluorophenyl)-1-oxoisoindolin-2-yl)-3-methyl butanoic acid;

(S)-Methyl 2-(6-(2-fluoro-4-(4-(trifluoromethoxy)benzamido)phenyl)-1-oxo isoindolin-2-yl)-3-methylbutanoate;

(S)-2-(6-(2-Fluoro-4-(4-(trifluoromethoxy)benzamido)phenyl)-1-oxoisoindolin-2-yl)-3-methylbutanoic acid;

(S)-Methyl 2-(6-(2-fluoro-4-(4-pentylbenzamido)phenyl)-1-oxoisoindolin-2-yl)-3-methylbutanoate;

(S)-2-(6-(2-Fluoro-4-(4-pentylbenzamido)phenyl)-1-oxoisoindolin-2-yl)-3-methyl butanoic acid;

(S)-Methyl 3-methyl-2-(1-oxo-6-(4-(5-phenylthiazole-2-carboxamido)phenyl)isoindolin-2-yl)butanoate;

(S)-3-Methyl-2-(1-oxo-6-(4-(5-phenylthiazole-2-carboxamido)phenyl)isoindolin-2-yl)butanoic acid;

(S)-Methyl 3-methyl-2-(1-oxo-6-(4-(5-phenyloxazole-2-carboxamido)phenyl)isoindolin-2-yl)butanoate;

(S)-3-Methyl-2-(1-oxo-6-(4-(5-phenyloxazole-2-carboxamido)phenyl)isoindolin-2-yl)butanoic acid;

(S)-Methyl 2-(6-(4-(3-(4-fluorophenyl)isoxazole-5-carboxamido)phenyl)-1-oxoisoindolin-2-yl)-3-methylbutanoate;

(S)-2-(6-(4-(3-(4-Fluorophenyl)isoxazole-5-carboxamido)phenyl)-1-oxo isoindolin-2-yl)-3-methylbutanoic acid;

(S)-Methyl 2-(6-(4-(3-(4-chlorophenyl)isoxazole-5-carboxamido)phenyl)-1-oxoisoindolin-2-yl)-3-methylbutanoate;

(S)-2-(6-(4-(3-(4-Chlorophenyl)isoxazole-5-carboxamido)phenyl)-1-oxo isoindolin-2-yl)-3-methylbutanoic acid;

(S)-Methyl 3-methyl-2-(1-oxo-6-(4-(3-(4-(trifluoromethyl)phenyl)isoxazole-5-carboxamido)phenyl)isoindolin-2-yl)butanoate;

(S)-3-Methyl-2-(1-oxo-6-(4-(3-(4-(trifluoromethyl)phenyl)isoxazole-5-carboxamido)phenyl)isoindolin-2-yl)butanoic acid;

(S)-Methyl 3-methyl-2-(6-(4-(4-(oxazol-5-yl)benzamido)phenyl)-1-oxoisoindolin-2-yl)butanoate;

(S)-3-Methyl-2-(6-(4-(4-(oxazol-5-yl)benzamido)phenyl)-1-oxoisoindolin-2-yl)butanoic acid;

(S)-Methyl 3-methyl-2-(1-oxo-6-(4-(4-phenylthiazole-2-carboxamido)phenyl)isoindolin-2-yl)butanoate;

(S)-3-methyl-2-(1-oxo-6-(4-(4-phenylthiazole-2-carboxamido)phenyl)isoindolin-2-yl)butanoic acid;

(S)-Methyl 3-methyl-2-(1-oxo-6-(4-(5-phenyl-1,3,4-oxadiazole-2-carboxamido)phenyl)isoindolin-2-yl)butanoate;

(S)-Methyl 3-methyl-2-(1-oxo-6-(4-(5-phenyl-1,3,4-thiadiazole-2-carboxamido)phenyl)isoindolin-2-yl)butanoate;

(S)-3-Methyl-2-(1-oxo-6-(4-(5-phenyl-1,3,4-thiadiazole-2-carboxamido)phenyl)isoindolin-2-yl)butanoic acid;

(S)-Methyl 3-methyl-2-(1-oxo-6-(4-(5-phenyl-4H-1,2,4-triazole-3-carboxamido)phenyl)isoindolin-2-yl)butanoate;

(S)-3-Methyl-2-(1-oxo-6-(4-(5-phenyl-4H-1,2,4-triazole-3-carboxamido)phenyl)isoindolin-2-yl)butanoic acid;

(S)-Methyl 2-(6-(4-(4-(2-cyanopropan-2-yl)benzamido)phenyl)-1-oxoisoindolin-2-yl)-3-methylbutanoate;

(S)-2-(6-(4-(4-(2-Cyanopropan-2-yl)benzamido)phenyl)-1-oxoisoindolin-2-yl)-3-methylbutanoic acid;

(S)-Methyl 2-(6-(4-(4-(3-cyanopentan-3-yl)benzamido)phenyl)-1-oxoisoindolin-2-yl)-3-methylbutanoate;

(S)-2-(6-(4-(4-(3-Cyanopentan-3-yl)benzamido)phenyl)-1-oxoisoindolin-2-yl)-3-methylbutanoic acid;

(S)-Methyl 3-methyl-2-(1-oxo-6-(5-(5-phenyloxazole-2-carboxamido)pyridin-2-yl)isoindolin-2-yl)butanoate;

(S)-3-Methyl-2-(1-oxo-6-(5-(5-phenyloxazole-2-carboxamido)pyridin-2-yl)isoindolin-2-yl)butanoic acid;

(S)-Methyl 3-methyl-2-(1-oxo-6-(5-(5-phenylthiazole-2-carboxamido)pyridin-2-yl)isoindolin-2-yl)butanoate;

(S)-3-Methyl-2-(1-oxo-6-(5-(5-phenylthiazole-2-carboxamido)pyridin-2-yl)isoindolin-2-yl)butanoic acid;

(S)-Methyl 2-(6-(5-(3-(4-fluorophenyl)isoxazole-5-carboxamido)pyridin-2-yl)-1-oxo isoindolin-2-yl)-3-methylbutanaote;

(S)-2-(6-(5-(3-(4-Fluorophenyl)isoxazole-5-carboxamido)pyridin-2-yl)-1-oxo isoindolin-2-yl)-3-methylbutanoic acid;

(S)-Methyl 2-(6-(4-(4-(1,3,4-oxadiazol-2-yl)benzamido)phenyl)-1-oxoisoindolin-2-yl)-3-methylbutanoate;

(S)-2-(6-(4-(4-(1,3,4-Oxadiazol-2-yl)benzamido)phenyl)-1-oxoisoindolin-2-yl)-3-methylbutanoic acid;

(S)-Methyl 3-methyl-2-(6-(4-(5-methyl-2-phenyloxazole-4-carboxamido)phenyl)-1-oxoisoindolin-2-yl)butanoate;

(S)-3-Methyl-2-(6-(4-(5-methyl-2-phenyloxazole-4-carboxamido)phenyl)-1-oxoisoindolin-2-yl)butanoic acid;

(S)-Methyl 3-methyl-2-(1-oxo-6-(4-(2-phenyl-5-(trifluoromethyl)oxazole-4-carboxamido)phenyl)isoindolin-2-yl)butanoate;

(S)-3-Methyl-2-(1-oxo-6-(4-(2-phenyl-5-(trifluoromethyl)oxazole-4-carboxamido)phenyl)isoindolin-2-yl)butanoic acid;

(S)-Methyl 3-methyl-2-(6-(2-methyl-4-(4-pentylbenzamido)phenyl)-1-oxoisoindolin-2-yl)butanoate;

(S)-3-Methyl-2-(1-oxo-6-(4-(4-(thiazol-2-yl)benzamido) phenyl)isoindolin-2-yl)butanoic acid;

(S)-Methyl 2-(6-(4-(5-butylpicolinamido)phenyl)-1-oxoisoindolin-2-yl)-3-methylbutanoate;

(S)-2-(6-(4-(5-Butylpicolinamido)phenyl)-1-oxoisoindolin-2-yl)-3-methylbutanoic acid;

(S)-Methyl 3-methyl-2-(1-oxo-6-(4-(quinoline-3-carboxamido)phenyl)isoindolin-2-yl)butanoate;

(S)-3-Methyl-2-(1-oxo-6-(4-(quinoline-3-carboxamido)phenyl)isoindolin-2-yl)butanoic acid;

(S)-Methyl 3-methyl-2-(1-oxo-6-(4-(4-(pyrimidin-5-yl)benzamido)phenyl)isoindolin-2-yl)butanoate;

(S)-3-Methyl-2-(1-oxo-6-(4-(4-(pyrimidin-5-yl)benzamido)phenyl)isoindolin-2-yl)butanoic acid;

(S)-Methyl 3-methyl-2-(6-(5-(5-methyl-2-phenyloxazole-4-carboxamido)pyridin-2-yl)-1-oxoisoindolin-2-yl)butanoate;

(S)-3-Methyl-2-(6-(5-(5-methyl-2-phenyloxazole-4-carboxamido)pyridin-2-yl)-1-oxoisoindolin-2-yl)butanoic acid;
(S)-Methyl 3-methyl-2-(1-oxo-6-(5-(2-phenyl-5-(trifluoromethyl)oxazole-4-carboxamido)pyridin-2-yl)isoindolin-2-yl)butanoate;
(S)-3-Methyl-2-(1-oxo-6-(5-(2-phenyl-5-(trifluoromethyl)oxazole-4-carboxamido)pyridin-2-yl)isoindolin-2-yl)butanoic acid;
(S)-Methyl 3-methyl-2-(1-oxo-6-(4-(2-phenylacetamido)phenyl)isoindolin-2-yl)butanoate;
(S)-3-Methyl-2-(1-oxo-6-(4-(2-phenylacetamido)phenyl)isoindolin-2-yl)butanoic acid;
Methyl 2-(5-(4-biphenyl-4-ylcarboxamidophenyl)-1,3-dioxoisoindolin-2-yl)-3-methyl butanoate;
Methyl 2-(5-(4-(4-tert-butylbenzamido)phenyl)-1,3-dioxoisoindolin-2-yl)-3-methyl butanoate;
Methyl 2-(5-(4-(2,4-dimethoxybenzamido)phenyl)-1,3-dioxoisoindolin-2-yl)-3-methylbutanoate;
Methyl 2-(5-(4-(3-(2-chlorophenyl)ureido)phenyl)-1,3-dioxoisoindolin-2-yl)-3-methylbutanoate;
Methyl 2-(5-(4-(3-(3,4-dimethylphenyl)ureido)phenyl)-1,3-dioxoisoindolin-2-yl)-3-methylbutanoate;
Methyl 2-(5-(4-(4-tert-butylbenzamido)phenyl)isoindolin-2-yl)-3-methyl butanoate;
Methyl 3-methyl-2-(5-(4-(4-pentylbenzamido)phenyl)isoindolin-2-yl)butanoate,
Methyl 2-(5-(4-biphenyl-4-ylcarboxamidophenyl)isoindolin-2-yl)-3-methyl butanoate;
Methyl 2-(5-(4-(2,4-dimethoxyphenylsulfonamido)phenyl)isoindolin-2-yl)-3-methyl butanoate; and
Methyl 3-methyl-2-(5-(4-(3-(2-(trifluoromethyl)phenyl)ureido)phenyl)isoindolin-2-yl)butanoate;
or a stereoisomer, tautomer, pharmaceutically acceptable salt, pharmaceutically acceptable solvate, pharmaceutically acceptable polymorph, pharmaceutically acceptable prodrug, N-oxide or carboxylic acid isostere thereof.

In another embodiment, the present invention provides compounds of formula 1 selected from:
(S)-2-(6-(4-(3-(4-Fluorophenyl)ureido)phenyl)-1-oxoisoindolin-2-yl)-3-methyl butanoic acid;
(S)-2-(6-(4-(3-(2,4-Difluorophenyl)ureido)phenyl)-1-oxoisoindolin-2-yl)-3-methylbutanoic acid;
(S)-2-(6-(4-(3-(2-Fluorophenyl)ureido)phenyl)-1-oxoisoindolin-2-yl)-3-methyl butanoic acid;
(S)-2-(6-(4-(3-(3-Fluorophenyl)ureido)phenyl)-1-oxoisoindolin-2-yl)-3-methyl butanoic acid,
(S)-3-Methyl-2-(1-oxo-6-(4-(3-phenylureido)phenyl)isoindolin-2-yl)butanoic acid;
(S)-2-(6-(4-(3-Benzylureido)phenyl)-1-oxoisoindolin-2-yl)-3-methylbutanoic acid;
(S)-2-(6-(4-(3-(2,6-Difluorophenyl)ureido)phenyl)-1-oxoisoindolin-2-yl)-3-methylbutanoic acid;
(S)-3-Methyl-2-(1-oxo-6-(4-(3-p-tolylureido)phenyl)isoindolin-2-yl)butanoic acid;
(S)-2-(6-(4-(3-(3-Methoxyphenyl)ureido)phenyl)-1-oxoisoindolin-2-yl)-3-methyl butanoic acid;
(S)-2-(6-(4-(3-(4-Methoxyphenyl)ureido)phenyl)-1-oxoisoindolin-2-yl)-3-methylbutanoic acid;
(S)-2-(6-(4-(3-(3,5-Difluorophenyl)ureido)phenyl)-1-oxoisoindolin-2-yl)-3-methylbutanoic acid;
(S)-2-(6-(4-(3-(3,4-Difluorophenyl)ureido)phenyl)-1-oxoisoindolin-2-yl)-3-methylbutanoic acid;
(S)-2-(6-(4-(3-Cyclohexylureido)phenyl)-1-oxoisoindolin-2-yl)-3-methylbutanoic acid;
(S)-3-Methyl-2-(1-oxo-6-(4-(3-(4-(trifluoromethyl)phenyl)ureido)phenyl)isoindolin-2-yl)butanoic acid;
(S)-3-Methyl-2-(1-oxo-6-(4-(3-(3-(trifluoromethyl)phenyl)ureido)phenyl)isoindolin-2-yl)butanoic acid;
(S)-2-(6-(4-(3-(4-Cyanophenyl)ureido)phenyl)-1-oxoisoindolin-2-yl)-3-methyl butanoic acid;
(S)-2-(6-(4-(3-(3-Cyanophenyl)ureido)phenyl)-1-oxoisoindolin-2-yl)-3-methyl butanoic acid;
(S)-2-(6-(4-(3-(4-Chloro-2-phenoxyphenyl)ureido)phenyl)-1-oxoisoindolin-2-yl)-3-methylbutanoic acid;
(S)-2-(6-(4-(3-(5-Chloro-2-phenoxyphenyl)ureido)phenyl)-1-oxoisoindolin-2-yl)-3-methylbutanoic acid;
(S)-3-Methyl-2-(1-oxo-6-(4-(3-(2-phenoxyphenyl)ureido)phenyl)isoindolin-2-yl)butanoic acid;
(S)-3-Methyl-2-(1-oxo-6-(4-(3-(4-phenoxyphenyl)ureido)phenyl)isoindolin-2-yl)butanoic acid;
(S)-2-(6-(4-(3-(2-Fluorophenyl)thioureido)phenyl)-1-oxoisoindolin-2-yl)-3-methylbutanoic acid;
(S)-3-Methyl-2-(1-oxo-6-(4-(3-p-tolylthioureido)phenyl)isoindolin-2-yl)butanoic acid;
(S)-2-(6-(4-(3-(3-Fluorophenyl)thioureido)phenyl)-1-oxoisoindolin-2-yl)-3-methylbutanoic acid;
(S)-2-(6-(4-(3-(4-Methoxyphenyl)thioureido)phenyl)-1-oxoisoindolin-2-yl)-3-methylbutanoic acid;
(S)-2-(6-(4-(3-(3-Methoxyphenyl)thioureido)phenyl)-1-oxoisoindolin-2-yl)-3-methylbutanoic acid;
(S)-2-(6-(4-(3-(4-Chlorophenyl)thioureido)phenyl)-1-oxoisoindolin-2-yl)-3-methyl butanoic acid;
(S)-2-(6-(4-(3-(3-Chlorophenyl)thioureido)phenyl)-1-oxoisoindolin-2-yl)-3-methyl butanoic acid;
(S)-3-Methyl-2-(1-oxo-6-(4-(3-(2-trifluoromethyl)phenyl)thioureido)phenyl)isoindolin-2-yl)butanoic acid;
(S)-2-(6-(4-(3-(4-Cyanophenyl)thioureido)phenyl)-1-oxoisoindolin-2-yl)-3-methyl butanoic acid;
(S)-2-(6-(4-(3-(3-Cyanophenyl)thioureido)phenyl)-1-oxoisoindolin-2-yl)-3-methylbutanoic acid;
(S)-3-Methyl-2-(1-oxo-6-(4-(3-o-tolylthioureido)phenyl)isoindolin-2-yl)butanoic acid;
(S)-2-(6-(4-(3-(2-Methoxyphenyl)thioureido)phenyl)-1-oxoisoindolin-2-yl)-3-methylbutanoic acid;
(S)-3-Methyl-2-(1-oxo-6-(4-(3-(3-(trifluoromethyl)phenyl)thioureido)phenyl)isoindolin-2-yl)butanoic acid;
(S)-3-Methyl-2-(1-oxo-6-(4-(phenylsulfonamido)phenyl)isoindolin-2-yl)butanoic acid;
(S)-2-(6-(4-(4-Cyanophenylsulfonamido)phenyl)-1-oxoisoindolin-2-yl)-3-methyl butanoic acid;
(S)-2-(6-(4-(3,4-Difluorophenylsulfonamido)phenyl)-1-oxoisoindolin-2-yl)-3-methylbutanoic acid;
(S)-2-(6-(4-(2,4-Difluorophenylsulfonamido)phenyl)-1-oxoisoindolin-2-yl)-3-methylbutanoic acid;
(S)-2-(6-(4-(3,4-Dimethoxyphenylsulfonamido)phenyl)-1-oxoisoindolin-2-yl)-3-methylbutanoic acid;
(S)-2-(6-(4-(3-Chlorophenylsulfonamido)phenyl)-1-oxoisoindolin-2-yl)-3-methylbutanoic acid;
(S)-2-(6-(4-(4-Methoxyphenylsulfonamido)phenyl)-1-oxoisoindolin-2-yl)-3-methylbutanoic acid;
(S)-3-Methyl-2-(1-oxo-6-(4-(4-(trifluoromethyl)phenylsulfonamido)phenyl)isoindolin-2-yl)butanoic acid;
(S)-3-Methyl-2-(1-oxo-6-(4-(phenylmethylsulfonamido)phenyl)isoindolin-2-yl)butanoic acid;
(S)-3-Methyl-2-(6-(4-(1-methylethylsulfonamido)phenyl)-1-oxoisoindolin-2-yl)butanoic acid;
(S)-2-(6-(4-Benzamidophenyl)-1-oxoisoindolin-2-yl)-3-methylbutanoic acid;
(S)-2-(6-(4-(4-Fluorobenzamido)phenyl)-1-oxoisoindolin-2-yl)-3-methylbutanoic acid;
(S)-3-Methyl-2-(1-oxo-6-(4-(4-(trifluoromethyl)benzamido)phenyl)isoindolin-2-yl)butanoic acid;

(S)-2-(6-(4-(4-Methoxybenzamido)phenyl)-1-oxoisoindolin-2-yl)-3-methyl butanoic acid;
(S)-2-(6-(4-(3-Fluorobenzamido)phenyl)-1-oxoisoindolin-2-yl)-3-methylbutanoic acid;
(S)-2-(6-(4-(3-Chlorobenzamido)phenyl)-1-oxoisoindolin-2-yl)-3-methylbutanoic acid;
(S)-2-(6-(4-(2,4-Difluorobenzamido)phenyl)-1-oxoisoindolin-2-yl)-3-methyl butanoic acid;
(S)-3-Methyl-2-(6-(4-(4-methylbenzamido)phenyl)-1-oxoisoindolin-2-yl)butanoic acid;
(S)-2-(6-(4-(4-Chlorobenzamido)phenyl)-1-oxoisoindolin-2-yl)-3-methylbutanoic acid;
(S)-2-(6-(4-(4-tert-Butylbenzamido)phenyl)-1-oxoisoindolin-2-yl)-3-methyl butanoic acid;
(S)-2-(6-(4-(Cyclohexanecarboxamido)phenyl)-1-oxoisoindolin-2-yl)-3-methylbutanoic acid;
(S)-2-(6-(4-Biphenyl-4-ylcarboxamidophenyl)-1-oxoisoindolin-2-yl)-3-methyl butanoic acid;
(S)-2-(6-(4-(2-Naphthamido)phenyl)-1-oxoisoindolin-2-yl)-3-methylbutanoic acid;
(S)-3-Methyl-2-(1-oxo-6-(4-(4-pentylbenzamido)phenyl)isoindolin-2-yl)butanoic acid;
(S)-2-(6-(4-(2-Fluoro-6-(trifluoromethyl)benzamido)phenyl)-1-oxoisoindolin-2-yl)-3-methylbutanoic acid;
(S)-2-(6-(4-(Benzo[d][1,3]dioxole-5-carboxamido)phenyl)-1-oxoisoindolin-2-yl)-3-methylbutanoic acid;
(S)-2-(6-(4-(2,6-Dichlorobenzamido)phenyl)-1-oxoisoindolin-2-yl)-3-methyl butanoic acid;
(S)-2-(6-(4-(2-Chlorobenzamido)phenyl)-1-oxoisoindolin-2-yl)-3-methylbutanoic acid;
(S)-2-(6-(4-(2,4-Dichlorobenzamido)phenyl)-1-oxoisoindolin-2-yl)-3-methyl butanoic acid;
(S)-2-(6-(4-(4-Butoxybenzamido)phenyl)-1-oxoisoindolin-2-yl)-3-methyl butanoic acid;
(S)-2-(6-(4-(2,6-Difluorobenzamido)phenyl)-1-oxoisoindolin-2-yl)-3-methyl butanoic acid;
(S)-2-(6-(4-(3,4-Difluorobenzamido)phenyl)-1-oxoisoindolin-2-yl)-3-methyl butanoic acid;
(S)-2-(6-(4-(3,4-Dimethoxybenzamido)phenyl)-1-oxoisoindolin-2-yl)-3-methyl butanoic acid;
(S)-3-Methyl-2-(1-oxo-6-(4-(3,4,5-trimethoxybenzamido)phenyl)isoindolin-2-yl)butanoic acid;
(S)-2-(6-(4-(3,5-Diethoxybenzamido)phenyl)-1-oxoisoindolin-2-yl)-3-methyl butanoic acid;
(S)-3-Methyl-2-(1-oxo-6-(4-(3-phenoxybenzamido)phenyl)isoindolin-2-yl)butanoic acid;
(S)-3-Methyl-2-(1-oxo-6-(4-(4-phenoxybenzamido)phenyl)isoindolin-2-yl)butanoic acid;
(S)-3-Methyl-2-(1-oxo-6-(4-(2-phenoxybenzamido)phenyl)isoindolin-2-yl)butanoic acid;
(S)-3-Methyl-2-(1-oxo-6-(4-(2,4,6-trimethylbenzamido)phenyl)isoindolin-2-yl)butanoic acid;
(S)-2-(6-(4-(2,4-Dimethoxybenzamido)phenyl)-1-oxoisoindolin-2-yl)-3-methyl butanoic acid;
(S)-3-Methyl-2-(1-oxo-6-(4-(4-(trifluoromethoxy)benzamido)phenyl)isoindolin-2-yl)butanoic acid;
(S)-2-(6-(4-(2-Methoxybenzamido)phenyl)-1-oxoisoindolin-2-yl)-3-methyl butanoic acid;
(S)-2-(6-(4-(4-Fluoro-3-methylbenzamido)phenyl)-1-oxoisoindolin-2-yl)-3-methyl butanoic acid;
(S)-2-(6-(4-(4-Butylbenzamido)phenyl)-1-oxoisoindolin-2-yl)-3-methylbutanoic acid;
(S)-2-(6-(4-(2,6-Difluoro-3-methylbenzamido)phenyl)-1-oxoisoindolin-2-yl)-3-methylbutanoic acid;
(S)-2-(6-(4-(4-Ethylbenzamido)phenyl)-1-oxoisoindolin-2-yl)-3-methylbutanoic acid;
(S)-3-Methyl-2-(1-oxo-6-(4-(4-propylbenzamido)phenyl)isoindolin-2-yl)butanoic acid;
(S)-3-Methyl-2-(6-(4-(4-octylbenzamido)phenyl)-1-oxoisoindolin-2-yl)butanoic acid;
(S)-2-(6-(4-(4-Cyclohexylbenzamido)phenyl)-1-oxoisoindolin-2-yl)-3-methyl butanoic acid;
(S)-3-Methyl-2-(1-oxo-6-(4-(5,5,8,8-tetramethyl-5,6,7,8-tetrahydro naphthalene-2-carboxamido)phenyl)isoindolin-2-yl)butanoic acid;
(S)-2-(6-(4-(1-Naphthamido)phenyl)-1-oxoisoindolin-2-yl)-3-methylbutanoic acid;
(S)-2-(6-(4-(3,5-Dimethoxybenzamido)phenyl)-1-oxoisoindolin-2-yl)-3-methyl butanoic acid;
(S)-2-(6-(4-(4-Hexylbenzamido)phenyl)-1-oxoisoindolin-2-yl)-3-methylbutanoic acid;
(S)-2-(6-(4-(4-Heptylbenzamido)phenyl)-1-oxoisoindolin-2-yl)-3-methylbutanoic acid;
(S)-3-Methyl-2-(6-(4-(4-nonylbenzamido)phenyl)-1-oxoisoindolin-2-yl)butanoic acid;
(S)-2-(6-(4-(4-Decylbenzamido)phenyl)-1-oxoisoindolin-2-yl)-3-methyl butanoic acid;
(S)-2-(6-(4-(Adamantyl-2-carboxamido)phenyl)-1-oxoisoindolin-2-yl)-3-methylbutanoic acid;
(S)-2-(6-(4-(2-Fluoro-4-(trifluoromethyl)benzamido)phenyl)-1-oxoisoindolin-2-yl)-3-methylbutanoic acid;
(S)-2-(6-(4-(2-Fluoro-3-(trifluoromethyl)benzamido)phenyl)-1-oxoisoindolin-2-yl)-3-methylbutanoic acid;
(S)-2-(6-(4-(3-Fluoro-4-(trifluoromethyl)benzamido)phenyl)-1-oxoisoindolin-2-yl)-3-methylbutanoic acid;
(S)-2-(6-(4-(4-Fluoro-2-(trifluoromethyl)benzamido)phenyl)-1-oxoisoindolin-2-yl)-3-methylbutanoic acid;
(S)-3-Methyl-2-(1-oxo-6-(4-(2-(trifluoromethyl)benzamido)phenyl)isoindolin-2-yl)butanoic acid;
(S)-2-(6-(4-(2-Ethoxybenzamido)phenyl)-1-oxoisoindolin-2-yl)-3-methylbutanoic acid;
(S)-3-Methyl-2-(6-(4-(nicotinamido)phenyl)-1-oxoisoindolin-2-yl)butanoic acid;
(S)-2-(6-(4-(2-Chloronicotinamido)phenyl)-1-oxoisoindolin-2-yl)-3-methyl butanoic acid;
(S)-3-Methyl-2-(6-(4-(6-morpholinonicotinamido)phenyl)-1-oxoisoindolin-2-yl)butanoic acid;
(S)-3-Methyl-2-(1-oxo-6-(4-(6-(piperidin-1-yl)nicotinamido)phenyl)isoindolin-2-yl)butanoic acid;
(S)-3-Methyl-2-(1-oxo-6-(4-(6-(pyrrolidin-1-yl)nicotinamido)phenyl)isoindolin-2-yl)butanoic acid;
(S)-2-(5-(4-(3-(4-Fluorophenyl)ureido)phenyl)-1-oxoisoindolin-2-yl)-3-methylbutanoic acid;
(S)-2-(5-(4-(3-(2-Fluorophenyl)ureido)phenyl)-1-oxoisoindolin-2-yl)-3-methyl butanoic acid;
(S)-2-(5-(4-(3-(3-Fluorophenyl)ureido)phenyl)-1-oxoisoindolin-2-yl)-3-methyl butanoic acid,
(S)-3-Methyl-2-(1-oxo-5-(4-(3-phenylureido)phenyl)isoindolin-2-yl)butanoic acid;
(S)-2-(5-(4-(3-Cyclohexylureido)phenyl)-1-oxoisoindolin-2-yl)-3-methyl butanoic acid;
(S)-2-(5-(4-(3-(2,4-Difluorophenyl)ureido)phenyl)-1-oxoisoindolin-2-yl)-3-methylbutanoic acid;
(S)-2-(5-(4-(3-(3,4-Difluorophenyl)ureido)phenyl)-1-oxoisoindolin-2-yl)-3-methylbutanoic acid;
(S)-3-Methyl-2-(1-oxo-5-(4-(3-p-tolylureido)phenyl)isoindolin-2-yl)butanoic acid;
(S)-3-Methyl-2-(1-oxo-5-(4-(3-m-tolylureido)phenyl)isoindolin-2-yl)butanoic acid;
(S)-3-Methyl-2-(1-oxo-5-(4-(3-(4-(trifluoromethyl)phenyl)ureido)phenyl)isoindolin-2-yl)butanoic acid;
(S)-3-Methyl-2-(1-oxo-5-(4-(3-(3-(trifluoromethyl)phenyl)ureido)phenyl)isoindolin-2-yl)butanoic acid;

(S)-2-(5-(4-(3-(4-Methoxyphenyl)ureido)phenyl)-1-oxoisoindolin-2-yl)-3-methylbutanoic acid;
(S)-2-(5-(4-(3-(3-Methoxyphenyl)ureido)phenyl)-1-oxoisoindolin-2-yl)-3-methylbutanoic acid;
(S)-2-(5-(4-(3-(4-Cyanophenyl)ureido)phenyl)-1-oxoisoindolin-2-yl)-3-methylbutanoic acid;
(S)-2-(5-(4-(3-(3-Cyanophenyl)ureido)phenyl)-1-oxoisoindolin-2-yl)-3-methylbutanoic acid;
(S)-2-(5-(4-(3-(2-Fluorophenyl)thioureido)phenyl)-1-oxoisoindolin-2-yl)-3-methylbutanoic acid;
(S)-2-(5-(4-(3-(3-Fluorophenyl)thioureido)phenyl)-1-oxoisoindolin-2-yl)-3-methyl butanoic acid;
(S)-2-(5-(4-(3-(4-Methoxyphenyl)thioureido)phenyl)-1-oxoisoindolin-2-yl)-3-methylbutanoic acid;
(S)-2-(5-(4-(3-(3-Methoxyphenyl)thioureido)phenyl)-1-oxoisoindolin-2-yl)-3-methyl butanoic acid;
(S)-2-(5-(4-(3-(4-Chlorophenyl)thioureido)phenyl)-1-oxoisoindolin-2-yl)-3-methylbutanoic acid;
(S)-2-(5-(4-(3-(3-Chlorophenyl)thioureido)phenyl)-1-oxoisoindolin-2-yl)-3-methylbutanoic acid;
(S)-2-(5-(4-(3-(4-Cyanophenyl)thioureido)phenyl)-1-oxoisoindolin-2-yl)-3-methyl butanoic acid;
(S)-3-Methyl-2-(1-oxo-5-(4-(3-(2-(trifluoromethyl)phenyl)thioureido)phenyl)isoindolin-2-yl)butanoic acid;
(S)-3-Methyl-2-(1-oxo-5-(4-(3-o-tolylthioureido)phenyl)isoindolin-2-yl)butanoic acid;
(S)-3-Methyl-2-(1-oxo-5-(4-(3-p-tolylthioureido)phenyl)isoindolin-2-yl)butanoic acid;
(S)-2-(5-(4-(3-(3-Fluorophenyl)thioureido)phenyl)-1-oxoisoindolin-2-yl)-3-methyl butanoic acid;
(S)-2-(5-(4-(3-(3-Methoxyphenyl)thioureido)phenyl)-1-oxoisoindolin-2-yl)-3-methylbutanoic acid;
(S)-2-(5-(4-(3-(2-Methoxyphenyl)thioureido)phenyl)-1-oxoisoindolin-2-yl)-3-methylbutanoic acid;
(S)-3-Methyl-2-(1-oxo-5-(4-(3-(3-(trifluoromethyl)phenyl)thioureido)phenyl)isoindolin-2-yl)butanoic acid;
(S)-3-Methyl-2-(1-oxo-6-(4-(phenylsulfonamido)phenyl)isoindolin-2-yl)butanoic acid;
(S)-2-(5-(4-(4-Cyanophenylsulfonamido)phenyl)-1-oxoisoindolin-2-yl)-3-methyl butanoic acid;
(S)-2-(5-(4-(3,4-Difluorophenylsulfonamido)phenyl)-1-oxoisoindolin-2-yl)-3-methylbutanoic acid;
(S)-2-(5-(4-(2,4-Difluorophenylsulfonamido)phenyl)-1-oxoisoindolin-2-yl)-3-methylbutanoic acid;
(S)-2-(5-(4-(3,4-Dimethoxyphenylsulfonamido)phenyl)-1-oxoisoindolin-2-yl)-3-methylbutanoic acid;
(S)-2-(5-(4-(3-Chlorophenylsulfonamido)phenyl)-1-oxoisoindolin-2-yl)-3-methyl butanoic acid;
(S)-2-(5-(4-(4-Methoxyphenylsulfonamido)phenyl)-1-oxoisoindolin-2-yl)-3-methylbutanoic acid;
(S)-3-Methyl-2-(1-oxo-5-(4-(4-(trifluoromethyl)phenylsulfonamido)phenyl)isoindolin-2-yl)butanoic acid;
(S)-3-Methyl-2-(1-oxo-5-(4-(phenylmethylsulfonamido)phenyl)isoindolin-2-yl)butanoic acid;
(S)-2-(5-(4-(Cyclohexanesulfonamido)phenyl)-1-oxoisoindolin-2-yl)-3-methylbutanoic acid;
(S)-2-(5-(4-Benzamidophenyl)-1-oxoisoindolin-2-yl)-3-methylbutanoic acid;
(S)-2-(5-(4-(4-Fluorobenzamido)phenyl)-1-oxoisoindolin-2-yl)-3-methylbutanoic acid;
(S)-3-Methyl-2-(1-oxo-5-(4-(4-(trifluoromethyl)benzamido)phenyl)isoindolin-2-yl)butanoic acid;
(S)-2-(5-(4-(4-Methoxybenzamido)phenyl)-1-oxoisoindolin-2-yl)-3-methyl butanoic acid;
(S)-2-(5-(4-(3-Fluorobenzamido)phenyl)-1-oxoisoindolin-2-yl)-3-methylbutanoic acid;
(S)-2-(5-(4-(3-Chlorobenzamido)phenyl)-1-oxoisoindolin-2-yl)-3-methylbutanoic acid;
(S)-2-(5-(4-(2,4-Difluorobenzamido)phenyl)-1-oxoisoindolin-2-yl)-3-methylbutanoic acid;
(S)-3-Methyl-2-(5-(4-(4-methylbenzamido)phenyl)-1-oxoisoindolin-2-yl)butanoic acid;
(S)-2-(5-(4-(4-Chlorobenzamido)phenyl)-1-oxoisoindolin-2-yl)-3-methylbutanoic acid;
(S)-2-(5-(4-(4-tert-Butylbenzamido)phenyl)-1-oxoisoindolin-2-yl)-3-methyl butanoic acid;
(S)-3-Methyl-2-(1-oxo-5-(4-(4-pentylbenzamido)phenyl)isoindolin-2-yl)butanoic acid;
(R)-3-Methyl-2-(1-oxo-6-(4-(3-(3-(trifluoromethyl)phenyl)ureido)phenyl)iso indolin-2-yl)butanoic acid;
2-(1-Oxo-6-(4-(3-(3-(trifluoromethyl)phenyl)ureido)phenyl)isoindolin-2-yl)acetic acid;
(S)-2-(1-Oxo-6-(4-(3-(3-(trifluoromethyl)phenyl)ureido)phenyl)isoindolin-2-yl)propanoic acid;
2-Methyl-2-(1-oxo-6-(4-(3-(3-(trifluoromethyl)phenyl)ureido)phenyl)isoindolin-2-yl)propanoic acid;
1-(1-Oxo-6-(4-(3-(3-(trifluoromethyl)phenyl)ureido)phenyl)isoindolin-2-yl)cyclopentanecarboxylic acid;
(S)-2-(1-Oxo-6-(4-(3-(3-(trifluoromethyl)phenyl)ureido)phenyl)isoindolin-2-yl)-2-phenylacetic acid;
4-(1-Oxo-6-(4-(3-(3-(trifluoromethyl)phenyl)ureido)phenyl)isoindolin-2-yl)butanoic acid;
(S)-4-Methyl-2-(1-oxo-6-(4-(3-(3-(trifluoromethyl)phenyl)ureido)phenyl)iso indolin-2-yl)pentanoic acid;
(S)-3-Methoxy-2-(1-oxo-6-(4-(3-(3-(trifluoromethyl)phenyl)ureido)phenyl)iso indolin-2-yl)propanoic acid;
(R)-3-Methyl-2-(1-oxo-5-(4-(3-(3-(trifluoromethyl)phenyl)ureido)phenyl)isoindolin-2-yl)butanoic acid;
2-(1-Oxo-5-(4-(3-(3-(trifluoromethyl)phenyl)ureido)phenyl)isoindolin-2-yl)acetic acid;
(S)-2-(1-Oxo-5-(4-(3-(3-(trifluoromethyl)phenyl)ureido)phenyl)isoindolin-2-yl)propanoic acid;
1-(1-Oxo-5-(4-(3-(3-(trifluoromethyl)phenyl)ureido)phenyl)isoindolin-2-yl)cyclopentanecarboxylic acid;
(S)-2-(1-Oxo-5-(4-(3-(3-(trifluoromethyl)phenyl)ureido)phenyl)isoindolin-2-yl)-2-phenylacetic acid;
4-(1-Oxo-5-(4-(3-(3-(trifluoromethyl)phenyl)ureido)phenyl)isoindolin-2-yl)butanoic acid;
3-(1-Oxo-5-(4-(3-(3-(trifluoromethyl)phenyl)ureido)phenyl)isoindolin-2-yl)propanoic acid;
(S)-2-(1-Oxo-5-(4-(3-(3-(trifluoromethyl)phenyl)ureido)phenyl)isoindolin-2-yl)-3-phenylpropanoic acid;
(S)-3-Methoxy-2-(1-oxo-5-(4-(3-(3-(trifluoromethyl)phenyl)ureido)phenyl)isoindolin-2-yl)propanoic acid;
(S)-4-Methyl-2-(1-oxo-5-(4-(3-(3-(trifluoromethyl)phenyl)ureido)phenyl)iso indolin-2-yl)pentanoic acid;
(S)-2-(6-(5-(3-(2-Chlorophenyl)ureido)pyridin-2-yl)-1-oxoisoindolin-2-yl)-3-methylbutanoic acid;
(S)-2-(6-(5-(3-(4-Chloro-2-phenoxyphenyl)ureido)pyridin-2-yl)-1-oxoisoindolin-2-yl)-3-methylbutanoic acid;
(S)-2-(6-(5-(3-(3,4-Dimethylphenyl)ureido)pyridin-2-yl)-1-oxoisoindolin-2-yl)-3-methylbutanoic acid;
(S)-2-(6-(5-(3-(3,4-Difluorophenyl)ureido)pyridin-2-yl)-1-oxoisoindolin-2-yl)-3-methylbutanoic acid;
(S)-2-(6-(5-(3-(2,3-Dihydro-1H-inden-5-yl)ureido)pyridin-2-yl)-1-oxoisoindolin-2-yl)-3-methylbutanoic acid;
(S)-2-(6-(5-(4-tert-Butylbenzamido)pyridin-2-yl)-1-oxoisoindolin-2-yl)-3-methyl butanoic acid;
(S)-3-Methyl-2-(1-oxo-6-(5-(4-pentylbenzamido)pyridin-2-yl)isoindolin-2-yl)butanoic acid;

(S)-2-(6-(5-Biphenyl-4-ylcarboxamidopyridin-2-yl)-1-oxoisoindolin-2-yl)-3-methylbutanoic acid; (S)-2-(6-(5-(2-Naphthamido)pyridin-2-yl)-1-oxoisoindolin-2-yl)-3-methylbutanoic acid;
(S)-2-(6-(5-(4-Butoxybenzamido)pyridin-2-yl)-1-oxoisoindolin-2-yl)-3-methylbutanoic acid;
(S)-2-(6-(4-(3-(2-Chlorophenyl)ureido)-2-(trifluoromethyl)phenyl)-1-oxoisoindolin-2-yl)-3-methylbutanoic acid;
(S)-2-(6-(4-(3-(3,4-Difluorophenyl)ureido)-2-(trifluoromethyl)phenyl)-1-oxoisoindolin-2-yl)-3-methylbutanoic acid;
(S)-2-(6-(4-(3-(2,3-Dihydro-1H-inden-5-yl)ureido)-2-(trifluoromethyl)phenyl)-1-oxoisoindolin-2-yl)-3-methylbutanoic acid;
(S)-2-(6-(4-(3-(3,4-Dimethylphenyl)ureido)-2-(trifluoromethyl)phenyl)-1-oxoisoindolin-2-yl)-3-methylbutanoic acid;
(S)-2-(6-(4-(4-tert-Butylbenzamido)-2-(trifluoromethyl)phenyl)-1-oxoisoindolin-2-yl)-3-methylbutanoic acid;
(S)-2-(6-(4-Biphenyl-4-ylcarboxamido-2-(trifluoromethyl)phenyl)-1-oxoisoindolin-2-yl)-3-methylbutanoic acid;
(S)-2-(6-(4-(2-Naphthamido)-2-(trifluoromethyl)phenyl)-1-oxoisoindolin-2-yl)-3-methylbutanoic acid;
(S)-3-Methyl-2-(1-oxo-6-(4-(4-pentylbenzamido)-2-(trifluoromethyl)phenyl)isoindolin-2-yl)butanoic acid;
(S)-2-(6-(4-(4-Butoxybenzamido)-2-(trifluoromethyl)phenyl)-1-oxoisoindolin-2-yl)-3-methylbutanoic acid;
(S)-2-(6-(4-(3-(3,4-Dimethylphenyl)ureido)-3-fluorophenyl)-1-oxoisoindolin-2-yl)-3-methylbutanoic acid;
(S)-2-(6-(4-(3-(2,3-Dihydro-1H-inden-5-yl)ureido)-3-fluorophenyl)-1-oxoisoindolin-2-yl)-3-methylbutanoic acid; (S)-2-(6-(4-(3-(3,4-Difluorophenyl)ureido)-3-fluorophenyl)-1-oxoisoindolin-2-yl)-3-methylbutanoic acid;
(S)-2-(6-(4-(3-(2-Chlorophenyl)ureido)-3-fluorophenyl)-1-oxoisoindolin-2-yl)-3-methylbutanoic acid;
(S)-2-(6-(4-(4-tert-Butylbenzamido)-3-fluorophenyl)-1-oxoisoindolin-2-yl)-3-methylbutanoic acid;
(S)-2-(6-(3-Fluoro-4-(4-pentylbenzamido)phenyl)-1-oxoisoindolin-2-yl)-3-methylbutanoic acid;
(S)-2-(6-(4-Biphenyl-4-ylcarboxamido-3-fluorophenyl)-1-oxoisoindolin-2-yl)-3-methylbutanoic acid;
(S)-2-(6-(4-(2-Naphthamido)-3-fluorophenyl)-1-oxoisoindolin-2-yl)-3-methyl butanoic acid;
(S)-2-(6-(4-(4-Butoxybenzamido)-3-fluorophenyl)-1-oxoisoindolin-2-yl)-3-methyl butanoic acid;
(S)-2-(6-(4-(4-tert-Butylbenzamido)-2-methoxyphenyl)-1-oxoisoindolin-2-yl)-3-methylbutanoic acid;
(S)-2-(6-(4-Biphenyl-4-ylcarboxamido-2-methoxyphenyl)-1-oxoisoindolin-2-yl)-3-methylbutanoic acid;
(S)-2-(6-(4-(4-Butoxybenzamido)-2-methoxyphenyl)-1-oxoisoindolin-2-yl)-3-methylbutanoic acid;
(S)-2-(6-(2-Methoxy-4-(4-pentylbenzamido)phenyl)-1-oxoisoindolin-2-yl)-3-methylbutanoic acid;
(S)-2-(6-(2-Methoxy-4-(4-(trifluoromethoxy)benzamido)phenyl)-1-oxoisoindolin-2-yl)-3-methylbutanoic acid;
(S)-2-(6-(4-(4-tert-Butylbenzamido)-2-methylphenyl)-1-oxoisoindolin-2-yl)-3-methylbutanoic acid;
(S)-2-(6-(4-Biphenyl-4-ylcarboxamido-2-methylphenyl)-1-oxoisoindolin-2-yl)-3-methylbutanoic acid;
(S)-2-(6-(4-(4-Butoxybenzamido)-2-methylphenyl)-1-oxoisoindolin-2-yl)-3-methylbutanoic acid;
(S)-3-Methyl-2-(6-(2-methyl-4-(4-pentylbenzamido)phenyl)-1-oxoisoindolin-2-yl)butanoic acid;
(S)-3-Methyl-2-(6-(2-methyl-4-(4-(trifluoromethoxy)benzamido)phenyl)-1-oxoisoindolin-2-yl)butanoic acid;
(S)-2-(6-(4-(4-tert-Butylbenzamido)-2-chlorophenyl)-1-oxoisoindolin-2-yl)-3-methylbutanoic acid;
(S)-2-(6-(4-Biphenyl-4-ylcarboxamido-2-chlorophenyl)-1-oxoisoindolin-2-yl)-3-methylbutanoic acid;
(S)-2-(6-(4-(4-Butoxybenzamido)-2-chlorophenyl)-1-oxoisoindolin-2-yl)-3-methylbutanoic acid;
(S)-2-(6-(2-Chloro-4-(4-pentylbenzamido)phenyl)-1-oxoisoindolin-2-yl)-3-methylbutanoic acid;
(S)-2-(6-(2-Chloro-4-(4-(trifluoromethoxy)benzamido)phenyl)-1-oxoisoindolin-2-yl)-3-methylbutanoic acid;
(S)-2-(6-(6-(4-tert-Butylbenzamido)pyridin-3-yl)-1-oxoisoindolin-2-yl)-3-methylbutanoic acid;
(S)-2-(6-(6-(4-tert-Butylbenzamido)pyridazin-3-yl)-1-oxoisoindolin-2-yl)-3-methylbutanoic acid;
(S)-3-Methyl-2-(1-oxo-6-(6-(4-pentylbenzamido)pyridazin-3-yl)isoindolin-2-yl)butanoic acid;
(S)-3-Methyl-2-(1-oxo-6-(6-(4-(trifluoromethoxy)benzamido)pyridazin-3-yl)isoindolin-2-yl)butanoic acid;
(S)-2-(6-(5-(4-tert-Butylbenzamido)pyrazin-2-yl)-1-oxoisoindolin-2-yl)-3-methylbutanoic acid;
(S)-2-(6-(5-Biphenyl-4-ylcarboxamidopyrazin-2-yl)-1-oxoisoindolin-2-yl)-3-methylbutanoic acid;
(S)-2-(6-(5-(4-Butoxybenzamido)pyrazin-2-yl)-1-oxoisoindolin-2-yl)-3-methylbutanoic acid;
(S)-3-Methyl-2-(1-oxo-6-(5-(4-pentylbenzamido)pyrazin-2-yl)isoindolin-2-yl)butanoic acid;
(S)-3-Methyl-2-(1-oxo-6-(5-(4-(trifluoromethoxy)benzamido)pyrazin-2-yl)isoindolin-2-yl)butanoic acid;
2-(6-(4-([1,1'-Biphenyl]-4-ylcarboxamido)phenyl)-1-oxoisoindolin-2-yl)-2-methyl propanoic acid;
2-(6-(4-(4-(tert-Butyl)benzamido)phenyl)-1-oxoisoindolin-2-yl)-2-methyl propanoic acid;
2-(6-(4-(4-Chlorobenzamido)phenyl)-1-oxoisoindolin-2-yl)-2-methylpropanoic acid;
2-Methyl-2-(1-oxo-6-(4-(4-(trifluoromethoxy)benzamido)phenyl)isoindolin-2-yl)propanoic acid;
2-Methyl-2-(1-oxo-6-(4-(4-pentylbenzamido)phenyl)isoindolin-2-yl)propanoic acid;
1-(6-(4-([1,1'-Biphenyl]-4-ylcarboxamido)phenyl)-1-oxoisoindolin-2-yl)cyclopentane carboxylic acid;
1-(6-(4-(4-(tert-Butyl)benzamido)phenyl)-1-oxoisoindolin-2-yl)cyclopentane carboxylic acid;
1-(6-(4-(4-Chlorobenzamido)phenyl)-1-oxoisoindolin-2-yl)cyclopentane carboxylic acid,
1-(1-Oxo-6-(4-(4-(trifluoromethoxy)benzamido)phenyl)isoindolin-2-yl)cyclopentane carboxylic acid;
1-(1-Oxo-6-(4-(4-pentylbenzamido)phenyl)isoindolin-2-yl)cyclopentane carboxylic acid;
(R)-2-(6-(4-([1,1'-Biphenyl]-4-ylcarboxamido)phenyl)-1-oxoisoindolin-2-yl)-3-methylbutanoic acid;
3-(6-(4-([1,1'-Biphenyl]-4-ylcarboxamido)phenyl)-1-oxoisoindolin-2-yl)cyclo hexane carboxylic acid;
3-(6-(4-(3-Chlorobenzamido)phenyl)-1-oxoisoindolin-2-yl)cyclohexane carboxylic acid;
3-(6-(4-(4-Chlorobenzamido)phenyl)-1-oxoisoindolin-2-yl)cyclohexane carboxylic acid;
3-(1-Oxo-6-(4-(4-(trifluoromethyl)benzamido)phenyl)isoindolin-2-yl)cyclo hexanecarboxylic acid;
3-(6-(4-(5-Methyl-2-phenyloxazole-4-carboxamido)phenyl)-1-oxoisoindolin-2-yl)cyclohexanecarboxylic acid;
(1r,4r)-4-(6-(4-([1,1'-Biphenyl]-4-ylcarboxamido)phenyl)-1-oxoisoindolin-2-yl)cyclohexanecarboxylic acid;
(1r,4r)-4-(6-(4-(3-Chlorobenzamido)phenyl)-1-oxoisoindolin-2-yl)cyclohexane carboxylic acid;
(1r,4r)-4-(6-(4-(4-Chlorobenzamido)phenyl)-1-oxoisoindolin-2-yl)cyclohexane carboxylic acid;
(1r,4r)-4-(1-Oxo-6-(4-(4-(trifluoromethyl)benzamido)phenyl)isoindolin-2-yl)cyclohexanecarboxylic acid;

(1r,3s,5R,7S)-3-(6-(4-(3-Chlorobenzamido)phenyl)-1-ox-oisoindolin-2-yl)adamantane-1-carboxylic acid;
(1r,3s,5R,7S)-3-(6-(4-(4-Chlorobenzamido)phenyl)-1-ox-oisoindolin-2-yl)adamantane-1-carboxylic acid;
(1r,3s,5R,7S)-3-(1-Oxo-6-(4-(4-(trifluoromethyl)benza-mido)phenyl)isoindolin-2-yl)adamantane-1-carboxylic acid;
(1r,3s,5R,7S)-3-(6-(4-(4-Methylbenzamido)phenyl)-1-ox-oisoindolin-2-yl)adamantane-1-carboxylic acid;
1-(6-(4-([1,1'-Biphenyl]-4-ylcarboxamido)phenyl)-1-ox-oisoindolin-2-yl)cyclobutane carboxylic acid;
1-(6-(4-(4-Chlorobenzamido)phenyl)-1-oxoisoindolin-2-yl)cyclobutane carboxylic acid;
1-(1-Oxo-6-(4-(4-(trifluoromethyl)benzamido)phenyl)isoindolin-2-yl)cyclo butanecarboxylic acid;
1-(6-(4-(4-Methylbenzamido)phenyl)-1-oxoisoindolin-2-yl)cyclobutane carboxylic acid;
1-(6-(4-([1,1'-Biphenyl]-4-ylcarboxamido)phenyl)-1-ox-oisoindolin-2-yl)cyclopropanecarboxylic acid;
1-(6-(4-(4-Chlorobenzamido)phenyl)-1-oxoisoindolin-2-yl)cyclopropane carboxylic acid;
1-(1-Oxo-6-(4-(4-(trifluoromethyl)benzamido)phenyl)isoindolin-2-yl)cyclopropane carboxylic acid;
(1S,2R)-2-(6-(4-(4-Chlorobenzamido)phenyl)-1-oxoisoin-dolin-2-yl)cyclopentane carboxylic acid;
(1S,2R)-2-(1-Oxo-6-(4-(4-(trifluoromethyl)benzamido)phe-nyl)isoindolin-2-yl)cyclopentanebcarboxylic acid;
(S)-2-(6-(4-([1,1'-Biphenyl]-4-ylcarboxamido)-2-fluo-rophenyl)-1-oxoisoindolin-2-yl)-3-methylbutanoic acid;
(S)-2-(6-(4-(4-(tert-Butyl)benzamido)-2-fluorophenyl)-1-oxoisoindolin-2-yl)-3-methylbutanoic acid;
(S)-2-(6-(4-(4-Chlorobenzamido)-2-fluorophenyl)-1-ox-oisoindolin-2-yl)-3-methyl butanoic acid;
(S)-2-(6-(2-Fluoro-4-(4-(trifluoromethoxy)benzamido)phe-nyl)-1-oxoisoindolin-2-yl)-3-methylbutanoic acid;
(S)-2-(6-(2-Fluoro-4-(4-pentylbenzamido)phenyl)-1-ox-oisoindolin-2-yl)-3-methyl butanoic acid;
(S)-3-Methyl-2-(1-oxo-6-(4-(5-phenylthiazole-2-carboxa-mido)phenyl)isoindolin-2-yl)butanoic acid;
(S)-3-Methyl-2-(1-oxo-6-(4-(5-phenyloxazole-2-carboxa-mido)phenyl)isoindolin-2-yl)butanoic acid;
(S)-2-(6-(4-(3-(4-Fluorophenyl)isoxazole-5-carboxamido)phenyl)-1-oxo isoindolin-2-yl)-3-methylbutanoic acid;
(S)-2-(6-(4-(3-(4-Chlorophenyl)isoxazole-5-carboxamido)phenyl)-1-oxo isoindolin-2-yl)-3-methylbutanoic acid;
(S)-3-Methyl-2-(1-oxo-6-(4-(3-(4-(trifluoromethyl)phenyl)isoxazole-5-carboxamido)phenyl)isoindolin-2-yl)bu-tanoic acid;
(S)-3-Methyl-2-(6-(4-(4-(oxazol-5-yl)benzamido)phenyl)-1-oxoisoindolin-2-yl)butanoic acid;
(S)-3-Methyl-2-(1-oxo-6-(4-(4-phenylthiazole-2-carboxa-mido)phenyl)isoindolin-2-yl)butanoic acid;
(S)-3-Methyl-2-(1-oxo-6-(4-(5-phenyl-1,3,4-thiadiazole-2-carboxamido)phenyl)isoindolin-2-yl)butanoic acid;
(S)-3-Methyl-2-(1-oxo-6-(4-(5-phenyl-4H-1,2,4-triazole-3-carboxamido)phenyl)isoindolin-2-yl)butanoic acid;
(S)-2-(6-(4-(4-(2-Cyanopropan-2-yl)benzamido)phenyl)-1-oxoisoindolin-2-yl)-3-methylbutanoic acid;
(S)-2-(6-(4-(4-(3-Cyanopentan-3-yl)benzamido)phenyl)-1-oxoisoindolin-2-yl)-3-methylbutanoic acid;
(S)-3-Methyl-2-(1-oxo-6-(5-(5-phenyloxazole-2-carboxa-mido)pyridin-2-yl)isoindolin-2-yl)butanoic acid;
(S)-3-Methyl-2-(1-oxo-6-(5-(5-phenylthiazole-2-carboxa-mido)pyridin-2-yl)isoindolin-2-yl)butanoic acid;
(S)-2-(6-(5-(3-(4-Fluorophenyl)isoxazole-5-carboxamido)pyridin-2-yl)-1-oxo isoindolin-2-yl)-3-methylbutanoic acid;
(S)-2-(6-(4-(4-(1,3,4-Oxadiazol-2-yl)benzamido)phenyl)-1-oxoisoindolin-2-yl)-3-methylbutanoic acid;
(S)-3-Methyl-2-(6-(4-(5-methyl-2-phenyloxazole-4-car-boxamido)phenyl)-1-oxoisoindolin-2-yl)butanoic acid;
(S)-3-Methyl-2-(1-oxo-6-(4-(2-phenyl-5-(trifluoromethyl)oxazole-4-carboxamido)phenyl)isoindolin-2-yl)butanoic acid;
(S)-3-Methyl-2-(1-oxo-6-(4-(4-(thiazol-2-yl)benzamido)phenyl)isoindolin-2-yl)butanoic acid;
(S)-2-(6-(4-(5-Butylpicolinamido)phenyl)-1-oxoisoindolin-2-yl)-3-methylbutanoic acid;
(S)-3-Methyl-2-(1-oxo-6-(4-(quinoline-3-carboxamido)phenyl)isoindolin-2-yl)butanoic acid,
(S)-3-Methyl-2-(1-oxo-6-(4-(4-(pyrimidin-5-yl)benzamido)phenyl)isoindolin-2-yl)butanoic acid;
(S)-3-Methyl-2-(6-(5-(5-methyl-2-phenyloxazole-4-car-boxamido)pyridin-2-yl)-1-oxoisoindolin-2-yl)butanoic acid;
(S)-3-Methyl-2-(1-oxo-6-(5-(2-phenyl-5-(trifluoromethyl)oxazole-4-carboxamido)pyridin-2-yl)isoindolin-2-yl)bu-tanoic acid; and
(S)-3-Methyl-2-(1-oxo-6-(4-(2-phenylacetamido)phenyl)isoindolin-2-yl)butanoic acid;
or a stereoisomer, tautomer, pharmaceutically acceptable salt, pharmaceutically acceptable solvate, pharmaceutically acceptable polymorph, pharmaceutically acceptable prodrug, N-oxide or carboxylic acid isostere thereof.

The compounds of the present invention also include all stereoisomeric and tautomeric forms and mixtures thereof in all ratios and their pharmaceutically acceptable salts, solvates, polymorphs, prodrugs, carboxylic acid isosteres and N-oxides.

According to another aspect of present invention, a compound of formula 1 can be prepared in a number of ways including using methods well known to the person skilled in the art. Examples of methods to prepare the present compounds are described below and illustrated in Schemes 1 to 10 but not limited thereto. It will be appreciated by persons skilled in the art that within certain of the processes described herein, the order of the synthetic steps employed may be varied and will depend inter alia on factors such as the nature of functional groups present in a particular substrate and the protecting group strategy (if any) to be adopted. Clearly, such factors will also influence the choice of reagent to be used in the synthetic steps.

The reagents, reactants and intermediates used in the following processes are either commercially available or can be prepared according to standard literature procedures known in the art. The starting compounds and the intermediates used for the synthesis of compounds of the present invention are referred to numerically. Throughout the process description, the corresponding substituent groups in the various formulae representing starting compounds and intermediates have the same meanings as that for the compound of formula I unless stated otherwise.

The schemes of the present invention are referred to numerically (1A to 1E; 2A to 2E; 3A to 3E; 4A to 4E; 5A to 5E; 6A to 6E; 7A to 7E; 8A to 8E; 9A to 9E and 10A to 10E). The processes used in various schemes of the present invention, are referred to with general symbols such as 1a to 1t, 2a to 2s, 3a to 3y, 4a to 4n, 5a to 5q, 6a to 6q, 7a to 7q, 8a to 8s, 9a, 9b and 10a. The schemes depict the preparation of compounds of formula 1, wherein m is 1. The compounds of formula 1, wherein m is an integer selected from 2 to 4, may be analogously prepared. Processes for the preparation of compounds of the present invention are set forth in the following schemes:

Scheme 1A: Preparation of Compound of Formula 1; Wherein $Y_1=CH_2$, $Y_2=C(O)$; $X_1$, $X_2$, $X_4$ and $X_5$ are Selected from CH or CR, $X_3=C$; L=NHC(O)NH; m=1; A, n, R, $R_1$, $R_2$ and $R_9$ are as Defined in Formula 1;

Scheme 1A

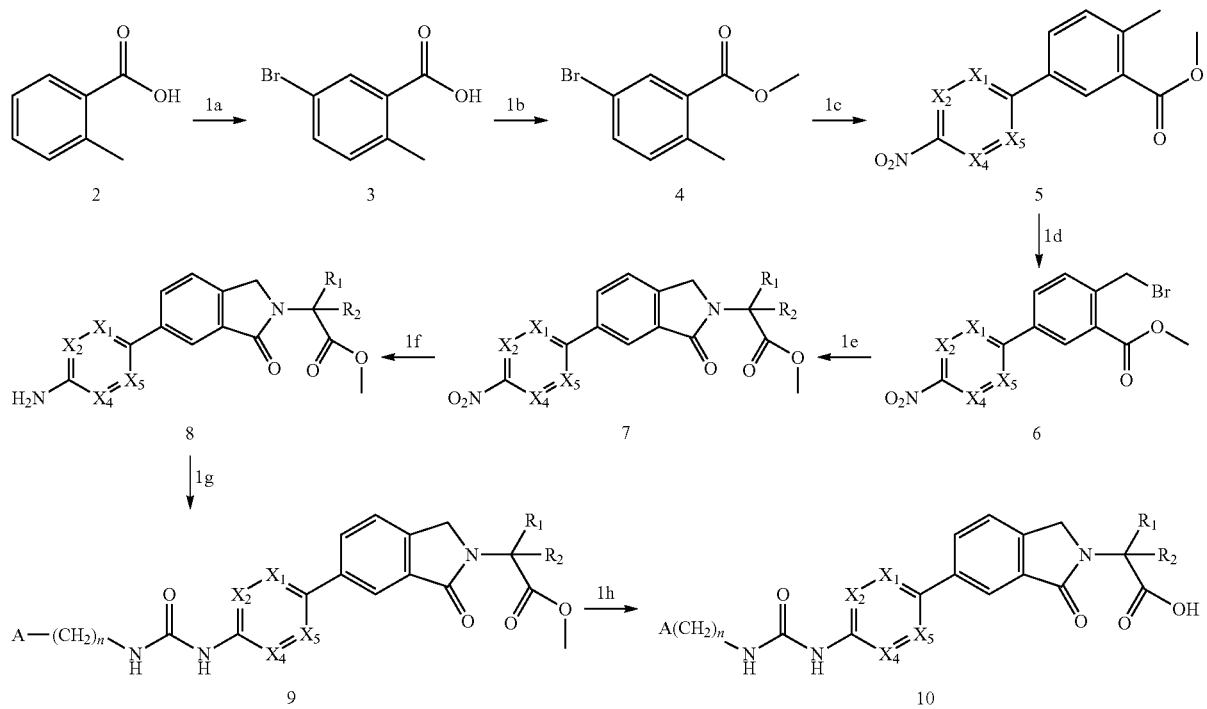

Step 1
Preparation of Compound of Formula 3:

Commercially available compound of formula 2 can be subjected to bromination using bromine in presence of suitable catalyst such as Fe at temperature ranging from 0-30° C. to yield compound of formula 3 (Reaction 1a).

Step 2
Preparation of Compound of Formula 4:

Compound of formula 3 can be converted to its corresponding methyl ester by reaction with methanol and $SOCl_2$ at temperature ranging from 0-30° C. or by heating with methanol and inorganic acid such as sulfuric acid or hydrochloric acid at temperature ranging from 50-100° C. to yield compound of formula 4 (Reaction 1b).

Step 3
Preparation of Compound of Formula 5:

Compound of formula 4 can be treated with compound of formula 4P:

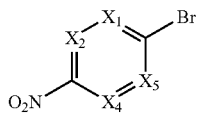

4P and bis(pinacolo)diboron, in presence of suitable reagent such as palladium acetate or tetrakis palladium and a suitable base such as potassium acetate, sodium carbonate or cesium carbonate in a suitable solvent such as toluene, dioxane, dimethoxyethane, DMF or acetone at a temperature ranging from 70-120° C. to obtain compound of formula 5 (Reaction 1c).

Step 4
Preparation of Compound of Formula 6:

Compound of formula 5 can be refluxed with N-bromosuccinimide and a catalytic amount of AIBN or benzoyl peroxide in a suitable solvent such as $CCl_4$ using irradiation (200 watt bulb) at a temperature ranging from 80-100° C. to obtain compound of formula 6 (Reaction 1d).

Step 5
Preparation of Compound of Formula 7:

Compound of formula 6 can be treated with compound of formula 6P:

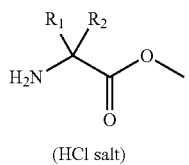

6P (HCl salt)

wherein $R_1$ and $R_2$ are as defined in formula 1;
in presence of a suitable base such as triethylamine in a suitable solvent such as benzene or toluene at a temperature ranging from 70-120° C. to obtain compound of formula 7 (Reaction 1e).

Alternatively, potassium carbonate may be used as a base in a suitable solvent such as DMF or THF at a temperature ranging from 50-80° C.

Step 6
Preparation of Compound of Formula 8:

Compound of formula 7 can be reduced using a suitable reducing agent such as Fe and ammonium chloride in a suitable solvent such as aqueous EtOH or $EtOH:THF:H_2O$ at a temperature ranging from 70-100° C. to obtain compound of formula 8 (Reaction 1f).

Alternatively, other reducing agents such as Fe and HCl in a solvent such as H₂O or ethanol or combination thereof; SnCl₂ in a solvent such as ethyl acetate; hydrogen over Raney Ni, Pd/C or Pt/C catalyst in a solvent such as methanol (pressure ranging from 50-80 psi and temperature ranging from 20-65° C.); or cobalt chloride and zinc in a solvent such as DMF or water (temperature ranging from 20-100° C.) may be used.

Step 7
Preparation of Compound of Formula 9:
Compound of formula 8 can be treated with compound of formula 8P:

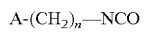

A-(CH₂)ₙ—NCO          8P wherein A and n are as defined in formula 1;
in a suitable solvent such as dichloromethane or THF at a temperature ranging from 20-35° C. to obtain compound of formula 9 (Reaction 1g).

Step 8
Preparation of Compound of Formula 10:
Compound of formula 9 can be hydrolysed using a suitable reagent such as 1N LiOH or 1N NaOH in a suitable solvent such as MeOH or THF at a temperature ranging from 20-35° C. to obtain compound of formula 10 (Reaction 1h).

Step 9
The carboxylic acid (compound of formula 10) may be optionally converted to its corresponding ester prodrugs by any suitable method well known in the art.

Scheme 1B: Preparation of Compound of Formula 1; Wherein Y₁=CH₂, Y₂=C(O); X₁, X₂, X₄ and X₅ are Selected from CH or CR, X₃=C; L=NHC(S)NH; m=1, A, n, R, R₁, R₂ and R₉ are as Defined in Formula 1;

Scheme 1B

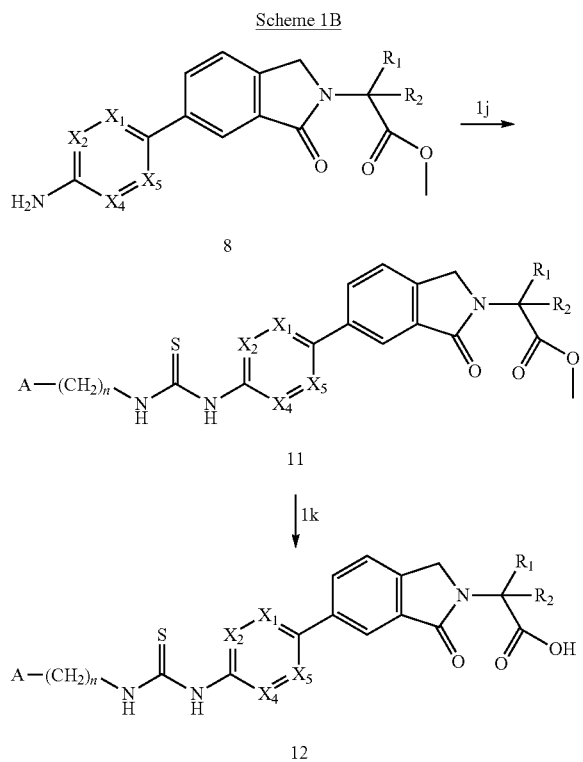

Step 1
Preparation of Compound of Formula 11:
Compound of formula 8 (obtained in Step 6 of Scheme 1A) can be treated with compound of formula 8Q:

A-(CH₂)ₙ—NCS          8Q wherein A and n are as defined in formula 1;
in presence of a suitable solvent such as THF or dichloromethane at temperature ranging from 20-35° C. to obtain compound of formula 11 (Reaction 1j).

Step 2
Preparation of Compound of Formula 12:
Compound of formula 11 can be hydrolysed using suitable reagent such as 1N LiOH or 1N NaOH in a suitable solvent such as MeOH or THF at temperature ranging from 20-35° C. to obtain compound of formula 12 (Reaction 1k).

Step 3
The carboxylic acid (compound of formula 12) may be optionally converted to its corresponding ester prodrugs by any suitable method well known in the art.

Scheme 1C: Preparation of Compound of Formula 1; Wherein Y₁=CH₂, Y₂=C(O); X₁, X₂, X₄ and X₅ are Selected from CH or CR, X₃=C; L=*SO₂NH; m=1; A, n, R, R₁, R₂ and R₉ are as Defined in Formula 1;

Scheme 1C

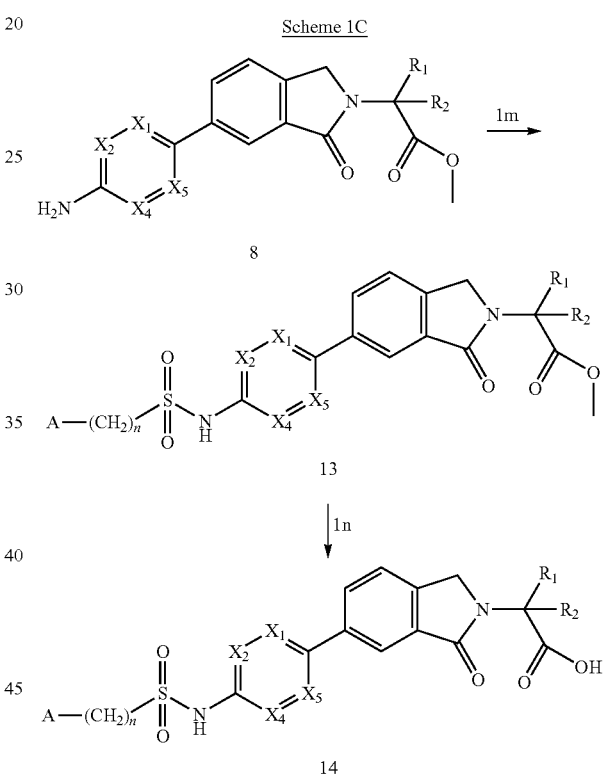

Step 1
Preparation of Compound of Formula 13:
Compound of formula 8 (obtained in Step 6 of Scheme 1A) can be treated with compound of formula 8R:

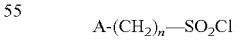

A-(CH₂)ₙ—SO₂Cl          8R wherein A and n are as defined in formula 1;
in presence of a suitable base such as pyridine or triethylamine in a suitable solvent such as dichloromethane at temperature ranging from 20-35° C. to obtain compound of formula 13 (Reaction 1m).

Step 2
Preparation of Compound of Formula 14:
Compound of formula 13 can be hydrolysed using suitable reagent such as 1N LiOH or 1N NaOH in a suitable solvent such as MeOH or THF at temperature ranging from 20-35° C. to obtain compound of formula 14 (Reaction 1n).

Step 3

The carboxylic acid (compound of formula 14) may be optionally converted to its corresponding ester prodrugs by any suitable method well known in the art.

Scheme 1D: Preparation of Compound of Formula 1; Wherein $Y_1$=$CH_2$, $Y_2$=C(O); $X_1$, $X_2$, $X_4$ and $X_5$ are Selected from CH or CR, $X_3$=C; L=*CONH; m=1; A, n, R, $R_1$, $R_2$ and $R_9$ are as Defined in Formula 1;

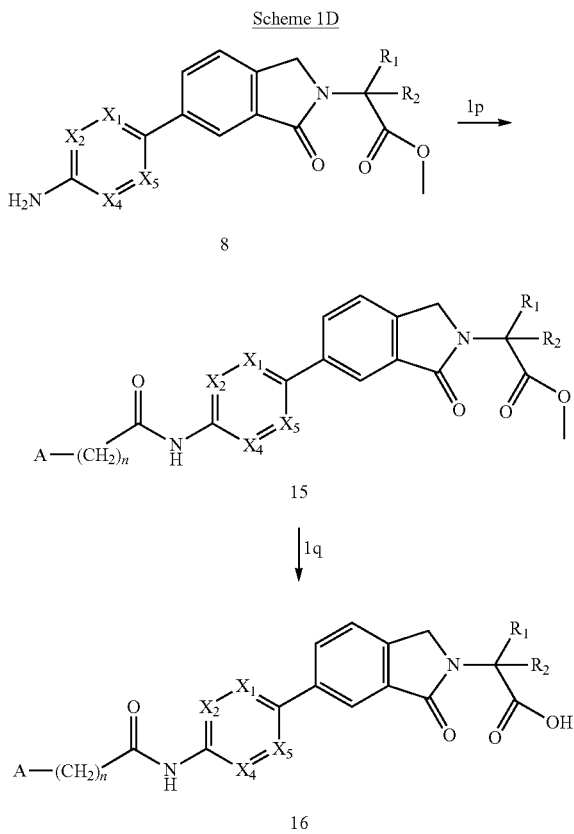

Step 1
Preparation of Compound of Formula 15:
Compound of formula 8 (obtained in Step 6 of Scheme 1A) can be treated with compound of formula 8S:

A-(CH$_2$)$_n$—COCl         8S wherein A and n are as defined in formula 1;

in presence of a suitable base such as pyridine in a suitable solvent such as dichloromethane or THF at temperature ranging from 20-35° C. to obtain compound of formula 15 (Reaction 1p).

Alternatively, compound of formula 8 (obtained in Step 6 of Scheme 1A) can be treated with the acid A-(CH$_2$)$_n$—COOH, wherein A and n are as defined in formula 1; in presence of a reagent such as isobutylchloroformate and a base such as N-methylmorpholine in a suitable solvent such as THF at a temperature range of 0° C. to room temperature (20-35° C.) for about 2-4 h to obtain compound of formula 15.

Alternatively, compound of formula 8 (obtained in Step 6 of Scheme 1A) may be heated with the ester A-(CH$_2$)$_n$COO—(C$_1$-C$_6$)-alkyl, wherein A represents a 5-membered heteroaryl ring containing one or more heteroatoms selected from 1-3 N, O and S, and substituted with a phenyl group, wherein both phenyl and heteroaryl rings may be substituted with one or more groups selected from halogen, hydroxy, (C$_1$-C$_{12}$)-alkoxy, cyano, (C$_1$-C$_{12}$)-alkyl, CF$_3$ and OCF$_3$; n is as defined in formula 1; in a solution of 2M AlMe$_3$ in toluene at 60-80° C. in a sealed tube for about 2-4 h to obtain compound of example 15.

In another alternate scheme, compound of formula 8 (obtained in Step 6 of Scheme 1A) may be heated with ester A-(CH$_2$)$_n$COO—(C$_1$-C$_6$)-alkyl, wherein A represents a phenyl group substituted with a 5-membered heteroaryl ring optionally containing heteroatoms selected from 1-3 N, O and S, and substituted with a phenyl group; wherein both phenyl and heteroaryl rings may be substituted with one or more groups selected from halogen, hydroxy, (C$_1$-C$_{12}$)-alkoxy, cyano, (C$_1$-C$_{12}$)-alkyl, CF$_3$ and OCF$_3$; n is as defined in formula 1; in presence of carbonyl chloride in a solvent mixture of dichloromethane and DMF at 20-35° C. for about 2-4 h to obtain compound of example 15, Step 2
Preparation of Compound of Formula 16:
Compound of formula 15 can be hydrolysed using suitable reagent such as 1N LiOH or 1N NaOH in a suitable solvent such as MeOH or THF at temperature ranging from 20-35° C. to obtain compound of formula 16 (Reaction 1q).

Step 3
The carboxylic acid (compound of formula 16) may be optionally converted to its corresponding ester prodrugs by any suitable method well known in the art.

Scheme 1E: Preparation of Compound of Formula 1; Wherein $Y_1$=$CH_2$, $Y_2$=C(O); $X_1$, $X_2$, $X_4$ and $X_5$ are Selected from CH or CR, $X_3$=C; L=*NHSO$_2$; m=1; A, n, R, $R_1$, $R_2$ and $R_9$ are as Defined in Formula 1;

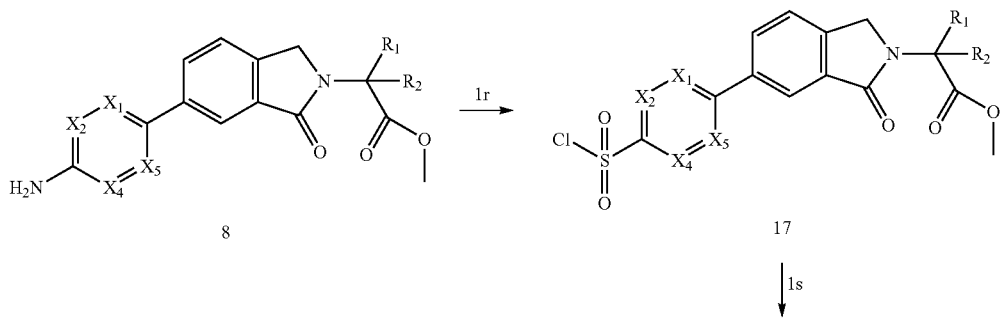

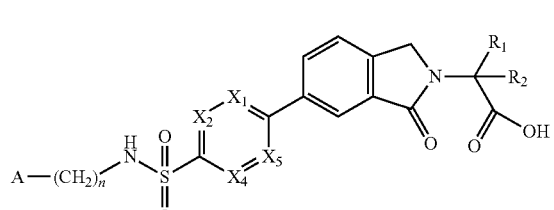

19

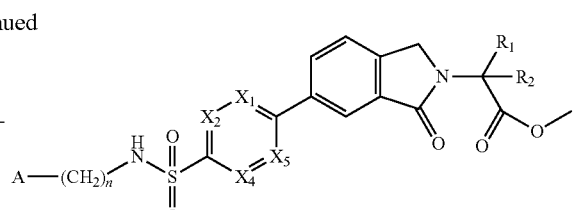

18

Step 1
Preparation of Compound of Formula 17:

Compound of formula 8 (obtained in Step 6 of Scheme 1A) can be treated with $NaNO_2$ and concentrated HCl to form a diazonium salt, which is treated with acetic acid saturated with $SO_2$ gas, followed by treatment with $CuCl_2$ at a temperature ranging from 0-35° C. to obtain compound of formula 17 (Reaction 1r).

Step 2
Preparation of Compound of Formula 18:

Compound of formula 17 can be treated with compound of formula 8T:

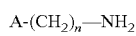      8T wherein A and n are as defined in formula 1;

in a suitable solvent such as dichloromethane and a base such as pyridine at temperature ranging from 20-35° C. to obtain compound of formula 18 (Reaction 1s).

Step 3
Preparation of Compound of Formula 19:

Compound of formula 18 can be hydrolysed using suitable reagent such as 1N LiOH or 1N NaOH in a suitable solvent such as MeOH or THF at temperature ranging from 20-35° C. to obtain compound of formula 19 (Reaction 1t).

Step 4
The carboxylic acid (compound of formula 19) may be optionally converted to its corresponding ester prodrugs by any suitable method well known in the art.

Scheme 2A: Preparation of Compound of Formula 1; Wherein $Y_1$=C(O), $Y_2$=$CH_2$; $X_1$, $X_2$, $X_4$ and $X_5$ are Selected from CH or CR, $X_3$=C; L=NHC(O)NH; m=1; A, n, R, $R_1$, $R_2$ and $R_9$ are as Defined in Formula 1;

<u>Scheme 2A</u>

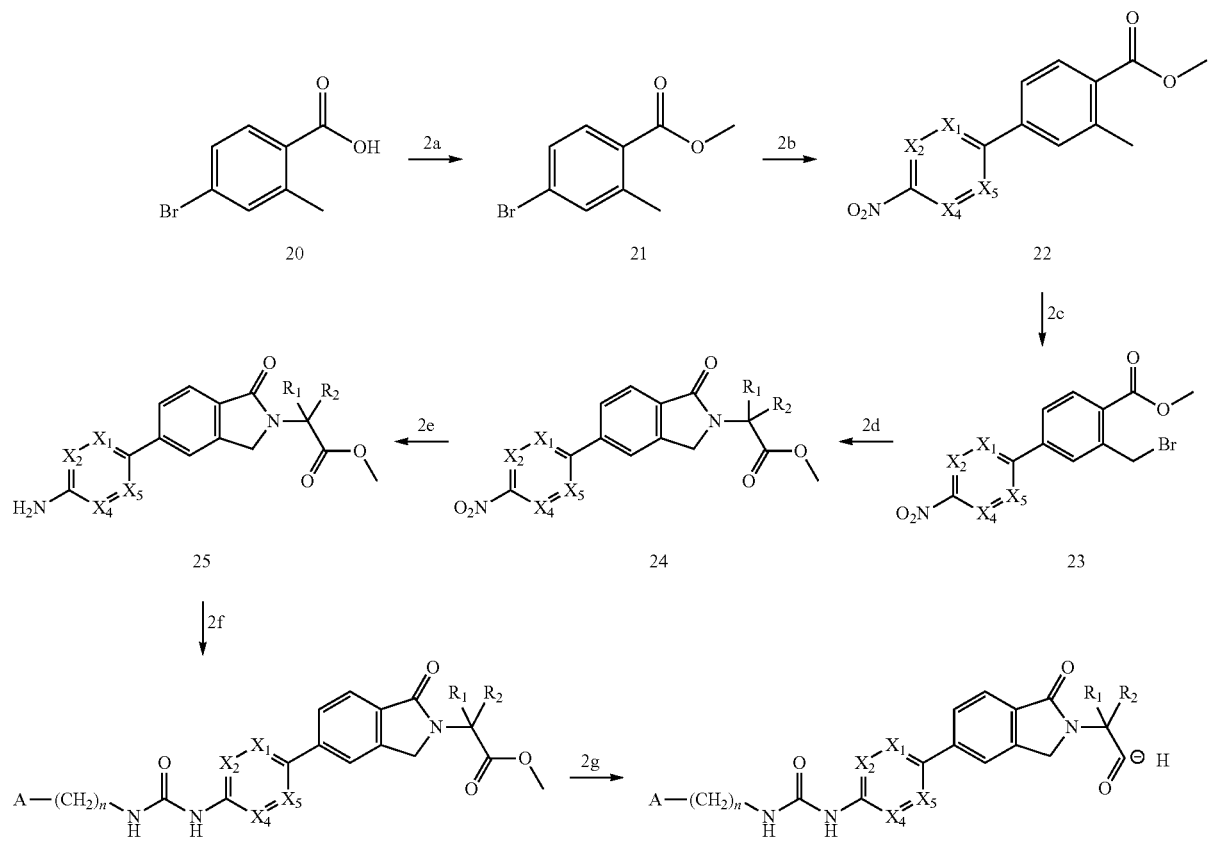

Step 1
Preparation of Compound of Formula 21:

Commercially available compound of formula 20 can be converted to its corresponding methyl ester by reaction with methanol and $SOCl_2$ at temperature ranging from 0-30° C. or by heating with methanol and inorganic acid such as sulfuric acid or hydrochloric acid at a temperature ranging from 50-100° C. to yield compound of formula 21 (Reaction 2a).

Step 2
Preparation of Compound of Formula 22:

The preparation involves two steps.

i) Preparation of Compound of Formula 21B Wherein $X_1$, $X_2$, $X_4$ and $X_5$ are Selected from CH or CR; R is Defined in Formula 1:

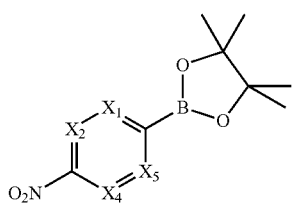

21B

Compound of formula 21A:

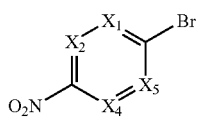

21A wherein $X_1$, $X_2$, $X_4$ and $X_5$ are selected from CH or CR, R is as defined in formula 1; can be treated with bis(pinacolo) diboron with a suitable catalyst such as palladium acetate and a suitable base such as potassium acetate, sodium carbonate or cesium carbonate in a solvent such as toluene, dioxane, dimethoxyethane, DMF or acetone at a temperature ranging from 70-120° C. to obtain compound of formula 21B.

ii) Preparation of Compound of Formula 22:

Compound of formula 21 can be treated with compound of formula 21B in presence of a catalyst such as $Pd(dppf)Cl_2$: $CH_2Cl_2$ and a base such as potassium carbonate, cesium carbonate or 2M $Na_2CO_3$ (in water) in a suitable solvent such as DMF, dioxane, dimethoxyethane or acetone at a temperature ranging from 70-120° C. under an atmosphere of argon, to obtain compound of formula 22 (Reaction 2b).

Alternatively, compound of formula 21 can be treated with compound of formula 21A in presence of bis(pinacolo)diboron with a suitable catalyst such as palladium acetate or tetrakis palladium and a suitable base such as potassium acetate, sodium carbonate or cesium carbonate in a solvent such as toluene, dioxane, dimethoxyethane, DMF or acetone at a temperature ranging from 70-120° C. to obtain compound of formula 22.

Step 3
Preparation of Compound of Formula 23:

Compound of formula 22 can be refluxed with N-bromosuccinimide and a catalytic amount of AIBN or benzoyl peroxide in a suitable solvent such as $CCl_4$ using irradiation (200 watt bulb) at a temperature ranging from 80-100° C. to obtain compound of formula 23 (Reaction 2c).

Step 4
Preparation of Compound of Formula 24:

Compound of formula 23 can be treated with compound of formula 6P:

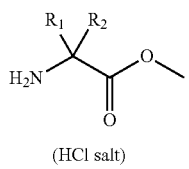

6P (HCl salt)

wherein $R_1$ and $R_2$ are as defined in formula 1;

in presence of a suitable base such as triethylamine in a suitable solvent such as benzene or toluene at a temperature ranging from 70-120° C. to obtain compound of formula 24 (Reaction 2d).

Alternatively, potassium carbonate may be used as a base in a suitable solvent such as DMF or THF at a temperature ranging from 50-80° C.

Step 5
Preparation of Compound of Formula 25:

Compound of formula 24 can be reduced using a suitable reducing agent such as Fe and ammonium chloride in a suitable solvent such as aqueous EtOH or $EtOH:THF:H_2O$ at a temperature ranging from 70-100° C. to obtain compound of formula 25 (Reaction 2e).

Alternatively, other reducing agents such as Fe and HCl in a solvent such as $H_2O$ or ethanol or combination thereof; $SnCl_2$ in a solvent such as ethyl acetate; hydrogen over Raney Ni, Pd/C or Pt/C catalyst in a solvent such as methanol (pressure ranging from 50-80 psi and temperature ranging from 20-65° C.); or cobalt chloride and zinc in a solvent such as DMF or water (temperature ranging from 20-100° C.) may be used.

Step 6
Preparation of Compound of Formula 26:

Compound of formula 25 can be treated with compound of formula 8P:

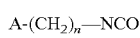

A-(CH_2)_n—NCO      8P wherein A and n are as defined in formula 1;

in a suitable solvent such as dichloromethane or THF at temperature ranging from 20-35° C. to obtain compound of formula 26 (Reaction 2f).

Step 7
Preparation of Compound of Formula 27:

Compound of formula 26 can be hydrolysed using suitable reagent such as 1N LiOH or 1N NaOH in a suitable solvent such as MeOH or THF at temperature ranging from 20-35° C. to obtain compound of formula 27 (Reaction 2g).

Step 8

The carboxylic acid (compound of formula 27) may be optionally converted to its corresponding ester prodrugs by any suitable method well known in the art.

Scheme 2B: Preparation of Compound of Formula 1; Wherein $Y_1$=C(O), $Y_2$=$CH_2$; $X_1$, $X_2$, $X_4$ and $X_5$ are Selected from CH or CR, $X_3$=C; L=NHC(S)NH; m=1; A, n, R, $R_1$, $R_2$ and $R_9$ are as Defined in Formula 1;

Scheme 2B

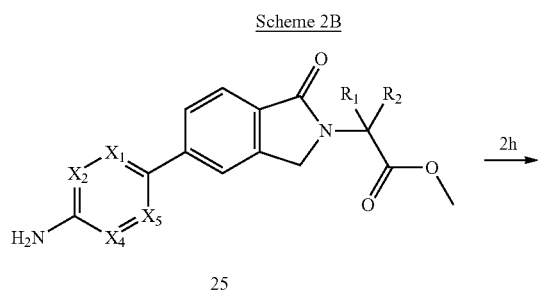

Scheme 2C

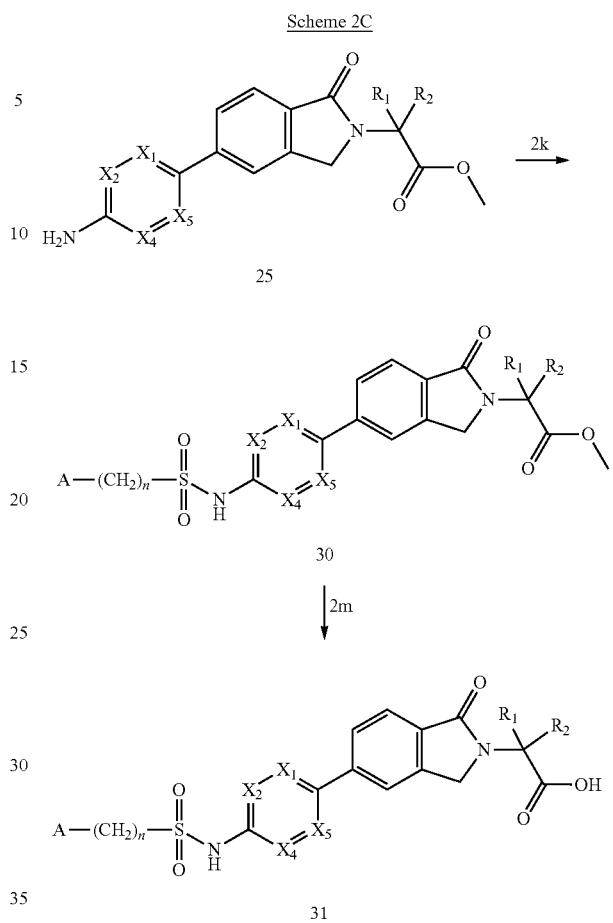

Step 1

Preparation of Compound of Formula 28:

Compound of formula 25 (obtained in Step 5 of Scheme 2A) can be treated with compound of formula 8Q:

A-(CH$_2$)$_n$—NCS     8Q wherein A and n are as defined in formula 1;

in presence of a suitable solvent such as THF or dichloromethane at temperature ranging from 20-35° C. to obtain compound of formula 28 (Reaction 2h).

Step 2

Preparation of Compound of Formula 29:

Compound of formula 28 can be hydrolysed using suitable reagent such as 1N LiOH or 1N NaOH in a suitable solvent such as MeOH or THF at temperature ranging from 20-35° C. to obtain compound of formula 29 (Reaction 2j).

Step 3

The carboxylic acid (compound of formula 29) may be optionally converted to its corresponding ester prodrugs by any suitable method well known in the art.

Scheme 2C: Preparation of Compound of Formula 1; Wherein Y$_1$=C(O), Y$_2$=CH$_2$; X$_1$, X$_2$, X$_4$ and X$_5$ are Selected from CH or CR, X$_3$=C; L=*SO$_2$NH; m=1; A, n, R, R$_1$, R$_2$ and R$_9$ are as Defined in Formula 1;

Step 1

Preparation of Compound of Formula 30:

Compound of formula 25 (obtained in Step 5 of Scheme 2A) can be treated with compound of formula 8R:

A-(CH$_2$)$_n$—SO$_2$Cl     8R wherein A and n are as defined in formula 1;

in presence of a suitable base such as pyridine or triethylamine in a suitable solvent such as dichloromethane at temperature ranging from 20-35° C. to obtain compound of formula 30 (Reaction 2k).

Step 2

Preparation of Compound of Formula 31:

Compound of formula 30 can be hydrolysed using suitable reagent such as 1N LiOH or 1N NaOH in a suitable solvent such as MeOH or THF at temperature ranging from 20-35° C. to obtain compound of formula 31 (Reaction 2m).

Step 3

The carboxylic acid (compound of formula 31) may be optionally converted to its corresponding ester prodrugs by any suitable method well known in the art.

Scheme 2D: Preparation of Compound of Formula 1; Wherein Y$_1$=C(O), Y$_2$=CH$_2$; X$_1$, X$_2$, X$_4$ and X$_5$ are Selected from CH or CR, X$_3$=C; L=*CONH; m=1; A, n, R, R$_1$, R$_2$ and R$_9$ are as Defined in Formula 1;

59

Scheme 2D

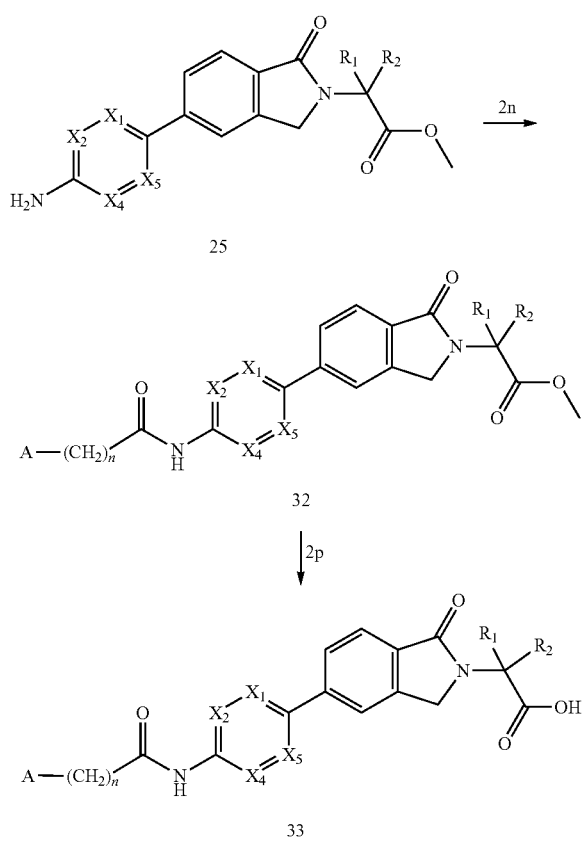

60

Step 1
Preparation of Compound of Formula 32:

Compound of formula 25 (obtained in Step 5 of Scheme 2A) can be treated with optionally substituted benzoyl chloride of formula 8S:

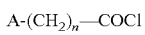

A-(CH$_2$)$_n$—COCl          8S wherein A and n are as defined in formula 1;

in presence of a suitable base such as pyridine in a suitable solvent such as dichloromethane or THF at temperature ranging from 20-35° C. to obtain compound of formula 32 (Reaction 2n).

Step 2
Preparation of Compound of Formula 33:

Compound of formula 32 can be hydrolysed using suitable reagent such as 1N LiOH or 1N NaOH in a suitable solvent such as MeOH or THF at temperature ranging from 20-35° C. to obtain compound of formula 33 (Reaction 2p).

Step 3

The carboxylic acid (compound of formula 33) may be optionally converted to its corresponding ester prodrugs by any suitable method well known in the art.

Scheme 2E: Preparation of Compound of Formula 1; Wherein Y$_1$=C(O), Y$_2$=CH$_2$; X$_1$, X$_2$, X$_4$ and X$_5$ are Selected from CH or CR, X$_3$=C; L=*NHSO$_2$; m=1; A, n, R, R$_1$, R$_2$ and R$_9$ are as Defined in Formula 1;

Scheme 2E

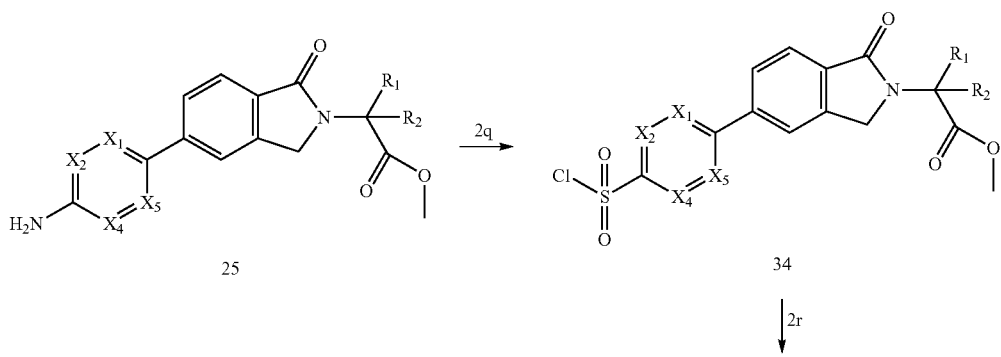

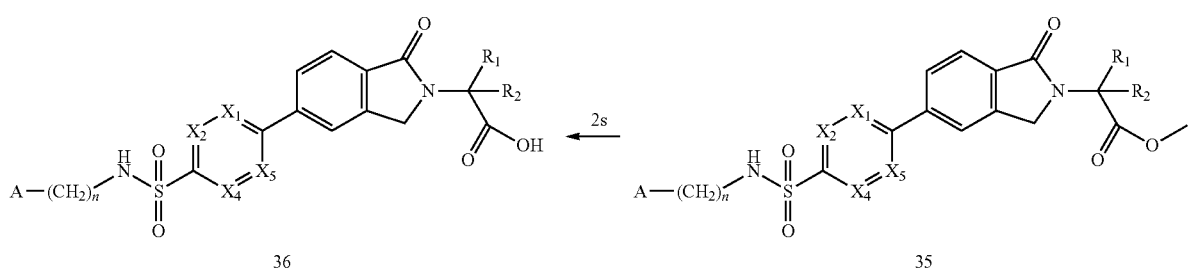

Step 1
Preparation of Compound of Formula 34:
Compound of formula 25 (obtained in Step 5 of Scheme 2A) can be treated with $NaNO_2$ and concentrated HCl to form a diazonium salt, which is treated with acetic acid saturated with $SO_2$ gas, followed by treatment with $CuCl_2$ at a temperature ranging from 0-35° C. to obtain compound of formula 34 (Reaction 2q).
Step 2
Preparation of Compound of Formula 35:
Compound of formula 34 can be treated with compound of formula 8T:

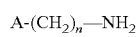

wherein A and n are as defined in formula 1;

in a suitable solvent such as dichloromethane and a base such as pyridine at temperature ranging from 20-35° C. to obtain compound of formula 35 (Reaction 2r).
Step 3
Preparation of Compound of Formula 36:
Compound of formula 35 can be hydrolysed using suitable reagent such as 1N LiOH or 1N NaOH in a suitable solvent such as MeOH or THF at temperature ranging from 20-35° C. to obtain compound of formula 36 (Reaction 2s).
Step 4
The carboxylic acid (compound of formula 36) may be optionally converted to its corresponding ester prodrugs by any suitable method well known in the art.
Scheme 3A: Preparation of Compound of Formula 1; Wherein $Y_1=CH_2$, $Y_2=C(O)$; $X_1$, $X_2$, $X_4$ and $X_5$ are Selected from CH or CR, $X_3=C$; L=NHC(O)NH; m=1; A, n, R, $R_1$, $R_2$ and $R_9$ are as Defined in Formula 1;

Scheme 3A

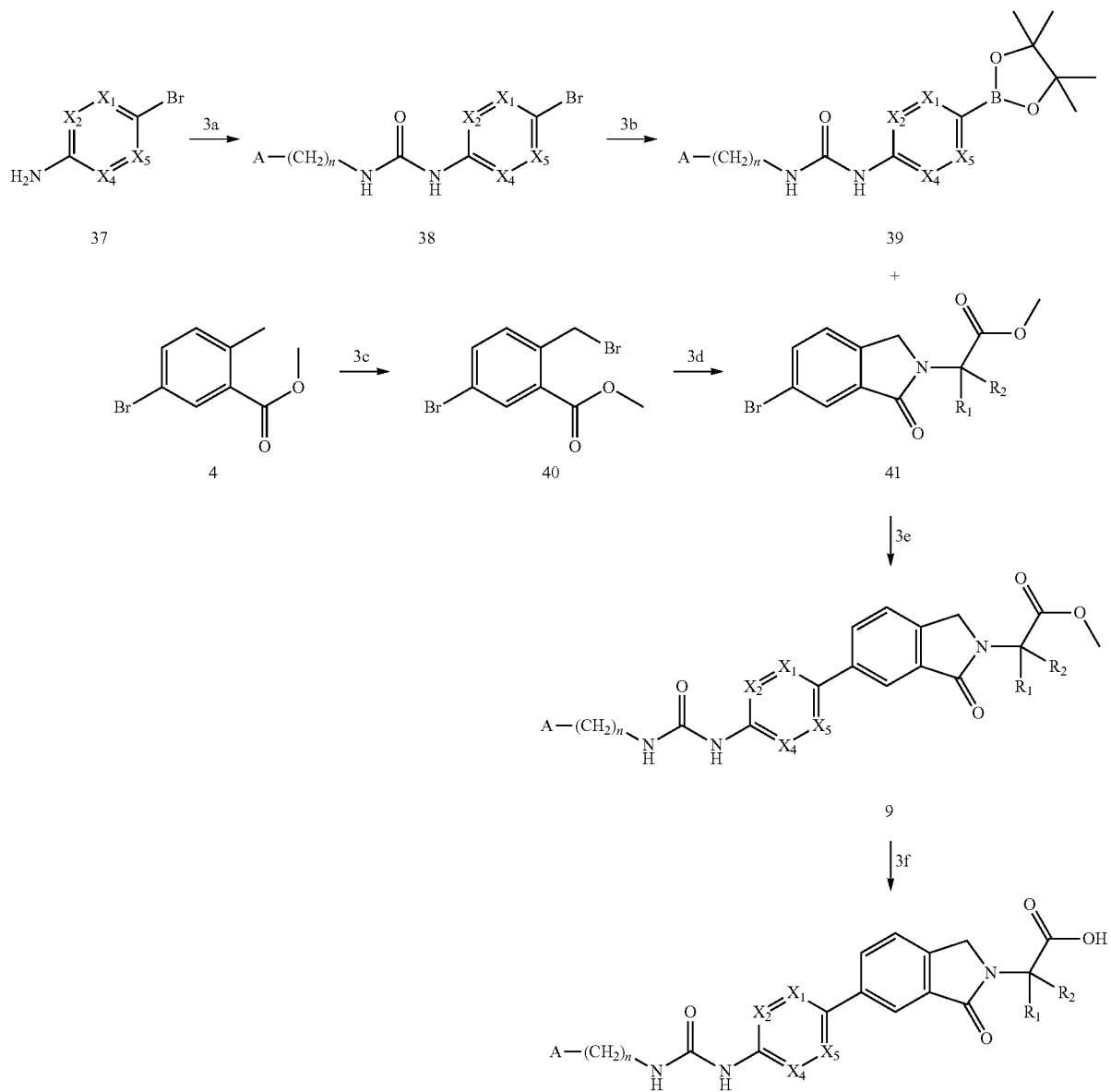

Step 1
Preparation of Compound of Formula 38:
Compound of formula 37 is reacted with compound of formula 8P:

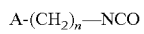  8P wherein A and n are as defined in formula 1;
in a suitable solvent such as dichloromethane or THF at temperature ranging from 20-35° C. to obtain compound of formula 38 (Reaction 3a).

Step 2
Preparation of Compound of Formula 39:
Compound of formula 38 can be treated with bis(pinacolato)diboron, Pd(dppf)Cl$_2$ and Pd(dppf)Cl$_2$:CH$_2$Cl$_2$ in a suitable solvent such as dioxane, dimethoxyethane, DMSO or DMF at temperature ranging from 50-100° C. to obtain compound of formula 39 (Reaction 3b).

Step 3
Preparation of Compound of Formula 40:
Compound of formula 4 can be refluxed with N-bromosuccinimide and a catalytic amount of AIBN or benzoyl peroxide in a suitable solvent such as CCl$_4$ using irradiation (200 watt bulb) at a temperature ranging from 80-100° C. to obtain compound of formula 40 (Reaction 3c).

Step 4
Preparation of Compound of Formula 41:
Compound of formula 40 can be treated with compound of formula 6P:

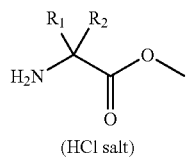  6P (HCl salt)

wherein R$_1$ and R$_2$ are as Defined in Formula 1;

in presence of a suitable base such as triethylamine in a suitable solvent such as benzene or toluene at a temperature ranging from 70-120° C. to obtain compound of formula 41 (Reaction 3d).

Alternatively, potassium carbonate may be used as a base in a suitable solvent such as DMF or THF at a temperature ranging from 50-80° C.

Step 5
Preparation of Compound of Formula 9:
Compound of formula 39 can be reacted with compound of formula 41 in presence of Pd(dppf)Cl$_2$:CH$_2$Cl$_2$ and a suitable base such as potassium carbonate, cesium carbonate or 2M Na$_2$CO$_3$ (in water) in a suitable solvent such as DMF, dioxane, dimethoxyethane or acetone under an atmosphere of argon at temperature ranging from 50-100° C. to obtain compound of formula 9 (Reaction 3e).

Step 6
Preparation of Compound of Formula 10:
Compound of formula 9 can be can be hydrolysed using suitable reagent such as 1N NaOH or 1N LiOH in a suitable solvent such as MeOH or THF at temperature ranging from 20-35° C. to obtain compound of formula 10 (Reaction 3f).

Step 7
The carboxylic acid (compound of formula 10) may be optionally converted to its corresponding ester prodrugs by any suitable method well known in the art.

Scheme 3B: Preparation of Compound of Formula 1; Wherein Y$_1$=CH$_2$, Y$_2$=C(O); X$_1$, X$_2$, X$_4$ and X$_5$ are Selected from CH or CR, X$_3$=C; L=NHC(S)NH; m=1; A, n, R, R$_1$, R$_2$ and R$_9$ are as Defined in Formula 1;

Scheme 3B

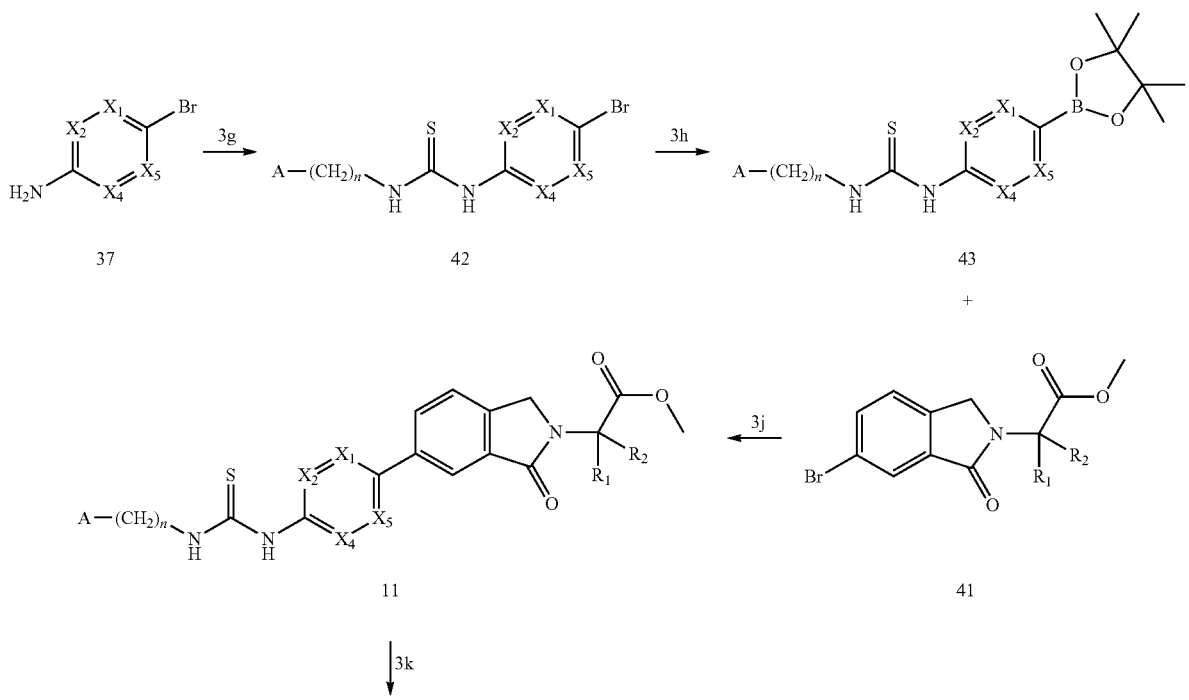

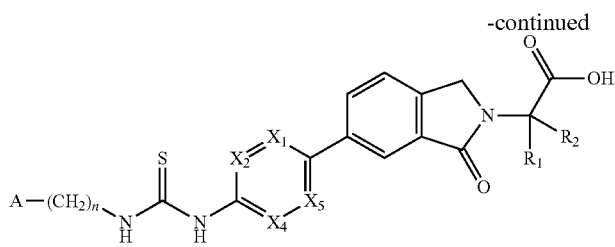

12

Step 1
Preparation of Compound of Formula 42:
Compound of formula 37 is reacted with compound of formula 8Q:

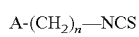 8Q wherein A and n are as defined in formula 1;
in a suitable solvent such as dichloromethane or THF at temperature ranging from 20-35° C. to obtain compound of formula 42 (Reaction 3g).

Step 2
Preparation of Compound of Formula 43:
Compound of formula 42 can be treated with bis(pinacolato)diboron, Pd(dppf)Cl$_2$ and Pd(dppf)Cl$_2$:CH$_2$Cl$_2$ in a suitable solvent such as dioxane, dimethoxyethane, DMSO or DMF at temperature ranging from 50-100° C. to obtain compound of formula 43 (Reaction 3h).

Step 3
Preparation of Compound of Formula 11:
Compound of formula 43 can be reacted with compound of formula 41 (obtained in Step 4 of Scheme 3A) in presence of Pd(dppf)Cl$_2$:CH$_2$Cl$_2$ and a suitable base such as potassium carbonate, cesium carbonate or 2M Na$_2$CO$_3$ (in water) in a suitable solvent such as DMF, dioxane, dimethoxyethane or acetone under an atmosphere of argon at temperature ranging from 50-100° C. to obtain compound of formula 11 (Reaction 3j).

Step 4
Preparation of Compound of Formula 12:
Compound of formula 11 can be can be hydrolysed using suitable reagent such as 1N NaOH or 1N LiOH in a suitable solvent such as MeOH or THF at temperature ranging from 20-35° C. to obtain compound of formula 12 (Reaction 3k).

Step 5
The carboxylic acid (compound of formula 12) may be optionally converted to its corresponding ester prodrugs by any suitable method well known in the art.

Scheme 3C: Preparation of Compound of Formula 1; Wherein Y$_1$=CH$_2$, Y$_2$=C(O); X$_1$, X$_2$, X$_4$ and X$_5$ are Selected from CH or CR, X$_3$=C; L=*SO$_2$NH; m=1; A, n, R, R$_1$, R$_2$ and R$_9$ are as Defined in Formula 1;

Scheme 3C

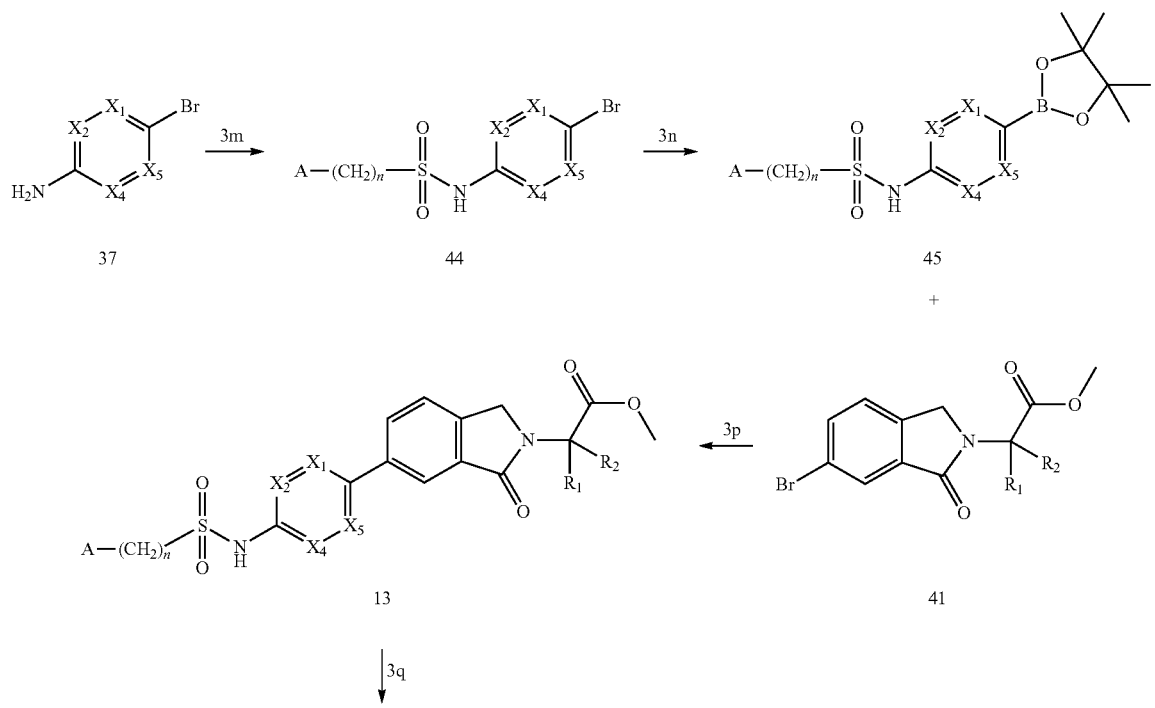

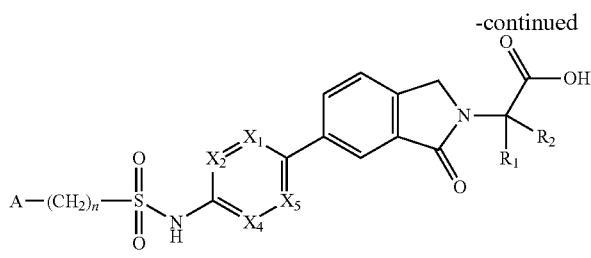

14

Step 1
Preparation of Compound of Formula 44:

Compound of formula 37 is reacted with compound of formula 8R:

wherein A and n are as defined in formula 1;
in presence of a suitable base such as pyridine or triethylamine in a suitable solvent such as dichloromethane at temperature ranging from 20-35° C. to obtain compound of formula 44 (Reaction 3m).

Step 2
Preparation of Compound of Formula 45:

Compound of formula 44 can be treated with bis(pinacolato)diboron, Pd(dppf)Cl$_2$ and Pd(dppf)Cl$_2$:CH$_2$Cl$_2$ in a suitable solvent such as dioxane, dimethoxyethane, DMSO or DMF at temperature ranging from 50-100° C. to obtain compound of formula 45 (Reaction 3n).

Step 3
Preparation of Compound of Formula 13:

Compound of formula 45 can be reacted with compound of formula 41 (obtained in Step 4 of Scheme 3A) in presence of Pd(dppf)Cl$_2$:CH$_2$Cl$_2$ and a suitable base such as potassium carbonate, cesium carbonate or 2M Na$_2$CO$_3$ (in water) in a suitable solvent such as DMF, dioxane, dimethoxyethane or acetone under an atmosphere of argon at temperature ranging from 50-100° C. to obtain compound of formula 13 (Reaction 3p).

Step 4
Preparation of Compound of Formula 14:

Compound of formula 13 can be can be hydrolysed using suitable reagent such as 1N NaOH or 1N LiOH in a suitable solvent such as MeOH or THF at temperature ranging from 20-35° C. to obtain compound of formula 14 (Reaction 3q).

Step 5

The carboxylic acid (compound of formula 14) may be optionally converted to its corresponding ester prodrugs by any suitable method well known in the art.

Scheme 3D: Preparation of Compound of Formula 1; Wherein Y$_1$=CH$_2$, Y$_2$=C(O); X$_1$, X$_2$, X$_4$ and X$_5$ are Selected from CH or CR, X$_3$=C; L=*CONH, m=1; A, n, R, R$_1$, R$_2$ and R$_9$ are as Defined in Formula 1;

Scheme 3D

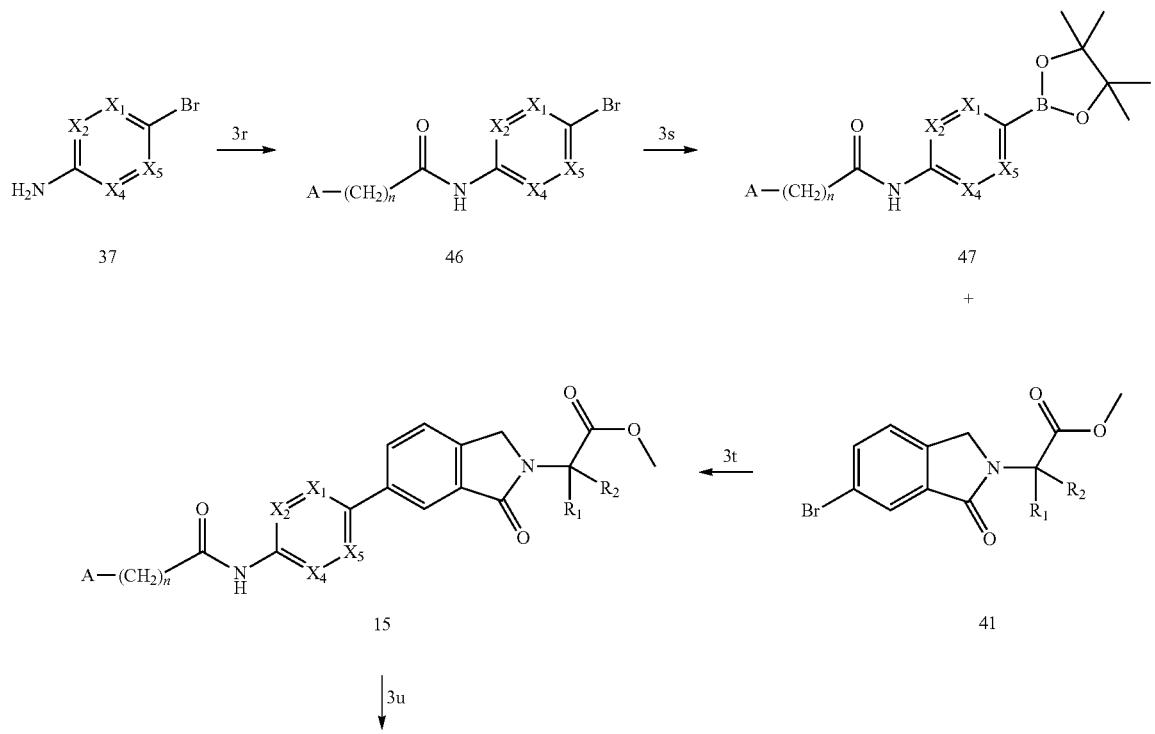

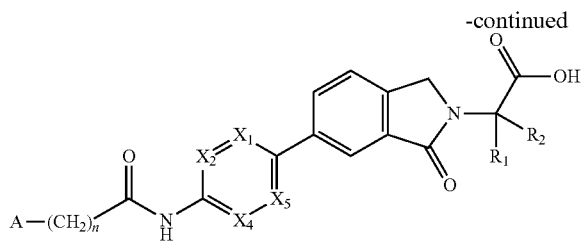

16

Step 1
Preparation of Compound of Formula 46:
Compound of formula 37 is reacted with compound of formula 8S:

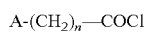

A-(CH$_2$)$_n$—COCl       8S wherein A and n are as defined in formula 1;
in presence of a suitable base such as pyridine in a suitable solvent such as dichloromethane or THF at temperature ranging from 20-35° C. to obtain compound of formula 46 (Reaction 3r).

Step 2
Preparation of Compound of Formula 47:
Compound of formula 46 can be treated with bis(pinacolato)diboron, Pd(dppf)Cl$_2$ and Pd(dppf)Cl$_2$:CH$_2$Cl$_2$ in a suitable solvent such as dioxane, dimethoxyethane, DMSO or DMF at temperature ranging from 50-100° C. to obtain compound of formula 47 (Reaction 3s).

Step 3
Preparation of Compound of Formula 15:
Compound of formula 47 can be reacted with compound of formula 41 (obtained in Step 4 of Scheme 3A) in presence of Pd(dppf)Cl$_2$:CH$_2$Cl$_2$ and a suitable base such as potassium carbonate, cesium carbonate or 2M Na$_2$CO$_3$ (in water) in a suitable solvent such as DMF, dioxane, dimethoxyethane or acetone under an atmosphere of argon at temperature ranging from 50-100° C. to obtain compound of formula 15 (Reaction 3t).

Step 4
Preparation of Compound of Formula 16:
Compound of formula 15 can be can be hydrolysed using suitable reagent such as 1N NaOH or 1N LiOH in a suitable solvent such as MeOH or THF at temperature ranging from 20-35° C. to obtain compound of formula 16 (Reaction 3u).

Step 5
The carboxylic acid (compound of formula 16) may be optionally converted to its corresponding ester prodrugs by any suitable method well known in the art.

Scheme 3E: Preparation of Compound of Formula 1;
Wherein Y$_1$=CH$_2$, Y$_2$=C(O); X$_1$, X$_2$, X$_4$ and X$_5$ are Selected from CH or CR, X$_3$=C; L=*NHSO$_2$; m=1; A, n, R, R$_1$, R$_2$ and R$_9$ are as Defined in Formula 1;

Scheme 3E

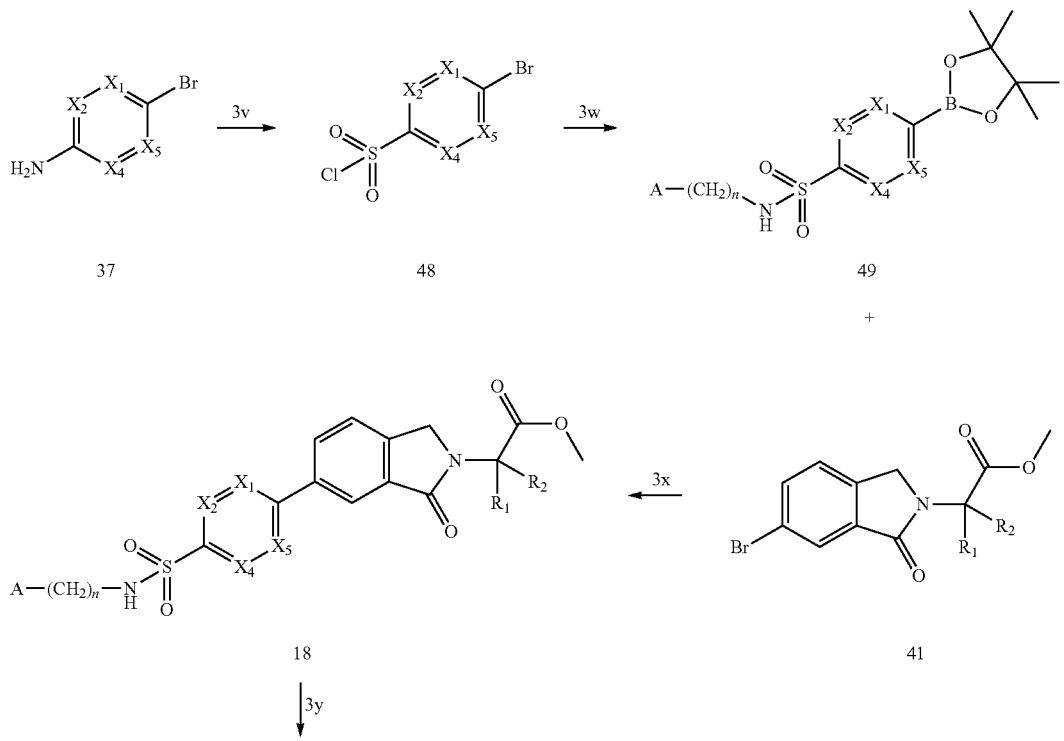

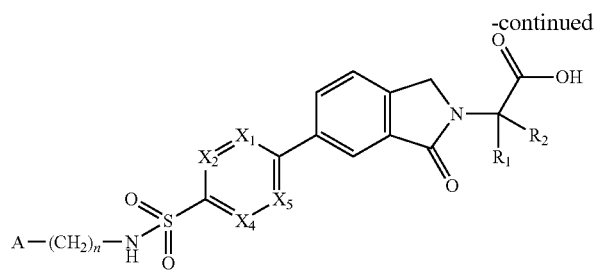

19

Step 1
Preparation of Compound of Formula 48:
Compound of formula 37 can be treated with NaNO$_2$ and concentrated HCl to form a diazonium salt, which is treated with acetic acid saturated with SO$_2$ gas, followed by treatment with CuCl$_2$ at a temperature ranging from 0-35° C. to obtain compound of formula 48 (Reaction 3v).

Step 2
Preparation of Compound of Formula 49:
The preparation involves two steps.
i) Preparation of Compound of Formula 48A where in X$_1$, X$_2$, X$_4$ and X$_5$ are Selected from CH or CR, X$_3$=C; A, n and R are as Defined in Formula 1:

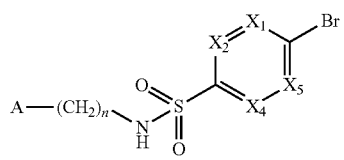

48A

Compound of formula 48 can be treated with compound of formula 8T:

A-(CH$_2$)$_n$—NH$_2$      8T wherein A and n are as defined in formula 1;
in a suitable solvent such as dichloromethane and a base such as pyridine at temperature ranging from 20-35° C. to obtain compound of formula 48A.

ii) Preparation of Compound of Formula 49:
Compound of formula 48A can be treated with bis(pinacolato)diboron, Pd(dppf)Cl$_2$ and Pd(dppf)Cl$_2$:CH$_2$Cl$_2$ in a suitable solvent such as dioxane, dimethoxyethane, DMSO or DMF at temperature ranging from 50-100° C. to obtain compound of formula 49 (Reaction 3w).

Step 3
Preparation of Compound of Formula 18:
Compound of formula 49 can be reacted with compound of formula 41 (obtained in Step 4 of Scheme 3A) in presence of Pd(dppf)Cl$_2$:CH$_2$Cl$_2$ and a suitable base such as potassium carbonate, cesium carbonate or 2M Na$_2$CO$_3$ (in water) in a suitable solvent such as DMF, dioxane, dimethoxyethane or acetone under an atmosphere of argon at temperature ranging from 50-100° C. to obtain compound of formula 18 (Reaction 3x).

Step 4
Preparation of Compound of Formula 19:
Compound of formula 18 can be can be hydrolysed using suitable reagent such as 1N NaOH or 1N LiOH in a suitable solvent such as MeOH or THF at temperature ranging from 20-35° C. to obtain compound of formula 19 (Reaction 3y).

Step 5
The carboxylic acid (compound of formula 19) may be optionally converted to its corresponding ester prodrugs by any suitable method well known in the art.

Scheme 4A: Preparation of Compound of Formula 1;
Wherein Y$_1$=C(O), Y$_2$=CH$_2$; X$_1$, X$_2$, X$_4$ and X$_5$ are Selected from CH or CR, X$_3$=C; L=NHC(O)NH; m=1; A, n, R, R$_1$, R$_2$ and R$_9$ are as Defined in Formula 1;

Scheme 4A

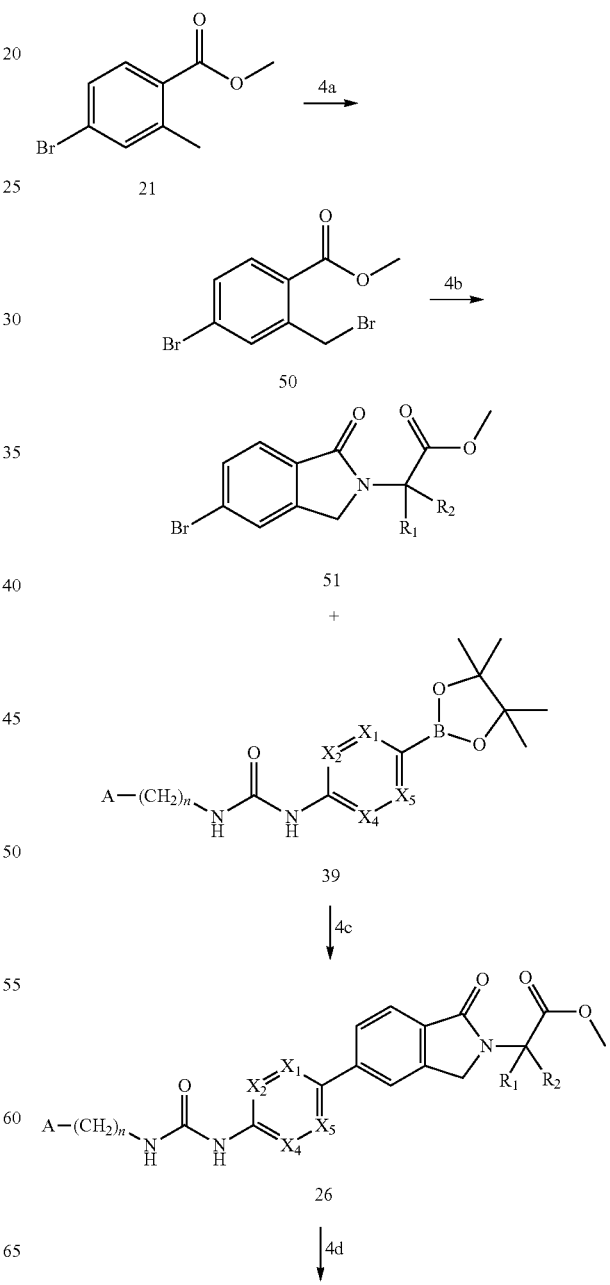

-continued

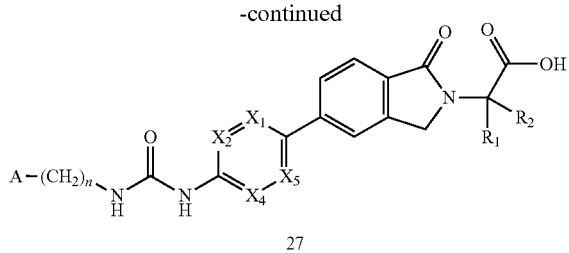

27

Step 1
Preparation of Compound of Formula 50:

Compound of formula 21 can be refluxed with N-bromosuccinimide and a catalytic amount of AIBN or benzoyl peroxide in a suitable solvent such as $CCl_4$ using irradiation (200 watt bulb) at a temperature ranging from 80-100° C. to obtain compound of formula 50 (Reaction 4a).

Step 2
Preparation of Compound of Formula 51:

Compound of formula 50 can be treated with compound of formula 6P:

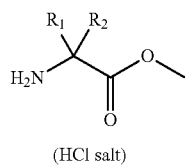

(HCl salt)

wherein $R_1$ and $R_2$ are as Defined in Formula 1;

in presence of a suitable base such as triethylamine in a suitable solvent such as benzene or toluene at a temperature ranging from 70-120° C. to obtain compound of formula 51 (Reaction 4b).

Alternatively, potassium carbonate may be used as a base in a suitable solvent such as DMF or THF at a temperature ranging from 50-80° C.

Step 3
Preparation of Compound of Formula 26:

Compound of formula 51 can be reacted with compound of formula 39 in presence of $Pd(dppf)Cl_2:CH_2Cl_2$ in a suitable base such as potassium carbonate, cesium carbonate or 2M $Na_2CO_3$ (in water) in a suitable solvent such as DMF, dioxane, dimethoxyethane or acetone under an atmosphere of argon at temperature ranging from 50-100° C. to obtain compound of formula 26 (Reaction 4c).

Step 4
Preparation of Compound of Formula 27:

Compound of formula 26 can be can be hydrolysed using suitable reagent such as 1N NaOH or 1N LiOH in a suitable solvent such as MeOH or THF at temperature ranging from 20-35° C. to obtain compound of formula 27 (Reaction 4d).

Step 5

The carboxylic acid (compound of formula 27) may be optionally converted to its corresponding ester prodrugs by any suitable method well known in the art.

Scheme 4B: Preparation of Compound of Formula 1; Wherein $Y_1$=C(O), $Y_2$=$CH_2$; $X_1$, $X_2$, $X_4$ and $X_5$ are Selected from CH or CR, $X_3$=C; L=NHC(S)NH; m=1; A, n, R, $R_1$, $R_2$ and $R_9$ are as Defined in Formula 1;

Scheme 4B

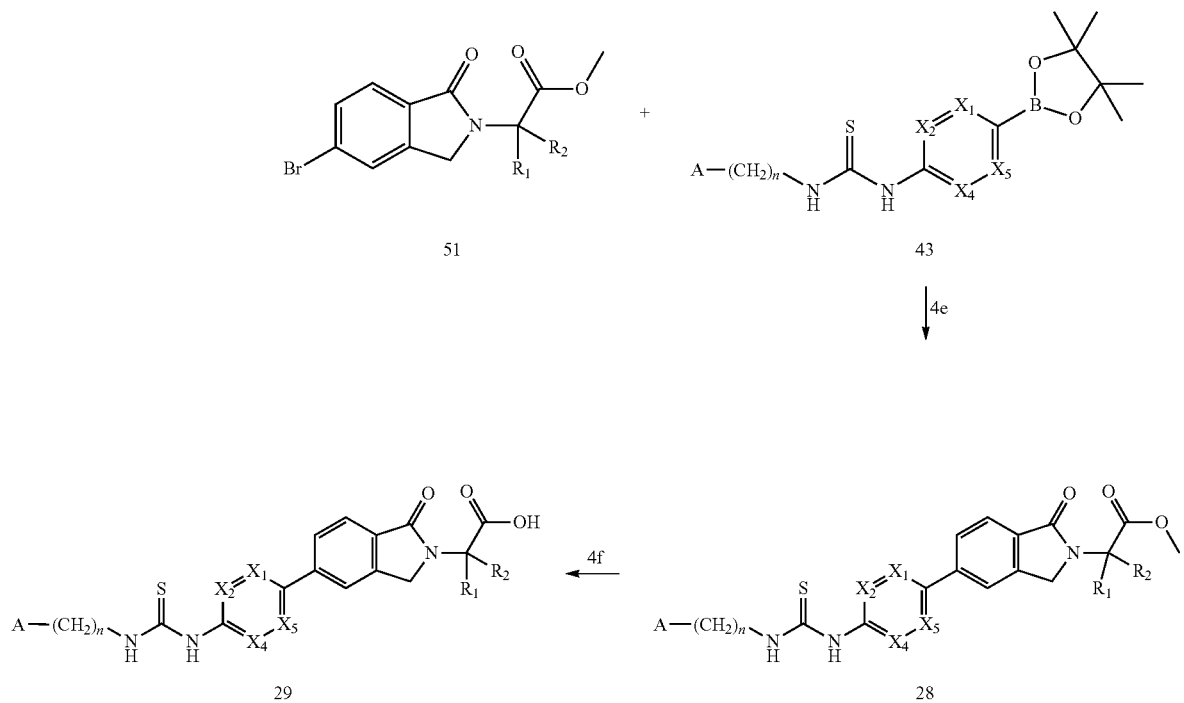

Step 1

Preparation of Compound of Formula 28:

Compound of formula 51 can be reacted with compound of formula 43 in presence of $Pd(dppf)Cl_2:CH_2Cl_2$ in a suitable base such as potassium carbonate, cesium carbonate or 2M $Na_2CO_3$ (in water) in a suitable solvent such as DMF, dioxane, dimethoxyethane or acetone under an atmosphere of argon at temperature ranging from 50-100° C. to obtain compound of formula 28 (Reaction 4e).

Step 2

Preparation of Compound of Formula 29:

Compound of formula 28 can be can be hydrolysed using suitable reagent such as 1N NaOH or 1N LiOH in a suitable solvent such as MeOH or THF at temperature ranging from 20-35° C. to obtain compound of formula 29 (Reaction 4f).

Step 3

The carboxylic acid (compound of formula 29) may be optionally converted to its corresponding ester prodrugs by any suitable method well known in the art.

Scheme 4C: Preparation of Compound of Formula 1; Wherein $Y_1$=C(O), $Y_2$=CH$_2$; $X_1$, $X_2$, $X_4$ and $X_5$ are Selected from CH or CR, $X_3$=C; L=*SO$_2$NH; m=1; A, n, $R_1$, $R_2$ and $R_9$ are as Defined in Formula 1;

Step 1

Preparation of Compound of Formula 30:

Compound of formula 51 can be reacted with compound of formula 45 in presence of $Pd(dppf)Cl_2:CH_2Cl_2$ in a suitable base such as potassium carbonate, cesium carbonate or 2M $Na_2CO_3$ (in water) in a suitable solvent such as DMF, dioxane, dimethoxyethane or acetone under an atmosphere of argon at temperature ranging from 50-100° C. to obtain compound of formula 30 (Reaction 4g).

Step 2

Preparation of Compound of Formula 31:

Compound of formula 30 can be can be hydrolysed using suitable reagent such as 1N NaOH or 1N LiOH in a suitable solvent such as MeOH or THF at temperature ranging from 20-35° C. to obtain compound of formula 31 (Reaction 4h).

Step 3

The carboxylic acid (compound of formula 31) may be optionally converted to its corresponding ester prodrugs by any suitable method well known in the art.

Scheme 4D: Preparation of Compound of Formula 1; Wherein $Y_1$=C(O), $Y_2$=CH$_2$; $X_1$, $X_2$, $X_4$ and $X_5$ are Selected from CH or CR, $X_3$=C; L=*CONH; m=1; A, n, R, $R_1$, $R_2$ and $R_9$ are as Defined in Formula 1;

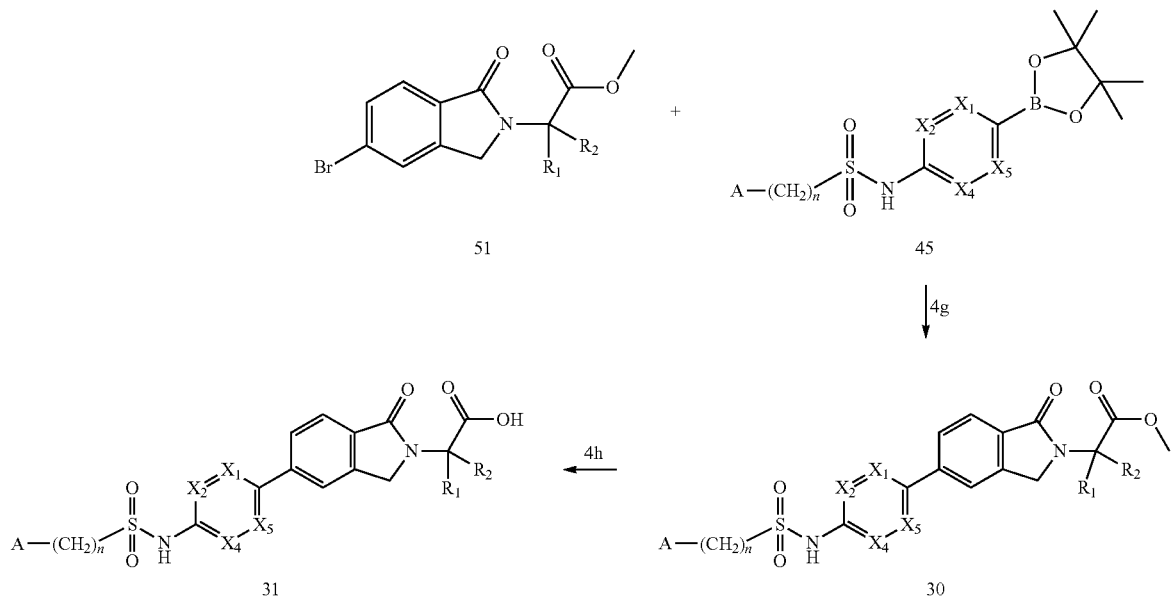

Scheme 4C

Scheme 4D

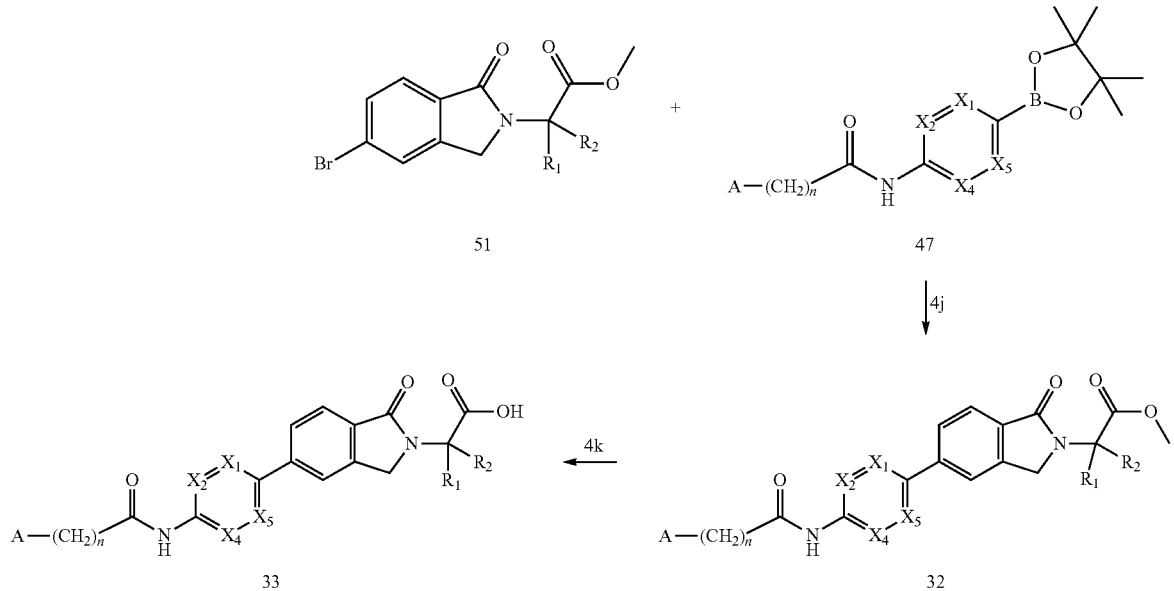

Step 1
Preparation of Compound of Formula 32:
Compound of formula 51 can be reacted with compound of formula 47 in presence of Pd(dppf)Cl$_2$:CH$_2$Cl$_2$ in a suitable base such as potassium carbonate, cesium carbonate or 2M Na$_2$CO$_3$ (in water) in a suitable solvent such as DMF, dioxane, dimethoxyethane or acetone under an atmosphere of argon at temperature ranging from 50-100° C. to obtain compound of formula 32 (Reaction 4j).

Step 2
Preparation of Compound of Formula 33:
Compound of formula 32 can be can be hydrolysed using suitable reagent such as 1N NaOH or 1N LiOH in a suitable solvent such as MeOH or THF at temperature ranging from 20-35° C. to obtain compound of formula 33 (Reaction 4k).

Step 3

The carboxylic acid (compound of formula 33) may be optionally converted to its corresponding ester prodrugs by any suitable method well known in the art.

Scheme 4E: Preparation of Compound of Formula 1; Wherein Y$_1$=C(O), Y$_2$=CH$_2$; X$_1$, X$_2$, X$_4$ and X$_5$ are Selected from CH or CR, X$_3$=C; L=*NHSO$_2$; m=1; A, n, R, R$_1$, R$_2$ and R$_9$ are as Defined in Formula 1;

Scheme 4E

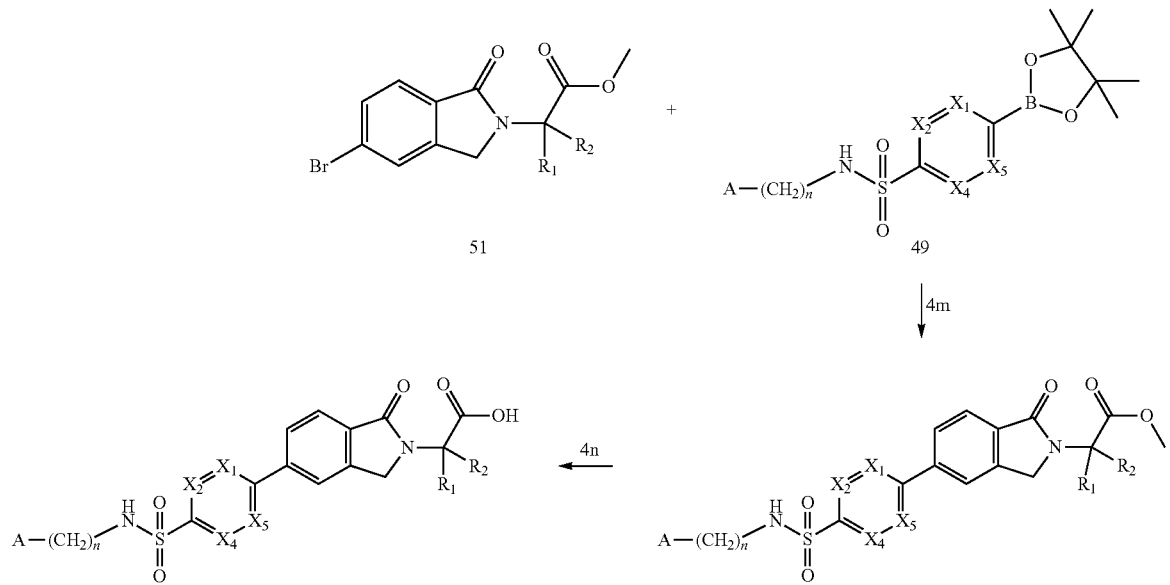

Step 1
Preparation of Compound of Formula 35:
Compound of formula 51 can be reacted with compound of formula 49 in presence of Pd(dppf)Cl$_2$:CH$_2$Cl$_2$ in a suitable base such as potassium carbonate, cesium carbonate or 2M Na$_2$CO$_3$ (in water) in a suitable solvent such as DMF, dioxane, dimethoxyethane or acetone under an atmosphere of argon at temperature ranging from 50-100° C. to obtain compound of formula 35 (Reaction 4m).

Step 2
Preparation of Compound of Formula 36:
Compound of formula 35 can be can be hydrolysed using suitable reagent such as 1N NaOH or 1N LiOH in a suitable solvent such as MeOH or THF at temperature ranging from 20-35° C. to obtain compound of formula 36 (Reaction 4n).

Step 3
The carboxylic acid (compound of formula 36) may be optionally converted to its corresponding ester prodrugs by any suitable method well known in the art.

Scheme 5A: Preparation of Compound of Formula 1; Wherein Y$_1$=CH$_2$, Y$_2$=C(O); X$_1$, X$_2$, X$_4$ and X$_5$ are Independently Selected from CH, CR and N, X$_3$=C; L=NHC(O)NH; m=1; A, n, R, R$_1$, R$_2$ and R$_9$ are as Defined in Formula 1;

Step 2
Preparation of Compound of Formula 54:
Compound of formula 52 can be treated with commercially available compound of formula 53 in presence of Pd(dppf)Cl$_2$:CH$_2$Cl$_2$ in a suitable base such as potassium carbonate, cesium carbonate or 2M Na$_2$CO$_3$ (in water) in a suitable solvent such as DMF, dioxane, dimethoxyethane or acetone under an atmosphere of argon at temperature ranging from 50-100° C. to obtain compound of formula 54 (Reaction 5b).

Step 3
Preparation of Compound of Formula 55:
Compound of formula 54 can be reduced using a suitable reducing agent such as Fe and ammonium chloride in a suitable solvent such as aqueous EtOH or EtOH:THF:H$_2$O at a temperature ranging from 70-100° C. to obtain compound of formula 55 (Reaction 5c).

Alternatively, other reducing agents such as Fe and HCl in solvent such as H$_2$O or ethanol or combination thereof, SnCl$_2$ in solvent such as ethyl acetate, hydrogen over Raney Ni, Pd/C or Pt/C catalyst in solvent such as methanol (pressure ranging from 50-80 psi and temperature ranging from 20-65° C.) or cobalt chloride and zinc in a solvent such as DMF or water (temperature ranging from 20-100° C.) may be used.

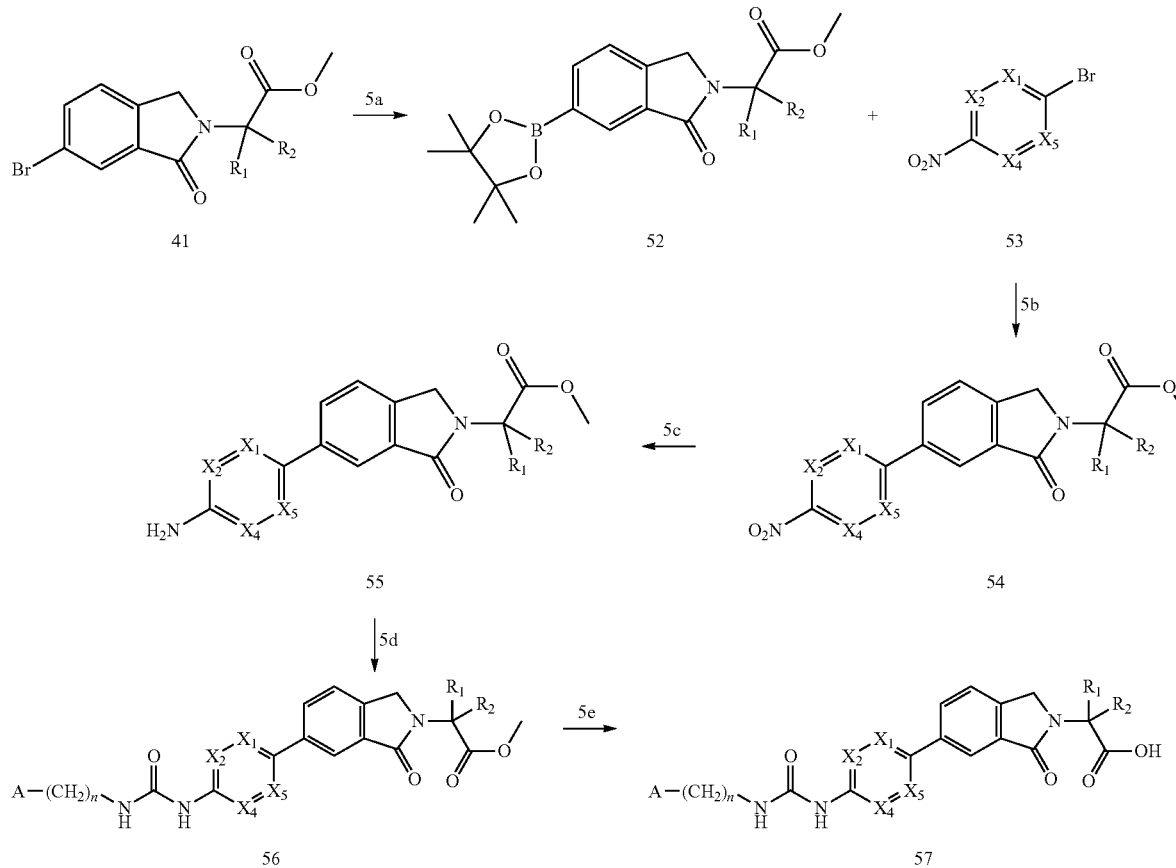

Scheme 5A

Step 1
Preparation of Compound of Formula 52:
Compound of formula 41 can be treated with bis(pinacolato)diboron, Pd(dppf)Cl$_2$ and Pd(dppf)Cl$_2$:CH$_2$Cl$_2$ in a suitable solvent such as dioxane, dimethoxyethane, DMSO or DMF at temperature ranging from 50-100° C. to obtain compound of formula 52 (Reaction 5a).

Step 4
Preparation of Compound of Formula 56:
Compound of formula 55 can be treated with compound of formula 8P:

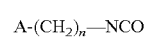   8P wherein A and n are as defined in formula 1;

in a suitable solvent such as dichloromethane or THF at temperature ranging from 20-35° C. to obtain compound of formula 56 (Reaction 5d).

Step 5
Preparation of Compound of Formula 57:
Compound of formula 56 can be hydrolysed using suitable reagent such as 1N NaOH or 1N LiOH in a suitable solvent such as MeOH or THF at temperature ranging from 20-35° C. to obtain compound of formula 57 (Reaction 5e).

Step 6
The carboxylic acid (compound of formula 57) may be optionally converted to its corresponding ester prodrugs by any suitable method well known in the art.

Scheme 5B: Preparation of Compound of Formula 1; Wherein $Y_1$=$CH_2$, $Y_2$=C(O); $X_1$, $X_2$, $X_4$ and $X_5$ are Independently Selected from CH, CR and N, $X_3$=C; L=—NHC(S)NH; m=1; A, n, R, $R_1$, $R_2$ and $R_9$ are as Defined in Formula 1;

Scheme 5B

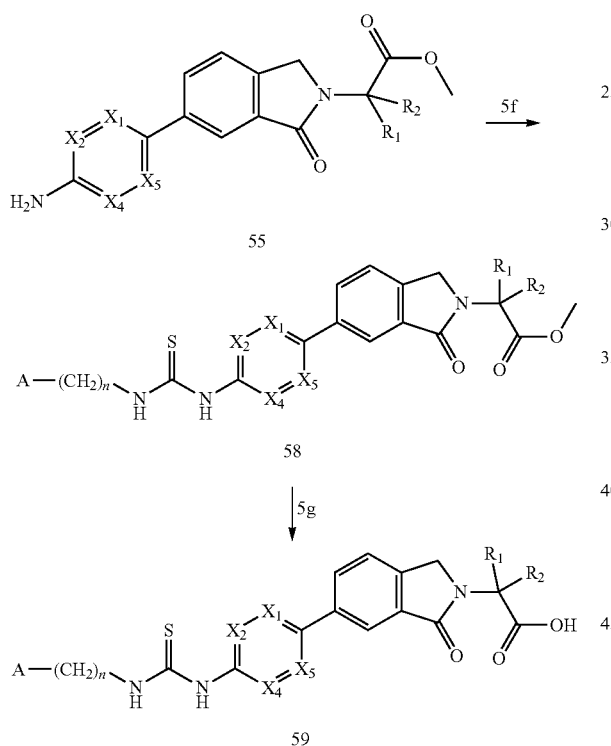

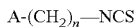

Step 1
Preparation of Compound of Formula 58:
Compound of formula 55 (as obtained in Step 3 of Scheme 5A) can be treated with compound of formula 8Q:

A-(CH$_2$)$_n$—NCS    8Q wherein A and n are as defined in formula 1;
in presence of a suitable solvent such as THF or dichloromethane at temperature ranging from 20-35° C. to obtain compound of formula 58 (Reaction 5f).

Step 2
Preparation of Compound of Formula 59:
Compound of formula 58 can be hydrolysed using suitable reagent such as 1N LiOH or 1N NaOH in a suitable solvent such as MeOH or THF at temperature ranging from 20-35° C. to obtain compound of formula 59 (Reaction 5g).

Step 3
The carboxylic acid (compound of formula 59) may be optionally converted to its corresponding ester prodrugs by any suitable method well known in the art.

Scheme 5C: Preparation of Compound of Formula 1; Wherein $Y_1$=$CH_2$, $Y_2$=C(O); $X_1$, $X_2$, $X_4$ and $X_5$ are Independently Selected from CH, CR and N, $X_3$=C; L=*SO$_2$NH; m=1; A, n, R, $R_1$, $R_2$ and $R_9$ are as Defined in Formula 1;

Scheme 5C

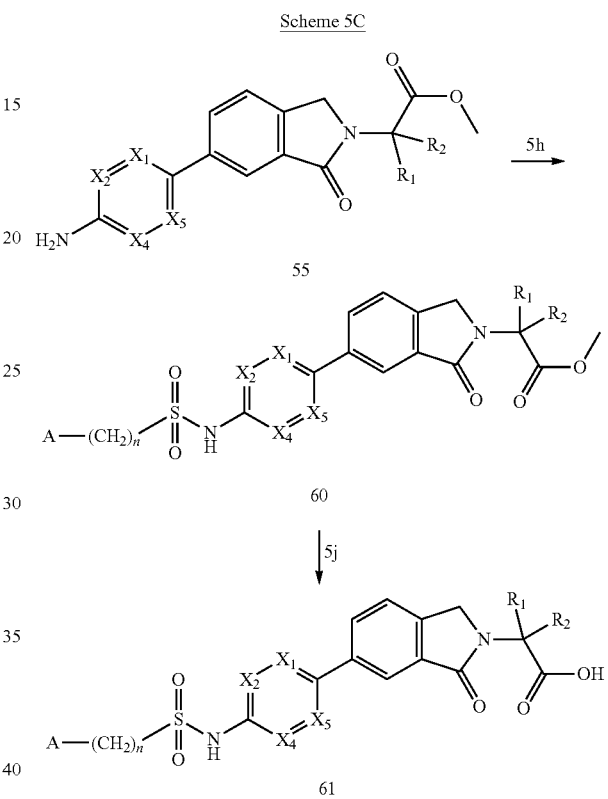

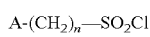

Step 1
Preparation of Compound of Formula 60:
Compound of formula 55 (as obtained in Step 3 of Scheme 5A) can be treated with compound of formula 8R:

A-(CH$_2$)$_n$—SO$_2$Cl    8R wherein A and n are as defined in formula 1;
in presence of a suitable base such as pyridine or triethylamine in a suitable solvent such as dichloromethane at temperature ranging from 20-35° C. to obtain compound of formula 60 (Reaction 5h).

Step 2
Preparation of Compound of Formula 61:
Compound of formula 60 can be hydrolysed using suitable reagent such as 1N LiOH or 1N NaOH in a suitable solvent such as MeOH or THF at temperature ranging from 20-35° C. to obtain compound of formula 61 (Reaction 5j).

Step 3
The carboxylic acid (compound of formula 61) may be optionally converted to its corresponding ester prodrugs by any suitable method well known in the art.

Scheme 5D: Preparation of Compound of Formula 1; Wherein $Y_1$=$CH_2$, $Y_2$=C(O); $X_1$, $X_2$, $X_4$ and $X_5$ are Independently Selected from CH, CR and N, $X_3$=C; L=*CONH, m=1; A, n, R, $R_1$, $R_2$ and $R_9$ are as Defined in Formula 1;

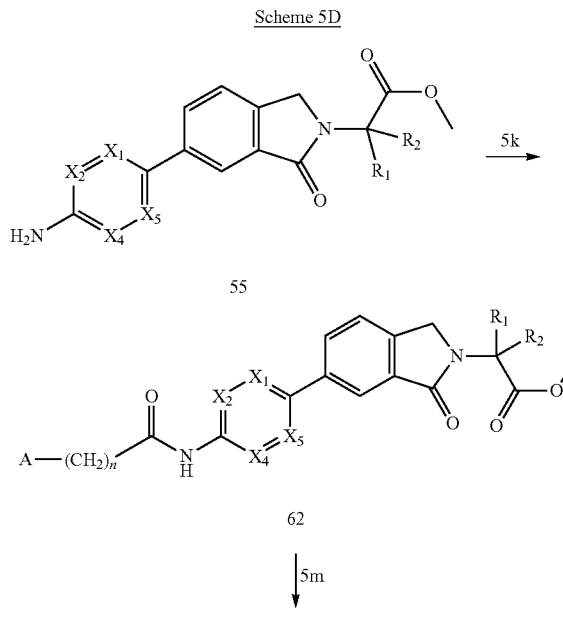

Step 1

Preparation of Compound of Formula 62:

Compound of formula 55 (as obtained in Step 3 of Scheme 5A) can be treated with compound of formula 8S:

$$A\text{-}(CH_2)_n\text{---}COCl \qquad 8S$$

wherein A and n are as defined in formula 1; in presence of a suitable base such as pyridine in a suitable solvent such as dichloromethane or THF at temperature ranging from 20-35° C. to obtain compound of formula 62 (Reaction 5k).

Step 2

Preparation of Compound of Formula 63:

Compound of formula 62 can be hydrolysed using suitable reagent such as 1N LiOH or 1N NaOH in a suitable solvent such as MeOH or THF at temperature ranging from 20-35° C. to obtain compound of formula 63 (Reaction 5m).

Step 3

The carboxylic acid (compound of formula 63) may be optionally converted to its corresponding ester prodrugs by any suitable method well known in the art.

Scheme 5E: Preparation of Compound of Formula 1; Wherein $Y_1$=$CH_2$, $Y_2$=C(O); $X_1$, $X_2$, $X_4$ and $X_5$ are Independently Selected from CH, CR and N, $X_3$=C; L=*NHSO_2; m=1; A, n, R, $R_1$, $R_2$ and $R_9$ are as Defined in Formula 1;

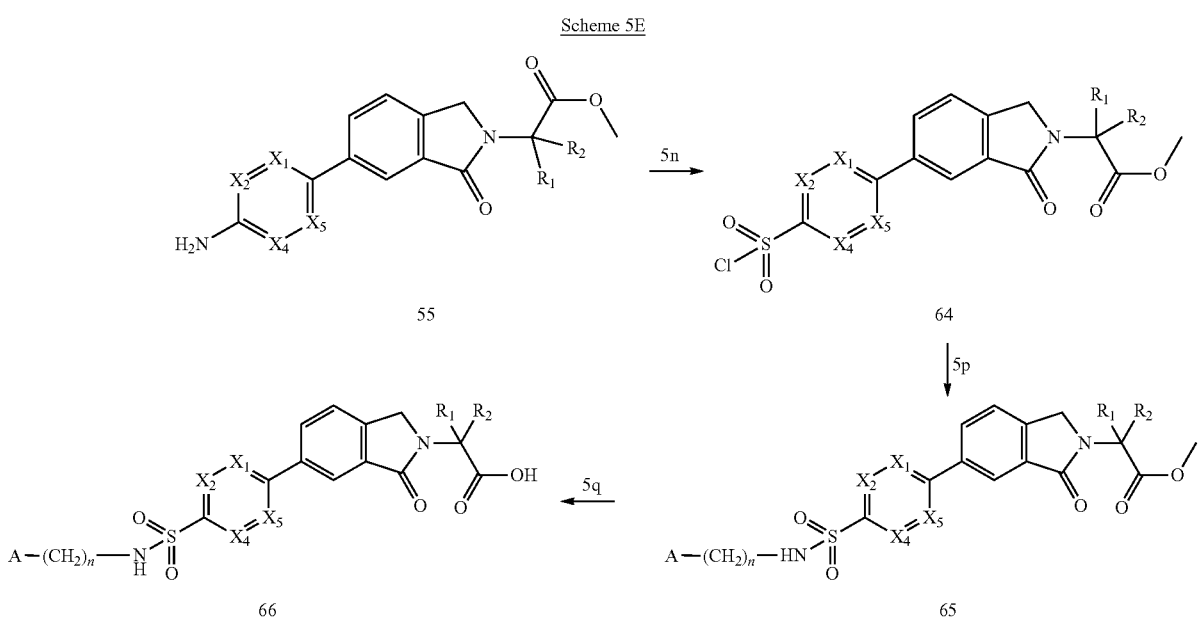

-continued

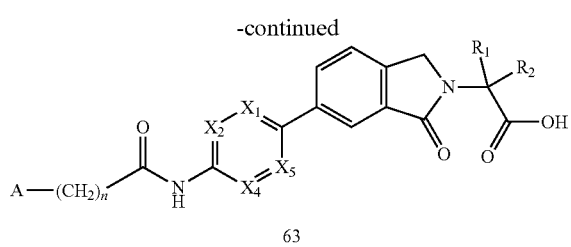

Step 1

Preparation of Compound of Formula 64:

Compound of formula 55 (obtained in Step 3 of Scheme 5A) can be treated with $NaNO_2$ and concentrated HCl to form a diazonium salt, which is treated with acetic acid saturated with $SO_2$ gas, followed by treatment with $CuCl_2$ at a temperature ranging from 0-35° C. to obtain compound of formula 64 (Reaction 5n).

85

Step 2
Preparation of Compound of Formula 65:
Compound of formula 64 can be treated with compound of formula 8T:

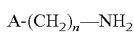
A-(CH$_2$)$_n$—NH$_2$    8T wherein A and n are as defined in formula 1;
in a suitable solvent such as dichloromethane and a base such as pyridine at temperature ranging from 20-35° C. to obtain compound of formula 65 (Reaction 5p).

Step 3
Preparation of Compound of Formula 66:
Compound of formula 65 can be hydrolysed using suitable reagent such as 1N LiOH or 1N NaOH in a suitable solvent such as MeOH or THF at temperature ranging from 20-35° C. to obtain compound of formula 66 (Reaction 5q).

Step 4
The carboxylic acid (compound of formula 66) may be optionally converted to its corresponding ester prodrugs by any suitable method well known in the art.

Scheme 6A: Preparation of Compound of Formula 1; Wherein Y$_1$=C(O), Y$_2$=CH$_2$; X$_1$, X$_2$, X$_4$ and X$_5$ are Independently Selected from CH, CR and N, X$_3$=C; L=NHC(O)NH; m=1; A, n, R, R$_1$, R$_2$ and R$_9$ are as Defined in Formula 1;

86

Step 1
Preparation of Compound of Formula 67:
Compound of formula 51 can be treated with bis(pinacolato)diboron, Pd(dppf)Cl$_2$ and Pd(dppf)Cl$_2$:CH$_2$Cl$_2$ in a suitable solvent such as dioxane, dimethoxyethane, DMSO or DMF at temperature ranging from 50-100° C. to obtain compound of formula 67 (Reaction 6a).

Step 2
Preparation of Compound of Formula 68:
Compound of formula 67 can be treated with compound of formula 53 in presence of Pd(dppf)Cl$_2$:CH$_2$Cl$_2$ in a suitable base such as potassium carbonate, cesium carbonate or 2M Na$_2$CO$_3$ (in water) in a suitable solvent such as DMF, dioxane, dimethoxyethane or acetone under an atmosphere of argon at temperature ranging from 50-100° C. to obtain compound of formula 68 (Reaction 6b).

Step 3
Preparation of Compound of Formula 69:
Compound of formula 68 can be reduced using a suitable reducing agent such as Fe and ammonium chloride in a suitable solvent such as aqueous EtOH or EtOH:THF:H$_2$O at a temperature ranging from 70-100° C. to obtain compound of formula 69 (Reaction 6c).

Alternatively, other reducing agents such as Fe and HCl in solvent such as H$_2$O or ethanol or combination thereof; Sn

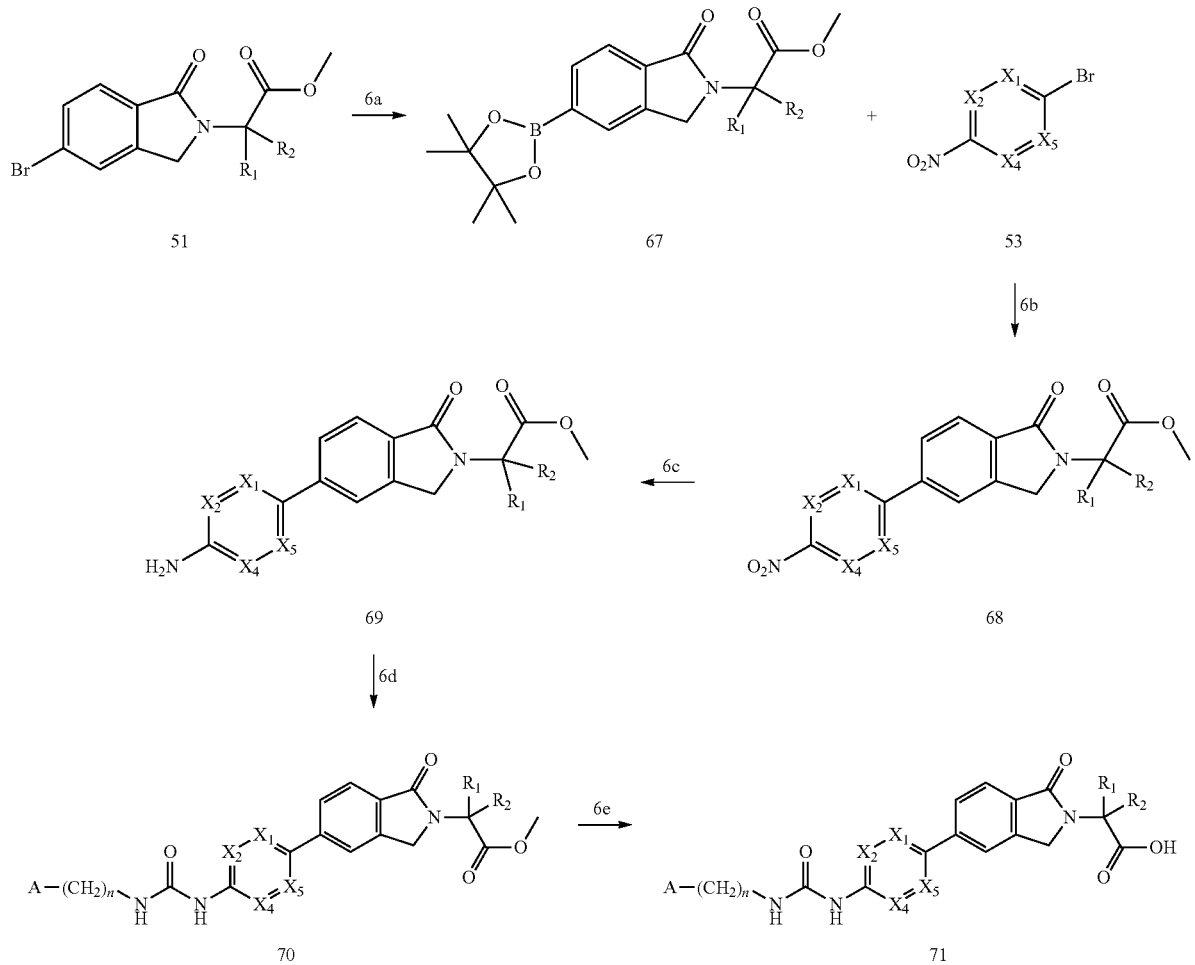
Scheme 6A

Cl$_2$ in solvent such as ethyl acetate; hydrogen over Raney Ni, Pd/C or Pt/C catalyst in solvent such as methanol (pressure ranging from 50-80 psi and temperature ranging from 20-65° C.); or cobalt chloride and zinc in a solvent such as DMF or water (temperature ranging from 20-100° C.) may be used.

Step 4
Preparation of Compound of Formula 70:

Compound of formula 69 can be treated with compound of formula 8P:

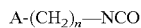   8P wherein A and n are as defined in formula 1;
in a suitable solvent such as dichloromethane or THF at temperature ranging from 20-35° C. to obtain compound of formula 70 (Reaction 6d).

Step 5
Preparation of Compound of Formula 71:

Compound of formula 70 can be hydrolysed using suitable reagent such as 1N NaOH or 1N LiOH in a suitable solvent such as MeOH or THF at temperature ranging from 20-35° C. to obtain compound of formula 71 (Reaction 6e).

Step 6

The carboxylic acid (compound of formula 71) may be optionally converted to its corresponding ester prodrugs by any suitable method well known in the art.

Scheme 6B: Preparation of Compound of Formula 1; Wherein Y$_1$=C(O), Y$_2$=CH$_2$; X$_1$, X$_2$, X$_4$ and X$_5$ are Independently Selected from CH, CR and N, X$_3$=C; L=NHC(S)NH; m=1; A, n, R, R$_1$, R$_2$ and R$_9$ are as Defined in Formula 1;

Step 1
Preparation of Compound of Formula 72:

Compound of formula 69 (obtained in Step 3 of Scheme 6A) can be treated with compound of formula 8Q:

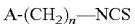   8Q wherein A and n are as defined in formula 1;
in presence of a suitable solvent such as THF or dichloromethane at temperature ranging from 20-35° C. to obtain compound of formula 72 (Reaction 5f).

Step 2
Preparation of Compound of Formula 73:

Compound of formula 72 can be hydrolysed using suitable reagent such as 1N LiOH or 1N NaOH in a suitable solvent such as MeOH or THF at temperature ranging from 20-35° C. to obtain compound of formula 73 (Reaction 5g).

Step 3

The carboxylic acid (compound of formula 73) may be optionally converted to its corresponding ester prodrugs by any suitable method well known in the art.

Scheme 6C: Preparation of Compound of Formula 1; Wherein Y$_1$=C(O), Y$_2$=CH$_2$; X$_1$, X$_2$, X$_4$ and X$_5$ are Independently Selected from CH, CR and N, X$_3$=C; L=*SO$_2$NH; m=1; A, n, R$_1$, R$_2$ and R$_9$ are as Defined in Formula 1;

Scheme 6C

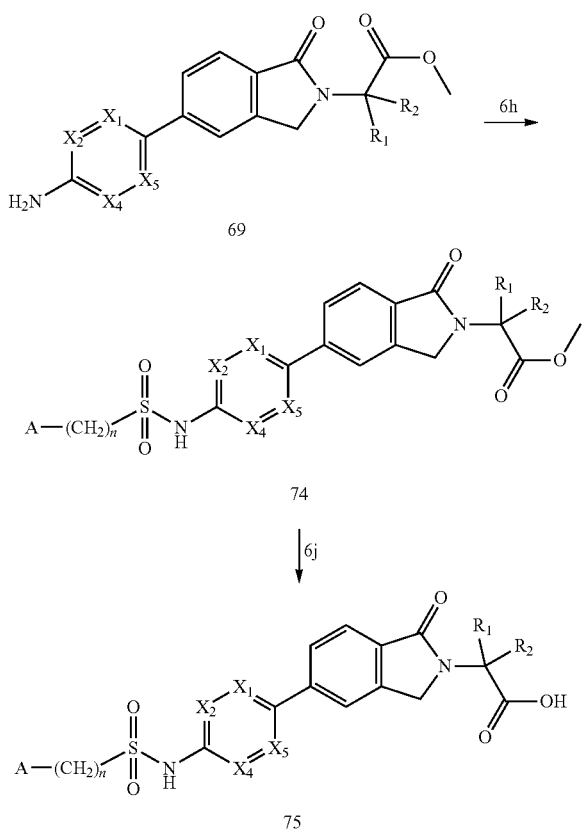

Scheme 6B

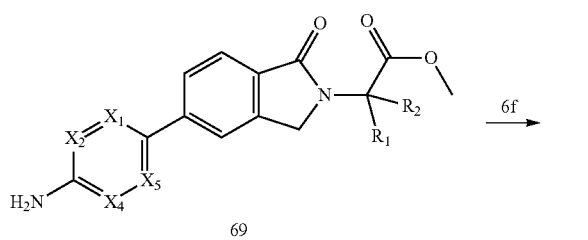

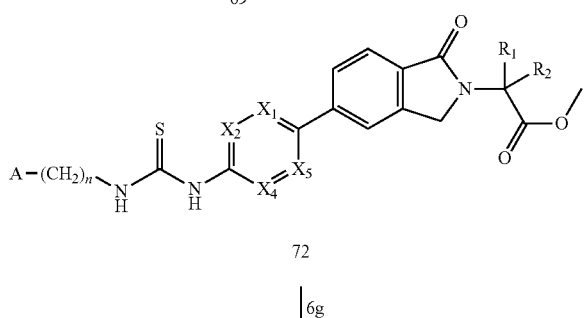

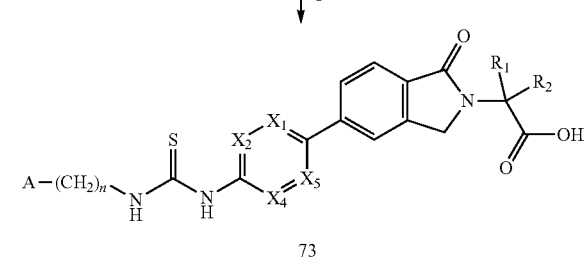

Step 1
Preparation of Compound of Formula 74:

Compound of formula 69 (obtained in Step 3 of Scheme 6A) can be treated with compound of formula 8R:

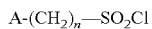   8R wherein A and n are as defined in formula 1;
in presence of a suitable base such as pyridine or triethylamine in a suitable solvent such as dichloromethane at temperature ranging from 20-35° C. to obtain compound of formula 74 (Reaction 6h).

Step 2
Preparation of Compound of Formula 75:

Compound of formula 74 can be hydrolysed using suitable reagent such as 1N LiOH or 1N NaOH in a suitable solvent such as MeOH or THF at temperature ranging from 20-35° C. to obtain compound of formula 75 (Reaction 6j).

Step 3

The carboxylic acid (compound of formula 75) may be optionally converted to its corresponding ester prodrugs by any suitable method well known in the art.

Scheme 6D: Preparation of Compound of Formula 1; Wherein $Y_1$=C(O), $Y_2$=CH$_2$; $X_1$, $X_2$, $X_4$ and $X_5$ are Independently Selected from CH, CR and N, $X_3$=C; L=*CONH; m=1; A, n, R, $R_1$, $R_2$ and $R_9$ are as Defined in Formula 1;

Scheme 6D

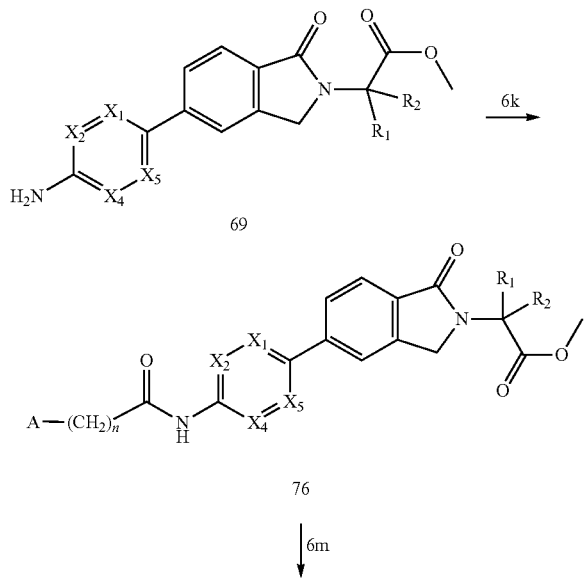

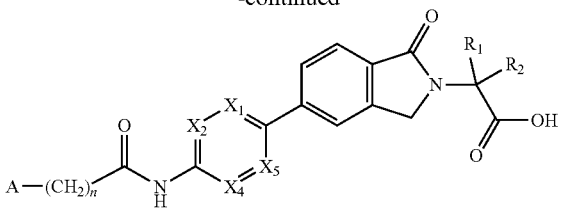

Step 1
Preparation of Compound of Formula 76:

Compound of formula 69 (obtained in Step 3 of Scheme 6A) can be treated with compound of formula 8S:

$$A\text{-}(CH_2)_n\text{—}COCl \qquad 8S$$

wherein A and n are as defined in formula 1;

in presence of a suitable base such as pyridine in a suitable solvent such as dichloromethane or THF at temperature ranging from 20-35° C. to obtain compound of formula 76 (Reaction 5k).

Step 2
Preparation of Compound of Formula 77:

Compound of formula 76 can be hydrolysed using suitable reagent such as 1N LiOH or 1N NaOH in a suitable solvent such as MeOH or THF at temperature ranging from 20-35° C. to obtain compound of formula 77 (Reaction 5m).

Step 3

The carboxylic acid (compound of formula 77) may be optionally converted to its corresponding ester prodrugs by any suitable method well known in the art.

Scheme 6E: Preparation of Compound of Formula 1; Wherein $Y_1$=C(O), $Y_2$=CH$_2$; $X_1$, $X_2$, $X_4$ and $X_5$ are Independently Selected from CH, CR and N, $X_3$=C; L=*NHSO$_2$; m=1; A, n, R, $R_1$, $R_2$ and $R_9$ are as Defined in Formula 1;

Scheme 6E

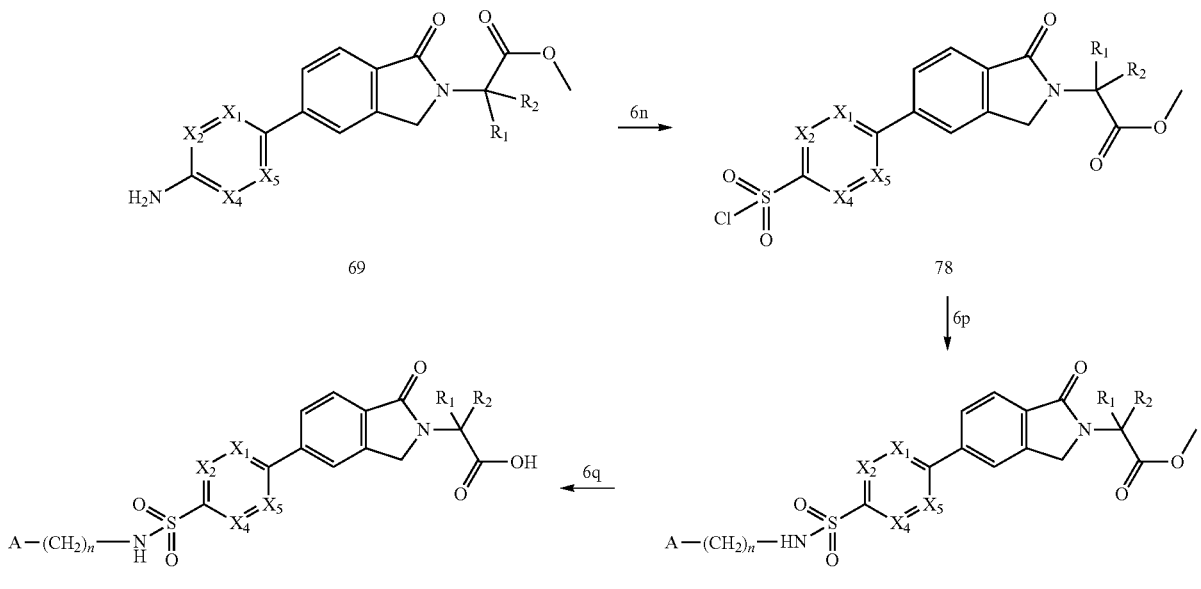

91

Step 1
Preparation of Compound of Formula 78:

Compound of formula 69 (obtained in Step 3 of Scheme 6A) can be treated with NaNO$_2$ and concentrated HCl to form a diazonium salt, which is treated with acetic acid saturated with SO$_2$ gas, followed by treatment with CuCl$_2$ at a temperature ranging from 0-35° C. to obtain compound of formula 78 (Reaction 6n).

92

Step 4
The carboxylic acid (compound of formula 80) may be optionally converted to its corresponding ester prodrugs by any suitable method well known in the art.

Scheme 7A: Preparation of Compound of Formula 1; Wherein Y$_1$=C(O), Y$_2$=C(O); X$_1$, X$_2$, X$_4$ and X$_5$ are Independently Selected from CH and CR, X$_3$=C; L=NHC(O)NH; m=1; A, n, R, R$_1$, R$_2$ and R$_9$ are as Defined in Formula 1;

Scheme 7A

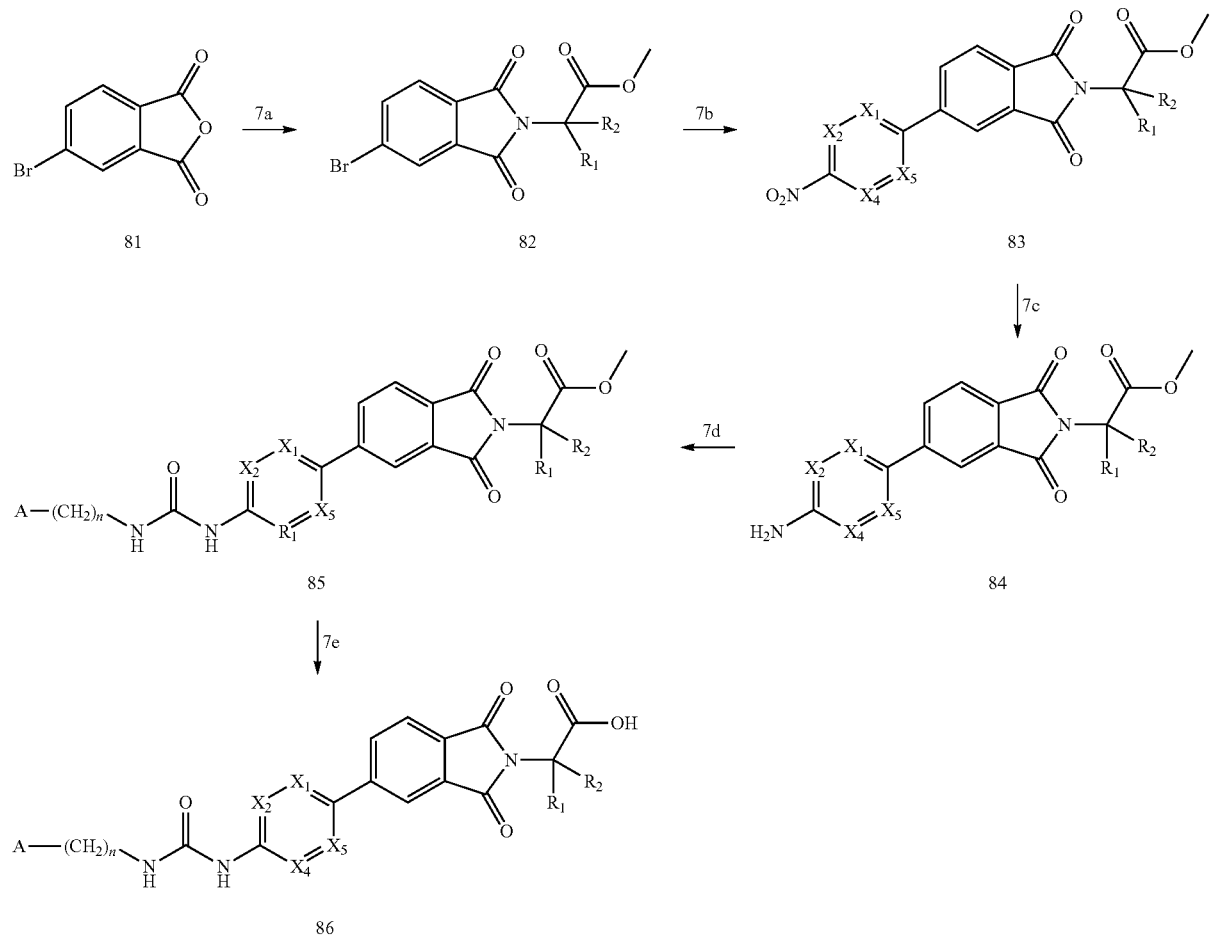

Step 2
Preparation of Compound of Formula 79:

Compound of formula 78 can be treated with compound of formula 8T:

A-(CH$_2$)$_n$—NH$_2$       8T wherein A and n are as defined in formula 1; in a suitable solvent such as dichloromethane and a base such as pyridine at temperature ranging from 20-35° C. to obtain compound of formula 79 (Reaction 6p).

Step 3
Preparation of Compound of Formula 80:

Compound of formula 79 can be hydrolysed using suitable reagent such as 1N LiOH or 1N NaOH in a suitable solvent such as MeOH or THF at temperature ranging from 20-35° C. to obtain compound of formula 80 (Reaction 6q).

Step 1
Preparation of Compound of Formula 82:

Commercially available compound of formula 81 can be treated with compound of formula 6P:

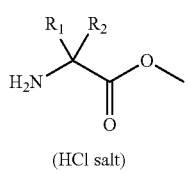

(HCl salt)

wherein R$_1$ and R$_2$ are as Defined in Formula 1;

in presence of a suitable base such as triethylamine in a suitable solvent such as benzene or toluene at a temperature ranging from 70-120° C. to obtain compound of formula 82 (Reaction 7a).

Alternatively, potassium carbonate may be used as a base in a suitable solvent such as DMF or THF at a temperature ranging from 50-80° C.

Step 2
Preparation of Compound of Formula 83:
Compound of formula 82 can be treated with compound of formula 21B:

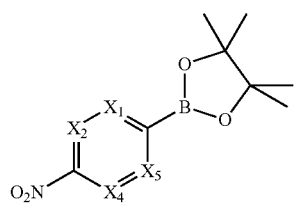
21B wherein $X_1$, $X_2$, $X_4$ and $X_5$ are selected from CH and CR; R is as defined in formula 1; in presence of a catalyst such as $Pd(dppf)Cl_2 \cdot CH_2Cl_2$ and a base such as potassium carbonate, cesium carbonate or 2M $Na_2CO_3$ (in water) in a suitable solvent such as DMF, dioxane, dimethoxyethane or acetone at a temperature ranging from 70-120° C. under an atmosphere of argon, to obtain compound of formula 83 (Reaction 7b). Alternatively, compound of formula 82 can be treated with compound of formula 21A:

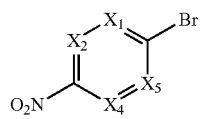
21A in presence of bis(pinacolo)diboron (to form compound of formula 21B in situ) with a suitable catalyst such as palladium acetate or tetrakis palladium and a suitable base such as potassium acetate, sodium carbonate and cesium carbonate in a solvent such as toluene, dioxane, dimethoxyethane, DMF or acetone at a temperature ranging from 70-120° C. to obtain compound of formula 83.

Step 3
Preparation of Compound of Formula 84:
Compound of formula 83 can be reduced using a suitable reducing agent such as Fe and ammonium chloride in a suitable solvent such as aqueous EtOH or EtOH:THF:$H_2O$ at a temperature ranging from 70-100° C. to obtain compound of formula 84 (Reaction 7c).

Alternatively, other reducing agents such as Fe and HCl in solvent such as $H_2O$ or ethanol or combination thereof; $SnCl_2$ in solvent such as ethyl acetate; hydrogen over Raney Ni, Pd/C or Pt/C catalyst in solvent such as methanol (pressure ranging from 50-80 psi and temperature ranging from 20-65° C.); or cobalt chloride and zinc in a solvent such as DMF or water (temperature ranging from 20-100° C.) may be used.

Step 4
Preparation of Compound of Formula 85:
Compound of formula 84 can be treated with compound of formula 8P:

A-$(CH_2)_n$—NCO  8P wherein A and n are as defined in formula 1;
in a suitable solvent such as dichloromethane or THF at temperature ranging from 20-35° C. to obtain compound of formula 85 (Reaction 7d).

Step 5
Preparation of Compound of Formula 86:
Compound of formula 85 can be hydrolysed using suitable reagent such as 1N NaOH or 1N LiOH in a suitable solvent such as MeOH or THF at temperature ranging from 20-35° C. to obtain compound of formula 86 (Reaction 7e).

Step 6
The carboxylic acid (compound of formula 86) may be optionally converted to its corresponding ester prodrugs by any suitable method well known in the art.

Scheme 7B: Preparation of Compound of Formula 1; Wherein $Y_1$=C(O), $Y_2$=C(O); $X_1$, $X_2$, $X_4$ and $X_5$ are Independently Selected from CH and CR, $X_3$=C; L=NHC(S)NH; m=1; A, n, R, $R_1$, $R_2$ and $R_9$ are as Defined in Formula 1;

Scheme 7B

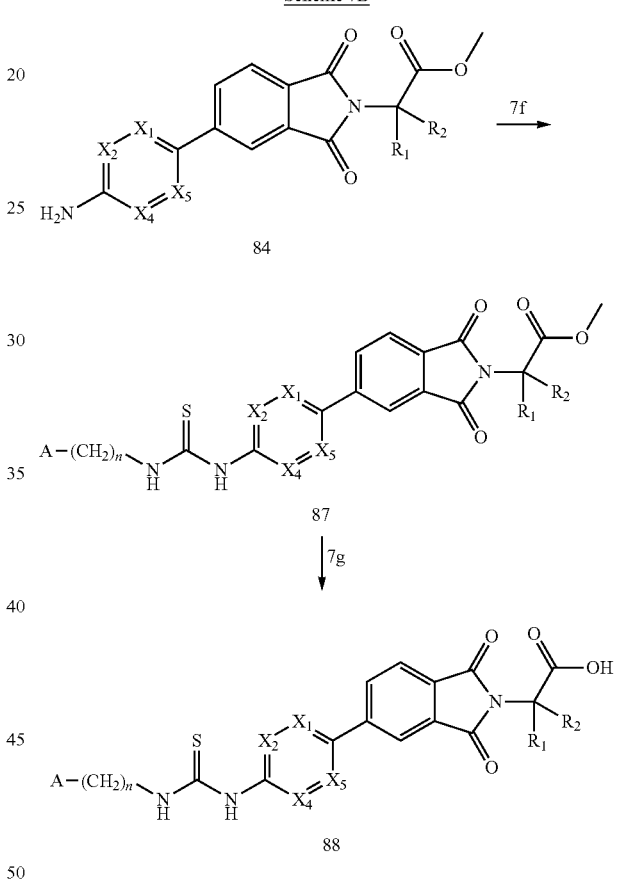

Step 1
Preparation of Compound of Formula 87:
Compound of formula 84 (obtained in Step 3 of Scheme 7A) can be treated with compound of formula 8Q:

A-$(CH_2)_n$—NCS  8Q wherein A and n are as defined in formula 1;
in presence of a suitable solvent such as THF or dichloromethane at temperature ranging from 20-35° C. to obtain compound of formula 87 (Reaction 7f).

Step 2
Preparation of Compound of Formula 88:
Compound of formula 87 can be hydrolysed using suitable reagent such as 1N LiOH or 1N NaOH in a suitable solvent such as MeOH or THF at temperature ranging from 20-35° C. to obtain compound of formula 88 (Reaction 7g).

Step 3

The carboxylic acid (compound of formula 88) may be optionally converted to its corresponding ester prodrugs by any suitable method well known in the art.

Scheme 7C: Preparation of Compound of Formula 1; Wherein $Y_1$=C(O), $Y_2$=C(O); $X_1$, $X_2$, $X_4$ and $X_5$ are Independently Selected from CH and CR, $X_3$=C; L=*SO$_2$NH; m=1; A, n, R, $R_1$, $R_2$ and $R_9$ are as Defined in Formula 1;

pendently Selected from CH and CR, $X_3$=C; L=*CONH; A, n, R, $R_1$, $R_2$ and $R_9$ are as Defined in Formula 1;

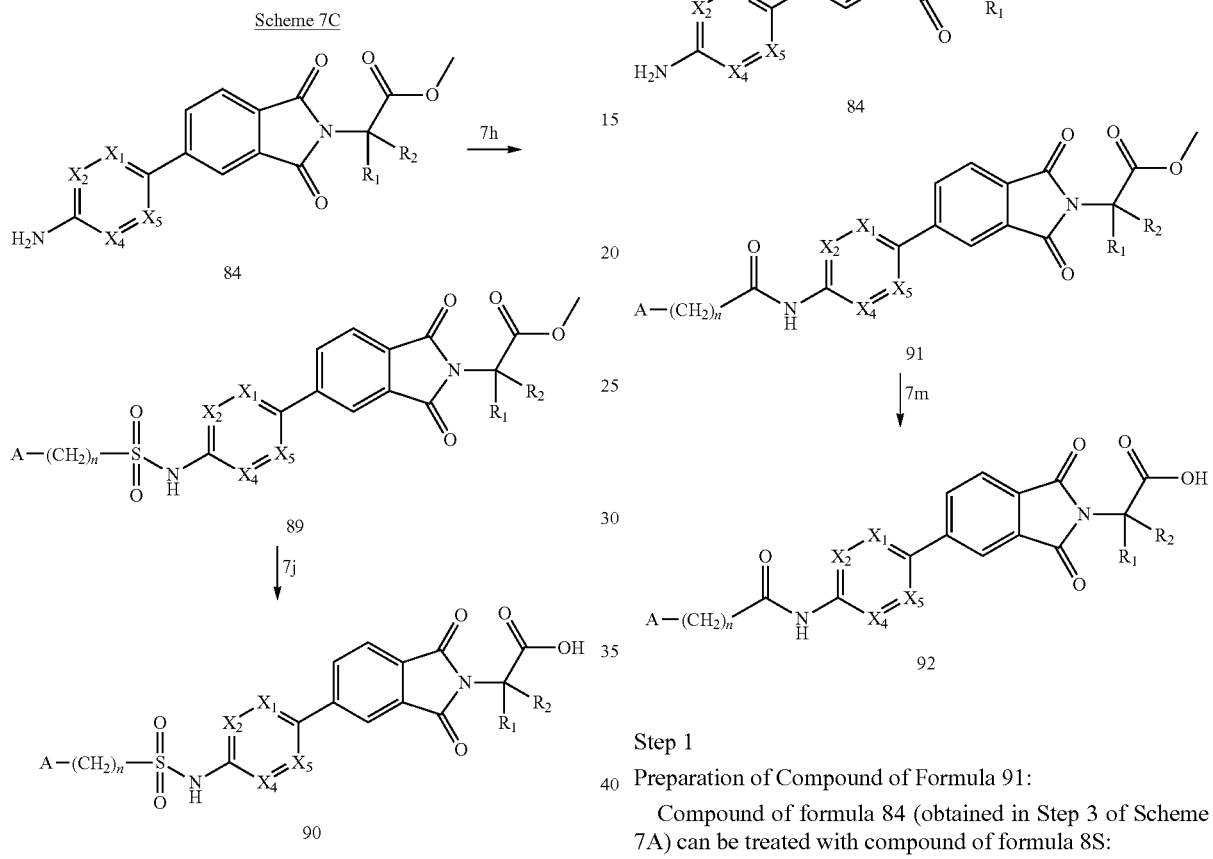

Step 1

Preparation of Compound of Formula 89:

Compound of formula 84 (obtained in Step 3 of Scheme 7A) can be treated with compound of formula 8R:

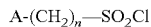    8R wherein A and n are as defined in formula 1;
in presence of a suitable base such as pyridine or triethylamine in a suitable solvent such as dichloromethane at temperature ranging from 20-35° C. to obtain compound of formula 89 (Reaction 7h).

Step 2

Preparation of Compound of Formula 90:

Compound of formula 89 can be hydrolysed using suitable reagent such as 1N LiOH or 1N NaOH in a suitable solvent such as MeOH or THF at temperature ranging from 20-35° C. to obtain compound of formula 90 (Reaction 7j).

Step 3

The carboxylic acid (compound of formula 90) may be optionally converted to its corresponding ester prodrugs by any suitable method well known in the art.

Scheme 7D: Preparation of Compound of Formula 1; Wherein $Y_1$=C(O), $Y_2$=C(O); $X_1$, $X_2$, $X_4$ and $X_5$ are Inde- Step 1

Preparation of Compound of Formula 91:

Compound of formula 84 (obtained in Step 3 of Scheme 7A) can be treated with compound of formula 8S:

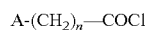    8S wherein A and n are as defined in formula 1;

in presence of a suitable base such as pyridine in a suitable solvent such as dichloromethane or THF at temperature ranging from 20-35° C. to obtain compound of formula 91 (Reaction 7k).

Step 2

Preparation of Compound of Formula 92:

Compound of formula 91 can be hydrolysed using suitable reagent such as 1N LiOH or 1N NaOH in a suitable solvent such as MeOH or THF at temperature ranging from 20-35° C. to obtain compound of formula 92 (Reaction 7m).

Step 3

The carboxylic acid (compound of formula 92) may be optionally converted to its corresponding ester prodrugs by any suitable method well known in the art.

Scheme 7E: Preparation of Compound of Formula 1; Wherein $Y_1$=C(O), $Y_2$=C(O); $X_1$, $X_2$, $X_4$ and $X_5$ are Independently Selected from CH and CR, $X_3$=C; L=*NHSO$_2$; m=1; A, n, R, $R_1$, $R_2$ and $R_9$ are as Defined in Formula 1;

Scheme 7E

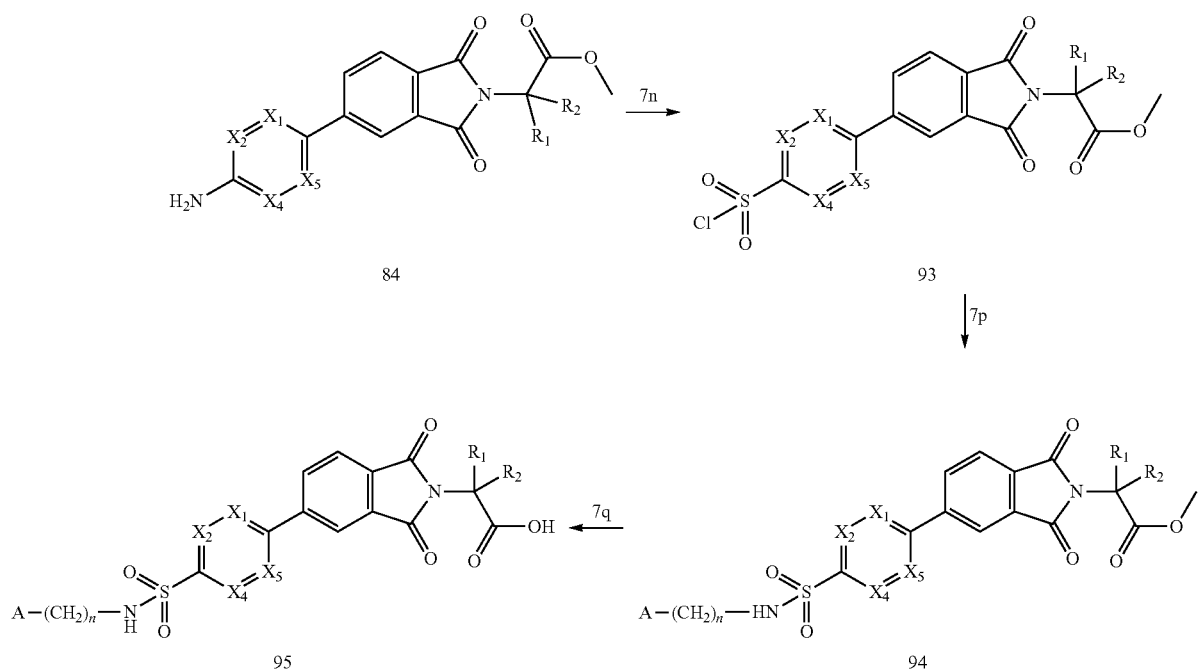

Step 1
Preparation of Compound of Formula 93:

Compound of formula 84 (obtained in Step 3 of Scheme 7A) can be treated with $NaNO_2$ and concentrated HCl to form a diazonium salt, which is treated with acetic acid saturated with $SO_2$ gas, followed by treatment with $CuCl_2$ at a temperature ranging from 0-35° C. to obtain compound of formula 93 (Reaction 7n).

Step 2
Preparation of Compound of Formula 94:

Compound of formula 93 can be treated with compound of formula 8T:

wherein A and n are as defined in formula 1;

in a suitable solvent such as dichloromethane and a base such as pyridine at temperature ranging from 20-35° C. to obtain compound of formula 94 (Reaction 7p).

Step 3
Preparation of Compound of Formula 95:

Compound of formula 94 can be hydrolysed using suitable reagent such as 1N LiOH or 1N NaOH in a suitable solvent such as MeOH or THF at temperature ranging from 20-35° C. to obtain compound of formula 95 (Reaction 7q).

Step 4

The carboxylic acid (compound of formula 95) may be optionally converted to its corresponding ester prodrugs by any suitable method well known in the art.

Scheme 8A: Preparation of Compound of Formula 1; Wherein $Y_1$=$CH_2$, $Y_2$=$CH_2$; $X_1$, $X_2$, $X_4$ and $X_5$ are Independently Selected from CH and CR, $X_3$=C; L=NHC(O)NH; m=1; A, n, R, $R_1$, $R_2$ and $R_9$ are as Defined in Formula 1;

Scheme 8A

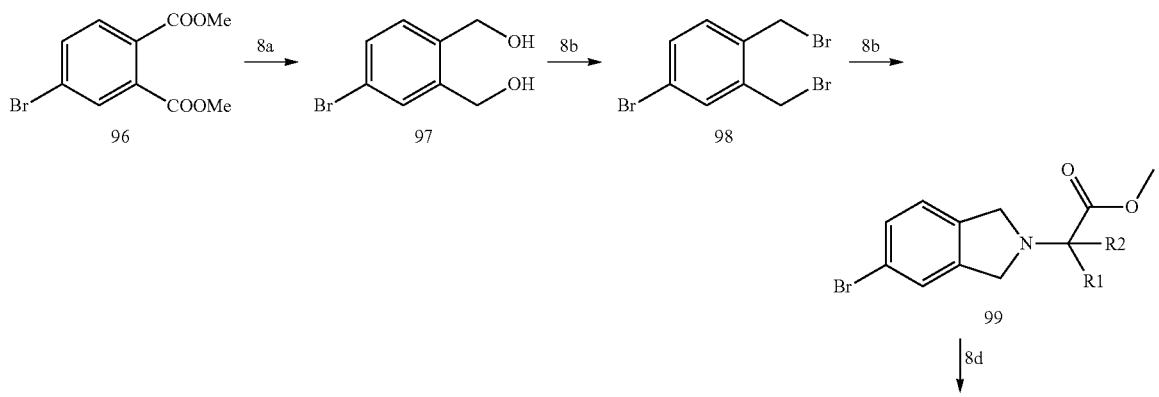

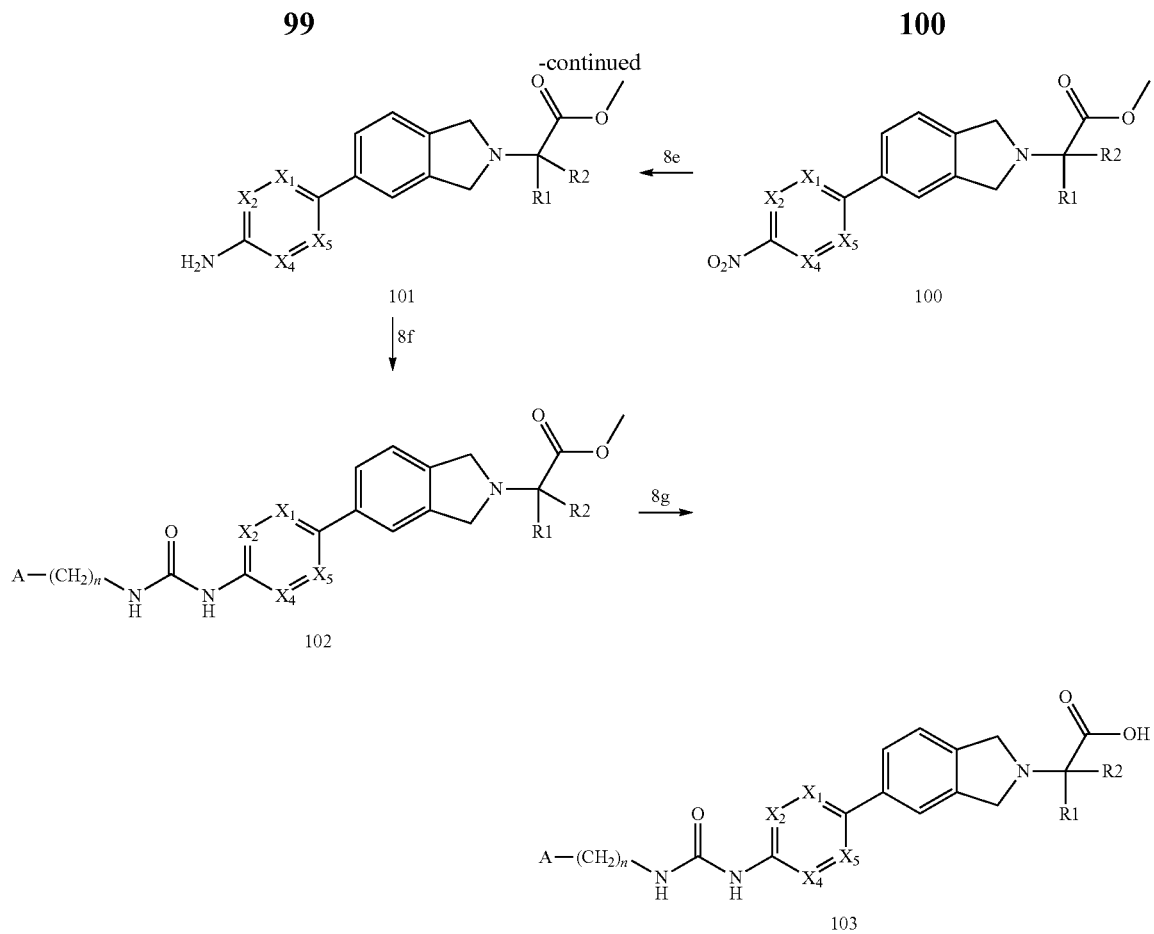

Step 1

Commercially available compound of formula 96 can be treated with LiAlH₄ in a suitable solvent such as THF or diethyl ether at the temperature ranging from 0-70° C. to obtain compound of formula 97.

Alternatively, commercially available compound of formula 81 can be treated with LiAlH₄ in a suitable solvent such as THF or diethyl ether at the temperature ranging from 0-70° C. to obtain compound of formula 97.

Step 2

Compound of formula 97 can be treated with N-bromosuccinimide in dichloromethane or PBr₃ in diethyl ether at temperature ranging from 0-35° C. to obtain compound of formula 98.

Step 3

Preparation of Compound of Formula 99:

Compound of formula 98 can be treated with compound of formula 6P:

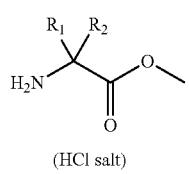

(HCl salt)

wherein R₁ and R₂ are as Defined in Formula 1;

in presence of a suitable base such as triethylamine in a suitable solvent such as benzene or toluene at a temperature ranging from 70-120° C. to obtain compound of formula 99 (Reaction 8c).

Alternatively, potassium carbonate may be used as a base in a suitable solvent such as DMF or THF at a temperature ranging from 50-80° C.

Step 4

Preparation of Compound of Formula 100:

Compound of formula 99 can be treated with compound of formula 21B:

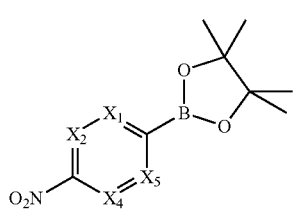

wherein X₁, X₂, X₄ and X₅ are selected from CH and CR, R is as defined in formula 1;

in presence of a catalyst such as Pd(dppf)Cl₂:CH₂Cl₂ and a base such as potassium carbonate, cesium carbonate or 2M Na₂CO₃ (in water) in a suitable solvent such as DMF, dioxane, dimethoxyethane or acetone at a temperature ranging from 70-120° C. under an atmosphere of argon, to obtain compound of formula 100 (Reaction 8d).

Alternatively, compound of formula 99 can be treated with compound of formula 21A:

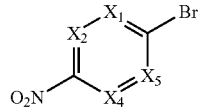
21A in presence of bis(pinacolo)diboron with a suitable catalyst such as palladium acetate or tetrakis palladium and a suitable base such as potassium acetate, sodium carbonate and cesium carbonate in a solvent such as toluene, dioxane, dimethoxyethane, DMF or acetone at a temperature ranging from 70-120° C. to obtain compound of formula 100.

Step 5
Preparation of Compound of Formula 101:

Compound of formula 100 can be reduced using a suitable reducing agent such as Fe and ammonium chloride in a suitable solvent such as aqueous EtOH or EtOH:THF:H$_2$O at a temperature ranging from 70-100° C. to obtain compound of formula 101 (Reaction 8e).

Alternatively, other reducing agents such as Fe and HCl in solvent such as H$_2$O or ethanol or combination thereof; SnCl$_2$ in solvent such as ethyl acetate; hydrogen over Raney Ni, Pd/C or Pt/C catalyst in solvent such as methanol (pressure ranging from 50-80 psi and temperature ranging from 20-65° C.); or cobalt chloride and zinc in a solvent such as DMF or water (temperature ranging from 20-100° C.) may be used.

Step 6
Preparation of Compound of Formula 102:

Compound of formula 101 can be treated with compound of formula 8P:

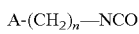
8P

Where in A and n are as defined in formula 1;
in a suitable solvent such as dichloromethane or THF at temperature ranging from 20-35° C. to obtain compound of formula 102 (Reaction 8f).

Step 7
Preparation of Compound of Formula 103:

Compound of formula 102 can be hydrolysed using suitable reagent such as 1N NaOH or 1N LiOH in a suitable solvent such as MeOH or THF at temperature ranging from 20-35° C. to obtain compound of formula 103 (Reaction 8g).

Step 8

The carboxylic acid (compound of formula 103) may be optionally converted to its corresponding ester prodrugs by any suitable method well known in the art.

Scheme 8B: Preparation of Compound of Formula 1; Wherein Y$_1$=CH$_2$, Y$_2$=CH$_2$; X$_1$, X$_2$, X$_4$ and X$_5$ are Independently Selected from CH and CR, X$_3$=C; L=NHC(S)NH; m=1; A, n, R, R$_1$, R$_2$ and R$_9$ are as Defined in Formula 1;

Scheme 8B

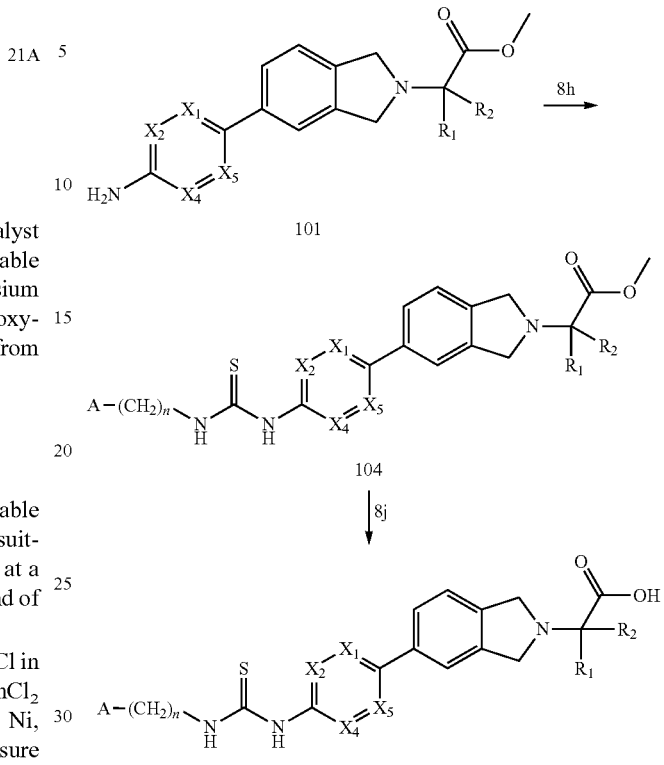

Step 1
Preparation of Compound of Formula 104:

Compound of formula 101 (obtained in Step 5 of Scheme 8A) can be treated with compound of formula 8Q:

8Q wherein A and n are as defined in formula 1;
in presence of a suitable solvent such as THF or dichloromethane at temperature ranging from 20-35° C. to obtain compound of formula 104 (Reaction 8h).

Step 2
Preparation of Compound of Formula 105:

Compound of formula 104 can be hydrolysed using suitable reagent such as 1N LiOH or 1N NaOH in a suitable solvent such as MeOH or THF at temperature ranging from 20-35° C. to obtain compound of formula 105 (Reaction 8j).

Step 3

The carboxylic acid (compound of formula 105) may be optionally converted to its corresponding ester prodrugs by any suitable method well known in the art.

Scheme 8C: Preparation of Compound of Formula 1; Wherein Y$_1$=CH$_2$, Y$_2$=CH$_2$; X$_1$, X$_2$, X$_4$ and X$_5$ are Independently Selected from CH and CR, X$_3$=C; L=*SO$_2$NH; m=1; A, n, R, R$_1$, R$_2$ and R$_9$ are as Defined in Formula 1;

Scheme 8C

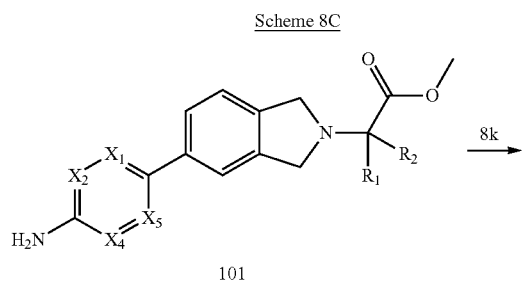

Scheme 8D

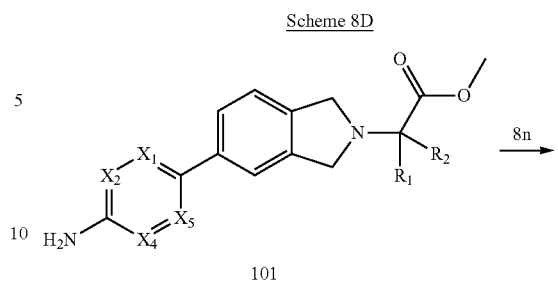

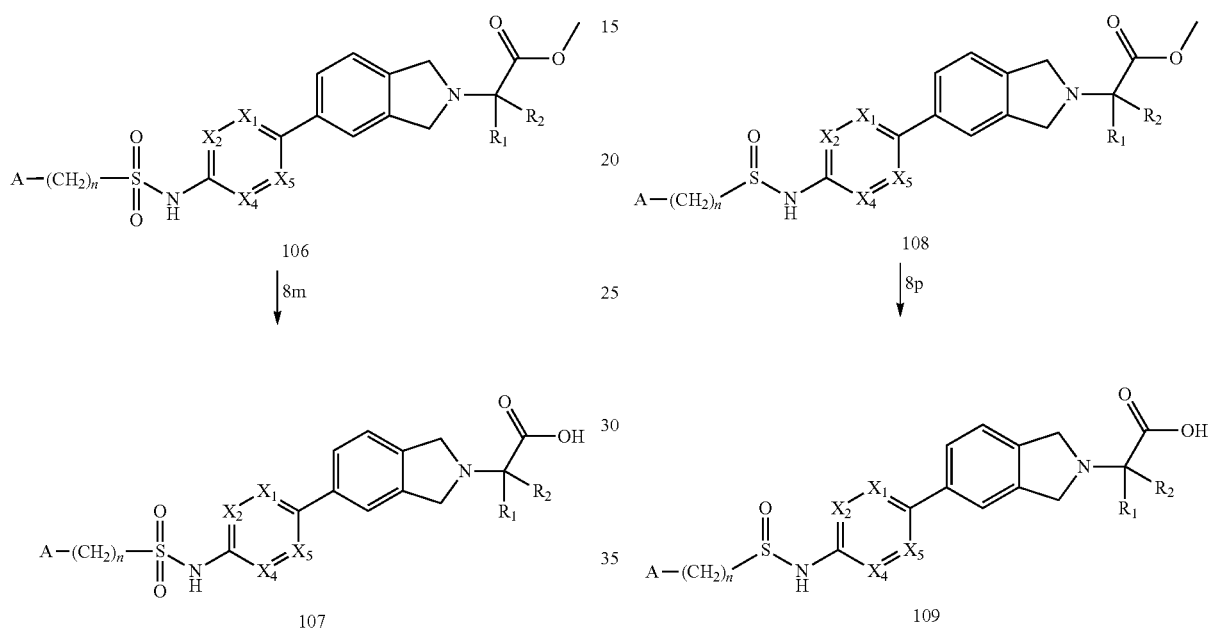

Step 1
Preparation of Compound of Formula 106:
Compound of formula 101 (obtained in Step 5 of Scheme 8A) can be treated with compound of formula 8R:

A-(CH$_2$)$_n$—SO$_2$Cl          8R wherein A and n are as defined in formula 1;
in presence of a suitable base such as pyridine or triethylamine in a suitable solvent such as dichloromethane at temperature ranging from 20-35° C. to obtain compound of formula 106 (Reaction 8k).

Step 2
Preparation of Compound of Formula 107:
Compound of formula 106 can be hydrolysed using suitable reagent such as 1N LiOH or 1N NaOH in a suitable solvent such as MeOH or THF at temperature ranging from 20-35° C. to obtain compound of formula 107 (Reaction 8m).

Step 3
The carboxylic acid (compound of formula 107) may be optionally converted to its corresponding ester prodrugs by any suitable method well known in the art.

Scheme 8D: Preparation of Compound of Formula 1;
Wherein Y$_1$=CH$_2$, Y$_2$=CH$_2$; X$_1$, X$_2$, X$_4$ and X$_5$ are Independently Selected from CH and CR, X$_3$=C; L=*CONH; m=1; A, n, R, R$_1$, R$_2$ and R$_9$ are as Defined in Formula 1;

Step 1
Preparation of Compound of Formula 108:
Compound of formula 101 (obtained in Step 5 of Scheme 8A) can be treated with compound of formula 8S:

A-(CH$_2$)$_n$—COCl          8S wherein A and n are as defined in formula 1;
in presence of a suitable base such as pyridine in a suitable solvent such as dichloromethane or THF at temperature ranging from 20-35° C. to obtain compound of formula 108 (Reaction 8n).

Step 2
Preparation of Compound of Formula 109:
Compound of formula 108 can be hydrolysed using suitable reagent such as 1N LiOH or 1N NaOH in a suitable solvent such as MeOH or THF at temperature ranging from 20-35° C. to obtain compound of formula 109 (Reaction 8p).

Step 3
The carboxylic acid (compound of formula 109) may be optionally converted to its corresponding ester prodrugs by any suitable method well known in the art.

Scheme 8E: Preparation of Compound of Formula 1;
Wherein Y$_1$=CH$_2$, Y$_2$=CH$_2$; X$_1$, X$_2$, X$_4$ and X$_5$ are Independently Selected from CH and CR, X$_3$=C; L=*NHSO$_2$; m=1; A, n, R, R$_1$, R$_2$ and R$_9$ are as Defined in Formula 1;

Scheme 8E

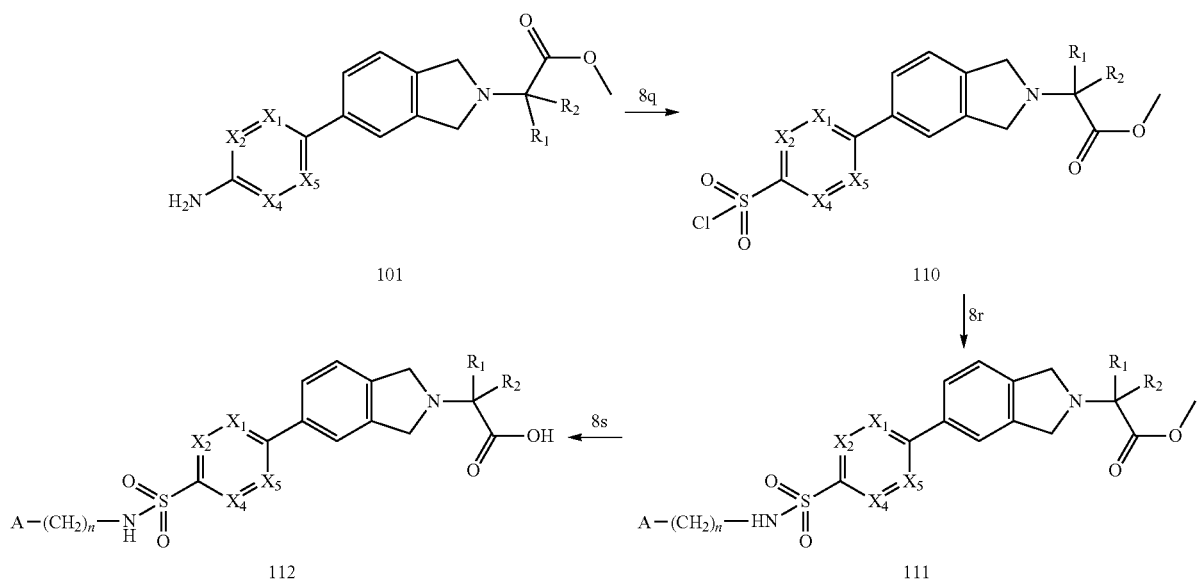

Step 1
Preparation of Compound of Formula 110:

Compound of formula 101 (obtained in Step 5 of Scheme 8A) can be treated with NaNO₂ and concentrated HCl to form a diazonium salt, which is treated with acetic acid saturated with SO₂ gas, followed by treatment with CuCl₂ at a temperature ranging from 0-35° C. to obtain compound of formula 110 (Reaction 8q).

Step 2
Preparation of Compound of Formula 111:

Compound of formula 110 can be treated with compound of formula 8T:

A-(CH₂)ₙ—NH₂    8T wherein A and n are as defined in formula 1;

in a suitable solvent such as dichloromethane and a base such as pyridine at temperature ranging from 20-35° C. to obtain compound of formula 111 (Reaction 8r).

Step 3
Preparation of Compound of Formula 112:

Compound of formula 111 can be hydrolysed using suitable reagent such as 1N LiOH or 1N NaOH in a suitable solvent such as MeOH or THF at temperature ranging from 20-35° C. to obtain compound of formula 112 (Reaction 8s).

Step 4

The carboxylic acid (compound of formula 112) may be optionally converted to its corresponding ester prodrugs by any suitable method well known in the art.

Scheme 9A: Preparation of Compound of Formula 1b; Wherein Y₁=CH₂, Y₂=C=O; X₁, X₂, X₄ and X₅ are Independently Selected from CH and CR, X₃=C; L=NHCONH; m=1-4; A, n, R and R₉ are as Defined in Formula 1;

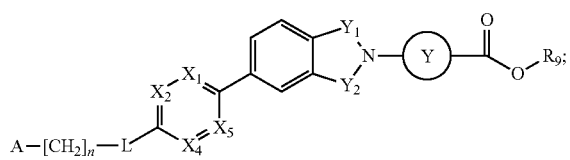

wherein Y is a cycloalkyl ring selected from:

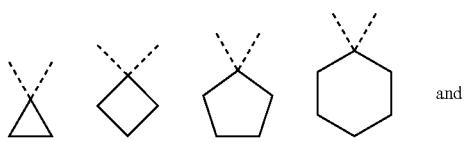

and wherein m = 1;

and

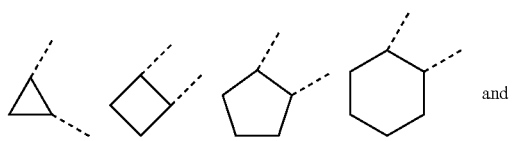

wherein m = 2;

-continued

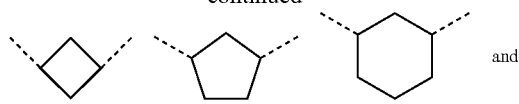

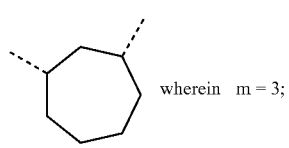

wherein m = 3;

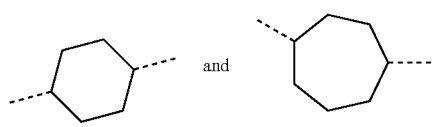

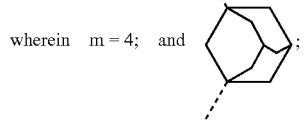

wherein m = 4; and

Step 1
Preparation of Compound of Formula 113:
Compound of formula 6 can be treated with compound M:

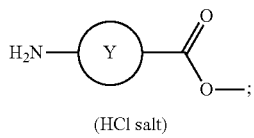

M (HCl salt)

in presence of a suitable base such as triethylamine in a suitable solvent such as benzene or toluene at a temperature ranging from 70-120° C. to obtain compound of formula 113 (Reaction 9a).

Alternatively, potassium carbonate may be used as a base in a suitable solvent such as DMF or THF at a temperature ranging from 50-80° C.

Step 2
Preparation of Compound of Formula 114:
Compound of formula 113 can be reduced using a suitable reducing agent such as Fe and ammonium chloride in a suitable solvent such as aqueous EtOH or EtOH:THF:$H_2O$ at a temperature ranging from 70-100° C. to obtain compound of formula 114 (Reaction 9b).

Scheme 9A

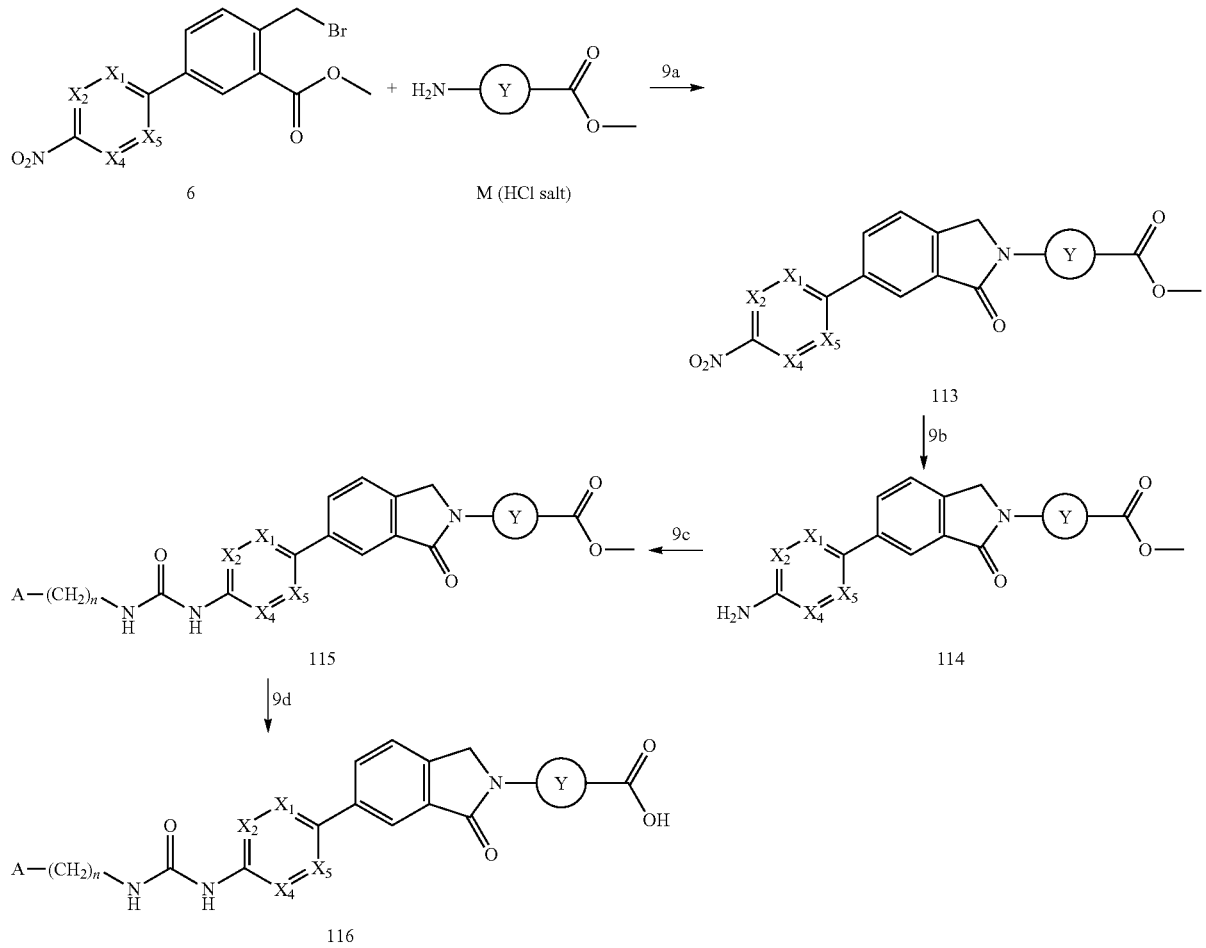

Alternatively, other reducing agents such as Fe and HCl in a solvent such as H$_2$O or ethanol or combination thereof; SnCl$_2$ in a solvent such as ethyl acetate; hydrogen over Raney Ni, Pd/C or Pt/C catalyst in a solvent such as methanol (pressure ranging from 50-80 psi and temperature ranging from 20-65° C.); or cobalt chloride and zinc in a solvent such as DMF or water (temperature ranging from 20-100° C.) may be used.

Step 3

Compound of formula 114 can be treated with compound of formula 8P:

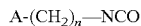

A-(CH$_2$)$_n$—NCO         8P wherein A and n are as defined in formula 1;
in a suitable solvent such as dichloromethane or THF at a temperature ranging from 20-35° C. to obtain compound of formula 115 (Reaction 9c).

Step 4
Preparation of Compound of Formula 116:

Compound of formula 115 can be hydrolysed using a suitable reagent such as 1N LiOH or 1N NaOH in a suitable solvent such as MeOH or THF at a temperature ranging from 20-35° C. to obtain compound of formula 116 (Reaction 9d).

Step 5

The carboxylic acid (compound of formula 116) may be optionally converted to its corresponding ester prodrugs by any suitable method well known in the art.

Scheme 9B: Preparation of Compound of Formula 1b; Wherein Y$_1$=CH$_2$, Y$_2$=C=O; X$_1$, X$_2$, X$_4$ and X$_5$ are Independently Selected from CH and CR, X$_3$=C; L=NHC(S)NH; m=1-4; A, n, R and R$_9$ are as Defined in Formula 1;

Scheme 9B

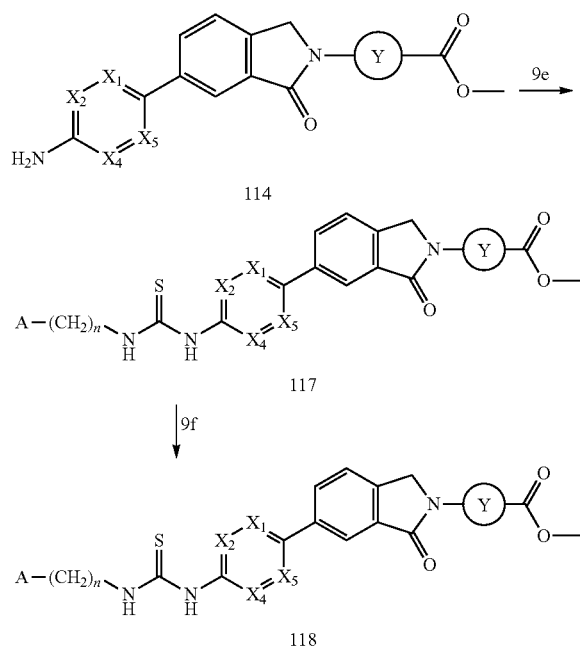

Step 1
Preparation of Compound of Formula 117:

Compound of formula 114 (obtained in Step 2 of Scheme 9A) can be treated with compound of formula 8Q:

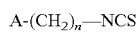

A-(CH$_2$)$_n$—NCS         8Q wherein A and n are as defined in formula 1;
in presence of a suitable solvent such as THF or dichloromethane at temperature ranging from 20-35° C. to obtain compound of formula 117 (Reaction 9e).

Step 2
Preparation of Compound of Formula 118:

Compound of formula 117 can be hydrolysed using suitable reagent such as 1N LiOH or 1N NaOH in a suitable solvent such as MeOH or THF at temperature ranging from 20-35° C. to obtain compound of formula 118 (Reaction 9f).

Step 3

The carboxylic acid (compound of formula 118) may be optionally converted to its corresponding ester prodrugs by any suitable method well known in the art.

Scheme 9C: Preparation of Compound of Formula 1b; Wherein Y$_1$=CH$_2$, Y$_2$=C=O; X$_1$, X$_2$, X$_4$ and X$_5$ are Independently Selected from CH and CR, X$_3$=C; L=*SO$_2$NH; m=1-4; A, n, R and R$_9$ are as Defined in Formula 1;

Scheme 9C

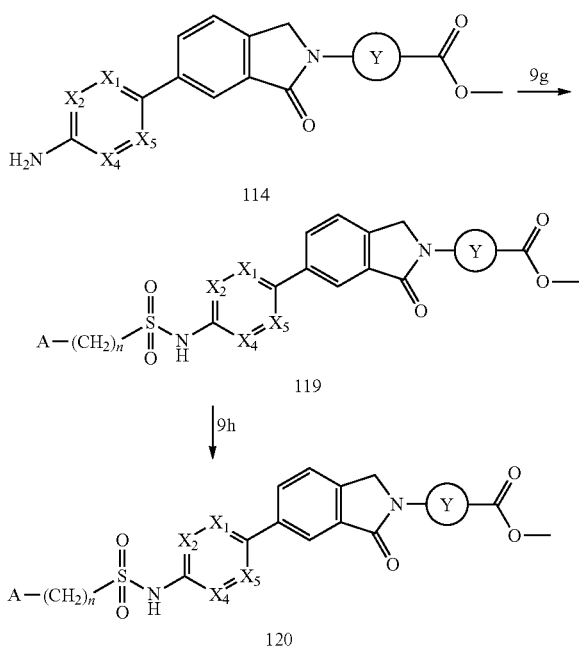

Step 1
Preparation of Compound of Formula 119:

Compound of formula 114 (obtained in Step 2 of Scheme 9A) can be treated with compound of formula 8R:

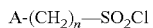

A-(CH$_2$)$_n$—SO$_2$Cl         8R wherein A and n are as defined in formula 1;
in presence of a suitable base such as pyridine or triethylamine in a suitable solvent such as dichloromethane at temperature ranging from 20-35° C. to obtain compound of formula 119 (Reaction 9g).

Step 2
Preparation of Compound of Formula 120:

Compound of formula 119 can be hydrolysed using suitable reagent such as 1N LiOH or 1N NaOH in a suitable solvent such as MeOH or THF at temperature ranging from 20-35° C. to obtain compound of formula 120 (Reaction 9h).

Step 3

The carboxylic acid (compound of formula 120) may be optionally converted to its corresponding ester prodrugs by any suitable method well known in the art.

Scheme 9D: Preparation of Compound of Formula 1b; Wherein $Y_1$=$CH_2$, $Y_2$=C=O; $X_1$, $X_2$, $X_4$ and $X_5$ are Independently Selected from CH and CR, $X_3$=C; L=*CONH; m=1-4; A, n, R and $R_9$ are as Defined in Formula 1;

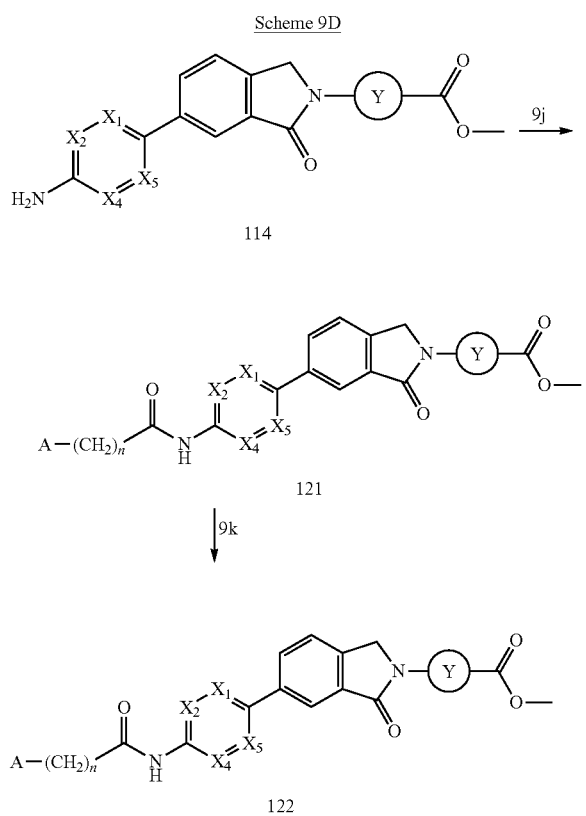

Step 1
Preparation of Compound of Formula 121:

Compound of formula 114 (obtained in Step 2 of Scheme 9A) can be treated with compound of formula 8S:

A-(CH$_2$)$_n$—COCl    8S wherein A and n are as defined in formula 1;
in presence of a suitable base such as pyridine in a suitable solvent such as dichloromethane or THF at temperature ranging from 20-35° C. to obtain compound of formula 121 (Reaction 9j).

Step 2
Preparation of Compound of Formula 122:

Compound of formula 121 can be hydrolysed using suitable reagent such as 1N LiOH or 1N NaOH in a suitable solvent such as MeOH or THF at temperature ranging from 20-35° C. to obtain compound of formula 122 (Reaction 9k).

Step 3

The carboxylic acid (compound of formula 122) may be optionally converted to its corresponding ester prodrugs by any suitable method well known in the art.

Scheme 9E: Preparation of Compound of Formula 1b; Wherein $Y_1$=$CH_2$, $Y_2$=C=O; $X_1$, $X_2$, $X_4$ and $X_5$ are Independently Selected from CH and CR, $X_3$=C; L=*NHSO$_2$; m=1-4; A, n, R and $R_9$ are as Defined in Formula 1;

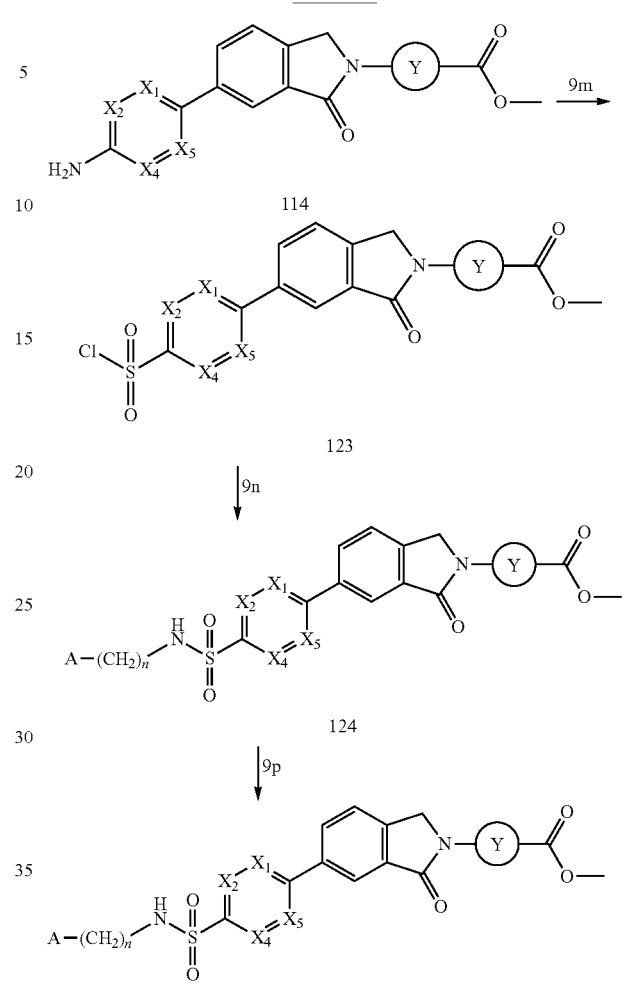

Step 1
Preparation of Compound of Formula 123:

Compound of formula 114 (obtained in Step 2 of Scheme 9A) can be treated with NaNO$_2$ and concentrated HCl to form a diazonium salt, which is treated with acetic acid saturated with SO$_2$ gas, followed by treatment with CuCl$_2$ at a temperature ranging from 0-35° C. to obtain compound of formula 123 (Reaction 9m).

Step 2
Preparation of Compound of Formula 124:

Compound of formula 123 can be treated with compound of formula 8T:

A-(CH$_2$)$_n$—NH$_2$    8T wherein A and n are as defined in formula 1;
in a suitable solvent such as dichloromethane and a base such as pyridine at temperature ranging from 20-35° C. to obtain compound of formula 124 (Reaction 9n).

Step 3
Preparation of Compound of Formula 125:

Compound of formula 124 can be hydrolysed using suitable reagent such as 1N LiOH or 1N NaOH in a suitable solvent such as MeOH or THF at temperature ranging from 20-35° C. to obtain compound of formula 125 (Reaction 9p).

Step 4

The carboxylic acid (compound of formula 125) may be optionally converted to its corresponding ester prodrugs by any suitable method well known in the art.

Scheme 10A: Preparation of Compound of Formula 1; Wherein $Y_1$=$CH_2$, $Y_2$=C(O); $X_1$, $X_2$, $X_4$ and $X_5$ are Selected from CH and CR, $X_3$=C; L=NHC(O)NH; m=1; A, n, R, $R_1$, $R_2$ and $R_9$ are as Defined in Formula 1;

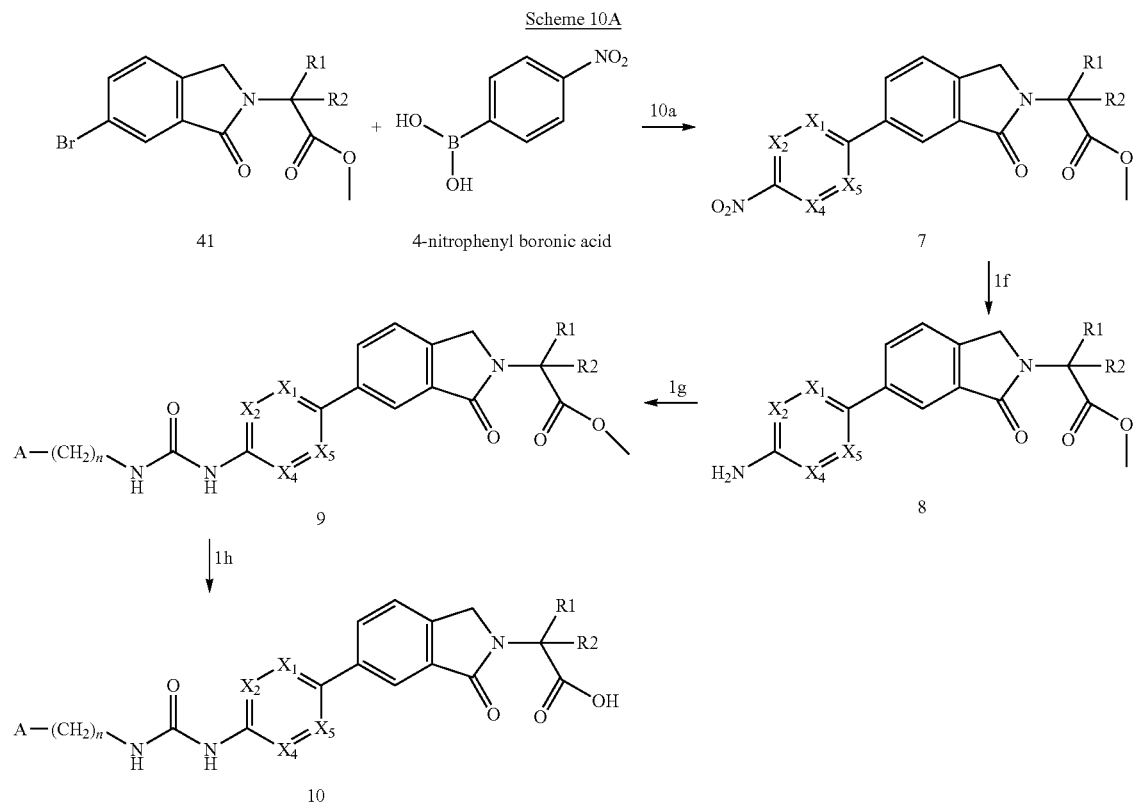

Scheme 10A

Step 1:
Preparation of Compound of Formula 7

The compound of formula 41 may be treated with a reagent such as commercially available 4-nitrophenyl boronic acid (Aldrich, USA) and commercially available Pd(dppf)Cl$_2$:CH$_2$Cl$_2$ (Aldrich, USA) in a suitable solvent such as DMF or dioxane at about 80° C. for about 3 h to obtain the compound of formula 7 (Reaction 10a).

Step 2:
Preparation of Compound of Formula 8

The compound of formula 8 is prepared analogous to Step 6 of Scheme 1A (Reaction 1f).

Step 3:
Preparation of Compound of Formula 10

The compound of formula 10 is prepared analogous to Steps 7, 8 and 9 of Scheme 1A (Reaction 1g and Reaction 1h).

In all the above mentioned schemes 1-10, the carboxylic acids formed may be optionally converted to their pharmaceutically acceptable salts.

The present invention also includes within its scope all isotopically labeled forms of compounds of formula 1, wherein one or more atoms of compounds of formula 1 are replaced by their respective isotopes. Examples of isotopes that may be incorporated into the compounds disclosed herein include, but are not limited to, isotopes of hydrogen such as $^2$H and $^3$H, carbon such as $^{11}$C, $^{13}$C and $^{14}$C, nitrogen such as $^{13}$N and $^{15}$N, oxygen such as $^{15}$O, $^{17}$O and $^{18}$O, chlorine such as $^{38}$Cl, fluorine such as $^{18}$F and sulphur such as $^{35}$S.

Substitution with heavier isotopes, for example, replacing one or more key carbon-hydrogen bonds with carbon-deuterium bond may show certain therapeutic advantages, for example, longer metabolism cycles, improved safety or greater effectiveness.

Isotopically labeled forms of compounds of formula 1, can be prepared by conventional techniques known to those skilled in the art or by processes analogous to those described above and in the subsequent section on examples by using an appropriate isotopically labeled reagent instead of non-labeled reagent.

The compounds of the present invention can also be converted into their corresponding pharmaceutically acceptable salts or solvates. The pharmaceutically acceptable salts of the compounds of the present invention are in particular salts, which can be used physiologically.

The term "pharmaceutically acceptable salts" is meant to include salts of the active compounds which are prepared with acids or bases, depending on the particular substituents found on the compounds described herein.

When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, magnesium, ammonium or organic base salt, or a similar salt. Examples of pharmaceutically acceptable organic base addition salts include those derived from organic bases like lysine, arginine, guanidine, diethanolamine and the like.

When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, glucuronic or galacturonic acids and the like. Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties. An example of physical properties that may differ is solubility in polar solvents.

Certain compounds of the present invention can exist in unsolvated forms as well as solvated forms, including hydrated forms. Certain compounds of the present invention may exist in multiple crystalline or amorphous forms. In general, all physical forms are equivalent for the uses contemplated by the present invention and are intended to be within the scope of the present invention.

Various polymorphs of compounds of formula 1 can be prepared by crystallization of the compounds under different conditions. The different conditions are, for example, using different commonly used solvents or their mixtures for crystallization; crystallization at different temperatures; various modes of cooling, ranging from very fast to very slow cooling during crystallizations. Polymorphs can also be obtained by heating or melting the compound followed by gradual or fast cooling. The presence of polymorphs can be determined by IR (Infra-red) spectroscopy, solid probe NMR (Nuclear Magnetic Resonance) spectroscopy, differential scanning calorimetry, powder X-ray diffraction or such other techniques.

As used herein, the term "stereoisomer" is a general term used for all isomers of individual compounds that differ only in the orientation of their atoms in space. The term stereoisomer includes mirror image isomers (enantiomers), mixtures of mirror image isomers (racemates, racemic mixtures), geometric (cis/trans or E/Z) isomers, and isomers of compounds with more than one chiral center that are not mirror images of one another (diastereoisomers). The compounds of the present invention may have asymmetric centers and occur as racemates, racemic mixtures, individual diastereoisomers, or enantiomers, or may exist as geometric isomers, with all isomeric forms of said compounds being included in the present invention. When a compound of formula 1 is desired as a single enantiomer, it may be obtained either by resolution of the final product or by stereospecific synthesis from either isomerically pure starting material or any convenient intermediate. Resolution of the final product, an intermediate or a starting material may be effected by any suitable method known in the art for example *Chiral reagents for Asymmetric Synthesis* by Leo A. Paquette; John Wiley & Sons Ltd.

Additionally, in situations wherein tautomers of the compounds of formula 1 are possible, the present invention is intended to include all tautomeric forms of the compounds.

The present invention also envisages prodrugs of the compound of formula 1. Prodrug derivatives of any compound of the invention are derivatives of said compounds which following administration release the parent compound in vivo via some chemical or physiological process, e.g., a prodrug on being brought to the physiological pH or through enzyme action is converted to the parent compound. The preferable prodrugs are those that are converted intracellularly, more preferably where the cellular converting location is the site of therapeutic action. For instance, preferred prodrugs are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters such as the pivaloyloxymethyl ester and the like conventionally used in the art (An introduction to Medicinal Chemistry, Graham. L. Patrick, Second Edition, Oxford University Press, pg 239-248; Prodrugs; Challenges and Rewards, Part 1 and Part 2, AAPS Press, Edited by Valentino J. Stella, Renald T. Borchardt, Michael J. Hagemon, Reza Oliyai, Hans Maag, Jefferson W. Tilley).

The present invention also envisages carboxylic acid isosteres of the compound of formula 1. The present invention further envisages N-oxide derivatives of the compound of formula 1.

The present invention furthermore relates to pharmaceutical compositions that contain an effective amount of at least one compound of formula 1 or its physiologically tolerable salt in addition to a customary pharmaceutically acceptable carrier, and to a process for the production of a pharmaceutical composition, which includes bringing at least one compound of formula 1, into a suitable administration form using a pharmaceutically suitable and physiologically tolerable excipient and, if appropriate, further suitable active compounds, additives or auxiliaries.

As used herein, the term "pharmaceutically acceptable carrier" refers to a material that is non-toxic, inert, solid, semi-solid or liquid filler, diluent, encapsulating material or formulation auxiliary of any type which is compatible with a subject, preferably a mammal, more preferably a human, and is suitable for delivering an active agent to the target site without terminating the activity of the agent.

The present invention also envisages the use of a compound of formula 1 or a pharmaceutically acceptable salt of the compound in combination with other pharmaceutically active compounds. For instance, a pharmaceutical composition including a compound of formula 1 or a pharmaceutically acceptable salt can be administered to a mammal, in particular a human, with any other anti-diabetic compound, in mixtures with one another or in the form of pharmaceutical preparations.

The term, "therapeutically effective amount" as used herein means an amount of compound or composition comprising compound of formula 1, effective in producing the desired therapeutic response in a particular patient suffering from DGAT1 mediated disorders. The therapeutically effective amount of the compound or composition will vary with the particular condition being treated, the age and physical condition of the end user, the severity of the condition being treated/prevented, the duration of the treatment, the nature of concurrent therapy, the specific compound or composition employed, the particular pharmaceutically acceptable carrier utilized, and like factors.

The term "subject" as used herein refers to an animal, preferably a mammal, and most preferably a human.

The term "mammal" used herein refers to warm-blooded vertebrate animals of the class Mammalia, including humans, characterized by a covering of hair on the skin and, in the female, milk-producing mammary glands for nourishing the young. The term mammal includes animals such as cat, dog, rabbit, bear, fox, wolf, monkey, deer, mouse, pig as well as human.

As used herein, the terms "treatment" "treat" and "therapy" and the like refer to alleviate, slow the progression, prophylaxis, attenuation or cure of existing disease (e.g., diabetes). "Prevent", as used herein, refers to delaying, slowing, inhibiting, reducing or ameliorating the onset of diseases or disorders mediated by diacylglycerol acyltransferase (DGAT), particularly DGAT1.

In an embodiment, the compounds of the present invention are particularly useful for the delay or treatment of a range of DGAT1 mediated diseases or disorders selected from obesity, diabetes, impaired glucose tolerance, diabetic neuropathy, diabetic nephropathy, diabetic retinopathy, anorexia nervosa, bulimia, cachexia, syndrome X, insulin resistance, hypoglycemia, hyperglycemia, hyperuricemia, hyperinsulinemia, hypercholesterolemia, hyperlipidemia, dyslipidemia, mixed dyslipidemia, hypertriglyceridemia, pancreatitis, metabolic acidosis, ketosis, steatosis, dysmetabolic syndrome and non-alcoholic fatty liver disease; cardiovascular diseases, such as atherosclerosis, arteriosclerosis, acute heart failure, congestive heart failure, coronary artery disease, cardiomyopathy, myocardial ischaemia, myocardial infarction, angina pectoris, hypertension, hypotension, stroke, ischemia, ischemic reperfusion injury, aneurysm, restenosis, peripheral vascular disease and vascular stenosis, diseases of the skin such as acne, infertility and polycystic ovary syndrome. The compounds of the present invention may be useful for the treatment of Hepatitis C infection.

In another embodiment, the DGAT1 mediated disorders of the present invention are selected from obesity, diabetes, impaired glucose tolerance, insulin resistance, impaired glucose tolerance, diabetic neuropathy, diabetic nephropathy, diabetic retinopathy, hypercholesterolemia, hypertriglyceridemia and hyperlipidemia.

In another embodiment, the present invention provides a method for the treatment of diseases or disorders mediated by DGAT1, comprising administering to a mammal in need thereof a therapeutically effective amount of a compound of formula 1, or a pharmaceutically acceptable salt or prodrug thereof.

In a further embodiment, the present invention provides a method for the treatment of obesity comprising administering to a mammal in need thereof a therapeutically effective amount of a compound of formula 1, or a pharmaceutically acceptable salt or prodrug thereof.

In an embodiment, the present invention provides the use of a compound of formula 1 in the treatment of diseases or disorders mediated by DGAT1.

In another embodiment, the present invention provides the use of a compound of formula 1 in the treatment of obesity.

In an embodiment, the present invention provides the use of a compound of formula 1 or a pharmaceutically acceptable salt or a prodrug thereof, for the manufacture of a medicament for the treatment of diseases or disorders mediated by DGAT1.

According to another embodiment of the present invention, there is provided the use of a compound of formula 1 or a pharmaceutically acceptable salt or a prodrug thereof, for the manufacture of a medicament for the treatment of obesity.

In an embodiment, the methods for treating DGAT1 associated disorders described herein use the pharmaceutical compositions described above and can be administered by the following administration routes, modes, etc.

Pharmaceutical Compositions and Methods:

The pharmaceuticals can be administered orally, for example in the form of pills, tablets, coated tablets, capsules, granules or elixirs. Administration, however, can also be carried out rectally, for example in the form of suppositories, or parenterally, for example intravenously, intramuscularly or subcutaneously, in the form of injectable sterile solutions or suspensions, or topically, for example in the form of solutions or transdermal patches, or in other ways, for example in the form of aerosols or nasal sprays.

As used herein, the term "pharmaceutically acceptable" means that the carrier, diluent, excipients, and/or salt must be compatible with the other ingredients of the formulation, and not deleterious to the recipient thereof.

The pharmaceutical preparations according to the invention are prepared in a manner known and familiar to one skilled in the art. Pharmaceutically acceptable inert inorganic and/or organic carriers and/or additives can be used in addition to the compound(s) of formula 1, and/or its (their) physiologically tolerable salt(s). For the production of pills, tablets, coated tablets and hard gelatin capsules it is possible to use, for example, lactose, corn starch or derivatives thereof, gum arabica, magnesia or glucose, etc. Carriers for soft gelatin capsules and suppositories are, for example, fats, waxes, natural or hardened oils, etc. Suitable carriers for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned.

The pharmaceutical preparations normally contain about 1 to 99%, for example, about 5 to 70%, or from about 10 to about 30% by weight of the compound of the formula 1 or its physiologically tolerable salt. The amount of the compound of the formula 1 or its physiologically tolerable salt in the pharmaceutical preparations normally is from about 5 to 500 mg. The dose of the compounds of this invention, which is to be administered, can cover a wide range. The dose to be administered daily is to be selected to suit the desired effect. A suitable dosage is about 0.001 to 100 mg/kg/day of the compound of formula 1 or their physiologically tolerable salt, for example, about 0.01 to 50 mg/kg/day of a compound of formula 1 or a pharmaceutically acceptable salt of the compound. If required, higher or lower daily doses can also be administered.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts.

In addition to the compound of the formula 1 or its physiologically acceptable salt and carrier substances, the pharmaceutical preparations can contain additives such as, for example, fillers, antioxidants, dispersants, emulsifiers, defoamers, flavors, preservatives, solubilizers or colorants. They can also contain two or more compounds of formula 1 or their physiologically tolerable salts. Furthermore, in addition to at least one compound of formula 1 or its physiologically tolerable salt, the pharmaceutical preparations can also contain one or more other therapeutically or prophylactically active ingredients.

It is understood that modifications that do not substantially affect the activity of the various embodiments of this invention are included within the invention disclosed herein. Accordingly, the following examples are intended to illustrate but not to limit the present invention.

The following abbreviations or terms are used herein:
AIBN 2,2'-Azobisisobutyronitrile
AlMe$_3$ Trimethylaluminium
CD$_3$OD Deuteriated methanol
CDCl$_3$ Deuteriated chloroform
CHCl$_3$ Chloroform
CCl$_4$ Carbon tetrachloride
CO$_2$ Carbon dioxide
CuCl$_2$ Cupric chloride
DCC N,N'-Dicyclohexyl carbodimide
DCM Dichloromethane
DMF N,N-Dimethylformamide
DMSO Dimethylsulfoxide
DMSO-d$_6$ Deuteriated dimethylsulfoxide
EtOH Ethanol
EtOAc Ethyl Acetate
eq equivalent
Fe Iron
g gram
h hour(s)
HCl Hydrochloric acid
H$_2$SO$_4$ Sulfuric acid
H$_2$O Water
LiAlH$_4$ Lithium aluminium hydride
LiOH Lithium hydroxide
mg/kg/day milligram/kilogram/day
MeOH Methanol
mg milligram(s)
mL milliliter
min minute(s)
mol Moles
mmol Millimoles
MgSO$_4$ Magnesium sulfate
N Normal
NBS N-bromosuccinimide
NaOH Sodium hydroxide
NaHCO$_3$ Sodium bicarbonate
Na$_2$CO$_3$ Sodium carbonate
NaNO$_2$ Sodium nitrite
Na$_2$SO$_4$ Sodium sulfate
nM nanomolar
Ni Nickel
PBr$_3$ phosphorus tribromide
Pd/C Palladium over activated carbon
Pd(dppf)Cl$_2$:CH$_2$Cl$_2$ [1,1'-bis(diphenylphosphino)-ferrocene]dichloropalladium (II), complex with dichloromethane, Sigma-Aldrich, USA
Pd(PPh$_3$) Triphenylphosphine Palladium
Pt/C platinum over activated carbon
Psi pounds per square inches
Room temperature 20-35° C.
SOCl$_2$ Thionyl chloride
SO$_2$ Sulfur dioxide
SnCl$_2$ Stannous chloride
TBAF Tributyl ammonium fluoride
TBDMS-Cl Tetrabutyl dimethyl silyl chloride
THF Tetrahydrofuran Example 1

5-Bromo-2-methyl benzoic acid

To a mixture of bromine (4 mL, 78 mmol) and iron (300 mg) cooled to 0° C., 2-methyl benzoic acid (5.0 g, 37 mmol) was added and the slurry was stirred at room temperature for about 16 h. The reaction mixture was triturated with water to provide a solid, which was isolated by filtration and dried at 50° C. for 4 h. The material obtained (8 g) was determined by $^1$H NMR to be a 60:40 mixture of the 5-bromo-2-methyl benzoic acid and 3-bromo-2-methyl benzoic acid isomers.

Further purification was performed on a separate batch of the 60:40 mixture by taking 12.5 g of the mixture and dissolving it in 200 mL of methanol. While stirring at room temperature, 250 mL of 0.1 N aqueous hydrochloric acid was added slowly producing a white solid. This solid was filtered and dried at 60° C. to afford the title compound.
Ref: —US2007/0213342 A1

Example 2

5-Bromo-2-methyl benzoic acid methyl ester

The compound of example 1 (20.3 g, 0.0944 mol) was dissolved in 150 mL methanol and cooled to 0° C. To this reaction mixture, thionyl chloride (28.07 g, 0.236 mol) was added slowly within 15-20 min. The reaction mixture was stirred at room temperature for 2-3 h. After completion of the reaction, MeOH was removed under vacuum. The oily material obtained was dissolved in ethyl acetate and washed with sodium bicarbonate, water and brine and dried over anhydrous sodium sulfate. The organic layer was concentrated to obtain the title compound.
Yield: 20.5 g (95.2%)
Ref: —US2007/0213342 A1

Example 3

Methyl 4-methyl-4'-nitrobiphenyl-3-carboxylate

The compound of example 2 (0.592 g, 0.0026 mol, 1.0 eq), bis(pinacolato)diboron (0.711 g, 0.0028 mol, 1.05 eq), palladium acetate (17.4 mg, 0.0007 mol, 3 mol % eq) and potassium acetate (0.765 g, 0.0078 mol, 3 eq) were taken in 10 mL of dry DMF. The mixture was degassed by gently bubbling argon through it for 30 min at room temperature. The mixture was then heated at 80° C. under argon atmosphere until completion of reaction (3 h). After completion of reaction, the reaction mixture was cooled to room temperature, followed by addition of 1-bromo-4-nitrobenzene (0.52 g, 0.0026 mol, 1.0 eq), cesium carbonate (1.27 g, 0.00039 mol, 1.5 eq) and Pd(PPh$_3$)$_4$ (0.090 g, 0.078 mol, 3 mol %). The reaction mixture was then heated at 80° C. for about 16 h under argon, then cooled to room temperature and diluted with water (20 mL) and ethyl acetate (20 mL). Black particles were removed by passing through a pad of celite. The organic layer was separated and washed twice with 15 mL of brine solution. After drying over anhydrous sodium sulfate, the solvent was removed to give crude 2-(4'-nitro-biphenyl-4-methyl)methyl benzoate, which was purified by column chromatography (silicagel, 1-5% ethyl acetate in petroleum ether) to obtain the title compound.

Yield: 0.650 mg (93%); $^1$H NMR (DMSO-d$_6$, 300 MHz): δ 8.282-8.244 (d, J=9 Hz, 2H), 8.126-8.191 (d, J=2.1 Hz, 1H), 7.947-7.917 (d, J=9 Hz, 2H), 7.844-7.850 (dd, J=2.1, 8.1 Hz, 1H), 7.474-7.448 (d, J=7.8 Hz, 1H), 3.853 (s, 3H), 2.539 (s, 3H); MS (ESI): m/z 272 (M+H).

Example 4

Methyl 4-(bromomethyl)-4'-nitrobiphenyl-3-carboxylate

The compound of example 3 (5.7 g, 0.021 mol) was dissolved in carbon tetrachloride (125 mL). AIBN (350 mg) and NBS (4.1 g, 0.0231 mol) were added and the reaction mixture was refluxed at 80° C. After completion of the reaction, the reaction mixture was cooled to room temperature and filtered through celite. The filtrate was concentrated to obtain a crude material containing 85% mono bromo and 10% dibromo product and 5% starting material. The crude was used directly without purification for the preparation of the compound of example 5.

Example 5

(S)-Methyl 3-methyl-2-(6-(4-nitrophenyl)-1-oxoisoindolin-2-yl)butanoate

A mixture of the compound of example 4 (1.54 g, 0.0044 mol) and L-valine methyl ester hydrochloride (0.813 g, 0.0048 mol) was taken in toluene (30 mL) in a round bottom flask. To this reaction mixture, triethyl amine (0.98 g, 0.0097 mol) was added and refluxed for 3-4 h. After completion of the reaction, the reaction mixture was diluted with ethyl acetate and washed with water and brine, dried over anhydrous sodium sulfate and concentrated to obtain an oily material, which was purified by column chromatography (silicagel, 30% ethyl acetate in petroleum ether).

Yield: 1.2 g (75%); $^1$H NMR (DMSO-d$_6$, 300 MHz): δ 8.312-8.283 (d, J=8.7 Hz, 2H), 8.077-8.019 (m, 4H), 7.789-7.761 (d, J=8.4 Hz, 1H), 4.698-4.568 (m, 3H), 3.668 (s, 3H), 2.353-2.233 (s, 1H), 0.995-0.973 (d, J=6.6 Hz, 3H), 0.847-0.825 (d, J=6.6 Hz, 3H); MS (ESI): m/z 369 (M+H).

Example 6

(S)-Methyl 2-(6-(4-aminophenyl)-1-oxoisoindolin-2-yl)-3-methylbutanoate

The compound of example 5 (0.9 g, 0.00244 mol), iron (0.32 g, 0.0057 mol) and ammonium chloride (0.551 g, 0.0103 mol) were taken in EtOH:THF:H$_2$O (15.5 mL, 9:4.5: 2.25). The reaction mixture was refluxed for about 16 h. After completion of the reaction, the reaction mixture was filtered through celite. The filtrate was concentrated to obtain a solid residue which was dissolved in ethyl acetate and washed with water and brine, dried over anhydrous sodium sulfate and concentrated to obtain a crude product, which was purified by column chromatography (silicagel, 30% ethyl acetate in petroleum ether).

Yield: 0.76 g (92%); $^1$H NMR (DMSO-d$_6$, 300 MHz): δ 7.824-7.785 (m, 2H), 7.627-7.601 (d, J=7.8 Hz, 1H), 7.433-7.404 (d, J=8.7 Hz, 2H), 6.673-6.644 (d, J=8.7 Hz, 2H), 5.302 (s, 2H), 4.625-4.495 (m, 3H), 3.680 (s, 3H), 2.380-2.258 (s, 1H), 1.007-0.985 (d, J=6.6 Hz, 3H), 0.854-0.831 (d, J=6.9 Hz, 3H); MS (ESI): m/z 339 (M+H).

Example 7

(S)-Methyl 2-(6-(4-(3-(4-fluorophenyl)ureido)phenyl)-1-oxoisoindolin-2-yl)-3-methyl butanoate The compound of example 6 (0.520 g, 0.00153 mol) was dissolved in 5 mL of dichloromethane and 4-fluorophenyl isocyanate (0.238 g, 0.00169 mol) was added and stirred at room temperature for 8-10 h. The reaction mixture was concentrated and purified by column chromatography (silicagel, 30-40% ethyl acetate in petroleum ether).

Yield: 0.690 g (94.5%)

Example 8

(S)-2-(6-(4-(3-(4-Fluorophenyl)ureido)phenyl)-1-oxoisoindolin-2-yl)-3-methyl butanoic acid The compound of example 7 (0.300 g, 0.00631 mol) was taken in THF (4 mL) and MeOH (1 mL) and to this reaction mixture, 1 N LiOH (0.0654 g, 0.001547 mol) was added and stirred at room temperature for 2-3 h. After completion of the reaction, the solvent was removed and the residue obtained was dissolved in water and acidified with 1 N HCl to obtain the title compound, which was filtered and dried.

Yield: 0.285 g (98%); $^1$H NMR (DMSO-d$_6$, 300 MHz): δ 13.061 (s, 1H), 8.868 (s, 1H), 8.833 (s, NH), 7.721-7.680 (t, J=3 Hz, 9 Hz, 2H), 7.638-7.630 (dd, J=3 Hz, 8 Hz, 1H), 7.630-7.600 (d, J=9 Hz, 2H), 7.614-7.581 (d, J=8.7 Hz, 2H), 7.581-7.552 (d, 8.7 Hz, 2H), 7.175-7.116 (t, J=9 Hz, 2H), 4.692-4.589 (dd, J=6.6 & 17.7 Hz, 2H), 4.548-4.515 (d, J=9.9 Hz, 1H), 2.416-2.291 (m, 1H), 1.036-1.014 (d, J=6.6 Hz, 3H), 0.868-0.846 (d, J=6.6 Hz, 3H); MS (ESI): m/z 460 (M−H), 462 (M+H)

Example 9

(S)-Methyl 2-(6-(4-(3-(2,4-difluorophenyl)ureido)phenyl)-1-oxoisoindolin-2-yl)-3-methylbutanoate The compound of example 9 was prepared analogous to compound of example 7 by reaction of compound of example 6 with 2,4-difluorophenyl isocyanate. The compound of example 9 was used directly without isolation for the preparation of compound of example 10.

Example 10

(S)-2-(6-(4-(3-(2,4-Difluorophenyl)ureido)phenyl)-1-oxoisoindolin-2-yl)-3-methylbutanoic acid The compound of example 10 was prepared analogous to compound of example 8 by hydrolysis of compound of example 7.

Yield: 83%; $^1$H NMR (DMSO-d$_6$, 300 MHz): δ 12.999 (s, 1H), 9.216 (s, 1H), 8.600 (s, NH), 8.125-8.086 (dd, J=2.7 Hz, 9 Hz, 1H), 7.719-7.677 (d, J=8 Hz, 2H), 7.635 (d, J=8 Hz, 2H), 7.597-7.588 (d, J=2.7 Hz, 1H), 7.635 (dd, J=2.7&8 Hz, 1H), 7.587-7.558 (d, 9 Hz, 1H), 7.370-7.293 (m, 1H), 7.099-7.045 (m, 1H), 4.686-4.667 (dd, J=6.6 & 17.7 Hz, 2H), 4.541-4.508 (d, J=9.9 Hz, 1H), 2.338-2.306 (m, 1H), 1.031-1.009

(d, J=6.6 Hz, 3H), 0.862-0.840 (d, J=6.6 Hz, 3H); MS (ESI): m/z 478 (M–H), m/z 480 (M+H).

Example 11

(S)-Methyl 2-(6-(4-(3-(2-fluorophenyl)ureido)phenyl)-1-oxoisoindolin-2-yl)-3-methyl butanoate The compound of example 11 was prepared analogous to compound of example 7 by reaction of compound of example 6 with 2-fluorophenyl isocyanate. The compound of example 11 was used directly without isolation for the preparation of compound of example 12.

Example 12

(S)-2-(6-(4-(3-(2-Fluorophenyl)ureido)phenyl)-1-oxoisoindolin-2-yl)-3-methyl butanoic acid The compound of example 12 was prepared analogous to compound of example 8 by hydrolysis of compound of example 11.
Yield: 83%; $^1$H NMR (DMSO-$d_6$, 300 MHz): δ 12.990 (s, 1H), 9.236 (s, 1H), 8.608 (s, NH), 8.158-8.125 (t, J=8 &8.5 Hz, 1H), 7.683-7.6 (d, J=9.5 Hz, 2H), 7.595-7.577 (d, J=9 Hz, 2H), 7.556 (d, 1H), 7.556-7.539 (d, 9 Hz, 2H), 7.241-7.202 (t, J=8.5 Hz, 1H), 7.144-7.113 (t, J=8 Hz, 1H), 7.013-6.973 (m, 1H), 4.693-4.601 (dd, J=6.6 & 17.7 Hz, 2H), 4.504-4.484 (d, J=10 Hz, 1H), 2.330-2.269 (m, 1H), 0.996-0.983 (d, J=6.5 Hz, 3H), 0.828-0.815 (d, J=6.6 Hz, 3H); MS (ESI): m/z 460 (M–H), m/z 462 (M+H).

Example 13

(S)-Methyl 2-(6-(4-(3-(3-fluorophenyl)ureido)phenyl)-1-oxoisoindolin-2-yl)-3-methylbutanoate The compound of example 13 was prepared analogous to compound of example 7 by reaction of compound of example 6 with 3-fluorophenyl isocyanate. The compound of example 13 was used directly without isolation for the preparation of compound of example 14.

Example 14

(S)-2-(6-(4-(3-(3-Fluorophenyl)ureido)phenyl)-1-oxoisoindolin-2-yl)-3-methyl butanoic acid The compound of example 14 was prepared analogous to compound of example 8 by hydrolysis of compound of example 13.
Yield: 95.8%; $^1$H NMR (DMSO-$d_6$, 300 MHz): δ 13.009 (s, 1H), 8.992 (s, 1H), 8.934 (s, NH), 7.723-7.720 (d, J=7.2 Hz, 2H), 7.679 (d, J=7.5 Hz, 1H), 7.637 (s, 1H), 7.612-7.603 (d, J=2.7 Hz, 2H), 7.587-7.557 (d, J=9 Hz, 2H), 7.557-7.529 (m, 1H), 7.362-7.284 (dd, J=8.1 Hz, 1H), 7.164-7.133 (d, J=8.1 Hz, 1H), 6.833-6.797 (dd, J=8.4 Hz, 1H), 4.747-4.609 (dd, J=6.3 & 17.7 Hz, 2H), 4.545-4.512 (d, J=9.9 Hz, 1H), 2.364-2.287 (m, 1H), 1.033-1.011 (d, J=6.6 Hz, 3H), 0.865-0.843 (d, J=6.6 Hz, 3H); MS (ESI): m/z 460 (M–H), m/z 462 (M+H)

Example 15

(S)-Methyl 3-methyl-2-(1-oxo-6-(4-(3-phenylureido)phenyl)isoindolin-2-yl)butanoate The compound of example 15 was prepared analogous to compound of example 7 by reaction of compound of example 6 with phenyl isocyanate. The compound of example 15 was used directly without isolation for the preparation of compound of example 16.

Example 16

(S)-3-Methyl-2-(1-oxo-6-(4-(3-phenylureido)phenyl)isoindolin-2-yl)butanoic acid

The compound of example 16 was prepared analogous to compound of example 8 by hydrolysis of compound of example 14.
Yield: 88%; $^1$H NMR (DMSO-$d_6$, 300 MHz): δ 13.042 (s, 1H), 8.949 (s, 1H), 8.736 (s, NH), 7.696-7.663 (t, J=9.9 Hz, 2H), 7.663-7.589 (d, J=8.5 Hz, 2H), 7.589 (s, 1H), 7.558-7.541 (d, J=0.7 Hz, 2H), 7.470-7.454 (d, J=8 Hz, 2H), 7.297-7.266 (t, J=5, 7.5, 12.5 Hz, 2H), 6.984-6.955 (t, J=7, 7.5, 14.5 Hz, 1H), 4.711-4.522 (dd, J=17.5 Hz, 2H), 4.522-4.502 (d, J=10 Hz, 1H), 2.32-2.301 (m, 1H), 1.012-0.999 (d, J=6.5 Hz, 3H), 0.844-0.831 (d, J=6.6 Hz, 3H); MS (ESI): m/z 442 (M+H).

Example 17

(S)-Methyl 2-(6-(4-(3-benzylureido)phenyl)-1-oxoisoindolin-2-yl)-3-methyl butanoate The compound of example 17 was prepared analogous to compound of example 7 by reaction of compound of example 6 with benzyl isocyanate. The compound of example 17 was used directly without isolation for the preparation of compound of example 18.

Example 18

(S)-2-(6-(4-(3-Benzylureido)phenyl)-1-oxoisoindolin-2-yl)-3-methylbutanoic acid

The compound of example 18 was prepared analogous to compound of example 8 by hydrolysis of compound of example 17.
Yield: 88.49%; $^1$H NMR (DMSO-$d_6$, 300 MHz): δ 13.124 (s, 1H), 8.803 (s, 1H), 7.698-7.674 (t, J=7.2 Hz, 2H), 7.618-7.593 (d, J=7.5 Hz, 1H), 7.583-7.568 (m, 1H), 7.554-7.520 (d, J=10.2 Hz, 2H), 7.520-7.491 (d, J=8.7 Hz, 1H), 7.375-7.292 (m, 2H), 7.248-7.197 (dd, J=2.7, 8.1 Hz, 2H), 6.799-6.680 (m, 1H), 4.725-4.596 (dd, J=2.7, 18 Hz, 2H), 4.532-4.499 (d, J=9.9 Hz, 1H), 4.338-4.319 (d, J=5.7 Hz, 2H), 4.244-4.224 (d, J=6 Hz, 1H), 2.378-2.279 (m, 1H), 1.027-1.005 (d, J=6.6 Hz, 3H), 0.856-0.834 (d, J=6.6 Hz, 3H); MS (ESI): m/z 458 (M+H).

Example 19

(S)-Methyl 2-(6-(4-(3-(2,6-difluorophenyl)ureido)phenyl)-1-oxoisoindolin-2-yl)-3-methylbutanoate The compound of example 19 was prepared analogous to compound of example 7 by reaction of compound of example 6 with 2,6-difluorophenyl isocyanate. The compound of example 19 was used directly without isolation for the preparation of compound of example 20.

Example 20

(S)-2-(6-(4-(3-(2,6-Difluorophenyl)ureido)phenyl)-1-oxoisoindolin-2-yl)-3-methylbutanoic acid The compound of example 20 was prepared analogous to compound of example 8 by hydrolysis of compound of example 19.

Yield: 90%; $^1$H NMR (DMSO-$d_6$, 300 MHz): δ 13.008 (s, 1H), 9.158 (s, 1H), 8.372 (s, NH), 7.717-7.713 (dd, J=1.3, 7.2 Hz, 2H), 7.629 (d, J=7.2 Hz, 2H), 7.598-7.572 (d, J=7.8 Hz, 1H), 7.572-7.542 (d, J=9 Hz, 2H), 7.378-7.280 (m, 1H), 7.196-7.143 (t, J=7.8 Hz, 2H), 4.741-4.602 (dd, J=6.3 & 17.7 Hz, 2H), 4.539-4.506 (d, J=9.9 Hz, 1H), 2.383-2.317 (m, 1H), 1.029-1.007 (d, J=6.6 Hz, 3H), 0.860-0.838 (d, J=6.6 Hz, 3H); MS (ESI): m/z 480 (M+H).

Example 21

(S)-Methyl 3-methyl-2-(1-oxo-6-(4-(3-m-tolylureido)phenyl)isoindolin-2-yl)butanoate The compound of example 21 was prepared analogous to compound of example 7 by reaction of compound of example 6 with 3-methyl phenyl isocyanate. The compound of example 21 was used directly without isolation for the preparation of compound of example 22.

Example 22

(S)-3-Methyl-2-(1-oxo-6-(4-(3-m-tolylureido)phenyl)isoindolin-2-yl)butanoic acid The compound of example 22 was prepared analogous to compound of example 8 by hydrolysis of compound of example 21.

Yield: 85%; $^1$H NMR (DMSO-$d_6$, 300 MHz): δ 13.013 (s, 1H), 8.842 (s, 1H), 8.670 (s, NH), 7.713-7.677 (dd, J=6, 7.2 Hz, 2H), 7.634-7.608 (dd, J=7.8, 7.8 Hz, 2H), 7.598-7.574 (d, J=7.2 Hz, 2H), 7.574-7.545 (d, J=8.7 Hz, 1H), 7.317 (s, 1H), 7.276-7.248 (d, J=8.4 Hz, 1H), 7.197-7.146 (t, J=7.5, 7.8 Hz, 1H), 6.813-6.793 (d, J=7.5 Hz, 1H), 4.747-4.610 (dd, J=5.7, 17.7 Hz, 2H), 4.547-4.514 (d, J=9.9 Hz, 1H), 2.365-2.320 (m, 1H), 2.290 (s, 3H), 1.034-1.012 (d, J=6.6 Hz, 3H), 0.866-0.844 (d, J=6.6 Hz, 3H); MS (ESI): m/z 456 (M−H), m/z 458 (M+H).

Example 23

(S)-Methyl 3-methyl-2-(1-oxo-6-(4-(3-p-tolylureido)phenyl)isoindolin-2-yl)butanoate The compound of example 23 was prepared analogous to compound of example 7 by reaction of compound of example 6 with 4-methyl phenyl isocyanate. The compound of example 23 was used directly without isolation for the preparation of compound of example 24.

Example 24

(S)-3-Methyl-2-(1-oxo-(6-(4-(3-p-tolylureido)phenyl)isoindolin-2-yl)butanoic acid The compound of example 22 was prepared analogous to compound of example 8 by hydrolysis of compound of example 21.

Yield: 90%; $^1$H NMR (DMSO-$d_6$, 300 MHz): δ 13.012 (s, 1H), 8.820 (s, 1H), 8.643 (s, NH), 7.714-7.674 (dd, J=0.9 Hz, 6 Hz, 2H), 7.632-7.591 (dd, J=3.3, 7.2 Hz, 2H), 7.591-7.569 (d, J=6.6 Hz, 2H), 7.569-7.540 (d, J=8.7 Hz, 1H), 7.375-7.347 (d, J=8.4 Hz, 2H), 7.114-7.087 (d, J=8.1 Hz, 2H), 4.745-4.609 (dd, J=5.4 & 17.7 Hz, 2H), 4.544-4.511 (d, J=9.9 Hz, 1H), 2.386-2.287 (m, 1H), 2.552 (s, 3H), 1.032-1.014 (d, J=6.3 Hz, 3H), 0.868-0.846 (d, J=6.6 Hz, 3H); MS (ESI): m/z 456 (M−H), m/z 458 (M+H).

Example 25

(S)-Methyl 2-(6-(4-(3-(3-methoxyphenyl)ureido)phenyl)-1-oxoisoindolin-2-yl)-3-methylbutanoate The compound of example 25 was prepared analogous to compound of example 7 by reaction of compound of example 6 with 4-methyl phenyl isocyanate. The compound of example 25 was used directly without isolation for the preparation of compound of example 26.

Example 26

(S)-2-(6-(4-(3-(3-Methoxyphenyl)ureido)phenyl)-1-oxoisoindolin-2-yl)-3-methyl butanoic acid The compound of example 26 was prepared analogous to compound of example 8 by hydrolysis of compound of example 25.

Yield: 96%; $^1$H NMR (DMSO-$d_6$, 300 MHz): δ 13.029 (s, 1H), 8.850 (s, 1H), 8.764 (s, NH), 7.721-7.677 (dd, J=1.2, 6.9 Hz, 2H), 7.636-7.611 (dd, J=3, 7.5 Hz, 2H), 7.596-7.577 (d, J=5.7 Hz, 2H), 7.577-7.548 (d, J=8.7 Hz, 1H), 7.218-7.203 (d, J=4.5 Hz, 1H), 7.210-7.195 (d, J=4.5 Hz, 1H), 6.975-6.945 (dd, J=0.9, 8.1 Hz, 1H), 6.587-6.533 (d, J=1.8, 8.1 Hz, 1H), 4.746-4.607 (dd, J=6.6, 17.7 Hz, 2H), 4.544-4.511 (d, J=9.9 Hz, 1H), 3.743 (s, 3H), 2.364-2.286 (m, 1H), 1.032-1.010 (d, J=6.6 Hz, 3H), 0.864-0.842 (d, J=6.6 Hz, 3H); MS (ESI): m/z 472 (M−H), m/z 474 (M+H).

Example 27

(S)-Methyl-2-(6-(4-(3-(4-methoxyphenyl)ureido)phenyl)-1-oxoisoindolin-2-yl)-3-methylbutanoate The compound of example 27 was prepared analogous to compound of example 7 by reaction of compound of example 6 with 4-methoxy phenyl isocyanate. The compound of example 27 was used directly without isolation for the preparation of compound of example 28.

Example 28

(S)-2-(6-(4-(3-(4-Methoxyphenyl)ureido)phenyl)-1-oxoisoindolin-2-yl)-3-methylbutanoic acid The compound of example 26 was prepared analogous to compound of example 8 by hydrolysis of compound of example 27.

Yield: 86%; 1H NMR (DMSO-$d_6$, 300 MHz): δ 13.072 (s, 1H), 8.864 (s, 1H), 8.634 (s, NH), 7.718-7.691 (dd, J=0.9, 8.1 Hz, 2H), 7.634-7.594 (dd, J=3.3, 7.2 Hz, 2H), 7.594-7.567 (d, J=8.1 Hz, 2H), 7.567-7.538 (d, J=8.7 Hz, 1H), 7.401-7.372 (d, J=8.7 Hz, 2H), 6.903-6.873 (d, J=9 Hz, 2H), 4.749-4.617 (dd, J=3.9, 17.7 Hz, 2H), 4.544-4.511 (d, J=9.9 Hz, 1H), 3.805 (s, 3H), 2.368-2.270 (m, 1H), 1.035-1.013 (d, J=6.6 Hz, 3H), 0.866-0.844 (d, J=6.6 Hz, 3H); MS (ESI): m/z 472 (M−H), m/z 474 (M+H).

Example 29

(S)-Methyl-2-(6-(4-(3-(3,5-difluorophenyl)ureido) phenyl)-1-oxoisoindolin-2-yl)-3-methylbutanoate The compound of example 29 was prepared analogous to compound of example 7 by reaction of compound of example 6 with 3,5-difluorophenyl isocyanate. The compound of example 29 was used directly without isolation for the preparation of compound of example 30.

Example 30

(S)-2-(6-(4-(3-(3,5-Difluorophenyl)ureido)phenyl)-1-oxoisoindolin-2-yl)-3-methylbutanoic acid The compound of example 30 was prepared analogous to compound of example 8 by hydrolysis of compound of example 29.
Yield: 94%; $^1$H NMR (DMSO-d$_6$, 300 MHz): δ 12.978 (s, 1H), 9.226 (s, 1H), 9.090 (s, NH), 7.728-7.702 (dd, J=0.9 Hz, 7.8 Hz, 2H), 7.681-7.565 (m, 5H), 7.261-7.239 (dd, J=5.1, 6.6 Hz, 2H), 6.814-6.775 (m, 1H), 4.686-4.667 (dd, J=6.6 & 17.7 Hz, 2H), 4.541-4.508 (d, J=9.9 Hz, 1H), 2.338-2.306 (m, 1H), 1.031-1.009 (d, J=6.6 Hz, 3H), 0.862-0.840 (d, J=6.6 Hz, 3H); MS (ESI) m/z: 478 (M−H), m/z 480 (M+H).

Example 31

(S)-Methyl 2-(6-(4-(3-(3,4-difluorophenyl)ureido) phenyl)-1-oxoisoindolin-2-yl)-3-methylbutanoate The compound of example 31 was prepared analogous to compound of example 7 by reaction of compound of example 6 with 3,4-difluorophenyl isocyanate. The compound of example 31 was used directly without isolation for the preparation of compound of example 32.

Example 32

(S)-2-(6-(4-(3-(3,4-Difluorophenyl)ureido)phenyl)-1-oxoisoindolin-2-yl)-3-methylbutanoic acid The compound of example 32 was prepared analogous to compound of example 8 by hydrolysis of compound of example 31.
Yield: 96%; $^1$H NMR (DMSO-d$_6$, 300 MHz): δ 13.020 (s, 1H), 8.997 (s, 1H), 8.961 (s, NH), 7.725-7.681 (dd, J=7.2, 2H), 7.658-7.559 (m, 6H), 7.417-7.321 (d, J=9.3 Hz, 1H), 7.173-7.144 (d, J=8.7 Hz, 1H), 4.751-4.611 (dd, J=6.6 & 17.7 Hz, 2H), 4.547-4.514 (d, J=9.9 Hz, 1H), 2.336-2.268 (m, 1H), 1.036-1.014 (d, J=6.6 Hz, 3H), 0.867-0.845 (d, J=6.6 Hz, 3H); MS (ESI): m/z 478 (M−H), m/z 480 (M+H).

Example 33

(S)-Methyl 2-(6-(4-(3-cyclohexylureido)phenyl)-1-oxoisoindolin-2-yl)-3-methylbutanoate The compound of example 33 was prepared analogous to compound of example 7 by reaction of compound of example 6 with cyclohexyl isocyanate. The compound of example 33 was used directly without isolation for the preparation of compound of example 34.

Example 34

(S)-2-(6-(4-(3-Cyclohexylureido)phenyl)-1-oxoisoindolin-2-yl)-3-methylbutanoic acid The compound of example 34 was prepared analogous to compound of example 8 by hydrolysis of compound of example 33.
Yield: 93%; $^1$H NMR (DMSO-d$_6$, 300 MHz): δ 13.063 (s, 1H), 8.441 (s, 1H), 7.891-7.866 (d, J=7.5 Hz, 1H), 7.866 (s, 1H), 7.682-7.655 (d, J=8.1 Hz, 1H), 7.626-7.597 (d, J=8.7 Hz, 2H), 7.500-7.471 (d, J=8.7 Hz, 2H), 6.130-6.104 (d, NH), 4.688-4.511 (dd, J=6.6 & 17.7 Hz, 2H), 4.554-4.521 (d, J=9.9 Hz, 1H), 3.493-3.432 (m, 1H), 2.338-2.306 (m, 1H), 1.834-1.796 (m, 2H), 1.737-1.646 (m, 2H), 1.569-1.528 (m, 2H), 1.376-1.300 (m, 2H), 1.189-1.122 (m, 2H), 1.041-1.019 (d, J=6.6 Hz, 3H), 0.873-0.851 (d, J=6.6 Hz, 3H); MS (ESI) m/z 450 (M+H)$^+$ Example 35

(S)-Methyl 3-methyl-2-(1-oxo-6-(4-(3-(4-(trifluoromethyl)phenyl)ureido)phenyl)isoindolin-2-yl)butanoate The compound of example 35 was prepared analogous to compound of example 7 by reaction of compound of example 6 with 4-trifluorophenyl isocyanate. The compound of example 35 was used directly without isolation for the preparation of compound of example 36.

Example 36

(S)-3-Methyl-2-(1-oxo-6-(4-(3-(4-(trifluoromethyl) phenyl)ureido)phenyl)isoindolin-2-yl)butanoic acid The compound of example 36 was prepared analogous to compound of example 8 by hydrolysis of compound of example 35.
Yield: 97%; $^1$H NMR (DMSO-d$_6$, 300 MHz): δ 13.060 (s, 1H), 9.205 (s, 1H), 9.008 (s, NH), 7.928-7.905 (d, J=6.9 Hz, 2H), 7.709-7.582 (m, 9H), 4.710-4.527 (m, 3H), 2.321-2.273 (m, 1H), 1.047-1.025 (d, J=6.6 Hz, 3H), 0.879-0.858 (d, J=6.6 Hz, 3H); MS (ESI): m/z 460 (M−H), m/z 512 (M+H).

Example 37

(S)-Methyl 3-methyl-2-(1-oxo-6-(4-(3-(3-(trifluoromethyl)phenyl)ureido)phenyl)isoindolin-2-yl)butanoate The compound of example 37 was prepared analogous to compound of example 7 by reaction of compound of example 6 with 3-trifluorophenyl isocyanate. The compound of example 37 was used directly without isolation for the preparation of compound of example 38.

Example 38

(S)-3-Methyl-2-(1-oxo-6-(4-(3-(3-(trifluoromethyl) phenyl)ureido)phenyl)isoindolin-2-yl)butanoic acid The compound of example 38 was prepared analogous to compound of example 8 by hydrolysis of compound of example 37.

Yield: 97%; ¹H NMR (DMSO-d₆, 300 MHz): δ 13.018 (s, 1H), 9.117 (s, 1H), 8.968 (s, NH), 8.039 (s, 1H), 7.927-7.905 (d, J=6.6 Hz, 2H), 7.709-7.682 (d, J=8.1 Hz, 3H), 7.610-7.582 (d, J=8.4 Hz, 3H), 7.551-7.498 (t, J=7.8, 8.1 Hz, 1H), 7.334-7.310 (d, J=7.2 Hz, 1H), 4.705-4.529 (dd, J=17.7, 18.6 Hz, 2H), 4.561-4.529 (d, J=9.6 Hz, 1H), 2.324-2.271 (m, 1H), 1.046-1.024 (d, J=6.6 Hz, 3H), 0.878-0.857 (d, J=6.6 Hz, 3H); MS (ESI): m/z 510 (M−H).

Example 39

(S)-Methyl 2-(6-(4-(3-(4-cyanophenyl)ureido)phenyl)-1-oxoisoindolin-2-yl)-3-methylbutanoate The compound of example 39 was prepared analogous to compound of example 7 by reaction of compound of example 6 with 4-cyanophenyl isocyanate. The compound of example 39 was used directly without isolation for the preparation of compound of example 40.

Example 40

(S)-2-(6-(4-(3-(4-Cyanophenyl)ureido)phenyl)-1-oxoisoindolin-2-yl)-3-methyl butanoic acid The compound of example 40 was prepared analogous to compound of example 8 by hydrolysis of compound of example 39.

Yield: 94%; ¹H NMR (DMSO-d₆, 300 MHz): δ 13.023 (s, 1H), 9.292 (s, 1H), 9.050 (s, NH), 7.926-7.904 (d, J=6.6 Hz, 2H), 7.763-7.734 (d, J=8.7 Hz, 2H), 7.718-7.671 (m, 4H), 7.642 (s, 1H), 7.604-7.575 (d, J=8.7 Hz, 2H), 4.701-4.526 (dd, J=7.2, 17.7 Hz, 2H), 4.559-4.526 (d, J=9.9 Hz, 1H), 2.366-2.45 (m, 1H), 1.179-1.168 (d, J=6.6 Hz, 3H), 0.876-0.854 (d, J=6.6 Hz, 3H); MS (ESI): m/z 467 (M−H), m/z 469 (M+H).

Example 41

(S)-Methyl 2-(6-(4-(3-(3-cyanophenyl)ureido)phenyl)-1-oxoisoindolin-2-yl)-3-methylbutanoate The compound of example 41 was prepared analogous to compound of example 7 by reaction of compound of example 6 with 3-cyanophenyl isocyanate. The compound of example 41 was used directly without isolation for the preparation of compound of example 42.

Example 42

(S)-2-(6-(4-(3-(3-Cyanophenyl)ureido)phenyl)-1-oxoisoindolin-2-yl)-3-methyl butanoic acid The compound of example 42 was prepared analogous to compound of example 8 by hydrolysis of compound of example 41.

Yield: 84%; ¹H NMR (DMSO-d₆, 300 MHz): δ 13.075 (s, 1H), 9.238 (s, 1H), 9.117 (s, NH), 7.998 (s, 1H), 7.928-7.906 (d, J=6.6 Hz, 2H), 7.709-7.686 (d, J=6.9 Hz, 4H), 7.604-7.576 (d, J=8.4 Hz, 2H), 7.536-7.467 (t, J=7.8, 8.1 Hz, 2H), 7.448-7.423 (d, J=7.5 Hz, 1H), 4.705-4.642 (dd, J=7.2, 17.7 Hz, 2H), 4.560-4.527 (d, J=9.9 Hz, 1H), 2.396-2.248 (m, 1H), 1.044-1.022 (d, J=6.6 Hz, 3H), 0.877-0.855 (d, J=6.6 Hz, 3H); MS (ESI): m/z 567 (M−H), m/z 569 (M+H).

Example 43

(S)-Methyl 2-(6-(4-(3-(4-chloro-2-phenoxyphenyl)ureido)phenyl)-1-oxo isoindolin-2-yl)-3-methylbutanoate The compound of example 43 was prepared analogous to compound of example 7 by reaction of compound of example 6 with 4-chloro-2-phenoxy phenyl isocyanate.

Yield: 96%; ¹H NMR (DMSO-d₆, 300 MHz): δ 9.509 (s, 1H), 8.718 (s, 1H), 8.426-8.418 (d, J=2.4 Hz, 1H), 7.939-7.907 (d, J=1.5, 9.6 Hz, 2H), 7.713-7.685 (d, J=8.4 Hz, 3H), 7.582-7.553 (d, J=8.7 Hz, 2H), 7.479-7.426 (t, J=7.8, 8.1 Hz, 2H), 7.234-7.184 (t, J=7.5 Hz, 1H), 7.121-7.095 (d, J=7.8 Hz, 2H), 7.027-7.019 (dd, J=2.4, 7.5 Hz, 1H), 6.861-6.832 (d, J=8.7 Hz, 1H), 4.641-4.607 (m, 3H), 3.688 (s, 3H), 2.410-2.273 (m, 1H), 1.016-0.994 (d, J=6.6 Hz, 3H), 0.866-0.844 (d, J=6.6 Hz, 3H); MS (ESI): m/z 582 (M−H), m/z 584 (M+H).

Example 44

(S)-2-(6-(4-(3-(4-Chloro-2-phenoxyphenyl)ureido)phenyl)-1-oxoisoindolin-2-yl)-3-methylbutanoic acid The compound of example 44 was prepared analogous to compound of example 8 by hydrolysis of compound of example 43.

Yield: 82%; ¹H NMR (DMSO-d₆, 300 MHz): δ 13.039 (s, 1H), 9.530 (s, 1H), 8.724 (s, 1H), 8.425-8.417 (d, J=2.4 Hz, 1H), 7.926-7.903 (d, J=6.9 Hz, 2H), 7.712-7.685 (d, J=8.1 Hz, 3H), 7.583-7.554 (d, J=9 Hz, 2H), 7.477-7.425 (t, J=7.5, 8.1 Hz, 2H), 7.232-7.207 (t, J=7.2, 7.5 Hz, 1H), 7.121-7.094 (d, J=8.1 Hz, 2H), 7.027-6.989 (dd, J=2.7, 8.7 Hz, 1H), 6.861-6.832 (d, J=8.7 Hz, 1H), 4.741-4.530 (dd, J=6.9, 17.4 Hz, 2H), 4.563-4.530 (d, d=9.9 Hz, 1H), 2.380-2.310 (m, 1H), 1.048-1.026 (d, J=6.6 Hz, 3H), 0.881-0.859 (d, J=6.6 Hz, 3H); MS (ESI) m/z 568 (M−H), m/z 570 (M+H).

Example 45

(S)-Methyl 2-(6-(4-(3-(5-chloro-2-phenoxyphenyl)ureido)phenyl)-1-oxoisoindolin-2-yl)-3-methylbutanoate The compound of example 45 was prepared analogous to compound of example 7 by reaction of compound of example 6 with 5-chloro-2-phenoxy phenyl isocyanate.

¹H NMR (DMSO-d₆, 300 MHz): δ 9.507 (s, 1H), 8.716 (s, 1H), 8.426-8.418 (d, J=2.4 Hz, 1H), 7.933-7.907 (d, J=7.8 Hz, 2H), 7.712-7.684 (d, J=8.4 Hz, 3H), 7.582-7.553 (d, J=8.7 Hz, 2H), 7.478-7.426 (t, J=7.8 Hz, 2H), 7.233-7.184 (t, J=7.2, 7.5 Hz, 1H), 7.121-7.095 (d, J=7.8 Hz, 2H), 7.026-6.989 (dd, J=2.4, 8.7 Hz, 1H), 6.860-6.831 (d, J=8.7 Hz, 1H), 4.641-4.608 (m, 3H), 3.687 (s, 3H), 2.371-2.316 (m, 1H), 1.016-0.994 (d, J=6.6 Hz, 3H), 0.866-0.844 (d, J=6.6 Hz, 3H); MS (ESI): m/z 582 (M−H), m/z 584 (M+H).

Example 46

(S)-2-(6-(4-(3-(5-Chloro-2-phenoxyphenyl)ureido)phenyl)-1-oxoisoindolin-2-yl)-3-methylbutanoic acid The compound of example 46 was prepared analogous to compound of example 8 by hydrolysis of compound of example 45.

Yield: 85%; ¹H NMR (DMSO-d₆, 300 MHz): δ 13.060 (s, 1H), 9.527 (s, 1H), 8.725 (s, 1H), 8.426-8.417 (d, J=2.7 Hz, 1H), 7.926-7.902 (d, J=7.2 Hz, 2H), 7.713-7.685 (d, J=8.4 Hz, 3H), 7.583-7.554 (d, J=9 Hz, 2H), 7.477-7.425 (t, J=7.5, 8.1 Hz, 2H), 7.232-7.207 (t, J=7.2, 7.5 Hz, 1H), 7.121-7.095 (d, J=7.8 Hz, 2H), 7.026-6.989 (dd, J=2.4, 8.7 Hz, 1H), 6.860-6.831 (d, J=8.7 Hz, 1H), 4.741-4.530 (dd, J=6.9, 17.4 Hz, 2H), 4.563-4.530 (d, J=9.9 Hz, 1H), 2.380-2.310 (m, 1H), 1.048-1.026 (d, J=6.6 Hz, 3H), 0.881-0.859 (d, J=6.6 Hz, 3H); MS (ESI): m/z 568 (M−H), m/z 570 (M+H).

Example 47

(S)-Methyl 3-methyl-2-(1-oxo-6-(4-(3-(2-phenoxyphenyl)ureido)phenyl)isoindolin-2-yl)butanoate The compound of example 47 was prepared analogous to compound of example 7 by reaction of compound of example 6 with 2-phenoxy phenyl isocyanate.

Yield: 98%; ¹H NMR (DMSO-d₆, 300 MHz): δ 9.424 (s, 1H), 8.516 (s, 1H), 8.321-8.294 (d, J=7.2 Hz, 1H), 7.927-7.900 (d, J=8.1 Hz, 2H), 7.700-7.670 (dd, J=2.1, 6.9 Hz, 3H), 7.579-7.550 (d, J=8.7 Hz, 2H), 7.460-7.407 (t, J=7.8, 8.1 Hz, 2H), 7.199-7.153 (t, J=6.6, 7.2 Hz, 1H), 7.131-7.103 (d, J=8.4 Hz, 1H), 7.081-7.055 (d, J=7.8 Hz, 2H), 7.002-6.946 (m, 1H), 6.867-6.841 (dd, J=0.6, 7.8 Hz, 1H), 4.640-4.598 (m, 3H), 3.687 (s, 3H), 2.371-2.293 (m, 1H), 1.016-0.994 (d, J=6.6 Hz, 3H), 0.866-0.844 (d, J=6.6 Hz, 3H); MS (ESI): m/z 548 (M−H), m/z 550 (M+H).

Example 48

(S)-3-Methyl-2-(1-oxo-6-(4-(3-(2-phenoxyphenyl)ureido)phenyl)isoindolin-2-yl)butanoic acid The compound of example 48 was prepared analogous to compound of example 8 by hydrolysis of compound of example 47.

Yield: 68%; ¹H NMR (DMSO-d₆, 300 MHz): δ 13.039 (s, COOH), 9.428 (s, NH), 8.519 (s, NH), 8.325-8.295 (dd, J=0.9, 8.7 Hz, 1H), 7.920-7.896 (d, J=7.2 Hz, 2H), 7.701-7.673 (d, J=8.4 Hz, 3H), 7.580-7.551 (d, J=8.7 Hz, 2H), 7.460-7.407 (t, J=7.8, 8.1 Hz, 2H), 7.200-7.103 (m, 2H), 7.081-7.055 (d, J=7.8 Hz, 2H), 7.002-6.946 (m, 1H), 6.865-6.841 (d, J=7.2 Hz, 1H), 4.703-4.529 (dd, J=6.9, 17.7, 18.3 Hz, 2H), 4.562-4.529 (d, J=9.9 Hz, 1H), 2.325-2.294 (m, 1H), 1.048-1.026 (d, J=6.6 Hz, 3H), 0.881-0.859 (d, J=6.6 Hz, 3H); MS (ESI): m/z 534 (M−H), m/z 536 (M+H).

Example 49

(S)-Methyl 3-methyl-2-(1-oxo-6-(4-(3-(4-phenoxyphenyl)ureido)phenyl)isoindolin-2-yl)butanoate The compound of example 49 was prepared analogous to compound of example 7 by reaction of compound of example 6 with 4-phenoxy phenyl isocyanate.

Yield: 98%; ¹H NMR (DMSO-d₆, 300 MHz): δ 8.816 (s, NH), 8.743 (s, NH), 7.931-7.905 (d, J=7.8 Hz, 1H), 7.709-7.669 (m, 2H), 7.597-7.568 (d, J=8.7 Hz, 3H), 7.514-7.461 (m, 2H), 7.398-7.345 (t, J=7.5, 8.4 Hz, 2H), 7.121-7.096 (t, J=7.5 Hz, 1H), 7.015-6.953 (m, 5H), 4.641-4.608 (m, 3H), 3.687 (s, 3H), 2.478-2.293 (m, 1H), 1.016-0.994 (d, J=6.6 Hz, 3H), 0.866-0.844 (d, J=6.6 Hz, 3H); MS (ESI): m/z 548 (M−H), m/z 550 (M+H).

Example 50

(S)-3-Methyl-2-(1-oxo-6-(4-(3-(4-phenoxyphenyl)ureido)phenyl)isoindolin-2-yl)butanoic acid The compound of example 50 was prepared analogous to compound of example 8 by hydrolysis of compound of example 49.

Yield: 71.9%; ¹H NMR (DMSO-d₆, 300 MHz): δ 13.102 (s, COOH), 8.849 (s, NH), 8.779 (s, NH), 7.923-7.901 (d, J=6.6 Hz, 2H), 7.700-7.671 (d, J=8.7 Hz, 3H), 7.600-7.571 (d, J=8.7 Hz, 2H), 7.517-7.488 (d, J=8.7 Hz, 2H), 7.398-7.345 (t, J=7.5, 8.4 Hz, 2H), 7.120-7.071 (t, J=7.2, 7.5 Hz, 1H), 7.015-6.955 (m, 4H), 4.710-4.531 (dd, J=17.7, 19.8 Hz, 2H), 4.564-4.531 (d, J=9.9 Hz, 1H), 2.328-2.296 (m, 1H), 1.050-1.028 (d, J=6.6 Hz, 3H), 0.882-0.860 (d, J=6.6 Hz, 3H); MS (ESI): m/z 534 (M−H), m/z 536 (M+H).

Example 51

(S)-Methyl 2-(6-(4-(3-(2-fluorophenyl)thioureido)phenyl)-1-oxoisoindolin-2-yl)-3-methylbutanoate The compound of example 6 (0.150, g, 0.000443 mol) was taken in THF (3 mL) and to this solution was added 2-fluorophenyl isothiocyanate (0.074 g, 0.000448 mol). The reaction mixture was stirred at room temperature for 8-10 h. The reaction mixture was concentrated and directly used for next step without isolation.

Example 52

(S)-2-(6-(4-(3-(2-Fluorophenyl)thioureido)phenyl)-1-oxoisoindolin-2-yl)-3-methylbutanoic acid The compound of example 51 (0.224 g, 0.000456 mol) was taken in THF (4 mL) and MeOH (1 mL). To this reaction mixture, 1 N LiOH (0.095 g, 0.0022 mol) was added and the reaction mixture was stirred at room temperature for 2-3 h. After completion of the reaction, the solvent was evaporated and the residue obtained was dissolved in water and acidified with 1 N HCl to obtain the title compound, which was filtered and dried.

Yield: 0.180 g (90%); ¹H NMR (DMSO-d₆, 300 MHz): δ 13.152 (s, COOH), 10.184 (s, NH), 9.662 (s, NH), 7.945-7.89 (t, J=6.9 Hz, 2H), 7.745-7.591 (m, 6H), 7.289-7.165 (m, 3H), 4.724-4.521 (dd, J=18, 21.6 Hz, 2H), 4.553-4.521 (d, J=9.6 Hz, 1H), 2.346-2.270 (m, 1H), 1.046-1.024 (d, J=6.6 Hz, 3H), 0.880-0.858 (d, J=6.6 Hz, 3H); MS (ESI): m/z 476 (M−H), m/z 478 (M+H).

Example 53

(S)-Methyl 3-methyl-2-(1-oxo-6-(4-(3-p-tolylthioureido)phenyl)isoindolin-2-yl)butanoate The compound of example 53 was prepared analogous to compound of example 51 by reaction of compound of example 6 with 4-methyl phenyl isothiocyanate. The compound of example 53 was used directly without isolation for the preparation of compound of example 54.

Example 54

(S)-3-Methyl-2-(1-oxo-6-(4-(3-p-tolylthioureido)phenyl)isoindolin-2-yl)butanoic acid The compound of example 54 was prepared analogous to compound of example 52 by hydrolysis of compound of example 53.

Yield: 83%; $^1$H NMR (DMSO-d$_6$, 300 MHz): δ 12.987 (s, COOH), 9.854 (s, NH), 9.817 (s, NH), 7.942-7.919 (d, J=6.9 Hz, 2H), 7.724-7.69 (d, J=8.1 Hz, 3H), 7.629-7.600 (d, J=8.7 Hz, 2H), 7.378-7.350 (d, J=8.4 Hz, 2H), 7.165-7.137 (d, J=8.4 Hz, 2H), 4.714-4.528 (dd, J=18, 18.9 Hz, 2H), 4.560-4.528 (d, J=9.6 Hz, 1H), 2.348-2.325 (m, 1H), 2.250 (s, 3H), 1.046-1.025 (d, J=6.3 Hz, 3H), 0.882-0.860 (d, J=6.3 Hz, 3H); MS (ESI): m/z 472 (M−H), m/z 474 (M+H).

Example 55

(S)-Methyl 2-(6-(4-(3-(3-fluorophenyl)thioureido) phenyl)-1-oxoisoindolin-2-yl)-3-methylbutanoate The compound of example 55 was prepared analogous to compound of example 51 by reaction of compound of example 6 with 3-fluorophenyl isothiocyanate. The compound of example 55 was used directly without isolation for the preparation of compound of example 56.

Example 56

(S)-2-(6-(4-(3-(3-Fluorophenyl)thioureido)phenyl)-1-oxoisoindolin-2-yl)-3-methylbutanoic acid The compound of example 56 was prepared analogous to compound of example 52 by hydrolysis of compound of example 55.
Yield: 93%; $^1$H NMR (DMSO-d$_6$, 300 MHz): δ 13.127 (s, COOH), 10.173 (s, NH), 10.140 (s, NH), 7.945-7.923 (d, J=6.6 Hz, 1H), 7.923 (s, 1H), 7.743-7.698 (m, 3H), 7.626-7.597 (d, J=8.4 Hz, 2H), 7.597-7.551 (m, 1H), 7.430-7.358 (dd, J=6.6, 8.1 Hz, 1H), 7.305-7.277 (d, J=8.4 Hz, 1H), 6.983-6.929 (m, 1H), 4.726-4.524 (dd, J=18, 22.2 Hz, 2H), 4.556-4.524 (d, J=9.6 Hz, 1H), 2.391-2.250 (m, 1H), 1.048-1.026 (d, J=6.6 Hz, 3H), 0.882-0.860 (d, J=6.6 Hz, 3H); MS (ESI): m/z: 476 (M−H), m/z: 478 (M+H).

Example 57

(S)-Methyl 2-(6-(4-(3-(4-methoxyphenyl)thioureido) phenyl)-1-oxoisoindolin-2-yl)-3-methylbutanoate The compound of example 57 was prepared analogous to compound of example 51 by reaction of compound of example 6 with 4-methoxyphenyl isothiocyanate. The compound of example 57 was used directly without isolation for the preparation of compound of example 58.

Example 58

(S)-2-(6-(4-(3-(4-Methoxyphenyl)thioureido)phenyl)-1-oxoisoindolin-2-yl)-3-methylbutanoic acid The compound of example 58 was prepared analogous to compound of example 52 by hydrolysis of compound of example 57.
Yield: 85%; $^1$H NMR (DMSO-d$_6$, 300 MHz): δ 12.941 (s, COOH), 9.756 (s, NH), 9.694 (s, NH), 7.941-7.919 (d, J=6.6 Hz, 2H), 7.723-7.695 (d, J=8.4, 3H), 7.623-7.594 (d, J=8.7 Hz, 2H), 7.368-7.338 (d, J=9.2H), 6.936-6.906 (d, J=9 Hz, 2H), 4.710-4.530 (dd, J=17.7, 18 Hz, 2H), 4.562-4.530 (d, J=9.6 Hz, 1H), 3.754 (s, 3H), 2.370-2.251 (m, 1H), 1.046-1.024 (d, J=6.6 Hz, 3H), 0.882-0.860 (d, J=6.6 Hz, 3H); MS (ESI): m/z 488 (M−H), m/z 490 (M+H).

Example 59

(S)-Methyl 2-(6-(4-(3-(3-methoxyphenyl)thioureido) phenyl)-1-oxoisoindolin-2-yl)-3-methylbutanoate The compound of example 59 was prepared analogous to compound of example 51 by reaction of compound of example 6 with 3-methoxyphenyl isothiocyanate. The compound of example 59 was used directly without isolation for the preparation of compound of example 60.

Example 60

(S)-2-(6-(4-(3-(3-Methoxyphenyl)thioureido)phenyl)-1-oxoisoindolin-2-yl)-3-methylbutanoic acid The compound of example 60 was prepared analogous to compound of example 52 by hydrolysis of compound of example 59.
Yield: 87%; $^1$H NMR (DMSO-d$_6$, 300 MHz): δ 13.023 (s, COOH), 9.955 (s, NH), 9.916 (s, NH), 7.945-7.922 (d, J=6.9 Hz, 1H), 7.922 (s, 1H), 7.732-7.704 (d, J=8.4 Hz, 3H), 7.626-7.597 (d, J=8.7 Hz, 2H), 7.273-7.206 (d, J=8.1 Hz, 2H), 7.070-7.043 (d, J=8.1 Hz, 1H), 6.734-6.707 (dd, J=1.8, 8.1 Hz, 1H), 4.715-4.528 (dd, J=17.7, 19.2 Hz, 2H), 4.559-4.528 (d, J=9.3 Hz, 1H), 3.745 (s, 3H), 2.348-2.272 (m, 1H), 1.046-1.025 (d, J=6.3 Hz, 3H), 0.881-0.860 (d, J=6.3 Hz, 3H); MS (ESI): m/z 488 (M−H), m/z 490 (M+H)

Example 61

(S)-Methyl 2-(6-(4-(3-(4-chlorophenyl)thioureido) phenyl)-1-oxoisoindolin-2-yl)-3-methylbutanoate The compound of example 61 was prepared analogous to compound of example 51 by reaction of compound of example 6 with 4-chlorophenyl isothiocyanate. The compound of example 61 was used directly without isolation for the preparation of compound of example 62.

Example 62

(S)-2-(6-(4-(3-(4-Chlorophenyl)thioureido)phenyl)-1-oxoisoindolin-2-yl)-3-methyl butanoic acid The compound of example 62 was prepared analogous to compound of example 52 by hydrolysis of compound of example 61.
Yield: 84%; $^1$H NMR (DMSO-d$_6$, 300 MHz): δ 10.319 (s, NH), 10.276 (s, NH), 7.928 (s, 2H), 7.716-7.689 (d, J=8.1 Hz, 3H), 7.635-7.607 (d, J=8.4 Hz, 2H), 7.586-7.556 (d, J=9 Hz, 2H), 7.400-7.370 (d, J=9 Hz, 2H), 4.748-4.520 (dd, J=18, 32.4 Hz, 2H), 4.539-4.507 (d, J=9.6 Hz, 1H), 2.366-2.247 (m, 1H), 1.047-1.025 (d, J=6.6 Hz, 3H), 0.877-0.855 (d, J=6.6 Hz, 3H); MS (ESI): m/z 492 (M−H), m/z: 494 (M+H).

Example 63

(S)-Methyl 2-(6-(4-(3-(4-chlorophenyl)thioureido) phenyl)-1-oxoisoindolin-2-yl)-3-methylbutanoate The compound of example 63 was prepared analogous to compound of example 51 by reaction of compound of example 6 with 3-chlorophenyl isothiocyanate. The compound of example 63 was used directly without isolation for the preparation of compound of example 64.

Example 64

(S)-2-(6-(4-(3-(3-Chlorophenyl)thioureido)phenyl)-1-oxoisoindolin-2-yl)-3-methyl butanoic acid The compound of example 64 was prepared analogous to compound of example 52 by hydrolysis of compound of example 63.

Yield: 86%; $^1$H NMR (DMSO-$d_6$, 300 MHz): δ 12.900 (s, 1H), 10.277 (s, NH), 10.199 (s, NH), 7.940 (s, 2H), 7.738-7.710 (m, 4H), 7.625-7.597 (d, J=8.4 Hz, 2H), 7.457-7.430 (d, J=8.1 Hz, 1H), 7.384-7.331 (d, J=7.8, 8.1 Hz, 1H), 7.189-7.163 (d, J=7.8 Hz, 1H), 4.733-4.518 (dd, J=18, 25.5 Hz, 2H), 4.539-4.507 (d, J=9.3 Hz, 1H), 2.346-2.272 (m, 1H), 1.047-1.025 (d, J=6.6 Hz, 3H), 0.879-0.858 (d, J=6.3 Hz, 3H); MS (ESI): m/z 492 (M−H), m/z: 494 (M+H).

Example 65

(S)-Methyl 3-methyl-2-(1-oxo-6-(4-(3-(2-(trifluoromethyl)phenyl)thioureido)phenyl)isoindolin-2-yl) butanoate The compound of example 65 was prepared analogous to compound of example 51 by reaction of compound of example 6 with 2-trifluorophenyl isothiocyanate. The compound of example 65 was used directly without isolation for the preparation of compound of example 66.

Example 66

(S)-3-Methyl-2-(1-oxo-6-(4-(3-(2-trifluoromethyl)phenyl)thioureido)phenyl)isoindolin-2-yl)butanoic acid The compound of example 66 was prepared analogous to compound of example 52 by hydrolysis of compound of example 65.

Yield: 96%; $^1$H NMR (DMSO-$d_6$, 300 MHz): δ 13.064 (s, COOH), 10.192 (s, NH), 9.492 (s, NH), 7.952-7.929 (d, J=6.9 Hz, 2H), 7.766-7.664 (m, 7H), 7.613-7.587 (d, J=7.8 Hz, 1H), 7.521-7.471 (t, J=7.5 Hz, 1H), 4.720-4.556 (d, J=17.7, 21 Hz, 2H), 4.556-4.524 (d, J=9.6 Hz, 1H), 2.324-2.270 (m, 1H), 1.046-1.024 (d, J=6.6 Hz, 3H), 0.880-0.858 (d, J=6.6 Hz, 3H); MS (ESI): m/z 526 (M−H), m/z 428 (M+H).

Example 67

(S)-Methyl 2-(6-(4-(3-(4-cyanophenyl)thioureido)phenyl)-1-oxoisoindolin-2-yl)-3-methylbutanoate The compound of example 67 was prepared analogous to compound of example 51 by reaction of compound of example 6 with 4-cyanophenyl isothiocyanate. The compound of example 67 was used directly without isolation for the preparation of compound of example 66.

Example 68

(S)-2-(6-(4-(3-(4-Cyanophenyl)thioureido)phenyl)-1-oxoisoindolin-2-yl)-3-methyl butanoic acid The compound of example 68 was prepared analogous to compound of example 52 by hydrolysis of compound of example 69.

Yield: 96%; $^1$H NMR (DMSO-$d_6$, 300 MHz): δ 13.002 (s, COOH), 10.394 (s, 2NH), 7.948-7.927 (d, J=6.3 Hz, 2H), 7.792 (m, 4H), 7.757-7.700 (t, J=8.7, 8.4 Hz, 3H), 7.634-7.606 (d, J=8.4 Hz, 2H), 4.724-4.557 (dd, J=18, 21.6 Hz, 2H), 4.557-4.525 (d, J=9.6 Hz, 1H), 2.349-2.273 (m, 1H), 1.047-1.025 (d, J=6.6 Hz, 3H), 0.882-0.859 (d, J=6.9 Hz, 3H); MS (ESI): m/z 483 (M−H), m/z 485 (M+H).

Example 69

(S)-Methyl 2-(6-(4-(3-(3-cyanophenyl)thioureido)phenyl)-1-oxoisoindolin-2-yl)-3-methylbutanoate The compound of example 69 was prepared analogous to compound of example 51 by reaction of compound of example 6 with 3-cyanophenyl isothiocyanate. The compound of example 69 was used directly without isolation for the preparation of compound of example 70.

Example 70

(S)-2-(6-(4-(3-(3-Cyanophenyl)thioureido)phenyl)-1-oxoisoindolin-2-yl)-3-methylbutanoic acid The compound of example 70 was prepared analogous to compound of example 52 by hydrolysis of compound of example 69.

Yield: 86%; $^1$H NMR (DMSO-$d_6$, 300 MHz): δ 12.941 (s, COOH), 10.275 (s, NH), 10.177 (s, NH), 8.039 (s, 1H), 7.950 (d, J=6.6 Hz, 2H), 7.826-7.794 (m, 1H), 7.757-7.700 (d, J=8.4, 8.7 Hz, 3H), 7.621-7.517 (m, 4H), 4.722-4.526 (dd, J=18, 20.4 Hz, 2H), 4.558-4.526 (d, J=9.6 Hz, 1H), 2.348-2.273 (m, 1H), 1.047-1.025 (d, J=6.6 Hz, 3H), 0.881-0.859 (d, J=6.6 Hz, 3H); MS (ESI): m/z 483 (M−H), m/z 485 (M+H).

Example 71

(S)-Methyl 3-methyl-2-(1-oxo-6-(4-(3-o-tolylthioureido)phenyl)isoindolin-2-yl)butanoate The compound of example 71 was prepared analogous to compound of example 51 by reaction of compound of example 6 with 2-methyl phenyl isothiocyanate. The compound of example 71 was used directly without isolation for the preparation of compound of example 72.

Example 72

(S)-3-Methyl-2-(1-oxo-6-(4-(3-o-tolylthioureido)phenyl)isoindolin-2-yl)butanoic acid The compound of example 72 was prepared analogous to compound of example 52 by hydrolysis of compound of example 73.

Yield: 88%; $^1$H NMR (DMSO-$d_6$, 300 MHz): δ 12.941 (s, COOH), 9.846 (s, NH), 9.479 (s, NH), 7.940-7.917 (d, J=6.9 Hz, 2H), 7.728-7.700 (m, 3H), 7.646-7.618 (d, J=8.4 Hz, 2H), 7.284-7.148 (m, 4H), 4.715-4.525 (dd, J=18, 19.8 Hz, 2H), 4.557-4.525 (d, J=9.6 Hz, 1H), 2.368-2.313 (m, 1H), 2.269 (s, 3H), 1.045-1.023 (d, J=6.6 Hz, 3H), 0.879-0.857 (d, J=6.6 Hz, 3H); MS (ESI): m/z 472 (M−H), m/z 474 (M+H).

Example 73

(S)-Methyl 2-(6-(4-(3-(2-methoxyphenyl)thioureido)phenyl)-1-oxoisoindolin-2-yl)-3-methylbutanoate The compound of example 73 was prepared analogous to compound of example 51 by reaction of compound of example 6 with 2-methoxyphenyl isothiocyanate. The compound of example 73 was used directly without isolation for the preparation of compound of example 74.

Example 74

(S)-2-(6-(4-(3-(2-Methoxyphenyl)thioureido)phenyl)-1-oxoisoindolin-2-yl)-3-methylbutanoic acid The compound of example 74 was prepared analogous to compound of example 52 by hydrolysis of compound of example 75.

Yield: 80%; $^1$H NMR (DMSO-$d_6$, 300 MHz): δ 3.525 (s, COOH), 10.074 (s, NH), 9.255 (s, NH), 7.952-7.902 (t, J=6.9, 8.1 Hz, 3H), 7.745-7.632 (m, 5H), 7.201-7.144 (m, 1H), 7.088-7.064 (d, J=7.2 Hz, 1H), 6.968-6.918 (d, J=7.2, 8.1 Hz, 1H), 4.712-4.563 (dd, J=17.4, 17.7 Hz, 2H), 4.653-4.532 (d, J=9.3 Hz, 1H), 3.854 (s, 3H), 2.370-2.251 (m, 1H), 1.047-1.025 (d, J=6.6 Hz, 3H), 0.883-0.861 (d, J=6.6 Hz, 3H); MS (ESI): m/z 488 (M−H), m/z 490 (M+H).

Example 75

(S)-Methyl 3-methyl-2-(1-oxo-6-(4-(3-(3-(trifluoromethyl)phenyl)thioureido)phenyl)isoindolin-2-yl)butanoate The compound of example 75 was prepared analogous to compound of example 51 by reaction of compound of example 6 with 3-trifluorophenyl isothiocyanate. The compound of example 75 was used directly without isolation for the preparation of compound of example 76.

Example 76

(S)-3-Methyl-2-(1-oxo-6-(4-(3-(3-(trifluoromethyl)phenyl)thioureido)phenyl)isoindolin-2-yl)butanoic acid The compound of example 76 was prepared analogous to compound of example 52 by hydrolysis of compound of example 75.

Yield: 67%; $^1$H NMR (DMSO-$d_6$, 300 MHz): δ 13.070 (s, COOH), 10.213 (s, NH), 10.143 (s, NH), 7.987 (s, 1H), 7.958-7.930 (m, 2H), 7.804-7.702 (m, 4H), 7.617-7.627 (d, J=8.4 Hz, 3H), 7.483-7.457 (d, J=9 Hz, 1H), 4.712-4.529 (dd, J=16.8, 18 Hz, 2H), 4.561-4.529 (d, J=9.6 Hz, 1H), 2.348-2.272 (m, 1H), 1.046-1.024 (d, J=6.6 Hz, 3H), 0.882-0.860 (d, J=6.6 Hz, 3H); MS (ESI): m/z: 526 (M−H), m/z: 528 (M+H).

Example 77

(S)-Methyl 3-methyl-2-(1-oxo-6-(4-(phenylsulfonamido)phenyl)isoindolin-2-yl)butanoate To a solution of compound of example 6 (0.250 g, 0.0073 mol) in dichloromethane (5 mL), pyridine (0.174 g, 0.00219 mol) was added and stirred for 5 min. To this reaction mixture, benzene sulfonyl chloride was added and stirred for about 16 h. After completion of the reaction, solvent was evaporated and the crude title compound obtained was directly used for the preparation of compound of example 78.

Example 78

(S)-3-Methyl-2-(1-oxo-6-(4-(phenylsulfonamido)phenyl)isoindolin-2-yl)butanoic acid The compound of example 77 (0.400 g, 0.000749 mol) was taken in THF (4 mL) and MeOH (1 mL) and to this reaction mixture, 1 N LiOH (0.157 g, 0.0037 mol) was added and stirred at room temperature for 2-3 h. After completion of the reaction, the solvent was evaporated and the residue obtained was dissolved in water and acidified with 1 N HCl to obtain the title compound, which was filtered and dried.

Yield: 0.310 g (80%); $^1$H NMR (DMSO-$d_6$, 300 MHz): δ 13.052 (s, COOH), 10.491 (s, NH), 7.854-7.808 (m, 4H), 7.675-7.547 (m, 6H), 7.221-7.192 (d, J=8.7 Hz, 2H), 4.680-4.506 (dd, J=17.4, 18 Hz, 2H), 4.539-4.506 (d, J=9.9 Hz, 1H), 2.349-2.230 (m, 1H), 1.030-1.008 (d, J=6.6 Hz, 3H), 0.858-0.836 (d, J=6.6 Hz, 3H); MS (ESI): m/z 465 (M+H), m/z 463 (M−H).

Example 79

(S)-Methyl 2-(6-(4-(4-cyanophenylsulfonamido)phenyl)-1-oxoisoindolin-2-yl)-3-methylbutanoate The compound of example 79 was prepared analogous to compound of example 77 by reaction of compound of example 6 with 4-cyanobenzene sulfonyl chloride. The compound of example 79 was used directly without isolation for the preparation of compound of example 80.

Example 80

(S)-2-(6-(4-(4-Cyanophenylsulfonamido)phenyl)-1-oxoisoindolin-2-yl)-3-methyl butanoic acid The compound of example 80 was prepared analogous to compound of example 78 by hydrolysis of compound of example 79.

Yield: 93%; $^1$H NMR (DMSO-$d_6$, 300 MHz): δ 13.016 (s, COOH), 10.627 (s, NH), 7.904-7.872 (m, 1H), 7.872 (s, 1H), 7.758 (m, 2H), 7.697-7.684 (m, 2H), 7.666-7.637 (d, J=8.7 Hz, 3H), 7.251-7.222 (d, J=8.7 Hz, 2H), 4.697-4.510 (dd, J=17.7, 20.4 Hz, 2H), 4.532-4.499 (d, J=9.9 Hz, 1H), 2.308-2.275 (m, 1H), 1.032-1.010 (d, J=6.6 Hz, 3H), 0.862-0.839 (d, J=6.9 Hz, 3H); MS (ESI): m/z 490 (M+H), m/z 488 (M−H).

Example 81

(S)-Methyl 2-(6-(4-(3,4-difluorophenylsulfonamido)phenyl)-1-oxoisoindolin-2-yl)-3-methylbutanoate The compound of example 81 was prepared analogous to compound of example 77 by reaction of compound of example 6 with 3,4-difluorobenzene sulfonyl chloride. The compound of example 81 was used directly without isolation for the preparation of compound of example 82.

Example 82

(S)-2-(6-(4-(3,4-Difluorophenylsulfonamido)phenyl)-1-oxoisoindolin-2-yl)-3-methylbutanoic acid The compound of example 82 was prepared analogous to compound of example 78 by hydrolysis of compound of example 81.

Yield: 96%; ¹H NMR (DMSO-d₆, 300 MHz): δ 13.016 (s, COOH), 10.589 (s, NH), 7.860-7.843 (m, 3H), 7.689-7.649 (m, 5H), 7.232-7.203 (d, J=8.7 Hz, 2H), 4.688-4.511 (dd, J=17.1, 18 Hz, 2H), 4.543-4.511 (d, J=9.6 Hz, 1H), 2.331-2.255 (m, 1H), 1.033-1.011 (d, J=6.6 Hz, 3H), 0.862-0.840 (d, J=6.6 Hz, 3H); MS (ESI) m/z: 501 (M+H), m/z 499 (M−H).

Example 83

(S)-Methyl 2-(6-(4-(2,4-difluorophenylsulfonamido)phenyl)-1-oxoisoindolin-2-yl)-3-methylbutanoate The compound of example 83 was prepared analogous to compound of example 77 by reaction of compound of example 6 with 2,4-difluorobenzene sulfonyl chloride. The compound of example 83 was used directly without isolation for the preparation of compound of example 84.

Example 84

(S)-2-(6-(4-(2,4-Difluorophenylsulfonamido)phenyl)-1-oxoisoindolin-2-yl)-3-methylbutanoic acid The compound of example 84 was prepared analogous to compound of example 78 by hydrolysis of compound of example 85.
Yield: 93%; ¹H NMR (DMSO-d₆, 300 MHz): δ 12.986 (s, COOH), 10.848 (s, NH), 7.995-7.917 (m, 1H), 7.860-7.839 (m, 2H), 7.761-7.634 (m, 3H), 7.588-7.514 (td, J=2.4, 11.1 Hz, 1H), 7.341-7.247 (m, 1H), 7.228-7.199 (d, J=8.7 Hz, 2H), 4.684-4.509 (dd, J=17.4, 18 Hz, 2H), 4.542-4.509 (d, J=9.9 Hz, 1H), 2.350-2.232 (m, 1H), 1.032-1.010 (d, J=6.6 Hz, 3H), 0.861-0.839 (d, J=6.6 Hz, 3H); MS (ESI): m/z 501 (M+H).

Example 85

(S)-Methyl 2-(6-(4-(3,4-dimethoxyphenylsulfonamido)phenyl)-1-oxoisoindolin-2-yl)-3-methylbutanoate The compound of example 85 was prepared analogous to compound of example 77 by reaction of compound of example 6 with 3,4-dimethoxybenzene sulfonyl chloride. The compound of example 85 was used directly without isolation for the preparation of compound of example 86.

Example 86

(S)-2-(6-(4-(3,4-Dimethoxyphenylsulfonamido)phenyl)-1-oxoisoindolin-2-yl)-3-methylbutanoic acid The compound of example 86 was prepared analogous to compound of example 78 by hydrolysis of compound of example 85.
Yield: 89%; ¹H NMR (DMSO-d₆, 300 MHz): δ 13.041 (s, COOH), 10.267 (s, NH), 7.856-7.835 (dd, J=1.8, 2.4 Hz, 2H), 7.679-7.664 (d, J=4.5 Hz, 1H), 7.647-7.617 (d, J=9 Hz, 2H), 7.393-7.358 (dd, J=2.1, 8.4 Hz, 1H), 7.292-7.285 (d, J=2.1 Hz, 1H), 7.233-7.204 (d, J=8.7 Hz, 2H), 7.088-7.059 (d, J=8.7 Hz, 1H), 4.683-4.509 (dd, J=17.4, 18 Hz, 2H), 4.542-4.505 (d, J=9.9 Hz, 1H), 3.784 (s, 3H), 3.754 (s, 3H), 2.353-2.232 (m, 1H), 1.032-1.010 (d, J=6.6 Hz, 3H), 0.861-0.839 (d, J=6.6 Hz, 3H); MS (ESI): m/z 525 (M+H), m/z 523 (M−H).

Example 87

(S)-Methyl 2-(6-(4-(3-chlorophenylsulfonamido)phenyl)-1-oxoisoindolin-2-yl)-3-methylbutanoate The compound of example 87 was prepared analogous to compound of example 77 by reaction of compound of example 6 with 3-chlorobenzene sulfonyl chloride. The compound of example 87 was used directly without isolation for the preparation of compound of example 88.

Example 88

(S)-2-(6-(4-(3-Chlorophenylsulfonamido)phenyl)-1-oxoisoindolin-2-yl)-3-methylbutanoic acid The compound of example 88 was prepared analogous to compound of example 78 by hydrolysis of compound of example 87.
Yield: 89%; ¹H NMR (DMSO-d₆, 300 MHz): δ 13.037 (s, COOH), 10.578 (s, NH), 7.869-7.851 (m, 3H), 7.771-7.709 (m, 2H), 7.686-7.611 (m, 3H), 7.536-7.530 (d, J=1.8 Hz, 1H), 7.228-7.199 (d, J=8.7 Hz, 2H), 4.658-4.529 (dd, J=9.6, 17.1 Hz, 2H), 4.543-4.511 (d, J=9.6 Hz, 1H), 2.332-2.233 (m, 1H), 1.033-1.011 (d, J=6.6 Hz, 3H), 0.862-0.840 (d, J=6.6 Hz, 3H); MS (ESI): m/z 497 (M−H).

Example 89

(S)-Methyl 2-(6-(4-(4-methoxyphenylsulfonamido)phenyl)-1-oxoisoindolin-2-yl)-3-methylbutanoate The compound of example 89 was prepared analogous to compound of example 77 by reaction of compound of example 6 with 4-methoxybenzene sulfonyl chloride. The compound of example 89 was used directly without isolation for the preparation of compound of example 90.

Example 90

(S)-2-(6-(4-(4-Methoxyphenylsulfonamido)phenyl)-1-oxoisoindolin-2-yl)-3-methylbutanoic acid The compound of example 90 was prepared analogous to compound of example 78 by hydrolysis of compound of example 89.
Yield: 87%; ¹H NMR (DMSO-d₆, 300 MHz): δ 13.074 (s, COOH), 10.330 (s, NH), 7.847-7.830 (dd, J=3.3, 1.8 Hz, 2H), 7.752-7.722 (d, J=9 Hz, 2H), 7.669-7.640 (d, J=8.7 Hz, 1H), 7.631-7.602 (d, J=8.7 Hz, 2H), 7.206-7.178 (d, J=8.4 Hz, 2H), 7.084-7.055 (d, J=8.7 Hz, 2H), 4.615-4.500 (dd, J=18 Hz, 2H), 4.532-4.500 (d, J=9.6 Hz, 1H), 3.781 (s, 3H), 2.299-2.277 (m, 1H), 1.023-1.002 (d, J=6.3 Hz, 3H), 0.852-0.830 (d, J=6.9 Hz, 3H); MS (ESI): m/z 495 (M+H), m/z 493 (M−H).

Example 91

(S)-Methyl 3-methyl-2-(1-oxo-6-(4-(4-(trifluoromethyl)phenylsulfonamido)phenyl)isoindolin-2-yl)butanoate The compound of example 91 was prepared analogous to compound of example 77 by reaction of compound of example 6 with 4-trifluoromethylbenzene sulfonyl chloride.

The compound of example 91 was used directly without isolation for the preparation of compound of example 92.

Example 92

(S)-3-Methyl-2-(1-oxo-6-(4-(4-(trifluoromethyl) phenylsulfonamido)phenyl)isoindolin-2-yl)butanoic acid The compound of example 92 was prepared analogous to compound of example 78 by hydrolysis of compound of example 91.

Yield: 93%; $^1$H NMR (DMSO-d$_6$, 300 MHz): δ 13.074 (s, COOH), 10.714 (s, NH), 8.500-7.965 (dd, J=3.6, 8.7 Hz, 4H), 7.864-7.843 (dd, J=2.4, 1.8 Hz, 2H), 7.684-7.674 (d, J=3 Hz, 2H), 7.655-7.646 (d, J=2.7 Hz, 1H), 7.234-7.205 (d, J=8.7 Hz, 2H), 4.685-4.508 (dd, J=17.4, 18 Hz, 2H), 4.541-4.508 (d, J=9.9 Hz, 1H), 2.308-2.231 (m, 1H), 1.031-1.009 (d, J=6.6 Hz, 3H), 0.860-0.838 (d, J=6.6 Hz, 3H); MS (ESI): m/z 533 (M+H).

Example 93

(S)-Methyl 3-methyl-2-(1-oxo-6-(4-(phenylmethylsulfonamido)phenyl)isoindolin-2-yl)butanoate The compound of example 93 was prepared analogous to compound of example 77 by reaction of compound of example 6 with benzyl sulfonyl chloride. The compound of example 93 was used directly without isolation for the preparation of compound of example 94.

Example 94

(S)-3-Methyl-2-(1-oxo-6-(4-(phenylmethylsulfonamido)phenyl)isoindolin-2-yl)butanoic acid The compound of example 94 was prepared analogous to compound of example 78 by hydrolysis of compound of example 93.

Yield: 96%; $^1$H NMR (DMSO-d$_6$, 300 MHz): δ 12.803 (s, COOH), 10.008 (s, NH), 7.932-7.915 (m, 2H), 7.738-7.695 (m, 3H), 7.373-7.355 (m, 3H), 7.324-7.275 (m, 4H), 4.710-4.551 (dd, J=17.7, 17.4 Hz, 2H), 4.565-4.532 (d, J=9.9 Hz, 1H), 4.516 (s, 2H), 2.350-2.273 (m, 1H), 1.047-1.025 (d, J=6.6 Hz, 3H), 0.88-0.859 (d, J=6.6 Hz, 3H); MS (ESI): m/z 479 (M+H).

Example 95

(S)-Methyl 3-methyl-2-(6-(4-(1-methylethylsulfonamido)phenyl)-1-oxoisoindolin-2-yl)butanoate The compound of example 95 was prepared analogous to compound of example 77 by reaction of compound of example 6 with isopropyl sulfonyl chloride. The compound of example 95 was used directly without isolation for the preparation of compound of example 96.

Example 96

(S)-3-Methyl-2-(6-(4-(1-methylethylsulfonamido) phenyl)-1-oxoisoindolin-2-yl)butanoic acid The compound of example 96 was prepared analogous to compound of example 78 by hydrolysis of compound of example 95.

Yield: 49%; $^1$H NMR (DMSO-d$_6$, 300 MHz): δ 13.077 (s, COOH), 9.923 (s, NH), 7.909-7.887 (ms, 1H), 7.724-7.681 (m, 3H), 7.353-7.324 (d, J=8.7 Hz, 2H), 4.701-4.524 (m, 3H), 3.345-3.237 (m, 1H), 2.342-2.266 (m, 1H), 1.278-1.255 (d, J=6.9 Hz, 6H), 1.041-1.019 (d, J=6.6 Hz, 3H), 0.874-0.852 (d, J=6.6 Hz, 3H); MS (ESI): m/z 431 (M+H), m/z 429 (M−H).

Example 97

(S)-Methyl 2-(6-(4-benzamidophenyl)-1-oxoisoindolin-2-yl)-3-methylbutanoate

To a solution of compound of formula 6 (100 mg, 0.295 mmol) in dichloromethane (3 mL), pyridine (70.53 mg, 0.885 mmol) was added and stirred for 5 min. To this reaction mixture, benzoyl chloride (81.96 mg, 0.443 mmol) was added and stirred for about 16 h. After completion of the reaction, the solvent was evaporated and the crude title compound was directly used for the preparation of compound of example 98.

Example 98

(S)-2-(6-(4-Benzamidophenyl)-1-oxoisoindolin-2-yl)-3-methylbutanoic acid

The compound of example 97 (130 mg, 0.294 mmol) was taken in THF (4 mL) and MeOH (1 mL). To this reaction mixture, 1 N LiOH (61.89 mg, 1.475 mmol) was added and stirred at room temperature for 2-3 h. After completion of the reaction, the solvent was evaporated and the residue obtained was dissolved in water and acidified with 1 N HCl to obtain the title compound, which was filtered and dried.

Yield: 115 mg (88%); $^1$H NMR (DMSO-d$_6$, 300 MHz): δ 13.046 (s, COOH), 10.425 (s, NH), 8.008-7.981 (d, J=8.1 Hz, 2H), 7.936-7.887 (m, 4H), 7.756-7.727 (d, J=8.7 Hz, 2H), 7.686-7.658 (d, J=8.4 Hz, 1H), 7.634-7.523 (m, 3H), 4.889-4.828 (d, J=18.3, 1H), 4.482-4.421 (d, J=18.3 Hz, 1H), 4.392-4.361 (d, J=9.3 Hz, 1H), 2.294-2.218 (m, 1H), 1.015-0.993 (d, J=6.6 Hz, 3H), 0.826-0.804 (d, J=6.6 Hz, 3H); MS (ESI): m/z 427 (M−H), m/z 429 (M+H).

Example 99

(S)-Methyl 2-(6-(4-(4-fluorobenzamido)phenyl)-1-oxoisoindolin-2-yl)-3-methyl butanoate The compound of example 99 was prepared analogous to compound of example 97 by reaction of compound of example 6 with 4-fluorobenzoyl chloride. The compound of example 99 was used directly without isolation for the preparation of compound of example 100.

Example 100

(S)-2-(6-(4-(4-Fluorobenzamido)phenyl)-1-oxoisoindolin-2-yl)-3-methylbutanoic acid The compound of example 100 was prepared analogous to compound of example 98 by hydrolysis of compound of example 99.

Yield: 90.9%; $^1$H NMR (DMSO-d$_6$, 300 MHz): δ 13.126 (s, COOH), 10.394 (s, NH), 8.093 (m, 2H), 7.960-7.939 (d, J=6.3 Hz, 2H), 7.922-7.893 (d, J=8.7 Hz, 2H), 7.776-7.747 (d, J=8.7 Hz, 2H), 7.724-7.696 (d, J=8.4 Hz, 1H), 7.421-7.362 (t, J=8.7, 9 Hz, 2H), 4.735-4.533 (dd, J=18.3, 24.3 Hz, 2H), 4.593-4.565 (d, J=8.4 Hz, 1H), 2.372-2.251 (m, 1H), 1.048-1.026 (d, J=6.6 Hz, 3H), 0.881-0.859 (d, J=6.6 Hz, 3H); MS (ESI): m/z 445 (M–H), m/z 447 (M+H).

Example 101

(S)-Methyl 3-methyl-2-(1-oxo-6-(4-(4-(trifluoromethyl)benzamido)phenyl)isoindolin-2-yl)butanoate The compound of example 101 was prepared analogous to compound of example 97 by reaction of compound of example 6 with 4-trifluoromethylbenzoyl chloride. The compound of example 101 was used directly without isolation for the preparation of compound of example 102.

Example 102

(S)-3-Methyl-2-(1-oxo-6-(4-(4-(trifluoromethyl)benzamido)phenyl)isoindolin-2-yl)butanoic acid The compound of example 102 was prepared analogous to compound of example 98 by hydrolysis of compound of example 101.

Yield: 89%; $^1$H NMR (DMSO-$d_6$, 300 MHz): δ 13.002 (s, COOH), 10.769 (s, NH), 8.237-8.210 (d, J=8.1 Hz, 2H), 7.929-7.856 (m, 6H), 7.740-7.711 (d, J=8.7 Hz, 2H), 7.669-7.643 (d, J=8.7 Hz, 1H), 4.957-4.896 (d, J=18.1 Hz, 1H), 4.445-4.384 (d, J=18.3 Hz, 1H), 4.330-4.298 (d, J=9.6 Hz, 1H), 2.277-2.201 (m, 1H), 1.005-0.983 (d, J=6.6 Hz, 3H), 0.881-0.859 (d, J=6.6 Hz, 3H); MS (ESI): m/z 497 (M+H).

Example 103

(S)-Methyl 2-(6-(4-(4-methoxybenzamido)phenyl)-1-oxoisoindolin-2-yl)-3-methylbutanoate The compound of example 103 was prepared analogous to compound of example 97 by reaction of compound of example 6 with 4-methoxybenzoyl chloride. The compound of example 103 was used directly without isolation for the preparation of compound of example 104.

Example 104

(S)-2-(6-(4-(4-Methoxybenzamido)phenyl)-1-oxoisoindolin-2-yl)-3-methyl butanoic acid The compound of example 104 was prepared analogous to compound of example 98 by hydrolysis of compound of example 103.

Yield: 89%; $^1$H NMR (DMSO-$d_6$, 300 MHz): δ 10.233 (s, NH), 8.010-7.981 (d, J=8.7 Hz, 2H), 7.921-7.864 (d, J=8.4 Hz, 4H), 7.750-7.672 (d, J=8.4 Hz, 2H), 7.700-7.62 (d, J=8.4 Hz, 1H), 7.094-7.064 (d, J=9 Hz, 2H), 4.800-4.739 (d, J=18.3 Hz, 1H), 4.532-4.472 (d, J=18 Hz, 1H), 4.472-4.440 (d, J=9.6 Hz, 1H), 3.850 (s, 3H), 2.318-2.242 (m, 1H), 1.029-1.007 (d, J=6.6 Hz, 3H), 0.850-0.828 (d, J=6.6 Hz, 3H); MS (ESI): m/z 457 (M+H), m/z 459 (M+H).

Example 105

(S)-Methyl 2-(6-(4-(3-fluorobenzamido)phenyl)-1-oxoisoindolin-2-yl)-3-methylbutanoate The compound of example 105 was prepared analogous to compound of example 97 by reaction of compound of example 6 with 3-fluorobenzoyl chloride. The compound of example 105 was used directly without isolation for the preparation of compound of example 106.

Example 106

(S)-2-(6-(4-(3-Fluorobenzamido)phenyl)-1-oxoisoindolin-2-yl)-3-methylbutanoic acid The compound of example 106 was prepared analogous to compound of example 98 by hydrolysis of compound of example 105.

Yield: 84%; $^1$H NMR (DMSO-$d_6$, 300 MHz): δ 13.053 (s, COOH), 10.441 (s, NH), 7.693-7.943 (m, 2H), 7.928-7.899 (d, J=8.7 Hz, 2H), 7.858-7.832 (d, J=7.8 Hz, 1H), 7.785-7.756 (d, J=8.7 Hz, 3H), 7.727-7.699 (d, J=8.4 Hz, 1H), 7.650-7.577 (m, 1H), 7.500-7.437 (m, 1H), 4.714-4.534 (dd, J=17.7, 18 Hz, 2H), 4.566-4.534 (d, J=9.6 Hz, 1H), 2.351-2.274 (m, 1H), 1.049-1.027 (d, J=6.6 Hz, 3H), 0.882-0.860 (d, J=6.3 Hz, 3H); MS (ESI): m/z 445 (M+H), m/z 447 (M+H).

Example 107

(S)-Methyl 2-(6-(4-(3-chlorobenzamido)phenyl)-1-oxoisoindolin-2-yl)-3-methylbutanoate The compound of example 107 was prepared analogous to compound of example 97 by reaction of compound of example 6 with 3-chlorobenzoyl chloride. The compound of example 107 was used directly without isolation for the preparation of compound of example 108.

Example 108

(S)-2-(6-(4-(3-Chlorobenzamido)phenyl)-1-oxoisoindolin-2-yl)-3-methylbutanoic acid The compound of example 108 was prepared analogous to compound of example 98 by hydrolysis of compound of example 107.

Yield: 81%; $^1$H NMR (DMSO-$d_6$, 300 MHz): δ 10.606 (s, NH), 8.071-8.065 (d, J=1.8 Hz, 1H), 7.988-7.962 (d, J=7.8 Hz, 1H), 7.917-7.870 (m, 4H), 7.744-7.715 (d, J=8.7 Hz, 2H), 7.690-7.648 (m, 2H), 7.606-7.554 (t, J=7.8, 1H), 4.925-4.864 (d, J=18.3 Hz, 1H), 4.463-4.402 (d, J=18.3 Hz, 1H), 4.363-4.331 (d, J=9.6 Hz, 1H), 2.286-2.210 (m, 1H), 1.012-0.990 (d, J=6.6 Hz, 3H), 0.818-0.796 (d, J=6.6 Hz, 3H); MS (ESI): m/z 461 (M+H), m/z 463 (M+H).

Example 109

(S)-Methyl 2-(6-(4-(2,4-difluorobenzamido)phenyl)-1-oxoisoindolin-2-yl)-3-methylbutanoate The compound of example 109 was prepared analogous to compound of example 97 by reaction of compound of example 6 with 2,4-difluorobenzoyl chloride. The compound of example 109 was used directly without isolation for the preparation of compound of example 110.

Example 110

(S)-2-(6-(4-(2,4-Difluorobenzamido)phenyl)-1-oxoisoindolin-2-yl)-3-methyl butanoic acid The compound of example 110 was prepared analogous to compound of example 98 by hydrolysis of compound of example 109.

Yield: 84%; ¹H NMR (DMSO-d₆, 300 MHz): δ 10.549 (s, NH), 7.950-7.931 (m, 2H), 7.852-7.824 (d, J=8.4 Hz, 2H), 7.773-7.744 (d, J=8.7 Hz, 2H), 7.725-7.696 (d, J=8.7 Hz, 2H), 7.486-7.412 (td, J=2.4, 10.2 Hz, 1H), 7.282-7.218 (td, J=2.1, 8.7 Hz, 1H), 4.716-4.527 (dd, J=18, 19.8 Hz, 2H), 4.559-4.527 (d, J=9.6 Hz, 1H), 2.409-2.316 (m, 1H), 1.046-1.024 (d, J=6.6 Hz, 3H), 0.878-0.856 (d, J=6.6 Hz, 3H); MS (ESI): m/z 465 (M+H).

Example 111

(S)-Methyl 3-methyl-2-(6-(4-(4-methylbenzamido)phenyl)-1-oxoisoindolin-2-yl)butanoate The compound of example 111 was prepared analogous to compound of example 97 by reaction of compound of example 6 with 4-methylbenzoyl chloride. The compound of example 111 was used directly without isolation for the preparation of compound of example 110.

Example 112

(S)-3-Methyl-2-(6-(4-(4-methylbenzamido)phenyl)-1-oxoisoindolin-2-yl)butanoic acid The compound of example 112 was prepared analogous to compound of example 98 by hydrolysis of compound of example 111.

Yield: 84%; ¹H NMR (DMSO-d₆, 300 MHz): δ 10.320 (s, NH), 7.923-7.898 (m, 6H), 7.744-7.717 (d, J=8.1, 2H), 7.681-7.653 (d, J=8.4 Hz, 1H), 7.360-7.335 (d, J=7.5 Hz, 2H), 4.882-4.821 (d, J=18.3 Hz, 1H), 4.478-4.416 (d, J=18.6 Hz, 1H), 4.384-4.353 (d, J=9.3 Hz, 1H), 2.394 (s, 3H), 2.282-2.238 (m, 1H), 1.009-0.988 (d, J=6.3 Hz, 3H), 0.820-0.799 (d, J=6.3 Hz, 3H); MS (ESI): m/z 441 (M−H), m/z 443 (M+H).

Example 113

(S)-Methyl 2-(6-(4-(4-chlorobenzamido)phenyl)-1-oxoisoindolin-2-yl)-3-methylbutanoate The compound of example 113 was prepared analogous to compound of example 97 by reaction of compound of example 6 with 4-chlorobenzoyl chloride. The compound of example 113 was used directly without isolation for the preparation of compound of example 114.

Example 114

(S)-2-(6-(4-(4-Chlorobenzamido)phenyl)-1-oxoisoindolin-2-yl)-3-methylbutanoic acid The compound of example 114 was prepared analogous to compound of example 98 by hydrolysis of compound of example 113.

Yield: 89%; ¹H NMR (DMSO-d₆, 300 MHz): δ 10.524 (s, NH), 8.047-8.019 (d, J=8.4 Hz, 2H), 7.916-7.751 (m, 3H), 7.684-7.655 (d, J=8.7 Hz, 2H), 7.633-7.605 (m, 4H), 4.883-4.822 (d, J=18.1 Hz, 1H), 4.483-4.422 (d, J=18.1 Hz, 1H), 4.393-4.361 (d, J=9.6 Hz, 1H), 2.316-2.220 (m, 1H), 1.013-0.992 (d, J=6.3 Hz, 3H), 0.824-0.802 (d, J=6.6 Hz, 3H); MS (ESI): m/z 461 (M+H), m/z 463 (M+H).

Example 115

(S)-Methyl 2-(6-(4-(4-tert-butylbenzamido)phenyl)-1-oxoisoindolin-2-yl)-3-methylbutanoate The compound of example 115 was prepared analogous to compound of example 97 by reaction of compound of example 6 with 4-(t-butyl)benzoyl chloride. The compound of example 115 was used directly without isolation for the preparation of compound of example 116.

Example 116

(S)-2-(6-(4-(4-tert-Butylbenzamido)phenyl)-1-oxoisoindolin-2-yl)-3-methyl butanoic acid The compound of example 116 was prepared analogous to compound of example 98 by hydrolysis of compound of example 115.

Yield: 87%; ¹H NMR (DMSO-d₆, 300 MHz): δ 13.044 (s, COOH), 10.302 (s, NH), 7.958-7.902 (m, 6H), 7.767-7.738 (d, J=8.7 Hz, 2H), 7.724-7.696 (d, J=8.4 Hz, 1H), 7.580-7.552 (d, J=7.8 Hz, 2H), 4.680-4.535 (dd, J=16.8, 17.1 Hz, 2H), 4.567-4.535 (d, J=9.6 Hz, 1H), 2.327-2.253 (m, 1H), 1.333 (s, 9H), 1.049-1.027 (d, J=6.6 Hz, 3H), 0.882-0.860 (d, J=6.6 Hz, 3H); MS (ESI): m/z 483 (M+H), m/z 485 (M+H).

Example 117

(S)-Methyl 2-(6-(4-(cyclohexanecarboxamido)phenyl)-1-oxoisoindolin-2-yl)-3-methylbutanoate The compound of example 117 was prepared analogous to compound of example 97 by reaction of compound of example 6 with cyclohexoyl chloride.

Yield: 75.96%; %; ¹H NMR (DMSO-d₆, 300 MHz): δ 9.949 (s, 1H), 7.896 (m, 2H), 7.715-7.688 (m, 5H), 4.632-4.599 (m, 3H), 3.682 (s, 3H), 2.347 (m, 2H), 1.791-1.676 (m, 5H), 1.443-1.234 (m, 5H), 1.009-0.990 (d, J=5.7 Hz, 3H), 0.856-0.837 (d, J=5.7 Hz, 3H); MS (ESI): m/z 447 (M−H), m/z 449 (M+H).

Example 118

(S)-2-(6-(4-(Cyclohexanecarboxamido)phenyl)-1-oxoisoindolin-2-yl)-3-methylbutanoic acid The compound of example 118 was prepared analogous to compound of example 98 by hydrolysis of compound of example 117.

Yield: 78%; ¹H NMR (DMSO-d₆, 300 MHz): δ 13.033 (s, 1H), 9.938 (s, 1H), 7.894 (m, 2H), 7.712-7.692 (m, 5H), 4.697-4.524 (dd, J=17.7 Hz, 2H), 4.558-4.524 (d, J=10.2 Hz, 1H), 2.345 (m, 2H), 1.792-1.676 (m, 5H), 1.444-1.236 (m, 5H), 1.041-1.023 (d, J=5.4 Hz, 3H), 0.872-0.853 (d, J=5.7 Hz, 3H); MS (ESI): m/z 433 (M−H), m/z 435 (M+H).

Example 119

(S)-Methyl 2-(6-(4-biphenyl-4-ylcarboxamidophenyl)-1-oxoisoindolin-2-yl)-3-methylbutanoate The compound of example 119 was prepared analogous to compound of example 97 by reaction of compound of example 6 with 4-phenyl benzoyl chloride.

Example 120

(S)-2-(6-(4-Biphenyl-4-ylcarboxamidophenyl)-1-oxoisoindolin-2-yl)-3-methyl butanoic acid The compound of example 120 was prepared analogous to compound of example 98 by hydrolysis of compound of example 119.

Yield: 82%; $^1$H NMR (DMSO-d$_6$, 300 MHz): δ 13.060 (bs, 1H), 10.435 (s, 1H), 8.106-8.082 (d, J=7.2 Hz, 2H), 7.943 (m, 4H), 7.873-7.849 (d, J=7.2 Hz, 2H), 7.748-7.726 (m, 5H), 7.521-7.433 (m, 3H), 4.661-4.526 (dd, J=21.9 Hz, 2H), 4.556-4.526 (d, J=9 Hz, 1H), 2.318 (m, 1H), 1.042-1.025 (d, J=5.1 Hz, 3H), 0.875-0.857 (d, J=5.4 Hz, 3H); MS (ESI): m/z 503 (M−H), m/z 505 (M+H).

Yield: 98%; $^1$H NMR (DMSO-d$_6$, 300 MHz): δ 10.458 (s, 1H), 8.893-8.882 (d, J=3.3 Hz, 2H), 8.491 (m, 1H), 8.116-8.091 (d, J=7.5 Hz, 2H), 7.955 (m, 3H), 7.877-7.852 (d, J=7.5 Hz, 2H), 7.787-7.710 (m, 3H), 7.525-7.503 (d, J=6.6 Hz, 2H), 7.458-7.437 (d, J=6.3 Hz, 1H), 4.615 (m, 3H), 3.690 (s, 3H), 2.349 (m, 1H), 1.016-0.998 (d, J=5.4 Hz, 3H), 0.867-0.848 (d, J=5.7 Hz, 3H); MS (ESI): m/z 517 (M−H), m/z 519 (M+H).

Example 121

(S)-Methyl 2-(6-(4-(2-naphthamido)phenyl)-1-oxoisoindolin-2-yl)-3-methyl butanoate The compound of example 121 was prepared analogous to compound of example 97 by reaction of compound of example 6 with 2-naphthoyl chloride.

Yield: 93%; $^1$H NMR (DMSO-d$_6$, 300 MHz): δ 10.599 (s, 1H), 8.899-8.887 (d, J=3.6 Hz, 2H), 8.631 (m, 1H), 8.503 (m, 1H), 8.069-7.968 (m, 7H), 7.801-7.775 (d, J=7.8 Hz, 1H), 7.737-7.712 (d, J=7.5 Hz, 1H), 7.654 (m, 1H), 4.617 (m, 3H), 3.692 (s, 3H), 2.349 (m, 1H), 1.017-0.999 (d, J=5.4 Hz, 3H), 0.869-0.850 (d, J=5.7 Hz, 3H); MS (ESI): m/z 491 (M−H), m/z 493 (M+H).

Example 122

(S)-2-(6-(4-(2-Naphthamido)phenyl)-1-oxoisoindolin-2-yl)-3-methylbutanoic acid

The compound of example 122 was prepared analogous to compound of example 98 by hydrolysis of compound of example 121.

Yield: 87%; $^1$H NMR (DMSO-d$_6$, 300 MHz): δ 10.645 (s, 1H), 8.651 (s, 1H), 8.099-8.011 (m, 4H), 7.979-7.952 (d, J=8.1 Hz, 2H), 7.904 (m, 2H), 7.768-7.744 (d, J=7.2 Hz, 2H), 7.652 (m, 3H), 4.949-4.888 (d, J=18.3 Hz, 1H), 4.449-4.388 (d, J=18.3 Hz, 1H), 4.328-4.298 (d, J=9 Hz, 1H), 2.253 (m, 1H), 1.000-0.983 (d, J=5.1 Hz, 3H), 0.807-0.789 (d, J=5.4 Hz, 3H); MS (ESI): m/z 477 (M−H), m/z 479 (M+H).

Example 123

(S)-Methyl 3-methyl-2-(1-oxo-6-(4-(4-pentylbenzamido)phenyl)isoindolin-2-yl)butanoate The compound of example 123 was prepared analogous to compound of example 97 by reaction of compound of example 6 with 4-(n-pentyl)benzoyl chloride.

Yield: 86%; $^1$H NMR (DMSO-d$_6$, 300 MHz): δ 10.325 (s, 1H), 8.893 (s, 2H), 8.517 (m, 1H), 8.003-7.910 (m, 5H), 7.761-7.732 (d, J=8.7 Hz, 2H), 7.374-7.351 (d, J=6.9 Hz, 1H), 4.610 (m, 3H), 3.687 (s, 3H), 2.661 (m, 2H), 2.346 (m, 1H), 1.611 (m, 2H), 1.301 (m, 4H), 1.012-0.994 (d, J=5.4 Hz, 3H), 0.866-0.847 (d, J=5.7 Hz, 6H); MS (ESI) m/z: 511 (M−H), m/z 513 (M+H).

Example 124

(S)-3-Methyl-2-(1-oxo-6-(4-(4-pentylbenzamido)phenyl)isoindolin-2-yl)butanoic acid The compound of example 124 was prepared analogous to compound of example 98 by hydrolysis of compound of example 123.

Yield: 82%; $^1$H NMR (DMSO-d$_6$, 300 MHz): δ 13.092 (bs, 1H), 10.300 (s, 1H), 7.934 (m, 6H), 7.763-7.735 (m, 3H), 7.375-7.351 (d, J=7.2 Hz, 2H), 4.715-4.531 (m, 3H), 2.661 (m, 2H), 2.301 (m, 1H), 1.613 (m, 2H), 1.302 (m, 4H), 1.045-1.028 (d, J=5.1 Hz, 3H), 0.873 (m, 6H); MS (ESI): m/z 497 (M−H), m/z 499 (M+H)

Example 125

(S)-Methyl 2-(6-(4-(2-fluoro-6-(trifluoromethyl)benzamido)phenyl)-1-oxoisoindolin-2-yl)-3-methylbutanoate The compound of example 125 was prepared analogous to compound of example 97 by reaction of compound of example 6 with 2-fluoro-6-trifluoro benzoyl chloride.

Yield: 76%; $^1$H NMR (DMSO-d$_6$, 300 MHz): δ 10.948 (s, 1H), 7.951-7.930 (m, 2H), 7.880-7.833 (m, 1H), 7.773-7.719 (m, 7H), 4.646-4.611 (m, 3H), 3.689 (s, 3H), 2.375-2.298 (m, 1H), 1.018-0.996 (d, J=6.6 Hz, 3H), 0.869-0.847 (d, J=6.6 Hz, 3H); MS (ESI): m/z 527 (M−H), m/z 529 (M+H).

Example 126

(S)-2-(6-(4-(2-Fluoro-6-(trifluoromethyl)benzamido)phenyl)-1-oxoisoindolin-2-yl)-3-methylbutanoic acid The compound of example 126 was prepared analogous to compound of example 98 by hydrolysis of compound of example 125.

Yield: 62%; $^1$H NMR (DMSO-d$_6$, 300 MHz): δ 13.049 (s, 1H), 10.952 (s, 1H), 7.948-7.927 (m, 2H), 7.775-7.706 (m, 8H), 4.716-4.567 (dd, J=17.4, 18 Hz, 2H), 4.567-4.536 (d, J=9.3 Hz, 1H), 2.395-2.275 (m, 1H), 1.049-1.027 (d, J=6.6 Hz, 3H), 0.882-0.860 (d, J=6.6 Hz, 3H); MS (ESI) m/z: 513 (M−H), m/z 515 (M+H).

Example 127

(S)-Methyl 2-(6-(4-(benzo[d][1,3]dioxole-5-carboxamido)phenyl)-1-oxo isoindolin-2-yl)-3-methylbutanoate The compound of example 127 was prepared analogous to compound of example 97 by reaction of compound of example 6 with benzo[d][1,3]dioxole-5-carbonyl chloride.

Yield: 83.7%; $^1$H NMR (DMSO-d$_6$, 300 MHz): δ 10.203 (s, 1H), 7.964-7.885 (m, 4H), 7.759-7.729 (d, J=9 Hz, 2H), 7.729-7.697 (d, J=9.6 Hz, 1H), 7.626-7.593 (dd, J=1.8, 8.1 Hz, 1H), 7.549-7.543 (d, J=1.8 Hz, 1H), 7.093-7.066 (d, J=8.1 Hz, 1H), 6.149 (s, 2H), 4.643-4.609 (m, 3H), 3.688 (s, 3H), 2.351-2.317 (m, 1H), 1.016-0.994 (d, J=6.6 Hz, 3H), 0.866-0.844 (d, J=6.6 Hz, 3H); MS (ESI): m/z 485 (M–H), m/z 487 (M+H).

Example 128

(S)-2-(6-(4-(Benzo[d][1,3]dioxole-5-carboxamido)phenyl)-1-oxoisoindolin-2-yl)-3-methylbutanoic acid The compound of example 128 was prepared analogous to compound of example 98 by hydrolysis of compound of example 127.

Yield: 64.6%; $^1$H NMR (DMSO-$d_6$, 300 MHz): δ 13.097 (s, 1H), 10.196 (s, 1H), 7.957-7.936 (d, J=6.3 Hz, 2H), 7.914-7.885 (d, J=8.7 Hz, 2H), 7.762-7.733 (d, J=8.7 Hz, 2H), 7.722-7.693 (d, J=8.7 Hz, 1H), 7.620-7.593 (d, J=8.1 Hz, 1H), 7.547-7.543 (d, J=1.2 Hz, 1H), 7.095-7.068 (d, J=8.1 Hz, 1H), 6.150 (s, 2H), 4.713-4.566 (dd, J=17.7, 18.3 Hz, 2H), 4.566-4.534 (d, J=9.6 Hz, 1H), 2.394-2.250 (m, 1H), 1.049-1.027 (d, J=6.6 Hz, 3H), 0.882-0.860 (d, J=6.6 Hz, 3H); MS (ESI): m/z 471 (M–H), m/z 473 (M+H).

Example 129

(S)-Methyl 2-(6-(4-(2,6-dichlorobenzamido)phenyl)-1-oxoisoindolin-2-yl)-3-methylbutanoate The compound of example 129 was prepared analogous to compound of example 97 by reaction of compound of example 6 with 2,6-dichloro benzoyl chloride.

Yield: 78%; $^1$H NMR (DMSO-$d_6$, 300 MHz): δ 10.897 (s, 1H), 8.884-8.867 (d, J=5.1 Hz, 2H), 7.981-7.955 (d, J=7.8 Hz, 2H), 7.835-7.7748 (dd, J=8.7 Hz, 4H), 7.737-7.708 (d, J=8.7 Hz, 1H), 7.625-7.619 (d, J=1.8 Hz, 1H), 4.644-4.611 (m, 3H), 3.688 (s, 3H), 2.375-2.317 (m, 1H), 1.017-0.995 (d, J=6.6 Hz, 3H), 0.866-0.844 (d, J=6.6 Hz, 3H); MS (ESI): m/z 509 (M–H), m/z 511 (M+H).

Example 130

(S)-2-(6-(4-(2,6-Dichlorobenzamido)phenyl)-1-oxoisoindolin-2-yl)-3-methyl butanoic acid The compound of example 130 was prepared analogous to compound of example 98 by hydrolysis of compound of example 129.

Yield: 43%; $^1$H NMR (DMSO-$d_6$, 300 MHz): δ 13.052 (s, 1H), 10.889 (s, 1H), 7.943-7.928 (m, 2H), 7.826-7.751 (dd, J=7.8, 8.7 Hz, 4H), 7.734-7.706 (d, J=8.4 Hz, 1H), 7.621-7.597 (d, J=7.2 Hz, 2H), 7.550-7.528 (d, J=6.6 Hz, 1H), 4.716-4.569 (dd, J=17.4, 18 Hz, 2H), 4.569-4.537 (d, J=9.6 Hz, 1H), 2.375-2.276 (m, 1H), 1.050-1.028 (d, J=6.6 Hz, 3H), 0.882-0.860 (d, J=6.6 Hz, 3H); MS (ESI): m/z 495 (M–H), m/z 497 (M+H).

Example 131

(S)-Methyl 2-(6-(4-(2-chlorobenzamido)phenyl)-1-oxoisoindolin-2-yl)-3-methylbutanoate The compound of example 131 was prepared analogous to compound of example 97 by reaction of compound of example 6 with 2-chloro benzoyl chloride.

Yield: 89%; $^1$H NMR (DMSO-$d_6$, 300 MHz): δ 10.646 (s, 1H), 8.856 (s, 1H), 7.931 (m, 2H), 7.856-7.831 (d, J=7.5 Hz, 1H), 7.762-7.732 (d, J=9 Hz, 3H), 7.600-7.474 (m, 4H), 4.606 (m, 3H), 3.682 (s, 3H), 2.343 (m, 1H), 1.009-0.991 (d, J=5.4 Hz, 3H), 0.859-0.839 (d, J=6 Hz, 3H); MS (ESI): m/z 475 (M–H), m/z 477 (M+H).

Example 132

(S)-2-(6-(4-(2-Chlorobenzamido)phenyl)-1-oxoisoindolin-2-yl)-3-methyl butanoic acid The compound of example 132 was prepared analogous to compound of example 98 by hydrolysis of compound of example 131.

Yield: 84%; $^1$H NMR (DMSO-$d_6$, 300 MHz): δ 10.657 (s, 1H), 7.897-7.882 (d, J=7.5 Hz, 2H), 7.854-7.837 (d, J=8.5 Hz, 1H), 7.756-7.739 (d, J=8.5 Hz, 2H), 7.686-7.671 (d, J=7.5 Hz, 1H), 7.627-7.580 (dd, J=7.5, 8 Hz, 2H), 7.542-7.511 (t, J=4.2 Hz, 1H), 7.491-7.462 (d, J=7 Hz, 2H), 4.884-4.848 (d, J=18 Hz, 1H), 4.465-4.428 (d, J=18.5 Hz, 1H), 4.368-4.349 (d, J=9.5 Hz, 1H), 2.272-2.186 (m, 1H), 1.005-0.992 (d, J=6.5 Hz, 3H), 0.814-0.801 (d, J=6.5 Hz, 3H); MS (ESI): m/z 461 (M–H), m/z 463 (M+H).

Example 133

(S)-Methyl 2-(6-(4-(2,4-dichlorobenzamido)phenyl)-1-oxoisoindolin-2-yl)-3-methylbutanoate The compound of example 133 was prepared analogous to compound of example 97 by reaction of compound of example 6 with 2,4-dichloro benzoyl chloride.

Yield: 92%; $^1$H NMR (DMSO-$d_6$, 300 MHz): δ 10.685 (s, 1H), 8.829 (s, 1H), 7.932 (m, 2H), 7.810-7.653 (m, 6H), 7.591-7.566 (J=7.5 Hz, 1H), 4.609 (m, 3H), 3.685 (s, 3H), 2.345 (m, 1H), 1.012-0.993 (d, J=5.7 Hz, 3H), 0.861-0.842 (d, J=5.7 Hz, 3H); MS (ESI): m/z 509 (M–H), m/z 511 (M+H).

Example 134

(S)-2-(6-(4-(2,4-Dichlorobenzamido)phenyl)-1-oxoisoindolin-2-yl)-3-methyl butanoic acid The compound of example 134 was prepared analogous to compound of example 98 by hydrolysis of compound of example 133.

Yield: 70%; $^1$H NMR (DMSO-$d_6$, 300 MHz): δ 10.701 (s, 1H), 7.904-7.885 (d, J=5.7 Hz, 2H), 7.840-7.811 (d, J=8.7 Hz, 2H), 7.793-7.787 (d, J=1.8 Hz, 1H), 7.765-7.736 (d, J=8.7 Hz, 2H), 7.697-7.660 (m, 2H), 7.592-7.5559 (dd, J=1.8, 8.1 Hz, 1H), 4.854-4.793 (d, J=18.3 Hz, 1H), 4.497-4.436 (d, J=18.3 Hz, 1H), 4.410-4.379 (d, J=9.3 Hz, 1H), 2.274-2.242 (m, 1H), 1.014-0.992 (d, J=6.6 Hz, 3H), 0.828-0.806 (d, J=6.6 Hz, 3H); MS (ESI): m/z 495 (M–H), m/z 497 (M+H).

Example 135

(S)-Methyl 2-(6-(4-(4-butoxybenzamido)phenyl)-1-oxoisoindolin-2-yl)-3-methyl butanoate The compound of example 135 was prepared analogous to compound of example 97 by reaction of compound of example 6 with 4-n-butoxy benzoyl chloride.

Yield: 85%; $^1$H NMR (DMSO-$d_6$, 300 MHz): δ 10.225 (s, 1H), 8.889-8.876 (d, J=3.9 Hz, 1H), 7.694-7.901 (m, 5H), 7.751-7.723 (m, 3H), 7.079-7.052 (d, J=8.1 Hz, 2H), 4.638-4.607 (m, 3H), 4.064 (m, 2H), 3.685 (s, 3H), 2.326 (m, 1H), 1.730-1.709 (m, 2H), 1.467-1.444 (m, 2H), 1.011-0.925 (m, 6H), 0.862-0.842 (d, J=6 Hz, 3H); MS (ESI): m/z 515 (M+H).

Example 136

(S)-2-(6-(4-(4-Butoxybenzamido)phenyl)-1-oxoisoindolin-2-yl)-3-methyl butanoic acid The compound of example 136 was prepared analogous to compound of example 98 by hydrolysis of compound of example 135.

Yield: 80%; $^1$H NMR (DMSO-$d_6$, 300 MHz): δ 10.255 (s, 1H), 7.996-7.979 (d, J=8.5 Hz, 2H), 7.915-7.878 (m, 4H), 7.733-7.716 (d, J=8.5 Hz, 2H), 7.672-7.656 (d, J=8 Hz, 1H), 7.072-7.055 (d, J=8.5 Hz, 2H), 4.913-4.876 (d, J=18.5 Hz, 1H), 4.447-4.410 (d, J=18.5 Hz, 1H), 4.342-4.323 (d, J=9.5 Hz, 1H), 4.078-4.052 (t, J=6.5 Hz, 2H), 2.280-2.207 (m, 1H), 1.760-1.704 (q, J=6.5, 7 Hz, 2H), 1.497-1.423 (m, 2H), 1.003-0.990 (d, J=6.5 Hz, 3H), 0.967-0.937 (d, J=7.5 Hz, 3H), 0.809-0.796 (d, J=6.5 Hz, 3H); MS (ESI): m/z 499 (M−H), m/z 501 (M+H).

Example 137

(S)-Methyl 2-(6-(4-(2,6-difluorobenzamido)phenyl)-1-oxoisoindolin-2-yl)-3-methylbutanoate The compound of example 137 was prepared analogous to compound of example 97 by reaction of compound of example 6 with 2,4-difluoro benzoyl chloride.

Yield: 88%; $^1$H NMR (DMSO-$d_6$, 300 MHz): δ 10.935 (s, 1H), 7.937-7.708 (m, 7H), 7.636-7.589 (t, J=6.9, 7.2 Hz, 1H), 7.299-7.248 (t, J=7.5, 7.8 Hz, 2H), 4.611 (m, 3H), 3.687 (s, 3H), 2.347 (m, 1H), 1.014-0.995 (d, J=5.7 Hz, 3H), 0.861-0.842 (d, J=6 Hz, 3H); MS (ESI): m/z 477 (M−H), m/z 479 (M+H).

Example 138

(S)-2-(6-(4-(2,6-Difluorobenzamido)phenyl)-1-oxoisoindolin-2-yl)-3-methyl butanoic acid The compound of example 138 was prepared analogous to compound of example 98 by hydrolysis of compound of example 137.

Yield: 77%; $^1$H NMR (DMSO-$d_6$, 300 MHz): δ 10.960 (s, 1H), 7.886 (m, 8H), 7.293-7.269 (m, 2H), 4.962-4.901 (d, J=18.3 Hz, 1H), 4.436-4.375 (d, J=18.3 Hz, 1H), 4.310-4.280 (d, J=9 Hz, 1H), 2.239 (m, 1H), 0.994-0.977 (d, J=5.1 Hz, 3H), 0.797-0.780 (d, J=5.1 Hz, 3H); MS (ESI): m/z 463 (M−H), m/z 465 (M+H).

Example 139

(S)-Methyl 2-(6-(4-(3,4-difluorobenzamido)phenyl)-1-oxoisoindolin-2-yl)-3-methylbutanoate The compound of example 139 was prepared analogous to compound of example 97 by reaction of compound of example 6 with 3,4-difluoro benzoyl chloride.

Yield: 85%; $^1$H NMR (DMSO-$d_6$, 300 MHz): δ 10.447 (s, 1H), 8.070-8.040 (m, 1H), 7.946-7.884 (m, 5H), 7.784-7.630 (m, 4H), 4.612 (m, 3H), 3.688 (s, 3H), 2.348 (m, 1H), 1.014-0.996 (d, J=5.4 Hz, 3H), 0.861-0.842 (d, J=5.7 Hz, 3H); MS (ESI) m/z: 477 (M−H), m/z 479 (M+H).

Example 140

(S)-2-(6-(4-(3,4-Difluorobenzamido)phenyl)-1-oxoisoindolin-2-yl)-3-methyl butanoic acid The compound of example 140 was prepared analogous to compound of example 98 by hydrolysis of compound of example 139.

Yield: 71%; $^1$H NMR (DMSO-$d_6$, 300 MHz): δ 10.457 (s, 1H), 8.073-8.035 (t, J=9 Hz, 1H), 7.954-7.942 (d, J=6 Hz, 2H), 7.983-7.876 (d, J=8.5 Hz, 3H), 7.773-7.756 (d, J=8.5 Hz, 2H), 7.724-7.707 (d, J=8.5 Hz, 1H), 7.659-7.605 (dd, J=6, 8.5 Hz, 1H), 4.697-4.661 (d, J=18 Hz, 1H), 4.585-4.548 (d, J=18.5 Hz, 1H), 4.548-4.527 (d, J=10.5 Hz, 1H), 2.330-2.284 (m, 1H), 1.038-1.025 (d, J=6.5 Hz, 3H), 0.871-0.858 (d, J=6.5 Hz, 3H); MS (ESI): m/z 463 (M−H), m/z 465 (M+H).

Example 141

(S)-Methyl 2-(6-(4-(3,4-dimethoxybenzamido)phenyl)-1-oxoisoindolin-2-yl)-3-methylbutanoate The compound of example 141 was prepared analogous to compound of example 97 by reaction of compound of example 6 with 3,4-dimethoxy benzoyl chloride.

Yield: 87%; $^1$H NMR (DMSO-$d_6$, 300 MHz): δ 10.205 (s, 1H), 7.946 (m, 2H), 7.916-7.889 (d, J=8.1 Hz, 2H), 7.769-7.741 (m, 3H), 7.668-7.642 (d, J=7.8 Hz, 1H), 7.559 (s, 1H), 7.119-7.093 (d, J=7.8 Hz, 1H), 4.611 (m, 3H), 3.856 (s, 6H), 3.688 (s, 3H), 2.346 (m, 1H), 1.013-0.995 (d, J=5.4 Hz, 3H), 0.864-0.845 (d, J=5.7 Hz, 3H); MS (ESI): m/z 501 (M−H), m/z 503 (M+H).

Example 142

(S)-2-(6-(4-(3,4-Dimethoxybenzamido)phenyl)-1-oxoisoindolin-2-yl)-3-methyl butanoic acid The compound of example 142 was prepared analogous to compound of example 98 by hydrolysis of compound of example 141.

Yield: 79%; $^1$H NMR (DMSO-$d_6$, 300 MHz): δ 10.204 (s, 1H), 7.960-7.946 (d, J=7 Hz, 2H), 7.914-7.896 (d, J=9 Hz, 2H), 7.769-7.751 (d, J=9 Hz, 2H), 7.719-7.702 (d, J=8.5 Hz, 1H), 7.668-7.648 (dd, J=1.5, 8 Hz, 1H), 7.565-7.562 (d, J=1.5 Hz, 1H), 7.111-7.101 (d, J=5 Hz, 1H), 4.703-4.668 (d, J=17.5 Hz, 1H), 4.585-4.557 (d, J=17.5 Hz, 1H), 4.557-4.538 (d, J=9.5 Hz, 1H), 3.865 (s, 3H), 3.853 (s, 3H), 2.336-2.277 (m, 1H), 1.046-1.033 (d, J=6.5 Hz, 3H), 0.879-0.865 (d, J=7 Hz, 3H); MS (ESI): m/z 487 (M−H), m/z 489 (M+H).

Example 143

(S)-Methyl 3-methyl-2-(1-oxo-6-(4-(3,4,5-trimethoxybenzamido)phenyl)isoindolin-2-yl)butanoate The compound of example 143 was prepared analogous to compound of example 97 by reaction of compound of example 6 with 3,4,5-trimethoxy benzoyl chloride.

Yield: 89%; $^1$H NMR (DMSO-$d_6$, 300 MHz): δ 10.256 (s, 1H), 7.946 (m, 2H), 7.898-7.872 (d, J=7.8 Hz, 2H), 7.789-7.763 (d, J=7.8 Hz, 2H), 7.730-7.705 (d, J=7.5 Hz, 1H), 7.306 (s, 2H), 4.612 (m, 3H), 3.888 (s, 6H), 3.741 (s, 3H), 3.688 (s, 3H), 2.340 (m, 1H), 1.014-0.996 (d, J=5.4 Hz, 3H), 0.864-0.845 (d, J=5.7 Hz, 3H); MS (ESI): m/z 531 (M−H), m/z 533 (M+H).

Example 144

(S)-3-Methyl-2-(1-oxo-6-(4-(3,4,5-trimethoxybenzamido)phenyl)isoindolin-2-yl)butanoic acid The compound of example 144 was prepared analogous to compound of example 98 by hydrolysis of compound of example 143.

Yield: 83%; $^1$H NMR (DMSO-$d_6$, 300 MHz): δ 10.277 (s, 1H), 7.942 (s, 2H), 7.894-7.878 (d, J=8 Hz, 2H), 7.779-7.763 (d, J=8 Hz, 2H), 7.710-7.694 (d, J=8 Hz, 1H), 7.316 (s, 2H), 4.745-4.709 (d, J=18 Hz, 1H), 4.558-4.516 (d, J=18 Hz, 1H), 4.516-4.496 (d, J=10 Hz, 1H), 3.890 (s, 6H), 3.744 (s, 3H), 2.305-2.289 (m, 1H), 1.036-1.023 (d, J=6.5 Hz, 3H), 0.863-0.850 (d, J=6.5 Hz, 3H); MS (ESI): m/z 517 (M−H), m/z 519 (M+H).

Example 145

(S)-Methyl 2-(6-(4-(3,5-diethoxybenzamido)phenyl)-1-oxoisoindolin-2-yl)-3-methylbutanoate The compound of example 145 was prepared analogous to compound of example 97 by reaction of compound of example 6 with 3,5-dimethoxy benzoyl chloride.

Yield: 77%; $^1$H NMR (DMSO-$d_6$, 300 MHz): δ 10.266 (s, 1H), 7.943-7.740 (m, 7H), 7.108 (s, 2H), 6.697 (s, 1H), 4.610 (m, 3H), 4.109-4.088 (d, J=6.3 Hz, 4H), 3.687 (s, 3H), 2.339 (m, 1H), 1.356 (m, 6H), 1.013-0.995 (d, J=5.4 Hz, 3H), 0.863-0.845 (d, J=5.4 Hz, 3H); MS (ESI): m/z 531 (M+H).

Example 146

(S)-2-(6-(4-(3,5-Diethoxybenzamido)phenyl)-1-oxoisoindolin-2-yl)-3-methyl butanoic acid The compound of example 146 was prepared analogous to compound of example 98 by hydrolysis of compound of example 145.

Yield: 82%; $^1$H NMR (DMSO-$d_6$, 300 MHz): δ 10.410 (s, 1H), 7.877 (s, 4H), 7.715-7.689 (d, J=7.8 Hz, 2H), 7.657-7.633 (d, J=7.2 Hz, 1H), 7.754 (s, 2H), 6.682 (s, 1H), 4.990-4.361 (dd, J=18.1 Hz, 2H), 4.299-4.269 (d, J=9 Hz, 1H), 4.112-4.090 (m, 4H), 2.218 (m, 1H), 1.353 (m, 6H), 0.998-0.980 (d, J=5.4 Hz, 3H), 0.796-0.777 (d, J=5.7 Hz, 3H); MS (ESI): m/z 515 (M−H), m/z 517 (M+H).

Example 147

(S)-Methyl 3-methyl-2-(1-oxo-6-(4-(3-phenoxybenzamido)phenyl)isoindolin-2-yl)butanoate The compound of example 147 was prepared analogous to compound of example 97 by reaction of example 6 with 3-phenoxy benzoyl chloride.

Yield: 70%; $^1$H NMR (DMSO-$d_6$, 300 MHz): δ 10.406 (s, 1H), 7.939-7.886 (m, 4H), 7.768-7.738 (m, 4H), 7.616-7.546 (m, 2H), 7.445-7.422 (m, 2H), 7.258-7.199 (m, 2H), 7.103-7.078 (d, J=7.5 Hz, 2H), 4.608 (m, 3H), 3.685 (s, 3H), 2.336 (m, 1H), 1.011-0.993 (d, J=5.4 Hz, 3H), 0.862-0.842 (d, J=6 Hz, 3H); MS (ESI): m/z 535 (M+H).

Example 148

(S)-3-Methyl-2-(1-oxo-6-(4-(3-phenoxybenzamido)phenyl)isoindolin-2-yl)butanoic acid The compound of example 148 was prepared analogous to compound of example 98 by hydrolysis of compound of example 147.

Yield: 83.44%; $^1$H NMR (DMSO-$d_6$, 300 MHz): δ 10.406 (s, 1H), 7.933-7.886 (m, 4H), 7.768-7.692 (m, 4H), 7.617-7.545 (m, 2H), 7.444-7.421 (d, J=6.9 Hz, 2H), 7.257-7.199 (m, 2H), 7.103-7.078 (d, J=7.5 Hz, 2H), 4.719-4.523 (m, 3H), 2.296 (m, 1H), 1.042-1.024 (d, J=5.4 Hz, 3H), 0.874-0.855 (d, J=5.7 Hz, 3H); MS (ESI): m/z 521 (M+H).

Example 149

(S)-Methyl 3-methyl-2-(1-oxo-6-(4-(4-phenoxybenzamido)phenyl)isoindolin-2-yl)butanoate The compound of example 149 was prepared analogous to compound of example 97 by reaction of compound of example 6 with 4-phenoxy benzoyl chloride.

Yield: 76%; $^1$H NMR (DMSO-$d_6$, 300 MHz): δ 10.336 (s, 1H), 8.044-8.018 (d, J=7.8 Hz, 2H), 7.941-7.900 (m, 4H), 7.766-7.702 (m, 3H), 7.467-7.444 (d, J=6.9 Hz, 2H), 7.260-7.237 (d, J=6.9 Hz, 1H), 7.129 (m, 4H), 4.610 (m, 3H), 3.687 (s, 3H), 2.339 (m, 1H), 1.013-0.994 (d, J=5.7 Hz, 3H), 0.863-0.844 (d, J=5.7 Hz, 3H); MS (ESI): m/z 533 (M−H), m/z 535 (M+H).

Example 150

(S)-3-Methyl-2-(1-oxo-6-(4-(4-phenoxybenzamido)phenyl)isoindolin-2-yl)butanoic acid The compound of example 150 was prepared analogous to compound of example 98 by hydrolysis of compound of example 149.

Yield: 77%; $^1$H NMR (DMSO-$d_6$, 300 MHz): δ 13.030 (s, 1H), 10.329 (s, 1H), 8.044-8.017 (d, J=8.1 Hz, 2H), 7.937-7.899 (m, 4H), 7.768-7.698 (m, 3H), 7.468-7.444 (d, J=7.2 Hz, 2H), 7.260-7.237 (d, J=6.9 Hz, 1H), 7.131-7.113 (m, 4H), 4.711-4.567 (dd, J=17.7, 2H), 4.567-4.535 (d, J=9.6 Hz, 1H), 2.323 (m, 1H), 1.047-1.028 (d, J=5.7 Hz, 3H), 0.880-0.861 (d, J=5.7 Hz, 3H); MS (ESI) m/z 519 (M−H), m/z 521 (M+H).

Example 151

(S)-Methyl 3-methyl-2-(1-oxo-6-(4-(2-phenoxybenzamido)phenyl)isoindolin-2-yl)butanoate The compound of example 151 was prepared analogous to compound of example 97 by reaction of compound of example 6 with 2-phenoxy benzoyl chloride.

Yield: 92%; $^1$H NMR (DMSO-$d_6$, 300 MHz): δ 10.456 (s, 1H), 7.908 (s, 2H), 7.779 (m, 2H), 7.715-7.694 (d, J=6.1 Hz, 4H), 7.513-7.289 (m, 4H), 7.137-7.061 (m, 3H), 6.993-6.967 (d, J=7.8 Hz, 1H), 4.631-4.600 (m, 3H), 3.681 (s, 3H), 2.333 (m, 1H), 1.007-0.988 (d, J=5.7 Hz, 3H), 0.855-0.835 (d, J=6 Hz, 3H); MS (ESI): m/z 533 (M−H), m/z 535 (M+H).

Example 152

(S)-3-Methyl-2-(1-oxo-6-(4-(2-phenoxybenzamido)phenyl)isoindolin-2-yl)butanoic acid The compound of example 152 was prepared analogous to compound of example 98 by hydrolysis of compound of example 151.

Yield: 76%; ¹H NMR (DMSO-d₆, 300 MHz): δ 13.028 (s, 1H), 10.452 (s, 1H), 7.905 (s, 2H), 7.805-7.780 (d, J=7.5 Hz, 2H), 7.698 (m, 4H), 7.513-7.289 (m, 4H), 7.161-7.968 (m, 4H), 4.701-4.526 (m, 3H), 2.292 (m, 1H), 1.040-1.022 (d, J=5.4 Hz, 3H), 0.871-0.852 (d, J=5.7 Hz, 3H); MS (ESI): m/z 519 (M−H), m/z 521 (M+H).

Example 153

(S)-Methyl 3-methyl-2-(1-oxo-6-(4-(2,4,6-trimethyl-benzamido)phenyl)isoindolin-2-yl)butanoate The compound of example 153 was prepared analogous to compound of example 97 by reaction of compound of example 6 with 2,4,6-trimethyl benzoyl chloride.

Yield: 77%; ¹H NMR (DMSO-d₆, 300 MHz): δ 10.448 (s, 1H), 7.922 (s, 2H), 7.868 (m, J=7.8 Hz; 2H), 7.737 (m, 3H), 6.942 (s, 2H), 4.608 (m, 3H), 3.686 (s, 3H), 2.256 (m, 10H), 1.013-0.995 (d, J=5.4 Hz, 3H), 0.862-0.843 (d, J=5.7 Hz, 3H); MS (ESI) m/z 483 (M−H), m/z 485 (M+H).

Example 154

(S)-3-Methyl-2-(1-oxo-6-(4-(2,4,6-trimethylbenzamido)phenyl)isoindolin-2-yl)butanoic acid The compound of example 154 was prepared analogous to compound of example 98 by hydrolysis of compound of example 153.

Yield: 81%; ¹H NMR (DMSO-d₆, 300 MHz): δ 13.021 (s, 1H), 10.445 (s, 1H), 7.922-7.717 (m, 7H), 6.942 (s, 2H), 4.708-4.565 (dd, J=17.7 Hz, 2H), 4.565-4.533 (d, d=9.6 Hz, 1H), 2.257 (s, 10H), 1.045-1.027 (d, J=5.4 Hz, 3H), 0.877-0.859 (d, J=5.4 Hz, 3H); MS (ESI): m/z 469 (M−H), m/z 471 (M+H).

Example 155

(S)-Methyl 2-(6-(4-(2,4-dimethoxybenzamido)phenyl)-1-oxoisoindolin-2-yl)-3-methylbutanoate The compound of example 155 was prepared analogous to compound of example 97 by reaction of compound of example 6 with 2,4-dimethoxy benzoyl chloride.

Yield: 73%; ¹H NMR (DMSO-d₆, 300 MHz): δ 10.048 (s, 1H), 8.863 (s, 2H), 7.936 (s, 2H), 7.877-7.851 (d, J=7.8 Hz, 2H), 7.781-7.722 (m, 3H), 6.721-6.673 (m, 1H), 4.608 (m, 3H), 3.972 (s, 3H), 3.853 (s, 3H), 3.686 (s, 3H), 2.346 (m, 1H), 1.012-0.994 (d, J=5.4 Hz, 3H), 0.861-0.843 (d, J=5.4 Hz, 3H); MS (ESI): m/z 503 (M−H).

Example 156

(S)-2-(6-(4-(2,4-Dimethoxybenzamido)phenyl)-1-oxoisoindolin-2-yl)-3-methyl butanoic acid The compound of example 156 was prepared analogous to compound of example 98 by hydrolysis of compound of example 155.

Yield: 80%; ¹H NMR (DMSO-d₆, 300 MHz): δ 13.009 (s, 1H), 10.046 (s, 1H), 7.934 (s, 2H), 7.877-7.852 (d, J=7.5 Hz, 2H), 7.874-7.7.721 (d, 4H), 6.722-6.674 (s, 2H), 4.710-4.568 (dd, J=17.7, 18 Hz, 2H), 4.568-4.535 (d, J=9.9 Hz, 1H), 3.974 (s, 3H), 3.854 (s, 3H), 2.304 (m, 1H), 1.047-1.029 (d, J=5.4 Hz, 3H), 0.879-0.861 (d, J=5.4 Hz, 3H); MS (ESI) m/z 487 (M−H), m/z 489 (M+H).

Example 157

(S)-Methyl 3-methyl-2-(1-oxo-6-(4-(4-(trifluoromethoxy)benzamido)phenyl)isoindolin-2-yl)butanoate The compound of example 157 was prepared analogous to compound of example 97 by reaction of compound of example 6 with 4-trifluoromethoxy benzoyl chloride.

Yield: 84%; ¹H NMR (DMSO-d₆, 300 MHz): δ 10.490 (s, 1H), 8.123-8.097 (d, J=7.8 Hz, 2H), 7.946-7.894 (m, 4H), 7.782-7.756 (d, J=7.8 Hz, 2H), 7.731-7.708 (d, J=6.9 Hz, 1H), 7.569-7.544 (d, J=7.5 Hz, 2H), 4.612 (m, 3H), 3.688 (s, 3H), 2.372-2.186 (m, 1H), 1.014-0.996 (d, J=5.4 Hz, 3H), 0.865-0.846 (d, J=5.7 Hz, 3H); MS (ESI): m/z 525 (M−H), m/z 527 (M+H).

Example 158

(S)-3-Methyl-2-(1-oxo-6-(4-(4-(trifluoromethoxy)benzamido)phenyl)isoindolin-2-yl)butanoic acid The compound of example 158 was prepared analogous to compound of example 98 by hydrolysis of compound of example 157.

Yield: 84%; ¹H NMR (DMSO-d₆, 300 MHz): δ 13.124 (s, 1H), 10.491 (s, 1H), 8.125-8.098 (d, J=8.1 Hz, 2H), 7.941-7.896 (m, 4H), 7.785-7.758 (d, J=8.1 Hz, 2H), 7.727-7.701 (d, J=7.8 Hz, 1H), 7.570-7.545 (d, J=7.5 Hz, 2H), 4.718-4.562 (dd, J=17.7, 19.8 Hz, 2H), 4.562-4.531 (d, J=9.3 Hz, 1H), 2.322 (m, 1H), 1.046-1.027 (d, J=5.7 Hz, 3H), 0.879-0.860 (d, J=5.7 Hz, 3H); MS (ESI): m/z 511 (M−H), m/z 513 (M+H).

Example 159

(S)-Methyl 2-(6-(4-(2-methoxybenzamido)phenyl)-1-oxoisoindolin-2-yl)-3-methylbutanoate The compound of example 159 was prepared analogous to compound of example 97 by reaction of compound of example 6 with 2-methoxy benzoyl chloride.

Yield: 90%; ¹H NMR (DMSO-d₆, 300 MHz): δ 10.246 (s, 1H), 8.883-8.871 (d, J=3 Hz, 1H), 8.473-8.450 (t, J=6.9 Hz, 1H), 7.962-7.936 (d, J=7.8 Hz, 2H), 7.882-7.856 (d, J=7.8 Hz, 2H), 7.750-7.724 (d, J=7.8 Hz, 2H), 7.520-7.497 (t, J=6.9 Hz, 1H), 7.211-7.184 (d, J=8.1 Hz, 1H), 7.105-7.059 (t, J=6.9 Hz, 1H), 4.640 (m, 3H), 3.916 (s, 3H), 3.687 (s, 3H), 2.349 (m, 1H), 1.015-0.996 (d, J=5.7 Hz, 3H), 0.865-0.845 (d, J=6 Hz, 3H); MS (ESI): m/z 473 (M+H).

Example 160

(S)-2-(6-(4-(2-Methoxybenzamido)phenyl)-1-oxoisoindolin-2-yl)-3-methyl butanoic acid The compound of example 160 was prepared analogous to compound of example 98 by hydrolysis of compound of example 159.

Yield: 84%; ¹H NMR (DMSO-d₆, 300 MHz): δ 10.246 (s, 1H), 7.916-7.855 (m, 4H), 7.747-7.677 (m, 4H), 7.519 (m, 1H), 7.209-7.183 (d, J=7.8 Hz, 1H), 7.083 (m, 1H), 4.777-4.464 (m, 3H), 3.917 (s, 3H), 2.277 (m, 1H), 1.013-0.996 (d, J=5.1 Hz, 3H), 0.853-0.836 (d, J=5.1 Hz, 3H); MS (ESI): m/z 457 (M−H), m/z 459 (M+H).

Example 161

(S)-Methyl 2-(6-(4-(4-fluoro-3-methylbenzamido)phenyl)-1-oxoisoindolin-2-yl)-3-methylbutanoate The compound of example 161 was prepared analogous to compound of example 97 by reaction of compound of example 6 with 4-fluoro-3-methyl benzoyl chloride.

Yield: 85%; $^1$H NMR (DMSO-$d_6$, 300 MHz): δ 10.349 (s, 1H), 7.942-7.890 (m, 6H), 7.770-7.703 (m, 3H), 7.346-7.287 (t, J=8.7, 9 Hz, 1H), 4.612 (m, 3H), 3.688 (s, 3H), 2.336 (m, 4H), 1.015-0.996 (d, J=5.7 Hz, 3H), 0.866-0.847 (d, J=5.7 Hz, 3H); MS (ESI) m/z 473 (M−H), m/z 475 (M+H).

Example 162

(S)-2-(6-(4-(4-Fluoro-3-methylbenzamido)phenyl)-1-oxoisoindolin-2-yl)-3-methyl butanoic acid The compound of example 162 was prepared analogous to compound of example 98 by hydrolysis of compound of example 161.

Yield: 85%; $^1$H NMR (DMSO-$d_6$, 300 MHz): δ 13.014 (s, 1H), 10.339 (s, 1H), 7.938-7.888 (m, 6H), 7.770-7.698 (m, 3H), 7.345-7.287 (t, J=8.7 Hz, 1H), 4.713-4.567 (dd, J=17.7, 18.6 Hz, 2H), 4.567-4.535 (d, J=9.6 Hz, 1H), 2.335 (m, 4H), 1.047-1.030 (d, J=5.1 Hz, 3H), 0.881-0.863 (d, J=5.4 Hz, 3H); MS (ESI): m/z 459 (M−H), m/z 461 (M+H).

Example 163

(S)-Methyl 2-(6-(4-(4-butylbenzamido)phenyl)-1-oxoisoindolin-2-yl)-3-methyl butanoate The compound of example 163 was prepared analogous to compound of example 97 by reaction of compound of example 6 with 4-(n-butyl)benzoyl chloride.

Yield: 75%; $^1$H NMR (DMSO-$d_6$, 300 MHz): δ 10.295 (s, 1H), 7.937 (m, 5H), 7.761-7.733 (d, J=8.4 Hz, 4H), 7.378-7.355 (d, J=6.9 Hz, 2H), 4.612 (m, 3H), 3.688 (s, 3H), 2.672 (m, 2H), 2.343 (m, 1H), 1.598 (m, 2H), 1.336-1.314 (m, 2H), 1.015-0.889 (m, 6H), 0.867-0.848 (d, J=5.7 Hz, 3H); MS (ESI): m/z 497 (M−H), m/z 499 (M+H).

Example 164

(S)-2-(6-(4-(4-Butylbenzamido)phenyl)-1-oxoisoindolin-2-yl)-3-methylbutanoic acid The compound of example 164 was prepared analogous to compound of example 98 by hydrolysis of compound of example 163.

Yield: 91%; $^1$H NMR (DMSO-$d_6$, 300 MHz): δ 13.044 (s, 1H), 10.294 (s, 1H), 7.932-7.904 (m, 6H), 7.763-7.736 (m, 3H), 7.378-7.355 (d, J=6.9 Hz, 2H), 4.716 (dd, J=17.7, 20.4 Hz, 2H), 4.564-4.532 (d, J=9.6 Hz, 1H), 2.671 (m, 2H), 2.303 (m, 1H), 1.597 (m, 2H), 1.336-1.313 (m, 2H), 1.029-0.863 (m, 9H); MS (ESI): m/z 483 (M−H).

Example 165

(S)-Methyl 2-(6-(4-(2,6-difluoro-3-methylbenzamido)phenyl)-1-oxoisoindolin-2-yl)-3-methylbutanoate The compound of example 165 was prepared analogous to compound of example 97 by reaction of compound of example 6 with 2,6-difluoro-3-methyl benzoyl chloride.

Yield: 89%; $^1$H NMR (DMSO-$d_6$, 300 MHz): δ 10.896 (s, 1H), 8.857 (m, 1H), 7.936 (m, 2H), 7.803-7.707 (m, 4H), 7.486-7.462 (m, 1H), 7.191-7.136 (t, J=8.1, 8.4 Hz, 1H), 4.611 (m, 3H), 3.686 (s, 3H), 2.275 (m, 4H), 1.014-0.995 (d, J=6 Hz, 3H), 0.864-0.845 (d, J=5.7 Hz, 3H); MS (ESI): m/z 493 (M+H).

Example 166

(S)-2-(6-(4-(2,6-Difluoro-3-methylbenzamido)phenyl)-1-oxoisoindolin-2-yl)-3-methylbutanoic acid The compound of example 166 was prepared analogous to compound of example 98 by hydrolysis of compound of example 165.

Yield: 78%; $^1$H NMR (DMSO-$d_6$, 300 MHz): δ 10.932 (s, 1H), 7.875-7.764 (m, 6H), 7.671-7.648 (d, J=6.9 Hz, 1H), 7.479-7.456 (m, 1H), 7.186-7.133 (t, J=8.1, 7.8 Hz, 1H), 5.008-4.348 (dd, J=18.3 Hz, 2H), 4.273-4.243 (d, J=9 Hz, 1H), 2.274 (m, 4H), 0.989-0.972 (d, J=5.1 Hz, 3H), 0.789-0.771 (d, J=5.4 Hz, 3H); MS (ESI): m/z 477 (M−H).

Example 167

(S)-Methyl 2-(6-(4-(4-ethylbenzamido)phenyl)-1-oxoisoindolin-2-yl)-3-methyl butanoate The compound of example 167 was prepared analogous to compound of example 97 by reaction of compound of example 6 with 4-ethyl benzoyl chloride.

Yield: 86%; $^1$H NMR (DMSO-$d_6$, 300 MHz): δ 10.292 (s, 1H), 7.963-7.874 (m, 7H), 7.762-7.745 (d, J=8.5 Hz, 2H), 7.379-7.381 (d, J=8 Hz, 2H), 4.658-4.569 (m, 3H), 3.692 (s, 3H), 2.725-2.680 (q, J=7.5 Hz, 2H), 2.361-2.302 (m, 1H), 1.243-1.213 (t, J=7.5 Hz, 3H), 1.015-1.002 (d, J=6.5 Hz, 3H), 0.867-0.854 (d, J=6.5 Hz, 3H); MS (ESI): m/z 469 (M−H), m/z 471 (M+H).

Example 168

(S)-2-(6-(4-(4-Ethylbenzamido)phenyl)-1-oxoisoindolin-2-yl)-3-methylbutanoic acid The compound of example 168 was prepared analogous to compound of example 98 by hydrolysis of compound of example 167.

Yield: 82%; $^1$H NMR (DMSO-$d_6$, 300 MHz): δ 10.316 (s, 1H), 7.935-7.881 (m, 6H), 7.745-7.728 (d, J=8.5 Hz, 2H), 7.675-7.659 (d, J=8 Hz, 1H), 7.392-7.376 (d, J=8 Hz, 2H), 4.922-4.406 (dd, J=18.5 Hz, 2H), 4.331-4.312 (d, J=9.5 Hz, 1H), 2.723-2.678 (q, J=7.5 Hz, 2H), 2.264-2.218 (m, 1H), 1.242-1.212 (t, J=7.5 Hz, 3H), 1.001-0.988 (d, J=6.5 Hz, 3H), 0.809-0.795 (d, J=7 Hz, 3H); MS (ESI): m/z 455 (M−H), m/z 457 (M+H).

Example 169

(S)-Methyl 3-methyl-2-(1-oxo-6-(4-(4-propylbenzamido)phenyl)isoindolin-2-yl)butanoate The compound of example 169 was prepared analogous to compound of example 97 by reaction of compound of example 6 with 4-(n-propyl)benzoyl chloride.

Yield: 91%; $^1$H NMR (DMSO-$d_6$, 300 MHz): δ 10.281 (s, 1H), 7.946-7.874 (m, 6H), 7.745-7.716 (d, J=8.7 Hz, 2H), 7.707-7.687 (d, J=8.7 Hz, 1H), 7.360-7.333 (d, J=8.1 Hz, 2H), 4.626-4.593 (m, 3H), 3.699 (s, 3H), 2.653-2.603 (t, J=7.2 Hz, 2H), 2.361-2.398 (m, 1H), 1.654-1.580 (m, 2H), 0.997-0.975 (d, J=6.6 Hz, 3H), 0.919-0.870 (t, J=7.2, 7.5 Hz, 3H), 0.848-0.825 (d, J=6.9 Hz, 3H); MS (ESI): m/z 483 (M−H), m/z 485 (M+H).

Example 170

(S)-3-Methyl-2-(1-oxo-6-(4-(4-propylbenzamido)phenyl)isoindolin-2-yl)butanoic acid The compound of example 170 was prepared analogous to compound of example 98 by hydrolysis of compound of example 169.
Yield: 80%; $^1$H NMR (DMSO-d$_6$, 300 MHz): δ 10.333 (s, 1H), 7.931-7.893 (m, 6H), 7.751-7.722 (d, J=8.7 Hz, 2H), 7.690-7.662 (d, J=8.4 Hz, 1H), 7.373-7.346 (d, J=8.1 Hz, 2H), 4.860-4.437 (dd, J=18, 18.3 Hz, 2H), 4.437-4.417 (d, J=6 Hz, 1H), 2.670-2.620 (t, J=7.2 Hz, 2H), 2.279-2.248 (m, 1H), 1.673-1.598 (m, 2H), 1.019-0.997 (d, J=6.6 Hz, 3H), 0.938-0.889 (t, J=7.2, 7.5 Hz, 3H), 0.833-0.811 (d, J=6.6 Hz, 3H); MS (ESI): m/z 469 (M−H), m/z 471 (M+H).

Example 171

(S)-Methyl 3-methyl-2-(6-(4-(4-octylbenzamido)phenyl)-1-oxoisoindolin-2-yl)butanoate The compound of example 171 was prepared analogous to compound of example 97 by reaction of compound of example 6 with 4-(n-octyl)benzoyl chloride.
Yield: 98%; $^1$H NMR (DMSO-d$_6$, 300 MHz): δ 10.290 (s, 1H), 7.962-7.945 (d, J=8.5 Hz, 2H), 7.927-7.900 (dd, J=2.5, 6, 8.5 Hz, 4H), 7.760-7.742 (d, J=9 Hz, 2H), 7.722-7.706 (d, J=8 Hz, 1H), 7.370-7.354 (d, J=8 Hz, 2H), 4.657-4.569 (m, 3H), 3.691 (s, 3H), 2.678-2.648 (t, J=7.5 Hz, 2H), 2.362-2.315 (m, 1H), 1.608 (m, 2H), 1.297 (m, 5H), 1.266-1.250 (m, 5H), 1.016-1.002 (d, J=7 Hz, 3H), 0.867-0.847 (m, 6H); MS (ESI): m/z 553 (M−H), m/z 555 (M+H).

Example 172

(S)-3-Methyl-2-(6-(4-(4-octylbenzamido)phenyl)-1-oxoisoindolin-2-yl)butanoic acid The compound of example 172 was prepared analogous to compound of example 98 by hydrolysis of compound of example 171.
Yield: 82%; $^1$H NMR (DMSO-d$_6$, 300 MHz): δ 10.295 (s, 1H), 7.951-7.893 (m, 6H), 7.762-7.733 (d, J=8.7 Hz, 2H), 7.718-7.690 (d, J=8.4 Hz, 1H), 7.371-7.344 (d, J=8.1 Hz, 2H), 4.729-4.550 (dd, J=18 Hz, 2H), 4.550-4.518 (d, J=9.6 Hz, 1H), 2.683-2.597 (t, J=7.2, 7.8 Hz, 2H), 2.344-2.268 (m, 1H), 1.603 (m, 2H), 1.289-1.249 (m, 10H), 1.045-1.023 (d, J=6.6 Hz, 3H), 0.876-0.834 (m, 6H); MS (ESI): m/z 539 (M−H), m/z 541 (M+H).

Example 173

(S)-Methyl 2-(6-(4-(4-cyclohexylbenzamido)phenyl)-1-oxoisoindolin-2-yl)-3-methylbutanoate The compound of example 173 was prepared analogous to compound of example 97 by reaction of compound of example 6 with 4-cyclohexyl benzoyl chloride.
Yield: 65%; $^1$H NMR (DMSO-d$_6$, 300 MHz): δ 10.276 (s, 1H), 7.945-7.872 (m, 6H), 7.744-7.714 (d, J=9 Hz, 2H), 7.708-7.679 (d, J=8.7 Hz, 1H), 7.389-7.362 (d, J=8.1 Hz, 2H), 4.626-4.593 (m, 3H), 3.669 (s, 3H), 2.584 (m, 1H), 2.331-2.298 (m, 1H), 1.812-1.685 (m, 5H), 1.459-1.303 (m, 5H), 1.028-1.006 (d, J=6.6 Hz, 3H), 0.860-0.838 (d, J=6.6 Hz, 3H); MS (ESI): m/z 523 (M−H), m/z 525 (M+H).

Example 174

(S)-2-(6-(4-(4-Cyclohexylbenzamido)phenyl)-1-oxoisoindolin-2-yl)-3-methyl butanoic acid The compound of example 174 was prepared analogous to compound of example 98 by hydrolysis of compound of example 173.
Yield: 82%; $^1$H NMR (DMSO-d$_6$, 300 MHz): δ 12.968 (s, 1H), 10.270 (s, 1H), 7.935-7.869 (m, 6H), 7.742-7.713 (d, J=8.7 Hz, 2H), 7.701-7.672 (d, J=8.7 Hz, 1H), 7.386-7.359 (d, J=8.1 Hz, 2H), 4.694-4.543 (dd, J=18, 19.2 Hz, 2H), 4.543-4.511 (d, J=9.6 Hz, 1H), 2.613-2.543 (m, 1H), 2.328-2.252 (m, 1H), 1.810-1.683 (m, 5H), 1.457-1.126 (m, 5H), 1.027-1.005 (d, J=6.6 Hz, 3H), 0.860-0.838 (d, J=6.6 Hz, 3H); MS (ESI): m/z 509 (M−H).

Example 175

(S)-Methyl 3-methyl-2-(1-oxo-6-(4-(5,5,8,8-tetramethyl-5,6,7,8-tetrahydro naphthalene-2-carboxamido)phenyl)isoindolin-2-yl)butanoate The compound of example 175 was prepared analogous to compound of example 97 by reaction of compound of example 6 with 5,5,8,8-tetramethyl-5,6,7,8-tetra hydronaphthalene-2-carbonyl chloride.
Yield: 76%; $^1$H NMR (DMSO-d$_6$, 300 MHz): δ 10.276 (s, 1H), 7.954-7.861 (m, 6H), 7.755-7.726 (d, J=8.7 Hz, 2H), 7.668-7.640 (m, 1H), 7.483-7.456 (d, J=8.1 Hz, 1H), 4.593-4.530 (m, 3H), 3.671 (s, 3H), 2.378-2.256 (m, 1H), 1.668 (s, 4H), 1.301 (s, 6H), 1.267 (s, 6H), 0.999-0.977 (d, J=6.6 Hz, 3H), 0.926-0.909 (d, J=5.1 Hz, 3H); MS (ESI): m/z 553 (M−H).

Example 176

(S)-3-Methyl-2-(1-oxo-6-(4-(5,5,8,8-tetramethyl-5,6,7,8-tetrahydro naphthalene-2-carboxamido)phenyl)isoindolin-2-yl)butanoic acid The compound of example 176 was prepared analogous to compound of example 98 by hydrolysis of compound of example 175.
Yield: 77%; $^1$H NMR (DMSO-d$_6$, 300 MHz): δ 13.055 (s, 1H), 10.212 (s, 1H), 7.945-7.868 (m, 5H), 7.754-7.726 (d, J=8.4 Hz, 2H), 7.702-7.677 (d, J=7.5 Hz, 2H), 7.748-7.453 (d, J=8.4 Hz, 1H), 4.693-4.548 (dd, J=17.7 Hz, 2H), 4.548-4.516 (d, J=9.6 Hz, 1H), 2.309-2.278 (m, 1H), 1.665 (s, 4H), 1.299 (s, 6H), 1.265 (s, 6H), 1.029-1.008 (d, J=6.3 Hz, 3H), 0.863-0.841 (d, J=6.6 Hz, 3H); MS (ESI): m/z 537 (M−H), m/z 539 (M+H).

Example 177

(S)-Methyl 2-(6-(4-(1-naphthamido)phenyl)-1-oxoisoindolin-2-yl)-3-methyl butanoate The compound of example 177 was prepared analogous to compound of example 97 by reaction of compound of example 6 with 1-naphthoyl chloride.

Yield: 76%; ¹H NMR (DMSO-d₆, 300 MHz): δ 10.722 (s, 1H), 8.868 (m, 2H), 8.556-8.381 (m, 1H), 8.139-7.957 (m, 5H), 7.793-7.616 (m, 6H), 4.617 (m, 3H), 3.692 (s, 3H), 2.332 (m, 1H), 1.000-0.982 (d, J=5.4 Hz, 3H), 0.870-0.852 (d, J=5.4 Hz, 3H); MS (ESI): m/z 491 (M–H), m/z 493 (M+H).

Example 178

(S)-2-(6-(4-(1-Naphthamido)phenyl)-1-oxoisoindolin-2-yl)-3-methylbutanoic acid

The compound of example 178 was prepared analogous to compound of example 98 by hydrolysis of compound of example 177.

Yield: 65%; ¹H NMR (DMSO-d₆, 300 MHz): δ 13.058 (s, 1H), 10.717 (s, 1H), 8.197-7.954 (m, 7H), 7.797-7.617 (m, 7H), 4.720-4.574 (dd, J=17.7 Hz, 2H), 4.574-4.542 (d, J=9.6 Hz, 1H), 2.332 (m, 1H), 1.052-1.034 (d, J=5.4 Hz, 3H), 0.886-0.868 (d, J=5.4 Hz, 3H); MS (ESI): m/z 477 (M–H), m/z 479 (M+H).

Example 179

(S)-Methyl 2-(6-(4-(3,5-dimethoxybenzamido)phenyl)-1-oxoisoindolin-2-yl)-3-methylbutanoate The compound of example 179 was prepared analogous to compound of example 97 by reaction of compound of example 6 with 3,5-dimethoxy benzoyl chloride. The compound of example 179 was used directly without isolation for the preparation of compound of example 180.

Example 180

(S)-2-(6-(4-(3,6-Dimethoxybenzamido)phenyl)-1-oxoisoindolin-2-yl)-3-methyl butanoic acid The compound of example 180 was prepared analogous to compound of example 98 by hydrolysis of compound of example 179.

Yield: 64%; ¹H NMR (DMSO-d₆, 300 MHz): δ 13.015 (s, 1H), 10.300 (s, 1H), 7.943-7.891 (m, 4H), 7.777-7.749 (d, J=8.4 Hz, 2H), 7.727-7.700 (d, J=8.1 Hz, 1H), 7.130 (s, 2H), 7.733 (s, 1H), 4.713-4.567 (dd, J=17.7 Hz, 2H), 4.567-4.536 (d, J=9.3 Hz, 1H), 3.839 (s, 6H), 2.303 (m, 1H), 1.049-1.029 (d, J=6 Hz, 3H), 0.882-0.862 (d, J=5.4 Hz, 3H); MS (ESI): m/z 487 (M–H), m/z 489 (M+H).

Example 181

(S)-Methyl 2-(6-(4-(4-hexylbenzamido)phenyl)-1-oxoisoindolin-2-yl)-3-methyl butanoate The compound of example 181 was prepared analogous to compound of example 97 by reaction of compound of example 6 with 4-(n-hexyl)benzoyl chloride.

Yield: 80%; ¹H NMR (DMSO-d₆, 300 MHz): δ 10.293 (s, 1H), 7.962-7.945 (d, J=8.5 Hz, 2H), 7.292-7.901 (dd, J=6.5, 8.5 Hz, 4H), 7.760-7.743 (d, J=8.5 Hz, 2H), 7.721-7.705 (d, J=8 Hz, 1H), 7.372-7.356 (d, J=8 Hz, 2H), 4.657-4.569 (m, 3H), 3.691 (s, 3H), 2.681-2.650 (t, J=7.5, 8 Hz, 2H), 2.361-2.301 (m, 1H), 1.621-1.595 (m, 2H), 1.291 (m, 6H), 1.015-1.002 (d, J=6.5 Hz, 3H), 0.879-0.853 (m, 6H); MS (ESI): m/z 525 (M–H), m/z 527 (M+H).

Example 182

(S)-2-(6-(4-(4-Hexylbenzamido)phenyl)-1-oxoisoindolin-2-yl)-3-methylbutanoic acid The compound of example 182 was prepared analogous to compound of example 98 by hydrolysis of compound of example 181.

Yield: 73%; ¹H NMR (DMSO-d₆, 300 MHz): δ 10.304 (s, 1H), 7.948-7.862 (m, 6H), 7.762-7.733 (d, J=8.7 Hz, 2H), 7.688-7.665 (d, J=6.9 Hz, 1H), 7.375-7.348 (d, J=8.1 Hz, 2H), 4.740-4.514 (dd, J=18 Hz, 2H), 4.535-4.503 (d, J=9.6 Hz, 1H), 2.688-2.638 (t, J=7.2, 7.8 Hz, 2H), 2.317-2.264 (m, 1H), 1.607 (m, 2H), 1.294 (m, 6H), 1.042-1.020 (d, J=6.6 Hz, 3H), 0.871-0.850 (m, 6H); MS (ESI): m/z 511 (M–H), m/z 513 (M+H).

Example 183

(S)-Methyl 2-(6-(4-(4-heptylbenzamido)phenyl)-1-oxoisoindolin-2-yl)-3-methyl butanoate The compound of example 183 was prepared analogous to compound of example 97 by reaction of compound of example 6 with 4-(n-heptyl)benzoyl chloride.

Yield: 75%; ¹H NMR (DMSO-d₆, 300 MHz): δ 10.276 (s, 1H), 7.946-7.872 (m, 6H), 7.744-7.715 (d, J=8.7 Hz, 2H), 7.708-7.679 (d, J=8.7 Hz, 2H), 7.355-7.328 (d, J=8.1 Hz, 1H), 4.625-4.592 (m, 3H), 3.669 (s, 3H), 2.667-2.617 (t, J=7.2, 7.8 Hz, 2H), 2.391-2.256 (m, 1H), 1.610-1.564 (m, 2H), 1.270-1.238 (m, 8H), 0.997-0.975 (d, J=6.6 Hz, 3H), 0.847-0.825 (m, 6H); MS (ESI): m/z 539 (M–H), m/z 541 (M+H).

Example 184

(S)-2-(6-(4-(4-Heptylbenzamido)phenyl)-1-oxoisoindolin-2-yl)-3-methylbutanoic acid The compound of example 184 was prepared analogous to compound of example 98 by hydrolysis of compound of example 183.

Yield: 88%; ¹H NMR (DMSO-d₆, 300 MHz): δ 10.301 (s, 1H), 7.930-7.895 (m, 6H), 7.762-7.733 (d, J=8.7 Hz, 2H), 7.715-7.687 (d, J=8.4 Hz, 1H), 7.372-7.345 (d, J=8.1 Hz, 2H), 4.741-4.536 (dd, J=17.7 Hz, 2H), 4.536-4.505 (d, J=9.3 Hz, 1H), 2.685-2.635 (t, J=7.5 Hz, 2H), 2.339-2.263 (m, 1H), 1.605 (m, 2H), 1.357-1.172 (m, 8H), 1.042-1.021 (d, J=6.3 Hz, 3H), 0.870-0.849 (m, 6H); MS (ESI): m/z 525 (M–H), m/z 527 (M+H).

Example 185

(S)-Methyl 3-methyl-2-(6-(4-(4-nonylbenzamido)phenyl)-1-oxoisoindolin-2-yl)butanoate The compound of example 185 was prepared analogous to compound of example 97 by reaction of compound of example 6 with 4-(n-nonyl)benzoyl chloride.

Yield: 76%; ¹H NMR (DMSO-d₆, 300 MHz): δ 10.291 (s, 1H), 7.964-7.892 (m, 6H), 7.763-7.734 (d, J=8.7 Hz, 2H), 7.726-7.697 (d, J=8.7 Hz, 1H), 7.373-7.346 (d, J=8.1 Hz, 2H), 4.645-4.612 (m, 3H), 3.688 (s, 3H), 2.684-2.635 (t, J=7.2, 7.5 Hz, 2H), 2.337-2.267 (m, 1H), 1.603 (m, 2H), 1.291-1.246 (m, 12H), 1.017-0.995 (d, J=6.6 Hz, 3H), 0.868-0.834 (m, 6H); MS (ESI): m/z 567 (M−H), m/z 569 (M+H).

Example 186

(S)-3-Methyl-2-(6-(4-(4-nonylbenzamido)phenyl)-1-oxoisoindolin-2-yl)butanoic acid The compound of example 186 was prepared analogous to compound of example 98 by hydrolysis of compound of example 185.

Yield: 75%; $^1$H NMR (DMSO-d$_6$, 300 MHz): δ 10.294 (s, 1H), 7.950-7.893 (m, 6H), 7.762-7.733 (d, J=8.7 Hz, 2H), 7.717-7.689 (d, J=8.4 Hz, 1H), 7.371-7.344 (d, J=8.1 Hz, 2H), 4.732-4.544 (dd, J=17.7 Hz, 2H), 4.544-4.512 (d, J=9.6 Hz, 1H), 2.683-2.633 (t, J=7.5 Hz, 2H), 2.343-2.267 (m, 1H), 1.602 (m, 2H), 1.290-1.245 (m, 13H), 1.044-1.022 (d, J=6.6 Hz, 3H), 0.874-0.833 (m, 6H); MS (ESI): m/z: 553 (M−H), m/z 555 (M+H).

Example 187

(S)-Methyl 2-(6-(4-(4-decylbenzamido)phenyl)-1-oxoisoindolin-2-yl)-3-methyl butanoate The compound of example 187 was prepared analogous to compound of example 97 by reaction of compound of example 6 with 4-(n-decyl)benzoyl chloride.

Yield: 64%; $^1$H NMR (DMSO-d$_6$, 300 MHz): δ 10.290 (s, 1H), 7.965-7.892 (m, 6H), 7.763-7.734 (d, J=8.7 Hz, 2H), 7.726-7.697 (d, J=8.7 Hz, 1H), 7.373-7.345 (d, J=8.4 Hz, 2H), 4.645-4.612 (m, 3H), 3.688 (s, 3H), 2.684-2.634 (t, J=7.2, 7.8 Hz, 2H), 2.372-2.269 (m, 1H), 1.653-1.546 (m, 2H), 1.289-1.243 (m, 14H), 1.017-0.995 (d, J=6.6 Hz, 3H), 0.868-0.833 (m, 6H); MS (ESI): m/z 581 (M−H), m/z 583 (M+H).

Example 188

(S)-2-(6-(4-(4-Decylbenzamido)phenyl)-1-oxoisoindolin-2-yl)-3-methyl butanoic acid The compound of example 188 was prepared analogous to compound of example 98 by hydrolysis of compound of example 187.

Yield: 82%; $^1$H NMR (DMSO-d$_6$, 300 MHz): δ 13.043 (s, 1H), 10.287 (s, 1H), 7.953-7.899 (m, 6H), 7.760-7.743 (d, J=8.5 Hz, 2H), 7.718-7.702 (d, J=8 Hz, 1H), 7.368-7.352 (d, J=8 Hz, 2H), 4.700-4.550 (dd, J=18 Hz, 2H), 4.561-4.541 (d, J=10 Hz, 1H), 2.676-2.646 (t, J=7.5 Hz, 2H), 2.366-2.292 (m, 1H), 1.606 (m, 2H), 1.295-1.245 (m, 14H), 1.047-1.034 (d, J=6.5 Hz, 3H), 0.880-0.843 (m, 6H); MS (ESI): m/z 567 (M−H), m/z 569 (M+H).

Example 189

(S)-(Methyl 2-(6-(4-(adamantyl-2-carboxamido)phenyl)-1-oxoisoindolin-2-yl)-3-methylbutanoate The compound of example 189 was prepared analogous to compound of example 97 by reaction of compound of example 6 with adamantane-2-carbonyl chloride.

Yield: 52%; $^1$H NMR (DMSO-d$_6$, 300 MHz): δ 9.236 (s, 1H), 7.910 (m, 2H), 7.808-7.782 (d, J=7.8 Hz, 2H), 7.695 (m, 3H), 4.636-4.602 (m, 3H), 3.684 (s, 3H), 2.343 (m, 2H), 2.031 (s, 3H), 1.932 (m, 6H), 1.718 (m, 5H), 1.011-0.992 (d, J=5.7 Hz, 3H), 0.859-0.840 (d, J=5.7 Hz, 3H); MS (ESI): m/z 502 (M+H).

Example 190

(S)-2-(6-(4-(Adamantyl-2-carboxamido)phenyl)-1-oxoisoindolin-2-yl)-3-methylbutanoic acid The compound of example 190 was prepared analogous to compound of example 98 by hydrolysis of compound of example 189.

Yield: 73%; $^1$H NMR (DMSO-d$_6$, 300 MHz): δ 13.007 (s, 1H), 9.217 (s, 1H), 7.909-7.887 (m, 2H), 7.792-7.763 (d, J=8.7 Hz, 2H), 7.679-7.650 (d, J=8.7 Hz, 3H), 4.681-4.508 (d, J=17.7 Hz, 2H), 4.508-4.476 (d, J=9.6 Hz, 1H), 2.348-2.228 (m, 2H), 2.014 (s, 3H), 1.916 (m, 6H), 1.699 (m, 5H), 1.025-1.003 (d, J=6.6 Hz, 3H), 0.857-0.833 (d, J=6.6 Hz, 3H); MS (ESI): m/z 485 (M−H), m/z 487 (M+H).

Example 191

(S)-Methyl 2-(6-(4-(2-fluoro-4-(trifluoromethyl)benzamido)phenyl)-1-oxoisoindolin-2-yl)-3-methylbutanoate The compound of example 191 was prepared was prepared analogous to compound of example 97 by reaction of compound of example 6 with 2-fluoro-4-trifluoromethyl benzoyl chloride.

Yield: 73%; $^1$H NMR (DMSO-d$_6$, 300 MHz): δ 10.759 (s, 1H), 7.941-7.907 (m, 4H), 7.829-7.740 (m, 6H), 4.613 (m, 3H), 3.688 (s, 3H), 2.348 (m, 1H), 1.013-0.996 (d, J=5.1 Hz, 3H), 0.863-0.845 (d, J=5.4 Hz, 3H); MS (ESI): m/z 527 (M−H), m/z 529 (M+H).

Example 192

(S)-2-(6-(4-(2-Fluoro-4-(trifluoromethyl)benzamido)phenyl)-1-oxoisoindolin-2-yl)-3-methylbutanoic acid The compound of example 192 was prepared analogous to compound of example 98 by hydrolysis of compound of example 191.

Yield: 94%; $^1$H NMR (DMSO-d$_6$, 300 MHz): δ 10.413 (s, 1H), 7.934-7.834 (m, 4H), 7.765 (m, 4H), 7.471-7.424 (m, 2H), 4.713-4.534 (m, 3H), 2.304 (m, 1H), 1.046-1.028 (d, J=5.4 Hz, 3H), 0.879-0.860 (d, J=5.7 Hz, 3H); MS (ESI): m/z 513 (M−H), m/z 515 (M+H).

Example 193

(S)-Methyl 2-(6-(4-(2-fluoro-3-(trifluoromethyl)benzamido)phenyl)-1-oxoisoindolin-2-yl)-3-methylbutanoate The compound of example 193 was prepared analogous to compound of example 97 by reaction of compound of example 6 with 2-fluoro-3-trifluoromethyl benzoyl chloride.

Yield: 32%; $^1$H NMR (DMSO-d$_6$, 300 MHz): δ 10.783 (s, 1H), 8.030-7.945 (m, 4H), 7.827-7.710 (m, 5H), 7.569 (m, 1H), 4.613 (m, 3H), 3.688 (s, 3H), 2.349 (m, 1H), 1.014-0.997

Example 194

(S)-2-(6-(4-(2-Fluoro-3-(trifluoromethyl)benzamido) phenyl)-1-oxoisoindolin-2-yl)-3-methylbutanoic acid The compound of example 194 was prepared analogous to compound of example 98 by hydrolysis of compound of example 193.

Yield: 69%; $^1$H NMR (DMSO-$d_6$, 300 MHz): δ 13.029 (s, 1H), 10.676 (s, 1H), 7.938-7.731 (m, 9H), 7.420 (m, 1H), 4.716-4.534 (m, 3H), 2.327 (m, 1H), 1.047-1.029 (d, J=5.4 Hz, 3H), 0.881-0.862 (d, J=5.7 Hz, 3H); MS (ESI): m/z 513 (M−H).

Example 195

(S)-Methyl 2-(6-(4-(3-fluoro-4-(trifluoromethyl) benzamido)phenyl)-1-oxoisoindolin-2-yl)-3-methylbutanoate The compound of example 195 was prepared analogous to compound of example 97 by reaction of compound of example 6 with 3-fluoro-4-trifluoromethyl benzoyl chloride.

Yield: 78%; $^1$H NMR (DMSO-$d_6$, 300 MHz): δ 10.644 (s, 1H), 8.109-7.901 (m, 7H), 7.804-7.780 (d, J=7.2 Hz, 2H), 7.734-7.710 (d, J=7.2 Hz, 1H), 4.613 (m, 3H), 3.688 (s, 3H), 2.347 (m, 1H), 1.013-0.996 (d, J=5.1 Hz, 3H), 0.864-0.846 (d, J=5.4 Hz, 3H); MS (ESI): m/z 527 (M−H), m/z 529 (M+H).

Example 196

(S)-2-(6-(4-(3-Fluoro-4-(trifluoromethyl)benzamido) phenyl)-1-oxoisoindolin-2-yl)-3-methylbutanoic acid The compound of example 196 was prepared analogous to compound of example 98 by hydrolysis of compound of example 195.

Yield: 78%; $^1$H NMR (DMSO-$d_6$, 300 MHz): δ 10.837 (s, 1H), 8.172-8.135 (m, 1H), 8.028-7.987 (m, 2H), 7.907-7.889 (m, 4H), 7.749-7.724 (d, J=7.5 Hz, 2H), 7.686-7.662 (d, J=7.2 Hz, 1H), 4.860-4.394 (m, 3H), 2.273 (m, 1H), 1.021-1.004 (d, J=5.1 Hz, 3H), 0.834-0.816 (d, J=5.4 Hz, 3H); MS (ESI): m/z 513 (M−H), m/z 515 (M+H).

Example 197

(S)-Methyl 2-(6-(4-(4-fluoro-2-(trifluoromethyl) benzamido)phenyl)-1-oxoisoindolin-2-yl)-3-methylbutanoate The compound of example 197 was prepared analogous to compound of example 97 by reaction of compound of example 6 with 4-fluoro-2-trifluoromethyl benzoyl chloride.

Yield: 64%; $^1$H NMR (DMSO-$d_6$, 300 MHz): δ 10.721 (s, 1H), 7.934 (s, 2H), 7.789 (s, 8H), 4.611 (m, 3H), 3.687 (s, 3H), 2.346 (m, 1H), 1.013-0.996 (d, J=5.1 Hz, 3H), 0.863-0.845 (d, J=5.4 Hz, 3H); MS (ESI): m/z 527 (M−H), m/z 529 (M+H).

Example 198

(S)-2-(6-(4-(4-Fluoro-2-(trifluoromethyl)benzamido) phenyl)-1-oxoisoindolin-2-yl)-3-methylbutanoic acid The compound of example 198 was prepared analogous to compound of example 98 by hydrolysis of compound of example 197.

Yield: 91%; $^1$H NMR (DMSO-$d_6$, 300 MHz): δ 13.0006 (s, 1H), 10.719 (s, 1H), 7.933 (s, 2H), 7.791-7.710 (s, 8H), 4.716-4.532 (m, 3H), 2.321-2.302 (m, 1H), 1.046-1.028 (d, J=5.4 Hz, 3H), 0.878-0.860 (d, J=5.4 Hz, 3H); MS (ESI): m/z 513 (M−H), m/z 515 (M+H).

Example 199

(S)-Methyl 3-methyl-2-(1-oxo-6-(4-(2-(trifluoromethyl)benzamido)phenyl)iso indolin-2-yl)butanoate The compound of example 199 was prepared analogous to compound of example 97 by reaction of compound of example 6 with 2-trifluoromethyl benzoyl chloride.

Yield: 73%; $^1$H NMR (DMSO-$d_6$, 300 MHz): δ 10.709 (s, 1H), 7.935 (s, 2H), 7.885-7.735 (s, 9H), 4.611 (m, 3H), 3.687 (s, 3H), 2.346 (m, 1H), 1.014-0.995 (d, J=5.7 Hz, 3H), 0.863-0.844 (d, J=5.7 Hz, 3H); MS (ESI): m/z 509 (M−H), m/z 511 (M+H).

Example 200

(S)-3-Methyl-2-(1-oxo-6-(4-(2-(trifluoromethyl) benzamido)phenyl)isoindolin-2-yl)butanoic acid The compound of example 200 was prepared analogous to compound of example 98 by hydrolysis of compound of example 199.

Yield: 81%; $^1$H NMR (DMSO-$d_6$, 300 MHz): δ 10.713 (s, 1H), 7.890-7.800 (m, 6H), 7.754-7.730 (m, 4H), 7.689-7.663 (d, J=78 Hz, 1H), 4.917-4.856 (d, J=18.3 Hz, 1H), 4.462-4.401 (d, J=18.3 Hz, 1H), 4.353-4.322 (d, J=9.3 Hz, 1H), 2.255 (m, 1H), 1.003-0.984 (d, J=5.7 Hz, 3H), 0.811-0.792 (d, J=5.7 Hz, 3H); MS (ESI): m/z 495 (M−H), m/z 497 (M+H).

Example 201

(S)-Methyl 2-(6-(4-(2-ethoxybenzamido)phenyl)-1-oxoisoindolin-2-yl)-3-methyl butanoate The compound of example 201 was prepared analogous to compound of example 97 by reaction of compound of example 6 with 2-ethoxy benzoyl chloride.

Yield: 87%; $^1$H NMR (DMSO-$d_6$, 300 MHz): δ 10.267 (s, 1H), 7.934 (s, 2H), 7.868-7.842 (d, J=7.8 Hz, 2H), 7.762-7.706 (m, 4H), 7.511-7.488 (t, J=6.9 Hz, 1H), 7.202-7.175 (d, J=8.1 Hz, 1H), 7.106-7.060 (t, J=6.6, 7.2 Hz, 1H), 4.610 (m, 3H), 4.210-4.189 (q, J=6.3 Hz, 2H), 3.687 (s, 3H), 2.347 (m, 1H), 1.426 (t, 3H), 1.014-0.995 (d, J=5.7 Hz, 3H), 0.864-0.845 (d, J=5.7 Hz, 3H); MS (ESI): m/z 487 (M+H).

Example 202

(S)-2-(6-(4-(2-Ethoxybenzamido)phenyl)-1-oxoisoindolin-2-yl)-3-methylbutanoic acid The compound of example 202 was prepared analogous to compound of example 98 by hydrolysis of compound of example 201.

Yield: 83%; ¹H NMR (DMSO-d₆, 300 MHz): δ 10.262 (s, 1H), 7.932 (s, 2H), 7.867-7.843 (d, J=7.2 Hz, 2H), 7.762-7.734 (m, 4H), 7.511-7.488 (t, J=6.9 Hz, 1H), 7.201-7.175 (d, J=8.1 Hz, 1H), 7.106-7.084 (t, J=6.6, 7.2 Hz, 1H), 4.712-4.534 (m, 3H), 4.212-4.191 (q, J=6.3 Hz, 2H), 2.302 (m, 1H), 1.426 (t, 3H), 1.047-1.029 (d, J=5.4 Hz, 3H), 0.880-0.862 (d, J=5.4 Hz, 3H); MS (ESI): m/z 471 (M−H), m/z 473 (M+H).

Example 203

(S)-Methyl 2-(6-(4-(4-cyanobenzamido)phenyl)-1-oxoisoindolin-2-yl)-3-methyl butanoate The compound of example 203 was prepared analogous to compound of example 97 by reaction of compound of example 6 with 4-cyano benzoyl chloride.

Yield: 92%; ¹H NMR (DMSO-d₆, 300 MHz): δ 10.616 (s, 1H), 8.153-8.124 (d, J=8.7 Hz, 2H), 8.065-8.037 (d, J=8.4 Hz, 2H), 7.971-7.901 (m, 4H), 7.794-7.765 (d, J=9 Hz, 2H), 7.732-7.703 (d, J=8.7 Hz, 1H), 4.645-4.550 (m, 3H), 3.688 (s, 3H), 2.372-2.295 (m, 1H), 1.016-0.994 (d, J=6.6 Hz, 3H), 0.866-0.844 (d, J=6.6 Hz, 3H); MS (ESI): m/z 466 (M−H), m/z 468 (M+H).

Example 204

(S)-Methyl 2-(6-(4-(3-chloro-2-fluorobenzamido) phenyl)-1-oxoisoindolin-2-yl)-3-methylbutanoate The compound of example 204 was prepared analogous to compound of example 97 by reaction of compound of example 6 with 3-chloro-2-fluoro benzoyl chloride.

Yield: 77%; ¹H NMR (DMSO-d₆, 300 MHz): δ 10.707 (s, 1H), 7.971-7.943 (m, 2H), 7.961-7.832 (d, J=8.7 Hz, 2H), 7.788-7.754 (d, J=9 Hz, 2H), 7.764-7.736 (d, J=8.4 Hz, 1H), 7.707-7.645 (m, 2H), 7.414-7.361 (t, J=7.8, 8.1 Hz, 1H), 4.648-4.614 (m, 3H), 3.692 (s, 3H), 2.377-2.299 (m, 1H), 1.020-0.998 (d, J=6.6 Hz, 3H), 0.869-0.847 (d, J=6.6 Hz, 3H); MS (ESI): m/z 493 (M−H), m/z 495 (M+H).

Example 205

(S)-Methyl 2-(6-(4-(4-fluoro-3-(trifluoromethyl) benzamido)phenyl)-1-oxoisoindolin-2-yl)-3-methylbutanoate The compound of example 205 was prepared analogous to compound of example 97 by reaction of compound of example 6 with 4-fluoro-3-trifluoromethyl benzoyl chloride.

Yield: 74%; ¹H NMR (DMSO-d₆, 300 MHz): δ 10.605 (s, 1H), 8.401-8.384 (d, J=5.1 Hz, 2H), 7.952 (s, 2H), 7.917-7.887 (d, J=7.8 Hz, 2H), 7.798-7.769 (d, J=8.7 Hz, 2H), 7.731 (s, 2H), 4.613 (m, 3H), 3.688 (s, 3H), 2.347 (m, 1H), 1.014-0.996 (d, J=5.4 Hz, 3H), 0.866-0.847 (d, J=5.7 Hz, 3H); MS (ESI): m/z 527 (M−H), m/z 529 (M+H).

Example 206

(S)-Methyl 3-methyl-2-(6-(4-(nicotinamido)phenyl)-1-oxoisoindolin-2-yl)butanoate The compound of example 206 was prepared analogous to compound of example 97 by reaction of compound of example 6 with nicotinoyl chloride.

Yield: 91%; ¹H NMR (DMSO-d₆, 300 MHz): δ 10.902 (s, 1H), 9.334 (s, 1H), 8.936 (m, 2H), 8.711-8.687 (d, J=7.2 Hz, 1H), 8.089 (s, 1H), 7.955-7.887 (m, 3H), 7.807-7.780 (d, J=8.1 Hz, 2H), 7.736-7.712 (d, J=7.2 Hz, 1H), 4.612 (m, 3H), 3.686 (s, 3H), 2.347 (m, 1H), 1.012-0.993 (d, J=5.7 Hz, 3H), 0.863-0.843 (d, J=6 Hz, 3H); MS (ESI): m/z 442 (M−H).

Example 207

(S)-3-Methyl-2-(6-(4-(nicotinamido)phenyl)-1-oxoisoindolin-2-yl)butanoic acid

The compound of example 207 was prepared analogous to compound of example 98 by hydrolysis of compound of example 206.

Yield: 51.63%; ¹H NMR (DMSO-d₆, 300 MHz): δ 12.764 (s, 1H), 10.688 (s, 1H), 9.214 (s, 1H), 8.842 (s, 1H), 8.497-8.476 (d, J=6.3 Hz, 1H), 7.946 (m, 4H), 7.800-7.775 (d, J=7.5 Hz, 2H), 7.730 (s, 2H), 4.716 (dd, J=17.7 Hz, 2H), 4.569-4.538 (d, J=9.3 Hz, 1H), 2.308 (m, 1H), 1.047-1.031 (d, J=4.8 Hz, 3H), 0.881-0.864 (d, J=5.1 Hz, 3H); MS (ESI): m/z 428 (M−H), m/z 430 (M+H).

Example 208

(S)-Methyl-2-(6-(4-(2-chloronicotinamido)phenyl)-1-oxoisoindolin-2-yl)-3-methylbutanoate The compound of example 208 was prepared analogous to compound of example 97 by reaction of compound of example 6 with 2-chloro nicotinoyl chloride.

Yield: 96%; ¹H NMR (DMSO-d₆, 300 MHz): δ 10.797 (s, 1H), 8.862 (s, 1H), 8.552 (s, 1H), 8.127-8.104 (d, J=6.9 Hz, 1H), 7.939 (s, 2H), 7.817-7.708 (m, 4H), 7.589 (m, 1H), 4.611 (m, 3H), 3.687 (s, 3H), 2.339 (m, 1H), 1.013-0.994 (d, J=5.7 Hz, 3H), 0.863-0.843 (d, J=6 Hz, 3H); MS (ESI): m/z 476 (M−H), m/z 478 (M+H).

Example 209

(S)-2-(6-(4-(2-Chloronicotinamido)phenyl)-1-oxoisoindolin-2-yl)-3-methyl butanoic acid The compound of example 209 was prepared analogous to compound of example 98 by hydrolysis of compound of example 208.

Yield: 85%; ¹H NMR (DMSO-d₆, 300 MHz): δ 13.073 (s, 1H), 10.314 (s, 1H), 8.343-8.320 (dd, J=1.8, 4.8 Hz, 1H), 8.070-8.039 (dd, J=1.8, 7.2 Hz, 1H), 7.936-7.916 (m, 2H), 7.854-7.825 (d, J=8.7 Hz, 2H), 7.753-7.724 (d, J=8.7 Hz, 2H), 7.706-7.678 (d, J=8.4 Hz, 1H), 7.168-7.127 (dd, J=5.1, 7.5 Hz, 1H), 4.697-4.544 (dd, J=18, 19.2 Hz, 2H), 4.544-4.512 (d, J=9.6 Hz, 1H), 2.330-2.254 (m, 1H), 1.028-1.006 (d, J=6.6 Hz, 3H), 0.860-0.838 (d, J=6.6 Hz, 3H); MS (ESI): m/z 462 (M−H); m/z 464 (M+H).

Example 210

(S)-Methyl 3-methyl-2-(1-oxo-5-(4-(6-(trifluoromethyl)nicotinamido)phenyl)iso indolin-2-yl)butanoate The compound of example 210 was prepared analogous to compound of example 97 by reaction of compound of example 6 with 6-trifluoromethyl nicotinoyl chloride.

Yield: 65%; ¹H NMR (DMSO-d₆, 300 MHz): δ 10.776 (s, 1H), 9.279 (s, 1H), 8.613-8.589 (d, J=7.2 Hz, 1H), 8.141-8.115 (d, J=7.8 Hz, 1H), 7.956-7.903 (m, 4H), 7.813-7.788 (d, J=7.5 Hz, 2H), 7.737-7.712 (d, J=7.5 Hz, 1H), 4.615 (m, 3H), 3.689 (s, 3H), 2.351 (m, 1H), 1.016-0.997 (d, J=5.7 Hz, 3H), 0.867-0.848 (d, J=5.7 Hz, 3H); MS (ESI): m/z 510 (M−H), m/z 512 (M+H).

Example 211

(S)-Methyl 2-(6-(4-(6-chloronicotinamido)phenyl)-1-oxoisoindolin-2-yl)-3-methyl butanoate The compound of example 211 was prepared analogous to compound of example 97 by reaction of compound of example 6 with 6-chloro nicotinoyl chloride.

Yield: 88%; $^1$H NMR (DMSO-d$_6$, 300 MHz): δ 10.622 (s, 1H), 8.979 (s, 1H), 8.398-8.373 (d, J=7.5 Hz, 1H), 7.950-7.885 (m, 4H), 7.798-7.771 (d, J=8.1 Hz, 2H), 7.751-7.727 (d, J=7.2 Hz, 2H), 4.613 (m, 3H), 3.688 (s, 3H), 2.349 (m, 1H), 1.014-0.996 (d, J=5.4 Hz, 3H), 0.864-0.845 (d, J=5.7 Hz, 3H); MS (ESI): m/z 477 (M−H), m/z 479 (M+H).

Example 212

(S)-Methyl 3-methyl-2-(6-(4-(6-morpholinonicotinamido)phenyl)-1-oxoisoindolin-2-yl)butanoate The compound of example 211 (150 mg, 0.313 mmol) was taken in 3 mL DMSO and to this solution, morpholine (82.01 mg, 0.941 mmol) was added and stirred at 85-90° C. for about 16 h. After completion of the reaction, NaHCO$_3$ was added to it and stirred for 5 min. The solid obtained was filtered and dried to obtain the title compound.

Yield: 120 mg (73%); $^1$H NMR (DMSO-d$_6$, 300 MHz): δ 10.153 (s, 1H), 8.788-8.781 (d, J=2.1 Hz, 1H), 8.154-8.116 (dd, J=2.4, 9 Hz, 1H), 7.963-7.880 (m, 4H), 7.757-7.727 (d, J=9 Hz, 3H), 6.959-6.928 (d, J=9.3 Hz, 1H), 4.643-4.609 (m, 3H), 3.729-3.687 (m, 7H), 3.624-3.594 (m, 4H), 2.349-2.295 (m, 1H), 1.015-0.993 (d, J=6.6 Hz, 3H), 0.864-0.842 (d, J=6.6 Hz, 3H); MS (ESI) m/z: 527 (M−H), m/z 529 (M+H).

Example 213

(S)-3-Methyl-2-(6-(4-(6-morpholinonicotinamido)phenyl)-1-oxoisoindolin-2-yl)butanoic acid To a solution of compound of example 213 (70 mg, 0.132 mmol) in THF (3 mL) and MeOH (1 mL) was added 1 N LiOH (0.06 mL) and stirred at room temperature for about 16 h. After completion of the reaction, the solvent was evaporated and the solid obtained was dissolved in water and extracted with ethyl acetate. Ethyl acetate extract was washed with water and brine, dried over anhydrous sodium sulphate and concentrated to obtain the title compound.

Yield: 60 mg (88%); $^1$H NMR (DMSO-d$_6$, 300 MHz): δ 13.055 (s, 1H), 10.150 (s, 1H), 8.789-8.781 (d, J=2.4 Hz, 1H), 8.156-8.118 (dd, J=2.4, 9 Hz, 1H), 7.957-7.880 (m, 4H), 7.758-7.728 (d, J=9 Hz, 2H), 7.721-7.691 (d, J=9 Hz, 1H), 6.960-6.930 (d, J=9 Hz, 1H), 4.710-4.566 (dd, J=17.7 Hz, 2H), 4.566-4.534 (d, J=9.6 Hz, 1H), 3.730-3.701 (m, 4H), 3.625-3.599 (m, 4H), 2.328-2.296 (m, 1H), 1.049-1.027 (d, J=6.6 Hz, 3H), 0.882-0.860 (d, J=6.6 Hz, 3H); MS (ESI): m/z 513 (M−H), m/z 515 (M+H).

Example 214

(S)-Methyl 3-methyl-2-(1-oxo-6-(4-(6-(piperidin-1-yl)nicotinamido)phenyl)iso indolin-2-yl)butanoate The compound of example 214 was prepared analogous to compound of example 212 by reaction of compound of example 211 with piperidine.

Yield: 91%; $^1$H NMR (DMSO-d$_6$, 300 MHz): δ 10.091 (s, 1H), 8.747-8.739 (d, J=2.4 Hz, 1H), 8.088-8.050 (dd, J=2.4, 9 Hz, 1H), 7.961-7.874 (m, 4H), 7.748-7.720 (d, J=9 Hz, 3H), 6.922-6.892 (d, J=9 Hz, 1H), 4.642-4.609 (m, 3H), 3.687 (s, 3H), 3.665 (m, 4H), 2.329-2.275 (m, 1H), 1.654-1.639 (m, 2H), 1.561-1.549 (m, 4H), 1.015-0.993 (d, J=6.6 Hz, 3H), 0.865-0.843 (d, J=6.6 Hz, 3H); MS (ESI) m/z 525 (M−H), m/z 527 (M+H).

Example 215

(S)-3-Methyl-2-(1-oxo-6-(4-(6-(piperidin-1-yl)nicotinamido)phenyl)isoindolin-2-yl)butanoic acid The compound of example 215 was prepared analogous to compound of example 213 by hydrolysis of compound of example 214.

Yield: 62%; $^1$H NMR (DMSO-d$_6$, 300 MHz): δ 13.197 (s, 1H), 10.089 (s, 1H), 8.745 (s, 1H), 8.083-8.058 (d, J=9 Hz, 1H), 7.931-7.824 (m, 4H), 7.749-7.690 (m, 3H), 6.924-6.893 (d, J=9.3 Hz, 1H), 4.711-4.524 (m, 3H), 3.665 (m, 4H), 2.319-2.291 (m, 1H), 1.643 (m, 2H), 1.552 (m, 4H), 1.043-1.024 (d, J=5.7 Hz, 3H), 0.876-0.856 (d, J=6 Hz, 3H); MS (ESI): m/z 511 (M−H), m/z 513 (M+H).

Example 216

(S)-Methyl 3-methyl-2-(1-oxo-6-(4-(6-(pyrrolidin-1-yl)nicotinamido)phenyl)iso indolin-2-yl)butanoate The compound of example 216 was prepared analogous to compound of example 212 by reaction of compound of example 211 with pyrrolidine.

Yield: 67%; $^1$H NMR (DMSO-d$_6$, 300 MHz): δ 10.063 (s, 1H), 8.757-8.750 (d, J=2.1 Hz, 1H), 8.092-8.055 (dd, J=2.1, 8.7 Hz, 1H), 7.966-7.877 (m, 4H), 7.747-7.694 (t, J=7.2, 8.7 Hz, 3H), 6.550-6.520 (d, J=9 Hz, 1H), 4.646-4.613 (m, 3H), 3.689 (s, 3H), 3.474 (m, 4H), 2.375-2.275 (m, 1H), 1.997-1.954 (m, 4H), 1.018-0.996 (d, J=6.6 Hz, 3H), 0.869-0.847 (d, J=6.6 Hz, 3H); MS (ESI): m/z 511 (M−H), m/z 513 (M+H).

Example 217

(S)-3-Methyl-2-(1-oxo-6-(4-(6-(pyrrolidin-1-yl)nicotinamido)phenyl)isoindolin-2-yl)butanoic acid The compound of example 217 was prepared analogous to compound of example 213 by hydrolysis of compound of example 216.

Yield: 67%; $^1$H NMR (DMSO-d$_6$, 300 MHz): δ 13.031 (s, 1H), 10.068 (s, 1H), 8.757-8.751 (d, J=1.8 Hz, 1H), 8.093-8.057 (dd, J=1.8, 8.7 Hz, 1H), 7.957-7.879 (m, 4H), 7.750-7.691 (t, J=8.7, 9 Hz, 3H), 6.552-6.522 (d, J=9 Hz, 1H), 4.711-4.566 (dd, J=17.7, 18 Hz, 2H), 4.566-4.534 (d, J=9.6 Hz, 1H), 3.474 (m, 4H), 2.352-2.275 (m, 1H), 1.976 (m, 4H), 1.050-1.028 (d, J=6.6 Hz, 3H), 0.883-0.861 (d, J=6.6 Hz, 3H); MS (ESI): m/z 497 (M−H), m/z 499 (M+H).

Example 218

(S)-Methyl 3-methyl-2-(6-(4-(6-(4-methylpiperazin-1-yl)nicotinamido)phenyl)-1-oxoisoindolin-2-yl)butanoate The compound of example 218 was prepared analogous to compound of example 212 by reaction of compound of example 211 with N-methyl piperazine.

Yield: 97%; ¹H NMR (DMSO-d₆, 300 MHz): δ 10.123 (s, 1H), 8.764-8.756 (d, J=2.4 Hz, 1H), 8.088-8.050 (dd, J=2.4, 9 Hz, 1H), 7.962-7.876 (m, 4H), 7.753-7.693 (d, J=9 Hz, 3H), 6.949-6.919 (d, J=9 Hz, 1H), 4.643-4.610 (m, 3H), 3.687 (s, 3H), 3.657-3.625 (t, J=4.8, 4H), 2.415-2.382 (t, J=5.1, 4.8 Hz, 4H), 2.272-2.226 (m, 1H), 2.224 (s, 3H), 1.015-0.993 (d, J=6.6 Hz, 3H), 0.865-0.843 (d, J=6.6 Hz, 3H); MS (ESI): m/z 540 (M–H), m/z 542 (M+H).

Example 219

Methyl 4-bromo-2-methylbenzoate

To a solution of 4-bromo-2-methyl benzoic acid (25 g, 0.116 mol) in methanol (680 mL) was added H₂SO₄ (12.15 mL) and this reaction mixture was refluxed for about 16 h. The reaction mixture was cooled and the solvent was evaporated to obtain a residue, which was dissolved in ethyl acetate, washed with water and brine, dried over anhydrous sodium sulphate and filtered. The solvent was evaporated to obtain the title compound.

Example 220

Methyl 3-methyl-4'-nitrobiphenyl-4-carboxylate

The compound of example 219 (10 g, 0.044 mol), 4,4,5,5-tetramethyl-2-(4-nitrophenyl)-1,3,2-dioxaborolane (13.16 gm, 0.0528 mole) and Pd(dppf)Cl₂:CH₂Cl₂ (1.07 g, 0.00132 mol) were taken in DMF (250 mL) under an argon atmosphere. To this reaction mixture, degassed 2M solution of Na₂CO₃ (14 g, 0.132 mol, 66.5 mL) was added. The reaction mixture was stirred at 80-85° C. for 1 to 1.5 h. After completion of the reaction, water was added and the product obtained was extracted with ether. The combined ether layer was washed with brine and dried over anhydrous Na₂SO₄ or MgSO₄. The solvent was evaporated and the product was purified by column (silica gel, 20% ethyl acetate in petroleum ether) to obtain the title compound.
Yield: 11.3 g (95%); ¹H NMR (DMSO-d₆, 300 MHz): δ 8.298-8.280 (d, J=9 Hz, 2H), 7.998-7.981 (d, J=8.5 Hz, 2H), 7.928-7.912 (d, J=8 Hz, 1H), 7.744 (s, 1H), 7.702-7.684 (dd, J=1.8 Hz, 1H), 3.827 (s, 3H), 2.577 (s, 3H); MS (ESI): m/z 272 (M+H).

Example 221

Methyl 3-(bromomethyl)-4'-nitrobiphenyl-4-carboxylate

The compound of example 220 (5 g, 0.0184 mol) was dissolved in carbon tetrachloride (125 mL). Benzoyl peroxide (250 mg) and NBS (3.6 g, 0.0202 mol) were added and the reaction mixture was refluxed at 80° C. The reaction mixture was cooled to room temperature and filtered through celite. The filtrate was concentrated to yield crude residue containing 85% mono bromo and 10% dibromo product and 5% starting material. The crude title compound obtained was used directly for preparation of compound of example 222.

Example 222

(S)-Methyl 3-methyl-2-(5-(4-nitrophenyl)-1-oxoisoindolin-2-yl)butanoate

The compound of example 221 (1.54 g, 0.0044 mol) and L-Valine methyl ester hydrochloride (0.813 g, 0.0048 mol) were taken in toluene (30 mL). To this reaction mixture, triethyl amine (0.98 g, 0.0097 mol) was added and refluxed for 3-4 h. After completion of the reaction, the reaction mixture was diluted with ethyl acetate and washed with water and brine, dried over anhydrous sodium sulfate, filtered and concentrated to obtain a crude material, which was purified by column chromatography (silicagel, 30% ethyl acetate in petroleum ether to obtain the title compound.
Yield: 1.2 g (75%); ¹H NMR (DMSO-d₆, 300 MHz): δ 8.375-8.346 (d, J=8.7 Hz, 2H), 8.019-7.992 (d, J=8.1 Hz, 1H), 7.811-7.721 (m, 4H), 4.883-4.498 (m, 3H), 3.761 (s, 3H), 2.453-2.323 (s, 1H), 1.106-1.084 (d, J=6.6 Hz, 3H), 0.978-0.956 (d, J=6.6 Hz, 3H); MS (ESI): m/z 369 (M+H).

Example 223

(S)-Methyl 2-(5-(4-aminophenyl)-1-oxoisoindolin-2-yl)-3-methylbutanoate

The compound of example 222 (0.5 g, 0.00135 mol), iron (0.178 g, 0.00319 mol) and ammonium chloride (0.312 g, 0.00585 mol) are taken in EtOH:THF:H₂O (7.5 mL; 5:2.5). The reaction mixture was refluxed for about 16 h. After completion of the reaction, the reaction mixture was filtered through celite. The filtrate was concentrated to obtain a solid residue, which was dissolved in ethyl acetate and washed with water and brine, dried over anhydrous sodium sulfate and concentrated. The residue obtained was purified by column chromatography (silicagel, 30% ethyl acetate in petroleum ether) to obtain the title compound.
Yield: 0.380 mg (82%); ¹H NMR (DMSO-d₆, 300 MHz): δ 7.770 (s, 1H), 7.704-7.648 (m, 2H), 7.461-7.433 (d, J=8.4 Hz, 2H), 6.688-6.660 (d, J=8.4 Hz, 2H), 5.412 (s, 2H), 4.639-4.503 (m, 3H), 3.682 (s, 3H), 2.356-2.278 (s, 1H), 1.007-0.985 (d, J=6.6 Hz, 3H), 0.856-0.833 (d, J=6.9 Hz, 3H); MS (ESI): m/z 339 (M+H).

Example 224

(S)-Methyl 2-(5-(4-(3-(4-fluorophenyl)ureido)phenyl)-1-oxoisoindolin-2-yl)-3-methylbutanoate The compound of example 223 (0.230 g, 0.00153 mol) was dissolved in 5 mL dichloromethane and to this reaction mixture, 4-fluorophenyl isocyanate (0.102 g, 0.000744 mol) was added and stirred at room temperature for 8-10 h. The reaction mixture was concentrated and purified by column chromatography (silicagel, 30-40% ethyl acetate in petroleum ether to obtain the title compound.
Yield: 0.300 g (93%).

Example 225

(S)-2-(5-(4-(3-(4-Fluorophenyl)ureido)phenyl)-1-oxoisoindolin-2-yl)-3-methylbutanoic acid The compound of example 224 (0.500 g, 0.00102 mol) was taken in THF (8 mL) and MeOH (1 mL) and to this reaction mixture, 1 N LiOH (0.213 g, 0.0051 mol) was added and stirred at room temperature for 2-3 h. After completion of the reaction, solvent was evaporated and the residue obtained was dissolved in water and acidified with 1 N HCl to obtain the title compound, which was filtered and dried.
Yield: 0.460 g (95%); ¹H NMR (DMSO-d₆, 300 MHz): δ 9.015 (s, 1H), 8.936 (s, 1H), 7.883 (s, 1H), 7.761 (s, 2H), 7.695-7.666 (d, J=8.7 Hz, 2H), 7.611-7.582 (d, J=8.7 Hz, 2H), 7.519-7.473 (m, 2H), 7.166-7.107 (d, 8.7 Hz, 2H), 4.753-4.493 (dd, J=18 Hz, 2H), 4.538-4.507 (d, J=9.3 Hz, 1H), 2.327-2.295 (m, 1H), 1.050-1.028 (d, J=6.6 Hz, 3H), 0.880-0.858 (d, J=6.6 Hz, 3H); MS (ESI): m/z 460 (M–H), m/z 462 (M+H).

Example 226

(S)-Methyl 2-(5-(4-(3-(2-fluorophenyl)ureido)phenyl)-1-oxoisoindolin-2-yl)-3-methylbutanoate The compound of example 226 was prepared analogous to compound of example 224 by reaction of compound of example 223 with 2-fluoro phenyl isocyanate. The compound of example 226 was used directly without isolation for the preparation of compound of example 227.

Example 227

(S)-2-(5-(4-(3-(2-Fluorophenyl)ureido)phenyl)-1-oxoisoindolin-2-yl)-3-methyl butanoic acid The compound of example 227 was prepared analogous to compound of example 225 by hydrolysis of compound of example 226.
Yield: 84%; $^1$H NMR (DMSO-$d_6$, 300 MHz): δ 13.074 (s, 1H), 9.250 (s, 1H), 8.623 (s, 1H), 8.197-8.142 (td, J=6.9, 8.4 Hz, 1H), 7.884 (s, 1H), 7.796-7.765 (t, J=9.1 Hz, 2H), 7.714-7.685 (d, J=8.7 Hz, 2H), 7.614-7.585 (d, J=8.7 Hz, 2H), 7.284-7.246 (dd, J=0.9, 8.7 Hz, 1H), 7.183-7.133 (t, J=7.5 Hz, 1H), 7.054-6.991 (m, 1H), 4.723-4.534 (dd, J=6.6 & 17.7 Hz, 2H), 4.546-4.514 (d, J=9.6 Hz, 1H), 2.364-2.245 (m, 1H), 1.049-1.021 (d, J=6.6 Hz, 3H), 0.877-0.855 (d, J=6.6 Hz, 3H); MS (ESI): m/z 460 (M–H), m/z 462 (M+H).

Example 228

(S)-Methyl 2-(5-(4-(3-(3-fluorophenyl)ureido)phenyl)-1-oxoisoindolin-2-yl)-3-methylbutanoate The compound of example 228 was prepared analogous to compound of example 224 by reaction of compound of example 223 with 3-fluoro phenyl isocyanate. The compound of example 228 was used directly without isolation for the preparation of compound of example 229.

Example 229

(S)-2-(5-(4-(3-(3-Fluorophenyl)ureido)phenyl)-1-oxoisoindolin-2-yl)-3-methyl butanoic acid The compound of example 229 was prepared analogous to compound of example 225 by hydrolysis of compound of example 228.
Yield: 86%; $^1$H NMR (DMSO-$d_6$, 300 MHz): δ 13.054 (s, 1H), 8.990 (s, 1H), 8.937 (s, 1H), 7.884 (s, 1H), 7.764-7.737 (d, J=8.1 Hz, 2H), 7.707-7.678 (d, J=8.7 Hz, 2H), 7.612-7.583 (d, J=8.7 Hz, 2H), 7.532-7.492 (m, 1H), 7.358-7.281 (dd, J=6.9, 8.1 Hz, 1H), 7.158-7.129 (d, J=8.7 Hz, 1H), 6.831-6.768 (td, J=2.1, 8.7 Hz, 1H), 4.723-4.545 (dd, J=6.3 & 17.7 Hz, 2H), 4.545-4.513 (d, J=9.6 Hz, 1H), 2.397-2.246 (m, 1H), 1.044-1.022 (d, J=6.6 Hz, 3H), 0.878-0.856 (d, J=6.6 Hz, 3H); MS (ESI): m/z 460 (M–H), m/z 462 (M+H).

Example 230

(S)-Methyl 3-methyl-2-(1-oxo-5-(4-(3-phenylureido)phenyl)isoindolin-2-yl)butanoate The compound of example 230 was prepared analogous to compound of example 224 by reaction of compound of example 223 with phenyl isocyanate. The compound of example 230 was used directly without isolation for the preparation of compound of example 231.

Example 231

(S)-3-Methyl-2-(1-oxo-5-(4-(3-phenylureido)phenyl)isoindolin-2-yl)butanoic acid

The compound of example 231 was prepared analogous to compound of example 225 by hydrolysis of compound of example 230.
Yield: 97%; $^1$H NMR (DMSO-$d_6$, 300 MHz): δ 9.825 (s, 1H), 9.632 (s, 1H), 7.874 (s, 1H), 7.721-7.695 (d, J=7.8 Hz, 2H), 7.641-7.569 (dd, J=3.6, 9 Hz, 4H), 7.538-7.512 (d, J=7.8 Hz, 2H), 7.297-7.244 (t, J=7.8, 8.1 Hz, 2H), 6.974-6.925 (t, J=7.2, 7.5 Hz, 1H), 4.928-4.868 (d, J=18 Hz, 1H), 4.574-4.514 (d, J=18 Hz, 1H), 4.478-4.445 (d, J=9.9 Hz, 1H), 2.353-2.277 (m, 1H), 1.063-1.041 (d, J=6.6 Hz, 3H), 0.879-0.857 (d, J=6.6 Hz, 3H); MS (ESI): m/z 444 (M+H).

Example 232

(S)-Methyl 2-(5-(4-(3-benzylureido)phenyl)-1-oxoisoindolin-2-yl)-3-methyl butanoate The compound of example 232 was prepared analogous to compound of example 224 by reaction of compound of example 223 with benzyl isocyanate. The compound of example 232 was used directly without isolation for the preparation of compound of example 233.

Example 233

(S)-2-(5-(4-(3-Benzylureido)phenyl)-1-oxoisoindolin-2-yl)-3-methylbutanoic acid

The compound of example 233 was prepared analogous to compound of example 225 by hydrolysis of compound of example 232.
Yield: 86%; $^1$H NMR (DMSO-$d_6$, 300 MHz): δ 9.132 (s, 1H), 7.847 (s, 1H), 7.725 (s, 2H), 7.630-7.602 (d, J=8.4 Hz, 2H), 7.561-7.533 (d, J=8.4, 2H), 7.319 (s, 4H), 7.265-7.238 (m, 1H), 7.033 (m, 1H), 4.771-4.490 (dd, J=18 Hz, 2H), 4.490-4.456 (d, J=10.2 Hz, 1H), 4.324-4.305 (d, J=5.7 Hz, 2H), 2.299-2.271 (m, 1H), 1.031-1.010 (d, J=6.6 Hz, 3H), 0.856-0.834 (d, J=6.6 Hz, 3H); MS (ESI): m/z 458 (M+H).

Example 234

(S)-Methyl 2-(5-(4-(3-cyclohexylureido)phenyl)-1-oxoisoindolin-2-yl)-3-methyl butanoate The compound of example 234 was prepared analogous to compound of example 224 by reaction of compound of example 223 with cyclohexyl isocyanate. The compound of example 234 was used directly without isolation for the preparation of compound of example 235.

Example 235

(S)-2-(5-(4-(3-Cyclohexylureido)phenyl)-1-oxoisoindolin-2-yl)-3-methyl butanoic acid The compound of example 235 was prepared analogous to compound of example 225 by hydrolysis of compound of example 234.

Yield: 95%; ¹H NMR (DMSO-d₆, 300 MHz): δ 13.101 (s, 1H), 8.507 (s, 1H), 7.899 (s, 1H), 7.736 (s, 2H), 7.632-7.603 (d, J=8.7 Hz, 2H), 7.518-7.489 (d, J=8.7 Hz, 2H), 6.172-6.147 (d, NH), 4.887-4.518 (dd, J=21.6, 33 Hz, 2H), 4.537-4.505 (d, J=9.6 Hz, 1H), 2.336-2.260 (m, 1H), 1.832-1.7940 (m, 2H), 1.688-1.646 (m, 2H), 1.567-1.527 (m, 1H), 1.432-1.300 (m, 2H), 1.260-1.124 (m, 4H), 1.038-1.017 (d, J=6.3 Hz, 3H), 0.871-0.849 (d, J=6.6 Hz, 3H); MS (ESI): m/z 450 (M+H).

Example 236

(S)-Methyl 2-(5-(4-(3-(2,4-difluorophenyl)ureido) phenyl)-1-oxoisoindolin-2-yl)-3-methylbutanoate The compound of example 236 was prepared analogous to compound of example 224 by reaction of compound of example 223 with 2,4-difluorophenyl isocyanate. The compound of example 236 was used directly without isolation for the preparation of compound of example 237.

Example 237

(S)-2-(5-(4-(3-(2,4-Difluorophenyl)ureido)phenyl)-1-oxoisoindolin-2-yl)-3-methylbutanoic acid The compound of example 237 was prepared analogous to compound of example 225 by hydrolysis of compound of example 236.
Yield: 89%; ¹H NMR (DMSO-d₆, 300 MHz): δ 13.043 (s, 1H), 9.217 (s, 1H), 8.583 (s, 1H), 8.141 (m, 1H), 7.918 (s, 1H), 7.794-7.737 (t, J=9.1 Hz, 2H), 7.709-7.680 (d, J=8.7 Hz, 2H), 7.605-7.577 (d, J=8.4 Hz, 2H), 7.368-7.261 (m, 1H), 7.090-7.035 (m, 1H), 4.719-4.534 (dd, J=17.7, 20.4 Hz, 2H), 4.543-4.511 (d, J=9.6 Hz, 1H), 2.382-2.273 (m, 1H), 1.041-1.020 (d, J=6.3 Hz, 3H), 0.875-0.853 (d, J=6.6 Hz, 3H); MS (ESI): m/z 480 (M+H), m/z 478 (M−H)

Example 238

(S)-Methyl 2-(5-(4-(3-(3,4-difluorophenyl)ureido) phenyl)-1-oxoisoindolin-2-yl)-3-methylbutanoate The compound of example 238 was prepared analogous to compound of example 224 by reaction of compound of example 223 with 2,4-difluorophenyl isocyanate. The compound of example 238 was used directly without isolation for the preparation of compound of example 239.

Example 239

(S)-2-(5-(4-(3-(3,4-Difluorophenyl)ureido)phenyl)-1-oxoisoindolin-2-yl)-3-methylbutanoic acid The compound of example 239 was prepared analogous to compound of example 225 by hydrolysis of compound of example 238.
Yield: 95%; ¹H NMR (DMSO-d₆, 300 MHz): δ 13.027 (s, 1H), 8.975 (s, 1H), 8.943 (s, 1H), 7.881 (s, 1H), 7.790 (s, 2H), 7.762-7.704 (m, 2H), 7.607-7.578 (d, J=8.7 Hz, 2H), 7.408-7.312 (m, 2H), 7.210-7.131 (m, 1H), 4.719-4.533 (dd, J=17.7, 20.7 Hz, 2H), 4.544-4.512 (d, J=9.6 Hz, 1H), 2.362-2.243 (m, 1H), 1.042-1.020 (d, J=6.3 Hz, 3H), 0.875-0.853 (d, J=6.6 Hz, 3H); MS (ESI) m/z: 480 (M+H), (ESI) m/z: 478 (M−H).

Example 240

(S)-Methyl 3-methyl-2-(1-oxo-5-(4-(3-p-tolylureido) phenyl)isoindolin-2-yl)butanoate The compound of example 240 was prepared analogous to compound of example 224 by reaction of compound of example 223 with 2,4-difluorophenyl isocyanate. The compound of example 240 was used directly without isolation for the preparation of compound of example 241.

Example 241

(S)-3-Methyl-2-(1-oxo-5-(4-(3-p-tolylureido)phenyl) isoindolin-2-yl)butanoic acid The compound of example 241 was prepared analogous to compound of example 225 by hydrolysis of compound of example 240.
Yield: 98%; ¹H NMR (DMSO-d₆, 300 MHz): δ 12.995 (s, 1H), 8.939 (s, 1H), 8.748 (s, 1H), 7.878 (s, 1H), 7.691-7.662 (d, J=8.7 Hz, 2H), 7.602-7.573 (d, J=8.7 Hz, 2H), 7.372-7.343 (d, J=8.7 Hz, 2H), 7.343-7.312 (d, J=9.3 Hz, 1H), 7.109-7.082 (d, J=8.1 Hz, 2H), 7.082-7.058 (d, J=7.2 Hz, 1H), 4.716-4.530 (dd, J=17.7, 20.4 Hz, 2H), 4.543-4.510 (d, J=9.9 Hz, 1H), 2.339-2.258 (m, 1H), 2.248 (s, 3H), 1.041-1.019 (d, J=6.6 Hz, 3H), 0.874-0.852 (d, J=6.6 Hz, 3H); MS (ESI): m/z 456 (M−H), m/z 458 (M+H).

Example 242

(S)-Methyl 3-methyl-2-(1-oxo-5-(4-(3-m-tolylureido)phenyl)isoindolin-2-yl)butanoate The compound of example 242 was prepared analogous to compound of example 224 by reaction of compound of example 223 with 3-methyl phenyl isocyanate. The compound of example 242 was used directly without isolation for the preparation of compound of example 243.

Example 243

(S)-3-Methyl-2-(1-oxo-5-(4-(3-m-tolylureido)phenyl)isoindolin-2-yl)butanoic acid The compound of example 243 was prepared analogous to compound of example 225 by hydrolysis of compound of example 242.
Yield: 96%; ¹H NMR (DMSO-d₆, 300 MHz): δ 13.041 (s, 1H), 8.837 (s, 1H), 8.557 (s, 1H), 7.881 (s, 1H), 7.792-7.734 (t, J=8.1, 9.3 Hz, 2H), 7.697-7.668 (d, J=8.7 Hz, 2H), 7.608-7.579 (d, J=8.7 Hz, 2H), 7.319 (s, 1H), 7.266-7.238 (d, J=8.4 Hz, 1H), 7.168-7.117 (t, J=7.4, 7.5 Hz, 1H), 6.815-6.791 (d, J=7.2 Hz, 1H), 4.719-4.531 (dd, J=17.7, 21 Hz, 2H), 4.545-4.513 (d, J=9.6 Hz, 1H), 2.381-2.274 (m, 1H), 2.251 (s, 3H), 1.043-1.021 (d, J=6.6 Hz, 3H), 0.876-0.854 (d, J=6.6 Hz, 3H); MS (ESI): m/z 456 (M−H), m/z 458 (M+H).

Example 244

(S)-Methyl 3-methyl-2-(1-oxo-5-(4-(3-(4-(trifluoromethyl)phenyl)ureido)phenyl)isoindolin-2-yl)butanoate The compound of example 244 was prepared analogous to compound of example 224 by reaction of compound of example 223 with 4-trifluoromethyl phenyl isocyanate. The compound of example 244 was used directly without isolation for the preparation of compound of example 245.

Example 245

(S)-3-Methyl-2-(1-oxo-5-(4-(3-(4-(trifluoromethyl)phenyl)ureido)phenyl)isoindolin-2-yl)butanoic acid The compound of example 245 was prepared analogous to compound of example 225 by hydrolysis of compound of example 244.

Yield: 96%; $^1$H NMR (DMSO-$d_6$, 300 MHz): δ 13.077 (s, 1H), 9.236 (s, 1H), 9.052 (s, 1H), 7.888 (s, 1H), 7.796-7.738 (t, J=8.4, 9 Hz, 2H), 7.715-7.598 (m, 8H), 4.724-4.543 (dd, J=17.7, 21.3 Hz, 2H), 4.543-4.512 (d, J=9.3 Hz, 1H), 2.342-2.245 (m, 1H), 1.043-1.021 (d, J=6.6 Hz, 3H), 0.876-0.854 (d, J=6.6 Hz, 3H); MS (ESI): m/z 509 (M–H), m/z 511 (M+H).

Example 246

(S)-Methyl 3-methyl-2-(1-oxo-5-(4-(3-(3-(trifluoromethyl)phenyl)ureido)phenyl)isoindolin-2-yl)butanoate The compound of example 246 was prepared analogous to compound of example 224 by reaction of compound of example 223 with 3-trifluoromethyl phenyl isocyanate. The compound of example 246 was used directly without isolation for the preparation of compound of example 247.

Example 247

(S)-3-Methyl-2-(1-oxo-5-(4-(3-(3-(trifluoromethyl)phenyl)ureido)phenyl)isoindolin-2-yl)butanoic acid The compound of example 247 was prepared analogous to compound of example 225 by hydrolysis of compound of example 246.

Yield: 88%; $^1$H NMR (DMSO-$d_6$, 300 MHz): δ 13.018 (s, 1H), 9.160 (s, 1H), 9.024 (s, 1H), 8.043 (s, 1H), 7.889 (s, 1H), 7.797-7.739 (t, J=8.1, 9.3 Hz, 2H), 7.712-7.683 (d, J=8.7 Hz, 2H), 7.630-7.601 (t, J=8.7 Hz, 3H), 7.553-7.500 (t, J=7.8, 8.1 Hz, 1H), 7.338-7.314 (d, J=7.2 Hz, 1H), 4.728-4.544 (dd, J=17.7, 22.5 Hz, 2H), 4.544-4.512 (d, J=9.6 Hz, 1H), 2.343-2.268 (m, 1H), 1.044-1.022 (d, J=6.6 Hz, 3H), 0.877-0.855 (d, J=6.6 Hz, 3H); MS (ESI): m/z 509.7 (M–H).

Example 248

(S)-Methyl 2-(5-(4-(3-(4-methoxyphenyl)ureido)phenyl)-1-oxoisoindolin-2-yl)-3-methylbutanoate The compound of example 248 was prepared analogous to compound of example 224 by reaction of compound of example 223 with 4-methoxy phenyl isocyanate. The compound of example 248 was used directly without isolation for the preparation of compound of example 249.

Example 249

(S)-2-(5-(4-(3-(4-Methoxyphenyl)ureido)phenyl)-1-oxoisoindolin-2-yl)-3-methylbutanoic acid The compound of example 249 was prepared analogous to compound of example 225 by hydrolysis of compound of example 248.

Yield: 95%; $^1$H NMR (DMSO-$d_6$, 300 MHz): δ 13.072 (s, 1H), 8.793 (s, 1H), 8.566 (s, 1H), 7.977 (s, 1H), 7.779 (dd, J=2, 8.5 Hz, 2H), 7.681-7.664 (dd, J=8.5 Hz, 2H), 7.595-7.578 (d, J=8.5 Hz, 2H), 7.388-7.370 (d, J=8.5 Hz, 2H), 6.894-6.876 (d, J=9 Hz, 2H), 4.708-4.548 (dd, J=17.5, 18 Hz, 2H), 4.538-4.519 (d, J=9.5 Hz, 1H), 3.726 (s, 3H), 2.367-2.270 (m, 1H), 1.041-1.028 (d, J=6.5 Hz, 3H), 0.875-0.861 (d, J=7 Hz, 3H); MS (ESI): m/z 472 (M–H), m/z 474 (M+H).

Example 250

(S)-Methyl 2-(5-(4-(3-(3-methoxyphenyl)ureido)phenyl)-1-oxoisoindolin-2-yl)-3-methylbutanoate The compound of example 250 was prepared analogous to compound of example 224 by reaction of compound of example 223 with 3-methoxy phenyl isocyanate. The compound of example 250 was used directly without isolation for the preparation of compound of example 251.

Example 251

(S)-2-(5-(4-(3-(3-Methoxyphenyl)ureido)phenyl)-1-oxoisoindolin-2-yl)-3-methylbutanoic acid The compound of example 251 was prepared analogous to compound of example 225 by hydrolysis of compound of example 250.

Yield: 86%; $^1$H NMR (DMSO-$d_6$, 300 MHz): δ 13.016 (s, 1H), 8.893 (s, 1H), 8.762 (s, 1H), 7.934 (s, 1H), 7.783-7.747 (dd, J=8.5, 9.5 Hz, 2H), 7.693-7.676 (d, J=8.5 Hz, 2H), 7.605-7.588 (d, J=8.5, 2H), 7.214-7.210 (d, J=2 Hz, 1H), 7.177-7.155 (d, J=11 Hz, 1H), 6.965-6.949 (d, J=8 Hz, 1H), 6.578-6.561 (d, J=8.5 Hz, 1H), 4.709-4.551 (dd, J=18, 61 Hz, 2H), 4.542-4.522 (d, J=10 Hz, 1H), 3.745 (s, 3H), 2.368-2.271 (m, 1H), 1.042-1.029 (d, J=6.5 Hz, 3H), 0.875-0.862 (d, J=6.5 Hz, 3H); MS (ESI): m/z 471 (M–H), m/z 473 (M+H).

Example 252

(S)-Methyl 2-(5-(4-(3-(4-cyanophenyl)ureido)phenyl)-1-oxoisoindolin-2-yl)-3-methylbutanoate The compound of example 252 was prepared analogous to compound of example 224 by reaction of compound of example 223 with 4-cyanophenyl isocyanate. The compound of example 252 was used directly without isolation for the preparation of compound of example 253.

Example 253

(S)-2-(5-(4-(3-(4-Cyanophenyl)ureido)phenyl)-1-oxoisoindolin-2-yl)-3-methylbutanoic acid The compound of example 253 was prepared analogous to compound of example 225 by hydrolysis of compound of example 252.

Yield: 76%; $^1$H NMR (DMSO-$d_6$, 300 MHz): δ 13.039 (s, 1H), 9.399 (s, 1H), 9.160 (s, 1H), 7.886 (s, 1H), 7.764-7.717 (m, 4H), 7.688-7.672 (m, 3H), 7.642-7.593 (m, 3H), 4.719-4.542 (dd, J=17.7, 20.4 Hz, 2H), 4.542-4.511 (d, J=9.3 Hz, 1H), 2.317-2.264 (m, 1H), 1.040-1.018 (d, J=6.6 Hz, 3H), 0.873-0.851 (d, J=6.6 Hz, 3H); MS (ESI): m/z 466 (M−H), m/z 468 (M+H).

Example 254

(S)-Methyl 2-(5-(4-(3-(3-cyanophenyl)ureido)phenyl)-1-oxoisoindolin-2-yl)-3-methylbutanoate The compound of example 254 was prepared analogous to compound of example 224 by reaction of compound of example 223 with 3-cyanophenyl isocyanate. The compound of example 254 was used directly without isolation for the preparation of compound of example 255.

Example 255

(S)-2-(5-(4-(3-(3-Cyanophenyl)ureido)phenyl)-1-oxoisoindolin-2-yl)-3-methylbutanoic acid The compound of example 255 was prepared analogous to compound of example 225 by hydrolysis of compound of example 254.

Yield: 86%; $^1$H NMR (DMSO-$d_6$, 300 MHz): δ 13.072 (s, 1H), 9.285 (s, 1H), 9.192 (s, 1H), 8.002 (s, 1H), 7.887 (s, 1H), 7.795-7.737 (t, J=9 Hz, 2H), 7.714-7.686 (d, J=8.4 Hz, 3H), 7.623-7.594 (d, J=8.7 Hz, 2H), 7.536-7.484 (t, J=7.5, 8.1 Hz, 1H), 7.449-7.424 (d, J=7.5 Hz, 1H), 4.720-4.534 (dd, J=18, 20.4 Hz, 2H), 4.544-4.512 (d, J=9.6 Hz, 1H), 2.363-2.243 (m, 1H), 1.041-1.019 (d, J=6.6 Hz, 3H), 0.875-0.852 (d, J=6.9 Hz, 3H); MS (ESI): m/z 567 (M−H), m/z 569 (M+H).

Example 256

(S)-Methyl 2-(5-(4-(3-(2-fluorophenyl)thioureido)phenyl)-1-oxoisoindolin-2-yl)-3-methylbutanoate The compound of example 223 (0.150 g, 0.000443 mol) was taken in THF (3 mL) and 2-fluorophenyl isothiocyanate (0.074 g, 0.000448 mol) was added and stirred at room temperature for 8-10 h. The reaction mixture was concentrated and directly used for preparation of compound of example 257.

Example 257

(S)-2-(5-(4-(3-(2-Fluorophenyl)thioureido)phenyl)-1-oxoisoindolin-2-yl)-3-methylbutanoic acid The compound of example 256 (0.224 g, 0.000456 mol) was taken in THF (4 mL) and MeOH (1 mL) and to this reaction mixture, 1 N LiOH (0.095 g, 0.0022 mol) was added and stirred at room temperature for 2-3 h. After completion of the reaction, the solvent was evaporated and the residue obtained was dissolved in water and acidified with 1 N HCl to obtain the title compound, which was filtered and dried.

Yield: 0.195 g (89%); $^1$H NMR (DMSO-$d_6$, 300 MHz): δ 13.065 (s, 1H), 11.288 (s, 1H), 10.135 (s, 1H), 7.909 (s, 1H), 7.857-7.784 (t, J=12.3, 9.6 Hz, 2H), 7.756-7.655 (m, 4H), 7.620-7.594 (d, J=7.8, 1H), 7.294-7.170 (m, 3H), 4.735-4.547 (dd, J=18, 21 Hz, 2H), 4.547-4.515 (d, J=9.6 Hz, 1H), 2.369-2.248 (m, 1H), 1.044-1.023 (d, J=6.3 Hz, 3H), 0.880-0.858 (d, J=6.6 Hz, 3H); MS (ESI): m/z 460 (M−H), m/z 462 (M+H).

Example 258

(S)-Methyl 2-(5-(4-(3-(3-fluorophenyl)thioureido)phenyl)-1-oxoisoindolin-2-yl)-3-methylbutanoate The compound of example 258 was prepared analogous to compound of example 256 by reaction of compound of example 223 with 3-fluorophenyl isothiocyanate. The compound of example 258 was used directly without isolation for the preparation of compound of example 259.

Example 259

(S)-2-(5-(4-(3-(3-Fluorophenyl)thioureido)phenyl)-1-oxoisoindolin-2-yl)-3-methyl butanoic acid The compound of example 259 was prepared analogous to compound of example 257 by hydrolysis of compound of example 258.

Yield: 82%; $^1$H NMR (DMSO-$d_6$, 300 MHz): δ 13.065 (s, 1H), 10.140 (s, 1H), 10.106 (s, 1H), 7.908 (s, 1H), 7.816-7.757 (t, J=9.6, 8.1 Hz, 2H), 7.739-7.710 (d, J=8.7 Hz, 2H), 7.651-7.622 (d, J=8.7 Hz, 2H), 7.581-7.543 (m, 1H), 7.385-7.336 (t, J=6.9, 7.8 Hz, 1H), 7.301-7.272 (d, J=8.7 Hz, 1H), 7.989-6.933 (m, 1H), 4.739-4.547 (dd, J=17.7, 22.5 Hz, 2H), 4.515-4.492 (d, J=6.9 Hz, 1H), 2.368-2.251 (m, 1H), 1.046-1.024 (d, J=6.6 Hz, 3H), 0.881-0.859 (d, J=6.6 Hz, 3H); MS (ESI): m/z 476 (M−H), m/z 478 (M+H).

Example 260

(S)-Methyl 2-(5-(4-(3-(4-methoxyphenyl)thioureido)phenyl)-1-oxoisoindolin-2-yl)-3-methylbutanoate The compound of example 260 was prepared analogous to compound of example 256 by reaction of compound of example 223 with 4-methoxy phenyl isothiocyanate. The compound of example 260 was used directly without isolation for the preparation of compound of example 261.

Example 261

(S)-2-(5-(4-(3-(4-Methoxyphenyl)thioureido)phenyl)-1-oxoisoindolin-2-yl)-3-methylbutanoic acid The compound of example 261 was prepared analogous to compound of example 257 by hydrolysis of compound of example 260.

Yield: 63%; $^1$H NMR (DMSO-$d_6$, 300 MHz): δ 13.068 (s, 1H), 9.867 (s, 1H), 9.804 (s, 1H), 7.899 (s, 1H), 7.807-7.749 (t, J=9.3 Hz, 2H), 7.715-7.686 (d, J=8.7 Hz, 2H), 7.656-7.627 (d, J=8.7 Hz, 2H), 7.373-7.343 (d, J=9 Hz, 2H), 6.936-6.906 (d, J=9 Hz, 2H), 4.741-4.541 (dd, J=18, 24.6 Hz, 2H), 4.541-4.509 (d, J=9.6 Hz, 1H), 3.755 (s, 3H), 2.367-2.247 (m, 1H), 1.044-1.023 (d, J=6.3 Hz, 3H), 0.879-0.857 (d, J=6.6 Hz, 3H); MS (ESI): m/z 488 (M−H), m/z 490 (M+H)

Example 262

(S)-Methyl 2-(5-(4-(3-(3-methoxyphenyl)thioureido)phenyl)-1-oxoisoindolin-2-yl)-3-methylbutanoate The compound of example 262 was prepared analogous to compound of example 256 by reaction of compound of example 223 with 3-methoxy phenyl isothiocyanate. The compound of example 262 was used directly without isolation for the preparation of compound of example 263.

Example 263

(S)-2-(5-(4-(3-(3-Methoxyphenyl)thioureido)phenyl)-1-oxoisoindolin-2-yl)-3-methyl butanoic acid The compound of example 263 was prepared analogous to compound of example 257 by hydrolysis of compound of example 262.

Yield: 82%; $^1$H NMR (DMSO-d$_6$, 300 MHz): δ 13.085 (s, 1H), 9.999 (s, 1H), 9.962 (s, 1H), 7.904 (s, 1H), 7.810-7.758 (t, J=9 Hz, 2H), 7.725-7.696 (d, J=8.7 Hz, 2H), 7.654-7.625 (d, J=8.7, 2H), 7.275-7.207 (m, 2H), 7.072-7.045 (d, J=8.1 Hz, 1H), 6.737-6.703 (dd, J=2.1, 8.1 Hz, 1H), 4.739-4.544 (dd, J=18, 23.1 Hz, 2H), 4.544-4.512 (d, J=9.6 Hz, 1H), 3.745 (s, 3H), 2.381-2.271 (m, 1H), 1.045-1.023 (d, J=6.6 Hz, 3H), 0.880-0.858 (d, J=6.6 Hz, 3H); MS (ESI): m/z 488 (M−H), m/z 490 (M+H).

Example 264

(S)-Methyl 2-(5-(4-(3-(4-chlorophenyl)thioureido)phenyl)-1-oxoisoindolin-2-yl)-3-methylbutanoate The compound of example 264 was prepared analogous to compound of example 256 by reaction of compound of example 223 with 4-chlorophenyl isothiocyanate. The compound of example 264 was used directly without isolation for the preparation of compound of example 265.

Example 265

(S)-2-(5-(4-(3-(4-Chlorophenyl)thioureido)phenyl)-1-oxoisoindolin-2-yl)-3-methylbutanoic acid The compound of example 265 was prepared analogous to compound of example 257 by hydrolysis of compound of example 264.

Yield: 94%; $^1$H NMR (DMSO-d$_6$, 300 MHz): δ 12.930 (s, 1H), 10.098 (s, 1H), 10.039 (s, 1H), 7.905 (s, 1H), 7.781-7.704 (t, J=14.7, 8.4 Hz, 2H), 7.649-7.620 (d, J=8.7 Hz, 2H), 7.562-7.533 (d, J=8.7 Hz, 2H), 7.410-7.381 (t, J=1.8, 6.9 Hz, 2H), 6.936-6.906 (d, J=9 Hz, 2H), 4.740-4.544 (dd, J=17.7, 23.7 Hz, 2H), 4.544-4.512 (d, J=9.6 Hz, 1H), 2.387-2.247 (m, 1H), 1.045-1.023 (d, J=6.6 Hz, 3H), 0.880-0.858 (d, J=6.6 Hz, 3H); MS (ESI): m/z 492 (M−H), m/z 494 (M+H).

Example 266

(S)-Methyl 2-(5-(4-(3-(3-chlorophenyl)thioureido)phenyl)-1-oxoisoindolin-2-yl)-3-methylbutanoate The compound of example 266 was prepared analogous to compound of example 256 by reaction of compound of example 223 with 3-chlorophenyl isothiocyanate. The compound of example 266 was used directly without isolation for the preparation of compound of example 267.

Example 267

(S)-2-(5-(4-(3-(3-Chlorophenyl)thioureido)phenyl)-1-oxoisoindolin-2-yl)-3-methylbutanoic acid The compound of example 267 was prepared analogous to compound of example 257 by hydrolysis of compound of example 266.

Yield: 92%; $^1$H NMR (DMSO-d$_6$, 300 MHz): δ 12.930 (s, 1H), 10.179 (s, 1H), 10.092 (s, 1H), 7.908 (s, 1H), 7.815-7.755 (t, J=8.4, 9.6 Hz, 2H), 7.738-7.710 (m, 3H), 7.645-7.617 (d, J=8.4 Hz, 2H), 7.446-7.418 (d, J=8.4 Hz, 1H), 7.390-7.337 (d, J=7.8, 8.1 Hz, 1H), 7.199-7.173 (d, J=7.8 Hz, 1H), 4.741-4.545 (dd, J=18, 23.1 Hz, 2H), 4.545-4.512 (d, J=9.9 Hz, 1H), 2.346-2.271 (m, 1H), 1.045-1.023 (d, J=6.6 Hz, 3H), 0.880-0.858 (d, J=6.6 Hz, 3H); MS (ESI): m/z 492 (M−H), m/z 494 (M+H).

Example 268

(S)-Methyl 2-(5-(4-(3-(4-cyanophenyl)thioureido)phenyl)-1-oxoisoindolin-2-yl)-3-methylbutanoate The compound of example 268 was prepared analogous to compound of example 256 by reaction of compound of example 223 with 4-cyanophenyl isothiocyanate. The compound of example 268 was used directly without isolation for the preparation of compound of example 269.

Example 269

(S)-2-(5-(4-(3-(4-Cyanophenyl)thioureido)phenyl)-1-oxoisoindolin-2-1)-3-methyl butanoic acid The compound of example 269 was prepared analogous to compound of example 257 by hydrolysis of compound of example 268.

Yield: 86%; $^1$H NMR (DMSO-d$_6$, 300 MHz): δ 12.982 (s, 1H), 10.327 (s, 1H), 10.321 (s, 1H), 7.911 (s, 1H), 7.790 (m, 6H), 7.753-7.724 (d, J=8.7 Hz, 2H), 7.658-7.629 (d, J=8.7 Hz, 2H), 4.734-4.549 (dd, J=18, 20.4 Hz, 2H), 4.549-4.517 (d, J=9.6 Hz, 1H), 2.346-2.270 (m, 1H), 1.044-1.022 (d, J=6.6 Hz, 3H), 0.880-0.858 (d, J=6.6 Hz, 3H); MS (ESI): m/z 483 (M−H), m/z 485 (M+H).

Example 270

(S)-Methyl 3-methyl-2-(1-oxo-5-(4-(3-(2-(trifluoromethyl)phenyl)thioureido)phenyl)isoindolin-2-yl)butanoate The compound of example 270 was prepared analogous to compound of example 256 by reaction of compound of example 223 with 2-trifluoromethyl phenyl isothiocyanate. The compound of example 270 was used directly without isolation, for the preparation of compound of example 271.

Example 271

(S)-3-Methyl-2-(1-oxo-5-(4-(3-(2-(trifluoromethyl)phenyl)thioureido)phenyl)isoindolin-2-yl)butanoic acid The compound of example 271 was prepared analogous to compound of example 257 by hydrolysis of compound of example 270.

Yield: 91%; $^1$H NMR (DMSO-d$_6$, 300 MHz): δ 12.983 (s, 1H), 10.205 (s, 1H), 9.480 (s, 1H), 7.961 (s, 1H), 7.868-7.679 (m, 8H), 7.617-7.590 (d, J=8.1 Hz, 1H), 7.525-7.454 (d, J=7.5, 1H), 4.734-4.549 (dd, J=17.7, 21.3 Hz, 2H), 4.549-4.518 (d, J=9.3 Hz, 1H), 2.369-2.229 (m, 1H), 1.045-1.023 (d, J=6.6 Hz, 3H), 0.881-0.859 (d, J=6.6 Hz, 3H); MS (ESI): m/z 526 (M−H), m/z 528 (M+H).

Example 272

(S)-Methyl 3-methyl-2-(1-oxo-5-(4-(3-o-tolylthio-ureido)phenyl)isoindolin-2-yl)butanoate The compound of example 272 was prepared analogous to compound of example 256 by reaction of compound of example 223 with 2-methyl phenyl isothiocyanate. The compound of example 272 was used directly without isolation, for the preparation of compound of example 273.

Example 273

(S)-3-Methyl-2-(1-oxo-5-(4-(3-o-tolylthioureido)phenyl)isoindolin-2-yl)butanoic acid The compound of example 273 was prepared analogous to compound of example 257 by hydrolysis of compound of example 272.

Yield: 88%; $^1$H NMR (DMSO-$d_6$, 300 MHz): δ 13.091 (s, 1H), 9.856 (s, 1H), 9.482 (s, 1H), 7.903 (s, 1H), 7.780 (m, 2H), 7.726-7.648 (dd, J=8.7, 6 Hz, 4H), 7.289-7.177 (m, 4H), 4.729-4.547 (d, J=17.7, 20.1 Hz, 2H), 4.547-4.516 (d, J=9.3 Hz, 1H), 2.345-2.322 (m, 1H), 2.270 (s, 3H), 1.044-1.022 (d, J=6.6 Hz, 3H), 0.879-0.857 (d, J=6.6 Hz, 3H); MS (ESI): m/z: 472 (M–H), m/z 474 (M+H).

Example 274

(S)-Methyl 3-methyl-2-(1-oxo-5-(4-(3-p-tolylthio-ureido)phenyl)isoindolin-2-yl)butanoate The compound of example 274 was prepared analogous to compound of example 256 by reaction of compound of example 223 with 4-methyl phenyl isothiocyanate. The compound of example 274 was used directly without isolation, for the preparation of compound of example 275.

Example 275

(S)-3-Methyl-2-(1-oxo-5-(4-(3-p-tolylthioureido)phenyl)isoindolin-2-yl)butanoic acid The compound of example 275 was prepared analogous to compound of example 257 by hydrolysis of compound of example 274.

Yield: 75%; $^1$H NMR (DMSO-$d_6$, 300 MHz): δ 13.011 (s, 1H), 9.892 (s, 1H), 9.855 (s, 1H), 7.954 (s, 1H), 7.809-7.752 (t, J=9, 8.1 Hz, 2H), 7.720-7.691 (d, J=8.7 Hz, 2H), 7.657-7.628 (d, J=8.7 Hz, 2H), 7.378-7.351 (d, J=8.1 Hz, 2H), 7.166-7.139 (d, J=8.1 Hz, 2H), 4.732-4.544 (dd, J=17.7, 22.3 Hz, 2H), 4.545-4.514 (d, J=9.3, 1H), 2.366-2.344 (m, 1H), 2.288 (s, 3H), 1.043-1.021 (d, J=6.6 Hz, 3H), 0.878-0.857 (d, J=6.3 Hz, 3H); MS (ESI): m/z 472 (M–H), m/z 474 (M+H).

Example 276

(S)-Methyl 2-(5-(4-(3-(3-fluorophenyl)thioureido)phenyl)-1-oxoisoindolin-2-yl)-3-methylbutanoate The compound of example 276 was prepared analogous to compound of example 256 by reaction of compound of example 223 with 4-fluorophenyl isothiocyanate. The compound of example 276 was used directly without isolation, for the preparation of compound of example 277.

Example 277

(S)-2-(5-(4-(3-(3-Fluorophenyl)thioureido)phenyl)-1-oxoisoindolin-2-yl)-3-methyl butanoic acid The compound of example 277 was prepared analogous to compound of example 257 by hydrolysis of compound of example 276.

Yield: 60%; $^1$H NMR (DMSO-$d_6$, 300 MHz): δ 13.070 (s, 1H), 10.107 (s, 1H), 10.074 (s, 1H), 7.910 (s, 1H), 7.818-7.758 (t, J=8.1, 9.9 Hz, 2H), 7.741-7.712 (d, J=8.7 Hz, 2H), 7.650-7.621 (d, J=8.7 Hz, 2H), 7.578-7.533 (m, 1H), 7.413-7.337 (dd, J=6.6, 8.1 Hz, 1H), 7.297-7.269 (d, J=8.4 Hz, 1H), 6.963-6.929 (m, 1H), 4.733-4.548 (dd, J=18, 20.1 Hz, 2H), 4.548-4.517 (d, J=9.3 Hz, 1H), 2.348-2.272 (m, 1H), 1.045-1.023 (d, J=6.6 Hz, 3H), 0.881-0.859 (d, J=6.6 Hz, 3H); MS (ESI): m/z 476 (M–H), m/z 478 (M+H).

Example 278

(S)-Methyl 2-(5-(4-(3-(3-methoxyphenyl)thioureido)phenyl)-1-oxoisoindolin-2-yl)-3-methylbutanoate The compound of example 278 was prepared analogous to compound of example 256 by reaction of compound of example 223 with 3-methoxyphenyl isothiocyanate. The compound of example 278 was used directly without isolation, for the preparation of compound of example 279.

Example 279

(S)-2-(5-(4-(3-(3-Methoxyphenyl)thioureido)phenyl)-1-oxoisoindolin-2-yl)-3-methylbutanoic acid The compound of example 279 was prepared analogous to compound of example 257 by hydrolysis of compound of example 278.

Yield: 69%; $^1$H NMR (DMSO-$d_6$, 300 MHz): δ 13.070 (s, 1H), 10.112 (s, 1H), 10.079 (s, 1H), 7.910 (s, 1H), 7.817-7.758 (t, J=8.1, 9.6 Hz, 2H), 7.740-7.712 (d, J=8.4 Hz, 2H), 7.650-7.621 (d, J=8.7 Hz, 2H), 7.579-7.541 (m, 1H), 7.413-7.337 (dd, J=6.9, 8.1 Hz, 1H), 7.297-7.269 (d, J=8.4 Hz, 1H), 6.991-6.928 (m, 1H), 4.733-4.548 (dd, J=18, 20.1 Hz, 2H), 4.548-4.516 (d, J=9.6 Hz, 1H), 3.350 (s, 3H), 2.398-2.248 (m, 1H), 1.044-1.022 (d, J=6.6 Hz, 3H), 0.88-0.859 (d, J=6.6 Hz, 3H); MS (ESI): m/z 488 (M–H), m/z 490 (M+H).

Example 280

(S)-Methyl 2-(5-(4-(3-(2-methoxyphenyl)thioureido)phenyl)-1-oxoisoindolin-2-yl)-3-methylbutanoate The compound of example 280 was prepared analogous to compound of example 256 by reaction of compound of example 223 with 2-methoxyphenyl isothiocyanate. The compound of example 280 was used directly without isolation, for the preparation of compound of example 281.

Example 281

(S)-2-(5-(4-(3-(2-Methoxyphenyl)thioureido)phenyl)-1-oxoisoindolin-2-yl)-3-methylbutanoic acid The compound of example 281 was prepared analogous to compound of example 257 by hydrolysis of compound of example 280.

Yield: 76%; ¹H NMR (DMSO-d₆, 300 MHz): δ 13.050 (s, 1H), 10.097 (s, 1H), 9.281 (s, 1H), 7.914 (s, 1H), 7.914-7.894 (d, J=6 Hz, 1H), 7.818-7.677 (m, 6H), 7.201-7.149 (t, J=7.5, 8.1 Hz, 1H), 7.092-7.065 (d, J=8.1 Hz, 1H), 6.969-6.918 (d, J=7.8, 7.5 Hz, 1H), 4.731-4.548 (dd, J=17.7, 19.8, 2H), 4.548-4.516 (d, J=9.6 Hz, 1H), 3.854 (s, 3H), 2.347-2.272 (m, 1H), 1.044-1.022 (d, J=6.6 Hz, 3H), 0.88-0.859 (d, J=6.6 Hz, 3H); MS (ESI): m/z 488 (M−H), m/z 490 (M+H).

Example 282

(S)-Methyl 3-methyl-2-(1-oxo-5-(4-(3-(3-(trifluoromethyl)phenyl)thioureido)phenyl)isoindolin-2-yl)butanoate The compound of example 282 was prepared analogous to compound of example 256 by reaction of compound of example 223 with 3-trifluoromethyl phenyl isothiocyanate. The compound of example 282 was used directly without isolation, for the preparation of compound of example 283.

Example 283

(S)-3-Methyl-2-(1-oxo-5-(4-(3-(3-(trifluoromethyl)phenyl)thioureido)phenyl)isoindolin-2-yl)butanoic acid The compound of example 283 was prepared analogous to compound of example 257 by hydrolysis of compound of example 282.
Yield: 77%; ¹H NMR (DMSO-d₆, 300 MHz): δ 13.070 (s, 1H), 10.284 (s, 1H), 10.228 (s, 1H), 8.002 (s, 1H), 7.912 (s, 1H), 7.809-7.722 (m, 5H), 7.665-7.627 (d, J=8.4 Hz, 2H), 7.603-7.550 (d, J=7.8, 8.1 Hz, 1H), 7.485-7.460 (d, J=7.5 Hz, 1H), 4.734-4.548 (dd, J=18, 20.1 Hz, 2H), 4.548-4.516 (d, J=9.6 Hz, 1H), 2.346-2.270 (m, 1H), 1.044-1.022 (d, J=6.6 Hz, 3H), 0.880-0.858 (d, J=6.6 Hz, 3H); MS (ESI): m/z 526 (M−H), m/z 528 (M+H).

Example 284

(S)-Methyl 3-methyl-2-(1-oxo-6-(4-(phenylsulfonamido)phenyl)isoindolin-2-yl)butanoate The compound of example 223 (0.250 g, 0.0073 mol) was taken in dichloromethane (5 mL) to which pyridine (0.174 g, 0.00219 mol) was added and stirred for 5 min. To this reaction mixture, benzene sulfonyl chloride was added and the reaction mixture was stirred for about 16 h. After completion of the reaction, the solvent was evaporated to obtain the title compound, which was directly used for preparation of compound of example 285.

Example 285

(S)-3-Methyl-2-(1-oxo-6-(4-phenylsulfonamido)phenyl)isoindolin-2-yl)butanoic acid The compound of example 284 (0.400 g, 0.000749 mol) was taken in THF (4 mL) and MeOH (1 mL) and to this reaction mixture, 1 N LiOH (0.157 g, 0.0037 mol) was added and stirred at room temperature for 2-3 h. After completion of the reaction, the solvent was evaporated and the residue obtained was dissolved in water and acidified with 1 N HCl to obtain the title compound, which was filtered and dried
Yield: 0.310 g (80%); ¹H NMR (DMSO-d₆, 300 MHz): δ 13.071 (s, 1H), 10.531 (s, 1H), 7.832-7.810 (d, J=6.6 Hz, 3H), 7.743-7.679 (dd, J=3, 7.8 Hz, 2H), 7.630-7.547 (m, 5H), 7.237-7.209 (d, J=8.4 Hz, 2H), 4.688-4.493 (dd, J=17.7, 21.3 Hz, 2H), 4.493-4.438 (d, J=16.5 Hz, 1H), 2.344-2.226 (m, 1H), 1.028-1.006 (d, J=6.6 Hz, 3H), 0.855-0.833 (d, J=6.6 Hz, 3H); MS (ESI): m/z 465 (M+H), m/z 463 (M−H).

Example 286

(S)-Methyl 2-(5-(4-(4-cyanophenylsulfonamido)phenyl)-1-oxoisoindolin-2-yl)-3-methylbutanoate The compound of example 286 was prepared analogous to compound of example 284 by reaction of compound of example 223 with 4-cyanobenzene sulfonyl chloride. The compound of example 286 was used directly without isolation, for the preparation of compound of example 287.

Example 287

(S)-2-(5-(4-(4-Cyanophenylsulfonamido)phenyl)-1-oxoisoindolin-2-yl)-3-methyl butanoic acid The compound of example 287 was prepared analogous to compound of example 285 by hydrolysis of compound of example 286.
Yield: 93%; ¹H NMR (DMSO-d₆, 300 MHz): δ 13.016 (s, 1H), 10.780 (s, 1H), 8.092-8.064 (d, J=6.6 Hz, 2H), 7.978-7.949 (d, J=8.7 Hz, 2H), 7.893 (s, 1H), 7.734-7.723 (d, J=3.3 Hz, 2H), 7.662-7.634 (d, J=8.4 Hz, 2H), 7.242-7.213 (d, J=8.7 Hz, 2H), 4.698-4.511 (dd, J=17.7, 20.4 Hz, 2H), 4.533-4.501 (d, J=9.6 Hz, 1H), 2.309-2.277 (m, 1H), 1.034-1.012 (d, J=6.6 Hz, 3H), 0.863-0.841 (d, J=6.6 Hz, 3H); MS (ESI): m/z 490 (M+H), m/z 488 (M−H)

Example 288

(S)-Methyl 2-(5-(4-(3,4-difluorophenylsulfonamidyl)-1-oxoisoindolin-2-yl)-3-methylbutanoate The compound of example 288 was prepared analogous to compound of example 284 by reaction of compound of example 223 with 3,4-difluoro benzene sulfonyl chloride. The compound of example 288 was used directly without isolation, for the preparation of compound of example 289.

Example 289

(S)-2-(5-(4-(3,4-Difluorophenylsulfonamido)phenyl)-1-oxoisoindolin-2-yl)-3-methylbutanoic acid The compound of example 289 was prepared analogous to compound of example 285 by hydrolysis of compound of example 288.
Yield: 98%; ¹H NMR (DMSO-d₆, 300 MHz): δ 13.036 (s, 1H), 10.734 (s, 1H), 8.086-8.057 (d, J=8.7 Hz, 2H), 7.971-7.942 (d, J=8.7 Hz, 2H), 7.888-7.843 (m, 2H), 7.688-7.627 (m, 2 Hz, 2H), 7.221-7.192 (d, J=8.7 Hz, 2H), 4.687-4.510 (dd, J=17.1, 18 Hz, 2H), 4.542-4.510 (d, J=9.6 Hz, 1H), 2.331-2.255 (m, 1H), 1.032-1.010 (d, J=6.6 Hz, 3H), 0.862-0.839 (d, J=6.9 Hz, 3H); MS (ESI): m/z 501 (M+H), m/z 499 (M−H).

Example 290

(S)-Methyl 2-(5-(4-(2,4-difluorophenylsulfonamido)phenyl)-1-oxoisoindolin-2-yl)-3-methylbutanoate The compound of example 290 was prepared analogous to compound of example 284 by reaction of compound of example 223 with 2,4-difluoro benzene sulfonyl chloride. The compound of example 290 was used directly without isolation, for the preparation of compound of example 291.

Example 291

(S)-2-(5-(4-(2,4-Difluorophenylsulfonamido)phenyl)-1-oxoisoindolin-2-yl)-3-methylbutanoic acid The compound of example 291 was prepared analogous to compound of example 285 by hydrolysis of compound of example 290.

Yield: 98%; $^1$H NMR (DMSO-$d_6$, 300 MHz): δ 13.038 (s, 1H), 10.889 (s, 1H), 8.004-7.885 (m, 1H), 7.819 (s, 1H), 7.750-7.685 (dd, J=2.4, 8.1 Hz, 2H), 7.651-7.622 (d, J=8.7 Hz, 2H), 7.589-7.516 (m, 1H), 7.316-7.281 (dd, J=2.1, 8.4 Hz, 1H), 7.244-7.215 (d, J=8.7 Hz, 2H), 4.691-4.497 (dd, J=10.5, 17.7 Hz, 2H), 4.529-4.497 (d, J=9.6 Hz, 1H), 2.349-2.229 (m, 1H), 1.031-1.009 (d, J=6.6 Hz, 3H), 0.859-0.837 (d, J=6.6 Hz, 3H); MS (ESI): m/z 501 (M+H), m/z 499 (M−H).

Example 292

(S)-Methyl 2-(5-(4-(3,4-dimethoxyphenylsulfonamido)phenyl)-1-oxoisoindolin-2-yl)-3-methylbutanoate The compound of example 292 was prepared analogous to compound of example 284 by reaction of compound of example 223 with 3,4-dimethoxy benzene sulfonyl chloride. The compound of example 292 was used directly without isolation, for the preparation of compound of example 293.

Example 293

(S)-2-(5-(4-(3,4-Dimethoxyphenylsulfonamido)phenyl)-1-oxoisoindolin-2-yl)-3-methylbutanoic acid The compound of example 293 was prepared analogous to compound of example 285 by hydrolysis of compound of example 292.

Yield: 98%; $^1$H NMR (DMSO-$d_6$, 300 MHz): δ 12.988 (s, 1H), 10.308 (s, 1H), 7.815 (s, 1H), 7.784-7.684 (d, J=3, 8.1 Hz, 2H), 7.634-7.606 (d, J=8.4 Hz, 2H), 7.396-7.361 (dd, J=2.1, 8.4 Hz, 1H), 7.296-7.289 (d, J=2.1 Hz, 1H), 7.248-7.220 (d, J=8.4 Hz, 2H), 7.089-7.061 (d, J=8.4 Hz, 1H), 4.691-4.529 (dd, J=17.7, 20.7 Hz, 2H), 4.529-4.497 (d, J=9.6 Hz, 1H), 3.785 (s, 3H), 3.756 (s, 3H), 2.350-2.251 (m, 1H), 1.031-1.009 (d, J=6.6 Hz, 3H), 0.860-0.838 (d, J=6.6 Hz, 3H); MS (ESI): m/z 525 (M+H), m/z 523 (M−H).

Example 294

(S)-Methyl 2-(5-(4-(3-chlorophenylsulfonamido)phenyl)-1-oxoisoindolin-2-yl)-3-methylbutanoate The compound of example 294 was prepared analogous to compound of example 284 by reaction of compound of example 223 with 3,4-dimethoxy benzene sulfonyl chloride. The compound of example 294 was used directly without isolation, for the preparation of compound of example 295.

Example 295

(S)-2-(5-(4-(3-Chlorophenylsulfonamido)phenyl)-1-oxoisoindolin-2-yl)-3-methyl butanoic acid The compound of example 295 was prepared analogous to compound of example 285 by hydrolysis of compound of example 292.

Yield: 93%; $^1$H NMR (DMSO-$d_6$, 300 MHz): δ 13.015 (s, 1H), 10.617 (s, 1H), 7.827-7.807 (m, 2H), 7.770-7.694 (m, 4H), 7.664-7.636 (d, J=8.4 Hz, 2H), 7.611-7.585 (d, J=7.8 Hz, 1H), 7.247-7.218 (d, J=8.7 Hz, 2H), 4.694-4.499 (dd, J=9.6, 17.7 Hz, 2H), 4.531-4.499 (d, J=9.6 Hz, 1H), 2.372-2.232 (m, 1H), 1.031-1.009 (d, J=6.6 Hz, 3H), 0.860-0.838 (d, J=6.6 Hz, 3H); MS (ESI): m/z 499 (M+H), m/z 497 (M−H).

Example 296

(S)-Methyl 2-(5-(4-(4-methoxyphenylsulfonamido)phenyl)-1-oxoisoindolin-2-yl)-3-methylbutanoate The compound of example 296 was prepared analogous to compound of example 284 by reaction of compound of example 223 with 4-methoxy benzene sulfonyl chloride. The compound of example 296 was used directly without isolation, for the preparation of compound of example 297.

Example 297

(S)-2-(5-(4-(4-Methoxyphenylsulfonamido)phenyl)-1-oxoisoindolin-2-yl)-3-methylbutanoic acid The compound of example 297 was prepared analogous to compound of example 285 by hydrolysis of compound of example 296.

Yield: 95%; $^1$H NMR (DMSO-$d_6$, 300 MHz): δ 13.074 (s, 1H), 10.380 (s, 1H), 7.854 (s, 1H), 7.813-7.681 (d, 4H), 7.628-7.600 (d, J=8.4 Hz, 2H), 7.231-7.203 (d, J=8.4 Hz, 2H), 7.093-7.064 (d, J=8.7 Hz, 2H), 4.690-4.497 (dd, J=17.7, 21.3 Hz, 2H), 4.528-4.497 (d, J=9.3 Hz, 1H), 3.791 (s, 3H), 2.396-2.229 (m, 1H), 1.030-1.008 (d, J=6.6 Hz, 3H), 0.859-0.836 (d, J=6.9 Hz, 3H); MS (ESI): m/z 495 (M+H), m/z 493 (M−H).

Example 298

(S)-Methyl 3-methyl-2-(1-oxo-5-(4-(4-(trifluoromethyl)phenylsulfonamido)phenyl)isoindolin-2-yl)butanoate The compound of example 298 was prepared analogous to compound of example 284 by reaction of compound of example 223 with 4-trifluoromethyl benzene sulfonyl chloride. The compound of example 298 was used directly without isolation, for the preparation of compound of example 299.

Example 299

(S)-3-Methyl-2-(1-oxo-5-(4-(4-(trifluoromethyl)phenylsulfonamido)phenyl)isoindolin-2-yl)butanoic acid The compound of example 299 was prepared analogous to compound of example 285 by hydrolysis of compound of example 298.

Yield: 84%; ¹H NMR (DMSO-d₆, 300 MHz): δ 13.004 (s, 1H), 10.748 (s, 1H), 8.039-7.967 (dd, J=3.9, 8.7 Hz, 4H), 7.822 (s, 1H), 7.753-7.689 (d, J=8.1 Hz, 2H), 7.661-7.633 (d, J=8.4 Hz, 2H), 7.252-7.223 (d, J=8.7 Hz, 2H), 4.693-4.497 (dd, J=18, 21 Hz, 2H), 4.529-4.497 (d, J=9.6 Hz, 1H), 2.350-2.228 (m, 1H), 1.030-1.008 (d, J=6.6 Hz, 3H), 0.858-0.836 (d, J=6.6 Hz, 3H); MS (ESI): m/z 533 (M+H), m/z 531 (M−H).

Example 300

(S)-Methyl 3-methyl-2-(1-oxo-5-(4-(phenylmethylsulfonamido)phenyl)iso indolin-2-yl)butanoate The compound of example 300 was prepared analogous to compound of example 284 by reaction of compound of example 223 with benzyl sulfonyl chloride. The compound of example 300 was used directly without isolation, for the preparation of compound of example 301.

Example 301

(S)-3-Methyl-2-(1-oxo-5-(4-(phenylmethylsulfonamido)phenyl)isoindolin-2-yl)butanoic acid The compound of example 301 was prepared analogous to compound of example 285 by hydrolysis of compound of example 300.

Yield: 87%; ¹H NMR (DMSO-d₆, 300 MHz): δ 13.027 (s, 1H), 10.45 (s, 1H), 7.955 (s, 1H), 7.776 (s, 2H), 7.725-7.696 (d, J=8.7 Hz, 2H), 7.388 (m, 6H), 4.903-4.549 (dd, J=13.8, 17.7 Hz, 2H), 4.530-4.499 (d, J=9.3 Hz, 1H), 4.517 (s, 2H), 2.325-2.202 (m, 1H), 1.045-1.023 (d, J=6.6 Hz, 3H), 0.880-0.858 (d, J=6.6 Hz, 3H); MS (ESI): m/z 479 (M+H), m/z 477 (M−H).

Example 302

(S)-Methyl 2-(5-(4-(cyclohexanesulfonamido)phenyl)-1-oxoisoindolin-2-yl)-3-methylbutanoate The compound of example 302 was prepared analogous to compound of example 284 by reaction of compound of example 223 with cyclohexyl sulfonyl chloride. The compound of example 302 was used directly without isolation, for the preparation of compound of example 303.

Example 303

(S)-2-(5-(4-(Cyclohexanesulfonamido)phenyl)-1-oxoisoindolin-2-yl)-3-methylbutanoic acid The compound of example 303 was prepared analogous to compound of example 285 by hydrolysis of compound of example 302.

Yield: 60%; ¹H NMR (DMSO-d₆, 300 MHz): δ 12.977 (s, 1H), 9.962 (s, 1H), 7.869 (s, 1H), 7.812 (m, 2H), 7.708-7.680 (d, J=8.4 Hz, 2H), 7.359-7.330 (d, J=8.7 Hz, 2H), 4.718-4.510 (m, 3H), 3.088-3.010 (t, J=11.7 Hz, 1H), 2.362-2.243 (m, 1H), 2.064-2.026 (m, 2H), 1.785-1.744 (m, 2H), 1.601-1.569 (m, 1H), 1.491-1.380 (m, 2H), 1.286-1.087 (m, 3H), 1.040-1.018 (d, J=6.6 Hz, 3H), 0.873-0.851 (d, J=6.6 Hz, 3H); MS (ESI): m/z 471 (M+H), m/z 469 (M−H).

Example 304

(S)-Methyl 2-(5-(4-benzamidophenyl)-1-oxoisoindolin-2-yl)-3-methylbutanoate

To a solution of compound of example 223 (100 mg, 0.295 mmol) in dichloromethane (3 mL), pyridine (70.53 mg, 0.885 mmol) was added and stirred for 5 min followed by addition of benzoyl bromide (81.96 mg, 0.443 mmol). The reaction mixture was stirred for about 16 h. After completion of the reaction, the solvent was evaporated to obtain the title compound, which was directly used for the preparation of compound of example 305.

Example 305

(S)-2-(5-(4-Benzamidophenyl)-1-oxoisoindolin-2-yl)-3-methylbutanoic acid

The compound of example 304 (130 mg, 0.294 mmol) was taken in THF (4 mL) and MeOH (1 mL) and to this reaction mixture, 1 N LiOH (61.89 mg, 1.475 mmol) was added and stirred at room temperature for 2-3 h. After completion of reaction, the solvent was evaporated and the residue obtained was dissolved in water and acidified with 1 N HCl to obtain the title compound, which was filtered and dried.

Yield: 110 mg (87%); ¹H NMR (DMSO-d₆, 300 MHz): δ 13.046 (s, 1H), 10.408 (s, 1H), 7.996-7.927 (m, 5H), 7.827-7.744 (m, 4H), 7.619-7.482 (m, 3H), 4.733-4.549 (dd, J=17.7, 21.3 Hz, 2H), 4.549-4.518 (d, J=9.3 Hz, 1H), 2.369-2.273 (m, 1H), 1.047-1.025 (d, J=6.6 Hz, 3H), 0.881-0.859 (d, J=6.6 Hz, 3H); MS (ESI): m/z 427 (M−H), m/z 429 (M+H).

Example 306

(S)-Methyl 2-(5-(4-(4-fluorobenzamido)phenyl)-1-oxoisoindolin-2-yl)-3-methyl butanoate The compound of example 306 was prepared analogous to compound of example 304 by reaction of compound of example 223 with 4-fluorobenzoyl bromide. The compound of example 306 was used directly without isolation, for the preparation of compound of example 307.

Example 307

(S)-2-(5-(4-(4-Fluorobenzamido)phenyl)-1-oxoisoindolin-2-yl)-3-methylbutanoic acid The compound of example 307 was prepared analogous to compound of example 305 by hydrolysis of compound of example 306.

Yield: 84%; ¹H NMR (DMSO-d₆, 300 MHz): δ 13.042 (s, 1H), 10.420 (s, 1H), 8.091-8.043 (dd, J=5.7, 3 Hz, 2H), 8.028-7.980 (dd, J=5.7, 3 Hz, 1H), 7.938-7.909 (m, 2H), 7.798-7.744 (m, 3H), 7.423-7.364 (t, J=9, 8.7 Hz, 2H), 7.353-7.298 (t, J=9, 7.5 Hz, 1H), 4.731-4.549 (dd, J=17.7, 21 Hz, 2H), 4.549-4.517 (d, J=9.6 Hz, 1H), 2.324-2.271 (m, 1H), 1.045-1.024 (d, J=6.3 Hz, 3H), 0.879-0.857 (d, J=6.6 Hz, 3H); MS (ESI): m/z 445 (M–H), m/z 447 (M+H).

Example 308

(S)-Methyl 3-methyl-2-(1-oxo-5-(4-(4-(trifluoromethyl)benzamido)phenyl)isoindolin-2-yl)butanoate The compound of example 308 was prepared analogous to compound of example 304 by reaction of compound of example 223 with 4-trifluoromethyl benzoyl bromide. The compound of example 308 was used directly without isolation, for the preparation of compound of example 309.

Example 309

(S)-3-Methyl-2-(1-oxo-5-(4-(4-(trifluoromethyl)benzamido)phenyl)isoindolin-2-yl)butanoic acid The compound of example 309 was prepared analogous to compound of example 305 by hydrolysis of compound of example 308.
Yield: 95%; $^1$H NMR (DMSO-$d_6$, 300 MHz): δ 13.002 (s, 1H), 10.632 (s, 1H), 8.194-8.167 (d, J=8.1 Hz, 2H), 7.956-7.928 (m, 5H), 7.835-7.764 (m, 4H), 4.735-4.551 (dd, J=18, 20.4 Hz, 2H), 4.551-4.519 (d, J=9.6 Hz, 1H), 2.324-2.271 (m, 1H), 1.047-1.025 (d, J=6.6 Hz, 3H), 0.881-0.859 (d, J=6.6 Hz, 3H); MS (ESI): m/z 497 (M+H).

Example 310

(S)-Methyl 2-(5-(4-(4-methoxybenzamido)phenyl)-1-oxoisoindolin-2-yl)-3-methylbutanoate The compound of example 310 was prepared analogous to compound of example 304 by reaction of compound of example 223 with 4-methoxy benzoyl bromide. The compound of example 310 was used directly without isolation, for the preparation of compound of example 311.

Example 311

(S)-2-(5-(4-(4-Methoxybenzamido)phenyl)-1-oxoisoindolin-2-yl)-3-methyl butanoic acid The compound of example 311 was prepared analogous to compound of example 305 by hydrolysis of compound of example 310.
Yield: 79%; $^1$H NMR (DMSO-$d_6$, 300 MHz): δ 13.288 (s, 1H), 10.243 (s, 1H), 8.005-7.976 (d, J=8.7 Hz, 2H), 7.942-7.914 (d, J=8.4 Hz, 3H), 7.794-7.779 (d, J=4.5 Hz, 2H), 7.757-7.729 (d, J=8.4 Hz, 2H), 7.099-7.070 (d, J=8.4 Hz, 2H), 4.732-4.545 (dd, J=17.7, 22.5 Hz, 2H), 4.545-4.513 (d, J=9.6 Hz, 1H), 3.852 (s, 3H), 2.346-2.271 (m, 1H), 1.045-1.023 (d, J=6.6 Hz, 3H), 0.879-0.857 (d, J=6.6 Hz, 3H); MS (ESI): m/z: 457 (M+H), m/z: 459 (M+H).

Example 312

(S)-Methyl 2-(5-(4-(3-fluorobenzamido)phenyl)-1-oxoisoindolin-2-yl)-3-methyl butanoate The compound of example 312 was prepared analogous to compound of example 304 by reaction of compound of example 223 with 3-fluoro benzoyl bromide. The compound of example 312 was used directly without isolation, for the preparation of compound of example 313.

Example 313

(S)-2-(5-(4-(3-Fluorobenzamido)phenyl)-1-oxoisoindolin-2-yl)-3-methylbutanoic acid The compound of example 313 was prepared analogous to compound of example 305 by hydrolysis of compound of example 312.
Yield: 84%; $^1$H NMR (DMSO-$d_6$, 300 MHz): δ 13.280 (s, 1H), 10.466 (s, 1H), 7.941-7.920 (m, 3H), 7.853-7.750 (m, 6H), 7.649-7.544 (m, 1H), 7.501-7.483 (m, 1H), 4.771-4.579 (dd, J=17.7, 21 Hz, 2H), 4.545-4.513 (d, J=9.6 Hz, 1H), 2.438-2.300 (m, 1H), 1.042-1.021 (d, J=6.3 Hz, 3H), 0.876-0.855 (d, J=6.3 Hz, 3H); MS (ESI): m/z 445 (M+H), m/z 447 (M+H).

Example 314

(S)-Methyl 2-(5-(4-(3-chlorobenzamido)phenyl)-1-oxoisoindolin-2-yl)-3-methyl butanoate The compound of example 314 was prepared analogous to compound of example 304 by reaction of compound of example 223 with 3-chloro benzoyl bromide. The compound of example 314 was used directly without isolation, for the preparation of compound of example 315.

Example 315

(S)-2-(5-(4-(3-Chlorobenzamido)phenyl)-1-oxoisoindolin-2-yl)-3-methylbutanoic acid The compound of example 315 was prepared analogous to compound of example 305 by hydrolysis of compound of example 314.
Yield: 84%; $^1$H NMR (DMSO-$d_6$, 300 MHz): δ 13.107 (s, 1H), 10.501 (s, 1H), 8.042-8.031 (t, J=1.5, 1.8 Hz, 1H), 7.958-7.886 (m, 4H), 7.801-7.764 (m, 4H), 7.620-7.563 (J=7.5, 5.7 Hz, 1H), 7.620-7.594 (d, J=7.8 Hz, 1H), 4.733-4.551 (dd, J=18, 20.4 Hz, 2H), 4.551-4.519 (d, J=9.6 Hz, 1H), 2.371-2.251 (m, 1H), 1.047-1.025 (d, J=6.6 Hz, 3H), 0.882-0.860 (d, J=6.6 Hz, 3H); MS (ESI): m/z 461 (M+H), m/z 463 (M+H).

Example 316

(S)-Methyl 2-(5-(4-(2,4-difluorobenzamido)phenyl)-1-oxoisoindolin-2-yl)-3-methylbutanoate The compound of example 316 was prepared analogous to compound of example 304 by reaction of compound of example 223 with 2,4-difluoro benzoyl bromide. The compound of example 316 was used directly without isolation, for the preparation of compound of example 317.

Example 317

(S)-2-(5-(4-(2,4-Difluorobenzamido)phenyl)-1-oxoisoindolin-2-yl)-3-methyl butanoic acid The compound of example 317 was prepared analogous to compound of example 305 by hydrolysis of compound of example 316.

Yield: 87%; $^1$H NMR (DMSO-d$_6$, 300 MHz): δ 12.915 (s, 1H), 10.580 (s, 1H), 7.915-7.743 (m, 8H), 7.489-7.415 (td, J=2.1, 9.6, 10.2 Hz, 1H), 7.285-7.221 (td, J=2.1, 8.4, 8.7 Hz, 1H), 4.732-4.546 (dd, J=18, 20.7 Hz, 2H), 4.546-4.515 (d, J=9.3 Hz, 1H), 2.346-2.270 (m, 1H), 1.044-1.022 (d, J=6.6 Hz, 3H), 0.878-0.856 (d, J=6.6 Hz, 3H); MS (ESI): m/z 465 (M+H).

Example 318

(S)-Methyl 3-methyl-2-(5-(4-(4-methylbenzamido) phenyl)-1-oxoisoindolin-2-yl)butanoate The compound of example 318 was prepared analogous to compound of example 304 by reaction of compound of example 223 with 4-methyl benzoyl bromide. The compound of example 318 was used directly without isolation, for the preparation of compound of example 319.

Example 319

(S)-3-Methyl-2-(5-(4-(4-methylbenzamido)phenyl)-1-oxoisoindolin-2-yl)butanoic acid The compound of example 319 was prepared analogous to compound of example 305 by hydrolysis of compound of example 318.

Yield: 93%; $^1$H NMR (DMSO-d$_6$, 300 MHz): δ 13.040 (s, 1H), 10.312 (s, 1H), 7.949-7.889 (t, J=9 Hz, 5H), 7.745-7.732 (m, 4H), 7.371-7.344 (d, J=8.1 Hz, 2H), 4.669-4.484 (d, J=15.9, 20.4 Hz, 2H), 4.516-4.490 (d, J=7.8 Hz, 1H), 2.456 (s, 3H), 2.399-2.270 (m, 1H), 1.044-1.023 (d, J=6.3 Hz, 3H), 0.879-0.857 (d, J=6.6 Hz, 3H); MS (ESI): m/z 441 (M+H), m/z 443 (M+H).

Example 320

(S)-Methyl 2-(5-(4-(4-chlorobenzamido)phenyl)-1-oxoisoindolin-2-yl)-3-methyl butanoate The compound of example 320 was prepared analogous to compound of example 304 by reaction of compound of example 223 with 4-chloro benzoyl bromide. The compound of example 320 was used directly without isolation, for the preparation of compound of example 321.

Example 321

(S)-2-(5-(4-(4-Chlorobenzamido)phenyl)-1-oxoisoindolin-2-yl)-3-methylbutanoic acid The compound of example 321 was prepared analogous to compound of example 305 by hydrolysis of compound of example 320.

Yield: 84%; $^1$H NMR (DMSO-d$_6$, 300 MHz): 13.040 (s, 1H), 10.469 (s, 1H), 8.027-7.999 (d, J=8.4 Hz, 2H), 7.936-7.910 (m, 3H), 7.824-7.745 (m, 4H), 7.647-7.619 (d, J=8.4 Hz, 2H), 4.705-4.572 (dd, J=19.5, 20.7 Hz, 2H), 4.546-4.515 (d, J=9.3 Hz, 1H), 2.364-2.270 (m, 1H), 1.044-1.022 (d, J=6.6 Hz, 3H), 0.877-0.856 (d, J=6.6 Hz, 3H); MS (ESI): m/z 461 (M+H), m/z 463 (M+H).

Example 322

(S)-Methyl 2-(5-(4-(4-tert-butylbenzamido)phenyl)-1-oxoisoindolin-2-yl)-3-methylbutanoate The compound of example 322 was prepared analogous to compound of example 304 by reaction of compound of example 223 with 4-(t-butyl)benzoyl bromide. The compound of example 322 was used directly without isolation, for the preparation of compound of example 323.

Example 323

(S)-2-(5-(4-(4-tert-Butylbenzamido)phenyl)-1-oxoisoindolin-2-yl)-3-methyl butanoic acid The compound of example 323 was prepared analogous to compound of example 305 by hydrolysis of compound of example 322.

Yield: 76%; $^1$H NMR (DMSO-d$_6$, 300 MHz): δ 13.035 (s, 1H), 10.329 (s, 1H), 7.947-7.902 (m, 5H), 7.825-7.737 (m, 4H), 7.582-7.554 (d, J=8.4 Hz, 2H), 4.731-4.550 (dd, J=10.8, 17.7 Hz, 2H), 4.550-4.519 (d, J=9.3 Hz, 1H), 2.369-2.216 (m, 1H), 1.334 (s, 9H), 1.047-1.026 (d, J=6.3 Hz, 3H), 0.881-0.859 (d, J=6.6 Hz, 3H); MS (ESI): m/z 483 (M+H), m/z 485 (M+H).

Example 324

(S)-Methyl 3-methyl-2-(1-oxo-5-(4-(4-pentylbenzamido)phenyl)isoindolin-2-yl)butanoate The compound of example 324 was prepared analogous to compound of example 304 by reaction of compound of example 223 with 4-(n-pentyl)benzoyl bromide. The compound of example 324 was used directly without isolation, for the preparation of compound of example 325.

Yield: 52%; $^1$H NMR (DMSO-d$_6$, 300 MHz): δ 10.308 (s, 1H), 7.934-7.874 (d, J=9 Hz, 5H), 7.786-7.767 (d, J=5.7 Hz, 2H), 7.747-7.718 (d, J=8.7 Hz, 2H), 7.364-7.337 (d, J=8.1 Hz, 2H), 4.613-4.578 (m, 3H), 3.670 (s, 3H), 2.697-2.638 (t, J=7.2, 7.8 Hz, 2H), 2.371-2.260 (m, 1H), 1.687-1.607 (m, 2H), 1.301-1.270 (m, 4H), 0.997-0.975 (d, J=6.6 Hz, 3H), 0.877-0.849 (m, 6H); MS (ESI): m/z 511 (M−H), m/z 513 (M+H).

Example 325

(S)-3-Methyl-2-(1-oxo-5-(4-(4-pentylbenzamido) phenyl)isoindolin-2-yl)butanoic acid The compound of example 325 was prepared analogous to compound of example 305 by hydrolysis of compound of example 324.

Yield: 71.7%; $^1$H NMR (DMSO-d$_6$, 300 MHz): δ 12.994 (s, 1H), 10.306 (s, 1H), 7.932-7.875 (d, J=8.7 Hz, 5H), 7.808-7.718 (m, 4H), 7.364-7.337 (d, J=8.1 Hz, 2H), 4.715-4.532 (dd, J=18, 20.7 Hz, 2H), 4.532-4.501 (d, J=9.3 Hz, 1H), 2.672-2.622 (t, J=7.5 Hz, 2H), 2.308-2.256 (m, 1H), 1.620-1.575 (m, 2H), 1.339-1.283 (m, 4H), 1.029-1.008 (d, J=6.3 Hz, 3H), 0.862-0.841 (m, 6H); MS (ESI): m/z 497 (M−H), m/z 499 (M+H).

Example 326

1-(4-Bromophenyl)-3-(3-(trifluoromethyl)phenyl) urea

In a round bottom flask, 4-bromoaniline (12 g, 0.0697 mol) was dissolved in 120 mL THF and to this solution, 3-trifluorophenyl isocyanate (14.36 g, 0.0767 mol) was added and stirred at room temperature for 8-10 h. The reaction mixture was concentrated and purified by column chromatography (silica gel, 30-40% ethyl acetate in petroleum ether) to obtain the title compound.

Yield: 21.66 g (96%); $^1$H NMR (DMSO-$d_6$, 300 MHz): δ 9.078 (s, NH), 8.939 (s, NH), 8.002 (s, 1H), 7.592-7.564 (d, J=8.4 Hz, 1H), 7.539-7.513 (d, J=7.8 Hz, 1H), 7.487-7.426 (m, 4H), 7.330-7.306 (d, J=7.2 Hz, 1H); MS (ESI): m/z 357.7 (M−H), m/z 359 (M+H).

Example 327

1-(4-(4,4,5,5-Tetramethyl-1,3,2-dioxaborolan-2-yl) phenyl)-3-(3-(trifluoromethyl)phenyl)urea The compound of example 326 (21 g, 0.0584 mol) bis (pinacolato)diborane, Pd(dppf)Cl$_2$:CH$_2$Cl$_2$ and potassium acetate were taken in dry DMF and heated at 85-90° C. under an atmosphere of argon. After completion of the reaction (8-10 h), DMF was evaporated and the residue obtained was dissolved in dichloromethane and filtered through celite. The filtrate was concentrated and purified by column chromatography (silica gel, 10% ethyl acetate in CHCl$_3$) to obtain the title compound.

$^1$H NMR (DMSO-$d_6$, 300 MHz): δ 9.085 (s, NH), 8.959 (s, NH), 8.030 (s, 1H), 7.615-7.587 (d, J=8.4 Hz, 2H), 7.557-7.541 (d, J=4.8 Hz, 1H), 7.515-7.465 (m, 3H), 7.333-7.309 (d, J=7.2 Hz, 1H), 1.283 (s, 12H); MS (ESI): m/z 406 (M+H), m/z 407 (M+H).

Example 328

Methyl 5-bromo-2-(bromomethyl)benzoate

Methyl 5-bromo-2-methylbenzoate (1.0 g, 0.45 mol) was dissolved in carbon tetrachloride (15 mL) to which benzoyl peroxide (40 mg) and NBS (1.49 g, 0.83 mol) were added and the reaction mixture was refluxed at 80° C. After completion of the reaction, the reaction mixture was cooled to room temperature and filtered through celite. The filtrate was concentrated to obtain a crude material containing 95% mono bromo and 5% dibromo product. The crude material was used directly for the preparation of compound of example 329 without purification.

Example 329

(R)-Methyl 2-(6-bromo-1-oxoisoindolin-2-yl)-3-methylbutanoate

The compound of example 328 (650 mg, 2.12 mmol) and D-valine methyl ester hydrochloride (527 mg, 3.15 mmol) was taken in toluene (6.5 mL) and to this reaction mixture, triethyl amine (428 mg, 4.24 mmol) was added and refluxed for about 16 h. After completion of the reaction, the reaction mixture was diluted with ethyl acetate and washed with water and brine, dried over anhydrous sodium sulfate and evaporated to obtain a residue, which was purified by column chromatography (silica gel, 30% ethyl acetate in petroleum ether) to obtain the title compound.

Yield: 550 mg (80%); $^1$H NMR (CDCl$_3$, 300 MHz): δ 8.019-8.014 (d, J=1.5 Hz, 1H), 7.705-7.672 (dd, J=1.8, 8.1 Hz, 1H), 7.380-7.353 (d, J=8.1 Hz, 1H), 4.823-4.789 (d, J=10.2 Hz, 1H), 4.743-4.685 (d, J=17.4 Hz, 1H), 4.415-4.357 (d, J=17.4 Hz, 1H), 3.743 (s, 3H), 2.377-2.298 (m, 1H), 1.077-1.055 (d, J=6.6 Hz, 3H), 0.938-0.916 (d, J=6.6 Hz, 3H); MS (ESI): m/z 326 (M+H).

Example 330

(R)-Methyl-3-methyl-2-(1-oxo-6-(4-(3-(3-(trifluoromethyl)phenyl)ureido)phenyl)isoindolin-2-yl)butanoate The compound of example 329 (288 mg, 0.886 mmol), compound of example 327 (300 mg, 0.738 mmole) and Pd(dppf)Cl$_2$: CH$_2$Cl$_2$ (18 mg, 0.022 mmol) were taken in DMF (5 mL) under an argon atmosphere. To this reaction mixture, 2M solution of Na$_2$CO$_3$ (234 mg, 2.214 mmole, 1.1 mL) was added. The reaction mixture was stirred at 80-85° C. for 1 to 1.5 h. After completion of the reaction, water was added and the product obtained was extracted with ether. The ether layer was washed with water, brine and dried over anhydrous Na$_2$SO$_4$ or anhydrous MgSO$_4$. The solvent was evaporated and the residue obtained was purified by column chromatography (silica gel, 30% ethyl acetate in petroleum ether) obtain the title compound.

Yield: 300 mg (77%); $^1$H NMR (DMSO-$d_6$, 300 MHz): δ 9.108 (s, NH), 8.985 (s, NH), 8.093-8.008 (m, 1H), 7.939-7.912 (d, J=8.1 Hz, 1H), 7.766-7.685 (m, 3H), 7.612-7.502 (m, 4H), 7.556-7.502 (t, J=8.1 Hz, 1H), 7.340-7.314 (d, J=7.8 Hz, 1H), 4.641-4.609 (m, 3H), 3.688 (s, 3H), 2.372-2.294 (m, 1H), 1.016-0.994 (d, J=6.6 Hz, 3H), 0.866-0.844 (d, J=6.6 Hz, 3H); MS (ESI): m/z 524.1 (M−H), m/z 526 (M+H).

Example 331

(R)-3-Methyl-2-(1-oxo-6-(4-(3-(3-(trifluoromethyl) phenyl)ureido)phenyl)iso indolin-2-yl)butanoic acid The compound of example 330 (150 mg, 0.293 mmol) was taken in THF (4 mL) and MeOH (1 mL) and to this reaction mixture, 1 N LiOH (61.58 mg, 1.46 mmol) was added and stirred at room temperature for 2-3 h. After completion of the reaction, the solvent was evaporated and the residue obtained was dissolved in water and acidified with 1 N HCl to obtain the title compound, which was filtered and dried.

Yield: 135 mg (78%); $^1$H NMR (DMSO-$d_6$, 300 MHz): δ 13.028 (s, 1H), 9.170 (s, 1H), 9.137 (s, 1H), 8.037 (s, 1H), 7.926-7.904 (d, J=6.6 Hz, 2H), 7.709-7.681 (d, J=8.1 Hz, 2H), 7.612-7.584 (d, J=8.4 Hz, 3H), 7.550-7.498 (m, 2H), 7.334-7.308 (m, 1H), 4.715-4.528 (m, 3H), 2.421-2.394 (m, 1H), 1.046-1.024 (d, J=6.6 Hz, 3H), 0.878-0.857 (d, J=6.6 Hz, 3H); MS (ESI): m/z 510.1 (M−H), m/z 512.2 (M+H).

Example 332

Methyl 2-(6-bromo-1-oxoisoindolin-2-yl)acetate

The compound of example 332 was prepared analogous to compound of example 329 by reaction of the compound of example 328 and glycine methyl ester hydrochloride.

Yield: 280 mg (68.5%); $^1$H NMR (CDCl$_3$, 300 MHz): δ 8.026-8.020 (d, J=1.8 Hz, 1H), 7.715-7.682 (dd, J=1.8, 8.1 Hz, 1H), 7.375-7.348 (d, J=8.1 Hz, 1H), 4.500 (s, 2H), 4.423 (s, 2H), 3.783 (s, 3H); MS (ESI): m/z 284 (M+H).

Example 333

Methyl 2-(1-oxo-6-(4-(3-(3-(trifluoromethyl)phenyl) ureido)phenyl)isoindolin-2-yl)acetate The compound of example 333 was prepared analogous to compound of example 330 by reaction of the compound of example 332, compound of example 327 and Pd(dppf)Cl$_2$:

CH₂Cl₂. The compound of example 333 was used directly without isolation for the preparation of compound of example 334.

Example 334

2-(1-Oxo-6-(4-(3-(3-(trifluoromethyl)phenyl)ureido) phenyl)isoindolin-2-yl)acetic acid The compound of example 334 was prepared analogous to compound of example 331 by hydrolysis of the compound of example 333.

Yield: 91%; ¹H NMR (DMSO-d₆, 300 MHz): δ 9.670 (s, 1H), 9.464 (s, 1H), 8.060 (s, 1H), 7.901-7.882 (d, J=5.7 Hz, 2H), 7.685-7.581 (m, 6H), 7.531-7.479 (d, J=7.5, 8.1 Hz, 1H), 7.309-7.285 (d, J=7.2 Hz, 1H), 4.575 (s, 2H), 4.254 (s, 2H); MS (ESI): m/z 468 (M−H), m/z 470 (M+H).

Example 335

(S)-Methyl 2-(6-bromo-1-oxoisoindolin-2-yl)propanoate

The compound of example 335 was prepared analogous to compound of example 329 by reaction of the compound of example 328 and L-alanine methyl ester hydrochloride.

Yield: 505 mg (86.7%); ¹H NMR (CDCl₃, 300 MHz): δ 8.017-8.012 (d, J=1.5 Hz, 1H), 7.706-7.673 (dd, J=1.8, 8.1 Hz, 1H), 7.381-7.354 (d, J=8.1 Hz, 1H), 5.242-5.167 (q, J=7.5 Hz, 1H), 4.598-4.543 (d, J=16.5 Hz, 1H), 4.419-4.364 (d, J=16.5 Hz, 1H), 3.747 (s, 3H), 1.612-1.587 (d, J=7.5 Hz, 3H); MS (ESI): m/z 298 (M+H).

Example 336

(S)-Methyl 2-(1-oxo-6-(4-(3-(3-(trifluoromethyl) phenyl)ureido)phenyl)isoindolin-2-yl)propanoate The compound of example 336 was prepared analogous to compound of example 330 by reaction of the compound of example 335, compound of example 327 and Pd(dppf)Cl₂: CH₂Cl₂.

¹H NMR (DMSO-d₆, 300 MHz): δ 9.095 (s, 1H), 8.951 (s, 1H), 8.037 (s, 1H), 7.936-7.908 (d, J=8.4 Hz, 2H), 7.716-7.688 (m, 3H), 7.612-7.583 (d, J=8.7 Hz, 3H), 7.553-7.501 (t, J=7.8 Hz, 1H), 7.337-7.312 (d, J=7.5 Hz, 1H), 5.0051-4.934 (q, J=7.2, 1H), 4.626-4.480 (dd, J=17.4, 9 Hz, 2H), 3.669 (s, 3H), 1.550-1.526 (d, J=7.2 Hz, 3H); MS (ESI) m/z 498 (M+H).

Example 337

(S)-2-(1-Oxo-6-(4-(3-(3-(trifluoromethyl)phenyl) ureido)phenyl)isoindolin-2-yl)propanoic acid The compound of example 337 was prepared analogous to compound of example 331 by hydrolysis of the compound of example 336.

Yield: 82%; ¹H NMR (DMSO-d₆, 300 MHz): δ 12.965 (s, 1H), 9.107 (s, 1H), 8.962 (s, 1H), 8.038 (s, 1H), 7.928-7.902 (d, J=7.8 Hz, 2H), 7.715-7.687 (d, J=8.4 Hz, 3H), 7.611-7.583 (d, J=8.4 Hz, 3H), 7.551-7.499 (t, J=7.8 Hz, 1H), 7.335-7.311 (d, J=7.2 Hz, 1H), 4.879-4.854 (d, J=7.5 Hz, 1H), 4.547 (s, 2H), 1.540-1.516 (d, J=7.2 Hz, 3H); MS (ESI): m/z 482.1 (M−H), m/z 484.2 (M+H).

Example 338

Methyl 2-(6-bromo-1-oxoisoindolin-2-yl)-2-methylpropanoate

The compound of example 338 was prepared analogous to compound of example 329 by reaction of the compound of example 328 and 2,2-dimethyl glycine methyl ester hydrochloride.

Yield: 167 mg (27.3%); ¹H NMR (CDCl₃, 300 MHz): δ 7.952 (s, 1H), 7.694-7.661 (dd, J=1.8, 8.1 Hz, 1H), 7.366-7.339 (d, J=8.1 Hz, 1H), 4.486 (s, 2H), 3.768 (s, 3H), 1.673 (s, 6H); MS (ESI): m/z 312 (M+H).

Example 339

Methyl 2-methyl-2-(1-oxo-6-(4-(3-(3-(trifluoromethyl)phenyl)ureido)phenyl)isoindolin-2-yl)propanoate The compound of example 339 was prepared analogous to compound of example 330 by reaction of the compound of example 338, compound of example 327 and Pd(dppf)Cl₂: CH₂Cl₂.

¹H NMR (DMSO-d₆, 300 MHz): δ 9.110 (s, NH), 8.958 (s, NH), 8.037 (s, 1H), 7.919-7.893 (d, J=7.8 Hz, 1H), 7.836 (s, 1H), 7.703-7.659 (m, 3H), 7.607-7.579 (m, 3H), 7.551-7.499 (t, J=7.5 Hz, 1H), 7.335-7.311 (d, J=7.2 Hz, 1H), 4.679 (s, 2H), 3.621 (s, 3H), 1.575 (s, 6H); MS (ESI): m/z 510 (M−H), m/z 512 (M+H).

Example 340

2-Methyl-2-(1-oxo-6-(4-(3-(3-(trifluoromethyl)phenyl)ureido)phenyl)isoindolin-2-yl)propanoic acid The compound of example 340 was prepared analogous to compound of example 331 by hydrolysis of the compound of example 339.

Yield: 87%; ¹H NMR (DMSO-d₆, 300 MHz): δ 12.485 (s, 1H), 9.110 (s, 1H), 8.962 (s, 1H), 8.038 (s, 1H), 7.938-7.908 (d, J=9 Hz, 1H), 7.832 (s, 1H), 7.702-7.649 (t, J=7.5, 8.4 Hz, 3H), 7.609-7.581 (d, J=8.4 Hz, 3H), 7.552-7.500 (t, J=7.8, 1H), 7.335-7.311 (d, J=7.2 Hz, 1H), 4.656 (s, 2H), 1.579 (s, 6H); MS (ESI): m/z 496.1 (M−H), m/z 498.2 (M+H).

Example 341

Methyl 1-(6-bromo-1-oxoisoindolin-2-yl)cyclopentanecarboxylate

The compound of example 341 was prepared analogous to compound of example 329 by reaction of the compound of example 328 and methyl 1-aminocyclopentanecarboxylate hydrochloride.

Yield: 300 mg (45.3%); ¹H NMR (CDCl₃, 300 MHz): δ 7.598 (s, 1H), 7.693-7.662 (dd, J=1.5, 7.8 Hz, 1H), 7.359-7.332 (d, J=8.1 Hz, 1H), 4498 (s, 2H), 3.715 (s, 3H), 2.519 (m, 4H), 1.918 (m, 4H); MS (ESI): m/z 338 (M+H).

Example 342

Methyl 1-(1-oxo-6-(4-(3-(3-(trifluoromethyl)phenyl) ureido)phenyl)isoindolin-2-yl)cyclopentanecarboxylate The compound of example 342 was prepared analogous to compound of example 330 by reaction of the compound of example 341, compound of example 327 and Pd(dppf)Cl₂: CH₂Cl₂.

¹H NMR (DMSO-d₆, 300 MHz): δ 9.107 (s, 1H), 8.956 (s, 1H), 8.037 (s, 1H), 7.922-7.893 (dd, J=1.8, 8.1 Hz, 1H), 7.838 (s, 1H), 7.700-7.645 (t, J=7.8, 8.7 Hz, 3H), 7.606-7.578 (d, J=8.4 Hz, 3H), 7.552-7.498 (t, J=8.1 Hz, 1H), 7.334-7.309 (d, J=7.5 Hz, 1H), 4.651 (s, 2H), 3.593 (s, 3H), 2.296 (m, 4H), 1.748 (m, 4H); MS (ESI): m/z 536 (M−H), m/z 538 (M+H).

Example 343

1-(1-Oxo-6-(4-(3-(3-(trifluoromethyl)phenyl)ureido) phenyl)isoindolin-2-yl)cyclopentanecarboxylic acid The compound of example 343 was prepared analogous to compound of example 331 by hydrolysis of the compound of example 342.
Yield: 85%; ¹H NMR (DMSO-d₆, 300 MHz): δ 12.573 (s, 1H), 9.110 (s, 1H), 8.958 (s, 1H), 8.037 (s, 1H), 7.918-7.892 (d, J=7.8 Hz, 1H), 7.835 (s, 1H), 7.700-7.672 (d, J=8.4 Hz, 3H), 7.608-7.580 (d, J=8.4 Hz, 3H), 7.553-7.499 (t, J=8.1 Hz, 1H), 7.335-7.311 (d, J=7.2 Hz, 1H), 4.653-4.622 (d, J=9.3 Hz, 2H), 2.299 (s, 4H), 1.751 (s, 4H); MS (ESI): m/z 522.1 (M−H), m/z 524.2 (M+H).

Example 344

(S)-Methyl 2-(6-bromo-1-oxoisoindolin-2-yl)-2-phenylacetate

The compound of example 344 was prepared analogous to compound of example 329 by reaction of the compound of example 328 and 2-phenyl glycine methyl ester hydrochloride.
Yield: 646 mg (91.7%); ¹H NMR (CDCl₃, 300 MHz): δ 8.029-8.024 (d, J=1.5 Hz, 1H), 7.838-7.806 (dd, J=1.5, 8.1 Hz, 1H), 7.432-7.330 (m, 5H), 7.274-7.246 (d, J=8.4 Hz, 1H), 5.305 (s, 1H), 4.782-4.725 (d, J=17.1 Hz, 1H), 3.940-3.883 (d, J=17.1 Hz, 1H), 3.820 (s, 3H); MS (ESI): m/z 360 (M+H).

Example 345

(S)-Methyl 2-(1-oxo-6-(4-(3-(3-(trifluoromethyl) phenyl)ureido)phenyl)isoindolin-2-yl)-2-phenylacetate The compound of example 345 was prepared analogous to compound of example 330 by reaction of the compound of example 344, compound of example 327 and Pd(dppf)Cl₂: CH₂Cl₂.
¹H NMR (DMSO-d₆, 300 MHz): δ 9.110 (s, 1H), 8.958 (s, 1H), 8.092 (m, 2H), 7.933-7.886 (m, 1H), 7.761-7.395 (m, 12H), 7.337-7.311 (d, J=6 Hz, 1H), 5.458 (s, 1H), 4.660-4.602 (d, J=17.4 Hz, 1H), 4.027-3.969 (d, J=17.4 Hz, 1H), 3.752 (s, 3H); MS (ESI): m/z 558 (M−H), m/z 560 (M+H).

Example 346

(S)-2-(1-Oxo-6-(4-(3-(3-(trifluoromethyl)phenyl) ureido)phenyl)isoindolin-2-yl)-2-phenylacetic acid The compound of example 346 was prepared analogous to compound of example 331 by hydrolysis of the compound of example 345.
Yield: 82%; ¹H NMR (DMSO-d₆, 300 MHz): δ 10.200 (s, 1H), 9.902 (s, NH), 8.088 (s, 1H), 7.879 (s, 1H), 7.831-7.805 (d, J=7.8, 1H), 7.688-7.660 (d, J=8.4 Hz, 2H), 7.613-7.587 (d, J=7.8 Hz, 2H), 7.546-7.348 (m, 10H), 7.289-7.263 (d, J=7.8 Hz, 1H), 5.930 (s, 1H), 4.888-4.807 (d, J=17.7 Hz, 1H), 3.967-3.908 (d, J=17.7 Hz, 1H); MS (ESI): m/z 544.1 (M−H), m/z 546.2 (M+H).

Example 347

Methyl 4-(6-bromo-1-oxoisoindolin-2-yl)butanoate

The compound of example 347 was prepared analogous to compound of example 329 by reaction of the compound of example 328 and methyl 4-aminobutanoate hydrochloride.
Yield: 255 mg (41.8%); ¹H NMR (CDCl₃, 300 MHz): δ 7.984 (s, 1H), 7.677-7.651 (dd, J=7.8 Hz, 1H), 7.358-7.332 (d, J=7.8 Hz, 1H), 4.372 (s, 2H), 3.699-3.637 (m, 2H) 3.652 (s, 3H), 2.440-2.392 (t, J=7.2 Hz, 2H), 2.073-1.979 (m, 2H); MS (ESI): m/z 312 (M+H).

Example 348

Methyl 4-(1-oxo-6-(4-(3-(3-(trifluoromethyl)phenyl) ureido)phenyl)isoindolin-2-yl)butanoate The compound of example 348 was prepared analogous to compound of example 330 by reaction of the compound of example 347, compound of example 327 and Pd(dppf)Cl₂: CH₂Cl₂.
¹H NMR (DMSO-d₆, 300 MHz): δ 9.101 (s, 1H), 8.950 (s, 1H), 8.039 (s, 1H), 7.890-7.865 (d, J=7.5 Hz, 2H), 7.707-7.578 (m, 6H), 7.551-7.498 (t, J=7.8, 8.1 Hz, 1H), 7.335-7.311 (d, J=7.2 Hz, 1H), 4.501 (s, 2H), 3.588-3.565 (m, 2H), 3.544 (s, 3H), 2.383-2.335 (t, J=7.2 Hz, 2H), 1.912-1.865 (m, 2H); MS (ESI): m/z 510 (M−H), m/z 512 (M+H).

Example 349

4-(1-Oxo-6-(4-(3-(3-(trifluoromethyl)phenyl)ureido) phenyl)isoindolin-2-yl)butanoic acid The compound of example 349 was prepared analogous to compound of example 331 by hydrolysis of the compound of example 348.
Yield: 82%; ¹H NMR (DMSO-d₆, 300 MHz): δ 12.091 (s, 1H), 9.119 (s, 1H), 8.964 (s, 1H), 8.039 (s, 1H), 7.886-7.864 (d, J=6.6 Hz, 2H), 7.706-7.580 (m, 6H), 7.551-7.499 (t, J=7.8 Hz, 1H), 7.334-7.309 (d, J=7.5 Hz, 1H), 4.510 (s, 2H), 3.588-3.542 (t, J=6.9 Hz, 2H), 2.292-2.244 (t, J=7.2 Hz, 2H), 1.903-1.813 (m, 2H); MS (ESI): m/z 496.1 (M−H), m/z 498.2 (M+H).

Example 350

(S)-Methyl 2-(6-bromo-1-oxoisoindolin-2-yl)-4-methylpentanoate

The compound of example 350 was prepared analogous to compound of example 329 by reaction of the compound of example 328 and methyl 2-amino-3-methylbutanoate hydrochloride.
Yield: 450 mg (67.7%); ¹H NMR (CDCl₃, 300 MHz): δ 8.017 (s, 1H), 7.70-7.677 (dd, J=1.5, 8.1 Hz, 1H), 7.381-7.355 (d, J=7.8 Hz, 1H), 5.229-5.176 (t, J=7.8, 8.1 Hz, 1H), 4.689-4.307 (dd, J=16.8 Hz, 2H), 3.767 (s, 3H), 1.892-1.841

Example 351

(S)-Methyl 4-methyl-2-(1-oxo-6-(4-(3-(3-(trifluoromethyl)phenyl)ureido)phenyl)isoindolin-2-yl)-pentanoate The compound of example 348 was prepared analogous to compound of example 330 by reaction of the compound of example 347, compound of example 327 and Pd(dppf)Cl$_2$: CH$_2$Cl$_2$.
$^1$H NMR (DMSO-d$_6$, 300 MHz): δ 9.101 (s, 1H), 8.953 (s, 1H), 8.038 (s, 1H), 7.937-7.911 (d, J=7.8 Hz, 2H), 7.715-7.686 (m, 3H), 7.612-7.583 (m, 3H), 7.553-7.500 (t, J=7.8 Hz, 1H), 7.336-7.312 (d, J=7.2 Hz, 1H), 5.027-4.9743 (dd, J=4.2, 11.4 Hz, 1H), 4.531 (s, 2H), 3.671 (s, 3H), 2.087-1.908 (m, 1H), 1.806-1.727 (m, 1H), 1.443-1.412 (m, 1H), 0.939 (s, 6H); MS (ESI): m/z 538 (M−H), m/z 540 (M+H).

Example 352

(S)-4-Methyl-2-(1-oxo-6-(4-(3-(3-(trifluoromethyl)phenyl)ureido)phenyl)iso indolin-2-yl)pentanoic acid The compound of example 352 was prepared analogous to compound of example 331 by hydrolysis of the compound of example 351.
Yield: 75%; $^1$H NMR (DMSO-d$_6$, 300 MHz): δ 13.032 (s, 1H), 9.130 (s, 1H), 8.978 (s, 1H), 8.039 (s, 1H), 7.926-7.902 (d, J=7.2 Hz, 2H), 7.712-7.684 (t, J=8.4 Hz, 3H), 7.612-7.584 (d, J=8.4 Hz, 3H), 7.551-7.498 (d, J=7.8, 8.1 Hz, 1H), 7.334-7.309 (d, J=7.5 Hz, 1H), 4.923-4.872 (dd, J=3.9, 11.1 Hz, 1H), 4.615-4.451 (dd, J=13.82, 17.7 Hz, 2H), 1.971-1.888 (m, 1H), 1.806-1.726 (m, 1H), 1.461-1.432 (m, 1H), 0.939-0.901 (t, J=5.7 Hz, 6H); MS (ESI): m/z 524.7 (M−H), m/z 526.2 (M+H).

Example 353

(S)-Methyl 2-(6-bromo-1-oxoisoindolin-2-yl)-3-methoxypropanoate

The compound of example 353 was prepared analogous to compound of example 329 by reaction of the compound of example 328 and methyl 2-amino-3-methylbutanoate hydrochloride.
Yield: 65%; $^1$H NMR (CDCl$_3$, 300 MHz): δ 7.994-7.989 (d, J=1.5 Hz, 1H), 7.680-7.647 (dd, J=1.8, 8.1 Hz, 1H), 7.354-7.327 (d, J=8.1 Hz, 1H), 5.309-5.279 (m, 1H), 4.740-4.682 (d, J=17.4 Hz, 1H), 4.534-4.476 (d, J=17.4 Hz, 1H), 4.079-4.025 (dd, J=4.2, 6 Hz, 1H), 3.786-3.775 (d, J=3 Hz, 1H), 3.370 (s, 3H), 3.395 (s, 3H); MS (ESI): m/z 350 (M+Na).

Example 354

(S)-Methyl 3-methoxy-2-(1-oxo-6-(4-(3-(3-(trifluoromethyl)phenyl)ureido)phenyl)isoindolin-2-yl)propanoate The compound of example 354 was prepared analogous to compound of example 330 by reaction of the compound of example 353, compound of example 327 and Pd(dppf)Cl$_2$: CH$_2$Cl$_2$.
$^1$H NMR (DMSO-d$_6$, 300 MHz): δ 9.105 (s, 1H), 8.962 (s, 1H), 8.040 (s, 1H), 7.943-7.918 (d, J=7.5 Hz, 2H), 7.721-7.692 (d, J=8.7 Hz, 3H), 7.613-7.548 (d, J=8.7 Hz, 3H), 7.553-7.500 (t, J=7.8 Hz, 1H), 7.337-7.313 (d, J=7.2 Hz, 1H), 5.190-5.156 (dd, J=3.3, 3.6 Hz, 1H), 4.593 (s, 2H), 4.032-3.974 (dd, J=3.3, 7.2 Hz, 1H), 3.848-3.802 (dd, J=3.3, 7.2 Hz, 1H), 3.689 (s, 3H), 3.313 (s, 3H); MS (ESI): m/z 528 (M+H).

Example 355

(S)-3-Methoxy-2-(1-oxo-6-(4-(3-(3-(trifluoromethyl)phenyl)ureidophenyl)iso indolin-2-yl)propanoic acid The compound of example 355 was prepared analogous to compound of example 331 by hydrolysis of the compound of example 354.
Yield: 82%; $^1$H NMR (DMSO-d$_6$, 300 MHz): δ 13.197 (s, 1H), 9.116 (s, 1H), 9.089 (s, 1H), 8.040 (s, 1H), 7.934-7.911 (d, J=6.9 Hz, 2H), 7.715-7.691 (d, J=7.2 Hz, 3H), 7.614-7.585 (d, J=8.7 Hz, 3H), 7.553-7.501 (t, J=7.8 Hz, 1H), 7.336-7.312 (d, J=7.2 Hz, 1H), 5.076-5.042 (m, 1H), 4.663-4.525 (dd, J=17.7, 7.2 Hz, 2H), 4.031-3.971 (dd, J=7.5, 3 Hz, 1H), 3.830-3.785 (dd, J=6.6, 3.6 Hz, 1H), 3.429 (s, 3H); MS (ESI): m/z 512.1 (M−H), m/z 514.2 (M+H).

Example 356

1-(4-Bromophenyl)-3-(3-(trifluoromethyl)phenyl)urea 4-bromoaniline (12 g, 0.0697 mol) was taken in 120 mL THF to which 3-trifluorophenyl isocyanate (14.36 g, 0.0767 mol) was added and stirred at room temperature for 8-10 h. The reaction mixture was concentrated and purified by column chromatography (silica gel, 30-40% ethyl acetate in petroleum ether) to obtain the title compound.
Yield: 21.66 g (96%); $^1$H NMR (DMSO-d$_6$, 300 MHz): δ 9.078 (s, 1H), 8.939 (s, 1H), 8.002 (s, 1H), 7.592-7.564 (d, J=8.4 Hz, 1H), 7.539-7.513 (d, J=7.8 Hz, 1H), 7.487-7.426 (m, 4H), 7.330-7.306 (d, J=7.2 Hz, 1H); MS (ESI): m/z 357.7 (M−H), m/z 359 (M+H).

Example 357

1-(4-(4,4,5,5-Tetramethyl-1,3,2-dioxaborolan-2-yl)phenyl)-3-(3-(trifluoro methyl)phenyl)urea The compound of example 356 (21 g, 0.0584 mol), bis(pinacolato)diborane, Pd(dppf)Cl$_2$:CH$_2$Cl$_2$ and potassium acetate were taken in dry DMF and heated at 85-90° C. under argon atmosphere. After completion of the reaction (8-10 h), DMF was evaporated and the residue obtained was dissolved in dichloromethane and filtered through celite. The filtrate was concentrated and purified by column chromatography (silica gel, 10% ethyl acetate in CHCl$_3$) to obtain the title compound.
$^1$H NMR (DMSO-d$_6$, 300 MHz): δ 9.085 (s, 1H), 8.959 (s, 1H), 8.030 (s, 1H), 7.615-7.587 (d, J=8.4 Hz, 2H), 7.557-7.541 (d, J=4.8 Hz, 1H), 7.515-7.465 (m, 3H), 7.333-7.309 (d, J=7.2 Hz, 1H), 1.283 (s, 12H); MS (ESI): m/z 406 (M+H), m/z 407 (M+H).

Example 358

Methyl 4-bromo-2-(bromomethyl)benzoate

Methyl 4-bromo-2-methylbenzoate (9.6 g, 0.42 mol) was dissolved in carbon tetrachloride (150 mL). Benzoyl peroxide (250 mg) and NBS (7.6 g, 0.42 mol) were added and the (t, J=7.2 Hz, 2H), 1.533-1.433 (m, 1H), 1.006-0.967 (t, J=6.3 Hz, 6H); MS (ESI): m/z 340 (M+H).

reaction mixture was refluxed at 80° C. After completion of the reaction, the reaction mixture was cooled to room temperature and filtered through celite. The filtrate was concentrated to obtain a crude material containing 85% mono bromo and 10% dibromo product. The crude product obtained was used directly, without purification for preparation of compound of example 359.

Example 359

(R)-Methyl 2-(5-bromo-1-oxoisoindolin-2-yl)-3-methylbutanoate

Methyl 4-bromo-2-(bromomethyl)benzoate (650 mg, 2.12 mmol) and D-valine methyl ester hydrochloride (527 mg, 3.15 mmol) was taken in toluene (6.5 mL) and to this reaction mixture, triethyl amine (428 mg, 4.24 mmol) was added and refluxed for about 16 h. After completion of the reaction, the reaction mixture was diluted with ethyl acetate and washed with water and brine, dried over anhydrous sodium sulfate and concentrated to obtain an oil, which was purified by column chromatography (silica gel, 30% ethyl acetate in petroleum ether) to obtain the title compound.

Yield: 440 mg (63.7%); $^1$H NMR (CDCl$_3$, 300 MHz): δ 7.762-7.735 (d, J=8.1 Hz, 1H), 7.649-7.614 (m, 2H), 4.823-4.789 (d, J=10.2 Hz, 1H), 4.773-4.715 (d, J=17.4 Hz, 1H), 4.440-4.383 (d, J=17.1 Hz, 1H), 3.743 (s, 3H), 2.399-2.276 (m, 1H), 1.079-1.057 (d, J=6.6 Hz, 3H), 0.940-0.918 (d, J=6.6 Hz, 3H); MS (ESI): m/z 326 (M+H).

Example 360

(R)-Methyl 3-methyl-2-(1-oxo-5-(4-(3-(3-(trifluoromethyl)phenyl)ureido)phenyl)isoindolin-2-yl)butanoate The compound of example 359 (288 mg, 0.886 mmol), compound of example 357 (300 mg, 0.738 mmol) and Pd(dppf)Cl$_2$: CH$_2$Cl$_2$ (18 mg, 0.022 mmol) were taken in DMF (5 mL) under an argon atmosphere. To this reaction mixture, 2M solution of Na$_2$CO$_3$ (234 mg, 2.214 mmol, 1.1 mL) was added and the reaction mixture was stirred at 80-85° C. for 1 to 1.5 h. After completion of the reaction, water was added to the reaction mixture and the product obtained was extracted with ether. The combined ether layers were washed with water and brine, dried over anhydrous Na$_2$SO$_4$ or MgSO$_4$. The solvent was evaporated and the product was purified by column chromatography (silica gel, 30% ethyl acetate in petroleum ether) to obtain the title compound.

Yield: 300 mg (77%); $^1$H NMR (DMSO-d$_6$, 300 MHz): δ 9.117 (s, 1H), 8.983 (s, 1H), 8.046 (s, 1H), 7.896 (s, 1H), 7.803-7.745 (t, J=8.4, 9 Hz, 2H), 7.717-7.688 (d, J=8.7 Hz, 2H), 7.633-7.589 (m, 3H), 7.559-7.505 (t, J=8.1 Hz, 1H), 7.343-7.319 (d, J=7.2 Hz, 1H), 4.628-4.533 (m, 3H), 3.688 (s, 3H), 2.371-2.293 (m, 1H), 1.015-0.993 (d, J=6.6 Hz, 3H), 0.867-0.845 (d, J=6.6 Hz, 3H); MS (ESI): m/z 524.1 (M−H), m/z 526 (M+H).

Example 361

(R)-3-Methyl-2-(1-oxo-5-(4-(3-(3-(trifluoromethyl)phenyl)ureido)phenyl)isoindolin-2-yl)butanoic acid The compound of example 360 (150 mg, 0.293 mmol) was taken in THF (4 mL) and MeOH (1 mL) and to this reaction mixture, 1 N LiOH (61.58 mg, 1.46 mmol) was added and stirred at room temperature for 2-3 h. After completion of the reaction, the solvent was evaporated and the residue obtained was dissolved in water and acidified with 1 N HCl to obtain the title compound, which was filtered and dried.

Yield: 135 mg (85%); $^1$H NMR (DMSO-d$_6$, 300 MHz): δ 13.018 (s, 1H), 9.117 (s, 1H), 8.968 (s, 1H), 8.039 (s, 1H), 7.927-7.905 (d, J=6.6 Hz, 2H), 7.709-7.682 (d, J=8.1 Hz, 3H), 7.610-7.582 (d, J=8.4 Hz, 3H), 7.551-7.498 (t, J=7.8, 8.1 Hz, 1H), 7.334-7.310 (d, J=7.2 Hz, 1H), 4.705-4.529 (dd, J=17.7, 18.6 Hz, 2H), 4.561-4.529 (d, J=9.6 Hz, 1H), 2.324-2.271 (m, 1H), 1.046-1.024 (d, J=6.6 Hz, 3H), 0.878-0.857 (d, J=6.6 Hz, 3H); MS (ESI): m/z 509.7 (M−H).

Example 362

Methyl 2-(5-bromo-1-oxoisoindolin-2-yl)acetate

The compound of example 362 was prepared analogous to compound of example 359 by reaction of the compound of example 358 and glycine methyl ester hydrochloride.

Yield: 360 mg (65.0%); $^1$H NMR (CDCl$_3$, 300 MHz): δ 7.768-7.739 (d, J=9 Hz, 1H), 7.650-7.624 (m, 2H), 4.527 (s, 2H), 4.417 (s, 2H), 3.783 (s, 3H); MS (ESI): m/z 284 (M+H).

Example 363

Methyl 2-(1-oxo-5-(4-(3-(3-(trifluoromethyl)phenyl)ureido)phenyl)isoindolin-2-yl)acetate The compound of example 363 was prepared analogous to compound of example 360 by reaction of the compound of example 362, compound of example 357 and Pd(dppf)Cl$_2$: CH$_2$Cl$_2$.

$^1$H NMR (DMSO-d$_6$, 300 MHz): δ 9.113 (s, 1H), 8.981 (s, 1H), 8.041 (s, 1H), 7.899 (s, 1H), 7.806-7.740 (m, 2H), 7.730-7.701 (d, J=8.7 Hz, 2H), 7.627-7.588 (m, 3H), 7.553-7.501 (t, J=7.5, 8.1 Hz, 1H), 7.340-7.315 (d, J=7.5 Hz, 1H), 4.579 (s, 2H), 4.418 (s, 2H), 3.694 (s, 3H); MS (ESI): m/z 482.1 (M−H), m/z 484 (M+H).

Example 364

2-(1-Oxo-5-(4-(3-(3-(trifluoromethyl)phenyl)ureido)phenyl)isoindolin-2-yl)acetic acid The compound of example 364 was prepared analogous to the compound of example 361 by hydrolysis of the compound of example 363.

$^1$H NMR (DMSO-d$_6$, 300 MHz): δ 11.316 (s, 1H), 11.245 (s, 1H), 8.161 (s, 1H), 7.867-7.840 (d, J=8.1 Hz, 1H), 7.790 (s, 1H), 7.748-7.702 (d, J=7.8, 6 Hz, 3H), 7.540-7.511 (d, J=8.7 Hz, 2H), 7.467-7.439 (d, J=8.4 Hz, 2H), 7.259-7.233 (d, J=7.8 Hz, 1H), 4.647 (s, 2H), 4.058 (s, 2H); MS (ESI): m/z 468 (M−H), m/z 470 (M+H).

Example 365

(S)-Methyl 2-(5-bromo-1-oxoisoindolin-2-yl)propanoate

The compound of example 365 was prepared analogous to compound of example 359 by reaction of the compound of example 358 and alanine methyl ester hydrochloride.

Yield: 380 mg (65.29%); $^1$H NMR (CDCl$_3$, 300 MHz): δ 7.761-7.734 (d, J=8.1 Hz, 1H), 7.651-7.614 (m, 2H), 5.214-5.167 (q, J=7.2, 7.5 Hz, 1H), 4.629-4.573 (d, J=16.8 Hz, 1H), 4.442-4.386 (d, J=16.8 Hz, 1H), 3.748 (s, 3H), 1.633-1.612 (d, J=6.3 Hz, 3H); MS (ESI): m/z 298 (M+H).

Example 366

(S)-Methyl 2-(1-oxo-5-(4-(3-(3-(trifluoromethyl)phenyl)ureido)phenyl)isoindolin-2-yl)propanoate The compound of example 366 was prepared analogous to compound of example 360 by reaction of the compound of example 365, compound of example 357 and Pd(dppf)Cl$_2$:CH$_2$Cl$_2$.

$^1$H NMR (DMSO-d$_6$, 300 MHz): δ 9.108 (s, 1H), 8.979 (s, 1H), 8.040 (s, 1H), 7.883 (s, 1H), 7.773-7.735 (m, 2H), 7.721-7.692 (d, J=8.7 Hz, 2H), 7.629-7.586 (m, 3H), 7.554-7.502 (t, J=7.8 Hz, 1H), 7.340-7.315 (d, J=7.5 Hz, 1H), 4.970-4.946 (q, J=7.2 Hz, 1H), 4.677-4.988 (dd, J=7.5, 12 Hz, 2H), 3.667 (s, 3H), 1.548-1.523 (d, J=7.5 Hz, 3H); MS (ESI): m/z 496.1 (M−H), m/z 498 (M+H).

Example 367

(S)-2-(1-Oxo-5-(4-(3-(3-(trifluoromethyl)phenyl)ureido)phenyl)isoindolin-2-yl)propanoic acid The compound of example 367 was prepared analogous to the compound of example 361 by hydrolysis of the compound of example 366.

Yield: 82%; $^1$H NMR (DMSO-d$_6$, 300 MHz): δ 12.947 (s, 1H), 9.169 (s, 1H), 9.036 (s, 1H), 8.042 (s, 1H), 7.878 (s, 1H), 7.766-7.599 (m, 7H), 7.551-7.525 (d, J=7.8 Hz, 1H), 7.337-7.312 (d, J=7.5 Hz, 1H), 4.867-4.842 (d, J=7.5 Hz, 1H), 4.566 (s, 2H), 1.536-1.512 (d, J=7.2 Hz, 3H); MS (ESI) m/z 482.1 (M−H), m/z 484.2 (M+H).

Example 368

Methyl 1-(5-bromo-1-oxoisoindolin-2-yl)cyclopentanecarboxylate

The compound of example 368 was prepared analogous to compound of example 359 by reaction of the compound of example 358 and methyl 1-aminocyclopentanecarboxylate hydrochloride.

Yield: 160 mg (24.20%); $^1$H NMR (CDCl$_3$, 300 MHz): δ 7.712-7.685 (d, J=8.1 Hz, 1H), 7.625-7.598 (m, 2H), 4.521 (s, 2H), 3.714 (s, 3H), 2.524-2.430 (m, 2H), 2.387-2.300 (m, 2H), 1.960-1.882 (m, 2H), 1.848-1.728 (m, 2H); MS (ESI): m/z 338 (M+H).

Example 369

Methyl 1-(1-oxo-5-(4-(3-(3-(trifluoromethyl)phenyl)ureido)phenyl)isoindolin-2-yl)cyclopentanecarboxylate The compound of example 369 was prepared analogous to compound of example 360 by reaction of the compound of example 368, compound of example 357 and Pd(dppf)Cl$_2$:CH$_2$Cl$_2$.

$^1$H NMR (DMSO-d$_6$, 300 MHz): δ 9.119 (s, 1H), 8.987 (s, 1H), 8.042 (s, 1H), 7.841 (s, 1H), 7.777-7.750 (d, J=8.1 Hz, 1H), 7.704-7.680 (d, J=7.2 Hz, 3H), 7.629-7.586 (m, 3H), 7.554-7.502 (t, J=7.5, 8.1 Hz, 1H), 7.340-7.314 (d, J=7.8 Hz, 1H), 4.662 (s, 2H), 3.593 (s, 3H), 2.296 (m, 4H), 1.749 (m, 4H); MS (ESI): m/z 538 (M+H).

Example 370

1-(1-Oxo-5-(4-(3-(3-(trifluoromethyl)phenyl)ureido)phenyl)isoindolin-2-yl)cyclopentanecarboxylic acid The compound of example 370 was prepared analogous to the compound of example 361 by hydrolysis of the compound of example 369.

Yield: 83%; $^1$H NMR (DMSO-d$_6$, 300 MHz): δ 12.520 (s, 1H), 9.227 (s, 1H), 9.081 (s, 1H), 8.036 (s, 1H), 7.831 (s, 1H), 7.772-7.745 (d, J=8.1 Hz, 1H), 7.700-7.676 (d, J=7.2 Hz, 3H), 7.625-7.596 (d, J=8.7 Hz, 3H), 7.550-7.525 (t, J=7.2 Hz, 1H), 7.336-7.310 (d, J=8.7 Hz, 1H), 4.632 (s, 2H), 2.310 (s, 4H), 1.733 (s, 4H); MS (ESI) m/z 522.1 (M−H), m/z 524.2 (M+H).

Example 371

(S)-Methyl 2-(5-bromo-1-oxoisoindolin-2-yl)-2-phenylacetate

The compound of example 368 was prepared analogous to compound of example 359 by reaction of the compound of example 358 and 2-phenyl glycine methyl ester hydrochloride.

Yield: 580 mg (82.38%); $^1$H NMR (CDCl$_3$, 300 MHz): δ 7.771-7.745 (d, J=7.8 Hz, 1H), 7.624-7.593 (d, J=9.3 Hz, 1H), 7.542 (s, 1H), 7.463-7.327 (m, 5H), 6.333 (s, 1H), 4.811-4.754 (d, J=17.1 Hz, 1H), 3.966-3.909 (d, J=17.1 Hz, 1H), 3.822 (s, 3H); MS (ESI): m/z 360 (M+H).

Example 372

(S)-Methyl 2-(1-oxo-5-(4-(3-(3-(trifluoromethyl)phenyl)ureido)phenyl)isoindolin-2-yl)-2-phenylacetate The compound of example 372 was prepared analogous to compound of example 360 by reaction of the compound of example 371, compound of example 357 and Pd(dppf)Cl$_2$:CH$_2$Cl$_2$.

$^1$H NMR (DMSO-d$_6$, 300 MHz): δ 9.111 (s, 1H), 8.974 (s, 1H), 8.033 (s, 1H), 7.823 (s, 1H), 7.784 (s, 2H), 7.678-7.649 (d, J=8.7 Hz, 2H), 7.609-7.580 (d, J=8.7 Hz, 3H), 7.548-7.391 (m, 6H), 7.335-7.309 (d, J=7.8 Hz, 1H), 6.110 (s, 1H), 4.680-4.622 (d, J=17.4 Hz, 1H), 4.042-3.983 (d, J=17.7 Hz, 1H), 3.755 (s, 3H); MS (ESI): m/z 560 (M+H).

Example 373

(S)-2-(1-Oxo-5-(4-(3-(3-(trifluoromethyl)phenyl)ureido)phenyl)isoindolin-2-yl)-2-phenylacetic acid The compound of example 373 was prepared analogous to the compound of example 361 by hydrolysis of the compound of example 372.

Yield: 92%; $^1$H NMR (DMSO-d$_6$, 300 MHz): δ 13.148 (s, 1H), 9.201 (s, 1H), 9.054 (s, 1H), 8.029 (s, 1H), 7.812 (s, 1H), 7.777 (s, 1H), 7.674-7.644 (d, J=9 Hz, 4H), 7.606-7.577 (d, J=8.7 Hz, 2H), 7.546-7.403 (m, 5H), 7.331-7.306 (d, J=7.5 Hz, 1H), 6.011 (s, 1H), 4.717-4.659 (d, J=17.4 Hz, 1H), 3.998-3.940 (d, J=17.4 Hz, 1H); MS (ESI): m/z 544.1 (M−H), m/z 546.2 (M+H).

Example 374

Methyl 4-(5-bromo-1-oxoisoindolin-2-yl)butanoate

The compound of example 374 was prepared analogous to compound of example 359 by reaction of the compound of example 358 and methyl 4-aminobutanoate hydrochloride.

Yield: 335 mg (54.9%); $^1$H NMR (CDCl$_3$, 300 MHz): δ 7.731-7.703 (d, J=8.4 Hz, 1H), 7.631-7.605 (m, 2H), 4.396 (s, 2H), 3.692-3.668 (d, J=7.2 Hz, 2H), 3.634 (s, 3H), 2.441-2.393 (t, J=7.2 Hz, 2H), 2.071-2.001 (m, 2H): m/z 312 (M+H).

Example 375

Methyl 4-(1-oxo-5-(4-(3-(3-(trifluoromethyl)phenyl)ureido)phenyl)isoindolin-2-yl)butanoate The compound of example 375 was prepared analogous to compound of example 360 by reaction of the compound of example 374, compound of example 357 and Pd(dppf)Cl$_2$:CH$_2$Cl$_2$.

$^1$H NMR (DMSO-d$_6$, 300 MHz): δ 9.112 (s, 1H), 8.975 (s, 1H), 8.041 (s, 1H), 7.854 (s, 1H), 7.771-7.685 (m, 2H), 7.621-7.591 (d, J=7.2 Hz, 2H), 7.553-7.5 (m, 3H), 7.553-7.501 (t, J=7.8 Hz, 1H), 7.339-7.314 (d, J=7.5 Hz, 1H), 4.513 (s, 2H), 3.578 (m, 2H), 3.544 (s, 3H), 2.379 (t, J=7.2 Hz, 2H), 1.931-1.840 (m, 2H); MS (ESI): m/z 512 (M+H).

Example 376

4-(1-Oxo-5-(4-(3-(3-(trifluoromethyl)phenyl)ureido)phenyl)isoindolin-2-yl)butanoic acid The compound of example 376 was prepared analogous to the compound of example 361 by hydrolysis of the compound of example 375.

Yield: 89%; $^1$H NMR (DMSO-d$_6$, 300 MHz): δ 12.117 (s, 1H), 9.121 (s, 1H), 8.983 (s, 1H), 8.040 (s, 1H), 7.852 (s, 1H), 7.769-7.683 (m, 4H), 7.620-7.591 (d, J=8.7 Hz, 3H), 7.552-7.500 (t, J=8.1, 7.5 Hz, 1H), 7.338-7.313 (d, J=7.5 Hz, 1H), 4.522 (s, 2H), 3.576-3.531 (t, J=6.6, 6.9 Hz, 2H), 2.287-2.239 (t, J=7.2 Hz, 2H), 1.898-1.830 (m, 2H); MS (ESI): m/z 496.1 (M−H).

Example 377

Ethyl 3-(5-bromo-1-oxoisoindolin-2-yl)propanoate

The compound of example 377 was prepared analogous to compound of example 359 by reaction of the compound of example 358 and ethyl 3-aminopropanoate hydrochloride.

Yield: 280 mg (45.90%); $^1$H NMR (CDCl$_3$, 300 MHz): δ 7.729-7.700 (d, J=8.7 Hz, 1H), 7.620-7.599 (m, 2H), 4.471 (s, 2H), 4.197-4.125 (q, J=7.2 Hz, 2H), 3.924-3.881 (t, J=6.3, 6.6 Hz, 2H), 2.765-2.722 (t, J=6.3, 6.6 Hz, 2H), 1.284-1.260 (t, J=7.2 Hz, 3H); MS (ESI): m/z 312 (M+H).

Example 378

Ethyl 3-(1-oxo-5-(4-(3-(3-(trifluoromethyl)phenyl)ureido)phenyl)isoindolin-2-yl)propanoate The compound of example 378 was prepared analogous to compound of example 360 by reaction of the compound of example 377, compound of example 357 and Pd(dppf)Cl$_2$:CH$_2$Cl$_2$.

$^1$H NMR (DMSO-d$_6$, 300 MHz): δ 9.095 (s, 1H), 8.995 (s, 1H), 8.036 (s, 1H), 7.863 (s, 1H), 7.771-7.686 (m, 4H), 7.619-7.590 (d, J=8.7 Hz, 3H), 7.553-7.501 (t, J=7.5, 8.1 Hz, 1H), 7.337-7.313 (d, J=7.2 Hz, 1H), 4.540 (s, 2H), 4.109-4.038 (q, J=6.9, 7.2 Hz, 2H), 3.805-3.760 (t, J=6.6, 6.9 Hz, 2H), 2.720-2.674 (t, J=6.9 Hz, 2H), 1.189-1.142 (t, J=6.9, 7.2 Hz, 3H); MS (ESI): m/z 496 (M−H).

Example 379

3-(1-Oxo-5-(4-(3-(3-(trifluoromethyl)phenyl)ureido)phenyl)isoindolin-2-yl)propanoic acid The compound of example 379 was prepared analogous to the compound of example 361 by hydrolysis of the compound of example 378.

Yield: 95%; $^1$H NMR (DMSO-d$_6$, 300 MHz): δ 12.351 (s, 1H), 9.456 (s, 1H), 9.298 (s, 1H), 8.050 (s, 1H), 7.848 (s, 1H), 7.766-7.670 (m, 4H), 7.622-7.595 (d, J=8.1 Hz, 3H), 7.542-7.490 (t, J=7.8 Hz, 1H), 7.324-7.299 (d, J=7.5 Hz, 1H), 4.561 (s, 2H), 3.775-3.730 (t, J=6.6, 6.9 Hz, 2H), 2.631-2.586 (t, J=6.6, 6.9 Hz, 2H); MS (ESI): m/z 482.1 (M−H), m/z 484.2 (M+H).

Example 380

(S)-Methyl 2-(5-bromo-1-oxoisoindolin-2-yl)-3-phenylpropanoate

The compound of example 380 was prepared analogous to compound of example 359 by reaction of the compound of example 358 and 2-phenyl glycine methyl ester hydrochloride.

Yield: 500 mg (68.39%); $^1$H NMR (CDCl$_3$, 300 MHz): δ 7.697-7.668 (d, J=8.7 Hz, 1H), 7.592-7.571 (m, 2H), 7.292-7.175 (m, 6H), 5.429-5.318 (m, 1H), 4.562-4.506 (d, J=16.8 Hz, 1H), 4.331-4.275 (d, J=16.8 Hz, 1H), 3.750 (s, 3H), 3.553-3.485 (dd, J=5.7, 5.4 Hz, 1H), 3.231-3.147 (dd, J=10.5, 1H); MS (ESI): m/z 374 (M+H).

Example 381

(S)-Methyl 2-(1-oxo-5-(4-(3-(3-(trifluoromethyl)phenyl)ureido)phenyl)isoindolin-2-yl)-3-phenylpropanoate The compound of example 381 was prepared analogous to compound of example 360 by reaction of the compound of example 379, compound of example 357 and Pd(dppf)Cl$_2$:CH$_2$Cl$_2$.

$^1$H NMR (DMSO-d$_6$, 300 MHz): δ 9.115 (s, 1H), 8.977 (s, 1H), 8.039 (s, 1H), 7.822 (s, 1H), 7.748-7.664 (m, 4H), 7.613-7.584 (d, J=8.7 Hz, 3H), 7.552-7.500 (t, J=7.81 Hz, 1H), 7.338-7.313 (d, J=7.5 Hz, 1H) 7.263-7.215 (m, 3H), 7.188-7.139 (m, 2H), 5.273-5.220 (dd, J=4.8, 5.7 Hz, 2H), 4.569-4.394 (dd, J=17.7, 17.4 Hz, 2H), 3.687 (s, 3H), 3.299 (m, 1H), MS (ESI): m/z 572 (M−H).

Example 382

(S)-2-(1-Oxo-5-(4-(3-(3-(trifluoromethyl)phenyl)ureido)phenyl)isoindolin-2-yl)-3-phenylpropanoic acid The compound of example 382 was prepared analogous to the compound of example 361 by hydrolysis of the compound of example 381.

Yield: 87%; ¹H NMR (DMSO-d₆, 300 MHz): δ 13.002 (s, 1H), 9.145 (s, 1H), 9.003 (s, 1H), 8.038 (s, 1H), 7.741-7.660 (m, 5H), 7.610-7.581 (d, J=8.7 Hz, 3H), 7.549-7.497 (t, J=7.5, 8.1 Hz, 1H), 7.335-7.129 (m, 6H), 5.189-5.137 (dd, J=4.5, 6.6 Hz, 1H), 4.494 (s, 2H), 3.280-3.192 (m, 2H); MS (ESI): m/z 558.1 (M−H), m/z 560.2 (M+H).

Example 383

(S)-Methyl 2-(5-bromo-1-oxoisoindolin-2-yl)-3-methoxypropanoate

The compound of example 383 was prepared analogous to compound of example 359 by reaction of the compound of example 358 and methyl 2-amino-3-methoxypropanoate hydrochloride.

Yield: 340 mg (53%); ¹H NMR (CDCl₃, 300 MHz): δ 7.764-7.737 (d, J=8.1 Hz, 1H), 7.648-7.610 (m, 2H), 5.333-5.303 (m, 1H), 4.795-4737 (d, J=17.4 Hz, 1H), 4.585-4.527 (d, J=17.4 Hz, 1H), 4.103-4.049 (dd, J=4.2, 6 Hz, 1H), 3.808-3.763 (m, 1H), 3.777 (s, 3H), 3.395 (s, 3H); MS (ESI): m/z 326 (M−H).

Example 384

(S)-Methyl 3-methoxy-2-(1-oxo-5-(4-(3-(3-(trifluoromethyl)phenyl)ureido)phenyl)isoindolin-2-yl)propanoate The compound of example 384 was prepared analogous to compound of example 360 by reaction of the compound of example 383, compound of example 357 and Pd(dppf)Cl₂: CH₂Cl₂. The compound of example 384 was directly used for the preparation of compound of example 385 without purification.

Example 385

(S)-3-Methoxy-2-(1-oxo-5-(4-(3-(3-(trifluoromethyl)phenyl)ureido)phenyl)isoindolin-2-yl)propanoic acid The compound of example 385 was prepared analogous to the compound of example 361 by hydrolysis of the compound of example 384.

Yield: 89%; ¹H NMR (DMSO-d₆, 300 MHz): δ 13.296 (s, 1H), 9.205 (s, 1H), 9.062 (s, 1H), 8.040 (s, 1H), 7.901 (s, 1H), 7.800-7.590 (m, 7H), 7.553-7.500 (d, J=7.8, 8.1 Hz, 1H), 7.338-7.312 (d, J=7.8 Hz, 1H), 5.062-5.027 (m, 1H), 4.681-4.539 (dd, J=17.7, 7.2 Hz, 2H), 4.029-3.971 (dd, J=7.2, 3 Hz, 1H), 3.822-3.777 (dd, J=3.3, 6.9, Hz, 1H), 3.314 (s, 3H); MS (ESI): m/z 512.1 (M−H), m/z 514.2 (M+H).

Example 386

(S)-Methyl 2-(5-bromo-1-oxoisoindolin-2-yl)-4-methylpentanoate

The compound of example 386 was prepared analogous to compound of example 359 by reaction of the compound of example 358 and methyl 2-amino-4-methylpentanoate hydrochloride.

Yield: 250 mg (37.65%); ¹H NMR (CDCl₃, 300 MHz): δ 7.763-7.737 (d, J=7.8 Hz, 1H), 7.648-7.618 (dd, J=9 Hz, 2H), 5.229-5.176 (t, J=7.8, 8.1 Hz, 1H), 4.689-4.633 (d, J=16.8 Hz, 1H), 4.363-4.307 (d, J=16.8 Hz, 1H), 3.735 (s, 3H), 1.892-1.841 (t, J=7.2, 8.1 Hz, 2H), 1.533-1.433 (m, 1H), 1.006-0.967 (t, J=5.4, 6.3 Hz, 6H); MS (ESI): m/z 340 (M+H).

Example 387

(S)-Methyl 4-methyl-2-(1-oxo-5-(4-(3-(3-(trifluoromethyl)phenyl)ureido)phenyl)isoindolin-2-yl)pentanoate The compound of example 387 was prepared analogous to compound of example 360 by reaction of the compound of example 386, compound of example 357 and Pd(dppf)Cl₂: CH₂Cl₂.

Yield: 78%; ¹H NMR (DMSO-d₆, 300 MHz): δ 9.122 (s, 1H), 8.990 (s, 1H), 8.043 (s, 1H), 7.879 (s, 1H), 7.805-7.744 (t, J=9.3, 9 Hz, 2H), 7.717-7.689 (d, J=8.4 Hz, 3H), 7.631-7.586 (m, 2H), 7.556-7.505 (t, J=7.5, 7.8 Hz, 1H), 7.342-7.318 (d, J=7.2 Hz, 1H), 5.015-4.965 (dd, J=3.9, 12.9 Hz, 1H), 4.546 (s, 2H), 3.671 (s, 3H), 1.992 (m, 1H), 1.803 (m, 1H), 1.403 (m, 1H), 0.937-0.902 (t, J=5.1, 5.4 Hz, 6H); MS (ESI): m/z 540 (M+H).

Example 388

(S)-4-Methyl-2-(1-oxo-5-(4-(3-(3-(trifluoromethyl)phenyl)ureido)phenyl)iso indolin-2-yl)pentanoic acid The compound of example 388 was prepared analogous to the compound of example 361 by hydrolysis of the compound of example 387.

Yield: 88%; ¹H NMR (DMSO-d₆, 300 MHz): δ 13.022 (s, 1H), 9.139 (s, 1H), 9.089 (s, 1H), 8.040 (s, 1H), 7.872 (s, 1H), 7.821-7.764 (t, J=7.2, 9.9 Hz, 2H), 7.737-7.715 (d, J=8.4 Hz, 2H), 7.630-7.584 (m, 3H), 7.555-7.502 (d, J=7.8, 8.1 Hz, 1H), 7.338-7.314 (d, J=7.2 Hz, 1H), 4.913-4.861 (dd, J=4.2, 7.2 Hz, 1H), 4.633-4.462 (d, J=16.2, 17.7 Hz, 2H), 1.983-1.885 (m, 1H), 1.792-1.712 (m, 1H), 1.447-1.336 (m, 1H), 0.893 (t, 6H); MS (ESI): m/z 524.7 (M−H), m/z 526.2 (M+H).

Example 389

(S)-Methyl 2-(6-bromo-1-oxoisoindolin-2-yl)-3-methylbutanoate

The compound of example 328 (52 g, 0.169 mol) and L-valine methyl ester hydrochloride (42.71 g, 0.254 mol) were taken in toluene (502 mL) and to this reaction mixture triethyl amine (34.13 g, 0.338 mol) was added and refluxed for about 16 h. After completion of the reaction, the reaction mixture was diluted with ethyl acetate and washed with water and brine, dried over anhydrous sodium sulfate and concentrated to obtain an oily material, which was purified by column chromatography (silica gel, 30% ethyl acetate in petroleum ether) to obtain the title compound.

Yield: 38 g (68%); ¹H NMR (CDCl₃, 300 MHz): δ 8.021-8.016 (d, J=1.5 Hz, 1H), 7.706-7.673 (dd, J=1.8, 8.1 Hz, 1H), 7.380-7.353 (d, J=8.1 Hz, 1H), 4.824-4.790 (d, J=10.2 Hz, 1H), 4.744-4.686 (d, J=17.4 Hz, 1H), 4.416-4.359 (d, J=17.1 Hz, 1H), 3.743 (s, 3H), 2.356-2.321 (m, 1H), 1.078-1.056 (d, J=6.6 Hz, 3H), 0.939-0.917 (d, J=6.6 Hz, 3H); MS (ESI): m/z 326 (M+H).

Example 390

(S)-Methyl 3-methyl-2-(1-oxo-6-(4,4,5,5-tetramethyl-1,3,2-dioxaborolan-2-yl)isoindolin-2-yl)butanoate The compound of example 389 (5 g, 0.01534 mol), bis (pinacolato)diboron (3.98 g, 0.0168 mol), potassium acetate (4.50 g, 0.0459 mol) and 1,1'-Bis(diphenylphosphino)-ferrocene (0.424 g, 0.000765 mol) were taken in dry dioxane and degassed with argon for 20 min. To this solution, [1,1-Bis(diphenylphosphino)-ferrocene]dichloropalladium (II), complex with dichloromethane (0.624 g, 0.000765 mol) was added and degassed with argon for 5 min. The reaction mixture was stirred at 70-75° C. for 2 h followed by stirring at 120° C. for 16 h. After completion of the reaction, dioxane was evaporated and to the residue obtained, water was added and extracted with ethyl acetate. The ethyl acetate extract was washed with water and brine and dried over anhydrous $Na_2SO_4$ or $MgSO_4$. The solvent was evaporated and the product was purified by column chromatography (silica gel, 10% $CHCl_3$ in ethyl acetate) to obtain the title compound.

Yield: 4.6 g (80.7%); $^1$H NMR (DMSO-$d_6$, 300 MHz): δ 7.941 (s, 1H), 7.899-7.873 (d, J=7.8 Hz, 1H), 7.651-7.626 (d, J=7.5 Hz, 1H), 4.589-4.566 (m, 3H), 3.653 (s, 3H), 2.357-2.280 (m, 1H), 1.309 (s, 12H), 0.975-0.953 (d, J=6.6 Hz, 3H), 0.810-0.788 (d, J=6.6 Hz, 3H); MS (ESI): m/z 374 (M+H).

Example 391

(S)-Methyl 3-methyl-2-(6-(5-nitropyridin-2-yl)-1-oxoisoindolin-2-yl)butanoate

The compound of example 390 (3 g, 0.0084 mol), 2-bromo-5-nitropyridine (1.95 g, 0.0096 mol) and Pd(dppf)$Cl_2$:$CH_2Cl_2$ (0.196 g, 0.00024 mol) were taken in DMF (100 mL) under an argon atmosphere. To this reaction mixture, 2M solution of $Na_2CO_3$ (2.55 mg, 0.0241 mmol, 12 mL) was added. The reaction mixture was stirred at 80-85° C. for 1 to 1.5 h. After completion of the reaction, water was added and the product obtained was extracted with ether. The combined ether layers were washed with brine and dried over anhydrous $Na_2SO_4$ or anhydrous $MgSO_4$. The solvent was evaporated and the product obtained was purified by flash chromatography to obtain the title compound Yield: 1.8 g (62%); $^1$H NMR (DMSO-$d_6$, 300 MHz): δ 9.456-9.447 (d, J=2.7 Hz, 1H), 8.671-8.632 (dd, J=3.3, 9 Hz, 1H), 8.490 (s, 1H), 8.464-8.459 (t, J=1.5 Hz, 1H), 8.413-8.383 (d, J=9 Hz, 1H), 7.823-7.795 (d, J=8.4 Hz, 1H), 4.666-4.601 (m, 3H), 3.672 (s, 3H), 2.357-2.280 (m, 1H), 0.998-0.976 (d, J=6.6 Hz, 3H), 0.852-0.830 (d, J=6.6 Hz, 3H); MS (ESI): m/z 368 (M–H), m/z 370 (M+H).

Example 392

(S)-Methyl 2-(6-(5-aminopyridin-2-yl)-1-oxoisoindolin-2-yl)-3-methylbutanoate

The compound of example 391 (1.5 g, 0.0040 mol), iron (0.533 g, 0.0095 mol) and ammonium chloride (0.930 g, 0.0174 mol) in EtOH:$H_2O$ (22.5 mL, 15:7.5) was refluxed for about 16 h. After completion of the reaction, the reaction mixture was filtered through celite. The filtrate was concentrated to obtain a residue which was dissolved in ethyl acetate and washed with water and brine, dried over anhydrous sodium sulfate and concentrated to obtain a residue, which was purified by column chromatography (silica gel, 30% ethyl acetate in petroleum ether) to obtain the title compound.

Yield: 1.2 g (87%); $^1$H NMR (DMSO-$d_6$, 300 MHz): δ 8.200-8.180 (d, J=6 Hz, 2H), 8.031-8.022 (d, J=2.7 Hz, 1H), 7.734-7.706 (d, J=8.4 Hz, 1H), 7.631-7.603 (d, J=8.4 Hz, 1H), 7.010-6.973 (dd, J=2.3, 8.4 Hz, 1H), 5.531 (s, 2H), 4.610-4.555 (m, 3H), 3.663 (s, 3H), 2.387-2.285 (m, 1H), 0.988-0.967 (d, J=6.3 Hz, 3H), 0.836-0.814 (d, J=6.6 Hz, 3H); MS (ESI): m/z 337 (M–H), m/z 339 (M+H).

Example 393

(S)-Methyl 2-(6-(5-(3-(2-chlorophenyl)ureido)pyridin-2-yl)-1-oxoisoindolin-2-yl)-3-methylbutanoate The compound of example 392 (100 mg, 0.295 mmol) was dissolved in 3 mL THF and to this reaction mixture, 2-chlorophenyl isocyanate (49.83 mg, 0.324 mmol) was added and stirred at room temperature for 8-10 h. The reaction mixture was concentrated and purified by column chromatography (silica gel, 30-40% ethyl acetate in petroleum ether) to obtain the title compound.

Yield: 135 mg (93%); $^1$H NMR (DMSO-$d_6$, 300 MHz): δ 9.717 (s, 1H), 8.682-8.674 (d, J=2.4 Hz, 1H), 8.464 (s, 1H), 8.330-8.309 (m, 2H), 8.171-8.139 (dd, J=1.5, 8.4 Hz, 2H), 8.095-8.087 (d, J=2.4 Hz, 1H), 7.718-7.690 (d, J=8.4 Hz, 1H), 7.482-7.451 (dd, J=1.2, 7.8 Hz, 1H), 7.312 (m, 1H), 7.053-7.049 (m, 1H), 4.610-4.540 (m, 3H), 3.689 (s, 3H), 2.351-2.274 (m, 1H), 0.995-0.973 (d, J=6.6 Hz, 3H), 0.847-0.825 (d, J=6.6 Hz, 3H); MS (ESI): m/z 493 (M+H).

Example 394

(S)-2-(6-(5-(3-(2-Chlorophenyl)ureido)pyridin-2-yl)-1-oxoisoindolin-2-yl)-3-methylbutanoic acid The compound of example 393 (75 mg, 0.150 mmol) was taken in THF (3 mL) and MeOH (1 mL) and to this reaction mixture, 1 N LiOH (31.47 mg, 0.75 mmol) was added and stirred at room temperature for 2-3 h. After completion of the reaction, solvent was evaporated and the residue obtained was dissolved in water and acidified with 1 N HCl to obtain the title compound, which was filtered and dried.

Yield: 68 mg (93%); $^1$H NMR (DMSO-$d_6$, 300 MHz): δ 12.927 (s, 1H), 9.837 (s, 1H), 8.717-8.710 (d, J=2.1 Hz, 1H), 8.506 (s, 1H), 8.320 (s, 1H), 8.295-8.290 (d, J=1.5 Hz, 1H), 8.162-8.077 (m, 3H), 7.728-7.699 (d, J=8.7 Hz, 1H), 7.483-7.452 (dd, J=1.2, 7.8 Hz, 1H), 7.313 (m, 1H), 7.056-7.053 (m, 1H), 4.651-4.517 (m, 3H), 2.338-2.261 (m, 1H), 1.030-1.008 (d, J=6.6 Hz, 3H), 0.865-0.843 (d, J=6.6 Hz, 3H); MS (ESI) m/z: m/z 479 (M+H).

Example 395

(S)-Methyl 2-(6-(5-(3-(4-chloro-2-phenoxyphenyl)ureido)pyridin-2-yl)-1-oxoisoindolin-2-yl)-3-methylbutanoate The compound of example 395 was prepared analogous to the compound of example 393 by reaction of the compound of example 392 with 4-chloro-2-phenoxy phenyl isocyanate. The compound of example 395 was used directly for the preparation of compound of example 396 without purification.

Example 396

(S)-2-(6-(5-(3-(4-Chloro-2-phenoxyphenyl)ureido)pyridin-2-yl)-1-oxoisoindolin-2-yl)-3-methylbutanoic acid The compound of example 396 was prepared analogous to the compound of example 394 by hydrolysis of the compound of example 395.

Yield: 82%; ¹H NMR (DMSO-d₆, 300 MHz): δ 13.031 (s, 1H), 9.666 (s, 1H), 8.815 (s, 1H), 8.633-8.627 (d, J=1.8 Hz, 1H), 8.389-8.381 (d, J=2.4 Hz, 1H), 8.316-8.295 (d, J=6.3 Hz, 2H), 8.116-8.020 (m, 2H), 7.710-7.681 (d, J=8.7 Hz, 1H), 7.456-7.404 (t, J=7.8 Hz, 2H), 7.212-7.163 (d, J=7.5 Hz, 1H), 7.100-7.074 (d, J=7.8 Hz, 2H), 7.025-6.988 (dd, J=2.7, 8.7 Hz, 1H), 6.849-6.821 (d, J=8.4 Hz, 1H), 4.704-4.523 (dd, J=17.7, 18.6 Hz, 2H), 4.543-4.511 (d, J=9.6 Hz, 1H), 2.361-2.251 (m, 1H), 1.027-1.005 (d, J=6.6 Hz, 3H), 0.862-0.840 (d, J=6.6 Hz, 3H); MS (ESI): m/z 571 (M+H).

Example 397

(S)-Methyl 2-(6-(5-(3-(3,4-dimethylphenyl)ureido)pyridin-2-yl)-1-oxoisoindolin-2-yl)-3-methylbutanoate The compound of example 397 was prepared analogous to the compound of example 393 by reaction of the compound of example 392 with 3,4-dimethyl phenyl isocyanate. The compound of example 397 was used directly for the preparation of compound of example 398 without purification.

Example 398

(S)-2-(6-(5-(3-(3,4-Dimethylphenyl)ureido)pyridin-2-yl)-1-oxoisoindolin-2-yl)-3-methylbutanoic acid The compound of example 398 was prepared analogous to the compound of example 394 by hydrolysis of the compound of example 397.

Yield: 96%; ¹H NMR (DMSO-d₆, 300 MHz): δ 9.440 (s, 1H), 8.968 (s, 1H), 8.795 (s, 1H), 8.305-8.263 (m, 2H), 8.166-8.097 (m, 2H), 7.756-7.730 (d, J=7.8 Hz, 1H), 7.236-7.110 (m, 2H), 7.047-7.019 (d, J=8.4 Hz, 1H), 4.725-4.551 (dd, J=16.2, 18.3 Hz, 2H), 4.551-4.519 (d, J=9.6 Hz, 1H), 2.391-2.235 (m, 1H), 2.235 (s, 3H), 2.125 (s, 3H), 1.030-1.008 (d, J=6.6 Hz, 3H), 0.865-0.842 (d, J=6.9 Hz, 3H); MS (ESI) m/z: 473 (M+H).

Example 399

(S)-Methyl 2-(6-(5-(3-(3,4-difluorophenyl)ureido)pyridin-2-yl)-1-oxoisoindolin-2-yl)-3-methylbutanoate The compound of example 399 was prepared analogous to the compound of example 393 by reaction of the compound of example 392 with 3,4-difluoro phenyl isocyanate.

Yield: 89%; ¹H NMR (DMSO-d₆, 300 MHz): δ 9.079 (s, 1H), 8.949 (s, 1H), 8.690 (s, 1H), 8.314 (m, 2H), 8.137-8.097 (m, 2H), 7.714-7.633 (m, 2H), 7.367-7.315 (m, 1H), 7.167-7.100 (t, J=9.3 Hz, 1H), 4.623-4.596 (m, 3H), 3.669 (s, 3H), 2.351-2.259 (m, 1H), 0.994-0.973 (d, J=6.3 Hz, 3H), 0.845-0.824 (d, J=6.9 Hz, 3H); MS (ESI): m/z 493 (M−H), m/z 495 (M+H).

Example 400

(S)-2-(6-(5-(3-(3,4-Difluorophenyl)ureido)pyridin-2-yl)-1-oxoisoindolin-2-yl)-3-methylbutanoic acid The compound of example 400 was prepared analogous to the compound of example 394 by hydrolysis of the compound of example 399.

Yield: 86%; ¹H NMR (DMSO-d₆, 300 MHz): δ 13.004 (s, 1H), 9.106 (s, 1H), 8.981 (s, 1H), 8.696-8.691 (d, J=1.5 Hz, 1H), 8.315-8.295 (m, 2H), 8.051-8.036 (m, 2H), 7.712-7.636 (m, 2H), 7.377-7.282 (m, 1H), 7.167-7.126 (m, 1H), 4.643-4.526 (dd, J=12, 17.1 Hz, 2H), 4.546-4.514 (d, J=9.6 Hz, 1H), 2.354-2.262 (m, 1H), 1.028-1.006 (d, J=6.6 Hz, 3H), 0.863-0.841 (d, J=6.6 Hz, 3H); MS (ESI): m/z 481 (M+H).

Example 401

(S)-Methyl 2-(6-(5-(3-(2,3-dihydro-1H-inden-5-yl)ureido)pyridin-2-yl)-1-oxoisoindolin-2-yl)-3-methylbutanoate The compound of example 401 was prepared analogous to the compound of example 393 by reaction of the compound of example 392 with 2,3-dihydro-1H-indene-5-isocyanate. The compound of example 401 was used directly for the preparation of compound 402 without purification.

Example 402

(S)-2-(6-(5-(3-(2,3-Dihydro-1H-inden-5-yl)ureido)pyridin-2-yl)-1-oxoisoindolin-2-yl)-3-methylbutanoic acid The compound of example 402 was prepared analogous to the compound of example 394 by hydrolysis of the compound of example 401.

Yield: 89%; ¹H NMR (DMSO-d₆, 300 MHz): δ 12.947 (s, 1H), 8.938 (s, 1H), 8.707 (s, 1H), 8.681-8.674 (d, J=2.1 Hz, 1H), 8.312-8.291 (m, 2H), 8.054-7.991 (m, 2H), 7.707-7.679 (d, J=8.4 Hz, 1H), 7.384-7.347 (m, 1H), 7.140-7.087 (m, 2H), 4.641-4.515 (dd, J=17.1, 18.3 Hz, 2H), 4.547-4.515 (d, J=9.6 Hz, 1H), 2.847-2.739 (m, 4H), 2.330-2.248 (m, 1H), 2.012-1.950 (m, 2H), 1.028-1.007 (d, J=6.3 Hz, 3H), 0.864-0.841 (d, J=6.9 Hz, 3H); MS (ESI): m/z 485 (M+H).

Example 403

(S)-Methyl 2-(6-(5-(4-tert-butylbenzamido)pyridin-2-yl)-1-oxoisoindolin-2-yl)-3-methylbutanoate To a solution of compound of example 392 (100 mg, 0.295 mmol) in dichloromethane (3 mL), pyridine (70.53 mg, 0.885 mmol) was added and stirred for 5 min. To the reaction mixture, 4-tert-butylbenzoyl chloride (87.27 mg, 0.443 mmol) was added and stirred for about 16 h. After completion of the reaction, the solvent was evaporated and the crude material obtained was triturated with diethyl ether to obtain the title compound, which was filtered and dried.

Yield: 100 mg (68%); ¹H NMR (DMSO-d₆, 300 MHz): δ 10.670 (s, 1H), 9.122-9.115 (d, J=2.1 Hz, 1H), 8.928-8.911 (d, J=5.1 Hz, 1H), 8.450-8.414 (dd, J=2.1, 8.4 Hz, 1H), 8.185-8.156 (d, J=8.7 Hz, 1H), 8.084-8.037 (t, J=6.9, 7.2 Hz, 1H), 7.974-7.946 (d, J=8.4 Hz, 2H), 7.766-7.738 (d, J=8.4 Hz, 1H), 7.584-7.556 (d, J=8.4 Hz, 2H), 4.633-4.599 (m, 3H), 3.673 (s, 3H), 2.337-2.303 (m, 1H), 1.317 (s, 9H), 0.999-0.977 (d, J=6.6 Hz, 3H), 0.851-0.829 (d, J=6.6 Hz, 3H); MS (ESI) m/z: 498 (M−H), m/z 500 (M+H).

Example 404

(S)-2-(6-(5-(4-tert-Butylbenzamido)pyridin-2-yl)-1-oxoisoindolin-2-yl)-3-methyl butanoic acid The compound of example 403 (80 mg, 0.160 mmol) was taken in THF (4 mL) and MeOH (1 mL) and to this reaction mixture, 1N LiOH (33.59 mg, 0.800 mmol) was added and stirred at room temperature for 2-3 h. After completion of the reaction, the solvent was evaporated and the residue obtained was dissolved in water and acidified with 1 N HCl to obtain the title compound, which was filtered and dried.

Yield: 84 mg (84%); $^1$H NMR (DMSO-$d_6$, 300 MHz): δ 12.949 (s, 1H), 10.505 (s, 1H), 9.048-9.041 (d, J=2.1 Hz, 1H), 8.355-8.315 (m, 3H), 8.121-8.092 (d, J=8.7 Hz, 1H), 7.944-7.916 (d, J=8.4 Hz, 2H), 7.737-7.708 (d, J=8.7 Hz, 1H), 7.582-7.554 (d, J=8.4 Hz, 2H), 4.718-4.541 (dd, J=17.1, 18 Hz, 2H), 4.555-4.523 (d, J=9.6 Hz, 1H), 2.358-2.260 (m, 1H), 1.319 (s, 9H), 1.033-1.012 (d, J=6.3 Hz, 3H), 0.869-0.846 (d, J=6.9 Hz, 3H); MS (ESI) m/z: 484 (M−H), m/z 486 (M+H).

Example 405

(S)-Methyl 3-methyl-2-(1-oxo-6-(5-(4-pentylbenzamido)pyridin-2-yl)isoindolin-2-yl)butanoate The compound of example 405 was prepared analogous to the compound of example 403 by reaction of the compound of example 392 with 4-(n-pentyl)benzoyl chloride.

Yield: 83%; $^1$H NMR (DMSO-$d_6$, 300 MHz): δ 10.633 (s, 1H), 9.108-9.101 (d, J=2.1 Hz, 1H), 8.442-8.404 (dd, J=2.4, 9 Hz, 1H), 8.353-8.324 (m, 2H), 8.183-8.154 (d, J=8.7 Hz, 1H), 7.948-7.921 (d, J=8.1 Hz, 2H), 7.764-7.735 (d, J=8.7 Hz, 1H), 7.383-7.356 (d, J=8.1 Hz, 2H), 4.631-4.597 (m, 3H), 3.671 (s, 3H), 2.676-2.626 (t, J=7.2, 7.8 Hz, 2H), 2.334-2.301 (m, 1H), 1.621-1.573 (m, 2H), 1.289-1.242 (m, 4H), 0.997-0.975 (d, J=6.6 Hz, 3H), 0.873-0.827 (m, 6H); MS (ESI): m/z 512 (M−H), m/z 514 (M+H).

Example 406

(S)-3-Methyl-2-(1-oxo-6-(5-(4-pentylbenzamido)pyridin-2-yl)isoindolin-2-yl)butanoic acid The compound of example 406 was prepared analogous to the compound of example 404 by hydrolysis of the compound of example 405.

Yield: 88%; $^1$H NMR (DMSO-$d_6$, 300 MHz): δ 12.985 (s, 1H), 10.484 (s, 1H), 9.039-9.031 (d, J=2.4 Hz, 1H), 8.355-8.308 (m, 3H), 8.111-8.082 (d, J=8.7 Hz, 1H), 7.929-7.901 (d, J=8.4 Hz, 2H), 7.733-7.704 (d, J=8.7 Hz, 1H), 7.380-7.353 (d, J=8.1 Hz, 2H), 4.716-4.539 (dd, J=17.1, 18 Hz, 2H), 4.554-4.522 (d, J=9.6 Hz, 1H), 2.677-2.627 (t, J=7.2, 7.8 Hz, 2H), 2.336-2.291 (m, 1H), 1.649-1.576 (m, 2H), 1.292-1.217 (m, 4H), 1.033-1.011 (d, J=6.6 Hz, 3H), 0.868-0.83 (m, 6H); MS (ESI): m/z 498 (M−H), m/z 500 (M+H).

Example 407

(S)-Methyl 2-(6-(5-biphenyl-4-ylcarboxamidopyridin-2-yl)-1-oxoisoindolin-2-yl)-3-methylbutanoate The compound of example 407 was prepared analogous to the compound of example 403 by reaction of the compound of example 392 with 4-phenyl benzoyl chloride.

Yield: 95%; $^1$H NMR (DMSO-$d_6$, 300 MHz): δ 10.788 (s, 1H), 9.152-9.145 (d, J=2.1 Hz, 1H), 8.486-8.451 (dd, J=1.8, 8.4 Hz, 1H), 8.367-8.341 (d, J=7.8 Hz, 2H), 8.209-8.180 (d, J=8.7 Hz, 1H), 8.143-8.116 (d, J=8.1 Hz, 2H), 7.785-7.857 (d, J=8.1 Hz, 2H), 7.795-7.704 (m, 5H), 7.462-7.403 (m, 1H), 4.636-4.603 (m, 3H), 3.675 (s, 3H), 2.360-2.283 (m, 1H), 1.000-0.978 (d, J=6.6 Hz, 3H), 0.852-0.831 (d, J=6.3 Hz, 3H); MS (ESI) m/z 518 (M−H), m/z 520 (M+H).

Example 408

(S)-2-(6-(5-Biphenyl-4-ylcarboxamidopyridin-2-yl)-1-oxoisoindolin-2-yl)-3-methylbutanoic acid The compound of example 408 was prepared analogous to the compound of example 404 by hydrolysis of the compound of example 407.

Yield: 82%; $^1$H NMR (DMSO-$d_6$, 300 MHz): δ 10.626 (s, 1H), 9.073-9.066 (d, J=2.1 Hz, 1H), 8.360-8.339 (m, 3H), 8.128-8.090 (dd, J=3, 8.4 Hz, 3H), 7.878-7.851 (d, J=8.1 Hz, 2H), 7.778-7.754 (d, J=7.2 Hz, 2H), 7.732-7.704 (d, J=8.4 Hz, 1H), 7.532-7.483 (t, J=7.2, 7.5 Hz, 2H), 7.442-7.419 (d, J=7.2 Hz, 1H), 4740-4.533 (dd, J=17.7 Hz, 2H), 4.533-4.502 (d, J=9.3 Hz, 1H), 2.347-2.253 (m, 1H), 1.029-1.007 (d, J=6.6 Hz, 3H), 0.860-0.839 (d, J=6.3 Hz, 3H); MS (ESI): m/z 504 (M−H).

Example 409

(S)-Methyl 2-(6-(5-(2-naphthamido)pyridin-2-yl)-1-oxoisoindolin-2-yl)-3-methyl butanoate The compound of example 409 was prepared analogous to the compound of example 403 by reaction of the compound of example 392 with 2-naphthoyl chloride.

Yield: 86%; $^1$H NMR (DMSO-$d_6$, 300 MHz): δ 10.922 (s, 1H), 9.171-9.163 (d, J=2.4 Hz, 1H), 8.670 (s, 1H), 8.508-8.471 (dd, J=2.1, 8.7 Hz, 1H), 8.374-8.350 (d, J=7.2 Hz, 2H), 8.221-8.192 (d, J=8.7 Hz, 1H), 8.122-8.077 (m, 3H), 8.040-8.010 (d, J=2.1, 6.9 Hz, 1H), 7.775-7.747 (d, J=8.4 Hz, 1H), 7.669-7.628 (m, 2H), 4.637-4.603 (m, 3H), 3.675 (s, 3H), 2.339-2.306 (m, 1H), 1.001-0.979 (d, J=6.6 Hz, 3H), 0.854-0.832 (d, J=6.6 Hz, 3H); MS (ESI): m/z 492 (M−H), m/z 494 (M+H).

Example 410

(S)-2-(6-(5-(2-Naphthamido)pyridin-2-yl)-1-oxoisoindolin-2-yl)-3-methylbutanoic acid The compound of example 410 was prepared analogous to the compound of example 404 by hydrolysis of the compound of example 409.

Yield: 73%; $^1$H NMR (DMSO-$d_6$, 300 MHz): δ 10.764 (s, 1H), 9.098-9.090 (d, J=2.4 Hz, 1H), 8.634 (s, 1H), 8.408-8.349 (m, 3H), 8.149-8.120 (d, J=8.7 Hz, 1H), 8.101-8.010 (m, 4H), 7.743-7.715 (d, J=8.4 Hz, 1H), 7.684-7.609 (m, 2H), 4.727-4.545 (dd, J=18, 18.9 Hz, 2H), 4.558-4.526 (d, J=9.6 Hz, 1H), 2.362-2.243 (m, 1H), 1.036-1.015 (d, J=6.3 Hz, 3H), 0.872-0.850 (d, J=6.6 Hz, 3H); MS (ESI) m/z: 478 (M−H); m/z 480 (M+H).

Example 411

(S)-Methyl 2-(6-(5-(4-butoxybenzamido)pyridin-2-yl)-1-oxoisoindolin-2-yl)-3-methylbutanoate The compound of example 411 was prepared analogous to the compound of example 403 by reaction of the compound of example 392 with 4-n-butoxy benzoyl chloride.

Yield: 69%; $^1$H NMR (DMSO-$d_6$, 300 MHz): δ 10.598 (s, 1H), 9.132-9.124 (d, J=2.4 Hz, 1H), 8.474-8.437 (dd, J=2.4, 8.7 Hz, 1H), 8.351-8.320 (m, 2H), 8.200-8.171 (d, J=8.7 Hz, 1H), 8.026-7.997 (d, J=8.7 Hz, 2H), 7.772-7.457 (d, J=8.1 Hz, 1H), 7.090-7.060 (d, J=9 Hz, 2H), 4.631-4.598 (m, 3H), 4.079-4.036 (t, J=6.3, 6.6 Hz, 2H), 3.672 (s, 3H), 2.357-2.313

(m, 1H), 1.739-1.669 (m, 2H), 1.476-1.402 (m, 2H), 0.998-0.976 (d, J=6.6 Hz, 3H), 0.956-0.907 (t, J=7.2, 7.5 Hz, 3H), 0.850-0.827 (d, J=6.9 Hz, 3H); MS (ESI): m/z 514 (M–H), m/z 516 (M+H).

Example 412

(S)-2-(6-(5-(4-Butoxybenzamido)pyridin-2-yl)-1-oxoisoindolin-2-yl)-3-methylbutanoic acid The compound of example 412 was prepared analogous to the compound of example 404 by hydrolysis of the compound of example 411.
Yield: 78%; $^1$H NMR (DMSO-$d_6$, 300 MHz): δ 10.405 (s, 1H), 9.032-9.024 (d, J=2.4 Hz, 1H), 8.335-8.296 (m, 3H), 8.094-8.065 (d, J=8.7 Hz, 1H), 7.998-7.969 (d, J=8.7 Hz, 2H), 7.717-7.688 (d, J=8.7 Hz, 1H), 7.084-7.054 (d, J=9 Hz, 2H), 4.776-4.496 (dd, J=18.3 Hz, 2H), 4.483-4.451 (d, J=9.6 Hz, 1H), 4.079-4.036 (t, J=6.3, 6.6 Hz, 2H), 2.312-2.267 (m, 1H), 1.765-1.672 (m, 2H), 1.480-1.381 (m, 2H), 1.018-0.996 (d, J=6.6 Hz, 3H), 0.959-0.910 (t, J=7.2, 7.5 Hz, 3H), 0.845-0.823 (d, J=6.6 Hz, 3H); MS (ESI): m/z 500 (M–H), m/z 502 (M+H).

Example 413

(S)-Methyl 3-methyl-2-(6-(4-nitro-2-(trifluoromethyl)phenyl)-1-oxoisoindolin-2-yl)butanoate The compound of example 413 was prepared analogous to the compound of example 391 by reaction of the compound of example 390, 1-bromo-4-nitro-2-(trifluoromethyl)benzene and Pd(dppf)Cl$_2$·CH$_2$Cl$_2$.
Yield: 85%; $^1$H NMR (DMSO-$d_6$, 300 MHz): δ 8.561-8.537 (m, 2H), 7.782-7.748 (d, J=7.8 Hz, 2H), 7.661 (s, 1H), 7.638-7.610 (d, J=8.4 Hz, 1H), 4.666-4.544 (m, 3H), 3.673 (s, 3H), 2.383-2.238 (m, 1H), 0.997-0.975 (d, J=6.6 Hz, 3H), 0.860-0.838 (d, J=6.6 Hz, 3H); MS (ESI): m/z 436 (M–H).

Example 414

(S)-Methyl 2-(6-(4-amino-2-(trifluoromethyl)phenyl)-1-oxoisoindolin-2-yl)-3-methyl butanoate The compound of example 414 was prepared analogous to the compound of example 392 by reduction of the compound of example 413.
Yield: 95%; $^1$H NMR (DMSO-$d_6$, 300 MHz): δ 7.650-7.623 (d, J=8.1 Hz, 1H), 7.505-7.483 (d, J=6.6 Hz, 2H), 7.061-7.034 (d, J=8.1 Hz, 1H), 6.992 (s, 1H), 6.845-6.817 (d, J=8.4 Hz, 1H), 5.701 (s, 2H), 4.615-4.588 (m, 3H), 3.684 (s, 3H), 2.388-2.276 (m, 1H), 1.008-0.987 (d, J=6.3 Hz, 3H), 0.868-0.846 (d, J=6.6 Hz, 3H); MS (ESI): m/z 405 (M–H), m/z 407 (M+H).

Example 415

(S)-Methyl 2-(6-(4-(3-(2-chlorophenyl)ureido)-2-(trifluoromethyl)phenyl)-1-oxoisoindolin-2-yl)-3-methylbutanoate The compound of example 415 was prepared analogous to the compound of example 393 by reaction of the compound of example 414 with 2-chlorophenyl isocyanate.
Yield: 90%; $^1$H NMR (DMSO-$d_6$, 300 MHz): δ 9.851 (s, 1H), 8.423 (s, 1H), 8.186-8.155 (dd, J=1.2, 8.1 Hz, 1H), 8.124-8.117 (d, J=2.1 Hz, 1H), 7.716-7.656 (t, J=8.7, 9.6 Hz, 2H), 7.586-7.561 (d, J=7.5 Hz, 2H), 7.505-7.474 (dd, J=1.2, 8.1 Hz, 1H), 7.396-7.368 (d, J=8.4 Hz, 1H), 7.354-7.301 (t, J=7.2 Hz, 1H), 7.104-7.078 (m, 1H), 4.647-4.602 (m, 3H), 3.691 (s, 3H), 2.403-2.226 (m, 1H), 1.016-0.994 (d, J=6.6 Hz, 3H), 0.879-0.857 (d, J=6.6 Hz, 3H); MS (ESI): m/z 558 (M–H), m/z 560 (M+H).

Example 416

(S)-2-(6-(4-(3-(2-Chlorophenyl)ureido)-2-(trifluoromethyl)phenyl)-1-oxoisoindolin-2-yl)-3-methylbutanoic acid The compound of example 416 was prepared analogous to the compound of example 394 by hydrolysis of the compound of example 415.
Yield: 97%; $^1$H NMR (DMSO-$d_6$, 300 MHz): δ 13.044 (s, 1H), 9.861 (s, 1H), 8.413 (s, 1H), 8.178-8.162 (d, J=8 Hz, 1H), 8.122 (s, 1H), 7.707-7.691 (d, J=8 Hz, 1H), 7.678-7.661 (d, J=8.5 Hz, 1H), 7.583-7.560 (m, 2H), 7.499-7.483 (d, J=8 Hz, 1H), 7.394-7.377 (d, J=8.5 Hz, 1H), 7.347-7.316 (t, J=7.5, 8 Hz, 1H), 7.095-7.064 (t, J=7.5, 8 Hz, 1H), 4.730-4.594 (dd, J=17.5 Hz, 2H), 4.554-4.535 (d, J=9.5 Hz, 1H), 2.343-2.314 (m, 1H), 1.014-0.992 (d, J=6.6 Hz, 3H), 0.877-0.855 (d, J=6.6 Hz, 3H); MS (ESI): m/z 544 (M–H), m/z 546 (M+H).

Example 417

(S)-Methyl 2-(6-(4-(3-(3,4-difluorophenyl)ureido)-2-(trifluoromethyl)phenyl)-1-oxoisoindolin-2-yl)-3-methylbutanoate The compound of example 417 was prepared analogous to the compound of example 393 by reaction of the compound of example 414 with 3,4-difluorophenyl isocyanate.
Yield: 87%; $^1$H NMR (DMSO-$d_6$, 300 MHz): δ 9.230 (s, 1H), 9.072 (s, 1H), 8.102 (s, 1H), 7.684 (m, 3H), 7.579-7.555 (d, J=7.2 Hz, 2H), 7.418-7.322 (dd, J=8.4 Hz, 2H), 7.199-7.170 (m, 1H), 4.645-4.600 (m, 3H), 3.690 (s, 3H), 2.396-2.277 (m, 1H), 1.015-0.993 (d, J=6.6 Hz, 3H), 0.877-0.855 (d, J=6.6 Hz, 3H); MS (ESI): m/z 560 (M–H), m/z 562 (M+H).

Example 418

(S)-2-(6-(4-(3-(3,4-Difluorophenyl)ureido)-2-(trifluoromethyl)phenyl)-1-oxoisoindolin-2-yl)-3-methylbutanoic acid The compound of example 418 was prepared analogous to the compound of example 394 by hydrolysis of the compound of example 417.
Yield: 87%; $^1$H NMR (DMSO-$d_6$, 300 MHz): δ 13.045 (s, 1H), 9.241 (s, 1H), 9.084 (s, 1H), 8.102 (s, 1H), 7.688 (m, 3H), 7.579-7.554 (d, J=7.5 Hz, 2H), 7.379-7.340 (dd, J=8.4 Hz, 2H), 7.195 (m, 1H), 4.727-4.592 (dd, J=18 Hz, 2H), 4.555-4.536 (d, J=9.5 Hz, 1H), 2.329-2.313 (m, 1H), 1.048-1.035 (d, J=6.5 Hz, 3H), 0.896-0.884 (d, J=6 Hz, 3H); MS (ESI): m/z 546 (M–H), m/z 548 (M+H).

Example 419

(S)-Methyl 2-(6-(4-(3-(2,3-dihydro-1H-inden-5-yl)ureido)-2-(trifluoromethyl)phenyl)-1-oxoisoindolin-2-yl)-3-methylbutanoate The compound of example 419 was prepared analogous to the compound of example 393 by reaction of the compound of example 414 with 2,3-dihydro-1H-indene-5-isocyanate.

Yield: 93%; ¹H NMR (DMSO-d$_6$, 300 MHz): δ 9.081 (s, 1H), 8.686 (s, 1H), 8.129-8.122 (d, J=2.1 Hz, 1H), 7.710-7.681 (d, J=8.7 Hz, 1H), 7.660-7.627 (dd, J=1.5, 8.4 Hz, 1H), 7.578-7.554 (d, J=7.2 Hz, 2H), 7.518 (s, 1H), 7.359-7.330 (d, J=8.7 Hz, 1H), 7.187-7.116 (dd, J=3.6, 9.6 Hz, 2H), 4.642-4.583 (m, 3H), 3.691 (s, 3H), 2.868-2.779 (m, 4H), 2.397-2.275 (m, 1H), 2.058-1.960 (m, 2H), 1.016-0.994 (d, J=6.6 Hz, 3H), 0.878-0.856 (d, J=6.6 Hz, 3H); MS (ESI): m/z 564 (M–H), m/z 565 (M+H).

Example 420

(S)-2-(6-(4-(3-(2,3-Dihydro-1H-inden-5-yl)ureido)-2-(trifluoromethyl)phenyl)-1-oxoisoindolin-2-yl)-3-methylbutanoic acid The compound of example 420 was prepared analogous to the compound of example 394 by hydrolysis of the compound of example 419.
Yield: 97%; ¹H NMR (DMSO-d$_6$, 300 MHz): δ 13.036 (s, 1H), 9.086 (s, 1H), 8.689 (s, 1H), 8.125 (s, 1H), 7.700-7.685 (d, J=7.5 Hz, 1H), 7.654-7.640 (d, J=7 Hz, 1H), 7.576-7.553 (m, 2H), 7.420 (s, 1H), 7.357-7.340 (d, J=8.5 Hz, 1H), 7.178-7.127 (dd, J=8, 9.5 Hz, 2H), 4.725-4.591 (dd, J=18 Hz, 2H), 4.555-4.536 (d, J=9.5 Hz, 1H), 2.860-2.791 (m, 4H), 2.344-2.791 (m, 1H), 2.042-1.983 (m, 2H), 1.048-1.035 (d, J=6.5 Hz, 3H), 0.897-0.884 (d, J=6.5 Hz, 3H); MS (ESI): m/z 550 (M–H), m/z 552 (M+H).

Example 421

(S)-Methyl 2-(6-(4-(3-(3,4-dimethylphenyl)ureido)-2-(trifluoromethyl)phenyl)-1-oxoisoindolin-2-yl)-3-methylbutanoate The compound of example 421 was prepared analogous to the compound of example 393 by reaction of the compound of example 414 with 3,4-dimethyl phenyl isocyanate.
Yield: 98%; ¹H NMR (DMSO-d$_6$, 300 MHz): δ 9.077 (s, 1H), 8.640 (s, 1H), 8.127-8.121 (d, J=1.8 Hz, 1H), 7.710-7.681 (d, J=8.7 Hz, 1H), 7.658-7.624 (dd, J=1.8, 8.4 Hz, 1H), 7.577-7.554 (d, J=6.9 Hz, 2H), 7.357-7.329 (d, J=8.4 Hz, 1H), 7.274 (s, 1H), 7.204-7.170 (dd, J=2.1, 8.4 Hz, 1H), 7.060-7.033 (d, J=8.1 Hz, 1H), 4.643-4.600 (m, 3H), 3.690 (s, 3H), 2.375-2.320 (m, 1H), 2.204 (s, 3H), 2.167 (s, 3H), 1.015-0.993 (d, J=6.6 Hz, 3H), 0.878-0.856 (d, J=6.6 Hz, 3H); MS (ESI): m/z 552 (M–H), m/z 554 (M+H).

Example 422

(S)-2-(6-(4-(3-(3,4-Dimethylphenyl)ureido)-2-(trifluoromethyl)phenyl)-1-oxoisoindolin-2-yl)-3-methylbutanoic acid The compound of example 422 was prepared analogous to the compound of example 394 by hydrolysis of the compound of example 421.
Yield: 92%; ¹H NMR (DMSO-d$_6$, 300 MHz): δ 13.042 (s, 1H), 9.080 (s, 1H), 8.640 (s, 1H), 8.124 (s, 1H), 7.698-7.551 (m, 4H), 7.354-7.337 (d, J=8.5 Hz, 1H), 7.277 (s, 1H), 7.195-7.181 (d, J=7 Hz, 1H), 7.056-7.040 (d, J=8 Hz, 1H), 4.723-4.589 (dd, J=17.5 Hz, 2H), 4.555-4.536 (d, J=9.5 Hz, 1H), 2.328 (m, 1H), 2.202 (s, 3H), 2.168 (s, 3H), 1.046-1.033 (d, J=6.5 Hz, 3H), 0.896-0.882 (d, J=7 Hz, 3H); MS (ESI): m/z 538 (M–H), m/z 540 (M+H).

Example 423

(S)-Methyl 2-(6-(4-(4-tert-butylbenzamido)-2-(trifluoromethyl)phenyl)-1-oxoisoindolin-2-yl)-3-methylbutanoate The compound of example 423 was prepared analogous to the compound of example 403 by reaction of the compound of example 414 with 4-(t-butyl)benzoyl chloride.
Yield: 68%; ¹H NMR (DMSO-d$_6$, 300 MHz): δ 10.571 (s, 1H), 8.379-8.373 (d, J=1.8 Hz, 1H), 8.153-8.120 (dd, J=1.5, 8.4 Hz, 1H), 7.957-7.929 (d, J=8.4 Hz, 2H), 7.723-7.697 (d, J=7.8 Hz, 1H), 7.599-7.572 (d, J=8.1 Hz, 4H), 7.455-7.427 (d, J=8.4 Hz, 1H), 4.651-4.601 (m, 3H), 3.689 (s, 3H), 2.375-2.275 (m, 1H), 1.332 (s, 9H), 1.014-0.992 (d, J=6.6 Hz, 3H), 0.877-0.855 (d, J=6.6 Hz, 3H); MS (ESI): m/z 565 (M–H), m/z 567 (M+H).

Example 424

(S)-2-(6-(4-(4-tert-Butylbenzamido)-2-(trifluoromethyl)phenyl)-1-oxoisoindolin-2-yl)-3-methylbutanoic acid The compound of example 424 was prepared analogous to the compound of example 404 by hydrolysis of the compound of example 423.
Yield: 71%; ¹H NMR (DMSO-d$_6$, 300 MHz): δ 12.952 (s, 1H), 10.579 (s, 1H), 8.385-8.379 (d, J=1.8 Hz, 1H), 8.157-8.124 (dd, J=1.5, 8.4 Hz, 1H), 7.962-7.934 (d, J=8.4 Hz, 2H), 7.722-7.696 (d, J=7.8 Hz, 1H), 7.602-7.575 (m, 4H), 7.461-7.433 (d, J=8.4 Hz, 1H), 4.753-4.580 (d, J=16.2, 17.7 Hz, 2H), 4.559-4.528 (d, J=9.3 Hz, 1H), 2.336-2.305 (m, 1H), 1.298 (s, 9H), 1.051-1.029 (d, J=6.6 Hz, 3H), 0.900-0.877 (d, J=6.9 Hz, 3H); MS (ESI): m/z 551 (M–H), m/z 553 (M+H).

Example 425

(S)-Methyl 2-(6-(4-biphenyl-4-ylcarboxamido-2-(trifluoromethyl)phenyl)-1-oxoisoindolin-2-yl)-3-methylbutanoate The compound of example 425 was prepared analogous to the compound of example 403 by reaction of the compound of example 414 with 4-phenyl benzoyl chloride.
Yield: 72%; ¹H NMR (DMSO-d$_6$, 300 MHz): δ 10.701 (s, 1H), 8.412-8.406 (d, J=1.8 Hz, 1H), 8.198-8.165 (dd, J=1.2, 8.7 Hz, 1H), 8.138-8.110 (d, J=8.4 Hz, 2H), 7.904-7.876 (d, J=8.4 Hz, 2H), 7.801-7.776 (d, J=7.5 Hz, 2H), 7.733-7.707 (d, J=7.8 Hz, 1H), 7.615-7.589 (d, J=7.8 Hz, 2H), 7.554-7.505 (t, J=6.9, 7.8 Hz, 2H), 7.480-7.442 (m, 2H), 4.660-4.609 (m, 3H), 3.696 (s, 3H), 2.382-2.305 (m, 1H), 1.020-0.998 (d, J=6.6 Hz, 3H), 0.884-0.862 (d, J=6.6 Hz, 3H); MS (ESI): m/z 585 (M–H), m/z 587 (M+H).

Example 426

(S)-2-(6-(4-Biphenyl-4-ylcarboxamido-2-(trifluoromethyl)phenyl)-1-oxoisoindolin-2-yl)-3-methylbutanoic acid The compound of example 426 was prepared analogous to the compound of example 404 by hydrolysis of the compound of example 425.
Yield: 82%; ¹H NMR (DMSO-d$_6$, 300 MHz): δ 13.038 (s, 1H), 10.695 (s, 1H), 8.408-8.403 (d, J=1.5 Hz, 1H), 8.193-8.164 (d, J=8.7 Hz, 1H), 8.134-8.107 (d, J=8.1 Hz, 2H), 7.899-7.872 (d, J=8.1 Hz, 2H), 7.797-7.772 (d, J=7.5 Hz, 2H), 7.725-7.700 (d, J=7.5 Hz, 1H), 7.607-7.577 (d, J=9 Hz, 2H), 7.551-7.501 (t, J=7.2, 7.8 Hz, 2H), 7.461-7.414 (m, 2H), 4.751-4.583 (dd, J=14.4, 18 Hz, 2H), 4.564-4.532 (d, J=9.6 Hz, 1H), 2.381-2.283 (m, 1H), 1.050-1.029 (d, J=6.3 Hz, 3H), 0.900-0.878 (d, J=6.6 Hz, 3H); MS (ESI): m/z 571 (M−H), m/z 573 (M+H).

Example 427

(S)-Methyl 2-(6-(4-(2-naphthamido)-2-(trifluoromethyl)phenyl)-1-oxoisoindolin-2-yl)-3-methylbutanoate The compound of example 427 was prepared analogous to the compound of example 403 by reaction of the compound of example 414 with 2-naphthoyl chloride.

Yield: 70%; $^1$H NMR (DMSO-$d_6$, 300 MHz): δ 10.840 (s, 1H), 8.653 (s, 1H), 8.421-8.415 (d, J=1.8 Hz, 1H), 8.235-8.207 (dd, J=8.4 Hz, 1H), 8.138-8.030 (m, 4H), 7.738-7.711 (d, J=8.1 Hz, 1H), 7.688-7.648 (m, 2H), 7.624-7.599 (d, J=7.5 Hz, 2H), 7.498-7.470 (d, J=8.4 Hz, 1H), 4.661-4.611 (m, 3H), 3.697 (s, 3H), 2.361-2.305 (m, 1H), 1.021-0.999 (d, J=6.6 Hz, 3H), 0.886-0.864 (d, J=6.6 Hz, 3H); MS (ESI): m/z 559 (M−H), m/z 561 (M+H).

Example 428

(S)-2-(6-(4-(2-Naphthamido)-2-(trifluoromethyl)phenyl)-1-oxoisoindolin-2-yl)-3-methylbutanoic acid The compound of example 428 was prepared analogous to the compound of example 404 by hydrolysis of the compound of example 427.

Yield: 85%; $^1$H NMR (DMSO-$d_6$, 300 MHz): δ 13.060 (s, 1H), 10.839 (s, 1H), 8.652 (s, 1H), 8.414 (s, 1H), 8.228-8.202 (dd, J=7.8 Hz, 1H), 8.133-7.990 (m, 4H), 7.729-7.703 (d, J=7.8 Hz, 1H), 7.675-0.7586 (m, 4H), 7.495-7.467 (d, J=8.4 Hz, 1H), 4.753-4.585 (dd, J=14.7, 17.7 Hz, 2H), 4.566-4.534 (d, J=9.6 Hz, 1H), 2.382-2.269 (m, 1H), 1.051-1.030 (d, J=6.3 Hz, 3H), 0.902-0.880 (d, J=6.6 Hz, 3H); MS (ESI) m/z: 545 (M−H), m/z 547 (M+H).

Example 429

(S)-Methyl 3-methyl-2-(1-oxo-6-(4-(4-pentylbenzamido)-2-(trifluoromethyl)phenyl)isoindolin-2-yl)butanoate The compound of example 429 was prepared analogous to the compound of example 403 by reaction of the compound of example 414 with 4-(n-pentyl)benzoyl chloride.

Yield: 67%; $^1$H NMR (DMSO-$d_6$, 300 MHz): δ 10.560 (s, 1H), 8.368 (s, 1H), 8.156-8.128 (d, J=8.4 Hz, 1H), 7.941-7.915 (d, J=7.8 Hz, 2H), 7.721-7.695 (d, J=7.8 Hz, 1H), 7.599-7.573 (d, J=7.8 Hz, 2H), 7.452-7.425 (d, J=8.1 Hz, 1H), 7.397-7.370 (d, J=8.1 Hz, 2H), 4.649-4.601 (m, 3H), 3.688 (s, 3H), 2.692-2.642 (t, J=7.5 Hz, 2H), 2.374-2.298 (m, 1H), 1.638-1.592 (m, 2H), 1.307-1.297 (m, 4H), 1.013-0.992 (d, J=6.3 Hz, 3H), 0.875-0.854 (m, 6H); MS (ESI): m/z 579 (M−H), m/z 581 (M+H).

Example 430

(S)-3-Methyl-2-(1-oxo-6-(4-(4-pentylbenzamido)-2-(trifluoromethyl)phenyl)isoindolin-2-yl)butanoic acid The compound of example 430 was prepared analogous to the compound of example 404 by hydrolysis of the compound of example 429.

Yield: 79%; $^1$H NMR (DMSO-$d_6$, 300 MHz): δ 13.014 (s, 1H), 10.569 (s, 1H), 8.379-8.373 (d, J=1.8 Hz, 1H), 8.162-8.134 (d, J=8.4 Hz, 1H), 7.947-7.920 (d, J=8.1 Hz, 2H), 7.722-7.696 (d, J=7.8 Hz, 1H), 7.599-7.570 (d, J=8.7 Hz, 2H), 7.459-7.431 (d, J=8.4 Hz, 1H), 7.402-7.375 (d, J=8.1 Hz, 2H), 4.689-4.582 (dd, J=14.1, 18 Hz, 2H), 4.563-4.532 (d, J=9.3 Hz, 1H), 2.696-2.646 (t, J=7.2, 7.8 Hz, 2H), 2.360-2.283 (m, 1H), 1.643-1.573 (m, 2H), 1.355-1.236 (m, 4H), 1.051-1.029 (d, J=6.6 Hz, 3H), 0.900-0.878 (m, 6H); MS (ESI): m/z 565 (M−H), m/z 567 (M+H).

Example 431

(S)-Methyl 2-(6-(4-(4-butoxybenzamido)-2-(trifluoromethyl)phenyl)-1-oxoisoindolin-2-yl)-3-methylbutanoate The compound of example 431 was prepared analogous to the compound of example 403 by reaction of the compound of example 414 with 4-(n-butoxy)benzoyl chloride.

Yield: 71%; $^1$H NMR (DMSO-$d_6$, 300 MHz): δ 10.476 (s, 1H), 8.370-8.364 (d, J=1.8 Hz, 1H), 8.159-8.131 (d, J=8.4 Hz, 1H), 8.015-7.986 (d, J=8.7 Hz, 2H), 7.725-7.697 (d, J=8.7 Hz, 1H), 7.602-7.577 (d, J=7.5 Hz, 2H), 7.448-7.420 (d, J=8.4 Hz, 1H), 7.108-7.079 (d, J=8.7 Hz, 2H), 4.654-4.604 (m, 3H), 4.100-4.057 (t, J=6.3, 6.6 Hz, 2H), 3.693 (s, 3H), 2.356-2.323 (m, 1H), 1.762-1.691 (m, 2H), 1.449-1.424 (m, 2H), 1.017-0.995 (d, J=6.6 Hz, 3H), 0.978-0.929 (t, J=7.2, 7.5 Hz, 3H), 0.880-0.858 (d, J=6.6 Hz, 3H); MS (ESI): m/z 581 (M−H), m/z 583 (M+H).

Example 432

(S)-2-(6-(4-(4-Butoxybenzamido)-2-(trifluoromethyl)phenyl)-1-oxoisoindolin-2-yl)-3-methylbutanoic acid The compound of example 432 was prepared analogous to the compound of example 404 by hydrolysis of the compound of example 431.

Yield: 82%; $^1$H NMR (DMSO-$d_6$, 300 MHz): δ 13.014 (s, 1H), 10.476 (s, 1H), 8.366-8.361 (d, J=1.3 Hz, 1H), 8.154-8.126 (d, J=8.4 Hz, 1H), 8.012-7.982 (d, J=9 Hz, 2H), 7.715-7.690 (d, J=7.5 Hz, 1H), 7.592-7.565 (d, J=8.1 Hz, 2H), 7.446-7.418 (d, J=8.4 Hz, 1H), 7.104-7.075 (d, J=8.7 Hz, 2H), 4.747-4.575 (dd, J=15.6, 18 Hz, 2H), 4.556-4.524 (d, J=9.6 Hz, 1H), 4.097-4.057 (t, J=6.3, 6.6 Hz, 2H), 2.377-2.279 (m, 1H), 1.780-1.688 (m, 2H), 1.520-1.397 (m, 2H), 1.047-1.025 (d, J=6.6 Hz, 3H), 0.974-0.925 (t, J=7.2, 7.5 Hz, 3H), 0.896-0.874 (d, J=6.6 Hz, 3H); MS (ESI): m/z 567 (M−H), m/z 569 (M+H).

Example 433

(S)-Methyl 2-(6-(3-fluoro-4-nitrophenyl)-1-oxoisoindolin-2-yl)-3-methyl butanoate The compound of example 433 was prepared analogous to the compound of example 391 by reaction of the compound of example 390, 1-bromo-4-nitro-3-fluoro benzene and Pd(dppf)Cl$_2$: CH$_2$Cl$_2$.

Yield: 74%; $^1$H NMR (DMSO-$d_6$, 300 MHz): δ 8.275-8.220 (t, J=8.1, 8.4 Hz, 1H), 8.129 (s, 1H), 8.113-8.081 (m, 1H), 8.060-8.054 (d, J=1.8 Hz, 1H), 7.888-7.855 (dd, J=1.2, 8.4 Hz, 1H), 7.811-7.784 (d, J=8.1 Hz, 1H), 4.659-4.591 (m, 3H), 3.687 (s, 3H), 2.436-2.319 (m, 1H), 1.016-0.994 (d, J=6.6 Hz, 3H), 0.866-0.844 (d, J=6.6 Hz, 3H); MS (ESI): m/z 385 (M−H), m/z 387 (M+H).

Example 434

(S)-Methyl 2-(6-(4-amino-3-fluorophenyl)-1-oxoisoindolin-2-yl)-3-methyl butanoate The compound of example 434 was prepared analogous to the compound of example 392 by reduction of the compound of example 433.
Yield: 81.8%; $^1$H NMR (DMSO-d$_6$, 300 MHz): δ 7.866-7.833 (m, 2H), 8.645-7.619 (d, J=7.8 Hz, 1H), 7.449-7.399 (dd, J=1.8, 12 Hz, 1H), 7.322-7.289 (dd, J=1.8, 8.4 Hz, 1H), 6.881-6.822 (t, J=8.7, 9 Hz, 1H), 5.354 (s, 2H), 4.626-4.563 (m, 3H), 3.679 (s, 3H), 2.357-2.279 (m, 1H), 1.006-0.984 (d, J=6.6 Hz, 3H), 0.852-0.830 (d, J=6.6 Hz, 3H); MS (ESI): m/z 355 (M−H), m/z 357 (M+H).

Example 435

(S)-Methyl 2-(6-(4-(3-(3,4-dimethylphenyl)ureido)-3-fluorophenyl)-1-oxoisoindolin-2-yl)-3-methylbutanoate The compound of example 435 was prepared analogous to the compound of example 393 by reaction of the compound of example 434 with 3,4-dimethyl phenyl isocyanate.
Yield: 77%; $^1$H NMR (DMSO-d$_6$, 300 MHz): δ 8.946 (s, 1H), 8.625-8.617 (d, J=2.4 Hz, 1H), 8.317-8.259 (m, 1H), 7.971-7.954 (m, 2H), 7.719-7.668 (m, 2H), 7.583-7.555 (d, J=8.4 Hz, 1H), 7.179-7.123 (m, 2H), 7.065-6.994 (m, 1H), 4.641-4.608 (m, 3H), 3.686 (s, 3H), 2.370-2.269 (m, 1H), 2.206 (s, 3H), 2.167 (s, 3H), 1.015-0.993 (d, J=6.6 Hz, 3H), 0.863-0.841 (d, J=6.6 Hz, 3H); MS (ESI): m/z 502 (M−H), m/z 504 (M+H).

Example 436

(S)-2-(6-(4-(3-(3,4-Dimethylphenyl)ureido)-3-fluorophenyl)-1-oxoisoindolin-2-yl)-3-methylbutanoic acid The compound of example 436 was prepared analogous to the compound of example 394 by hydrolysis of the compound of example 435.
Yield: 82%; $^1$H NMR (DMSO-d$_6$, 300 MHz): δ 13.033 (s, 1H), 8.946 (s, 1H), 8.623 (s, 1H), 7.957-7.941 (d, J=8.7 Hz, 2H), 7.715-7.672 (m, 2H), 7.582-7.553 (d, J=8.7 Hz, 1H), 7.249-7.129 (m, 2H), 7.064-7.993 (d, J=8.4 Hz, 2H), 4.708-4.564 (d, J=17.7, 18 Hz, 2H), 4.564-4.531 (d, J=9.9 Hz, 1H), 2.323-2.269 (m, 1H), 2.206 (s, 3H), 2.166 (s, 3H), 1.046-1.024 (d, J=6.6 Hz, 3H), 0.878-0.856 (d, J=6.6 Hz, 3H); MS (ESI): m/z 488 (M−H), m/z 490 (M+H).

Example 437

(S)-Methyl 2-(6-(4-(3-(2,3-dihydro-1H-inden-5-yl)ureido)-3-fluorophenyl)-1-oxoisoindolin-2-yl)-3-methylbutanoate The compound of example 437 was prepared analogous to the compound of example 393 by reaction of the compound of example 434 with 2,3-dihydro-1H-indene-5-isocyanate.
Yield: 87%; $^1$H NMR (DMSO-d$_6$, 300 MHz): δ 8.989 (s, 1H), 8.629-8.621 (d, J=2.4 Hz, 1H), 7.971-7.949 (m, 2H), 7.719-7.669 (m, 2H), 7.584-7.551 (d, J=1.5, 8.4 Hz, 1H), 7.407-7.368 (d, J=8.4 Hz, 2H), 7.146-7.077 (m, 2H), 4.641-4.544 (m, 3H), 3.686 (s, 3H), 2.871-2.726 (m, 4H), 2.370-2.275 (m, 1H), 2.058-1.946 (m, 2H), 1.015-0.993 (d, J=6.6 Hz, 3H), 0.863-0.841 (d, J=6.6 Hz, 3H); MS (ESI): m/z 514 (M−H), m/z 516 (M+H).

Example 438

(S)-2-(6-(4-(3-(2,3-Dihydro-1H-inden-5-yl)ureido)-3-fluorophenyl)-1-oxoisoindolin-2-yl)-3-methylbutanoic acid The compound of example 438 was prepared analogous to the compound of example 394 by hydrolysis of the compound of example 437.
Yield: 82%; $^1$H NMR (DMSO-d$_6$, 300 MHz): δ 13.033 (s, 1H), 8.995 (s, 1H), 8.630-8.622 (d, J=2.4 Hz, 1H), 7.958-7.943 (m, 2H), 7.716-7.670 (m, 2H), 7.586-7.553 (d, J=1.5, 8.4 Hz, 1H), 7.408-7.368 (d, J=8.4 Hz, 2H), 7.146-7.107 (m, 2H), 4.648-4.531 (m, 3H), 2.870-2.760 (m, 4H), 2.370-2.270 (m, 1H), 2.033-1.970 (m, 2H), 1.046-1.025 (d, J=6.3 Hz, 3H), 0.878-0.856 (d, J=6.6 Hz, 3H); MS (ESI): m/z 500 (M−H), m/z 502 (M+H).

Example 439

(S)-Methyl 2-(6-(4-(3-(3,4-difluorophenyl)ureido)-3-fluorophenyl)-1-oxoisoindolin-2-yl)-3-methylbutanoate The compound of example 439 was prepared analogous to the compound of example 393 by reaction of the compound of example 434 with 3,4-difluorophenyl isocyanate.
Yield: 85%; $^1$H NMR (DMSO-d$_6$, 300 MHz): δ 9.308 (s, 1H), 8.728 (s, 1H), 8.263-8.206 (t, J=8.4, 8.7 Hz, 1H), 7.972-7.950 (m, 2H), 7.740-7.664 (m, 3H), 7.600-7.566 (m, 1H), 7.422-7.326 (m, 1H), 7.138-7.108 (m, 1H), 4.641-4.607 (m, 3H), 3.686 (s, 3H), 2.369-2.291 (m, 1H), 1.014-0.992 (d, J=6.6 Hz, 3H), 0.862-0.840 (d, J=6.6 Hz, 3H); MS (ESI): m/z 510 (M−H), m/z 512 (M+H).

Example 440

(S)-2-(6-(4-(3-(3,4-Difluorophenyl)ureido)-3-fluorophenyl)-1-oxoisoindolin-2-yl)-3-methylbutanoic acid The compound of example 440 was prepared analogous to the compound of example 394 by hydrolysis of the compound of example 439.
Yield: 93%; $^1$H NMR (DMSO-d$_6$, 300 MHz): δ 13.052 (s, 1H), 9.604 (s, 1H), 8.838 (s, 1H), 8.259-8.202 (t, J=8.4 Hz, 1H), 7.961-7.945 (m, 2H), 7.719-7.678 (m, 3H), 7.596-7.567 (d, J=8.7 Hz, 1H), 7.388-7.354 (m, 1H), 7.144-7.116 (m, 1H), 4.710-4.529 (m, 3H), 2.345-2.269 (m, 1H), 1.045-1.023 (d, J=6.6 Hz, 3H), 0.876-0.854 (d, J=6.6 Hz, 3H); MS (ESI): m/z 496 (M−H), m/z 498 (M+H).

Example 441

(S)-Methyl 2-(6-(4-(3-(2-chlorophenyl)ureido)-3-fluorophenyl)-1-oxoisoindolin-2-yl)-3-methylbutanoate The compound of example 441 was prepared analogous to the compound of example 393 by reaction of the compound of example 434 with 2-chlorophenyl isocyanate. The compound of example 441 was used directly for the preparation of the compound of example 442 without purification.

Example 442

(S)-2-(6-(4-(3-(2-Chlorophenyl)ureido)-3-fluorophenyl)-1-oxoisoindolin-2-yl)-3-methylbutanoic acid The compound of example 442 was prepared analogous to the compound of example 394 by hydrolysis of the compound of example 441.
Yield: 85%; $^1$H NMR (DMSO-d$_6$, 300 MHz): δ 13.033 (s, 1H), 9.485 (s, 1H), 9.038 (s, 1H), 8.319-8.262 (t, J=8.4 Hz, 8.7 Hz, 1H), 8.186-8.158 (d, J=8.4 Hz, 1H), 8.087-8.059 (d, J=8.4 Hz, 1H), 7.736-7.693 (m, 2H), 7.604-7.576 (d, J=8.4 Hz, 1H), 7.490-7.463 (d, J=8.1 Hz, 2H), 7.091-7.040 (t, J=7.5, 7.8 Hz, 2H), 4.713-4.532 (m, 3H), 2.347-2.271 (m, 1H), 1.047-1.025 (d, J=6.6 Hz, 3H), 0.879-0.857 (d, J=6.6 Hz, 3H); MS (ESI): m/z 494 (M−H), m/z 496 (M+H).

Example 443

(S)-Methyl 2-(6-(4-(4-tert-butylbenzamido)-3-fluorophenyl)-1-oxoisoindolin-2-yl)-3-methylbutanoate The compound of example 443 was prepared analogous to the compound of example 403 by reaction of the compound of example 434 with 4-(t-butyl)benzoyl chloride.
Yield: 83%; $^1$H NMR (DMSO-d$_6$, 300 MHz): δ 10.123 (s, 1H), 8.021-8.000 (m, 2H), 7.955-7.927 (d, J=8.4 Hz, 2H), 7.767-7.746 (m, 2H), 7.727-7.721 (d, J=1.8 Hz, 1H), 7.646-7.618 (d, J=8.4 Hz, 1H), 7.581-7.553 (d, J=8.4 Hz, 2H), 4.648-4.615 (m, 3H), 3.689 (s, 3H), 2.395-2.265 (m, 1H), 1.332 (s, 9H), 1.018-0.996 (d, J=6.6 Hz, 3H), 0.869-0.846 (d, J=6.9 Hz, 3H); MS (ESI): m/z 515 (M−H), m/z 517 (M+H).

Example 444

(S)-2-(6-(4-(4-tert-Butylbenzamido)-3-fluorophenyl)-1-oxoisoindolin-2-yl)-3-methylbutanoic acid The compound of example 444 was prepared analogous to the compound of example 404 by hydrolysis of the compound of example 443.
Yield: 86%; $^1$H NMR (DMSO-d$_6$, 300 MHz): δ 13.052 (s, 1H), 10.121 (s, 1H), 8.010-7.991 (d, J=5.7 Hz, 2H), 7.957-7.929 (d, J=8.4 Hz, 2H), 7.776-7.723 (m, 3H), 7.646-7.618 (d, J=8.4 Hz, 1H), 7.581-7.553 (d, J=8.4 Hz, 2H), 4.732-4.570 (dd, J=17.7, 19.2 Hz, 2H), 4.570-4.538 (d, J=9.6 Hz, 1H), 2.352-2.276 (m, 1H), 1.331 (s, 9H), 1.016-0.994 (d, J=6.6 Hz, 3H), 0.866-0.844 (d, J=6.6 Hz, 3H); MS (ESI): m/z 501 (M−H), m/z 503 (M+H).

Example 445

(S)-Methyl 2-(6-(3-fluoro-4-(4-pentylbenzamido)phenyl)-1-oxoisoindolin-2-yl)-3-methylbutanoate The compound of example 445 was prepared analogous to the compound of example 403 by reaction of the compound of example 434 with 4-(n-pentyl)benzoyl chloride.
Yield: 83%; $^1$H NMR (DMSO-d$_6$, 300 MHz): δ 10.124 (s, 1H), 8.020-7.999 (m, 2H), 7.939-7.912 (d, J=8.1 Hz, 2H), 7.575-7.708 (m, 3H), 7.644-7.610 (d, J=1.8, 8.4 Hz, 1H), 7.380-7.353 (d, J=8.1 Hz, 2H), 4.648-4.616 (m, 3H), 3.690 (s, 3H), 2.692-2.642 (t, J=7.5 Hz, 2H), 2.400-2.275 (m, 1H), 1.666-1.570 (m, 2H), 1.361-1.263 (m, 4H), 1.019-0.997 (d, J=6.6 Hz, 3H), 0.896-0.849 (m, 6H); MS (ESI): m/z 529 (M−H), m/z 531 (M+H).

Example 446

(S)-2-(6-(3-Fluoro-4-(4-pentylbenzamido)phenyl)-1-oxoisoindolin-2-yl)-3-methylbutanoic acid The compound of example 446 was prepared analogous to the compound of example 404 by hydrolysis of the compound of example 443.
Yield: 83%; $^1$H NMR (DMSO-d$_6$, 300 MHz): δ 13.014 (s, 1H), 10.118 (s, 1H), 8.009-7.991 (m, 2H), 7.939-7.912 (d, J=8.1 Hz, 2H), 7.764-7.712 (m, 3H), 7.644-7.617 (d, J=8.1 Hz, 1H), 7.380-7.353 (d, J=8.1 Hz, 2H), 4.730-4.549 (dd, J=18 Hz, 2H), 4.571-4.539 (d, J=9.6 Hz, 1H), 2.691-2.640 (t, J=7.5 Hz, 2H), 2.354-2.277 (m, 1H), 1.639-1.568 (m, 2H), 1.360-1.263 (m, 4H), 1.051-1.029 (d, J=6.6 Hz, 3H), 0.885-0.851 (m, 6H); MS (ESI): m/z 515 (M−H), m/z 517 (M+H).

Example 447

(S)-Methyl 2-(6-(4-biphenyl-4-ylcarboxamido-3-fluorophenyl)-1-oxoisoindolin-2-yl)-3-methylbutanoate The compound of example 447 was prepared analogous to the compound of example 403 by reaction of the compound of example 434 with 4-phenyl benzoyl chloride. The compound of example 447 was used directly for the preparation of the compound of example 448 without purification.

Example 448

(S)-2-(6-(4-Biphenyl-4-ylcarboxamido-3-fluorophenyl)-1-oxoisoindolin-2-yl)-3-methylbutanoic acid The compound of example 448 was prepared analogous to the compound of example 404 by hydrolysis of the compound of example 447.
Yield: 88%; $^1$H NMR (DMSO-d$_6$, 300 MHz): δ 13.035 (s, 1H), 10.268 (s, 1H), 8.125-8.097 (d, J=8.4 Hz, 2H), 8.022-8.004 (m, 2H), 7.883-7.885 (d, J=8.4 Hz, 2H), 7.815-7.731 (m, 5H), 7.667-7.634 (dd, J=1.8, 8.4 Hz, 1H), 7.552-7.503 (t, J=7.2, 7.5 Hz, 2H), 7.463-7.439 (d, J=7.2 Hz, 1H), 4.736-4.555 (dd, J=18, 18.3 Hz, 2H), 4.575-4.543 (d, J=9.6 Hz, 1H), 2.420-2.281 (m, 1H), 1.054-1.032 (d, J=6.6 Hz, 3H), 0.888-0.866 (d, J=6.6 Hz, 3H); MS (ESI): m/z 521 (M−H), m/z 523 (M+H).

Example 449

(S)-Methyl 2-(6-(4-(2-naphthamido)-3-fluorophenyl)-1-oxoisoindolin-2-yl)-3-methylbutanoate The compound of example 449 was prepared analogous to the compound of example 403 by reaction of the compound of example 434 with 2-naphthoyl chloride.
Yield: 77%; $^1$H NMR (DMSO-d$_6$, 300 MHz): δ 10.399 (s, 1H), 8.652 (s, 1H), 8.128-8.098 (dd, J=2.1, 9 Hz, 1H), 8.072-8.018 (m, 5H), 7.802-7.737 (m, 3H), 7.678-7.637 (m, 3H), 4.639-4.622 (m, 3H), 3.694 (s, 3H), 2.357-2.324 (m, 1H), 1.022-1.000 (d, J=6.6 Hz, 3H), 0.875-0.852 (d, J=6.9 Hz, 3H); MS (ESI): m/z 509 (M−H), m/z 511 (M+H).

Example 450

(S)-2-(6-(4-(2-Naphthamido)-3-fluorophenyl)-1-oxoisoindolin-2-yl)-3-methyl butanoic acid The compound of example 450 was prepared analogous to the compound of example 404 by hydrolysis of the compound of example 449.

Yield: 69%; $^1$H NMR (DMSO-d$_6$, 300 MHz): δ 10.403 (s, 1H), 8.654 (s, 1H), 8.127-8.001 (m, 6H), 7.830-7.728 (m, 3H), 7.695-7.617 (m, 3H), 4.766-4.544 (dd, J=18 Hz, 2H), 4.544-4.513 (d, J=9.3 Hz, 1H), 2.346-2.271 (m, 1H), 1.048-1.026 (d, J=6.6 Hz, 3H), 0.879-0.857 (d, J=6.6 Hz, 3H); MS (ESI): m/z 495 (M−H), m/z 497 (M+H).

Example 451

(S)-Methyl 2-(6-(4-(4-butoxybenzamido)-3-fluorophenyl)-1-oxoisoindolin-2-yl)-3-methyl butanoate The compound of example 451 was prepared analogous to the compound of example 403 by reaction of the compound of example 434 with 4-(n-butoxy)benzoyl chloride.

Yield: 73%; $^1$H NMR (DMSO-d$_6$, 300 MHz): δ 10.042 (s, 1H), 8.889-8.863 (dd, J=1.5, 6.3 Hz, 1H), 8.016-7.938 (m, 4H), 7.752-7.724 (d, J=8.4 Hz, 2H), 7.634-7.600 (dd, J=1.8, 8.4 Hz, 1H), 7.082-7.053 (d, J=8.7 Hz, 2H), 4.647-4.561 (m, 3H), 4.091-4.047 (t, J=6.6 Hz, 2H), 3.688 (s, 3H), 2.396-2.275 (m, 1H), 1.780-1.687 (m, 2H), 1.520-1.397 (m, 2H), 1.017-0.995 (d, J=6.6 Hz, 3H), 0.976-0.926 (t, J=7.5 Hz, 3H), 0.868-0.846 (d, J=6.6 Hz, 3H); MS (ESI) m/z 531 (M−H), m/z 533 (M+H).

Example 452

(S)-2-(6-(4-(4-Butoxybenzamido)-3-fluorophenyl)-1-oxoisoindolin-2-yl)-3-methyl butanoic acid The compound of example 452 was prepared analogous to the compound of example 404 by hydrolysis of the compound of example 451.

Yield: 60%; $^1$H NMR (DMSO-d$_6$, 300 MHz): δ 10.036 (s, 1H), 7.996-7.967 (m, 4H), 7.749-7.697 (m, 3H), 7.631-7.603 (d, J=8.4 Hz, 1H), 7.082-7.052 (d, J=9 Hz, 2H), 4.797-4.463 (m, 3H), 4.091-4.048 (t, J=6.3, 6.6 Hz, 2H), 2.326-2.250 (m, 1H), 1.781-1.688 (m, 2H), 1.522-1.423 (m, 2H), 1.034-1.012 (d, J=6.6 Hz, 3H), 0.977-0.928 (t, J=7.2, 7.5 Hz, 3H), 0.858-0.836 (d, J=6.6 Hz, 3H); MS (ESI): m/z 517 (M−H), m/z 519 (M+H).

Example 453

(S)-Methyl 2-(6-(2-methoxy-4-nitrophenyl)-1-oxoisoindolin-2-yl)-3-methyl butanoate The compound of example 453 was prepared analogous to the compound of example 391 by reaction of the compound of example 390, 1-bromo-2-methoxy-4-nitro benzene and Pd(dppf)Cl$_2$: CH$_2$Cl$_2$.

Yield: 73%; $^1$H NMR (DMSO-d$_6$, 300 MHz): δ 7.957-7.922 (dd, J=2.1, 8.4 Hz, 1H), 7.908-7.901 (d, J=2.1 Hz, 1H), 7.837 (s, 1H), 7.805-7.773 (dd, J=1.5, 8.1 Hz, 1H), 7.743-7.717 (d, J=7.8 Hz, 1H), 7.66-7.638 (d, J=8.4 Hz, 1H), 4.633-4.599 (m, 3H), 3.926 (s, 3H), 3.683 (s, 3H), 2.374-2.314 (m, 1H), 1.014-0.992 (d, J=6.6 Hz, 3H), 0.872-0.849 (d, J=6.9 Hz, 3H); MS (ESI) m/z 399 (M+H).

Example 454

(S)-Methyl 2-(6-(4-amino-2-methoxyphenyl)-1-oxoisoindolin-2-yl)-3-methyl butanoate The compound of example 454 was prepared analogous to the compound of example 392 by reduction of the compound of example 453.

Yield: 85%; $^1$H NMR (DMSO-d$_6$, 300 MHz): δ 7.679 (s, 1H), 7.621-7.536 (dd, J=1.2, 8.1 Hz, 1H), 7.576-7.548 (d, J=8.4 Hz, 1H), 7.016-6.989 (d, J=8.1 Hz, 1H), 6.337-6.332 (dd, J=1.5 Hz, 1H), 6.265-6.238 (d, J=1.5, 8.1 Hz, 1H), 5.306 (s, 2H), 4.612-4.542 (m, 3H), 3.691 (s, 3H), 3.675 (s, 3H), 2.362-2.272 (m, 1H), 1.004-0.982 (d, J=6.6 Hz, 3H), 0.857-0.835 (d, J=6.6 Hz, 3H); MS (ESI) m/z 369 (M+H).

Example 455

(S)-Methyl 2-(6-(4-(4-tert-butylbenzamido)-2-methoxyphenyl)-1-oxoisoindolin-2-yl)-3-methyl butanoate The compound of example 455 was prepared analogous to the compound of example 403 by reaction of the compound of example 454 with 4-(t-butyl)benzoyl chloride.

Yield: 78%; $^1$H NMR (DMSO-d$_6$, 300 MHz): δ 10.295 (s, 1H), 7.940-7.912 (d, J=8.4 Hz, 2H), 7.779 (s, 1H), 7.724-7.713 (m, 2H), 7.670-7.644 (d, J=7.8 Hz, 1H), 7.586-7.526 (m, 3H), 7.350-7.322 (d, J=8.4 Hz, 1H), 4.634-4.600 (m, 3H), 3.798 (s, 3H), 3.686 (s, 3H), 2.373-2.275 (m, 1H), 1.335 (s, 9H), 1.017-0.995 (d, J=6.6 Hz, 3H), 0.873-0.851 (d, J=6.6 Hz, 3H); MS (ESI): m/z 527 (M−H), m/z 529 (M+H).

Example 456

(S)-2-(6-(4-(4-tert-Butylbenzamido)-2-methoxyphenyl)-1-oxoisoindolin-2-yl)-3-methylbutanoic acid The compound of example 456 was prepared analogous to the compound of example 404 by hydrolysis of the compound of example 455.

Yield: 70%; $^1$H NMR (DMSO-d$_6$, 300 MHz): δ 13.022 (s, 1H), 10.290 (s, 1H), 7.941-7.914 (d, J=8.1 Hz, 2H), 7.780 (s, 1H), 7.746-7.713 (m, 2H), 7.668-7.642 (d, J=7.8 Hz, 1H), 7.587-7.527 (m, 3H), 7.354-7.326 (d, J=8.4 Hz, 1H), 4.700-4.526 (dd, J=17.4, 17.7 Hz, 2H), 4.558-4.526 (d, J=9.6 Hz, 1H), 3.798 (s, 3H), 2.331-2.277 (m, 1H), 1.339 (s, 9H), 1.051-1.030 (d, J=6.3 Hz, 3H), 0.891-0.869 (d, J=6.6 Hz, 3H); MS (ESI): m/z 513 (M−H), m/z 515 (M+H).

Example 457

(S)-Methyl 2-(6-(4-biphenyl-4-ylcarboxamido-2-methoxyphenyl)-1-oxoisoindolin-2-yl)-3-methylbutanoate The compound of example 457 was prepared analogous to the compound of example 403 by reaction of the compound of example 454 with 4-phenyl benzoyl chloride.

Yield: 82%; $^1$H NMR (DMSO-d$_6$, 300 MHz): δ 10.428 (s, 1H), 8.122-8.095 (d, J=8.1 Hz, 2H), 7.947-7.857 (m, 3H), 7.794-7.735 (m, 5H), 7.677-7.651 (d, J=7.8 Hz, 1H), 7.599-7.503 (m, 2H), 7.462-7.438 (d, J=7.2 Hz, 1H), 7.370-7.343 (d, J=8.1 Hz, 1H), 4.664-4.540 (m, 3H), 3.809 (s, 3H), 3.688 (s, 3H), 2.411-2.276 (m, 1H), 1.019-0.997 (d, J=6.6 Hz, 3H), 0.876-0.854 (d, J=6.6 Hz, 3H); MS (ESI): m/z 547 (M−H), m/z 549 (M+H).

Example 458

(S)-2-(6-(4-Biphenyl-4-ylcarboxamido-2-methoxyphenyl)-1-oxoisoindolin-2-yl)-3-methylbutanoic acid The compound of example 458 was prepared analogous to the compound of example 404 by hydrolysis of the compound of example 457.
Yield: 96.4%; $^1$H NMR (DMSO-$d_6$, 300 MHz): δ 13.013 (s, 1H), 10.416 (s, 1H), 8.121-8.094 (d, J=8.1 Hz, 2H), 7.887-7.860 (d, J=8.1 Hz, 2H), 7.796-7.732 (m, 5H), 7.676-7.649 (d, J=8.1 Hz, 1H), 7.594-7.506 (m, 2H), 7.462-7.440 (d, J=6.6 Hz, 1H), 7.375-7.347 (d, J=8.4 Hz, 2H), 4.705-4.530 (m, 3H), 3.814 (s, 3H), 2.354-2.302 (m, 1H), 1.053-1.032 (d, J=6.3 Hz, 3H), 0.894-0.872 (d, J=6.6 Hz, 3H); MS (ESI): m/z 533 (M−H), m/z 535 (M+H).

Example 459

(S)-Methyl 2-(6-(4-(4-butoxybenzamido)-2-methoxyphenyl)-1-oxoisoindolin-2-yl)-3-methylbutanoate The compound of example 459 was prepared analogous to the compound of example 403 by reaction of the compound of example 454 with 4-(n-butoxy)benzoyl chloride.
Yield: 95%; $^1$H NMR (DMSO-$d_6$, 300 MHz): δ 10.214 (s, 1H), 8.540-8.479 (m, 1H), 8.020-7.999 (d, J=6.3 Hz, 2H), 8.004-7.975 (d, J=8.7 Hz, 2H), 7.777 (s, 1H), 7.668-7.641 (d, J=8.1 Hz, 1H), 7.338-7.311 (d, J=8.1 Hz, 1H), 7.088-7.059 (d, J=8.7 Hz, 2H), 4.658-4.598 (m, 3H), 4.093-4.050 (t, J=6.3, 6.6 Hz, 2H), 3.786 (s, 3H), 3.733 (s, 3H), 2.372-2.294 (m, 1H), 1.784-1.689 (m, 2H), 1.523-1.424 (m, 2H), 1.015-0.993 (d, J=6.6 Hz, 3H), 0.977-0.928 (t, J=7.2, 7.5 Hz, 3H), 0.872-0.850 (d, J=6.6 Hz, 3H); MS (ESI): m/z 543 (M−H), m/z 545 (M+H).

Example 460

(S)-2-(6-(4-(4-Butoxybenzamido)-2-methoxyphenyl)-1-oxoisoindolin-2-yl)-3-methylbutanoic acid The compound of example 460 was prepared analogous to the compound of example 404 by hydrolysis of the compound of example 459.
Yield: 72%; $^1$H NMR (DMSO-$d_6$, 300 MHz): δ 10.197 (s, 1H), 8.001-7.973 (d, J=8.4 Hz, 2H), 7.771 (s, 1H), 7.731-7.630 (m, 3H), 7.553-7.525 (d, J=8.4 Hz, 1H), 7.343-7.316 (d, J=8.1 Hz, 1H), 7.092-7.064 (d, J=8.4 Hz, 2H), 4.739-4.483 (m, 3H), 4.097-4.055 (t, J=6.3 Hz, 2H), 3.796 (s, 3H), 2.314-2.285 (m, 1H), 1.764-1.694 (m, 2H), 1.502-1.429 (m, 2H), 1.042-1.021 (d, J=6.3 Hz, 3H), 0.983-0.934 (t, J=7.2, 7.5 Hz, 3H), 0.876-0.855 (d, J=6.3 Hz, 3H); MS (ESI): m/z 529 (M−H), m/z 531 (M+H).

Example 461

(S)-Methyl 2-(6-(2-methoxy-4-(4-pentylbenzamido)phenyl)-1-oxoisoindolin-2-yl)-3-methylbutanoate The compound of example 461 was prepared analogous to the compound of example 403 by reaction of the compound of example 454 with 4-(n-pentyl)benzoyl chloride.
Yield: 59%; $^1$H NMR (DMSO-$d_6$, 300 MHz): δ 10.296 (s, 1H), 7.992-7.967 (d, J=7.5 Hz, 1H), 7.970-7.945 (d, J=7.5 Hz, 1H), 7.931-7.904 (d, J=8.1 Hz, 2H), 7.778 (s, 1H), 7.751-7.643 (m, 2H), 7.567-7.534 (dd, J=1.5, 8.1 Hz, 1H), 7.384-7.356 (d, J=8.4 Hz, 2H), 4.660-4.633 (m, 3H), 3.792 (s, 3H), 3.686 (s, 3H), 2.642-2.518 (t, J=7.2, 7.8 Hz, 2H), 2.418-2.274 (m, 1H), 1.668-1.570 (m, 2H), 1.362-1.266 (m, 4H), 1.016-0.994 (d, J=6.6 Hz, 3H), 0.924-0.851 (m, 6H); MS (ESI): m/z 541 (M−H), m/z 543 (M+H).

Example 462

(S)-2-(6-(2-Methoxy-4-(4-pentylbenzamido)phenyl)-1-oxoisoindolin-2-yl)-3-methylbutanoic acid The compound of example 462 was prepared analogous to the compound of example 404 by hydrolysis of the compound of example 461.
Yield: 82.8%; $^1$H NMR (DMSO-$d_6$, 300 MHz): δ 13.013 (s, 1H), 10.278 (s, 1H), 7.928-7.901 (d, J=8.1 Hz, 2H), 7.782 (s, 1H), 7.746-7.640 (m, 3H), 7.565-7.537 (d, J=8.4 Hz, 1H), 7.385-7.358 (d, J=8.4 Hz, 2H), 7.352-7.324 (d, J=8.4 Hz, 1H), 4.699-4.526 (m, 3H), 3.796 (s, 3H), 2.693-2.643 (t, J=7.2, 7.8 Hz, 2H), 2.353-2.276 (m, 1H), 1.644-1.597 (m, 2H), 1.314-1.268 (m, 4H), 1.051-1.029 (d, J=6.6 Hz, 3H), 0.925-0.876 (m, 6H); MS (ESI): m/z 527 (M−H), m/z 529 (M+H).

Example 463

(S)-Methyl 2-(6-(2-methoxy-4-(4-(trifluoromethoxy)benzamido)phenyl)-1-oxo isoindolin-2-yl)-3-methylbutanoate The compound of example 463 was prepared analogous to the compound of example 403 by reaction of the compound of example 454 with 4-trifluoromethoxy benzoyl chloride.
Yield: 59%; $^1$H NMR (DMSO-$d_6$, 300 MHz): δ 10.474 (s, 1H), 8.131-8.101 (d, J=9 Hz, 2H), 7.781 (s, 1H), 7.754-7.723 (d, J=1.5, 8.1 Hz, 1H), 7.674-7.648 (d, J=7.8 Hz, 2H), 7.578-7.513 (m, 3H), 7.369-7.341 (d, J=8.4 Hz, 1H), 4.634-4.601 (m, 3H), 3.797 (s, 3H), 3.687 (s, 3H), 2.364-2.255 (m, 1H), 1.017-0.995 (d, J=6.6 Hz, 3H), 0.874-0.852 (d, J=6.6 Hz, 3H); MS (ESI): m/z 555 (M−H), m/z 557 (M+H).

Example 464

(S)-2-(6-(2-Methoxy-4-(4-(trifluoromethoxy)benzamido)phenyl)-1-oxoisoindolin-2-yl)-3-methylbutanoic acid The compound of example 464 was prepared analogous to the compound of example 404 by hydrolysis of the compound of example 463.
Yield: 82.2%; $^1$H NMR (DMSO-$d_6$, 300 MHz): δ 13.022 (s, 1H), 10.471 (s, 1H), 8.132-8.103 (d, J=8.7 Hz, 2H), 7.782 (s, 1H), 7.748-7.721 (d, J=8.1 Hz, 1H), 7.672-7.645 (d, J=8.1 Hz, 2H), 7.579-7.520 (m, 3H), 7.371-7.344 (d, J=8.1 Hz, 1H), 4.701-4.526 (m, 3H), 3.800 (s, 3H), 2.330-2.277 (m, 1H), 1.051-1.029 (d, J=6.6 Hz, 3H), 0.890-0.868 (d, J=6.6 Hz, 3H); MS (ESI): m/z 541 (M−H), m/z 543 (M+H).

Example 465

(S)-Methyl 3-methyl-2-(6-(2-methyl-4-nitrophenyl)-1-oxoisoindolin-2-yl)butanoate The compound of example 465 was prepared analogous to the compound of example 391 by reaction of the compound of example 390, 1-bromo-2-methyl-4-nitro benzene and Pd(dppf)Cl$_2$: CH$_2$Cl$_2$.

Yield: 75%; ¹H NMR (DMSO-d₆, 300 MHz): δ 8.243-8.238 (d, J=1.5 Hz, 1H), 8.147-8.113 (dd, J=1.8, 8.4 Hz, 1H), 7.777-7.752 (d, J=7.5 Hz, 1H), 7.691-7.666 (d, J=7.5 Hz, 2H), 7.554-7.526 (d, J=8.4 Hz, 1H), 4.720-4.607 (m, 3H), 3.688 (s, 3H), 2.355 (s, 3H), 2.301-2.279 (m, 1H), 1.016-0.994 (d, J=6.6 Hz, 3H), 0.877-0.856 (d, J=6.3 Hz, 3H); MS (ESI): m/z 383 (M+H).

Example 466

(S)-Methyl 2-(6-(4-amino-2-methylphenyl)-1-oxoisoindolin-2-yl)-3-methyl butanoate The compound of example 466 was prepared analogous to the compound of example 392 by reduction of the compound of example 465.
Yield: 94.7%; ¹H NMR (DMSO-d₆, 300 MHz): δ 7.630-7.604 (d, J=7.8 Hz, 1H), 7.534-7.505 (d, J=8.7 Hz, 2H), 6.917-6.891 (d, J=7.8 Hz, 1H), 6.490-6.461 (d, J=8.7 Hz, 2H), 5.119 (s, 2H), 4.620-4.578 (m, 3H), 3.679 (s, 3H), 2.361-2.258 (m, 1H), 2.124 (s, 3H), 1.007-0.985 (d, J=6.6 Hz, 3H), 0.865-0.843 (d, J=6.6 Hz, 3H); MS (ESI): m/z 353 (M+H).

Example 467

(S)-Methyl 2-(6-(4-(4-tert-butylbenzamido)-2-methylphenyl)-1-oxoisoindolin-2-yl)-3-methylbutanoate The compound of example 467 was prepared analogous to the compound of example 403 by reaction of the compound of example 466 with 4-(t-butyl)benzoyl chloride.
Yield: 82%; ¹H NMR (DMSO-d₆, 300 MHz): δ 10.219 (s, 1H), 7.931-7.903 (d, J=8.4 Hz, 2H), 7.756-7.690 (m, 3H), 7.637-7.609 (d, J=8.4 Hz, 2H), 7.578-7.550 (d, J=8.4 Hz, 2H), 7.246-7.218 (d, J=8.4 Hz, 1H), 4.640-4.608 (m, 3H), 3.692 (s, 3H), 2.407-2.324 (m, 1H), 2.256 (s, 3H), 1.335 (s, 9H), 1.021-0.999 (d, J=6.6 Hz, 3H), 0.882-0.860 (d, J=6.6 Hz, 3H); MS (ESI): m/z 511 (M−H), m/z 513 (M+H).

Example 468

(S)-2-(6-(4-(4-tert-Butylbenzamido)-2-methylphenyl)-1-oxoisoindolin-2-yl)-3-methylbutanoic acid The compound of example 468 was prepared analogous to the compound of example 404 by hydrolysis of the compound of example 467.
Yield: 82%; ¹H NMR (DMSO-d₆, 300 MHz): δ 12.981 (s, 1H), 10.210 (s, 1H), 7.925-7.897 (d, J=8.4 Hz, 2H), 7.750 (s, 1H), 7.719-7.680 (m, 2H), 7.618-7.600 (m, 2H), 7.572-7.543 (d, J=8.7 Hz, 2H), 7.242-7.214 (d, J=8.4 Hz, 1H), 4.723-4.559 (dd, J=16.8, 18 Hz, 2H), 4.559-4.527 (d, J=9.6 Hz, 1H), 2.352-2.300 (m, 1H), 2.253 (s, 3H), 1.329 (s, 9H), 1.047-1.025 (d, J=6.6 Hz, 3H), 0.893-0.871 (d, J=6.6 Hz, 3H); MS (ESI): m/z 497 (M−H), m/z 499 (M+H).

Example 469

(S)-Methyl 2-(6-(4-biphenyl-4-ylcarboxamido-2-methylphenyl)-1-oxoisoindolin-2-yl)-3-methylbutanoate The compound of example 469 was prepared analogous to the compound of example 403 by reaction of the compound of example 466 with 4-phenyl benzoyl chloride.
Yield: 93%; ¹H NMR (DMSO-d₆, 300 MHz): δ 10.355 (s, 1H), 8.113-8.085 (d, J=8.4 Hz, 2H), 7.926-7.904 (d, J=6.6 Hz, 1H), 7.877-7.849 (d, J=8.4 Hz, 2H), 7.793-7.768 (d, J=7.5 Hz, 3H), 7.741-7.725 (m, 1H), 7.645-7.622 (d, J=6.9 Hz, 2H), 7.552-7.503 (d, J=7.2, 7.5 Hz, 2H), 7.461-7.437 (d, J=7.2 Hz, 1H), 7.267-7.239 (d, J=8.4 Hz, 1H), 4.639-4.571 (m, 3H), 3.694 (s, 3H), 2.404-2.306 (m, 1H), 2.271 (s, 3H), 1.023-1.001 (d, J=6.6 Hz, 3H), 0.885-0.863 (d, J=6.6 Hz, 3H); MS (ESI): m/z 531 (M−H), m/z 533 (M+H).

Example 470

(S)-2-(6-(4-Biphenyl-4-ylcarboxamido-2-methylphenyl)-1-oxoisoindolin-2-yl)-3-methylbutanoic acid The compound of example 470 was prepared analogous to the compound of example 404 by hydrolysis of the compound of example 469.
Yield: 88%; ¹H NMR (DMSO-d₆, 300 MHz): δ 13.019 (s, 1H), 10.340 (s, 1H), 8.106-8.078 (d, J=8.4 Hz, 2H), 7.872-7.844 (d, J=8.4 Hz, 2H), 7.787-7.763 (m, 3H), 7.734-7.715 (m, 1H), 7.688 (s, 1H), 7.763-7.614 (m, 2H), 7.546-7.497 (t, J=6.9 Hz, 2H), 7.456-7.431 (d, J=7.5 Hz, 1H), 7.264-7.237 (d, J=8.1 Hz, 1H), 4.728-4.565 (d, J=16.5, 18 Hz, 2H), 4.565-4.533 (d, J=9.6 Hz, 1H), 2.357-2.303 (m, 1H), 2.269 (s, 3H), 1.051-1.029 (d, J=6.6 Hz, 3H), 0.898-0.876 (d, J=6.6 Hz, 3H); MS (ESI): m/z 517 (M−H), m/z 519 (M+H).

Example 471

(S)-Methyl 2-(6-(4-(4-butoxybenzamido)-2-methylphenyl)-1-oxoisoindolin-2-yl)-3-methylbutanoate The compound of example 471 was prepared analogous to the compound of example 403 by reaction of the compound of example 466 with 4-(n-butoxy)benzoyl chloride.
Yield: 80%; ¹H NMR (DMSO-d₆, 300 MHz): δ 10.130 (s, 1H), 7.992-7.963 (d, J=8.7 Hz, 2H), 7.748-7.686 (m, 3H), 7.636-7.609 (d, J=8.1 Hz, 2H), 7.236-7.209 (d, J=8.1 Hz, 1H), 7.081-7.052 (d, J=8.7 Hz, 2H), 4.640-4.564 (m, 3H), 4.090-4.047 (t, J=6.3, 6.6 Hz, 2H), 3.691 (s, 3H), 2.401-2.277 (m, 1H), 2.252 (s, 3H), 1.781-1.689 (m, 2H), 1.523-1.400 (m, 2H), 1.019-0.997 (d, J=6.6 Hz, 3H), 0.978-0.929 (t, J=7.2, 7.5 Hz, 3H), 0.881-0.859 (d, J=6.6 Hz, 3H); MS (ESI): m/z 527 (M−H), m/z 529 (M+H).

Example 472

(S)-2-(6-(4-(4-Butoxybenzamido)-2-methylphenyl)-1-oxoisoindolin-2-yl)-3-methylbutanoic acid The compound of example 472 was prepared analogous to the compound of example 404 by hydrolysis of the compound of example 471.
Yield: 92%; ¹H NMR (DMSO-d₆, 300 MHz): δ 13.043 (s, 1H), 10.111 (s, 1H), 7.982-7.953 (d, J=8.7 Hz, 2H), 7.739-7.677 (m, 3H), 7.618-7.599 (m, 2H), 7.233-7.205 (d, J=8.1 Hz, 1H), 7.076-7.047 (d, J=8.7 Hz, 2H), 4.721-4.547 (dd, J=16.8, 17.7 Hz, 2H), 4.559-4.527 (d, J=9.6 Hz, 1H), 4.084-4.041 (t, J=6.3, 6.6 Hz, 2H), 2.330-2.275 (m, 1H), 2.250 (s, 3H), 1.753-1.683 (m, 2H), 1.492-1.418 (m, 2H), 1.047-1.025 (d, J=6.6 Hz, 3H), 0.972-0.923 (t, J=7.2, 7.5 Hz, 3H), 0.893-0.871 (d, J=6.6 Hz, 3H); MS (ESI): m/z 513 (M−H), m/z 515 (M+H).

Example 473

(S)-Methyl 3-methyl-2-(6-(2-methyl-4-(4-pentylbenzamido)phenyl)-1-oxoisoindolin-2-yl)butanoate The compound of example 473 was prepared analogous to the compound of example 403 by reaction of the compound of example 466 with 4-(n-pentyl)benzoyl chloride.

Yield: 93%; $^1$H NMR (DMSO-$d_6$, 300 MHz): δ 10.211 (s, 1H), 7.919-7.892 (d, J=8.1 Hz, 2H), 7.755 (s, 1H), 7.732-7.689 (m, 2H), 7.633-7.610 (d, J=6.9 Hz, 2H), 7.376-7.348 (d, J=8.4 Hz, 2H), 7.245-7.217 (d, J=8.4 Hz, 1H), 4.640-4.609 (m, 3H), 3.692 (s, 3H), 2.688-2.638 (t, J=7.2, 7.8 Hz, 2H), 2.380-2.302 (m, 1H), 2.255 (s, 3H), 1.640-1.569 (m, 2H), 1.312-1.266 (m, 4H), 1.020-0.998 (d, J=6.6 Hz, 3H), 0.896-0.875 (m, 6H); MS (ESI): m/z 525 (M−H), m/z 527 (M+H).

Example 474

(S)-3-Methyl-2-(6-(2-methyl-4-(4-pentylbenzamido)phenyl)-1-oxoisoindolin-2-yl)butanoic acid The compound of example 474 was prepared analogous to the compound of example 404 by hydrolysis of the compound of example 473.

Yield: 89%; $^1$H NMR (DMSO-$d_6$, 300 MHz): δ 13.023 (s, 1H), 10.202 (s, 1H), 7.913-7.886 (d, J=8.1 Hz, 2H), 7.749 (s, 1H), 7.726-7.680 (m, 2H), 7.620-7.602 (m, 2H), 7.370-7.343 (d, J=8.1 Hz, 2H), 7.241-7.214 (d, J=8.1 Hz, 1H), 4.722-4.561 (d, J=16.5, 17.7 Hz, 2H), 4.561-4.529 (d, J=9.6 Hz, 1H), 2.726-2.657 (t, J=7.5, 13.2 Hz, 2H), 2.375-2.300 (m, 1H), 2.253 (s, 3H), 1.632-1.587 (m, 2H), 1.307-1.285 (m, 4H), 1.048-1.026 (d, J=6.6 Hz, 3H), 0.893-0.846 (m, 6H); MS (ESI): m/z 511 (M−H), m/z 513 (M+H).

Example 475

(S)-Methyl 3-methyl-2-(6-(2-methyl-4-(4-(trifluoromethoxy)benzamido)phenyl)-1-oxoisoindolin-2-yl)butanoate The compound of example 475 was prepared analogous to the compound of example 403 by reaction of the compound of example 466 with 4-trifluoromethoxy benzoyl chloride.

Yield: 65%; $^1$H NMR (DMSO-$d_6$, 300 MHz): δ 10.412 (s, 1H), 8.127-8.098 (d, J=8.7 Hz, 2H), 7.745 (s, 1H), 7.721-7.692 (d, J=8.7 Hz, 2H), 7.640-7.613 (m, 2H), 7.569-7.542 (d, J=8.1 Hz, 2H), 7.264-7.237 (d, J=8.1 Hz, 1H), 4.640-4.608 (m, 3H), 3.692 (s, 3H), 2.380-2.303 (m, 1H), 2.260 (s, 3H), 1.020-0.998 (d, J=6.6 Hz, 3H), 0.882-0.860 (m, 3H); MS (ESI): m/z 539 (M−H), m/z 541 (M+H).

Example 476

(S)-3-Methyl-2-(6-(2-methyl-4-(4-(trifluoromethoxy)benzamido)phenyl)-1-oxoisoindolin-2-yl)butanoic acid The compound of example 476 was prepared analogous to the compound of example 404 by hydrolysis of the compound of example 475.

Yield: 78%; $^1$H NMR (DMSO-$d_6$, 300 MHz): δ 13.022 (s, 1H), 10.397 (s, 1H), 8.120-8.091 (d, J=8.7 Hz, 2H), 7.738 (s, 1H), 7.713-7.685 (d, J=8.4 Hz, 2H), 7.624-7.605 (m, 2H), 7.563-7.536 (d, J=8.1 Hz, 2H), 7.262-7.235 (d, J=8.1 Hz, 1H), 4.725-4.554 (d, J=16.5, 18 Hz, 2H), 4.554-4.529 (d, J=7.5 Hz, 1H), 2.372-2.301 (m, 1H), 2.259 (s, 3H), 1.048-1.027 (d, J=6.3 Hz, 3H), 0.895-0.873 (m, 3H); MS (ESI): m/z 525 (M−H), m/z 527 (M+H).

Example 477

(S)-Methyl 2-(6-(2-chloro-4-nitrophenyl)-1-oxoisoindolin-2-yl)-3-methyl butanoate The compound of example 477 was prepared analogous to the compound of example 391 by reaction of the compound of example 390, 1-bromo-2-chloro-4-nitro benzene and Pd(dppf)Cl$_2$: CH$_2$Cl$_2$.

Yield: 87.5%; $^1$H NMR (DMSO-$d_6$, 300 MHz): δ 8.451-8.443 (d, J=2.4 Hz, 1H), 8.301-8.265 (dd, J=2.4, 8.4 Hz, 1H), 7.800-7.771 (m, 4H), 4.670-4.606 (m, 3H), 3.687 (s, 3H), 2.380-2.275 (m, 1H), 1.017-0.995 (d, J=6.6 Hz, 3H), 0.878-0.856 (d, J=6.3 Hz, 3H); MS (ESI): m/z 403 (M+H).

Example 478

(S)-Methyl 2-(6-(4-amino-2-chlorophenyl)-1-oxoisoindolin-2-yl)-3-methyl butanoate The compound of example 478 was prepared analogous to the compound of example 392 by reduction of the compound of example 477.

Yield: 77%; $^1$H NMR (DMSO-$d_6$, 300 MHz): δ 7.658-7.592 (m, 3H), 7.114-7.087 (d, J=8.1 Hz, 1H), 6.732-6.726 (d, J=1.8 Hz, 1H), 6.623-6.589 (dd, J=1.8, 8.1 Hz, 1H), 5.558 (s, 2H), 4.653-4.531 (m, 3H), 3.678 (s, 3H), 2.361-2.285 (m, 1H), 1.007-0.985 (d, J=6.6 Hz, 3H), 0.865-0.843 (d, J=6.6 Hz, 3H); MS (ESI): m/z 373 (M+H).

Example 479

(S)-Methyl 2-(6-(4-(4-tert-butylbenzamido)-2-chlorophenyl)-1-oxoisoindolin-2-yl)-3-methylbutanoate The compound of example 479 was prepared analogous to the compound of example 403 by reaction of the compound of example 478 with 4-(t-butyl)benzoyl chloride.

Yield: 84%; $^1$H NMR (DMSO-$d_6$, 300 MHz): δ 10.519 (s, 1H), 8.140-8.133 (d, J=2.1 Hz, 1H), 7.941-7.913 (d, J=8.4 Hz, 2H), 7.868-7.832 (dd, J=2.1, 8.4 Hz, 1H), 7.720-7.684 (m, 3H), 7.588-7.552 (d, J=2.1, 8.7 Hz, 2H), 7.480-7.452 (d, J=8.4 Hz, 1H), 4.699-4.603 (m, 3H), 3.686 (s, 3H), 2.369-2.275 (m, 1H), 1.330 (s, 9H), 1.014-0.993 (d, J=6.3 Hz, 3H), 0.876-0.854 (d, J=6.6 Hz, 3H); MS (ESI): m/z 531 (M−H), m/z 533 (M+H).

Example 480

(S)-2-(6-(4-(4-tert-Butylbenzamido)-2-chlorophenyl)-1-oxoisoindolin-2-yl)-3-methylbutanoic acid The compound of example 480 was prepared analogous to the compound of example 404 by hydrolysis of the compound of example 479.

Yield: 77%; $^1$H NMR (DMSO-$d_6$, 300 MHz): δ 13.043 (s, 1H), 10.437 (s, 1H), 8.129-8.123 (d, J=2.1 Hz, 1H), 7.931-7.903 (d, J=8.4 Hz, 2H), 7.856-7.822 (dd, J=1.8, 8.4 Hz, 1H), 7.715-7.706 (m, 3H), 7.589-7.561 (d, J=8.4 Hz, 2H), 7.481-7.453 (d, J=8.4 Hz, 1H), 4.737-4.555 (dd, J=16.8, 18 Hz, 2H), 4.555-4.523 (d, J=9.6 Hz, 1H), 2.329-2.275 (m, 1H), 1.329 (s, 9H), 1.046-1.024 (d, J=6.6 Hz, 3H), 0.891-0.869 (d, J=6.6 Hz, 3H); MS (ESI): m/z 517 (M–H), m/z 519 (M+H).

Example 481

(S)-Methyl 2-(6-(4-biphenyl-4-ylcarboxamido-2-chlorophenyl)-1-oxoisoindolin-2-yl)-3-methylbutanoate The compound of example 481 was prepared analogous to the compound of example 403 by reaction of the compound of example 478 with 4-phenyl benzoyl chloride.
Yield: 94%; $^1$H NMR (DMSO-$d_6$, 300 MHz): δ 10.573 (s, 1H), 8.167-8.161 (d, J=1.8 Hz, 1H), 8.113-8.016 (d, J=8.1 Hz, 2H), 7.910-7.862 (m, 4H), 7.792-7.730 (m, 4H), 7.549-7.412 (m, 4H), 4.639-4.580 (m, 3H), 3.688 (s, 3H), 2.418-2.277 (m, 1H), 1.017-0.995 (d, J=6.6 Hz, 3H), 0.879-0.857 (d, J=6.6 Hz, 3H); MS (ESI) m/z 551 (M–H), m/z 553 (M+H).

Example 482

(S)-2-(6-(4-Biphenyl-4-ylcarboxamido-2-chlorophenyl)-1-oxoisoindolin-2-yl)-3-methylbutanoic acid The compound of example 482 was prepared analogous to the compound of example 404 by hydrolysis of the compound of example 481.
Yield: 83%; $^1$H NMR (DMSO-$d_6$, 300 MHz): δ 13.043 (s, 1H), 10.563 (s, 1H), 8.164-8.158 (d, J=1.8 Hz, 1H), 8.110-8.012 (d, J=8.4 Hz, 2H), 7.888-7.861 (d, J=8.1 Hz, 3H), 7.790-7.766 (d, J=7.2 Hz, 2H), 7.728-7.718 (m, 3H), 7.548-7.435 (m, 4H), 4.740-4.562 (d, J=15.9, 18 Hz, 2H), 4.562-4.530 (d, J=9.6 Hz, 1H), 2.371-2.268 (m, 1H), 1.049-1.027 (d, J=6.6 Hz, 3H), 0.895-0.873 (d, J=6.6 Hz, 3H); MS (ESI): m/z 537 (M–H), m/z 539 (M+H).

Example 483

(S)-Methyl 2-(6-(4-(4-butoxybenzamido)-2-chlorophenyl)-1-oxoisoindolin-2-yl)-3-methylbutanoate The compound of example 483 was prepared analogous to the compound of example 403 by reaction of the compound of example 478 with 4-(t-butoxy)benzoyl chloride.
Yield: 79.6%; $^1$H NMR (DMSO-$d_6$, 300 MHz): δ 10.453 (s, 1H), 8.130-8.124 (d, J=1.8 Hz, 1H), 7.994-7.932 (m, 3H), 7.860-7.826 (d, J=1.8, 8.4 Hz, 1H), 7.740-7.783 (m, 2H), 7.468-7.441 (d, J=8.1 Hz, 1H), 7.091-7.062 (d, J=8.7 Hz, 2H), 4.634-4.572 (m, 3H), 4.089-4.046 (t, J=6.3, 6.6 Hz, 2H), 3.684 (s, 3H), 2.396-2.296 (m, 1H), 1.776-1.683 (m, 2H), 1.516-1.393 (m, 2H), 1.013-0.991 (d, J=6.6 Hz, 3H), 0.971-0.922 (t, J=7.2, 7.5 Hz, 3H), 0.874-0.852 (d, J=6.6 Hz, 3H); MS (ESI): m/z 547 (M–H), m/z 549 (M+H).

Example 484

(S)-2-(6-(4-(4-Butoxybenzamido)-2-chlorophenyl)-1-oxoisoindolin-2-yl)-3-methylbutanoic acid The compound of example 484 was prepared analogous to the compound of example 404 by hydrolysis of the compound of example 483.
Yield: 93%; $^1$H NMR (DMSO-$d_6$, 300 MHz): δ 13.043 (s, 1H), 10.333 (s, 1H), 8.123-8.117 (d, J=1.8 Hz, 1H), 7.986-7.957 (d, J=8.7 Hz, 2H), 7.853-7.818 (dd, J=1.8, 8.4 Hz, 1H), 7.736-7.705 (m, 3H), 7.470-7.442 (d, J=8.4 Hz, 1H), 7.092-7.063 (d, J=8.7 Hz, 2H), 4.732-4.558 (dd, J=15.9, 17.7 Hz, 2H), 4.558-4.525 (d, J=9.9 Hz, 1H), 4.088-4.045 (t, J=6.3, 6.6 Hz, 2H), 2.354-2.269 (m, 1H), 1.753-1.704 (m, 2H), 1.490-1.416 (m, 2H), 1.045-1.023 (d, J=6.6 Hz, 3H), 0.970-0.921 (t, J=7.2, 7.5 Hz, 3H), 0.891-0.869 (d, J=6.6 Hz, 3H); MS (ESI): m/z 533 (M–H), m/z 535 (M+H).

Example 485

(S)-Methyl 2-(6-(2-chloro-4-(4-pentylbenzamido)phenyl)-1-oxoisoindolin-2-yl)-3-methylbutanoate The compound of example 485 was prepared analogous to the compound of example 403 by reaction of the compound of example 478 with 4-(n-pentyl)benzoyl chloride.
Yield: 88%; $^1$H NMR (DMSO-$d_6$, 300 MHz): δ 10.468 (s, 1H), 8.137-8.130 (d, J=2.1 Hz, 1H), 7.934-7.905 (d, J=8.1 Hz, 2H), 7.867-7.839 (dd, J=1.8, 8.4 Hz, 1H), 7.719 (m, 3H), 7.476-7.448 (d, J=8.4 Hz, 1H), 7.383-7.356 (d, J=8.1 Hz, 2H), 4.634-4.601 (m, 3H), 3.684 (s, 3H), 2.685-2.635 (t, J=7.2, 7.8 Hz, 2H), 2.351-2.318 (m, 1H), 1.631-1.586 (m, 2H), 1.303-1.292 (m, 4H), 1.012-0.991 (d, J=6.3 Hz, 3H), 0.873-0.853 (m, 6H); MS (ESI): m/z 547 (M+H).

Example 486

(S)-2-(6-(2-Chloro-4-(4-pentylbenzamido)phenyl)-1-oxoisoindolin-2-yl)-3-methylbutanoic acid The compound of example 486 was prepared analogous to the compound of example 404 by hydrolysis of the compound of example 485.
Yield: 72%; $^1$H NMR (DMSO-$d_6$, 300 MHz): δ 13.051 (s, 1H), 10.428 (s, 1H), 8.130-8.124 (d, J=1.8 Hz, 1H), 7.918-7.891 (d, J=8.1 Hz, 2H), 7.858-7.824 (dd, J=1.8, 8.4 Hz, 1H), 7.738-7.676 (m, 3H), 7.479-7.451 (d, J=8.4 Hz, 1H), 7.386-7.359 (d, J=8.1 Hz, 2H), 4.736-4.558 (dd, J=16.5, 18 Hz, 2H), 4.558-4.525 (d, J=9.9 Hz, 1H), 2.686-2.636 (t, J=7.5 Hz, 2H), 2.351-2.276 (m, 1H), 1.658-1.561 (m, 2H), 1.353-1.257 (m, 4H), 1.046-1.024 (d, J=6.6 Hz, 3H), 0.916-0.890 (m, 6H); MS (ESI): m/z 531 (M–H), m/z 533 (M+H).

Example 487

(S)-Methyl 2-(6-(2-chloro-4-(4-(trifluoromethoxy)benzamido)phenyl)-1-oxo isoindolin-2-yl)-3-methylbutanoate The compound of example 487 was prepared analogous to the compound of example 403 by reaction of the compound of example 478 with 4-trifluoromethoxy benzoyl chloride.
Yield: 91%; $^1$H NMR (DMSO-$d_6$, 300 MHz): δ 10.641 (s, 1H), 8.134-8.105 (d, J=8.7 Hz, 2H), 8.121-8.114 (d, J=2.1 Hz, 1H), 7.853-7.818 (dd, J=2.1, 8.4 Hz, 1H), 7.748-7.685 (m, 3H), 7.579-7.552 (d, J=8.1 Hz, 2H), 7.498-7.470 (d, J=8.4 Hz, 1H), 4.635-4.576 (m, 3H), 3.684 (s, 3H), 2.396-2.275 (m, 1H), 1.014-0.992 (d, J=6.6 Hz, 3H), 0.875-0.853 (d, J=6.6 Hz, 3H); MS (ESI): m/z 559 (M–H), m/z 561 (M+H).

Example 488

(S)-2-(6-(2-Chloro-4-(4-(trifluoromethoxy)benzamido)phenyl)-1-oxoisoindolin-2-yl)-3-methylbutanoic acid The compound of example 488 was prepared analogous to the compound of example 404 by hydrolysis of the compound of example 487.

Yield: 72%; ¹H NMR (DMSO-d$_6$, 300 MHz): δ 13.043 (s, 1H), 10.614 (s, 1H), 8.125-8.096 (m, 3H), 7.844-7.809 (dd, J=3, 8.4 Hz, 1H), 7.719-7.710 (m, 3H), 7.582-7.555 (d, J=8.1 Hz, 2H), 7.502-7.473 (d, J=8.7 Hz, 1H), 4.677-4.558 (dd, J=15.9, 19.8 Hz, 2H), 4.558-4.525 (d, J=9.9 Hz, 1H), 2.356-2.268 (m, 1H), 1.046-1.025 (d, J=6.3 Hz, 3H), 0.892-0.870 (d, J=6.6 Hz, 3H); MS (ESI) m/z 545 (M–H), m/z 547 (M+H).

Example 489

(S)-Methyl 3-methyl-2-(6-(6-nitropyridin-3-yl)-1-oxoisoindolin-2-yl)butanoate

The compound of example 489 was prepared analogous to the compound of example 391 by reaction of the compound of example 390, 3-bromo-6-nitro pyridine and Pd(dppf)Cl$_2$:CH$_2$Cl$_2$.

Yield: 33%; ¹H NMR (DMSO-d$_6$, 300 MHz): δ 9.099 (s, 1H), 8.641-8.616 (d, J=7.5 Hz, 1H), 8.423-8.396 (d, J=8.1 Hz, 1H), 8.192 (s, 1H), 8.154-8.129 (d, J=7.5 Hz, 1H), 7.851-7.826 (d, J=7.5 Hz, 1H), 4.672-4.622 (m, 3H), 3.690 (s, 3H), 2.357 (m, 1H), 1.019-1.000 (d, J=5.7 Hz, 3H), 0.869-0.850 (d, J=5.7 Hz, 3H); MS (ESI): m/z 368 (M–H), m/z 370 (M+H).

Example 490

(S)-Methyl 2-(6-(6-aminopyridin-3-yl)-1-oxoisoindolin-2-yl)-3-methyl butanoate

The compound of example 490 was prepared analogous to the compound of example 392 by reduction of the compound of example 489.

Yield: 93%; ¹H NMR (DMSO-d$_6$, 300 MHz): δ 8.298 (s, 1H), 7.824 (m, 2H), 7.787-7.759 (d, J=8.4 Hz, 1H), 7.662-7.639 (d, J=6.9 Hz, 1H), 6.553-6.526 (d, J=8.1 Hz, 1H), 6.136 (s, 2H), 4.625-4.576 (m, 3H), 3.678 (s, 3H), 2.314 (m, 1H), 1.003-0.985 (d, J=5.4 Hz, 3H), 0.869-0.850 (d, J=5.4 Hz, 3H); MS (ESI): m/z 338 (M–H), m/z 340 (M+H).

Example 491

(S)-Methyl 2-(6-(6-(4-tert-butylbenzamido)pyridin-3-yl)-1-oxoisoindolin-2-yl)-3-methylbutanoate The compound of example 491 was prepared analogous to the compound of example 403 by reaction of the compound of example 490 with 4-(t-butyl)benzoyl chloride.

Yield: 88%; ¹H NMR (DMSO-d$_6$, 300 MHz): δ 10.879 (s, 1H), 8.807-8.803 (d, J=1.2 Hz, 1H), 8.341-8.315 (d, J=7.8 Hz, 1H), 8.274-8.246 (dd, J=1.8, 8.4 Hz, 1H), 8.045-8.004 (m, 4H), 7.773-7.747 (d, J=7.8 Hz, 1H), 7.560-7.533 (d, J=8.1 Hz, 2H), 4.652-4.621 (m, 3H), 3.692 (s, 3H), 2.394-2.278 (m, 1H), 1.329 (s, 9H), 1.019-0.997 (d, J=6.6 Hz, 3H), 0.868-0.846 (d, J=6.6 Hz, 3H); MS (ESI): m/z 498 (M–H), m/z 500 (M+H).

Example 492

(S)-2-(6-(6-(4-tert-Butylbenzamido)pyridin-3-yl)-1-oxoisoindolin-2-yl)-3-methylbutanoic acid P-6543

The compound of example 492 was prepared analogous to the compound of example 40 by hydrolysis of the compound of example 491.

Yield: 88%; ¹H NMR (DMSO-d$_6$, 300 MHz): δ 13.014 (s, 1H), 10.873 (s, 1H), 8.808-8.801 (d, J=2.1 Hz, 1H), 8.345-8.317 (d, J=8.4 Hz, 1H), 8.275-8.239 (dd, J=2.1, 8.4 Hz, 1H), 8.043-8.004 (m, 4H), 7.770-7.744 (d, J=7.8 Hz, 1H), 7.560-7.532 (d, J=8.4 Hz, 2H), 4.736-4.555 (dd, J=18, 18.3 Hz, 2H), 4.574-4.542 (d, J=9.6 Hz, 1H), 2.902-2.278 (m, 1H), 1.328 (s, 9H), 1.051-1.029 (d, J=6.6 Hz, 3H), 0.883-0.861 (d, J=6.6 Hz, 3H); MS (ESI): m/z 484 (M–H), m/z 486 (M+H).

Example 493

(S)-Methyl 2-(6-(6-biphenyl-4-ylcarboxamidopyridin-3-yl)-1-oxoisoindolin-2-yl)-3-methylbutanoate The compound of example 493 was prepared analogous to the compound of example 403 by reaction of the compound of example 490 with 4-phenyl benzoyl chloride.

Yield: 61%; ¹H NMR (DMSO-d$_6$, 300 MHz): δ 9.025 (s, 1H), 8.582 (s, 2H), 8.107 (s, 1H), 8.095-8.068 (d, J=8.1 Hz, 3H), 7.811-7.759 (m, 3H), 7.685-7.657 (d, J=8.4 Hz, 2H), 7.615-7.589 (d, J=7.8 Hz, 1H), 7.483-7.455 (d, J=7.5 Hz, 2H), 7.455-7.431 (d, J=7.2 Hz, 1H), 4.891-4.476 (m, 3H), 3.764 (s, 3H), 2.426-2.347 (m, 1H), 1.108-1.086 (d, J=6.6 Hz, 3H), 0.979-0.957 (d, J=6.6 Hz, 3H); MS (ESI): m/z 520 (M+H).

Example 494

(S)-Methyl 3-methyl-2-(1-oxo-6-(6-(4-pentylbenzamido)pyridin-3-yl)iso indolin-2-yl)butanoate The compound of example 494 was prepared analogous to the compound of example 403 by reaction of the compound of example 490 with 4-(n-pentyl)benzoyl chloride.

Yield: 70%; ¹H NMR (DMSO-d$_6$, 300 MHz): δ 10.867 (s, 1H), 8.804-8.791 (d, J=2.1 Hz, 1H), 8.335-8.306 (d, J=8.7 Hz, 1H), 8.271-8.239 (dd, J=2.1, 8.4 Hz, 1H), 8.044-7.979 (m, 3H), 7.863-7.837 (d, J=7.8 Hz, 1H), 7.772-7.746 (d, J=7.8 Hz, 1H), 7.357-7.297 (d, J=8.4 Hz, 2H), 4.651-4.620 (m, 3H), 3.961 (m, 3H), 2.682-2.632 (t, J=7.5 Hz, 2H), 2.392-2.298 (m, 1H), 1.633-1.563 (m, 2H), 1.310-1.232 (m, 4H), 1.019-0.997 (d, J=6.6 Hz, 3H), 0.894-0.847 (m, 6H); MS (ESI): m/z 514 (M+H).

Example 495

(S)-Methyl 3-methyl-2-(1-oxo-6-(6-(4-(trifluoromethoxy)benzamido)pyridin-3-yl)isoindolin-2-yl)butanoate The compound of example 495 was prepared analogous to the compound of example 403 by reaction of the compound of example 490 with 4-trifluoromethoxy benzoyl chloride.

Yield: 82%; ¹H NMR (DMSO-d$_6$, 300 MHz): δ 11.131 (s, 1H), 8.823-8.820 (d, J=0.9 Hz, 1H), 8.331-8.254 (m, 2H), 8.200-8.171 (d, J=8.7 Hz, 2H), 8.082-8.053 (d, J=8.7 Hz, 2H), 7.775-7.749 (d, J=7.8 Hz, 1H), 7.501-7.472 (d, J=8.7 Hz, 2H), 4.652-4.620 (m, 3H), 3.692 (s, 3H), 2.356-2.323 (m, 1H), 1.019-0.997 (d, J=6.6 Hz, 3H), 0.883-0.861 (d, J=6.6 Hz, 3H); MS (ESI) m/z 526 (M–H), m/z 528 (M+H).

Example 496

(S)-Methyl 2-(6-(6-aminopyridazin-3-yl)-1-oxoisoindolin-2-yl)-3-methyl butanoate The compound of example 496 was prepared analogous to the compound of example 391 by reaction of the compound of example 390, 6-bromopyridazin-3-amine and Pd(dppf)Cl$_2$:CH$_2$Cl$_2$.

Yield: 55%; ¹H NMR (DMSO-d$_6$, 300 MHz): δ 8.288-8.257 (dd, J=1.2, 8.1 Hz, 1H), 7.962-7.931 (d, J=9.3 Hz, 1H), 7.734-7.707 (d, J=8.1 Hz, 1H), 6.894-6.863 (d, J=9.3 Hz, 1H), 6.596-6.543 (m, 3H), 4.638-4.605 (m, 3H), 3.685 (s, 3H), 2.346-2.313 (m, 1H), 1.011-0.990 (d, J=6.3 Hz, 3H), 0.853-0.831 (d, J=6.6 Hz, 3H); MS (ESI): m/z 339 (M−H), m/z 341 (M+H).

Example 497

(S)-Methyl 2-(6-(6-(4-tert-butylbenzamido)py-ridazin-3-yl)-1-oxoisoindolin-2-yl)-3-methyl butanoate The compound of example 497 was prepared analogous to the compound of example 403 by reaction of the compound of example 496 with 4-(t-butyl)benzoyl chloride. The compound of example 497 was used directly for the preparation of the compound of example 498 without purification.

Example 498

(S)-2-(6-(6-(4-tert-Butylbenzamido)pyridazin-3-yl)-1-oxoisoindolin-2-yl)-3-methylbutanoic acid The compound of example 498 was prepared analogous to the compound of example 404 by hydrolysis of the compound of example 497.
Yield: 60%; ¹H NMR (DMSO-d$_6$, 300 MHz): δ 12.680 (s, 1H), 11.534 (s, 1H), 8.536-8.505 (d, J=9.3 Hz, 1H), 8.456-8.424 (m, 2H), 8.081-8.053 (d, J=8.4 Hz, 1H), 7.888-7.860 (d, J=8.4 Hz, 1H), 7.837-7.809 (d, J=8.4 Hz, 1H), 7.590-7.562 (d, J=8.4 Hz, 2H), 7.532-7.504 (d, J=8.4 Hz, 1H), 4.779-4.599 (d, J=17.7, 18 Hz, 2H), 4.581-4.549 (d, J=9.6 Hz, 1H), 2.361-2.288 (m, 1H), 1.336 (s, 9H), 1.056-1.235 (d, J=6.3 Hz, 3H), 0.892-0.870 (d, J=6.6 Hz, 3H); MS (ESI): m/z 485 (M−H), m/z 487 (M+H).

Example 499

(S)-Methyl 3-methyl-2-(1-oxo-6-(6-(4-pentylbenza-mido)pyridazin-3-yl)iso indolin-2-yl)butanoate The compound of example 499 was prepared analogous to the compound of example 403 by reaction of the compound of example 496 with 4-(n-pentyl)benzoyl chloride.
Yield: 59%; ¹H NMR (DMSO-d$_6$, 300 MHz): δ 11.525 (s, 1H), 8.556-8.427 (m, 3H), 8.274-7.227 (m, 1H), 8.056-8.029 (d, J=8.1 Hz, 2H), 7.843-7.815 (d, J=8.4 Hz, 1H), 7.389-7.363 (d, J=7.8 Hz, 2H); 4.676-4.614 (m, 3H), 3.700 (s, 3H), 2.698-2.648 (m, 2H), 2.389-2.313 (m, 1H), 1.644-1.598 (m, 2H), 1.316-1.295 (m, 4H), 1.027-1.005 (d, J=6.6 Hz, 3H), 0.898-0.857 (m, 6H); MS (ESI): m/z 513 (M−H), m/z 515 (M+H).

Example 500

(S)-3-Methyl-2-(1-oxo-6-(6-(4-pentylbenzamido) pyridazin-3-yl)isoindolin-2-yl)butanoic acid The compound of example 500 was prepared analogous to the compound of example 404 by hydrolysis of the compound of example 499.
Yield: 70%; ¹H NMR (DMSO-d$_6$, 300 MHz): δ 12.834 (s, 1H), 11.522 (s, 1H), 8.526-8.495 (d, J=9.3 Hz, 1H), 8.452-7.427 (m, 2H), 8.053-8.027 (d, J=7.8 Hz, 2H), 7.864-7.837 (d, J=8.1 Hz, 1H), 7.387-7.360 (d, J=8.1 Hz, 2H), 7.325-7.298 (d, J=8.1 Hz, 1H), 4.779-4.598 (dd, J=17.4, 18.3 Hz, 2H), 4.581-4.549 (d, J=9.6 Hz, 1H), 2.729-2.607 (m, 2H), 2.342-2.288 (m, 1H), 1.315-1.291 (m, 2H), 1.315-1.291 (m, 4H), 1.056-1.034 (d, J=6.6 Hz, 3H), 0.892-0.834 (m, 6H); MS (ESI) m/z 499 (M−H), m/z 501 (M+H).

Example 501

(S)-Methyl 3-methyl-2-(1-oxo-6-(6-(4-(trifluo-romethoxy)benzamido)pyridazin-3-yl)isoindolin-2-yl)butanoate The compound of example 501 was prepared analogous to the compound of example 403 by reaction of the compound of example 496 with 4-trifluoromethoxy benzoyl chloride. The compound of example 501 was used directly for the preparation of the compound of example 502 without purification.

Example 502

(S)-3-Methyl-2-(1-oxo-6-(6-(4-(trifluoromethoxy) benzamido)pyridazin-3-yl)isoindolin-2-yl)butanoic acid The compound of example 502 was prepared analogous to the compound of example 404 by hydrolysis of the compound of example 501.
Yield: 76%; ¹H NMR (DMSO-d$_6$, 300 MHz): δ 13.163 (s, 1H), 11.768 (s, 1H), 8.528-8.497 (d, J=9.3 Hz, 1H), 8.247-7.218 (d, J=8.7 Hz, 2H), 8.082-8.053 (d, J=8.7 Hz, 2H), 7.840-7.812 (d, J=8.4 Hz, 1H), 7.569-7.542 (d, J=8.1 Hz, 2H), 7.502-7.474 (d, J=8.4 Hz, 1H), 4.718-4.603 (dd, J=16.5, 18 Hz, 2H), 4.585-4.553 (d, J=9.6 Hz, 1H), 2.342-2.288 (m, 1H), 1.057-1.036 (d, J=6.3 Hz, 3H), 0.893-0.832 (d, J=6.3 Hz, 3H); MS (ESI): m/z 513 (M−H), m/z 515 (M+H).

Example 503

(S)-Methyl 2-(6-(5-aminopyrazin-2-yl)-1-oxoisoin-dolin-2-yl)-3-methyl butanoate

The compound of example 503 was prepared analogous to the compound of example 391 by reaction of the compound of example 390, 5-bromopyrazin-2-amine and Pd(dppf)Cl$_2$: CH$_2$Cl$_2$.
Yield: 66%; ¹H NMR (DMSO-d$_6$, 300 MHz): δ 8.609 (s, 1H), 8.211-8.188 (m, 2H), 7.980 (s, 1H), 7.682-7.654 (d, J=8.4 Hz, 1H), 6.647 (s, 2H), 4.629-4.587 (m, 3H), 3.681 (s, 3H), 2.359-2.282 (m, 1H), 1.006-0.984 (d, J=6.6 Hz, 3H), 0.853-0.831 (d, J=6.6 Hz, 3H); MS (ESI): m/z 341 (M+H).

Example 504

(S)-Methyl 2-(6-(5-(4-tert-butylbenzamido)pyrazin-2-yl)-1-oxoisoindolin-2-yl)-3-methylbutanoate The compound of example 504 was prepared analogous to the compound of example 403 by reaction of the compound of example 503 with 4-(t-butyl)benzoyl chloride.
Yield: 93.87%; ¹H NMR (DMSO-d$_6$, 300 MHz): δ 11.209 (s, 1H), 9.529-9.525 (d, J=1.2 Hz, 1H), 9.224-9.220 (d, J=1.2 Hz, 1H), 8.502 (d, J=8.1 Hz, 2H), 8.053-7.967 (m, 2H), 7.805-7.779 (d, J=7.8 Hz, 1H), 7.582-7.553 (d, J=8.7 Hz, 2H), 4.653-4.619 (m, 3H), 3.691 (s, 3H), 2.355-2.272 (m, 1H), 1.329 (s, 9H), 1.017-0.995 (d, J=6.6 Hz, 3H), 0.868-0.846 (d, J=6.6 Hz, 3H); MS (ESI): m/z 499 (M−H), m/z 501 (M+H).

Example 505

(S)-2-(6-(5-(4-tert-Butylbenzamido)pyrazin-2-yl)-1-oxoisoindolin-2-yl)-3-methylbutanoic acid The compound of example 505 was prepared analogous to the compound of example 404 by hydrolysis of the compound of example 504.

Yield: 31%; $^1$H NMR (DMSO-$d_6$, 300 MHz): δ 12.999 (s, 1H), 11.205 (s, 1H), 9.533-9.530 (d, J=0.9 Hz, 1H), 9.224-9.221 (d, J=0.9 Hz, 1H), 8.451 (s, 1H), 8.436-8.409 (d, J=8.1 Hz, 1H), 8.054-8.026 (d, J=8.4 Hz, 2H), 7.581-7.553 (d, J=8.4 Hz, 2H), 7.530-7.502 (d, J=8.4 Hz, 1H), 4.757-4.577 (d, J=16.5, 18.3 Hz, 2H), 4.577-4.545 (d, J=9.6 Hz, 1H), 2.356-2.284 (m, 1H), 1.329 (s, 9H), 1.051-1.029 (d, J=6.6 Hz, 3H), 0.885-0.863 (d, J=6.6 Hz, 3H); MS (ESI): m/z 487 (M+H).

Example 506

(S)-Methyl 2-(6-(5-biphenyl-4-ylcarboxamidopyrazin-2-yl)-1-oxoisoindolin-2-yl)-3-methylbutanoate The compound of example 506 was prepared analogous to the compound of example 403 by reaction of the compound of example 503 with 4-phenyl benzoyl chloride.

Yield: 65%; $^1$H NMR (DMSO-$d_6$, 300 MHz): δ 11.351 (s, 1H), 9.553-9.549 (d, J=1.2 Hz, 1H), 9.245-9.241 (d, J=1.2 Hz, 1H), 8.464 (s, 1H), 8.457-8.421 (dd, J=1.5, 9.3 Hz, 1H), 8.208-8.180 (d, J=8.4 Hz, 2H), 7.877-7.849 (d, J=8.4 Hz, 2H), 7.802-7.774 (m, 3H), 7.547-7.437 (m, 3H), 4.658-4.625 (m, 3H), 3.695 (s, 3H), 2.380-2.291 (m, 1H), 1.020-0.998 (d, J=6.6 Hz, 3H), 0.871-0.849 (d, J=6.6 Hz, 3H); MS (ESI): m/z 521 (M+H).

Example 507

(S)-2-(6-(5-Biphenyl-4-ylcarboxamidopyrazin-2-yl)-1-oxoisoindolin-2-yl)-3-methylbutanoic acid The compound of example 507 was prepared analogous to the compound of example 404 by hydrolysis of the compound of example 506.

Yield: 66.8%; $^1$H NMR (DMSO-$d_6$, 300 MHz): δ 11.351 (s, 1H), 9.553 (s, 1H), 9.242 (s, 1H), 8.459 (s, 1H), 8.441-8.415 (d, J=7.8 Hz, 1H), 8.208-8.121 (d, J=8.1 Hz, 2H), 8.036-8.008 (d, J=8.4 Hz, 1H), 7.876-7.848 (d, J=8.4 Hz, 2H), 7.748-7.723 (d, J=7.5 Hz, 2H), 7.546-7.460 (m, 3H), 4.774-4.566 (d, J=18.3 Hz, 2H), 4.566-4.534 (d, J=9.6 Hz, 1H), 2.351-2.277 (m, 1H), 1.050-1.028 (d, J=6.6 Hz, 3H), 0.882-0.860 (d, J=6.6 Hz, 3H); MS (ESI): m/z 507 (M+H).

Example 508

(S)-Methyl 2-(6-(5-(4-butoxybenzamido)pyrazin-2-yl)-1-oxoisoindolin-2-yl)-3-methylbutanoate The compound of example 508 was prepared analogous to the compound of example 403 by reaction of the compound of example 503 with 4-(t-butoxy)benzoyl chloride.

Yield: 56.2%; $^1$H NMR (DMSO-$d_6$, 300 MHz): δ 11.116 (s, 1H), 9.508-9.504 (d, J=1.2 Hz, 1H), 9.212-9.208 (d, J=1.2 Hz, 1H), 8.446 (s, 1H), 8.443-8.406 (dd, J=1.5, 9.6 Hz, 1H), 8.097-8.068 (d, J=8.7 Hz, 2H), 7.800-7.774 (d, J=7.8 Hz, 1H), 7.077-7.047 (d, J=9 Hz, 2H), 4.653-4.620 (m, 3H), 4.095-4.052 (t, J=6.3, 6.6 Hz, 2H), 3.691 (s, 3H), 2.376-2.321 (m, 1H), 1.753-1.683 (m, 2H), 1.490-1.416 (m, 2H), 1.017-0.995 (d, J=6.6 Hz, 3H), 0.972-0.922 (t, J=7.5 Hz, 3H), 0.868-0.846 (d, J=6.6 Hz, 3H); MS (ESI): m/z 517 (M+H).

Example 509

(S)-2-(6-(5-(4-Butoxybenzamido)pyrazin-2-yl)-1-oxoisoindolin-2-yl)-3-methylbutanoic acid The compound of example 509 was prepared analogous to the compound of example 404 by hydrolysis of the compound of example 508.

Yield: 77%; $^1$H NMR (DMSO-$d_6$, 300 MHz): δ 11.113 (s, 1H), 9.500 (s, 1H), 9.190 (s, 1H), 8.382 (s, 1H), 8.357-8.331 (d, J=7.8 Hz, 1H), 8.100-8.071 (d, J=8.7 Hz, 2H), 7.742-7.715 (d, J=8.1 Hz, 1H), 7.072-7.043 (d, J=8.7 Hz, 2H), 5.051 (d, J=18.6 Hz, 1H), 4.452-4.390 (d, J=18.6 Hz, 1H), 4.274-4.242 (d, J=9.6 Hz, 1H), 4.093-4.051 (t, J=6.3 Hz, 2H), 2.236-2.209 (m, 1H), 1.752-1.681 (m, 2H), 1.490-1.416 (m, 2H), 0.992-0.904 (m, 6H), 0.793-0.771 (d, J=6.6 Hz, 3H); MS (ESI): m/z 503 (M+H).

Example 510

(S)-Methyl 3-methyl-2-(1-oxo-6-(5-(4-pentylbenzamido)pyrazin-2-yl)isoindolin-2-yl)butanoate The compound of example 510 was prepared analogous to the compound of example 403 by reaction of the compound of example 503 with 4-(n-pentyl)benzoyl chloride.

Yield: 66.2%; $^1$H NMR (DMSO-$d_6$, 300 MHz): δ 11.199 (s, 1H), 9.518-9.513 (d, J=1.5 Hz, 1H), 9.220-9.216 (d, J=1.2 Hz, 1H), 8.540 (s, 1H), 8.445-8.408 (dd, J=1.5, 9.6 Hz, 1H), 8.027-8.000 (d, J=8.4 Hz, 2H), 7.802-7.776 (d, J=7.8 Hz, 1H), 7.377-7.349 (d, J=8.4 Hz, 2H), 4.653-4.620 (m, 3H), 3.691 (s, 3H), 2.686-2.636 (t, J=7.2, 7.8 Hz, 2H), 2.385-2.294 (m, 1H), 1.634-1.586 (m, 2H), 1.314-1.260 (m, 4H), 1.017-0.995 (d, J=6.6 Hz, 3H), 0.890-0.845 (m, 6H); MS (ESI): m/z 515 (M+H).

Example 511

(S)-3-Methyl-2-(1-oxo-6-(5-(4-pentylbenzamido)pyrazin-2-yl)isoindolin-2-yl)butanoic acid The compound of example 511 was prepared analogous to the compound of example 404 by hydrolysis of the compound of example 510.

Yield: 60.34%; $^1$H NMR (DMSO-$d_6$, 300 MHz): δ 12.934 (s, 1H), 11.199 (s, 1H), 9.519 (s, 1H), 9.220 (s, 1H), 8.450 (s, 1H), 8.433-8.406 (d, J=8.1 Hz, 1H), 8.205-8.178 (d, J=8.1 Hz, 1H), 7.860-7.834 (d, J=7.8 Hz, 2H), 7.377-7.351 (d, J=7.8 Hz, 2H), 4.756-4.513 (m, 3H), 2.687-2.631 (t, J=7.2, 7.8 Hz, 2H), 2.350-2.278 (m, 1H), 1.606-1.581 (m, 2H), 1.294-1.227 (m, 4H), 1.049-1.029 (d, J=6 Hz, 3H), 0.882-0.867 (m, 6H); MS (ESI): m/z 499 (M−H), m/z 501 (M+H).

Example 512

(S)-Methyl 3-methyl-2-(1-oxo-6-(5-(4-(trifluoromethoxy)benzamido)pyrazin-2-yl)isoindolin-2-yl)butanoate The compound of example 512 was prepared analogous to the compound of example 403 by reaction of the compound of example 503 with 4-trifluoromethoxy benzoyl chloride.

Yield: 51.6%; $^1$H NMR (DMSO-$d_6$, 300 MHz): δ 11.436 (s, 1H), 9.516-9.512 (d, J=1.2 Hz, 1H), 9.241-9.237 (d, J=1.2

Hz, 1H), 8.456 (s, 1H), 8.444-8.413 (dd, J=1.2, 9.3 Hz, 1H), 8.221-8.192 (d, J=8.7 Hz, 2H), 7.805-7.779 (d, J=7.8 Hz, 1H), 7.562-7.535 (d, J=8.1 Hz, 2H), 4.654-4.514 (m, 3H), 3.692 (s, 3H), 2.384-2.276 (m, 1H), 1.017-0.996 (d, J=6.3 Hz, 3H), 0.868-0.846 (t, J=6.6 Hz, 3H); MS (ESI): m/z 529 (M+H).

Example 513

(S)-3-Methyl-2-(1-oxo-6-(5-(4-(trifluoromethoxy) benzamido)pyrazin-2-yl)isoindolin-2-yl)butanoic acid The compound of example 513 was prepared analogous to the compound of example 404 by hydrolysis of the compound of example 512.
Yield: 38%; $^1$H NMR (DMSO-$d_6$, 300 MHz): δ 13.134 (s, 1H), 11.440 (s, 1H), 9.522-9.518 (d, J=1.2 Hz, 1H), 9.247-9.243 (d, J=1.2 Hz, 1H), 8.457 (s, 1H), 8.443-8.411 (dd, J=1.5, 9.6 Hz, 1H), 8.080-8.050 (d, J=9 Hz, 1H), 7.806-7.779 (d, J=8.1 Hz, 1H), 7.566-7.539 (d, J=8.1 Hz, 2H), 7.501-7.473 (d, J=8.4 Hz, 1H), 4.699-4.514 (m, 3H), 2.381-2.279 (m, 1H), 1.051-1.030 (d, J=6.3 Hz, 3H), 0.886-0.865 (t, J=6.3 Hz, 3H); MS (ESI): m/z 515 (M+H).

Example 514

Methyl 2-methyl-2-(6-(4-nitrophenyl)-1-oxoisoindolin-2-yl)propanoate

The compound of example 338 (2.4 g, 0.0076 mol), (4-nitrophenyl)boronic acid (1.649 g, 0.0098 mol) and Pd(dppf)Cl$_2$: CH$_2$Cl$_2$ (0.186 g, 0.00022 mol) were taken in DMF (60 mL) under an argon atmosphere. To this reaction mixture, 2M solution of Na$_2$CO$_3$ (2.33 g, 0.022 mol, 10.99 mL) was added and the reaction mixture was stirred at 80 to 85° C. for 1 to 1.5 h. After completion of the reaction, water was added to the reaction mixture and the product obtained was extracted with diethyl ether. The combined ether layers were washed with water and brine, dried over anhydrous Na$_2$SO$_4$. The solvent was evaporated and the product was purified by column chromatography (silica gel, 30% ethyl acetate in petroleum ether) to afford the title compound.
Yield: 95%; $^1$H NMR (DMSO-$d_6$, 300 MHz): δ 8.337-8.308 (d, J=8.7 Hz, 2H), 8.099-8.001 (m, 4H), 7.789-7.763 (d, J=7.8 Hz, 1H), 4.735 (s, 2H), 3.623 (s, 3H), 1.586-1.555 (s, 6H); MS (ESI): m/z 353 (M–H), m/z 355 (M+H).

Example 515

Methyl 2-(6-(4-aminophenyl)-1-oxoisoindolin-2-yl)-2-methylpropanoate

The compound of example 515 was prepared analogous to the compound of example 6 by reduction of the compound of example 514.
Yield: 78%; $^1$H NMR (DMSO-$d_6$, 300 MHz): δ 7.806-7.774 (dd, J=1.5, 8.1 Hz, 1H), 7.712 (s, 1H), 7.598-7.571 (d, J=8.1 Hz, 1H), 7.424-7.396 (d, J=8.4 Hz, 2H), 6.669-6.641 (d, J=8.4 Hz, 2H), 5.299 (s, 2H), 3.614 (s, 3H), 1.563 (s, 6H); MS (ESI): m/z 325 (M+H).

Example 516

Methyl 2-(6-(4-([1,1'-biphenyl]-4-ylcarboxamido) phenyl)-1-oxoisoindolin-2-yl)-2-methylpropanoate The compound of example 516 was prepared analogous to compound of example 97 by reaction of compound of example 515 with 4-phenylbenzoyl chloride.
Yield: 90%; $^1$H NMR (DMSO-$d_6$, 300 MHz): δ 10.437 (s, 1H), 8.112-8.084 (d, J=8.4 Hz, 2H), 7.965-7.849 (m, 6H), 7.789-7.570 (m, 3H), 7.706-7.680 (d, J=7.8 Hz, 2H), 7.549-7.500 (t, J=7.2, 7.5 Hz, 2H), 7.459-7.434 (d, J=7.5 Hz, 1H), 4.693 (s, 2H), 3.605 (s, 3H), 1.585 (s, 6H); MS (ESI): m/z 505 (M+H).

Example 517

2-(6-(4-([1,1'-Biphenyl]-4-ylcarboxamido)phenyl)-1-oxoisoindolin-2-yl)-2-methyl propanoic acid The compound of example 517 was prepared analogous to compound of example 98 by hydrolysis of compound of example 516.
Yield: 86%; $^1$H NMR (DMSO-$d_6$, 300 MHz): δ 12.548 (s, 1H), 10.430 (s, 1H), 8.111-8.083 (d, J=8.4 Hz, 2H), 7.965-7.928 (m, 3H), 7.878-7.850 (m, 3H), 7.798-7.769 (d, J=8.7 Hz, 2H), 7.767-7.738 (d, J=8.7 Hz, 2H), 7.696-7.670 (d, J=7.8 Hz, 1H), 7.550-7.500 (t, J=7.2 Hz, 2H), 7.459-7.435 (d, J=7.2 Hz, 1H), 4.670 (s, 2H), 1.588 (s, 6H); MS (ESI): m/z 589 (M–H), m/z 491 (M+H).

Example 518

Methyl 2-(6-(4-(4-(tert-butyl)benzamido)phenyl)-1-oxoisoindolin-2-yl)-2-methyl propanoate The compound of example 518 was prepared analogous to compound of example 97 by reaction of compound of example 515 with 4-(t-butyl)benzoyl chloride.
Yield: 96%; $^1$H NMR (DMSO-$d_6$, 300 MHz): δ 10.311 (s, 1H), 7.970-7.870 (m, 6H), 7.757-7.728 (d, J=8.7 Hz, 2H), 7.700-7.673 (d, J=8.1 Hz, 1H), 7.578-7.550 (d, J=8.4 Hz, 2H), 4.689 (s, 2H), 3.787 (s, 3H), 1.582 (s, 6H), 1.333 (s, 9H); MS (ESI): m/z 485 (M+H).

Example 519

2-(6-(4-(4-(tert-Butyl)benzamido)phenyl)-1-oxoisoindolin-2-yl)-2-methyl propanoic acid The compound of example 519 was prepared analogous to compound of example 98 by hydrolysis of compound of example 518.
Yield: 72%; $^1$H NMR (DMSO-$d_6$, 300 MHz): δ 12.477 (s, 1H), 10.300 (s, 1H), 7.928-7.866 (m, 6H), 7.756-7.727 (J=8.7 Hz, 2H), 7.689-7.663 (d, J=7.8 Hz, 1H), 7.579-7.551 (d, J=8.4 Hz, 2H), 4.665 (s, 2H), 1.584 (s, 6H), 1.333 (s, 9H); MS (ESI): m/z 471 (M+H).

Example 520

Methyl 2-(6-(4-(4-chlorobenzamido)phenyl)-1-oxoisoindolin-2-yl)-2-methyl propanoate The compound of example 520 was prepared analogous to compound of example 97 by reaction of compound of example 515 with 4-chloro-benzoyl chloride.
Yield: 96%; $^1$H NMR (DMSO-$d_6$, 300 MHz): δ 10.449 (s, 1H), 8.031-8.004 (d, J=8.1 Hz, 2H), 7.923-7.873 (m, 4H), 7.772-7.743 (d, J=8.7 Hz, 2H), 7.704-7.675 (d, J=8.7 Hz, 1H), 7.648-7.620 (d, J=8.4 Hz, 2H), 4.691 (s, 2H), 3.624 (s, 3H), 1.582 (s, 6H); MS (ESI): m/z 463 (M+H).

Example 521

2-(6-(4-(4-Chlorobenzamido)phenyl)-1-oxoisoindolin-2-yl)-2-methylpropanoic acid

The compound of example 521 was prepared analogous to compound of example 98 by hydrolysis of compound of example 520.

Yield: 68%; $^1$H NMR (DMSO-d$_6$, 300 MHz): δ 12.497 (s, 1H), 10.443 (s, 1H), 8.030-8.002 (d, J=8.4 Hz, 2H), 7.957-7.870 (m, 4H), 7.769-7.740 (d, J=8.7 Hz, 2H), 7.691-7.665 (d, J=8.7 Hz, 1H), 7.646-7.618 (d, J=8.4 Hz, 2H), 4.665 (s, 2H), 1.584 (s, 6H); MS (ESI): m/z 467 (M−H); m/z 489 (M+H).

Example 522

Methyl 2-methyl-2-(1-oxo-6-(4-(4-(trifluoromethoxy)benzamido)phenyl)iso indolin-2-yl)propanoate The compound of example 522 was prepared analogous to compound of example 97 by reaction of compound of example 515 with 4-trifluoromethoxy-benzoyl chloride.

Yield: 96%; $^1$H NMR (DMSO-d$_6$, 300 MHz): δ 10.494 (s, 1H), 8.128-8.099 (d, J=8.7 Hz, 2H), 7.957-7.876 (m, 4H), 7.776-7.747 (d, J=8.7 Hz, 2H), 7.704-7.677 (d, J=8.1 Hz, 1H), 7.568-7.541 (d, J=8.1 Hz, 2H), 4.691 (s, 2H), 3.625 (s, 3H), 1.583 (s, 6H); MS (ESI): m/z 513 (M+H).

Example 523

2-Methyl-2-(1-oxo-6-(4-(4-(trifluoromethoxy)benzamido)phenyl)isoindolin-2-yl)propanoic acid The compound of example 523 was prepared analogous to compound of example 98 by hydrolysis of compound of example 522.

Yield: 71%; $^1$H NMR (DMSO-d$_6$, 300 MHz): δ 12.497 (s, 1H), 10.484 (s, 1H), 8.124-8.095 (d, J=8.7 Hz, 2H), 7.940-7.871 (m, 4H), 7.774-7.745 (d, J=8.7 Hz, 2H), 7.694-7.667 (d, J=8.7 Hz, 1H), 7.568-7.541 (d, J=8.1 Hz, 2H), 4.667 (s, 2H), 1.584 (s, 6H); MS (ESI): m/z 497 (M−H); m/z 499 (M+H).

Example 524

Methyl 2-methyl-2-(1-oxo-6-(4-(4-pentylbenzamido)phenyl)isoindolin-2-yl)propanoate The compound of example 524 was prepared analogous to compound of example 97 by reaction of compound of example 515 with 4-(n-pentyl)-benzoyl chloride.

Yield: 93%; $^1$H NMR (DMSO-d$_6$, 300 MHz): δ 10.314 (s, 1H), 8.022-8.093 (d, J=8.7 Hz, 2H), 7.947-7.869 (m, 4H), 7.754-7.726 (d, J=8.4 Hz, 2H), 7.699-7.672 (d, J=8.1 Hz, 1H), 7.375-7.348 (d, J=8.1 Hz, 2H), 4.689 (s, 2H), 3.624 (s, 3H), 2.687-2.637 (t, J=7.2, 7.8 Hz, 2H), 1.637-1.612 (m, 2H), 1.581 (s, 6H), 1.359-1.263 (m, 4H), 0.893-0.848 (t, J=6.3, 7.2 Hz, 3H); MS (ESI): m/z 499 (M+H).

Example 525

2-Methyl-2-(1-oxo-6-(4-(4-pentylbenzamido)phenyl)isoindolin-2-yl)propanoic acid

The compound of example 525 was prepared analogous to compound of example 98 by hydrolysis of compound of example 524.

Yield: 77%; $^1$H NMR (DMSO-d$_6$, 300 MHz): δ 12.485 (s, 1H), 10.292 (s, 1H), 7.928-7.685 (m, 6H), 7.753-7.725 (d, J=8.4 Hz, 2H), 7.688-7.661 (d, J=8.1 Hz, 1H), 7.376-7.349 (d, J=8.1 Hz, 2H), 4.664 (s, 2H), 2.687-2.637 (t, J=7.5 Hz, 2H), 1.692-1.635 (m, 2H), 1.584 (s, 6H), 1.309-1.299 (m, 4H), 0.893-0.848 (t, J=6.3, 7.2 Hz, 3H); MS (ESI): m/z 483 (M+H); m/z 485 (M+H).

Example 526

Methyl 1-(6-(4-nitrophenyl)-1-oxoisoindolin-2-yl)cyclopentanecarboxylate

The compound of example 526 was prepared analogous to compound of example 514 by reaction of the compound of example 341 and Yield: 76%; $^1$H NMR (DMSO-d$_6$, 300 MHz): δ 8.339-8.310 (d, J=8.7 Hz, 2H), 8.067-8.001 (m, 4H), 7.776-7.750 (d, J=7.8 Hz, 1H), 4.705 (s, 2H), 3.597 (s, 3H), 2.307-2.285 (m, 4H), 1.756-1.520 (m, 4H); MS (ESI): m/z 379 (M−H), m/z 381 (M+H).

Example 527

Methyl 1-(6-(4-aminophenyl)-1-oxoisoindolin-2-yl)cyclopentanecarboxylate

The compound of example 527 was prepared analogous to the compound of example 6 by reduction of the compound of example 526.

Yield: 77%; $^1$H NMR (DMSO-d$_6$, 300 MHz): δ 7.807-7.775 (dd, J=1.8, 8.1 Hz, 1H), 7.713 (s, 1H), 7.588-7.561 (d, J=8.1 Hz, 1H), 7.422-7.394 (d, J=8.4 Hz, 2H), 6.670-6.642 (d, J=8.4 Hz, 2H), 5.292 (s, 2H), 4.609 (s, 2H), 3.588 (s, 3H), 2.287-2.265 (m, 4H), 1.764-1.742 (m, 4H); MS (ESI): m/z 350 (M+H).

Example 528

Methyl 1-(6-(4-([1,1'-biphenyl]-4-ylcarboxamido)phenyl)-1-oxoisoindolin-2-yl)cyclopentanecarboxylate The compound of example 528 was prepared analogous to compound of example 97 by reaction of compound of example 527 with 4-phenyl benzoyl chloride.

Yield: 84%; $^1$H NMR (DMSO-d$_6$, 300 MHz): δ 10.448 (s, 1H), 8.116-8.088 (d, J=8.4 Hz, 2H), 7.970-7.941 (m, 3H), 7.877-7.849 (m, 3H), 7.790-7.747 (m, 4H), 7.694-7.668 (d, J=7.8 Hz, 1H), 7.549-7.500 (t, J=6.9, 7.2 Hz, 2H), 7.459-

7.435 (d, J=7.2 Hz, 1H), 4.666 (s, 2H), 3.601 (s, 3H), 2.306-2.286 (m, 4H), 1.764-1.742 (m, 4H); MS (ESI): m/z 529 (M−H), m/z 531 (M+H).

Example 529

1-(6-(4-([1,1'-Biphenyl]-4-ylcarboxamido)phenyl)-1-oxoisoindolin-2-yl)cyclopentane carboxylic acid The compound of example 529 was prepared analogous to compound of example 98 by hydrolysis of compound of example 528.

Yield: 67%; $^1$H NMR (DMSO-$d_6$, 300 MHz): δ 12.572 (s, 1H), 10.431 (s, 1H), 8.109-8.081 (d, J=8.4 Hz, 2H), 7.963-7.920 (m, 3H), 7.876-7.848 (m, 3H), 7.789-7.743 (m, 4H), 7.679-7.653 (d, J=7.8 Hz, 1H), 7.548-7.498 (t, J=7.2, 7.8 Hz, 2H), 7.457-7.433 (d, J=7.2 Hz, 1H), 4.633 (s, 2H), 2.318-2.286 (m, 4H), 1.756-1.738 (m, 4H); MS (ESI): m/z 515 (M−H), m/z 517 (M+H).

Example 530

Methyl 1-(6-(4-(4-(tert-butyl)benzamido)phenyl)-1-oxoisoindolin-2-yl)cyclopentanecarboxylate The compound of example 530 was prepared analogous to compound of example 97 by reaction of compound of example 527 with 4-(t-butyl)benzoyl chloride.

Yield: 79%; $^1$H NMR (DMSO-$d_6$, 300 MHz): δ 10.320 (s, 1H), 7.934-7.907 (m, 5H), 7.869 (s, 1H), 7.754-7.725 (d, J=8.7 Hz, 2H), 7.687-7.660 (d, J=8.1 Hz, 1H), 7.577-7.549 (d, J=8.4 Hz, 2H), 4.661 (s, 2H), 3.597 (s, 3H), 2.303-2.284 (m, 4H), 1.753-1.765 (m, 4H), 1.332 (s, 9H); MS (ESI): m/z 509 (M−H), m/z 511 (M+H).

Example 531

1-(6-(4-(4-(tert-Butyl)benzamido)phenyl)-1-oxoisoindolin-2-yl)cyclopentane carboxylic acid The compound of example 531 was prepared analogous to compound of example 98 by hydrolysis of compound of example 530.

Yield: 62%; $^1$H NMR (DMSO-$d_6$, 300 MHz): δ 12.572 (s, 1H), 10.300 (s, 1H), 7.926-7.863 (m, 5H), 7.863 (s, 1H), 7.751-7.723 (d, J=8.4 Hz, 2H), 7.673-7.647 (d, J=7.8 Hz, 1H), 7.577-7.549 (d, J=8.4 Hz, 2H), 4.629 (s, 2H), 2.315-2.275 (m, 4H), 1.754-1.736 (m, 4H), 1.331 (s, 9H); MS (ESI): m/z 495 (M−H), m/z 497 (M+H).

Example 532

Methyl 1-(6-(4-(4-chlorobenzamido)phenyl)-1-oxoisoindolin-2-yl)cyclopentane carboxylate The compound of example 532 was prepared analogous to compound of example 97 by reaction of compound of example 527 with 4-chloro benzoyl chloride.

Yield: 74%; $^1$H NMR (DMSO-$d_6$, 300 MHz): δ 10.477 (s, 1H), 8.040-8.012 (d, J=8.4 Hz, 2H), 7.953-7.900 (m, 2H), 7.871 (s, 1H), 7.766-7.737 (d, J=8.7 Hz, 2H), 7.689-7.662 (d, J=8.1 Hz, 2H), 7.643-7.615 (d, J=8.4 Hz, 2H), 4.661 (s, 2H), 3.596 (s, 3H), 2.315-2.293 (m, 4H), 1.783-1.752 (m, 4H); MS (ESI): m/z 487 (M−H), m/z 489 (M+H).

Example 533

1-(6-(4-(4-Chlorobenzamido)phenyl)-1-oxoisoindolin-2-yl)cyclopentane carboxylic acid The compound of example 533 was prepared analogous to compound of example 98 by hydrolysis of compound of example 532.

Yield: 70%; $^1$H NMR (DMSO-$d_6$, 300 MHz): δ 12.572 (s, 1H), 10.443 (s, 1H), 8.028-8.000 (d, J=8.4 Hz, 2H), 7.917-7.890 (m, 3H), 7.867 (s, 1H), 7.764-7.736 (d, J=8.4 Hz, 2H), 7.675-7.648 (d, J=8.1 Hz, 1H), 7.646-7.618 (d, J=8.4 Hz, 2H), 4.629 (s, 2H), 2.313-2.298 (m, 4H), 1.753-1.735 (m, 4H); MS (ESI): m/z 473 (M−H), m/z 475 (M+H).

Example 534

Methyl 1-(1-oxo-6-(4-(4-(trifluoromethoxy)benzamido)phenyl)isoindolin-2-yl)cyclopentanecarboxylate The compound of example 534 was prepared analogous to compound of example 97 by reaction of compound of example 527 with 4-trifluoromethoxy benzoyl chloride.

Yield: 77%; $^1$H NMR (DMSO-$d_6$, 300 MHz): δ 10.513 (s, 1H), 8.133-8.104 (d, J=8.7 Hz, 2H), 7.926-7.898 (d, J=8.4 Hz, 3H), 7.874 (s, 1H), 7.771-7.742 (d, J=8.7 Hz, 2H), 7.691-7.662 (d, J=8.7 Hz, 1H), 7.566-7.539 (d, J=8.1 Hz, 2H), 4.663 (s, 2H), 3.597 (s, 3H), 2.303-2.280 (m, 4H), 1.775-1.754 (m, 4H); MS (ESI): m/z 537 (M−H), m/z 539 (M+H).

Example 535

1-(1-Oxo-6-(4-(4-(trifluoromethoxy)benzamido)phenyl)isoindolin-2-yl)cyclopentane carboxylic acid The compound of example 535 was prepared analogous to compound of example 98 by hydrolysis of compound of example 534.

Yield: 70%; $^1$H NMR (DMSO-$d_6$, 300 MHz): δ 12.572 (s, 1H), 10.485 (s, 1H), 8.122-8.093 (d, J=8.7 Hz, 2H), 7.917-7.869 (m, 4H), 7.769-7.740 (d, J=8.7 Hz, 2H), 7.677-7.650 (d, J=8.1 Hz, 1H), 7.567-7.540 (d, J=8.1 Hz, 2H), 4.630 (s, 2H), 2.315-2.310 (m, 4H), 1.754-1.736 (m, 4H); MS (ESI): m/z 523 (M−H), m/z 525 (M+H).

Example 536

Methyl 1-(1-oxo-6-(4-(4-pentylbenzamido)phenyl)isoindolin-2-yl)cyclopentane carboxylate The compound of example 536 was prepared analogous to compound of example 97 by reaction of compound of example 527 with 4-(n-pentyl)benzoyl chloride.

Yield: 85%; $^1$H NMR (DMSO-$d_6$, 300 MHz): δ 10.306 (s, 1H), 7.931-7.895 (m, 5H), 7.869 (s, 1H), 7.752-7.723 (d, J=8.7 Hz, 2H), 7.761-7.732 (d, J=8.7 Hz, 1H), 7.376-7.349 (d, J=8.1 Hz, 2H), 4.660 (s, 2H), 3.597 (s, 3H), 2.663 (m, 2H), 2.303-2.280 (m, 4H), 1.775-1.753 (m, 4H), 1.530-1.452 (m, 2H), 1.310-1.286 (t, J=3.3, 3.9 Hz, 4H), 0.953-0.883 (t, J=6.3, 6.9 Hz, 3H); MS (ESI): m/z 523 (M–H), m/z 525 (M+H).

Example 537

1-(1-Oxo-6-(4-(4-pentylbenzamido)phenyl)isoindolin-2-yl)cyclopentane carboxylic acid The compound of example 537 was prepared analogous to compound of example 98 by hydrolysis of compound of example 536.
Yield: 84%; $^1$H NMR (DMSO-$d_6$, 300 MHz): δ 12.600 (s, 1H), 10.294 (s, 1H), 7.927-7.890 (m, 5H), 7.863 (s, 1H), 7.750-7.721 (d, J=8.7 Hz, 2H), 7.672-7.646 (d, J=7.8 Hz, 1H), 7.376-7.349 (d, J=8.1 Hz, 2H), 4.628 (s, 2H), 2.687-2.636 (t, J=7.8, 7.5 Hz, 2H), 2.316-2.308 (m, 4H), 1.753-1.735 (m, 4H), 1.637-1.588 (m, 2H), 1.308-1.285 (m, 4H), 0.892-0.848 (t, J=6.3, 6.9 Hz, 3H); MS (ESI): m/z 509 (M–H), m/z 511 (M+H).

Example 538

(R)-Methyl 3-methyl-2-(6-(4-nitrophenyl)-1-oxoisoindolin-2-yl)butanoate

The compound of example 538 was prepared analogous to compound of example 5 by reaction of compound of example 4 with D-valine methyl ester hydrochloride.
Yield: 77%; $^1$H NMR (DMSO-$d_6$, 300 MHz): δ 8.335-8.306 (d, J=8.7 Hz, 2H), 8.072-7.987 (m, 4H), 7.811-7.782 (d, J=8.7 Hz, 1H), 4.657-4.588 (m, 3H), 3.687 (s, 3H), 2.374-2.207 (m, 1H), 1.015-0.993 (d, J=6.6 Hz, 3H), 0.928-0.904 (d, J=6.6 Hz, 3H); MS (ESI): m/z 369 (M–H).

Example 539

(R)-Methyl 2-(6-(4-aminophenyl)-1-oxoisoindolin-2-yl)-3-methylbutanoate

The compound of example 539 was prepared analogous to the compound of example 6 by reduction of the compound of example 538.
Yield: 77%; $^1$H NMR (DMSO-$d_6$, 300 MHz): δ 7.882-7.785 (dd, J=1.5, 8.1 Hz, 2H), 7.626-7.600 (d, J=7.8 Hz, 1H), 7.431-7.403 (d, J=8.4 Hz, 2H), 6.672-6.644 (d, J=8.4 Hz, 2H), 5.300 (s, 2H), 4.623-4.553 (m, 3H), 3.678 (s, 3H), 2.381-2.253 (m, 1H), 1.005-0.983 (d, J=6.6 Hz, 3H), 0.852-0.830 (d, J=6.6 Hz, 3H); MS (ESI): m/z 339 (M–H).

Example 540

(R)-Methyl 2-(6-(4-([1,1'-biphenyl]-4-ylcarboxamido)phenyl)-1-oxoisoindolin-2-yl)-3-methylbutanoate The compound of example 540 was prepared analogous to compound of example 97 by reaction of compound of example 539 with 4-phenyl benzoyl chloride.
Yield: 65%; $^1$H NMR (DMSO-$d_6$, 300 MHz): δ 10.435 (s, 1H), 8.111-8.084 (d, J=8.1 Hz, 1H), 7.977-7.939 (m, 4H), 7.879-7.815 (d, J=8.4 Hz, 4H), 7.788-7.765 (m, 3H), 7.733-7.705 (d, J=8.4 Hz, 1H), 7.550-7.500 (t, J=7.2, 7.8 Hz, 2H), 7.459-7.435 (d, J=7.2 Hz, 1H), 4.648-4.614 (m, 3H), 3.691 (s, 3H), 2.395-2.263 (m, 1H), 1.018-0.996 (d, J=6.6 Hz, 3H), 0.869-0.847 (d, J=6.6 Hz, 3H); MS (ESI): m/z 517 (M–H), m/z 519 (M+H).

Example 541

(R)-2-(6-(4-([1,1'-Biphenyl]-4-ylcarboxamido)phenyl)-1-oxoisoindolin-2-yl)-3-methylbutanoic acid The compound of example 541 was prepared analogous to compound of example 98 by hydrolysis of compound of example 540.
Yield: 87%; $^1$H NMR (DMSO-$d_6$, 300 MHz): δ 13.200 (s, 1H), 10.438 (s, 1H), 8.112-8.085 (d, J=8.1 Hz, 2H), 7.968-7.941 (m, 4H), 7.878-7.850 (d, J=8.4 Hz, 2H), 7.789-7.765 (m, 4H), 7.728-7.700 (d, J=8.4 Hz, 1H), 7.549-7.500 (t, J=7.2, 7.5 Hz, 2H), 7.458-7.410 (t, J=7.2 Hz, 1H), 4.723-4.531 (m, 3H), 2.349-2.050 (m, 1H), 1.048-1.026 (d, J=6.6 Hz, 3H), 0.881-0.859 (d, J=6.6 Hz, 3H); MS (ESI): m/z 503 (M–H), m/z 505 (M+H).

Example 542

Methyl 3-(6-(4-nitrophenyl)-1-oxoisoindolin-2-yl)cyclohexanecarboxylate

The compound of example 542 was prepared analogous to compound of example 5 by reaction of compound of example 4 with methyl 3-aminocyclohexanecarboxylate hydrochloride.
Yield: 59%; $^1$H NMR (DMSO-$d_6$, 300 MHz): δ 8.333-8.303 (d, J=9 Hz, 2H), 8.070-8.011 (m, 4H), 7.759-7.733 (d, J=7.8 Hz, 1H), 4.547 (s, 2H), 4.136-4.097 (m, 1H), 3.608 (s, 3H), 2.636-2.509 (s, 1H), 2.023-1.319 (m, 8H); MS (ESI): m/z 395 (M+H).

Example 543

Methyl 3-(6-(4-aminophenyl)-1-oxoisoindolin-2-yl)cyclohexanecarboxylate

The compound of example 543 was prepared analogous to the compound of example 6 by reduction of the compound of example 542.
Yield: 72%; $^1$H NMR (DMSO-$d_6$, 300 MHz): δ 7.769-7.746 (d, J=6.9 Hz, 2H), 7.571-7.543 (d, J=8.4 Hz, 1H), 7.425-7.397 (d, J=8.4 Hz, 2H), 6.666-6.638 (d, J=8.4 Hz, 2H), 5.288 (s, 2H), 4.450 (s, 2H), 4.132-4.095 (m, 1H), 3.603 (s, 3H), 2.582-2.503 (s, 1H), 1.990-1.325 (m, 8H); MS (ESI): m/z 363 (M–H); m/z 365 (M+H).

Example 544

Methyl 3-(6-(4-([1,1'-biphenyl]-4-ylcarboxamido)phenyl)-1-oxoisoindolin-2-yl)cyclohexanecarboxylate The compound of example 544 was prepared analogous to compound of example 97 by reaction of compound of example 543 with 4-phenyl benzoyl chloride.
Yield: 80%; $^1$H NMR (DMSO-$d_6$, 300 MHz): δ 10.431 (s, 1H), 8.111-8.084 (d, J=8.1 Hz, 2H), 7.962-7.904 (m, 4H), 7.877-7.849 (d, J=8.4 Hz, 2H), 7.789-7.753 (m, 4H), 7.677-7.649 (d, J=8.4 Hz, 1H), 7.549-7.500 (t, J=7.2, 7.5 Hz, 2H), 7.459-7.435 (d, J=7.2 Hz, 1H), 4.507 (s, 2H), 4.138-4.134 (m, 1H), 3.611 (s, 3H), 2.596-2.504 (m, 1H), 2.020-1.508 (m, 8H); MS (ESI): m/z 543 (M–H), m/z 545 (M+H).

Example 545

3-(6-(4-([1,1'-Biphenyl]-4-ylcarboxamido)phenyl)-1-oxoisoindolin-2-yl)cyclo hexane carboxylic acid The compound of example 545 was prepared analogous to compound of example 98 by hydrolysis of compound of example 544.

Yield: 86%; $^1$H NMR (DMSO-$d_6$, 300 MHz): δ 10.438 (s, 1H), 8.113-8.085 (d, J=8.4 Hz, 2H), 7.964-7.904 (m, 4H), 7.876-7.848 (d, J=8.4 Hz, 2H), 7.789-7.752 (m, 4H), 7.677-7.649 (d, J=8.4 Hz, 1H), 7.548-7.499 (t, J=7.2, 7.5 Hz, 2H), 7.458-7.434 (d, J=7.2 Hz, 1H), 4.506 (s, 2H), 4.128-4.118 (m, 1H), 2.441-2.414 (m, 1H), 2.006-1.330 (m, 8H); MS (ESI): m/z 529 (M–H), m/z 531 (M+H).

Example 546

Methyl 3-(6-(4-(3-chlorobenzamido)phenyl)-1-oxoisoindolin-2-yl)cyclohexane carboxylate The compound of example 546 was prepared analogous to compound of example 97 by reaction of compound of example 543 with 3-chloro benzoyl chloride.

Yield: 87%; $^1$H NMR (DMSO-$d_6$, 300 MHz): δ 10.494 (s, 1H), 8.044-8.038 (d, J=1.8 Hz, 2H), 7.988-7.895 (m, 4H), 7.777-7.748 (d, J=8.7 Hz, 2H), 7.675-7.647 (d, J=8.4 Hz, 2H), 7.616-7.590 (d, J=7.8 Hz, 1H), 4.505 (s, 2H), 4.131-4.093 (m, 1H), 3.608 (s, 3H), 2.730-2.593 (m, 1H), 2.017-1.504 (m, 8H); MS (ESI): m/z 501 (M–H), m/z 503 (M+H).

Example 547

3-(6-(4-(3-Chlorobenzamido)phenyl)-1-oxoisoindolin-2-yl)cyclohexane carboxylic acid The compound of example 547 was prepared analogous to compound of example 98 by hydrolysis of compound of example 546.

Yield: 82%; $^1$H NMR (DMSO-$d_6$, 300 MHz): δ 12.202 (s, 1H), 10.442 (s, 1H), 8.031-8.002 (d, J=8.7 Hz, 2H), 7.917-7.890 (m, 4H), 7.773-7.744 (d, J=8.7 Hz, 2H), 7.673-7.617 (t, J=8.1, 8.7 Hz, 3H), 4.504 (s, 2H), 4.135-4.119 (m, 1H), 2.503-2.462 (m, 1H), 2.009-1.251 (m, 8H); MS (ESI): m/z 487 (M–H), m/z 489 (M+H).

Example 548

Methyl 3-(6-(4-(4-chlorobenzamido)phenyl)-1-oxoisoindolin-2-yl)cyclohexane carboxylate The compound of example 548 was prepared analogous to compound of example 97 by reaction of compound of example 543 with 4-chloro benzoyl chloride.

Yield: 93%; $^1$H NMR (DMSO-$d_6$, 300 MHz): δ 10.470 (s, 1H), 8.040-8.012 (d, J=8.4 Hz, 2H), 7.925-7.897 (m, 4H), 7.772-7.743 (d, J=8.7 Hz, 2H), 7.674-7.617 (d, J=8.4, 8.7 Hz, 3H), 4.505 (s, 2H), 4.135-4.195 (m, 1H), 3.609 (s, 3H), 2.634-2.594 (m, 1H), 2.014-1.505 (m, 8H); MS (ESI): m/z 501 (M–H), m/z 503 (M+H).

Example 549

3-(6-(4-(4-Chlorobenzamido)phenyl)-1-oxoisoindolin-2-yl)cyclohexane carboxylic acid The compound of example 549 was prepared analogous to compound of example 98 by hydrolysis of compound of example 548.

Yield: 85%; $^1$H NMR (DMSO-$d_6$, 300 MHz): δ 12.200 (s, 1H), 10.474 (s, 1H), 8.040-8.035 (d, J=1.5 Hz, 1H), 7.920-7.893 (m, 5H), 7.780-7.751 (d, J=8.7 Hz, 2H), 7.703-7.648 (t, J=8.4, 8.7 Hz, 2H), 7.617-7.591 (d, J=7.8 Hz, 1H), 4.568 (s, 2H), 4.137-4.118 (m, 1H), 2.503-2.422 (m, 1H), 2.011-1.326 (m, 8H); MS (ESI): m/z 487 (M–H), m/z 489 (M+H).

Example 550

Methyl 3-(1-oxo-6-(4-(4-(trifluoromethyl)benzamido)phenyl)isoindolin-2-yl)cyclohexanecarboxylate The compound of example 550 was prepared analogous to compound of example 97 by reaction of compound of example 543 with 4-trifluoromethyl benzoyl chloride.

Yield: 82%; $^1$H NMR (DMSO-$d_6$, 300 MHz): δ 10.598 (s, 1H), 8.195-8.168 (d, J=8.1 Hz, 2H), 7.954-7.904 (m, 6H), 7.790-7.761 (d, J=8.7 Hz, 2H), 7.678-7.651 (d, J=8.1 Hz, 1H), 4.508 (s, 2H), 4.145-4.125 (m, 1H), 3.609 (s, 3H), 2.636-2.505 (m, 1H), 2.019-1.577 (m, 8H); MS (ESI): m/z 521 (M–H), m/z 523 (M+H).

Example 551

3-(1-Oxo-6-(4-(4-(trifluoromethyl)benzamido)phenyl)isoindolin-2-yl)cyclo hexanecarboxylic acid The compound of example 551 was prepared analogous to compound of example 98 by hydrolysis of compound of example 550.

Yield: 77%; $^1$H NMR (DMSO-$d_6$, 300 MHz): δ 12.197 (s, 1H), 10.599 (s, 1H), 8.195-8.168 (d, J=8.1 Hz, 2H), 7.954-7.905 (m, 6H), 7.791-7.763 (d, J=8.7 Hz, 2H), 7.680-7.652 (d, J=8.4 Hz, 1H), 4.509 (s, 2H), 4.140-4.120 (m, 1H), 2.637-2.505 (m, 1H), 2.010-1.27 (m, 8H); MS (ESI): m/z 535 (M–H), m/z 537 (M+H).

Example 552

Methyl 3-(6-(4-(5-methyl-2-phenyloxazole-4-carboxamido)phenyl)-1-oxo isoindolin-2-yl)cyclohexanecarboxylate The compound of example 552 was prepared analogous to compound of example 97 by reaction of compound of example 543 with 5-methyl-2-phenyloxazole-4-carbonyl chloride.

Yield: 65%; $^1$H NMR (DMSO-$d_6$, 300 MHz): δ 10.105 (s, 1H), 8.106-8.075 (m, 2H), 7.995-7.967 (d, J=8.4 Hz, 2H), 7.929-7.908 (m, 2H), 7.767-7.738 (d, J=8.7 Hz, 2H), 7.674-7.646 (d, J=8.4 Hz, 1H), 7.603-7.584 (m, 3H), 4.506 (s, 2H), 4.142-4.115 (m, 1H), 3.611 (s, 3H), 3.308 (s, 3H), 2.740 (s, 3H), 2.615-2.504 (m, 1H), 1.983-1.507 (m, 8H); MS (ESI): m/z 548 (M–H), m/z 550 (M+H).

Example 553

3-(6-(4-(5-Methyl-2-phenyloxazole-4-carboxamido) phenyl)-1-oxoisoindolin-2-yl)cyclohexanecarboxylic acid The compound of example 553 was prepared analogous to compound of example 98 by hydrolysis of compound of example 552.

Yield: 72%; $^1$H NMR (DMSO-d$_6$, 300 MHz): δ 12.194 (s, 1H), 10.105 (s, 1H), 8.106-8.075 (m, 2H), 7.995-7.966 (d, J=8.7 Hz, 2H), 7.922-7.908 (m, 2H), 7.768-7.739 (d, J=8.7 Hz, 2H), 7.676-7.648 (d, J=8.4 Hz, 1H), 7.603-7.584 (m, 3H), 4.508 (s, 2H), 4.132-4.105 (m, 1H), 2.740 (s, 3H), 2.611-2.524 (m, 1H), 2.013-1.252 (m, 8H); MS (ESI): m/z 534 (M–H), m/z 535 (M+H).

Example 554

(1r,4r)-Methyl 4-(6-(4-nitrophenyl)-1-oxoisoindolin-2-yl)cyclohexanecarboxylate

The compound of example 554 was prepared analogous to compound of example 5 by reaction of compound of example 4 with (1r,4r)-methyl 4-aminocyclohexanecarboxylate hydrochloride.

Yield: 53%; $^1$H NMR (DMSO-d$_6$, 300 MHz): δ 8.334-8.305 (d, J=8.7 Hz, 2H), 8.071-8.012 (m, 4H), 7.771-7.742 (d, J=8.7 Hz, 1H), 4.524 (s, 2H), 4.126-4.046 (m, 1H), 3.621 (s, 3H), 2.346-2.309 (s, 1H), 2.055-1.503 (m, 8H); MS (ESI): m/z 393 (M–H); m/z 395 (M+H).

Example 555

(1r,4r)-Methyl4-(6-(4-aminophenyl)-1-oxoisoindolin-2-yl)cyclohexane carboxylate

The compound of example 555 was prepared analogous to the compound of example 6 by reduction of the compound of example 554.

Yield: 76%; $^1$H NMR (DMSO-d$_6$, 300 MHz): δ 7.767-7.742 (d, J=7.5 Hz, 2H), 7.578-7.552 (d, J=7.8 Hz, 1H), 7.422-7.394 (d, J=8.4 Hz, 2H), 6.666-6.638 (d, J=8.4 Hz, 2H), 5.279 (s, 2H), 4.426 (s, 2H), 4.061-3.986 (m, 1H), 3.616 (s, 3H), 2.390-2.324 (s, 1H), 2.043-1.354 (m, 8H); MS (ESI): m/z 363 (M–H); m/z 365 (M+H).

Example 556

(1r,4r)-Methyl 4-(6-(4-([1,1'-biphenyl]-4-ylcarboxamido)phenyl)-1-oxoisoindolin-2-yl)cyclohexanecarboxylate The compound of example 556 was prepared analogous to compound of example 97 by reaction of compound of example 555 with 4-phenyl benzoyl chloride. The title compound was directly used for preparation of compound of example 557 without purification.

Example 557

(1r,4r)-4-(6-(4-([1,1'-Biphenyl]-4-ylcarboxamido) phenyl)-1-oxoisoindolin-2-yl)cyclohexanecarboxylic acid The compound of example 557 was prepared analogous to compound of example 98 by hydrolysis of compound of example 556.

Yield: 82%; $^1$H NMR (DMSO-d$_6$, 300 MHz): δ 12.166 (s, 1H), 10.429 (s, 1H), 8.110-8.082 (d, J=8.4 Hz, 2H), 7.960-7.931 (d, J=8.7 Hz, 2H), 7.917-7.911 (d, J=1.8 Hz, 2H), 7.876-7.849 (d, J=8.1 Hz, 2H), 7.789-7.750 (m, 4H), 7.684-7.656 (d, J=8.4 Hz, 1H), 7.549-7.499 (t, J=7.5 Hz, 2H), 7.458-7.434 (d, J=7.2 Hz, 1H), 4.483 (s, 2H), 4.136-3.997 (m, 1H), 2.278-2.198 (m, 1H), 2.047-1.431 (m, 8H); MS (ESI): m/z 529 (M–H), m/z 531 (M+H).

Example 558

(1r,4r)-Methyl 4-(6-(4-(3-chlorobenzamido)phenyl)-1-oxoisoindolin-2-yl)cyclo hexanecarboxylate The compound of example 558 was prepared analogous to compound of example 97 by reaction of compound of example 555 with 3-chloro benzoyl chloride.

Yield: 87%; $^1$H NMR (DMSO-d$_6$, 300 MHz): δ 10.476 (s, 1H), 8.041 (s, 1H), 7.921-7.892 (m, 5H), 7.776-7.747 (d, J=8.7 Hz, 2H), 7.681-7.654 (d, J=8.1 Hz, 2H), 7.617-7.565 (d, J=7.8 Hz, 1H), 4.480 (s, 2H), 4.041-4.003 (m, 1H), 3.621 (s, 3H), 2.400-2.269 (m, 1H), 2.051-1.458 (m, 8H); MS (ESI): m/z 501 (M–H), m/z 503 (M+H).

Example 559

(1r,4r)-4-(6-(4-(3-Chlorobenzamido)phenyl)-1-oxoisoindolin-2-yl)cyclohexane carboxylic acid The compound of example 559 was prepared analogous to compound of example 98 by hydrolysis of compound of example 558.

Yield: 85%; $^1$H NMR (DMSO-d$_6$, 300 MHz): δ 10.580 (s, 1H), 8.052 (s, 1H), 7.973-7.900 (m, 5H), 7.773-7.745 (d, J=8.4 Hz, 2H), 7.673-7.646 (d, J=8.1 Hz, 2H), 7.612-7.586 (d, J=7.8 Hz, 1H), 4.477 (s, 2H), 4.040-4.002 (m, 1H), 2.400-1.985 (m, 1H), 1.970-1.404 (m, 8H); MS (ESI): m/z 487 (M–H), m/z 489 (M+H).

Example 560

(1r,4r)-Methyl 4-(6-(4-(4-chlorobenzamido)phenyl)-1-oxoisoindolin-2-yl)cyclohexanecarboxylate The compound of example 560 was prepared analogous to compound of example 97 by reaction of compound of example 555 with 4-chloro benzoyl chloride.

Yield: 93%; $^1$H NMR (DMSO-d$_6$, 300 MHz): δ 10.438 (s, 1H), 8.031-8.003 (d, J=8.4 Hz, 1H), 7.917-7.889 (m, 4H), 7.770-7.741 (d, J=8.7 Hz, 2H), 7.708-7.679 (d, J=8.7 Hz, 2H), 7.646-7.617 (d, J=8.7 Hz, 1H), 4.478 (s, 2H), 4.041-4.003 (m, 1H), 3.620 (s, 3H), 2.398-2.318 (m, 1H), 1.843-1.459 (m, 8H); MS (ESI): m/z 501 (M–H), m/z 503 (M+H).

Example 561

(1r,4r)-4-(6-(4-(4-Chlorobenzamido)phenyl)-1-oxoisoindolin-2-yl)cyclohexane carboxylic acid The compound of example 561 was prepared analogous to compound of example 98 by hydrolysis of compound of example 560.

Yield: 84%; $^1$H NMR (DMSO-$d_6$, 300 MHz): δ 10.491 (s, 1H), 8.037-8.010 (d, J=8.7 Hz, 2H), 7.919-7.894 (m, 4H), 7.769-7.741 (d, J=8.4 Hz, 2H), 7.675-7.646 (d, J=8.7 Hz, 2H), 7.644-7.615 (d, J=8.7 Hz, 1H), 4.477 (s, 2H), 4.014-4.001 (m, 1H), 2.099-1.980 (m, 1H), 1.812-1.388 (m, 8H); MS (ESI): m/z 487 (M−H), m/z 489 (M+H).

Example 562

(1r,4r)-Methyl 4-(1-oxo-6-(4-(4-(trifluoromethyl)benzamido)phenyl)isoindolin-2-yl)cyclohexanecarboxylate The compound of example 562 was prepared analogous to compound of example 97 by reaction of compound of example 555 with 4-trifluoromethyl benzoyl chloride.

Yield: 93%; $^1$H NMR (DMSO-$d_6$, 300 MHz): δ 10.607 (s, 1H), 8.199-8.172 (d, J=8.1 Hz, 2H), 7.952-7.907 (m, 6H), 7.788-7.759 (d, J=8.7 Hz, 2H), 7.687-7.659 (d, J=8.4 Hz, 1H), 4.485 (s, 2H), 4.042-4.005 (m, 1H), 3.622 (s, 3H), 2.361-2.271 (m, 1H), 1.815-1.502 (m, 8H); MS (ESI): m/z 535 (M−H), m/z 537 (M+H).

Example 563

(1r,4r)-4-(1-Oxo-6-(4-(4-(trifluoromethyl)benzamido)phenyl)isoindolin-2-yl)cyclohexanecarboxylic acid The compound of example 563 was prepared analogous to compound of example 98 by hydrolysis of compound of example 562.

Yield: 82%; $^1$H NMR (DMSO-$d_6$, 300 MHz): δ 10.618 (s, 1H), 8.197-8.170 (d, J=8.1 Hz, 2H), 7.950-7.906 (m, 6H), 7.787-7.758 (d, J=8.7 Hz, 2H), 7.683-7.654 (d, J=8.7 Hz, 1H), 4.481 (s, 2H), 4.065-3.989 (m, 1H), 2.334-2.154 (m, 1H), 1.828-1.417 (m, 8H); MS (ESI): m/z 521 (M−H), m/z 523 (M+H).

Example 564

(1r,3s,5R,7S)-Methyl 3-(6-(4-nitrophenyl)-1-oxoisoindolin-2-yl)adamantane-1-carboxylate The compound of example 564 was prepared analogous to compound of example 5 by reaction of compound of example 4 with (1r,3s,5R,7S)-methyl 3-aminoadamantane-1-carboxylate hydrochloride.

Yield: 65%; $^1$H NMR (DMSO-$d_6$, 300 MHz): δ 8.332-8.303 (d, J=8.7 Hz, 2H), 8.040-7.937 (m, 4H), 7.727-7.701 (d, J=7.8 Hz, 1H), 4.676 (s, 2H), 3.613 (s, 3H), 2.386-1.688 (s, 14H); MS (ESI): m/z 445 (M−H); m/z 447 (M+H).

Example 565

(1r,3s,5R,7S)-Methyl 3-(6-(4-aminophenyl)-1-oxoisoindolin-2-yl)adamantane-1-carboxylate The compound of example 565 was prepared analogous to the compound of example 6 by reduction of the compound of example 564.

Yield: 86%; $^1$H NMR (DMSO-$d_6$, 300 MHz): δ 7.745-7.718 (d, J=8.1 Hz, 1H), 7.666 (s, 1H), 7.540-7.514 (d, J=7.8 Hz, 1H), 7.401-7.373 (d, J=8.4 Hz, 2H), 6.667-6.639 (d, J=8.4 Hz, 2H), 5.275 (s, 2H), 4.582 (s, 2H), 3.612 (s, 3H), 2.375-2.136 (m, 8H), 1.859-1.816 (m, 4H), 1.671-1.616 (m, 2H); MS (ESI): m/z 415 (M−H), m/z 417 (M+H).

Example 566

(1r,3s,5R,7S)-Methyl 3-(6-(4-(3-chlorobenzamido)phenyl)-1-oxoisoindolin-2-yl)adamantane-1-carboxylate The compound of example 566 was prepared analogous to compound of example 97 by reaction of compound of example 565 with 3-chloro benzoyl chloride.

Yield: 93%; $^1$H NMR (DMSO-$d_6$, 300 MHz): δ 10.495 (s, 1H), 8.040-8.014 (s, 1H), 7.989-7.869 (m, 5H), 7.749-7.721 (d, J=8.4 Hz, 2H), 7.671-7.644 (d, J=8.1 Hz, 1H), 7.615-7.561 (d, J=8.1 Hz, 2H), 4.636 (s, 2H), 3.615 (s, 3H), 2.387-2.152 (m, 8H), 1.866-1.775 (m, 4H), 1.668-1.492 (m, 2H); MS (ESI): m/z 553 (M−H), m/z 555 (M+H).

Example 567

(1r,3s,5R,7S)-3-(6-(4-(3-Chlorobenzamido)phenyl)-1-oxoisoindolin-2-yl)adamantane-1-carboxylic acid The compound of example 567 was prepared analogous to compound of example 98 by hydrolysis of compound of example 566.

Yield: 79%; $^1$H NMR (DMSO-$d_6$, 300 MHz): δ 12.208 (s, 1H), 10.477 (s, 1H), 8.040 (s, 1H), 7.957-7.875 (m, 4H), 7.824 (s, 1H), 7.755-7.726 (d, J=8.7 Hz, 2H), 7.702-7.675 (d, J=8.1 Hz, 1H), 7.641-7.590 (d, J=7.5, 7.8 Hz, 2H), 4.638 (s, 2H), 2.353-2.210 (m, 8H), 1.801-1.664 (m, 4H), 1.662-1.495 (m, 2H); MS (ESI): m/z 539 (M−H), m/z 541 (M+H).

Example 568

(1r,3s,5R,7S)-Methyl 3-(6-(4-(4-chlorobenzamido)phenyl)-1-oxoisoindolin-2-yl)adamantane-1-carboxylate The compound of example 568 was prepared analogous to compound of example 97 by reaction of compound of example 565 with 4-chloro benzoyl chloride.

Yield: 91%; $^1$H NMR (DMSO-$d_6$, 300 MHz): δ 10.480 (s, 1H), 8.040-7.982 (m, 4H), 7.925-7.896 (d, J=8.7 Hz, 2H), 7.818 (s, 1H), 7.742-7.713 (d, J=8.7 Hz, 2H), 7.640-7.612 (d, J=8.4 Hz, 2H), 4.634 (s, 2H), 3.614 (s, 3H), 2.387-2.152 (m, 8H), 1.865-1.777 (m, 4H), 1.668-1.485 (m, 2H); MS (ESI): m/z 553 (M−H), m/z 555 (M+H).

Example 569

(1r,3s,5R,7S)-3-(6-(4-(4-Chlorobenzamido)phenyl)-1-oxoisoindolin-2-yl)adamantane-1-carboxylic acid The compound of example 569 was prepared analogous to compound of example 98 by hydrolysis of compound of example 568.

Yield: 80%; $^1$H NMR (DMSO-$d_6$, 300 MHz): δ 12.166 (s, 1H), 10.449 (s, 1H), 8.028-8.000 (d, J=8.4 Hz, 2H), 7.915-7.863 (m, 3H), 7.821 (s, 1H), 7.745-7.716 (d, J=8.7 Hz, 2H), 7.642-7.614 (d, J=8.4 Hz, 3H), 4.633 (s, 2H), 2.352 (s, 2H), 2.352-2.170 (m, 6H), 1.844-1.751 (m, 4H), 1.704-1.640 (m, 2H); MS (ESI): m/z 539 (M−H), m/z 541 (M+H).

Example 570

(1r,3s,5R,7S)-Methyl 3-(1-oxo-6-(4-(4-(trifluoromethyl)benzamido)phenyl)isoindolin-2-yl)adamantane-1-carboxylate The compound of example 570 was prepared analogous to compound of example 97 by reaction of compound of example 565 with 4-trifluoromethyl benzoyl chloride.

Yield: 75%; $^1$H NMR (DMSO-$d_6$, 300 MHz): δ 10.680 (s, 1H), 8.205-8.178 (d, J=8.1 Hz, 2H), 8.031-7.984 (m, 5H), 7.825 (s, 1H), 7.760-7.731 (d, J=8.7 Hz, 2H), 7.745-7.719 (d, J=7.8 Hz, 1H), 4.637 (s, 2H), 3.615 (s, 3H), 2.388 (s, 2H), 2.321-2.153 (m, 6H), 1.868-1.712 (m, 4H), 1.669-1.607 (m, 2H); MS (ESI): m/z 587 (M−H), m/z 589 (M+H).

Example 571

(1r,3s,5R,7S)-3-(1-Oxo-6-(4-(4-(trifluoromethyl)benzamido)phenyl)isoindolin-2-yl)adamantane-1-carboxylic acid The compound of example 571 was prepared analogous to compound of example 98 by hydrolysis of compound of example 570.

Yield: 75%; $^1$H NMR (DMSO-$d_6$, 300 MHz): δ 12.266 (s, 1H), 10.602 (s, 1H), 8.192-8.165 (d, J=8.1 Hz, 2H), 7.952-7.872 (m, 5H), 7.828 (s, 1H), 7.765-7.736 (d, J=8.7 Hz, 2H), 7.643-7.617 (d, J=7.8 Hz, 1H), 4.639 (s, 2H), 2.354 (s, 2H), 2.292-2.209 (m, 6H), 1.846-1.765 (m, 4H), 1.704-1.666 (m, 2H); MS (ESI): m/z 573 (M−H), m/z 575 (M+H).

Example 572

(1r,3s,5R,7S)-3-(6-(4-(4-Methylbenzamido)phenyl)-1-oxoisoindolin-2-yl)adamantane-1-carboxylic acid The compound of example 572 was prepared analogous to compound of example 97 by reaction of compound of example 565 with 4-methyl benzoyl chloride.

Yield: 83%; $^1$H NMR (DMSO-$d_6$, 300 MHz): δ 10.297 (s, 1H), 7.918-7.892 (m, 5H), 7.816 (s, 1H), 7.732-7.704 (d, J=8.4 Hz, 2H), 7.632-7.606 (d, J=7.8 Hz, 1H), 7.366-7.340 (d, J=7.8 Hz, 2H), 4.630 (s, 2H), 2.397 (s, 3H), 2.335-2.212 (m, 8H), 1.790-1.659 (m, 4H), 1.695-1.235 (m, 2H); MS (ESI): m/z 519 (M−H), m/z 521 (M+H).

Example 573

Methyl 1-(6-(4-nitrophenyl)-1-oxoisoindolin-2-yl)cyclobutanecarboxylate

The compound of example 573 was prepared analogous to compound of example 5 by reaction of compound of example 4 with methyl 1-aminocyclobutanecarboxylate hydrochloride.

Yield: 71%; $^1$H NMR (DMSO-$d_6$, 300 MHz): δ 8.337-8.308 (d, J=8.7 Hz, 2H), 8.068-8.000 (m, 4H), 7.794-7.768 (d, J=7.8 Hz, 1H), 4.673 (s, 2H), 3.652 (s, 3H), 2.668-2.616 (t, J=7.2, 8.4 Hz, 4H), 2.138-1.198 (m, 2H); MS (ESI): m/z 365 (M−H), m/z 367 (M+H).

Example 574

Methyl 1-(6-(4-aminophenyl)-1-oxoisoindolin-2-yl)cyclobutanecarboxylate

The compound of example 574 was prepared analogous to the compound of example 6 by reduction of the compound of example 573.

Yield: 71%; $^1$H NMR (DMSO-$d_6$, 300 MHz): δ 7.813-7.782 (dd, J=1.5, 8.1 Hz, 1H), 7.713 (S, 1H), 7.606-7.579 (d, J=8.1 Hz, 1H), 7.426-7.398 (d, J=8.4 Hz, 2H), 6.672-6.644 (d, J=8.4 Hz, 2H), 5.293-5.274 (s, 2H), 4.581 (s, 2H), 3.645 (s, 3H), 2.650-2.599 (t; J=6.9, 8.4 Hz, 4H), 2.125-1.991 (m, 2H); MS (ESI): m/z 335 (M−H), m/z 337 (M+H).

Example 575

Methyl 1-(6-(4-([1,1'-biphenyl]-4-ylcarboxamido)phenyl)-1-oxoisoindolin-2-yl)cyclobutanecarboxylate The compound of example 575 was prepared analogous to compound of example 97 by reaction of compound of example 574 with 4-phenyl benzoyl chloride.

Yield: 92%; $^1$H NMR (DMSO-$d_6$, 300 MHz): δ 10.435 (s, 1H), 8.113-8.085 (J=8.4 Hz, 2H), 7.968-7.940 (d, J=8.4 Hz, 3H), 7.879-7.850 (m, 3H), 7.791-7.752 (m, 4H), 7.715-7.688 (d, J=8.1 Hz, 1H), 7.550-7.501 (t, J=6.9, 7.8 Hz, 2H), 7.460-7.436 (d, J=7.2 Hz, 1H), 4.638 (s, 2H), 3.658 (s, 3H), 2.672-2.619 (t, J=7.5, 8.4 Hz, 4H), 2.104-2.017 (m, 2H); MS (ESI): m/z 515 (M−H), m/z 517 (M+H).

Example 576

1-(6-(4-([1,1'-Biphenyl]-4-ylcarboxamido)phenyl)-1-oxoisoindolin-2-yl)cyclo butanecarboxylic acid The compound of example 576 was prepared analogous to compound of example 98 by hydrolysis of compound of example 575.

Yield: 89%; $^1$H NMR (DMSO-$d_6$, 300 MHz): δ 10.442 (s, 1H), 8.112-8.084 (J=8.4 Hz, 2H), 7.966-7.927 (m, 3H), 7.875-7.849 (m, 3H), 7.790-7.774 (m, 4H), 7.691-7.664 (d, J=8.1 Hz, 1H), 7.548-7.499 (t, J=7.2, 7.5 Hz, 2H), 7.458-7.434 (d, J=7.2 Hz, 1H), 4.584 (s, 2H), 2.642-2.592 (t, J=6.6, 8.4 Hz, 4H), 2.166-1.989 (m, 2H); MS (ESI): m/z 501 (M−H), m/z 503 (M+H).

Example 577

Methyl 1-(6-(4-(4-chlorobenzamido)phenyl)-1-oxoisoindolin-2-yl)cyclobutane carboxylate The compound of example 577 was prepared analogous to compound of example 97 by reaction of compound of example 574 with 4-chloro benzoyl chloride.

Yield: 96%; $^1$H NMR (DMSO-$d_6$, 300 MHz): δ 10.469 (s, 1H), 8.039-8.010 (J=8.7 Hz, 2H), 7.957-7.930 (d, J=8.1 Hz, 2H), 7.900-7.874 (d, J=7.8 Hz, 2H), 7.770-7.741 (d, J=8.7 Hz, 2H), 7.710-7.683 (d, J=8.1 Hz, 1H), 7.644-7.616 (d, J=8.4 Hz, 2H), 4.634 (s, 2H), 3.654 (s, 3H), 2.667-2.615 (t, J=7.2, 8.4 Hz, 4H), 2.100-1.984 (m, 2H); MS (ESI): m/z 473 (M−H), m/z 475 (M+H).

Example 578

1-(6-(4-(4-Chlorobenzamido)phenyl)-1-oxoisoindolin-2-yl)cyclobutane carboxylic acid The compound of example 578 was prepared analogous to compound of example 98 by hydrolysis of compound of example 577.

Yield: 93%; $^1$H NMR (DMSO-$d_6$, 300 MHz): δ 12.774 (s, 1H), 10.447 (s, 1H), 8.030-8.001 (J=8.7 Hz, 2H), 7.950-7.869 (m, 4H), 7.770-7.741 (d, J=7.8 Hz, 2H), 7.693-7.666 (d, J=8.1 Hz, 1H), 7.647-7.619 (d, J=8.4 Hz, 2H), 4.588 (s, 2H), 2.647-2.596 (t, J=6.9, 8.4 Hz, 4H), 2.129-1.997 (m, 2H); MS (ESI): m/z 459 (M–H), m/z 461 (M+H).

Example 579

Methyl 1-(1-oxo-6-(4-(4-(trifluoromethyl)benzamido)phenyl)isoindolin-2-yl)cyclobutanecarboxylate The compound of example 579 was prepared analogous to compound of example 97 by reaction of compound of example 574 with 4-trifluoromethyl benzoyl chloride.

Yield: 83%; $^1$H NMR (DMSO-$d_6$, 300 MHz): δ 10.613 (s, 1H), 8.199-8.172 (J=8.1 Hz, 2H), 7.964-7.882 (m, 6H), 7.789-7.760 (d, J=8.7 Hz, 2H), 7.715-7.689 (d, J=7.8 Hz, 1H), 4.637 (s, 2H), 3.656 (s, 3H), 2.669-2.617 (t, J=7.2, 8.4 Hz, 4H), 2.103-1.987 (m, 2H); MS (ESI): m/z 507 (M–H), m/z 509 (M+H).

Example 580

1-(1-Oxo-6-(4-(4-(trifluoromethyl)benzamido)phenyl)isoindolin-2-yl)cyclo butane carboxylic acid The compound of example 580 was prepared analogous to compound of example 98 by hydrolysis of compound of example 579.

Yield: 96%; $^1$H NMR (DMSO-$d_6$, 300 MHz): δ 10.737 (s, 1H), 8.232-8.206 (J=7.8 Hz, 2H), 7.936-7.832 (m, 6H), 7.741-7.713 (d, J=8.4 Hz, 2H), 7.652-7.626 (d, J=7.8 Hz, 1H), 4.637 (s, 2H), 3.656 (s, 3H), 2.669-2.617 (t, J=7.2, 8.4 Hz, 4H), 2.103-1.987 (m, 2H); MS (ESI): m/z 493 (M–H), m/z 495 (M+H).

Example 581

Methyl 1-(6-(4-(4-methylbenzamido)phenyl)-1-oxoisoindolin-2-yl)cyclobutane carboxylate The compound of example 581 was prepared analogous to compound of example 97 by reaction of compound of example 574 with 4-methyl benzoyl chloride.

Yield: 96%; $^1$H NMR (DMSO-$d_6$, 300 MHz): δ 10.305 (s, 1H), 8.005-7.897 (m, 6H), 7.756-7.727 (d, J=8.7 Hz, 2H), 7.707-7.680 (d, J=8.1 Hz, 1H), 7.369-7.342 (d, J=8.1 Hz, 2H), 4.633 (s, 2H), 3.654 (s, 3H), 2.667-2.614 (t, J=7.5, 8.4 Hz, 4H), 2.400 (s, 3H), 2.100-1.985 (m, 2H); MS (ESI): m/z 453 (M–H), m/z 455 (M+H).

Example 582

1-(6-(4-(4-Methylbenzamido)phenyl)-1-oxoisoindolin-2-yl)cyclobutane carboxylic acid The compound of example 582 was prepared analogous to compound of example 98 by hydrolysis of compound of example 581.

Yield: 87%; $^1$H NMR (DMSO-$d_6$, 300 MHz): δ 10.382 (s, 1H), 7.944-7.918 (m, 4H), 7.859-7.832 (d, J=8.1 Hz, 1H), 7.795 (s, 1H), 7.713-7.684 (d, J=8.4 Hz, 2H), 7.616-7.589 (d, J=8.1 Hz, 1H), 7.361-7.334 (d, J=8.1 Hz, 2H), 4.519 (s, 2H), 2.528-2.460 (t, J=7.5, 8.4 Hz, 4H), 2.396 (s, 3H), 2.183-1.812 (m, 2H); MS (ESI): m/z 439 (M–H), m/z 441 (M+H).

Example 583

Methyl 1-(6-(4-nitrophenyl)-1-oxoisoindolin-2-yl) cyclopropanecarboxylate

The compound of example 583 was prepared analogous to compound of example 5 by reaction of compound of example 4 with methyl 1-aminocyclopropanecarboxylate hydrochloride.

Yield: 65%; $^1$H NMR (DMSO-$d_6$, 300 MHz): δ 8.337-8.308 (J=8.7 Hz, 2H), 8.078-8.050 (d, J=8.4 Hz, 4H), 7.778-7.752 (d, J=7.8 Hz, 1H), 4.594 (s, 2H), 3.618 (s, 3H), 1.611-1.493 (m, 4H); MS (ESI): m/z 351 (M–H), m/z 353 (M+H).

Example 584

Methyl 1-(6-(4-aminophenyl)-1-oxoisoindolin-2-yl) cyclopropanecarboxylate

The compound of example 584 was prepared analogous to the compound of example 6 by reduction of the compound of example 583.

Yield: 61%; $^1$H NMR (DMSO-$d_6$, 300 MHz): δ 7.821-7.758 (m, 2H), 7.585-7.559 (d, J=7.8 Hz, 1H), 7.433-7.404 (d, J=8.7 Hz, 2H), 6.670-6.642 (d, J=8.4 Hz, 2H), 5.300 (s, 2H), 4.501 (s, 2H), 3.611 (s, 3H), 1.591-1.469 (m, 4H); MS (ESI): m/z 321 (M–H), m/z 323 (M+H).

Example 585

Methyl 1-(6-(4-biphenyl-4-ylcarboxamidophenyl)-1-oxoisoindolin-2-yl)cyclo propanecarboxylate The compound of example 585 was prepared analogous to compound of example 97 by reaction of compound of example 584 with 4-phenyl benzoyl chloride. The compound obtained was used directly for the preparation of the compound of example 586 without purification.

Example 586

1-(6-(4-([1,1'-Biphenyl]-4-ylcarboxamido)phenyl)-1-oxoisoindolin-2-yl)cyclopropanecarboxylic acid The compound of example 586 was prepared analogous to compound of example 98 by hydrolysis of compound of example 585.

Yield: 91%; $^1$H NMR (DMSO-$d_6$, 300 MHz): δ 10.437 (s, 1H), 8.113-8.085 (J=8.4 Hz, 2H), 7.964-7.908 (m, 4H), 7.877-7.849 (d, J=8.4 Hz, 2H), 7.791-7.753 (m, 4H), 7.673-7.646 (d, J=9 Hz, 1H), 7.550-7.500 (t, J=7.2, 7.8 Hz, 2H), 7.459-7.435 (d, J=7.2 Hz, 1H), 4.542 (s, 2H), 1.473 (m, 2H), 1.371 (m, 2H); MS (ESI): m/z 489 (M+H).

Example 587

Methyl 1-(6-(4-(4-chlorobenzamido)phenyl)-1-oxoisoindolin-2-yl)cyclopropane carboxylate The compound of example 587 was prepared analogous to compound of example 97 by reaction of compound of example 584 with 4-chloro benzoyl chloride.

Yield: 95%; ¹H NMR (DMSO-d₆, 300 MHz): δ 10.463 (s, 1H), 8.035-8.006 (J=8.7 Hz, 2H), 7.966-7.897 (m, 4H), 7.779-7.750 (d, J=8.7 Hz, 2H), 7.690-7.663 (d, J=8.1 Hz, 2H), 7.586-7.558 (d, J=8.4 Hz, 1H), 4.554 (s, 2H), 3.619 (s, 3H), 1.606-1.488 (m, 4H); MS (ESI): m/z 461 (M+H).

Example 588

1-(6-(4-(4-Chlorobenzamido)phenyl)-1-oxoisoindolin-2-yl)cyclopropane carboxylic acid The compound of example 588 was prepared analogous to compound of example 98 by hydrolysis of compound of example 587.

Yield: 88%; ¹H NMR (DMSO-d₆, 300 MHz): δ 12.910 (s, 1H), 10.446 (s, 1H), 8.031-8.002 (J=8.7 Hz, 2H), 7.956-7.893 (m, 4H), 7.777-7.748 (d, J=8.7 Hz, 2H), 7.646-7.618 (d, J=8.4 Hz, 2H), 7.585-7.557 (d, J=8.4 Hz, 1H), 4.541 (s, 2H), 1.524-1.354 (m, 4H); MS (ESI): m/z 445 (M−H), m/z 447 (M+H).

Example 589

Methyl 1-(1-oxo-6-(4-(4-(trifluoromethyl)benzamido)phenyl)isoindolin-2-yl)cyclopropane carboxylate The compound of example 588 was prepared analogous to compound of example 97 by reaction of compound of example 584 with 4-trifluoromethyl benzoyl chloride.

Yield: 93%; ¹H NMR (DMSO-d₆, 300 MHz): δ 10.610 (s, 1H), 8.196-8.169 (J=8.1 Hz, 2H), 7.974-7.910 (m, 6H), 7.798-7.769 (d, J=8.7 Hz, 2H), 7.696-7.669 (d, J=8.1 Hz, 1H), 4.558 (s, 2H), 3.621 (s, 3H), 1.608-1.490 (m, 4H); MS (ESI): m/z 495 (M+H).

Example 590

1-(1-Oxo-6-(4-(4-(trifluoromethyl)benzamido)phenyl)isoindolin-2-yl)cyclo propane carboxylic acid The compound of example 590 was prepared analogous to compound of example 98 by hydrolysis of compound of example 589.

Yield: 93%; ¹H NMR (DMSO-d₆, 300 MHz): δ 10.603 (s, 1H), 8.192-8.165 (J=8.1 Hz, 2H), 7.953-7.905 (m, 6H), 7.793-7.764 (d, J=8.7 Hz, 2H), 7.683-7.656 (d, J=8.1 Hz, 1H), 4.543 (s, 2H), 1.521-1.444 (m, 4H); MS (ESI): m/z 481 (M+H).

Example 591

(1S,2R)-Methyl 2-(6-(4-nitrophenyl)-1-oxoisoindolin-2-yl)cyclopentane carboxylate The compound of example 591 was prepared analogous to compound of example 5 by reaction of compound of example 4 with (1S,2R)-methyl 2-aminocyclopentanecarboxylate hydrochloride.

Yield: 75%; ¹H NMR (DMSO-d₆, 300 MHz): δ 8.333-7.304 (d, J=8.7 Hz, 2H), 8.072-8.007 (m, 4H), 7.768-7.739 (d, J=8.7 Hz, 1H), 4.901-4.827 (m, 1H), 4.644-4.585 (d, J=17.7 Hz, 1H), 4.431-4.372 (d, J=17.7 Hz, 1H), 3.352 (s, 3H), 3.259-3.147 (m, 1H), 2.104-1.646 (m, 6H); MS (ESI): m/z 379 (M−H), m/z 381 (M+H).

Example 592

(1S,2R)-Methyl 2-(6-(4-aminophenyl)-1-oxoisoindolin-2-yl)cyclopentane carboxylate The compound of example 592 was prepared analogous to the compound of example 6 by reduction of the compound of example 591.

Yield: 90%; ¹H NMR (DMSO-d₆, 300 MHz): δ 7.776-7.743 (m, 2H), 7.576-7.550 (d, J=7.8 Hz, 1H), 7.428-7.400 (d, J=8.4 Hz, 2H), 6.667-6.638 (d, J=8.7 Hz, 2H), 5.287 (s, 2H), 4.875-4.819 (m, 1H), 4.544-4.486 (d, J=17.4 Hz, 1H), 4.341-4.284 (d, J=17.4 Hz, 1H), 3.342 (s, 3H), 3.179-3.152 (m, 1H), 2.035-1.972 (m, 6H); MS (ESI): m/z 351 (M−H), m/z 353 (M+H).

Example 593

(1S,2R)-Methyl 2-(6-(4-([1,1'-biphenyl]-4-ylcarboxamido)phenyl)-1-oxo isoindolin-2-yl)cyclopentanecarboxylate The compound of example 593 was prepared analogous to compound of example 97 by reaction of compound of example 592 with 4-phenyl benzoyl chloride.

Yield: 96%; ¹H NMR (DMSO-d₆, 300 MHz): δ 10.429 (s, 1H), 8.110-8.082 (J=8.4 Hz, 2H), 7.964-7.909 (m, 4H), 7.877-7.849 (d, J=8.4 Hz, 2H), 7.784-7.755 (m, 4H), 7.684-7.655 (d, J=8.7 Hz, 1H), 7.548-7.499 (t, J=7.2, 7.5 Hz, 2H), 7.458-7.434 (d, J=7.2 Hz, 1H), 4.879-4.853 (m, 1H), 4.602-4.543 (d, J=17.7 Hz, 1H), 4.396-4.337 (d, J=17.7 Hz, 1H), 3.358 (s, 3H), 3.198-3.171 (m, 1H), 2.074-1.989 (m, 6H); MS (ESI): m/z 528 (M−H), m/z 530 (M+H).

Example 594

(1S,2R)-2-(6-(4-([1,1'-Biphenyl]-4-ylcarboxamido)phenyl)-1-oxoisoindolin-2-yl)cyclopentanecarboxylic acid The compound of example 594 was prepared analogous to compound of example 98 by hydrolysis of compound of example 593.

Yield: 92%; ¹H NMR (DMSO-d₆, 300 MHz): δ 12.196 (s, 1H), 10.432 (s, 1H), 8.110-8.082 (J=8.4 Hz, 2H), 7.963-7.934 (d, J=8.7 Hz, 2H), 7.913-7.851 (m, 4H), 7.791-7.747 (m, 4H), 7.724-7.695 (d, J=8.7 Hz, 1H), 7.526-7.501 (t, J=7.2, 7.5 Hz, 2H), 7.448-7.424 (d, J=7.2 Hz, 1H), 4.789-4.756 (m, 1H), 4.556 (s, 2H), 3.093-3.061 (m, 1H), 2.067-1.743 (m, 6H); MS (ESI): m/z 515 (M−H), m/z 517 (M+H).

Example 595

(1S,2R)-Methyl 2-(6-(4-(4-chlorobenzamido)phenyl)-1-oxoisoindolin-2-yl)cyclopentanecarboxylate The compound of example 595 was prepared analogous to compound of example 97 by reaction of compound of example 592 with 4-chloro benzoyl chloride.

Yield: 95%; ¹H NMR (DMSO-d₆, 300 MHz): δ 10.440 (s, 1H), 8.029-8.001 (J=8.4 Hz, 2H), 7.919-7.890 (m, 4H), 7.776-7.747 (d, J=8.7 Hz, 2H), 7.680-7.619 (m, 3H), 4.874-4.849 (m, 1H), 4.600-4.541 (d, J=17.7 Hz, 1H), 4.392-4.333

(d, J=17.7 Hz, 1H), 3.314 (s, 3H), 3.195-3.316 (m, 1H), 2.073-1.939 (m, 6H); MS (ESI): m/z 486 (M–H), m/z 488 (M+H).

Example 596

(1S,2R)-2-(6-(4-(4-Chlorobenzamido)phenyl)-1-oxoisoindolin-2-yl)cyclopentane carboxylic acid The compound of example 596 was prepared analogous to compound of example 98 by hydrolysis of compound of example 595.

Yield: 82%; $^1$H NMR (DMSO-d$_6$, 300 MHz): δ 12.214 (s, 1H), 10.445 (s, 1H), 8.030-8.001 (J=8.7 Hz, 2H), 7.919-7.889 (m, 4H), 7.767-7.738 (d, J=8.7 Hz, 2H), 7.696-7.667 (d, J=8.7 Hz, 1H), 7.648-7.619 (d, J=8.7 Hz, 2H), 4.778-4.749 (m, 1H), 4.552 (s, 2H), 3.017 (m, 1H), 2.082-1.738 (m, 6H); MS (ESI): m/z 473 (M–H), m/z 475 (M+H).

Example 597

(1S,2R)-Methyl 2-(1-oxo-6-(4-(4-(trifluoromethyl)benzamido)phenyl)isoindolin-2-yl)cyclopentanecarboxylate The compound of example 597 was prepared analogous to compound of example 97 by reaction of compound of example 592 with 4-trifluoromethyl benzoyl chloride.

Yield: 86%; $^1$H NMR (DMSO-d$_6$, 300 MHz): δ 10.596 (s, 1H), 8.193-8.166 (J=8.1 Hz, 2H), 7.954-7.960 (m, 6H), 7.793-7.765 (d, J=8.7 Hz, 2H), 7.685-7.657 (d, J=8.4 Hz, 1H), 4.875-4.835 (m, 1H), 4.603-4.544 (d, J=17.7 Hz, 1H), 4.395-4.336 (d, J=17.7 Hz, 1H), 3.355 (s, 3H), 3.196-3.170 (m, 1H), 2.054-1.979 (m, 6H); MS (ESI): m/z 520 (M–H), m/z 522 (M+H).

Example 598

(1S,2R)-2-(1-Oxo-6-(4-(4-(trifluoromethyl)benzamido)phenyl)isoindolin-2-yl)cyclopentanebcarboxylic acid The compound of example 598 was prepared analogous to compound of example 98 by hydrolysis of compound of example 597.

Yield: 88%; $^1$H NMR (DMSO-d$_6$, 300 MHz): δ 12.203 (s, 1H), 10.602 (s, 1H), 8.194-8.167 (J=8.1 Hz, 2H), 7.954-7.896 (m, 6H), 7.784-7.755 (d, J=8.7 Hz, 2H), 7.699-7.672 (d, J=8.1 Hz, 1H), 4.785-4.701 (m, 1H), 4.554 (s, 2H), 3.001-2.943 (m, 1H), 2.002-1.777 (m, 6H); MS (ESI): m/z 507 (M–H), m/z 509 (M+H).

Example 599

(S)-Methyl 2-(6-(2-fluoro-4-nitrophenyl)-1-oxoisoindolin-2-yl)-3-methyl butanoate The compound of example 599 was prepared analogous to the compound of example 391 by reaction of the compound of example 390, 1-bromo-2-fluoro-4-nitrobenzene and Pd(dppf)Cl$_2$: CH$_2$Cl$_2$.

Yield: 80%; $^1$H NMR (DMSO-d$_6$, 300 MHz): δ 8.293-8.286 (dd, J=2.1, 8.4 Hz, 1H), 8.210-8.174 (dd, J=2.1, 8.4 Hz, 1H), 7.963-7.891 (m, 3H), 7.827-7.801 (d, J=7.8 Hz, 2H), 4.671-4.611 (m, 3H), 3.689 (s, 3H), 2.378-2.301 (m, 1H), 1.017-0.995 (d, J=6.6 Hz, 3H), 0.874-0.852 (d, J=6.6 Hz, 3H); MS (ESI): m/z 385 (M–H).

Example 600

(S)-Methyl 2-(6-(4-amino-2-fluorophenyl)-1-oxoisoindolin-2-yl)-3-methyl butanoate The compound of example 600 was prepared analogous to the compound of example 6 by reduction of the compound of example 599.

Yield: 95%; $^1$H NMR (DMSO-d$_6$, 300 MHz): δ 7.704-7.655 (m, 3H), 7.239-7.212 (t, J=8.1 Hz, 1H), 6.503-6.476 (d, J=8.1 Hz, 1H), 6.453-6.426 (d, J=8.1 Hz, 1H), 5.617 (s, 2H), 4.639-4.513 (m, 3H), 3.677 (s, 3H), 2.402-2.281 (m, 1H), 1.005-0.983 (d, J=6.6 Hz, 3H), 0.856-0.834 (d, J=6.6 Hz, 3H); MS (ESI): m/z 355 (M–H).

Example 601

(S)-Methyl 2-(6-(4-([1,1'-biphenyl]-4-ylcarboxamido)-2-fluorophenyl)-1-oxo isoindolin-2-yl)-3-methylbutanoate The compound of example 601 was prepared analogous to compound of example 97 by reaction of compound of example 600 with 4-phenyl benzoyl chloride.

Yield: 93%; $^1$H NMR (DMSO-d$_6$, 300 MHz): δ 10.612 (s, 1H), 8.113-8.085 (d, J=8.4 Hz, 2H), 7.921-7.824 (m, 5H), 7.793-7.730 (m, 4H), 7.659-7.601 (t, J=8.7 Hz, 1H), 7.551-7.501 (t, J=7.2, 7.8 Hz, 2H), 7.462-7.414 (t, J=7.8 Hz, 1H), 4.697-4.570 (m, 3H), 3.690 (s, 3H), 2.377-2.277 (m, 1H), 1.018-0.996 (d, J=6.6 Hz, 3H), 0.874-0.852 (d, J=6.6 Hz, 3H); MS (ESI): m/z 535 (M–H), m/z 537 (M+H).

Example 602

(S)-2-(6-(4-([1,1'-Biphenyl]-4-ylcarboxamido)-2-fluorophenyl)-1-oxoisoindolin-2-yl)-3-methylbutanoic acid The compound of example 602 was prepared analogous to compound of example 98 by hydrolysis of compound of example 601.

Yield: 97%; $^1$H NMR (DMSO-d$_6$, 300 MHz): δ 10.811 (s, 1H), 8.148-8.122 (d, J=7.8 Hz, 2H), 7.971-7.926 (m, 1H), 7.793-7.730 (m, 4H), 7.659-7.601 (t, J=8.7 Hz, 1H), 7.551-7.501 (t, J=7.2, 7.8 Hz, 2H), 7.462-7.414 (t, J=7.8 Hz, 1H), 4.697-4.570 (m, 3H), 3.690 (s, 3H), 2.377-2.277 (m, 1H), 1.018-0.996 (d, J=6.6 Hz, 3H), 0.874-0.852 (d, J=6.6 Hz, 3H); MS (ESI): m/z 535 (M–H), m/z 537 (M+H).

Example 603

(S)-Methyl 2-(6-(4-(4-(tert-butyl)benzamido)-2-fluorophenyl)-1-oxoisoindolin-2-yl)-3-methylbutanoate The compound of example 603 was prepared analogous to compound of example 97 by reaction of compound of example 600 with 4-t-butyl benzoyl chloride.

Yield: 83%; $^1$H NMR (DMSO-d$_6$, 300 MHz): δ 10.488 (s, 1H), 7.934-7.906 (d, J=8.4 Hz, 3H), 7.837-7.814 (d, J=6.9 Hz, 2H), 7.752-7.694 (m, 3H), 7.638-7.564 (m, 3H), 4.634-4.565 (m, 3H), 3.688 (s, 3H), 2.398-2.220 (m, 1H), 1.333 (S, 9H), 1.017-0.995 (d, J=6.6 Hz, 3H), 0.871-0.849 (d, J=6.6 Hz, 3H); MS (ESI): m/z 515 (M–H), m/z 517 (M+H).

Example 604

(S)-2-(6-(4-(4-(tert-Butyl)benzamido)-2-fluorophenyl)-1-oxoisoindolin-2-yl)-3-methylbutanoic acid The compound of example 604 was prepared analogous to compound of example 98 by hydrolysis of compound of example 603.

Yield: 87%; $^1$H NMR (DMSO-d$_6$, 300 MHz): δ 13.037 (s, 1H), 10.472 (s, 1H), 7.927-7.899 (d, J=8.4 Hz, 2H), 7.887-7.881 (d, J=1.8 Hz, 1H), 7.832-7.805 (d, J=8.1 Hz, 2H), 7.746-7.716 (d, J=9 Hz, 1H), 7.686-7.680 (d, J=1.8 Hz, 1H), 7.638-7.609 (d, J=8.7 Hz, 1H), 7.591-7.563 (d, J=8.4 Hz, 2H), 4.668-4.528 (m, 3H), 2.253-2.259 (m, 1H), 1.332 (S, 9H), 1.047-1.025 (d, J=6.6 Hz, 3H), 0.885-0.863 (d, J=6.6 Hz, 3H); MS (ESI): m/z 501 (M−H), m/z 503 (M+H).

Example 605

(S)-Methyl 2-(6-(4-(4-chlorobenzamido)-2-fluorophenyl)-1-oxoisoindolin-2-yl)-3-methylbutanoate The compound of example 605 was prepared analogous to compound of example 97 by reaction of compound of example 600 with 4-chloro benzoyl chloride.

Yield: 98%; $^1$H NMR (DMSO-d$_6$, 300 MHz): δ 10.647 (s, 1H), 7.934-7.906 (d, J=8.4 Hz, 2H), 7.838-7.815 (d, J=6.9 Hz, 2H), 7.753-7.696 (m, 2H), 7.653-7.622 (m, 3H), 7.586-7.557 (d, J=8.7 Hz, 1H), 4.635-4.606 (m, 3H), 3.688 (s, 3H), 2.374-2.297 (m, 1H), 1.015-0.993 (d, J=6.6 Hz, 3H), 0.870-0.848 (d, J=6.6 Hz, 3H); MS (ESI): m/z 493 (M−H), m/z 495 (M+H).

Example 606

(S)-2-(6-(4-(4-Chlorobenzamido)-2-fluorophenyl)-1-oxoisoindolin-2-yl)-3-methyl butanoic acid The compound of example 606 was prepared analogous to compound of example 98 by hydrolysis of compound of example 605.

Yield: 87%; $^1$H NMR (DMSO-d$_6$, 300 MHz): δ 13.163 (s, 1H), 10.615 (s, 1H), 8.028-8.000 (d, J=8.4 Hz, 2H), 7.951-7.923 (d, J=8.4 Hz, 2H), 7.832-7.804 (d, J=8.4 Hz, 2H), 7.681-7.622 (m, 2H), 7.577-7.548 (d, J=8.7 Hz, 2H), 4.635-4.606 (m, 3H), 2.325-2.271 (m, 1H), 1.045-1.023 (d, J=6.6 Hz, 3H), 0.881-0.859 (d, J=6.6 Hz, 3H); MS (ESI): m/z 479 (M−H), m/z 481 (M+H).

Example 607

(S)-Methyl 2-(6-(2-fluoro-4-(4-(trifluoromethoxy)benzamido)phenyl)-1-oxo isoindolin-2-yl)-3-methylbutanoate The compound of example 607 was prepared analogous to compound of example 97 by reaction of compound of example 600 with 4-trifluoromethoxy benzoyl chloride.

Yield: 83%; $^1$H NMR (DMSO-d$_6$, 300 MHz): δ 10.664 (s, 1H), 8.128-8.099 (d, J=8.7 Hz, 2H), 7.915-7.817 (m, 3H), 7.756-7.728 (d, J=8.4 Hz, 1H), 7.711-7.628 (m, 2H), 7.583-7.556 (d, J=8.1 Hz, 2H), 4.695-4.568 (m, 3H), 3.688 (s, 3H), 2.354-2.186 (m, 1H), 1.017-0.995 (d, J=6.6 Hz, 3H), 0.872-0.850 (d, J=6.6 Hz, 3H); MS (ESI): m/z 543 (M−H), m/z 545 (M+H).

Example 608

(S)-2-(6-(2-Fluoro-4-(4-(trifluoromethoxy)benzamido)phenyl)-1-oxoisoindolin-2-yl)-3-methylbutanoic acid The compound of example 608 was prepared analogous to compound of example 98 by hydrolysis of compound of example 607.

Yield: 80%; $^1$H NMR (DMSO-d$_6$, 300 MHz): δ 10.692 (s, 1H), 8.130-8.101 (d, J=8.7 Hz, 2H), 7.914-7.868 (m, 1H), 7.821-7.790 (m, 2H), 7.734-7.707 (d, J=8.1 Hz, 2H), 7.644-7.615 (d, J=8.7 Hz, 1H), 7.574-7.546 (d, J=8.4 Hz, 2H), 4.774-4.481 (m, 3H), 2.334-2.258 (m, 1H), 1.036-1.014 (d, J=6.6 Hz, 3H), 0.867-0.845 (d, J=6.6 Hz, 3H); MS (ESI): m/z 529 (M−H), m/z 531 (M+H).

Example 609

(S)-Methyl 2-(6-(2-fluoro-4-(4-pentylbenzamido)phenyl)-1-oxoisoindolin-2-yl)-3-methylbutanoate The compound of example 609 was prepared analogous to compound of example 97 by reaction of compound of example 600 with 4-n-pentyl benzoyl chloride.

Yield: 83%; $^1$H NMR (DMSO-d$_6$, 300 MHz): δ 10.478 (s, 1H), 7.932-7.894 (m, 3H), 7.837-7.814 (d, J=6.9 Hz, 2H), 7.752-7.691 (t, J=8.4 Hz, 2H), 7.637-7.579 (t, J=8.4, 9 Hz, 1H), 7.391-7.364 (d, J=8.1 Hz, 2H), 4.633-4.608 (m, 3H), 3.688 (s, 3H), 2.377-2.299 (t, J=7.5 Hz, 2H), 2.377-2.299 (m, 1H), 1.638-1.591 (m, 2H), 1.310-1.300 (m, 4H), 1.017-0.995 (d, J=6.6 Hz, 3H), 0.893-0.850 (m, 6H); MS (ESI): m/z 529 (M−H), m/z 531 (M+H).

Example 610

(S)-2-(6-(2-Fluoro-4-(4-pentylbenzamido)phenyl)-1-oxoisoindolin-2-yl)-3-methyl butanoic acid The compound of example 610 was prepared analogous to compound of example 98 by hydrolysis of compound of example 609.

Yield: 81%; $^1$H NMR (DMSO-d$_6$, 300 MHz): δ 12.996 (s, 1H), 10.462 (s, 1H), 7.927-7.888 (m, 3H), 7.832-7.805 (d, J=8.1 Hz, 2H), 7.744-7.686 (t, J=8.1 Hz, 2H), 7.636-7.578 (t, J=8.7 Hz, 1H), 7.388-7.362 (d, J=7.8 Hz, 2H), 4.728-4.529 (m, 3H), 2.688-2.638 (t, J=7.5 Hz, 2H), 2.349-2.274 (m, 2H), 1.635-1.588 (m, 1H), 1.354-1.296 (m, 4H), 1.047-1.025 (d, J=6.6 Hz, 3H), 0.885-0.865 (m, 6H); MS (ESI): m/z 515 (M−H), m/z 517 (M+H).

Example 611

(S)-Methyl 3-methyl-2-(1-oxo-6-(4-(5-phenylthiazole-2-carboxamido)phenyl)isoindolin-2-yl)butanoate To a solution of the compound of example 6 (405 mg, 1.2 mmol) and ethyl 5-phenylthiazole-2-carboxylate (233 mg, 1 mmol) in toluene (15 mL) in a sealed tube, was added 2M solution of AlMe$_3$ (135 mg, 1.875 mmol) and the reaction mixture was heated at 80° C. for 2 h. After completion of the reaction, the reaction mixture was cooled to room temperature and quenched with saturated ammonium chloride. The resulting solution was extracted with ethyl acetate. The ethyl acetate extract was washed with water, brine, dried over anhydrous sodium sulphate and concentrated to obtain a crude material, which was purified using column chromatography (30% ethyl acetate in petroleum ether) to afford the title compound.

Yield: 29%; $^1$H NMR (DMSO-d$_6$, 300 MHz): δ 10.965 (s, 1H), 8.543 (s, 1H), 8.030-8.001 (d, J=9 Hz, 2H), 7.975-7.951 (m, 2H), 7.856-7.832 (d, J=6 Hz, 2H), 7.789-7.760 (d, J=8.7 Hz, 2H), 7.733-7.705 (d, J=8.4 Hz, 2H), 7.520-7.480 (m, 2H), 4.643-4.610 (m, 3H), 3.687 (s, 3H), 2.394-2.256 (m, 1H), 1.016-0.994 (d, J=6.6 Hz, 3H), 0.867-0.845 (d, J=6.6 Hz, 3H); MS (ESI): m/z 524 (M−H), m/z 526 (M+H).

Example 612

(S)-3-Methyl-2-(1-oxo-6-(4-(5-phenylthiazole-2-carboxamido)phenyl)isoindolin-2-yl)butanoic acid The compound of example 612 was prepared analogous to compound of example 98 by hydrolysis of compound of example 611.

Yield: 93%; $^1$H NMR (DMSO-d$_6$, 300 MHz): δ 10.954 (s, 1H), 8.538 (s, 1H), 8.027-7.998 (d, J=9 Hz, 2H), 7.941-7.920 (m, 2H), 7.852-7.829 (d, J=6.9 Hz, 2H), 7.783-7.754 (d, J=9 Hz, 2H), 7.711-7.683 (d, J=8.4 Hz, 1H), 7.540-7.429 (m, 3H), 4.793-4.733 (d, J=18 Hz, 1H), 4.541-4.481 (d, J=18 Hz, 1H), 4.481-4.449 (d, J=9.6 Hz, 1H), 2.342-2.224 (m, 1H), 1.029-1.007 (d, J=6.6 Hz, 3H), 0.852-0.828 (d, J=6.6 Hz, 3H); MS (ESI): m/z 512 (M+H).

Example 613

(S)-Methyl 3-methyl-2-(1-oxo-6-(4-(5-phenyloxazole-2-carboxamido)phenyl)isoindolin-2-yl)butanoate The compound of example 613 was prepared analogous to the compound of example 611 by reaction of compound of example 6 with ethyl 5-phenyloxazole-2-carboxylate.

Ethyl 5-phenyloxazole-2-carboxylate was prepared according to the method disclosed in the PCT publication WO2004/18428 A1.

Yield: 90%; $^1$H NMR (DMSO-d$_6$, 300 MHz): δ 10.999 (s, 1H), 8.053 (s, 1H), 8.002-7.962 (m, 4H), 7.916-7.892 (d, J=7.2 Hz, 2H), 7.807-7.779 (d, J=8.4 Hz, 2H), 7.743-7.715 (d, J=8.4 Hz, 1H), 7.594-7.544 (t, J=7.2, 7.8 Hz, 2H), 7.507-7.483 (d, J=7.2 Hz, 1H), 4.655-4.620 (m, 3H), 3.697 (s, 3H), 2.382-2.305 (m, 1H), 1.025-1.003 (d, J=6.6 Hz, 3H), 0.877-0.855 (d, J=6.6 Hz, 3H); MS (ESI): m/z 510 (M+H).

Example 614

(S)-3-Methyl-2-(1-oxo-6-(4-(5-phenyloxazole-2-carboxamido)phenyl)isoindolin-2-yl)butanoic acid The compound of example 614 was prepared analogous to compound of example 98 by hydrolysis of compound of example 613.

Yield: 72%; $^1$H NMR (DMSO-d$_6$, 300 MHz): δ 12.962 (s, 1H), 10.001 (s, 1H), 8.049 (s, 1H), 7.995-7.954 (m, 4H), 7.911-7.886 (d, J=7.5 Hz, 2H), 7.803-7.774 (d, J=8.7 Hz, 2H), 7.735-7.707 (d, J=8.4 Hz, 1H), 7.588-7.538 (t, J=7.2, 7.8 Hz, 2H), 7.501-7.477 (d, J=7.2 Hz, 1H), 4.718-4.537 (m, 3H), 2.374-2.261 (m, 1H), 1.050-1.028 (d, J=6.6 Hz, 3H), 0.884-0.862 (d, J=6.6 Hz, 3H); MS (ESI): m/z 494 (M−H), m/z 496 (M+H).

Example 615

(S)-Methyl 2-(6-(4-(3-(4-fluorophenyl)isoxazole-5-carboxamido)phenyl)-1-oxoisoindolin-2-yl)-3-methylbutanoate The compound of example 615 was prepared analogous to the compound of example 611 by reaction of compound of example 6 with ethyl 3-(4-fluorophenyl)isoxazole-5-carboxylate.

Ethyl 3-(4-fluorophenyl)isoxazole-5-carboxylate was prepared according to the method disclosed in Bioorganic and Medicinal Chemistry Letters, 2009, 19, 21, 6218-6221.

Yield: 78%; $^1$H NMR (DMSO-d$_6$, 300 MHz): δ 10.988 (s, 1H), 8.075-8.027 (m, 2H), 7.977-7.920 (m, 4H), 7.868 (s, 1H), 7.814-7.785 (d, J=8.7 Hz, 2H), 7.740-7.711 (d, J=8.7 Hz, 1H), 7.452-7.393 (d, J=8.7, 9 Hz, 2H), 4.645-4.612 (m, 3H), 3.688 (s, 3H), 2.375-2.272 (m, 1H), 1.016-0.994 (d, J=6.6 Hz, 3H), 0.867-0.845 (d, J=6.6 Hz, 3H); MS (ESI): m/z 526 (M−H), m/z 528 (M+H).

Example 616

(S)-2-(6-(4-(3-(4-Fluorophenyl)isoxazole-5-carboxamido)phenyl)-1-oxo isoindolin-2-yl)-3-methylbutanoic acid The compound of example 616 was prepared analogous to the compound of example 98 by hydrolysis of compound of example 615.

Yield: 93%; $^1$H NMR (DMSO-d$_6$, 300 MHz): δ 13.141 (s, 1H), 10.995 (s, 1H), 8.075-8.028 (m, 2H), 7.951-7.921 (m, 4H), 7.875 (s, 1H), 7.813-7.785 (d, J=8.4 Hz, 2H), 7.733-7.705 (d, J=8.4 Hz, 1H), 7.451-7.392 (t, J=8.7, 9 Hz, 2H), 4.727-4.529 (m, 3H), 2.400-2.252 (m, 1H), 1.016-0.994 (d, J=6.6 Hz, 3H), 0.881-0.859 (d, J=6.6 Hz, 3H); MS (ESI): m/z 512 (M−H), m/z 514 (M+H).

Example 617

(S)-Methyl 2-(6-(4-(3-(4-chlorophenyl)isoxazole-5-carboxamido)phenyl)-1-oxoisoindolin-2-yl)-3-methylbutanoate The compound of example 617 was prepared analogous to the compound of example 611 by reaction of compound of example 6 with ethyl 3-(4-chlorophenyl)isoxazole-5-carboxylate.

Yield: 48%; $^1$H NMR (DMSO-d$_6$, 300 MHz): δ 10.993 (s, 1H), 8.028-8.000 (d, J=8.4 Hz, 2H), 7.977 (s, 1H), 7.955-7.889 (m, 3H), 7.814-7.785 (d, J=8.7 Hz, 2H), 7.739-7.711 (d, J=8.4 Hz, 1H), 7.666-7.638 (d, J=8.4 Hz, 2H), 7.592-7.564 (d, J=8.4 Hz, 1H), 4.645-4.612 (m, 3H), 3.689 (s, 3H), 2.398-2.275 (m, 1H), 1.016-0.995 (d, J=6.3 Hz, 3H), 0.867-0.846 (d, J=6.3 Hz, 3H); MS (ESI): m/z 542 (M−H), m/z 544 (M+H).

Example 618

(S)-2-(6-(4-(3-(4-Chlorophenyl)isoxazole-5-carboxamido)phenyl)-1-oxo isoindolin-2-yl)-3-methylbutanoic acid The compound of example 618 was prepared analogous to the compound of example 98 by hydrolysis of compound of example 617.

Yield: 94%; ¹H NMR (DMSO-d₆, 300 MHz): δ 13.031 (s, 1H), 10.992 (s, 1H), 8.028-8.000 (d, J=8.4 Hz, 2H), 7.981-7.921 (m, 4H), 7.889 (s, 1H), 7.816-7.787 (d, J=8.7 Hz, 2H), 7.736-7.708 (d, J=8.4 Hz, 1H), 7.665-7.637 (d, J=8.4 Hz, 2H), 4.719-4.538 (m, 3H), 2.353-2.276 (m, 1H), 1.050-1.028 (d, J=6.6 Hz, 3H), 0.884-0.862 (d, J=6.6 Hz, 3H); MS (ESI): m/z 527 (M–H), m/z 529 (M+H).

Example 619

(S)-Methyl 3-methyl-2-(1-oxo-6-(4-(3-(4-(trifluoromethyl)phenyl)isoxazole-5-carboxamido)phenyl)isoindolin-2-yl)butanoate The compound of example 619 was prepared analogous to the compound of example 611 by reaction of compound of example 6 with ethyl 3-(4-(trifluoromethyl)phenyl)isoxazole-5-carboxylate.

Yield: 62%; ¹H NMR (DMSO-d₆, 300 MHz): δ 11.028 (s, 1H), 8.233-8.207 (d, J=7.8 Hz, 2H), 7.979-7.925 (m, 7H), 7.820-7.791 (d, J=8.7 Hz, 2H), 7.741-7.713 (d, J=8.4 Hz, 1H), 4.646-4.614 (m, 3H), 3.689 (s, 3H), 2.393-2.274 (m, 1H), 1.018-0.996 (d, J=6.6 Hz, 3H), 0.869-0.847 (d, J=6.6 Hz, 3H); MS (ESI): m/z 576 (M–H), m/z 578 (M+H).

Example 620

(S)-3-Methyl-2-(1-oxo-6-(4-(3-(4-(trifluoromethyl)phenyl)isoxazole-5-carboxamido)phenyl)isoindolin-2-yl)butanoic acid The compound of example 620 was prepared analogous to the compound of example 98 by hydrolysis of compound of example 619.

Yield: 82%; ¹H NMR (DMSO-d₆, 300 MHz): δ 13.019 (s, 1H), 11.026 (s, 1H), 8.229-8.208 (d, J=6.3 Hz, 2H), 8.118-7.960 (m, 7H), 7.820-7.795 (d, J=7.5 Hz, 2H), 7.738-7.710 (d, J=8.4 Hz, 1H), 4.718-4.540 (m, 3H), 2.394-2.293 (m, 1H), 1.049-1.032 (d, J=5.1 Hz, 3H), 0.883-0.865 (d, J=5.4 Hz, 3H); MS (ESI): m/z 562 (M–H), m/z 564 (M+H).

Example 621

(S)-Methyl 3-methyl-2-(6-(4-(4-(oxazol-5-yl)benzamido)phenyl)-1-oxoisoindolin-2-yl)butanoate The compound of example 621 was prepared analogous to the compound of example 611 by reaction of compound of example 6 with commercially available methyl 4-(oxazol-5-yl)benzoate (Ryan Scientific, USA).

Yield: 58%; ¹H NMR (DMSO-d₆, 300 MHz): δ 10.452 (s, 1H), 8.548 (s, 1H), 8.120-8.092 (d, J=8.4 Hz, 2H), 7.973-7.888 (m, 6H), 7.785-7.756 (d, J=8.7 Hz, 2H), 7.730-7.702 (d, J=8.4 Hz, 1H), 4.645-4.611 (m, 3H), 3.688 (s, 3H), 2.372-2.296 (m, 1H), 1.016-0.994 (d, J=6.6 Hz, 3H), 0.867-0.845 (d, J=6.6 Hz, 3H); MS (ESI): m/z 508 (M–H), m/z 510 (M+H).

Example 622

(S)-3-Methyl-2-(6-(4-(4-(oxazol-5-yl)benzamido)phenyl)-1-oxoisoindolin-2-yl)butanoic acid The compound of example 622 was prepared analogous to the compound of example 98 by hydrolysis of compound of example 621.

Yield: 73%; ¹H NMR (DMSO-d₆, 300 MHz): δ 13.047 (s, 1H), 10.453 (s, 1H), 8.550 (s, 1H), 8.122-8.094 (d, J=8.4 Hz, 2H), 8.048-7.948 (m, 7H), 7.789-7.760 (d, J=8.7 Hz, 2H), 7.729-7.701 (d, J=8.4 Hz, 1H), 4.717-4.495 (m, 3H), 2.370-2.298 (m, 1H), 1.050-1.028 (d, 0.6 Hz, 3H), 0.884-0.862 (d, J=6.6 Hz, 3H); MS (ESI): m/z 494 (M–H), m/z 496 (M+H).

Example 623

(S)-Methyl 3-methyl-2-(1-oxo-6-(4-(4-phenylthiazole-2-carboxamido)phenyl)isoindolin-2-yl)butanoate The compound of example 623 was prepared analogous to the compound of example 611 by reaction of compound of example 6 with commercially available methyl 4-phenylthiazole-2-carboxylate (J & W PFharmLab, USA).

Yield: 55%; ¹H NMR (DMSO-d₆, 300 MHz): δ 10.758 (s, 1H), 8.531 (s, 1H), 8.205-8.180 (d, J=7.5 Hz, 2H), 8.038-8.009 (d, J=8.7 Hz, 2H), 7.996-7.973 (m, 2H), 7.828-7.800 (d, J=8.4 Hz, 2H), 7.739-7.711 (d, J=8.4 Hz, 1H), 7.552-7.502 (t, J=7.2, 7.8 Hz, 2H), 7.453-7.404 (t, J=7.2, 7.5 Hz, 1H), 4.649-4.554 (m, 3H), 3.690 (s, 3H), 2.397-2.274 (m, 1H), 1.017-0.995 (d, J=6.6 Hz, 3H), 0.870-0.848 (d, J=6.6 Hz, 3H); MS (ESI): m/z 524 (M–H), m/z 526 (M+H).

Example 624

(S)-3-Methyl-2-(1-oxo-6-(4-(4-phenylthiazole-2-carboxamido)phenyl)isoindolin-2-yl)butanoic acid The compound of example 624 was prepared analogous to the compound of example 98 by hydrolysis of compound of example 623.

Yield: 82%; ¹H NMR (DMSO-d₆, 300 MHz): δ 13.091 (s, 1H), 10.759 (s, 1H), 8.531 (s, 1H), 8.206-8.181 (d, J=7.5 Hz, 2H), 8.132-8.105 (d, J=8.1 Hz, 2H), 8.040-7.972 (m, 2H), 7.830-7.801 (d, J=8.7 Hz, 2H), 7.738-7.710 (d, J=8.4 Hz, 1H), 7.553-7.503 (t, J=7.2, 7.8 Hz, 2H), 7.454-7.405 (t, J=7.2, 7.5 Hz, 1H), 4.721-4.541 (m, 3H), 2.377-2.278 (m, 1H), 1.052-1.030 (d, J=6.6 Hz, 3H), 0.887-0.865 (d, J=6.6 Hz, 3H); MS (ESI): m/z 510 (M–H), m/z 512 (M+H).

Example 625

(S)-Methyl 3-methyl-2-(1-oxo-6-(4-(5-phenyl-1,3,4-oxadiazole-2-carboxamido)phenyl)isoindolin-2-yl)butanoate The compound of example 625 was prepared analogous to the compound of example 611 by reaction of compound of example 6 with commercially available ethyl 5-phenyl-1,3,4-oxadiazole-2-carboxylate (Enamine Ltd, Ukraine, Europe).

Yield: 44%; ¹H NMR (DMSO-d₆, 300 MHz): δ 11.392 (s, 1H), 8.160-8.133 (d, J=8.1 Hz, 2H), 7.993-7.962 (m, 4H), 7.826-7.797 (d, J=8.7 Hz, 2H), 7.742-7.641 (m, 4H), 4.646-4.613 (m, 3H), 3.689 (s, 3H), 2.375-2.297 (m, 1H), 1.017-0.996 (d, J=6.3 Hz, 3H), 0.869-0.847 (d, J=6.6 Hz, 3H); MS (ESI): m/z 509 (M–H), m/z 511 (M+H).

Example 626

(S)-Methyl 3-methyl-2-(1-oxo-6-(4-(5-phenyl-1,3,4-thiadiazole-2-carboxamido phenyl)isoindolin-2-yl)butanoate The compound of example 626 was prepared analogous to the compound of example 611 by reaction of compound of example 6 with ethyl 5-phenyl-1,3,4-thiadiazole-2-carboxylate.

Yield: 51%; $^1$H NMR (DMSO-$d_6$, 300 MHz): δ 11.383 (s, 1H), 8.127-8.101 (dd, J=1.8, 7.8 Hz, 2H), 8.026-7.997 (d, J=8.7 Hz, 2H), 7.972-7.959 (m, 2H), 7.813-7.785 (d, J=8.4 Hz, 2H), 7.740-7.711 (d, J=8.7 Hz, 1H), 7.659-7.616 (m, 3H), 4.645-4.612 (m, 3H), 3.688 (s, 3H), 2.375-2.319 (m, 1H), 1.017-0.995 (d, J=6.6 Hz, 3H), 0.869-0.847 (d, J=6.6 Hz, 3H); MS (ESI): m/z 525 (M−H), m/z 527 (M+H).

Example 627

(S)-3-Methyl-2-(1-oxo-6-(4-(5-phenyl-1,3,4-thiadiazole-2-carboxamido)phenyl)isoindolin-2-yl)butanoic acid The compound of example 627 was prepared analogous to the compound of example 98 by hydrolysis of compound of example 626.

Yield: 91%; $^1$H NMR (DMSO-$d_6$, 300 MHz): δ 13.060 (s, 1H) 11.384 (s, 1H), 8.130-8.102 (dd, J=1.8, 7.8 Hz, 2H), 8.030-8.001 (d, J=8.7 Hz, 2H), 7.978-7.958 (m, 2H), 7.817-7.789 (d, J=8.4 Hz, 2H), 7.738-7.710 (d, J=8.4 Hz, 1H), 7.643-7.619 (m, 3H), 4.721-4.536 (m, 3H), 2.331-2.275 (m, 1H), 1.051-1.029 (d, J=6.6 Hz, 3H), 0.885-0.863 (d, J=6.6 Hz, 3H); MS (ESI): m/z 511 (M−H).

Example 628

(S)-Methyl 3-methyl-2-(1-oxo-6-(4-(5-phenyl-4H-1,2,4-triazole-3-carboxamido)phenyl)isoindolin-2-yl)butanoate The compound of example 628 was prepared analogous to the compound of example 611 by reaction of compound of example 6 with ethyl 5-phenyl-4H-1,2,4-triazole-3-carboxylate.

Ethyl 5-phenyl-4H-1,2,4-triazole-3-carboxylate is prepared according to the method disclosed in Tetrahedron Letters, 1982, 23, 33, 3357-3360.

Yield: 33%; $^1$H NMR (DMSO-$d_6$, 300 MHz): δ 15.288-15.021 (d, 1H), 10.865-10.529 (d, 1H), 8.130 (m, 2H), 8.018-7.957 (m, 3H), 7.790-7.750 (m, 2H), 7.737-7.709 (d, J=8.4 Hz, 2H), 7.586-7.485 (d, J=8.4 Hz, 3H), 4.681-4.553 (m, 3H), 3.690 (s, 3H), 2.377-2.276 (m, 1H), 1.019-0.997 (d, J=6.6 Hz, 3H), 0.872-0.850 (d, J=6.6 Hz, 3H); MS (ESI): m/z 508 (M−H), m/z 510 (M+H).

Example 629

(S)-3-Methyl-2-(1-oxo-6-(4-(5-phenyl-4H-1,2,4-triazole-3-carboxamido)phenyl)isoindolin-2-yl)butanoic acid The compound of example 629 was prepared analogous to the compound of example 98 by hydrolysis of compound of example 628.

Yield: 77%; $^1$H NMR (DMSO-$d_6$, 300 MHz): δ 15.278-15.028 (d, 1H), 13.027 (s, 1H), 10.871-10.540 (d, 1H), 8.143-8.120 (d, J=6.9 Hz, 2H), 8.021-7.992 (d, J=8.7 Hz, 2H), 7.974-7.953 (m, 2H), 7.796-7.768 (d, J=8.4 Hz, 2H), 7.734-7.705 (d, J=8.7 Hz, 1H), 7.565 (m, 3H), 4.717-4.537 (m, 3H), 2.360-2.277 (m, 1H), 1.050-1.028 (d, J=6.6 Hz, 3H), 0.885-0.863 (d, J=6.6 Hz, 3H); MS (ESI): m/z 494 (M−H), m/z 496 (M+H).

Example 630A

Methyl 4-(2-cyanopropan-2-yl)benzoate

To a solution of potassium tert-butoxide (8 g) in THF (25 mL) at −30° C. was added a solution of methyl iodide (5.35 mL) and methyl 4-(cyanomethyl)benzoate (5 g) in THF (25 mL) under nitrogen atmosphere over 20 min. The reaction mixture was allowed to warm to room temperature and stirred for 2 h. The reaction was quenched by the addition of water (10 mL) and ethyl acetate was added. The organic layer was washed successively with water, brine and dried over anhydrous sodium sulfate. The organic solvent was removed to obtain a residue, which was purified by column chromatography (silicagel, 20% ethyl acetate in petroleum ether) to obtain a crude solid. The crude solid was crystallized using chloroform in petroleum ether to afford the title compound.

Yield: 4 g (69%); $^1$H NMR (CDCl$_3$, 300 MHz): δ 8.06 (d, 2H), 7.58 (d, 2H), 3.97 (s, 3H), 1.76 (s, 6H); MS (ESI): m/z 204.1 (M+H).

Example 630B (S)-Methyl 2-(6-(4-(4-(2-cyanopropan-2-yl)benzamido)phenyl)-1-oxoisoindolin-2-yl)-3-methylbutanoate The compound of example 630B was prepared analogous to the compound of example 611 by reaction of compound of example 6 with compound of example 630A.

Yield: 58%; $^1$H NMR (DMSO-$d_6$, 300 MHz): δ 10.417 (s, 1H), 8.045-8.017 (d, J=8.4 Hz, 2H), 7.969-7.902 (m, 4H), 7.779-7.750 (d, J=8.7 Hz, 2H), 7.726-7.697 (d, J=8.7 Hz, 1H), 7.717-7.689 (d, J=8.4 Hz, 2H), 4.644-4.610 (m, 3H), 3.687 (s, 3H), 2.373-2.272 (m, 1H), 1.744 (s, 6H), 1.015-0.993 (d, J=6.6 Hz, 3H), 0.866-0.844 (d, J=6.6 Hz, 3H); MS (ESI): m/z 510 (M+H).

Example 631

(S)-2-(6-(4-(4-(2-Cyanopropan-2-yl)benzamido)phenyl)-1-oxoisoindolin-2-yl)-3-methylbutanoic acid The compound of example 631 was prepared analogous to the compound of example 98 by hydrolysis of compound of example 630.

Yield: 87%; $^1$H NMR (DMSO-$d_6$, 300 MHz): δ 13.026 (s, 1H), 10.418 (s, 1H), 8.044-8.016 (d, J=8.4 Hz, 2H), 7.963-7.901 (m, 4H), 7.780-7.751 (d, J=8.7 Hz, 2H), 7.725-7.696 (d, J=8.7 Hz, 1H), 7.717-7.689 (d, J=8.4 Hz, 2H), 4.652-4.533 (m, 3H), 2.363-2.232 (m, 1H), 1.744 (s, 6H), 1.048-1.026 (d, J=6.6 Hz, 3H), 0.881-0.859 (d, J=6.6 Hz, 3H); MS (ESI): m/z 494 (M−H), m/z 496 (M+H).

Example 632A

Methyl 4-(3-cyanopentan-3-yl)benzoate

To a solution of potassium tert-butoxide (4.81 g) in THF (15 mL) at −30° C. was added a solution of ethyl iodide (4.11 mL) and methyl 4-(cyanomethyl)benzoate (3 g) THF (15 mL) under nitrogen atmosphere over 20 min. The reaction mixture was allowed to warm to room temperature and stirred for 2 h. The reaction was quenched by the addition of water (10 mL) and ethyl acetate was added. The organic layer was washed successively with water, brine and dried over anhydrous sodium sulfate. The organic solvent was removed to obtain a residue, which was purified by column chromatography (silicagel, 20% ethyl acetate in petroleum ether) to obtain a crude solid. The crude solid was crystallized using chloroform in petroleum ether to afford the title compound.

Yield: 2.5 g (63%); $^1$H NMR (CDCl$_3$): 8.08-8.06 (d, 2H), 7.5-7.47 (d, 2H), 3.94 (s, 3H), 2.15-2.03 (m, 2H) 2.0-1.89 (m, 2H), 0.91 (t, 6H); MS (ESI): m/z 232.1 (M+H).

Example 632B (S)-Methyl 2-(6-(4-(4-(3-cyanopentan-3-yl)benzamido)phenyl)-1-oxoisoindolin-2-yl)-3-methylbutanoate The compound of example 632 was prepared analogous to the compound of example 611 by reaction of compound of example 6 with 4-(3-cyanopentan-3-yl)benzoyl chloride.

Yield: 49%; $^1$H NMR (DMSO-d$_6$, 300 MHz): δ 10.435 (s, 1H), 8.041-8.014 (d, J=8.1 Hz, 2H), 7.943-7.898 (m, 4H), 7.775-7.747 (d, J=8.4 Hz, 2H), 7.728-7.699 (d, J=8.7 Hz, 1H), 7.620-7.593 (d, J=8.1 Hz, 2H), 4.643-4.609 (m, 3H), 3.686 (s, 3H), 2.365-2.252 (m, 1H), 2.076-2.042 (q, J=2.7, 7.2 Hz, 4H), 1.014-0.992 (d, J=6.6 Hz, 3H), 0.865-0.793 (m, 9H); MS (ESI): m/z 538 (M+H).

Example 633

(S)-2-(6-(4-(4-(3-Cyanopentan-3-yl)benzamido)phenyl)-1-oxoisoindolin-2-yl)-3-methylbutanoic acid The compound of example 633 was prepared analogous to the compound of example 98 by hydrolysis of compound of example 632.

Yield: 79%; $^1$H NMR (DMSO-d$_6$, 300 MHz): δ 13.041 (s, 1H), 10.436 (s, 1H), 8.043-8.015 (d, J=8.4 Hz, 2H), 7.961-7.899 (m, 4H), 7.778-7.749 (d, J=8.7 Hz, 2H), 7.726-7.697 (d, J=8.7 Hz, 1H), 7.621-7.593 (d, J=8.4 Hz, 2H), 4.713-4.532 (m, 3H), 2.349-2.272 (m, 1H), 2.125-2.067 (m, 4H), 1.047-1.025 (d, J=6.6 Hz, 3H), 0.880-0.793 (m, 9H); MS (ESI): m/z 522 (M–H), m/z 524 (M+H).

Example 634

(S)-Methyl 3-methyl-2-(1-oxo-6-(5-(5-phenyloxazole-2-carboxamido)pyridin-2-yl)isoindolin-2-yl)butanoate The compound of example 634 was prepared analogous to the compound of example 611 by reaction of compound of example 392 with ethyl 5-phenyloxazole-2-carboxylate.

Yield: 83%; $^1$H NMR (DMSO-d$_6$, 300 MHz): δ 10.247 (s, 1H), 9.136-9.128 (d, J=2.4 Hz, 1H), 8.392-8.354 (m, 3H), 8.167-8.138 (d, J=8.7 Hz, 1H), 8.072 (s, 1H), 7.912-7.885 (d, J=8.1 Hz, 2H), 7.763-7.735 (d, J=8.4 Hz, 1H), 7.590-7.540 (t, J=7.2, 7.8 Hz, 2H), 7.505-7.480 (d, J=7.5 Hz, 1H), 4.648-4.616 (m, 3H), 3.691 (s, 3H), 2.396-2.270 (m, 1H), 1.017-0.995 (d, J=6.6 Hz, 3H), 0.869-0.847 (d, J=6.6 Hz, 3H); MS (ESI): m/z 509 (M–H), m/z 511 (M+H).

Example 635

(S)-3-Methyl-2-(1-oxo-6-(5-(5-phenyloxazole-2-carboxamido)pyridin-2-yl)isoindolin-2-yl)butanoic acid The compound of example 635 was prepared analogous to the compound of example 98 by hydrolysis of compound of example 634.

Yield: 77%; $^1$H NMR (DMSO-d$_6$, 300 MHz): δ 13.051 (s, 1H), 11.249 (s, 1H), 9.139-9.132 (d, J=2.1 Hz, 1H), 8.385-8.365 (m, 3H), 8.169-8.1340 (d, J=8.7 Hz, 1H), 8.072 (s, 1H), 7.909-7.885 (d, J=7.2 Hz, 2H), 7.759-7.730 (d, J=8.7 Hz, 1H), 7.589-7.540 (t, J=7.2, 7.5 Hz, 2H), 7.504-7.480 (d, J=7.2 Hz, 1H), 4.737-4.542 (m, 3H), 2.373-2.277 (m, 1H), 1.051-1.029 (d, J=6.6 Hz, 3H), 0.887-0.865 (d, J=6.6 Hz, 3H); MS (ESI): m/z 495 (M–H), m/z 497 (M+H).

Example 636

(S)-Methyl 3-methyl-2-(1-oxo-6-(5-(5-phenylthiazole-2-carboxamido)pyridin-2-yl)isoindolin-2-yl)butanoate The compound of example 636 was prepared analogous to the compound of example 611 by reaction of compound of example 392 with ethyl 5-phenylthiazole-2-carboxylate.

Yield: 39%; $^1$H NMR (DMSO-d$_6$, 300 MHz): δ 11.226 (s, 1H), 9.172-9.165 (d, J=2.1 Hz, 1H), 8.573 (s, 1H), 8.425-8.376 (m, 3H), 8.156-8.127 (d, J=8.7 Hz, 1H), 7.862-7.838 (d, J=7.2 Hz, 2H), 7.760-7.731 (d, J=8.7 Hz, 1H), 7.523-7.461 (m, 3H), 4.640-4.616 (m, 3H), 3.691 (s, 3H), 2.333-2.285 (m, 1H), 1.017-0.995 (d, J=6.6 Hz, 3H), 0.869-0.847 (d, J=6.6 Hz, 3H); MS (ESI): m/z 525 (M–H), m/z 527 (M+H).

Example 637

(S)-3-Methyl-2-(1-oxo-6-(5-(5-phenylthiazole-2-carboxamido)pyridin-2-yl)isoindolin-2-yl)butanoic acid The compound of example 637 was prepared analogous to the compound of example 98 by hydrolysis of compound of example 636.

Yield: 59%; $^1$H NMR (DMSO-d$_6$, 300 MHz): δ 13.201 (s, 1H), 11.099 (s, 1H), 9.177-9.169 (d, J=2.4 Hz, 1H), 8.577 (s, 1H), 8.428-8.326 (m, 3H), 8.161-8.132 (d, J=8.7 Hz, 1H), 7.869-7.842 (d, J=8.1 Hz, 2H), 7.713-7.684 (d, J=8.7 Hz, 1H), 7.552-7.438 (m, 3H), 4.677-4.538 (m, 3H), 2.374-2.277 (m, 1H), 1.051-1.029 (d, J=6.6 Hz, 3H), 0.852-0.829 (d, J=6.6 Hz, 3H); MS (ESI): m/z 511 (M–H), m/z 513 (M+H).

Example 638

(S)-Methyl 2-(6-(5-(3-(4-fluorophenyl)isoxazole-5-carboxamido)pyridin-2-yl)-1-oxo isoindolin-2-yl)-3-methylbutanaote The compound of example 638 was prepared analogous to the compound of example 611 by reaction of compound of example 392 with ethyl 3-(4-fluorophenyl)isoxazole-5-carboxylate. The title compound obtained was used directly without purification for the preparation of compound of example 639.

Example 639

(S)-2-(6-(5-(3-(4-Fluorophenyl)isoxazole-5-carboxamido)pyridin-2-yl)-1-oxo isoindolin-2-yl)-3-methylbutanoic acid The compound of example 639 was prepared analogous to the compound of example 98 by hydrolysis of compound of example 638.

Yield: 68%; $^1$H NMR (DMSO-d$_6$, 300 MHz): δ 12.960 (s, 1H), 11.252 (s, 1H), 9.084 (s, 1H), 8.382-8.337 (m, 3H), 8.177-8.148 (d, J=8.7 Hz, 1H), 8.080-8.034 (dd, J=8.1 Hz, 2H), 7.909 (s, 1H), 7.758-7.731 (d, J=8.1 Hz, 1H), 7.449-

7.392 (t, J=8.4, 8.7 Hz, 2H), 4.746-4.532 (m, 3H), 2.348-2.274 (m, 1H), 1.048-1.026 (d, J=6.6 Hz, 3H), 0.883-0.861 (d, J=6.6 Hz, 3H); MS (ESI): m/z 513 (M−H), m/z 515 (M+H).

Example 640

(S)-Methy 12-(6-(4-(4-(1,3,4-oxadiazol-2-yl)benzamido)phenyl)-1-oxoisoindolin-2-yl)-3-methyl butanoate To a solution of 4-(1,3,4-oxadiazol-2-yl)benzoic acid (150 mg, 0.789 mmol) in DCM (3 mL), oxalyl chloride (187.73, 1.578 mmol) was added followed by 1-2 drops of DMF and stirred at room temperature. The solvent was removed and the residue obtained was dissolved in DCM (5 mL). To this solution, was added compound of example 6 (240 mg, 0.760 mmole) and pyridine (188.64 mg, 2.367 mmol) and the reaction mixture was stirred at room temperature for 3-4 h. After completion of the reaction, the reaction mixture was concentrated and the residue obtained was purified by column chromatography (silicagel, 30% ethyl acetate in chloroform).
Yield: 40%; $^1$H NMR (DMSO-$d_6$, 300 MHz): δ 10.595 (s, 1H), 9.441 (s, 1H), 8.203 (m, 4H), 7.976-7.924 (m, 4H), 7.797-7.768 (d, J=8.7 Hz, 2H), 7.733-7.705 (d, J=8.4 Hz, 1H), 4.645-4.611 (m, 3H), 3.688 (s, 3H), 2.395-2.254 (m, 1H), 1.016-0.994 (d, J=6.6 Hz, 3H), 0.867-0.845 (d, J=6.6 Hz, 3H); MS (ESI): m/z 509 (M−H), m/z 511 (M+H).

Example 641

(S)-2-(6-(4-(4-(1,3,4-Oxadiazol-2-yl)benzamido) phenyl)-1-oxoisoindolin-2-yl)-3-methylbutanoic acid The compound of example 641 was prepared analogous to the compound of example 98 by hydrolysis of compound of example 640.

Example 642

(S)-Methyl 3-methyl-2-(6-(4-(5-methyl-2-phenyloxazole-4-carboxamido)phenyl)-1-oxoisoindolin-2-yl) butanoate The compound of example 642 was prepared analogous to the compound of example 640 by reaction of compound of example 6 with commercially available 5-methyl-2-phenyloxazole-4-carboxylic acid (Maybridge Chemical Company, Ltd., UK).
Yield: 43%; $^1$H NMR (DMSO-$d_6$, 300 MHz): δ 10.120 (s, 1H), 8.105-8.075 (m, 2H), 7.999-7.951 (m, 4H), 7.772-7.743 (d, J=8.7 Hz, 2H), 7.728-7.701 (d, J=8.1 Hz, 1H), 7.602-7.584 (m, 3H), 4.645-4.611 (m, 3H), 3.688 (s, 3H), 2.740 (s, 3H), 2.395-2.301 (m, 1H), 1.016-0.994 (d, J=6.6 Hz, 3H), 0.868-0.846 (d, J=6.6 Hz, 3H); MS (ESI): m/z 524 (M+H).

Example 643

(S)-3-Methyl-2-(6-(4-(5-methyl-2-phenyloxazole-4-carboxamido)phenyl)-1-oxoisoindolin-2-yl)butanoic acid The compound of example 643 was prepared analogous to the compound of example 98 by hydrolysis of compound of example 642.
Yield: 89%; $^1$H NMR (DMSO-$d_6$, 300 MHz): δ 13.073 (s, 1H), 10.108 (s, 1H), 8.092-7.949 (m, 6H), 7.770-7.589 (m, 6H), 4.714-4.526 (m, 3H), 2.740 (s, 3H), 2.326-2.307 (m, 1H), 1.048-1.030 (d, J=5.4 Hz, 3H), 0.883-0.865 (d, J=5.4 Hz, 3H); MS (ESI): m/z 508 (M−H), m/z 510 (M+H).

Example 644

(S)-Methyl 3-methyl-2-(1-oxo-6-(4-(2-phenyl-5-(trifluoromethyl)oxazole-4-carboxamido)phenyl) isoindolin-2-yl)butanoate The compound of example 644 was prepared analogous to the compound of example 640 by reaction of compound of example 6 with commercially available 2-phenyl-5-(trifluoromethyl)oxazole-4-carboxylic acid (Matrix Scientific, USA).
Yield: 62%; $^1$H NMR (DMSO-$d_6$, 300 MHz): δ 10.708 (s, 1H), 8.181-8.155 (d, J=7.8 Hz, 2H), 7.974-7.946 (m, 4H), 7.803-7.775 (d, J=8.4 Hz, 2H), 7.731-7.653 (m, 4H), 4.643-4.609 (m, 3H), 3.685 (s, 3H), 2.407-2.235 (m, 1H), 1.012-0.990 (d, J=6.6 Hz, 3H), 0.864-0.842 (d, J=6.6 Hz, 3H); MS (ESI): m/z 478 (M+H).

Example 645

(S)-3-Methyl-2-(1-oxo-6-(4-(2-phenyl-5-(trifluoromethyl)oxazole-4-carboxamido)phenyl)isoindolin-2-yl)butanoic acid The compound of example 645 was prepared analogous to the compound of example 98 by hydrolysis of compound of example 644.
Yield: 61%; $^1$H NMR (DMSO-$d_6$, 300 MHz): δ 13.105 (s, 1H), 10.714 (s, 1H), 7.979-7.877 (m, 4H), 7.812-7.783 (d, J=8.7 Hz, 2H), 7.767-7.639 (m, 4H), 7.573-7.503 (m, 2H), 4.720-4.526 (m, 3H), 2.375-2.277 (m, 1H), 1.043-1.022 (d, J=6.3 Hz, 3H), 0.886-0.865 (d, J=6.3 Hz, 3H); MS (ESI): m/z 562 (M−H), m/z 564 (M+H).

Example 646

(S)-Methyl 3-methyl-2-(6-(2-methyl-4-(4-pentylbenzamido)phenyl)-1-oxoisoindolin-2-yl)butanoate The compound of example 646 was prepared analogous to the compound of example 640 by reaction of compound of example 6 with commercially available 4-(thiazol-2-yl)benzoic acid (Maybridge Chemical Company, Ltd., UK).
Yield: 28%; $^1$H NMR (DMSO-$d_6$, 300 MHz): δ 10.505 (s, 1H), 8.126 (m, 4H), 8.024-8.013 (d, J=3 Hz, 1H), 7.976-7.952 (m, 5H), 7.790-7.761 (d, J=9 Hz, 2H), 7.733-7.705 (d, J=8.4 Hz, 1H), 4.645-4.612 (m, 3H), 3.688 (s, 3H), 2.381-2.263 (m, 1H), 1.017-0.995 (d, J=6 Hz, 3H), 0.868-0.846 (d, J=6 Hz, 3H); MS (ESI): m/z 524 (M−H), m/z 526 (M+H).

Example 647

(S)-3-Methyl-2-(1-oxo-6-(4-(4-(thiazol-2-yl)benzamido)phenyl)isoindolin-2-yl)butanoic acid The compound of example 647 was prepared analogous to the compound of example 98 by hydrolysis of compound of example 646.
Yield: 78%; $^1$H NMR (DMSO-$d_6$, 300 MHz): δ 10.535 (s, 1H), 8.127 (m, 4H), 8.023-8.012 (d, J=3 Hz, 1H), 7.952-7.898 (m, 5H), 7.780-7.751 (d, J=9 Hz, 2H), 7.705-7.678 (d, J=9 Hz, 1H), 4.821-4.758 (d, J=18.9 Hz, 1H), 4.528-4.465 (d, J=18.9 Hz, 1H), 4.457-4.425 (d, J=9 Hz, 1H), 2.317-2.221

(m, 1H), 1.027-1.005 (d, J=6.6 Hz, 3H), 0.847-0.825 (d, J=6.6 Hz, 3H); MS (ESI): m/z 510 (M–H), m/z 512 (M+H).

Example 648

(S)-Methyl 2-(6-(4-(5-butylpicolinamido)phenyl)-1-oxoisoindolin-2-yl)-3-methylbutanoate The compound of example 648 was prepared analogous to the compound of example 640 by reaction of compound of example 6 with commercially available 5-butylpicolinoyl chloride (Sigma Chemical Company, USA).

Yield: 60%; $^1$H NMR (DMSO-d$_6$, 300 MHz): δ 10.726 (s, 1H), 8.606-8.601 (d, J=1.5 Hz, 1H), 8.117-8.091 (d, J=7.8 Hz, 1H), 8.059-8.030 (d, J=8.7 Hz, 2H), 7.974-7.894 (m, 3H), 7.769-7.740 (d, J=8.7 Hz, 2H), 7.726-7.698 (d, J=8.4 Hz, 1H), 4.643-4.609 (m, 3H), 3.686 (s, 3H), 2.758-2.707 (t, J=7.5, 7.8 Hz, 2H), 2.380-2.257 (m, 1H), 1.645-1.594 (m, 2H), 1.372-1.298 (m, 2H), 1.014-0.992 (d, J=6.6 Hz, 3H), 0.945-0.896 (t, J=7.2, 7.5 Hz, 3H), 0.888-0.866 (d, J=6.6 Hz, 3H); MS (ESI): m/z 498 (M–H), m/z 500 (M+H).

Example 649

(S)-2-(6-(4-(5-Butylpicolinamido)phenyl)-1-oxoisoindolin-2-yl)-3-methylbutanoic acid The compound of example 649 was prepared analogous to the compound of example 98 by hydrolysis of compound of example 648.

Yield: 80.6%; $^1$H NMR (DMSO-d$_6$, 300 MHz): δ 13.125 (s, 1H), 10.756 (s, 1H), 8.607-8.603 (d, J=1.2 Hz, 1H), 8.119-8.092 (d, J=8.1 Hz, 1H), 8.060-8.032 (d, J=8.7 Hz, 2H), 7.963-7.896 (m, 3H), 7.771-7.742 (d, J=8.7 Hz, 2H), 7.724-7.695 (d, J=8.7 Hz, 1H), 4.652-4.534 (m, 3H), 2.760-2.709 (t, J=7.5, 7.8 Hz, 2H), 2.372-2.229 (m, 1H), 1.669-1.564 (m, 2H), 1.401-1.274 (m, 2H), 1.048-1.026 (d, J=6.6 Hz, 3H), 0.946-0.897 (t, J=7.2, 7.5 Hz, 3H), 0.882-0.860 (d, J=6.6 Hz, 3H); MS (ESI): m/z 484 (M–H), m/z 486 (M+H).

Example 650

(S)-Methyl 3-methyl-2-(1-oxo-6-(4-(quinoline-3-carboxamido)phenyl)isoindolin-2-yl)butanoate The compound of example 650 was prepared analogous to the compound of example 640 by reaction of compound of example 6 with commercially available quinoline-3-carbonyl chloride.

Yield: 20%; $^1$H NMR (DMSO-d$_6$, 300 MHz): δ 10.749 (s, 1H), 9.394-9.387 (d, J=2.1 Hz, 1H), 9.000-8.994 (d, J=1.8 Hz, 1H), 8.195-8.169 (d, J=7.8 Hz, 1H), 8.150-8.122 (d, J=8.4 Hz, 1H), 7.989-7.916 (m, 5H), 7.821-7.792 (d, J=8.7 Hz, 2H), 7.741-7.712 (d, J=8.7 Hz, 2H), 4.649-4.615 (m, 3H), 3.691 (s, 3H), 2.375-2.237 (m, 1H), 1.018-0.996 (d, J=6.6 Hz, 3H), 0.870-0.848 (d, J=6.6 Hz, 3H); MS (ESI): m/z 492 (M–H), m/z 494 (M+H).

Example 651

(S)-3-Methyl-2-(1-oxo-6-(4-(quinoline-3-carboxamido)phenyl)isoindolin-2-butanoic acid The compound of example 651 was prepared analogous to the compound of example 98 by hydrolysis of compound of example 650.

Yield: 66%; $^1$H NMR (DMSO-d$_6$, 300 MHz): δ 10.770 (s, 1H), 9.395-9.389 (d, J=1.8 Hz, 1H), 9.010 (s, 1H), 8.194-8.167 (d, J=8.1 Hz, 1H), 8.149-8.121 (d, J=8.4 Hz, 1H), 7.980-7.887 (m, 5H), 7.817-7.788 (d, J=8.7 Hz, 2H), 7.766-7.699 (d, J=8.7 Hz, 2H), 4.747-4.509 (m, 3H), 2.320-2.267 (m, 1H), 1.044-1.022 (t, J=6.6 Hz, 3H), 0.874-0.852 (d, J=6.6 Hz, 3H); MS (ESI): m/z 480 (M–H).

Example 652

(S)-Methyl 3-methyl-2-(1-oxo-6-(4-(4-(pyrimidin-5-yl)benzamido)phenyl)isoindolin-2-yl)butanoate The compound of example 652 was prepared analogous to the compound of example 640 by reaction of compound of example 6 with commercially available 4-(pyrimidin-5-yl)benzoyl chloride.

Yield: 37%; $^1$H NMR (DMSO-d$_6$, 300 MHz): δ 10.489 (s, 1H), 9.262-9.252 (m, 3H), 8.170-8.142 (d, J=8.4 Hz, 2H), 8.046-8.018 (d, J=8.4 Hz, 2H), 7.967-7.938 (m, 4H), 7.793-7.764 (d, J=8.7 Hz, 2H), 7.726-7.698 (d, J=8.4 Hz, 1H), 4.643-4.612 (m, 3H), 3.689 (s, 3H), 2.372-2.298 (m, 1H), 1.017-0.995 (d, J=6.6 Hz, 3H), 0.868-0.846 (d, J=6.6 Hz, 3H); MS (ESI): m/z 519 (M–H), m/z 521 (M+H).

Example 653

(S)-3-Methyl-2-(1-oxo-6-(4-(4-(pyrimidin-5-yl)benzamido)phenyl)isoindolin-2-yl)butanoic acid The compound of example 653 was prepared analogous to the compound of example 98 by hydrolysis of compound of example 652.

Yield: 97%; $^1$H NMR (DMSO-d$_6$, 300 MHz): δ 13.019 (s, 1H), 10.490 (s, 1H), 9.262-9.252 (m, 3H), 8.171-8.144 (d, J=8.1 Hz, 2H), 8.045-8.018 (d, J=8.1 Hz, 2H), 7.969-7.940 (m, 4H), 7.793-7.765 (d, J=8.4 Hz, 2H), 7.729-7.701 (d, J=8.4 Hz, 1H), 4.718-4.535 (m, 3H), 2.350-2.274 (m, 1H), 1.049-1.027 (d, J=6.6 Hz, 3H), 0.882-0.860 (d, J=6.6 Hz, 3H); MS (ESI): m/z 505 (M–H), m/z 507 (M+H).

Example 654

(S)-Methyl 3-methyl-2-(6-(5-(5-methyl-2-phenyloxazole-4-carboxamido)pyridin-2-yl)-1-oxoisoindolin-2-yl)butanoate The compound of example 654 was prepared analogous to the compound of example 640 by reaction of compound of example 392 with 5-methyl-2-phenyloxazole-4-carboxylic acid.

Yield: 64%; $^1$H NMR (DMSO-d$_6$, 300 MHz): δ 10.414 (s, 1H), 9.142-9.135 (d, J=2.1 Hz, 1H), 8.421-8.380 (m, 3H), 8.141-8.082 (m, 3H), 7.760-7.732 (d, J=8.4 Hz, 1H), 7.614-7.594 (m, 3H), 4.654-4.575 (m, 3H), 3.695 (s, 3H), 2.753 (s, 3H), 2.427-2.228 (m, 1H), 1.022-1.000 (d, J=6.6 Hz, 3H), 0.874-0.811 (d, J=6.6 Hz, 3H); MS (ESI): m/z 523 (M–H), m/z 525 (M+H).

Example 655

(S)-3-Methyl-2-(6-(5-(5-methyl-2-phenyloxazole-4-carboxamido)pyridin-2-yl)-1-oxoisoindolin-2-yl)butanoic acid The compound of example 655 was prepared analogous to the compound of example 98 by hydrolysis of compound of example 654.

Yield: 92%; ¹H NMR (DMSO-d$_6$, 300 MHz): δ 13.074 (s, 1H), 10.411 (s, 1H), 9.143-9.136 (d, J=2.1 Hz, 1H), 8.422-8.364 (m, 3H), 8.139-8.086 (m, 3H), 7.755-7.726 (d, J=8.7 Hz, 1H), 7.612-7.594 (m, 3H), 4.738-4.545 (m, 3H), 2.751 (s, 3H), 2.334-2.280 (m, 1H), 1.055-1.033 (d, J=6.6 Hz, 3H), 0.892-0.870 (d, J=6.6 Hz, 3H); MS (ESI): m/z 509 (M–H), m/z 511 (M+H).

Example 656

(S)-Methyl 3-methyl-2-(1-oxo-6-(5-(2-phenyl-5-(trifluoromethyl)oxazole-4-carboxamido)pyridin-2-yl)isoindolin-2-yl) butanoate The compound of example 654 was prepared analogous to the compound of example 640 by reaction of compound of example 392 with 2-phenyl-5-(trifluoromethyl)oxazole-4-carboxylic acid.

Yield: 43%; ¹H NMR (DMSO-d$_6$, 300 MHz): δ 10.964 (s, 1H), 9.110-9.102 (d, J=2.4 Hz, 1H), 8.401-8.384 (m, 3H), 8.187-8.144 (m, 3H), 7.764-7.736 (d, J=8.4 Hz, 1H), 7.710-7.663 (m, 3H), 4.648-4.618 (m, 3H), 3.692 (s, 3H), 2.393-2.264 (m, 1H), 1.018-0.996 (d, J=6.6 Hz, 3H), 0.870-0.848 (d, J=6.6 Hz, 3H); MS (ESI): m/z 577 (M–H), m/z 579 (M+H).

Example 657

(S)-3-Methyl-2-(1-oxo-6-(5-(2-phenyl-5-(trifluoromethyl)oxazole-4-carboxamido)pyridin-2-yl)isoindolin-2-yl)butanoic acid The compound of example 657 was prepared analogous to the compound of example 98 by hydrolysis of compound of example 656.

Yield: 85%; ¹H NMR (DMSO-d$_6$, 300 MHz): δ 13.011 (s, 1H), 10.967 (s, 1H), 9.114-9.107 (d, J=2.1 Hz, 1H), 8.389-8.325 (m, 3H), 8.229-8.147 (m, 3H), 8.075-8.047 (d, J=8.4 Hz, 1H), 7.763-7.614 (m, 4H), 4.741-4.544 (m, 3H), 2.379-2.280 (m, 1H), 1.053-1.032 (d, J=6.3 Hz, 3H), 0.889-0.868 (d, J=6.3 Hz, 3H); MS (ESI): m/z 563 (M–H), m/z 565 (M+H).

Example 658

(S)-Methyl 3-methyl-2-(1-oxo-6-(4-(2-phenylacetamido)phenyl)isoindolin-2-yl)butanoate To a solution of 2-phenylacetic acid (150 mg, 1.102 mmol) in THF (5 mL) was added N-methylmorpholine (0.182 mL, 1.653 mmol) and cooled to −20 to −30° C. To this solution was added isobutyl chloroformate (0.145 mL, 1.102 mmol) and the reaction mixture was stirred at −20° C. for 30 min. To the reaction mixture, a solution of compound of example 6 (336 mg, 0.992 mmol) in THF (2.5 mL) was added and stirred at room temperature for 2-3 h. After completion of the reaction, EtOAc was added to the reaction mixture and washed with brine water. The organic extract was dried over anhydrous sodium sulfate and concentrated to obtain a crude material, which was purified by column chromatography (silicagel, 30% ethyl acetate in chloroform).

Yield: 69.3%; ¹H NMR (DMSO-d$_6$, 300 MHz): δ 10.310 (s, 1H), 7.926-7.902 (d, J=7.2 Hz, 2H), 7.747-7.679 (m, 5H), 7.357-7.255 (m, 5H), 4.636-4.596 (m, 3H), 3.683 (s, 3H), 3.344 (s, 2H), 2.366-2.288 (m, 1H), 1.011-0.989 (d, J=6.6 Hz, 3H), 0.859-0.837 (d, J=6.6 Hz, 3H); MS (ESI): m/z 455 (M–H), m/z 457 (M+H).

Example 659

(S)-3-Methyl-2-(1-oxo-6-(4-(2-phenylacetamido)phenyl)isoindolin-2-yl)butanoic acid The compound of example 659 was prepared analogous to the compound of example 98 by hydrolysis of compound of example 658.

Yield: 90%; ¹H NMR (DMSO-d$_6$, 300 MHz): δ 13.044 (s, 1H), 10.321 (s, 1H), 7.918-7.897 (d, J=6.3 Hz, 2H), 7.746-7.676 (m, 5H), 7.356-7.311 (m, 4H), 7.282-7.234 (m, 1H), 4.699-4.523 (m, 3H), 3.675 (s, 2H), 2.341-2.266 (m, 1H), 1.042-1.020 (d, J=6.3 Hz, 3H), 0.872-0.850 (d, J=6.6 Hz, 3H); MS (ESI): m/z 441 (M–H), m/z 443 (M+H).

Example 660

Methyl 2-(5-bromo-1,3-dioxoisoindolin-2-yl)-3-methylbutanoate 5-bromoisobenzofuran-1,3-dione (3 g, 13.21 mmol), L-valine methyl ester (3.31 g, 19.82 mmol) and triethyl amine (2.75 mL, 19.82 mmol) were taken in acetonitrile and heated at 80° C. for 24 h. The solvent was removed by distillation and the crude material obtained was purified using column chromatography (silicagel, 20% dichloromethane in petroleum ether) to afford the title compound.

Yield: 2.5 g, 55.6%; ¹H NMR (300 MHz, DMSO-d$_6$): δ 8.145 (s, 1H), 8.117 (d, J=8.1 Hz, 1H), 7.881 (d, J=8.1 Hz, 1H), 4.616 (d, J=7.5 Hz, 1H), 3.614 (s, 3H), 2.505 (m, 1H), 1.055 (d, J=6.6 Hz, 3H), 0.840 (d, J=6.9 Hz, 3H), MS ES(+): m/z 340 (M+H).

Example 661

Methyl 3-methyl-2-(5-(4-nitrophenyl)-1,3-dioxoisoindolin-2-yl)butanoate

The compound of example 660 (2.5 g, 7.35 mmol); 4,4,5,5-tetramethyl-2-(4-nitrophenyl)-1,3,2-dioxaborolane (2.19 g, 8.82 mmol) and bis-Pinacolato diborane (180 mg, 0.22 mmol) were taken in dry DMF under argon atmosphere. Degassed 2M solution of sodium carbonate (1.94 g, 18.37 mmol) was added and the reaction mixture was heated to 80° C. for 2 h. The reaction mixture was cooled and the solvent was removed by distillation. The residue was taken in water and this aqueous mixture was extracted with ethyl acetate. The crude material was purified through column chromatography (silicagel, 30% dichloromethane in petroleum ether) to afford the title compound.

Yield: 2 g (71%); ¹H NMR (300 MHz, DMSO-d$_6$): δ 8.359 (d, J=8.7 Hz, 2H), 8.296 (s, 1H), 8.269 (s, 1H); 8.147 (d, J=8.7 Hz, 1H), 8.080 (d, 1H), 8.054 (d, 1H), 4.658 (d, J=7.8 Hz, 1H), 3.633 (s, 3H), 2.642 (m, 1H), 1.086 (d, J=6.6 Hz, 3H), 0.845 (d, J=6.9 Hz, 3H); MS ES(+): m/z 383 (M+H), 405 (M+Na); ES(−): m/z 381 (M–H).

Example 662

Methyl 2-(5-(4-aminophenyl)-1,3-dioxoisoindolin-2-yl)-3-methyl butanoate

The compound of example 661 (2 g, 5.23) was dissolved in ethanol (20 mL), tetrahydrofuran (8 mL) and water (8 mL). Then ammonium chloride (840 mg, 15.70 mmoL)) and iron (876 mg, 15.70 mmoL) were added and refluxed at 80° C. for 2 h. The reaction mixture was cooled and filtered through Celite®. The solvent was removed to obtain a dark brown residue. The residue was taken in water and extracted with ethyl acetate. The organic layer was separated, dried over anhydrous $Na_2SO_4$ and concentrated to obtain a dark brown residue which was purified by column chromatography (silicagel, 30% ethyl acetate in petroleum ether) to afford the title compound.

Yield: 1.1 g (60%); $^1$H NMR (300 MHz, DMSO-$d_6$): δ 8.045 (s, 1H), 8.022 (s, 1H), 7.888 (d, J=8.4 Hz, 1H), 7.583 (d, J=8.4 Hz, 2H), 6.692 (d, J=8.4 Hz, 2H), 5.572 (s, 2H), 4.600 (d, J=7.8 Hz, 1H), 3.619 (s, 3H), 2.505 (m, 1H), 1.076 (d, J=6.6 Hz, 3H), 0.845 (d, J=6.9 Hz, 3H); MS ES(+): m/z 352 (M+H).

Example 663

Methyl 2-(5-(4-biphenyl-4-ylcarboxamidophenyl)-1,3-dioxoisoindolin-2-yl)-3-methyl butanoate The compound of example 662 (100 mg, 0.284 mmol), biphenyl-4-carbonyl chloride (93 mg, 0.426 mmol) and pyridine (0.35 mL) were taken in dichloromethane and the reaction mixture was stirred at room temperature for about 16 h. The solvent was removed by distillation and the crude material obtained was purified through column chromatography (silicagel, 30% ethyl acetate in petroleum ether) to afford the title compound.

Yield: 100 mg (66.2%); $^1$H NMR (300 MHz, DMSO-$d_6$): δ 10.508 (s, 1H), 8.219 (bs, 2H), 8.144 (d, J=8.4 Hz, 2H), 8.014 (d, J=7.8 Hz, 3H), 7.917 (t, J=9 Hz, 4H), 7.794 (d, J=7.2 Hz, 2H), 7.553 (t, J=7.2 Hz, 2H), 7.463 (m, 1H), 4.646 (d, J=7.8 Hz, 1H), 3.635 (t, 3H), 2.504 (m, 1H), 1.093 (d, J=6.9 Hz, 3H), 0.847 (d, J=6.9 Hz, 3H); MS ES(+): m/z 533 (M+H); ES(−): m/z 531 (M−H).

Example 664

Methyl 2-(5-(4-(4-tert-butylbenzamido)phenyl)-1,3-dioxoisoindolin-2-yl)-3-methyl butanoate The compound of example 664 was prepared analogous to the compound of example 663 by reaction of compound of example 662 with 4-(t-butyl)benzoyl chloride.

Yield: 80 mg (55%); $^1$H NMR (300 MHz, DMSO-$d_6$): δ 10.380 (s, 1H), 8.208 (m, 2H), 8.006-7.933 (m, 4H), 7.904 (d, J=2.1 Hz, 2H), 7.867 (s, 1H), 7.587 (d, J=8.4 Hz, 2H), 4.642 (d, J=7.8 Hz, 1H), 3.632 (s, 3H), 2.639 (m, 1H), 1.334 (s, 9H), 1.090 (d, J=6.9 Hz, 3H), 0.866 (d, J=6.9 Hz, 3H); MS ES(+): m/z 513 (M+H); ES(+): m/z 511 (M−H).

Example 665

Methyl 2-(5-(4-(2,4-dimethoxybenzamido)phenyl)-1,3-dioxoisoindolin-2-yl)-3-methylbutanoate The compound of example 665 was prepared analogous to the compound of example 663 by reaction of compound of example 662 with 2,4-dimethoxy benzoyl chloride.

Yield: 75 mg (51%); $^1$H NMR (300 MHz, DMSO-$d_6$): δ 10.121 (s, 1H), 8.191 (bs, 2H), 8.003 (d, J=8.1 Hz, 1H), 7.930-7.849 (m, 4H), 7.778 (d, J=8.4 Hz, 2H), 6.726 (m, 2H), 4.642 (d, J=7.5 Hz, 1H), 3.974 (s, 3H), 3.856 (s, 3H), 3.632 (s, 3H), 2.615 (m, 1H), 1.089 (d, J=6.3 Hz, 3H), 0.865 (d, J=6.6 Hz, 3H); MS ES(+): m/z 517 (M+H); ES(+): m/z 515 (M−H).

Example 666

Methyl 2-(5-(4-(3-(2-chlorophenyl)ureido)phenyl)-1,3-dioxoisoindolin-2-yl)-3-methylbutanoate The compound of example 665 (100 mg. 0.284 mmol) was dissolved in tetrahydrofuran (10 mL) and to this solution, 2-chloro phenylisocyanate (65 mg. 0.426 mmol) was added. The reaction mixture was stirred at room temperature for 24 h. The solvent was removed completely to obtain a residue which was purified by column chromatography (silicagel, 30% ethyl acetate in chloroform) to afford the title compound.

Yield: 70 mg (48.9%); $^1$H NMR (300 MHz, DMSO-$d_6$): δ 9.653 (s, 1H), 8.399 (d, 1H), 8.197 (d, J=1.2 Hz, 1H), 8.175 (m, 2H), 7.989 (d, J=8.1 Hz, 1H), 7.850 (d, J=8.7 Hz, 2H), 7.650 (d, J=8.7 Hz, 2H), 7.495 (dd, J=1.2, 8.1 Hz, 1H), 7.352 (t, J=8.4 Hz, 1H), 7.085 (t, J=7.8 Hz, 1H), 4.635 (d, J=7.8 Hz, 1H), 3.630 (s, 3H), 2.613 (m, 1H), 1.087 (d, J=6.6 Hz, 3H), 0.862 (d, J=6.6 Hz, 3H); MS ES(+): m/z 506 (M+H); ES(−): m/z 504 (M−H).

Example 667

Methyl 2-(5-(4-(3-(3,4-dimethylphenyl)ureido)phenyl)-1,3-dioxoisoindolin-2-yl)-3-methyl butanoate The compound of example 667 was prepared analogous to the compound of example 666 by reaction of compound of example 662 with 3,4-dimethyl benzoyl chloride.

Yield: 70 mg (49.4%); $^1$H NMR (300 MHz, DMSO-$d_6$): δ 8.860 (s, 1H), 8.573 (d, 1H), 8.166 (bs, 2H), 7.980 (d, J=8.1 Hz, 1H), 7.819 (d, J=8.4 Hz, 2H), 7.626 (d, J=8.7 Hz, 2H), 7.253 (s, 1H), 7.204 (d, J=8.1 Hz, 1H), 7.054 (d, J=8.1 Hz, 1H), 4.635 (d, J=7.5 Hz, 1H), 3.626 (s, 3H), 2.615 (m, 1H), 2.268 (s, 3H), 2.163 (s, 3H), 1.086 (d, J=6.6 Hz, 3H), 0.862 (d, J=6.9 Hz, 3H); MS ES(+): m/z 500 (M+H); ES(−): m/z 498 (M−H).

Example 668

Dimethyl 4-bromophthalate 5-bromoisobenzofuran-1,3-dione (5 g) was taken in methanol (50 mL). To this solution, chlorosulfonic acid (5 drops) was added and the resultant reaction mixture was refluxed for about 16 h and concentrated to obtain a residue, which was purified by column chromatography (silicagel, 30% ethyl acetate in hexane) to afford the title compound.

Yield: 3 g (50%); $^1$H NMR (300 MHz, DMSO-$d_6$): δ 7.930 (m, 1H), 7.887 (d, J=2.1 Hz, 1H), 7.731 (d, J=8.1 Hz, 1H), 3.382 (s, 6H).

Example 669

(4-Bromo-1,2-phenylene)dimethanol

The compound of example 668 (2 g, 7.326 mmol) was taken in dry THF and was added to a slurry of $LiAlH_4$ (1.67 g, 43.95 mmol) in THF cooled to 0° C. The reaction mixture was stirred at room temperature for 1 h. The reaction mixture was quenched with aqueous NaOH solution followed by extraction with ethyl acetate. The solvent was removed by distillation to afford the title compound.

Yield: 0.789 mg (50%); $^1$H NMR (300 MHz, DMSO-d$_6$): δ 7.556 (s, 1H), 7.40 (d, 1H), 7.347 (d J=8.1 Hz, 1H), 5.253 (s, 1H), 5.175 (s, 1H), 4.530 (d, J=5.1 Hz, 2H), 4.476 (d, J=5.1 Hz, 2H).

Example 670

(4'-Nitrobiphenyl-3,4-diyl)dimethanol

The compound of example 669 (7 g, 32.25 mmol), 4,4,5,5-tetramethyl-2-(4-nitrophenyl)-1,3,2-dioxaborolane (9.63 g, 38.70 mmol) and [1,1-Bis(diphenylphosphino)-ferrocine] dichloropalladium(II), complex with dichloromethane (789 mg, 0.967 mmol) were taken in dry DMF under Argon atmosphere. Degassed 2M solution of sodium carbonate (8.54 g, 80.62 mmol) was added and the reaction mixture was heated to 80° C. for 3 h. The reaction mixture was cooled and the solvent was removed by distillation. The residue was taken in water and the aqueous mixture was extracted with ethyl acetate. The crude material obtained was purified using column chromatography (silicagel, 30% dichloromethane in petroleum ether) to afford the title compound.

Yield: 6 g (72%); $^1$H NMR (300 MHz, DMSO-d$_6$): δ 8.359 (d, J=8.7 Hz, 2H), 8.296 (s, 1H), 8.269 (s, 1H), 8.147 (d, J=8.7 Hz, 1H), 8.080 (d, 1H), 8.054 (d, 1H), 5.250 (s, 1H), 5.212 (s, 1H), 4.625 (d, J=5.4 Hz, 2H), 4.588 (d, J=5.7 Hz, 2H); MS ES(+): m/z 383 (M+H), 405 (M+Na); ES(−): m/z 381 (M−H).

Example 671

3,4-bis(Bromomethyl)-4'-nitrobiphenyl

In diethyl ether was dissolved compound of example 670 (6 g, 23.16 mmol) and to the solution was added phosphorus tribromide (5.8 g, 62.66 mmol) at 0° C. The resulting mixture was gradually brought to room temperature over the period of 1 h. The reaction mixture was added to ice water and the pH was adjusted to 7 with sodium hydrogen carbonate, followed by extraction with ethyl acetate. The organic layer thus obtained was washed with a saturated aqueous sodium chloride solution, dried over anhydrous sodium sulfate, and then distilled to remove the solvent. The crude material was purified with column chromatography (silicagel, 30% ethyl acetate in petroleum ether) to afford the title compound.

Yield: 3.2 g (36%); $^1$H NMR (300 MHz, DMSO-d$_6$): δ 8.351 (d, J=8.7 Hz, 2H), 8.030 (s, 2H), 7.981 (d, J=3 Hz, 1H), 7.814 (dd, J=1.8, 8.1 Hz, 1H), 7.665 (d, J=8.1 Hz, 1H), 4.918 (s, 2H), 4.903 (s, 2H); MS ES(+): m/z 383 (M+H).

Example 672

Methyl 3-methyl-2-(5-(4-nitrophenyl)isoindolin-2-yl)butanoate

The compound of example 671 (3 g, 7.79 mmol) was taken in acetonitrile and to the reaction mixture, potassium carbonate (3.25 g, 23.37 mmol) was added followed by the addition of valine methyl ester (1.56 g, 9.35 mmol). The reaction mixture was refluxed for about 16 h and water was added to quench the reaction. The aqueous mixture was extracted with ethyl acetate to obtain a crude material, which was purified using column chromatography (silicagel, 30% ethyl acetate in petroleum ether).

Yield: 2 g (73%); $^1$H NMR (300 MHz, DMSO-d$_6$): δ 8.314 (d, J=8.7 Hz, 2H), 7.948 (d, J=9 Hz, 2H), 7.667 (s, 1H), 7.641 (d, J=8.4 Hz, 1H), 7.418 (d, J=9 Hz, 1H), 4.214 (m, 2H), 4.024 (m, 2H), 3.649 (s, 3H), 3.210 (d, J=9.3 Hz, 1H), 2.123 (m, 1H), 1.016 (d, J=6.6 Hz, 3H), 0.917 (d, J=6.6 Hz, 3H); MS ES(+): m/z 355 (M+H).

Example 673

Methyl 2-(5-(4-aminophenyl)isoindolin-2-yl)-3-methylbutanoate

The compound of example 673 was prepared analogous to the compound of example 6 by reduction of the compound of example 672.

Yield: 55%; $^1$H NMR (300 MHz, DMSO-d$_6$): δ 7.362 (d, J=8.1 Hz, 2H), 7.330 (d, J=3 Hz, 1H), 7.292 (s, 1H), 7.227 (d, J=7.8 Hz, 1H), 6.633 (d, J=8.4 Hz, 2H), 5.182 (s, 2H), 4.095 (m, 2H), 3.940 (m, 2H), 3.639 (s, 3H), 3.178 (d, J=9.3 Hz, 1H), 2.086 (m, 1H), 1.016 (d, J=6.6 Hz, 3H), 0.907 (d, J=6.6 Hz, 3H); MS ES(+): m/z 325 (M+H).

Example 674

Methyl 2-(5-(4-(4-tert-butylbenzamido)phenyl)isoindolin-2-yl)-3-methyl butanoate The compound of example 674 was prepared analogous to the compound of example 663 by reaction of compound of example 673 with 4-(t-butyl)benzoyl chloride.

Yield: 36% $^1$H NMR (300 MHz, DMSO-d$_6$): δ 10.254 (s, 1H), 7.925-7.854 (m, 4H), 7.649 (d, J=8.7 Hz, 1H), 7.577 (s, 1H), 7.548 (d, J=3.6 Hz, 2H), 7.515 (d, J=7.8 Hz, 1H), 7.327 (d, J=7.8 Hz, 2H), 4.174 (m, 2H), 3.989 (m, 2H), 3.655 (s, 3H), 3.206 (d, 1H), 2.1 (m, 1H), 1.335 (s, 9H), 1.033 (d, J=6.6 Hz, 3H), 0.923 (d, J=6.6 Hz, 3H); MS ES(+): m/z 485 (M+H); ES(−): m/z 483 (M−H).

Example 675

Methyl 3-methyl-2-(5-(4-(4-pentylbenzamido)phenyl)isoindolin-2-yl)butanoate

The compound of example 675 was prepared analogous to the compound of example 663 by reaction of compound of example 673 with 4-(n-pentyl)benzoyl chloride.

Yield: 22%; $^1$H NMR (300 MHz, DMSO-d$_6$): δ 10.248 (s, 1H), 7.915 (t, J=8.4 Hz, 4H), 7.648 (d, J=8.4 Hz, 2H), 7.536 (s, 1H), 7.516 (d, J=8.7 Hz, 1H), 7.376 (d, J=8.1 Hz, 2H), 7.327 (d, J=7.8 Hz, 1H), 4.174 (m, 2H), 4.015 (m, 2H), 3.656 (s, 3H), 3.206 (d, 1H), 2.690 (t, J=7.5 Hz, 2H), 2.1 (m, 1H), 1.640 (m, 2H), 1.314 (m, 4H), 1.034 (d, J=6.6 Hz, 3H), 0.923 (d, J=6.6 Hz, 3H), 0.877 (m, 3H); MS ES(+): m/z 499 (M+H); ES(−): m/z 497 (M−H).

Example 676

Methyl 2-(5-(4-biphenyl-4-ylcarboxamidophenyl)isoindolin-2-yl)-3-methyl butanoate The compound of example 676 was prepared analogous to the compound of example 663 by reaction of compound of example 673 with 4-phenyl benzoyl chloride.

Yield: 21%; $^1$H NMR (300 MHz, DMSO-d$_6$): δ 11.448 (s, 1H), 8.106 (d, J=8.1 Hz, 2H), 7.950 (d, J=8.4 Hz, 2H), 7.870 (d, J=8.1 Hz, 2H), 7.784 (d, J=7.8 Hz, 2H), 7.692 (d, J=8.4 Hz, 4H), 7.545 (t, J=7.5 Hz, 2H), 7.452 (m, 2H), 4.652 (bs, 4H), 3.815 (s, 3H), 3.361 (bs, 1H), 2.495 (bs, 1H), 1.114 (d, J=6.6 Hz, 3H), 1.002 (d, J=6.6 Hz, 3H); Mass: ES(+): m/z 505 (M+H); ES(−): m/z 503 (M−H).

Example 677

Methyl 2-(5-(4-(2,4-dimethoxyphenylsulfonamido) phenyl)isoindolin-2-yl)-3-methyl butanoate The compound of example 677 was prepared analogous to the compound of example 77 by reaction of compound of example 673 with 2,4-dimethoxy benzene sulfonyl chloride.

Yield: 25%; $^1$H NMR (300 MHz, DMSO-$d_6$): δ 9.976 (s, 1H), 7.718 (d, J=8.7 Hz, 1H), 7.464-7.359 (m, 4H), 7.257 (d, J=7.8 Hz, 1H), 7.148 (d, J=8.7 Hz, 2H), 6.641 (d, J=1.8 Hz, 1H), 6.600 (dd, J=8.7, 0.9 Hz, 1H), 4.135 (bd, 2H), 3.942 (bd, 2H), 3.872 (s, 3H), 3.780 (s, 3H), 3.688 (s, 3H), 3.168 (d, J=9.6 Hz, 1H), 2.497 (m, 1H), 0.999 (d, J=6.6 Hz, 3H), 0.893 (d, J=6.6 Hz, 3H); MS ES(+): m/z 525 (M+H), ES(−): m/z 523 (M−H).

Example 678

Methyl 3-methyl-2-(5-(4-(3-(2-(trifluoromethyl) phenyl)ureido)phenyl)isoindolin-2-yl)butanoate The compound of example 678 was prepared analogous to the compound of example 7 by reaction of compound of example 673 with 2-trifluoromethyl phenyl isocyanate.

Yield: 34%; $^1$H NMR (300 MHz, DMSO-$d_6$): δ 9.073 (s, 1H), 8.891 (s, 1H), 8.021 (s, 1H), 7.592-7.553 (m, 5H), 7.520 (d, J=7.5 Hz, 2H), 7.475 (d, J=7.8 Hz, 1H), 7.325 (t, J=6.3 Hz, 2H), 4.199 (m, 2H), 3.999 (m, 2H), 3.643 (s, 3H), 3.192 (d, J=9.3 Hz, 1H), 2.1 (m, 1H), 1.021 (d, J=6.6 Hz, 3H), 0.911 (d, J=6.6 Hz, 3H); MS ES(−): m/z 546 (M−H).

Pharmacology Data

The efficacy of the compounds of the present invention can be determined by a number of pharmacological assays well known in the art, such as described below.

Materials:
Tissue culture materials, (Nunc)
Tissue culture media, (Gibco)
Fetal bovine serum (FBS), (Hyclone)
Bovine serum albumin (BSA), (Sigma)
sn-1,2-dioleoylglycerol (Sigma)
Sucrose (Sigma)
2-propanol (Qualigens)
Heptane (Qualigens)
$^{14}$C Oleoyl CoA (GE Healthcare)
Sf9 cells (*Spodoptera frugiperda*, American Type Culture Collection (ATCC), USA)
Bradford (Sigma)
Cellfectin (Invitrogen)

Abbreviations and Terms

FBS Fetal Bovine serum
ORF Open Reading Frame
DAB DGAT Assay Buffer
AESSM Alkaline Ethanol Stop Solution Mix
$KH_2PO_4$ Potassium Dihydrogen Phosphate
KCl Potassium chloride
EDTA Ethylene Diamine Tetraacetic Acid
LB Luria Bertani
BSA Bovine serum albumin
PPO 2,5-Diphenyloxazole
POPOP 1,4-bis(5-phenyloxazol-2-yl)benzene
μg/mL microgram per Milliliter
rpm revolutions per minute
CoA Coenzyme A
nCi nanoCurie
μM Micromolar
μL Microliter
Tris-HCl Tris(hydroxymethyl)aminomethane Hydrochloride
DMSO Dimethyl sulfoxide
p.o. Oral administration
Kcal/g Kilocalorie per gram
IU/L International units per liter Example 679

In-Vitro Protocol for DGAT1 Assay

Sf9 Culture and Treatment

Sf9 cells were grown in T25 flasks containing Graces's Insect media with 10% FBS with antibiotic (100 units/mL penicillin, 100 μg/mL streptomycin sulphate, 0.25 μg/mL Amptotericin B as Fungizone) grown in a 27° C. incubator.

Viral Stock Preparation hDGAT1 ORF expression clone (RZPDo839C09146 in pDEST vector) was obtained from RZPD (German Science Centre for Genome Research, Germany). hDGAT1 bacmid DNA was obtained by transformation of the hDGAT1 expression clone into DH10Bac *E. coli* competent cells. Approximately 1 μg of hDGAT1 bacmid DNA was infected into Sf9 (Store frozen cells) with Cellfectin (Invitrogen) reagent. Following infection, Sf9 cells were incubated at 27° C. for 30 min. Five hours after infection, the media was replaced with growth media containing antibiotics (100 units/mL penicillin, 100 μg/mL streptomycin sulphate, 0.25 μg/mL Amptotericin B as Fungizone) and incubated at 27° C. for 72 h. The supernatant containing the virus was centrifuged at 1500×g for 5 min, passed through 0.22 μm filter, and subsequently stored at 4° C. The virus was further amplified three more times by re-infection of Sf9 cells and the viral titer was determined by plaque assay.

Preparation of hDGAT1 Microsomes from Sf9 Cells

Sf9 cells were seeded in spinner flasks on day 0 at a cell density of 1×10$^6$ and infected on day 1 with hDGAT1 baculovirus at a multiplicity of infection (MOI) of 5 and a cell density of 2×10$^6$. On day 3 (or 66-72 h), cells were harvested and centrifuged at 2500×g for 10 min. Pellet was resuspended in lysis buffer (100 mM sucrose, 50 mM KCl, 40 mM KH$_2$PO$_4$, 30 mM EDTA, pH 7.2) and passed through 21-gauge needle approximately 10 times. The mixture was centrifuged at 12,000 rpm in a Sigma 12158-H rotor at 4° C. for 30 min. The supernatant was subjected to centrifugation at 35,000 rpm in a Beckman Ti-45 rotor at 4° C. for 1 h. The resultant pellet containing the microsomes wasere resuspended overnight in 1 mL of lysis buffer and total protein concentration was estimated using Bradford Reagent. Microsomes were aliquoted and stored at −80° C.

Measurement of DGAT1 Activity

Frozen aliquots of hDGAT1 containing microsomes were thawed (5-10 mg/mL total protein) on ice and diluted to a working stock of 1 mg/mL with DGAT Assay Buffer (DAB). The DGAT reaction assay was performed by following the procedure described in U.S. Pat. No. 6,607,893 with some modifications that are described below.

Preparation of DGAT1 Substrate Mixture:

1 mL stock solution of DGAT1 substrate mixture contains 5.6 μL of $^{14}$C oleoyl CoA (16.8 nCi) and 105 μL of 1,2-dioleoyl-sn-glycerol (1228.5 μM)

1,2-dioleoyl-sn-glycerol stock (19.5 mM) was prepared by dissolving 25 mg of 1,2-dioleoyl-sn-glycerol (Sigma, US) in 2060 μL of acetone.

The assay was performed in duplicates in a reaction volume of 100 μL. The reaction volume consisted of:
(i) 27.5 μL of DGAT assay buffer (0.25 M Sucrose, 1 mM EDTA (pH 8.0), 150 mM Tris-HCl, pH 7.4, 1.25 mg/mL fatty acid free BSA),
(ii) 10 μL of compound of present invention or standard (2-(4'-(6-fluorobenzo[d]thiazol-2-ylamino)biphenyl-4-ylcarboxamido)-3-methylbutanoic acid) dissolved in DMSO and diluted to 10× with DAB and screened at 10 μM, 5 μM and 1 μM,
(iii) 60 μL DGAT1 substrate mixture taken from a 1 mL stock (16.8 nCi of $^{14}C$ oleoyl CoA and 1228.5 μM of 1,2-dioleyl-sn-glycerol),
(iv) 2.5 μL of 1 mg/mL of microsomes (the amount of assay buffer was varied depending upon the concentration of microsome to make up the volume to 100 μL).

Procedure:

The reaction was started by the addition of 2.5 μL of 1 mg/mL of microsomes (iv) to the mixture and incubated at 37° C. for 10 min. The reaction was stopped by the addition of 300 μL of Alkaline Ethanol Stop Solution Mix [AESSM; [12.5% of 100% non-denatured ethanol, 10% deionized water, 2.5% 1N NaOH, 75% stop solution (78.4% isopropanol, 19.6% n-heptane, 2% deionized water)] followed by addition of 600 μL of n-heptane. The mixture was vortexed and the triglycerides formed were extracted into the organic heptane phase. 250 μL of the heptane phase was added into 4 mL scintillation cocktail (66.72% toluene, 33.3% TritonX-100, 0.5% PPO, 0.02% POPOP) and counted on a liquid scintillation counter for 1 min.

The % Inhibition of hDGAT1 at 1 μM is displayed in the following table (Table 1) for representative examples of the present invention.

TABLE 1

| Ex. No. | % Inhibition |
|---|---|
| 8 | + |
| 10 | + |
| 12 | + |
| 14 | + |
| 16 | + |
| 18 | + |
| 20 | + |
| 22 | + |
| 24 | + |
| 26 | + |
| 28 | + |
| 30 | + |
| 32 | + |
| 34 | ++ |
| 36 | ++ |
| 38 | ++ |
| 40 | ++ |
| 42 | ++ |
| 44 | ++ |
| 46 | ++ |
| 48 | ++ |
| 50 | ++ |
| 52 | + |
| 54 | + |
| 56 | + |
| 58 | ++ |
| 60 | ++ |
| 62 | + |
| 64 | + |
| 66 | ++ |
| 68 | ++ |
| 70 | + |
| 72 | ++ |
| 74 | + |
| 76 | ++ |
| 80 | + |
| 82 | + |
| 84 | + |
| 86 | + |
| 90 | + |
| 92 | + |
| 94 | + |
| 96 | + |
| 98 | + |
| 100 | ++ |
| 102 | ++ |
| 104 | ++ |
| 106 | ++ |
| 108 | ++ |
| 110 | ++ |
| 112 | ++ |
| 114 | ++ |
| 116 | ++ |
| 118 | ++ |
| 120 | ++ |
| 122 | ++ |
| 124 | ++ |
| 126 | + |
| 128 | ++ |
| 130 | + |
| 132 | + |
| 134 | + |
| 136 | ++ |
| 138 | + |
| 140 | ++ |
| 142 | + |
| 144 | ++ |
| 146 | ++ |
| 148 | ++ |
| 150 | ++ |
| 152 | ++ |
| 154 | + |
| 156 | ++ |
| 158 | ++ |
| 160 | ++ |
| 162 | ++ |
| 164 | ++ |
| 166 | ++ |
| 168 | ++ |
| 170 | ++ |
| 172 | ++ |
| 174 | ++ |
| 176 | ++ |
| 178 | + |
| 180 | ++ |
| 182 | ++ |
| 184 | ++ |
| 186 | ++ |
| 188 | ++ |
| 190 | ++ |
| 192 | ++ |
| 194 | + |
| 196 | ++ |
| 198 | + |
| 200 | + |
| 202 | ++ |
| 207 | ++ |
| 209 | ++ |
| 213 | + |
| 215 | ++ |
| 217 | ++ |
| 225 | ++ |
| 227 | ++ |
| 229 | ++ |
| 231 | + |
| 233 | + |
| 235 | + |
| 237 | ++ |

TABLE 1-continued

| Ex. No. | % Inhibition |
|---|---|
| 239 | ++ |
| 241 | ++ |
| 243 | ++ |
| 245 | ++ |
| 247 | ++ |
| 249 | ++ |
| 251 | ++ |
| 253 | ++ |
| 255 | ++ |
| 257 | + |
| 259 | + |
| 261 | + |
| 263 | + |
| 265 | + |
| 267 | + |
| 269 | + |
| 271 | + |
| 275 | + |
| 277 | + |
| 279 | + |
| 281 | ++ |
| 283 | ++ |
| 289 | + |
| 291 | + |
| 293 | + |
| 295 | + |
| 297 | + |
| 299 | + |
| 301 | + |
| 303 | + |
| 305 | + |
| 307 | + |
| 309 | + |
| 311 | + |
| 313 | + |
| 315 | + |
| 315 | + |
| 319 | + |
| 321 | ++ |
| 323 | + |
| 325 | + |
| 331 | ++ |
| 334 | + |
| 337 | ++ |
| 340 | + |
| 343 | + |
| 346 | + |
| 349 | + |
| 352 | + |
| 355 | + |
| 361 | + |
| 364 | + |
| 367 | ++ |
| 370 | + |
| 373 | + |
| 376 | + |
| 379 | + |
| 382 | + |
| 385 | + |
| 388 | + |
| 394 | ++ |
| 396 | ++ |
| 398 | ++ |
| 402 | ++ |
| 404 | ++ |
| 406 | ++ |
| 408 | ++ |
| 410 | ++ |
| 412 | ++ |
| 416 | + |
| 418 | + |
| 420 | + |
| 422 | + |
| 424 | + |
| 426 | + |
| 428 | + |
| 430 | + |

TABLE 1-continued

| Ex. No. | % Inhibition |
|---|---|
| 432 | + |
| 436 | ++ |
| 438 | ++ |
| 440 | ++ |
| 442 | ++ |
| 444 | ++ |
| 446 | ++ |
| 448 | ++ |
| 450 | ++ |
| 452 | ++ |
| 456 | + |
| 458 | ++ |
| 460 | + |
| 462 | + |
| 464 | + |
| 468 | ++ |
| 470 | ++ |
| 472 | ++ |
| 474 | ++ |
| 476 | ++ |
| 480 | ++ |
| 482 | ++ |
| 484 | ++ |
| 486 | ++ |
| 488 | ++ |
| 492 | ++ |
| 498 | ++ |
| 500 | ++ |
| 502 | ++ |
| 505 | + |
| 507 | ++ |
| 509 | ++ |
| 517 | ++ |
| 519 | ++ |
| 521 | ++ |
| 523 | + |
| 525 | + |
| 529 | ++ |
| 531 | ++ |
| 533 | ++ |
| 535 | ++ |
| 537 | ++ |
| 541 | ++ |
| 545 | ++ |
| 547 | ++ |
| 549 | ++ |
| 551 | ++ |
| 553 | ++ |
| 557 | ++ |
| 559 | ++ |
| 561 | + |
| 563 | + |
| 567 | + |
| 569 | + |
| 571 | ++ |
| 572 | ++ |
| 576 | ++ |
| 578 | ++ |
| 580 | ++ |
| 582 | ++ |
| 586 | ++ |
| 588 | ++ |
| 590 | ++ |
| 594 | ++ |
| 596 | ++ |
| 598 | ++ |
| 602 | ++ |
| 604 | ++ |
| 606 | + |
| 608 | ++ |
| 610 | ++ |
| 612 | ++ |
| 614 | ++ |
| 616 | ++ |
| 618 | ++ |
| 620 | ++ |
| 622 | ++ |

TABLE 1-continued

| Ex. No. | % Inhibition |
|---|---|
| 624 | ++ |
| 627 | ++ |
| 629 | + |
| 631 | ++ |
| 633 | ++ |
| 635 | ++ |
| 637 | ++ |
| 639 | ++ |
| 643 | ++ |
| 647 | ++ |
| 649 | ++ |
| 651 | + |
| 653 | + |
| 655 | ++ |
| 657 | ++ |
| 659 | + |

Ex. No.: Example Number
% Inhibition of hDGAT1 (Scoring Details)
+ 10-50% Inhibition
++ >50% Inhibition In-Vivo Protocol Animals were housed and cared for in accordance with the Guidelines in force published by CPCSEA (Committee for the Purpose of Control and Supervision of Experiments on Animals), Tamil Nadu, India. Procedures using laboratory animals were approved by the IAEC (Institutional Animal Ethics Committee) of the Research Centre of Piramal Life Sciences Limited, Mumbai, India.

Example 680

Study Protocol for Screening of Compounds for Fat Tolerance Test (ftt) in Mice

Swiss mice of age 4-5 weeks and body weight between 25-30 g were selected for study. After fasting for about 16 h, the animals were divided into three groups based on plasma triglyceride level with same mean and variation. Animals were administered with either vehicle [(1% tween 80 in 0.5% carboxy methylcellulose (CMC)]) or with compounds of the present invention (3 mg/kg, p.o.). Compounds of the present invention were prepared as suspension in 0.5% carboxy methylcellulose (CMC) with 1% tween 80. Olive oil (fat) load (10 mL/kg, p.o.) was given, 30 min after the treatment. Blood samples were collected at 1, 2, 3 and 4 h after the fat (olive oil) load. Plasma was separated and triglyceride level was measured using commercially available kits (diasys, Germany). Percentage reduction in area under curve ($AUC_{0-4h}$) of the test compound was calculated by taking $AUC_{0-4h}$ of the vehicle group as 100%. The compounds of the present invention were found to show reduction in levels of plasma triglyceride.

The % reduction in the levels of plasma triglyceride is displayed in the following table (Table 2) for representative examples of the present invention.

TABLE 2

| % Reduction (Plasma triglyceride) Scoring Details | |
|---|---|
| Example No. | % Reduction (Plasma triglyceride) |
| 116 | ++ |
| 120 | ++ |
| 124 | ++ |
| 148 | ++ |
| 150 | ++ |
| 170 | ++ |
| 406 | ++ |
| 408 | ++ |
| 410 | ++ |

++ >50% Reduction

References

1. Koji Ueshima, Hitomi Akihisa-Umeno, Akira Nagayoshi, Shoji Takakura, Masahiko Matsuo, Seitaro Mutoh. A gastrointestinal lipase inhibitor reduces progression of atherosclerosis in mice fed a western-type diet. European Journal of Pharmacology (2004), 501, 137-142.
2. L-K Han et al. "Anti-obesity effects in rodents of dietary teasaponin, a lipase inhibitor" International Journal of Obesity (2001), 25, 1459-1464.
3. Katherine J. D. Ashbourne Excoffon et al. "Correction of Hypertriglyceridemia and Impaired Fat Tolerance in Lipoprotein Lipase-Deficient Mice by Adenovirus-Mediated Expression of Human Lipoprotein Lipase" Arteriosclerosis, Thrombosis, and Vascular Biology (1997), 17, 2532-2539.

Additionally, one or more compounds of the present invention may be tested in any of the below-mentioned assays to determine their efficacy in obtaining a reduction in body weight, cumulative feed intake and/or biochemical parameters such as plasma glucose (mg/dL), plasma triglyceride (mg/dL), plasma cholesterol (mg/dL), plasma AST (IU/L), plasma ALT (IU/L) and liver weight (g).

Example 681

Chronic Study 1

Effect of the Test Compound on High Fat Diet Induced Weight Gain in ob/ob Mice

Meal-Fed Protocol

Male ob/ob mice aged 4-5 weeks with body weight range of 30-40 g are procured from the Jackson Laboratory, USA and kept in the central animal facility, Piramal Life Sciences Limited, Mumbai, India. Animals are housed in individually ventilated cages (IVC's) at a room temperature of 22±2° C., humidity 55±5% with a 12:12 h light-dark cycle and have access to water ad libitum. Mice (one/cage) are allowed to acclimatize on standard diet (normal pellet diet, NPD; Amrut Laboratory Animal Feed, India) for one week. Then animals are grouped based on body weight and plasma glucose with similar mean±S.E.M. with 10 animals per group.

Acclimatization Period

All the mice are housed individually in IVC's cages and subjected to 9 days acclimatization period. In brief, animals are provided with either low fat diet (LFD) or high fat diet (HFD). LFD provides 10% of the total calories obtained from lard (D12450B; Research Diets Inc., NJ, USA) with total energy provided as 3.85 Kcal/g of feed whereas HFD provides 60% of the total calories obtained from lard (D12492; Research Diets Inc., NJ, USA) with total energy provided as 5.24 Kcal/g of feed. Animals are provided with ad libitum feed from day 1 to day 3. From day 4 to day 6, food is restricted for 12 h. From day 7 to day 9, food is provided for three h in the morning and three h in the evening. During acclimatization period, mice are administered with vehicle (1% Tween 80 in 0.5% CMC; 10 mL/kg) twice daily, to acclimatize them to oral dosing and handling procedures.

Treatment Regimen

On day 10, high fat fed animals are regrouped to three groups based on body weight with similar mean±S.E.M. with 10 animals per group. The test compound is prepared as suspension with 1% Tween 80 in 0.5% CMC. Vehicle (0.5% CMC with 1% Tween 80; 10 ml/kg) or the test compound is administered twice daily in the morning and evening. The concentration of test compounds used is in the range of 0.1 to 1 mg/kg (p.o., b.i.d.). This dosing regimen is continued for 14 days. Daily body weight is recorded just before administration of test compound.

Food Intake Measurement

Food intake is measured twice daily. In the morning, random amount of LFD or HFD is kept in the metallic lid. It is weighed with food and is considered as food provided. At noon, lid weight with food is measured as food remaining. Food intake in morning is calculated as difference between food provided and food remaining. Mice are devoid of food for six hours. In the evening, again food is provided and food intake is measured at 9 pm as per the above procedure during morning session. Followed by this, food is removed from the cages for 12 h. Sum of the food intake in the morning and in the evening gives total food intake during the corresponding day.

Biochemical Parameters Estimation and Necropsy

Blood (~80 μL) is collected from the retro-orbital plexus of mice on day 15, 1 h after administration of the test compound. The plasma is separated by centrifugation at 8000×g for 7 min at 4° C. and plasma glucose, triglyceride, cholesterol, liver enzymes [alanine aminotransferase (ALT) and aspartate aminotransferase (AST)], LDL-C and HDL-C are estimated immediately using a biochemistry autoanalyser (Hitachi Science Systems Limited, Ibaraki, Japan). Plasma insulin (Linco Research, USA) is estimated as per manufacturer's protocol.

Observations are recorded for percent change in body weight gain and cumulative feed intake during 14 days of treatment. The biochemical parameters such as plasma glucose (mg/dL), plasma triglyceride (mg/dL), plasma cholesterol (mg/dL), plasma AST (IU/L), plasma ALT (IU/L) and liver weight (g) may be recorded at the end of 14 days.

Example 682

Chronic Study 2

Effect of the Test Compound on High Fat Diet Induced Weight Gain in Wistar Rats

Meal-Fed Protocol

Male Wistar rat mice aged 4 weeks with body weight range of 150-180 g are procured from the central animal house facility, Piramal Life Sciences Limited, Mumbai, India. Animals are housed in individually ventilated cages (IVC's) at a room temperature of 22±2° C., humidity 55±5% with a 12:12 h light-dark cycle and have access to water ad libitum. Rats (two/cage) are allowed to acclimatize on Standard diet (Normal Pellet Diet; NPD; Amrut Laboratory Animal Feed, India) for one week. Then, animals are grouped based on body weight and plasma glucose with similar mean±S.E.M. with 10 animals per group.

Acclimatization Period

All the rats are housed individually in IVC's cages and subjected to 9 days acclimatization period. In brief, animals are provided with either NPD or high fat diet (HFD, D12492; Research Diets Inc., NJ, USA). Animals are provided with ad libitum feed form day 1 to day 3. From day 4 to day 6, food is restricted for 12 hours. From day 7 to day 9, food is provided for three hours in the morning and three hours in the evening. During acclimatization period, rats are administered with vehicle (1% Tween 80 in 0.5% CMC; 10 ml/kg) twice daily, to acclimatize them to oral dosing and handling procedures.

Treatment Regimen

On day 10, high fat fed animals are regrouped to three groups based on body weight with similar mean±S.E.M. with 10 animals per group. The test compound is prepared as suspension with 1% Tween 80 in 0.5% CMC. Vehicle (0.5% CMC with 1% Tween 80; 10 mL/kg) or the test compound is administered twice daily in the morning and evening. The concentration of test compounds used is in the range of 1 to 10 mg/kg (p.o., b.i.d.). This dosing regimen is continued for 14 days. Daily body weight is recorded just before test compound administration.

Food Intake Measurement

Food intake is measured twice daily. In the morning, random amount of LFD or HFD is kept in the metallic lid. It is weighed with food and is considered as food provided. At noon, lid weight with food is measured as food remaining. Food intake in morning is calculated as difference between food provided and food remaining. Mice are devoid of food for six hours. In the evening, again food is provided and food intake is measured at 9 pm as per the above procedure during morning session. Followed by this, food is removed from the cages for twelve hours. Sum of the food intake in the morning and in the evening gives total food intake during the corresponding day.

Biochemical Parameters Estimation and Necropsy

Blood (~80 μL) is collected from the retro-orbital plexus of rats on day 15, 1 h after administration of the test compound. The plasma is separated by centrifugation at 8000×g for 7 min at 4° C. and plasma glucose, triglyceride, cholesterol, liver enzymes (ALT and AST), LDL-C and HDL-C are estimated immediately using a biochemistry autoanalyser (Hitachi Science Systems Limited, Ibaraki, Japan). Plasma insulin (Linco Research, USA) is estimated as per manufacturer's protocol. Observations are recorded for percent change in body weight gain and cumulative feed intake during 14 days of treatment. The biochemical parameters such as plasma glucose (mg/dL), plasma triglyceride (mg/dL), plasma cholesterol (mg/dL), plasma AST (IU/L), plasma ALT (IU/L) and liver weight (g) may be recorded at the end of 14 days.

Example 683

Chronic Study 3

Effect of Test Compound on High Fat Diet Induced Hyperlipidemia in Hamster

Protocol

Male hamsters aged 9-10 weeks with body weight range of 90-110 g are procured from the central animal house facility, Piramal Life Sciences Limited, Mumbai, India. Animals are housed in individually ventilated cages (IVC's) at a room temperature of 22±2° C., humidity 55±5% with a 12:12 h light-dark cycle and have access to water ad libitum. Hamsters (two/cage) are allowed to acclimatize on standard diet (normal pellet diet, NPD; Amrut Laboratory Animal Feed, India) for one week. Animals are then grouped based on plasma triglyceride and cholesterol with similar mean±S.E.M. with 10 animals per group.

Diet

Animals are provided with high cholesterol high fat diet (HCHF). HCHF is prepared in-house (cholesterol 1%, fructose 10%, coconut oil 25%, corn starch 5% and made to 100% by NPD) and is provided ad libitum for all the 14 days.

Treatment Regimen

The test compound is prepared as suspension with 1% Tween 80 in 0.5% CMC. Vehicle (0.5% CMC with 1% Tween 80; 10 mL/kg) or test compound are administered twice daily in the morning and evening. The concentration of test compounds used is in the range of 1 to 10 mg/kg (p.o., b.i.d.). This dosing regimen is continued for 14 days. Daily body weight is recorded just before test compound administration.

Biochemical Parameters Estimation and Necropsy

Blood (~80 μL) is collected from the retro-orbital plexus of hamster on day 15. Plasma is separated by centrifugation at 8000×g for 7 min at 4° C. and plasma glucose, triglyceride, cholesterol, liver enzymes (ALT and AST), LDL-C and HDL-C are estimated immediately using a biochemistry autoanalyser (Hitachi Science Systems Limited, Ibaraki, Japan). Plasma insulin (Linco Research, USA) is estimated as per manufacturer's protocol.

Observations are recorded for percent change in body weight gain and cumulative feed intake during 14 days of treatment. The biochemical parameters such as plasma glucose (mg/dL), plasma triglyceride (mg/dL), plasma cholesterol (mg/dL), plasma AST (IU/L), plasma ALT (IU/L) and liver weight (g) may be recorded at the end of 14 days.

Example 684

Acute Study 1

Effect of Test Compound on Feed Intake in Sprague Dawley Rats Fed on High Fat Diet Protocol Male Sprague Dawley rat aged 5-6 weeks with body weight range of 200-220 g are procured from the central animal house facility, Piramal Life Sciences Limited, Mumbai, India. Animals are housed in individually ventilated cages (IVC's) at a room temperature of 22±2° C., humidity 55±5% with a 12:12 h light-dark cycle and have access to water ad libitum. After a 12 h fasting period, animals are grouped based on body weight with similar mean±S.E.M. with 9 animals per group.

Treatment

The test compound is prepared as suspension with 1% Tween 80 in 0.5% CMC. Vehicle (0.5% CMC with 1% Tween 80; 10 mL/kg) or test compound are administered in the morning (9 am). The concentration of test compounds used is in the range of 1 to 10 mg/kg (p.o.). High Fat diet (HFD) is immediately provided to the animals after dosing. Food intake is measured at 1, 2, 4, 6 and 8 h post dose.

Food Intake Measurement

Random amount of HFD is kept in the metallic lid. It is weighed with food and is considered as food provided. At 1, 2, 4, 6 and 8 h lid weight with food is measured as food remaining. Food intake is calculated as difference between food provided and food remaining.

Percent Inhibition of Food Intake

Percentage inhibition is calculated separately for 1, 2, 4, 6 and 8 h. It is calculated with respect to HFD fed vehicle group using the formula % inhibition=(Mean feed intake of vehicle group of respective hour–feed intake of each animal in treatment group of respective hour)/Mean feed intake of vehicle group of respective hour×100.

We claim:
1. A compound of formula 1,

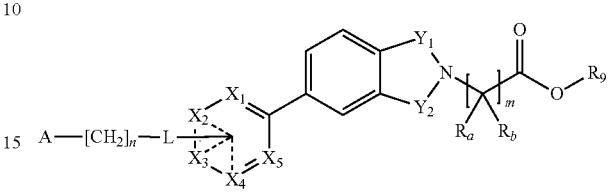

Formula 1 wherein,

A is selected from $(C_1-C_{12})$-alkyl, $(C_3-C_{12})$-cycloalkyl, aryl, and heterocyclyl; wherein the aryl group may be fused with an unsubstituted or substituted 5 or 6-membered cycloalkyl ring optionally containing heteroatoms selected from O, N or S;

n is 0 or 1;

L is selected from NHC(O)NH, NHC(S)NH, *NHSO$_2$, *CONH and *SO$_2$NH; wherein * indicates the point of attachment to A-[CH$_2$]$_n$—;

$X_1$ and $X_5$ are independently selected from N, N-oxide, CH and CR; $X_2$, $X_3$, and $X_4$ are independently selected from N, N-oxide, C, CH and CR; wherein R is selected from halogen, hydroxy, $(C_1-C_{12})$-alkoxy, cyano, $(C_1-C_{12})$-alkyl, CF$_3$, OCF$_3$, $(C_2-C_{12})$-alkenyl, $(C_2-C_{12})$-alkynyl, $(C_3-C_{12})$-cycloalkyl, aryl, aryloxy, heterocyclyl, O-heterocyclyl, $C(O)R_p$, $C(O)OR_p$, $NR_pR_q$, $SR_p$, $S(O)R_p$, $SO_2R_p$ and $C(O)NR_pR_q$;

$R_p$ and $R_q$ are independently selected from hydrogen, $(C_1-C_{12})$-alkyl, aryl, aralkyl and heterocyclyl, or $R_p$ and $R_q$ can optionally form a 3-7 membered ring;

$Y_1$ and $Y_2$ are independently selected from C=O and CH$_2$;

m is an integer selected from 1 to 4; wherein:
when m is 1, $R_a$ and $R_b$ may be independently selected from $R_1$ and $R_2$;
when m is 2, $R_a$ and $R_b$ may be independently selected from $R_1$, $R_2$, $R_3$ and $R_4$;
when m is 3, $R_a$ and $R_b$ may be independently selected from $R_1$, $R_2$, $R_3$, $R_4$, $R_5$ and $R_6$;
when m is 4, $R_a$ and $R_b$ may be independently selected from $R_1$, $R_2$, $R_3$, $R_4$, $R_5$, $R_6$, $R_7$ and $R_8$; and $R_1$, $R_2$, $R_3$, $R_4$, $R_5$, $R_6$, $R_7$ and $R_8$ are independently selected from hydrogen, $(C_1-C_{12})$-alkyl, aryl, aralkyl and heterocyclyl;

or any two of $R_1$, $R_2$, $R_3$, $R_4$, $R_5$, $R_6$, $R_7$ and $R_8$ can form a $(C_3-C_{12})$ cycloalkyl ring;

$R_9$ is selected from hydrogen, $(C_1-C_{12})$-alkyl, aryl, aralkyl, and heterocyclyl;

wherein, $(C_1-C_{12})$-alkyl is unsubstituted or substituted with one or more groups selected from halogen, hydroxy, unsubstituted or substituted $(C_1-C_{12})$-alkoxy, cyano, nitro, unsubstituted or substituted $(C_3-C_{12})$-cycloalkyl, unsubstituted or substituted aryl, $C(O)R_p$, $C(O)OR_p$, $NR_pR_q$, $SR_p$, $S(O)R_p$ and $SO_2R_p$;

$(C_3-C_{12})$-cycloalkyl is unsubstituted or substituted with one or more groups selected from halogen, hydroxy, unsubstituted or substituted $(C_1-C_{12})$-alkoxy cyano, nitro, unsubstituted or substituted aryl, unsubstituted or substituted heterocyclyl, $C(O)R_p$, $C(O)OR_p$, $NR_pR_q$, $SR_p$, $S(O)R_p$ and $SO_2R_p$;

aryl is unsubstituted or substituted with one or more groups selected from halogen, hydroxy, unsubstituted or substituted ($C_1$-$C_{12}$)-alkoxy, cyano, nitro, unsubstituted or substituted ($C_1$-$C_{12}$)-alkyl, $CF_3$, $OCF_3$, ($C_2$-$C_{12}$)-alkenyl, ($C_2$-$C_{12}$)-alkynyl, unsubstituted or substituted ($C_3$-$C_{12}$)-cycloalkyl, unsubstituted or substituted aryl, unsubstituted or substituted aryloxy, unsubstituted or substituted heterocyclyl, unsubstituted or substituted O-heterocyclyl, $C(O)R_p$, $C(O)OR_p$, $NR_pR_q$, $SR_p$, $S(O)R_p$ and $SO_2R_p$, or aryl may be fused with an unsubstituted or substituted 5 or 6-membered cycloalkyl ring optionally containing heteroatoms selected from O, N and S;

heterocyclyl is unsubstituted or substituted with one or more groups selected from halogen, hydroxy, unsubstituted or substituted ($C_1$-$C_{12}$)-alkoxy, cyano, nitro, unsubstituted or substituted ($C_1$-$C_{12}$)-alkyl, $CF_3$, $OCF_3$, ($C_2$-$C_{12}$)-alkenyl, ($C_2$-$C_{12}$)-alkynyl, unsubstituted or substituted ($C_3$-$C_{12}$)-cycloalkyl, unsubstituted or substituted aryl, unsubstituted or substituted aryloxy, unsubstituted or substituted heterocyclyl, unsubstituted or substituted O-heterocyclyl, $C(O)R_p$, $C(O)OR_p$, $NR_pR_q$, $SR_p$, $S(O)R_p$ and $SO_2R_p$; or a stereoisomer, tautomer or a pharmaceutically acceptable salt, prodrug, carboxylic acid isostere or N-oxide thereof.

2. The compound according to claim 1, represented by formula 1a;

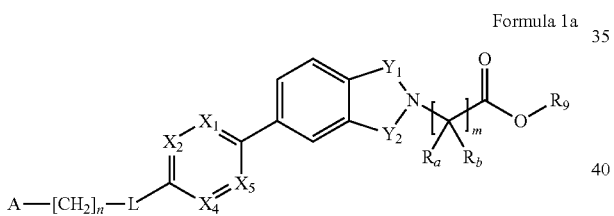

Formula 1a wherein,
A is selected from ($C_1$-$C_{12}$)-alkyl, ($C_3$-$C_{12}$)-cycloalkyl, aryl and heterocyclyl; wherein the aryl group may be fused with an unsubstituted or substituted 5 or 6-membered cycloalkyl ring optionally containing heteroatoms selected from O, N or S;

n is 0 or 1;

L is selected from NHC(O)NH, NHC(S)NH, *NHSO$_2$, *CONH and *SO$_2$NH; wherein* indicates the point of attachment to A-[CH$_2$]$_n$—;

$X_1$, $X_2$, $X_4$ and $X_5$ are independently selected from N, N-oxide, CH and CR; wherein R is selected from halogen, hydroxy, ($C_1$-$C_{12}$)-alkoxy, cyano, ($C_1$-$C_{12}$)-alkyl, $CF_3$, $OCF_3$, ($C_2$-$C_{12}$)-alkenyl, ($C_2$-$C_{12}$)-alkynyl, ($C_3$-$C_{12}$)-cycloalkyl, aryl, aryloxy, heterocyclyl, O-heterocyclyl, $C(O)R_p$, $C(O)OR_p$, $NR_pR_q$, $SR_p$, $S(O)R_p$, $SO_2R_p$ and $C(O)NR_pR_q$;

$R_p$ and $R_q$ are independently selected from hydrogen, ($C_1$-$C_{10}$-alkyl, aryl, aralkyl and heterocyclyl, or $R_p$ and $R_q$ can optionally form a 3-7 membered ring;

$Y_1$ and $Y_2$ are independently selected from C=O and CH$_2$;

m is an integer selected from 1 to 4; wherein:
when m is 1, $R_a$ and $R_b$ may be independently selected from $R_1$ and $R_2$;

when m is 2, $R_a$ and $R_b$ may be independently selected from $R_1$, $R_2$, $R_3$ and $R_4$;

when m is 3, $R_a$ and $R_b$ may be independently selected from $R_1$, $R_2$, $R_3$, $R_4$, $R_5$ and $R_6$;

when m is 4, $R_a$ and $R_b$ may be independently selected from $R_1$, $R_2$, $R_3$, $R_4$, $R_5$, $R_6$, $R_7$ and $R_8$;

$R_1$, $R_2$, $R_3$, $R_4$, $R_5$, $R_6$, $R_7$ and $R_8$ are independently selected from hydrogen, ($C_1$-$C_{12}$)-alkyl, aryl, aralkyl, and heterocyclyl;

or any two of $R_1$, $R_2$, $R_3$, $R_4$, $R_5$, $R_6$, $R_7$ and $R_8$ can form a ($C_3$-$C_{12}$)cycloalkyl ring;

$R_9$ is selected from hydrogen, ($C_1$-$C_{12}$)-alkyl, aryl, aralkyl and heterocyclyl;

wherein,
($C_1$-$C_{12}$)-alkyl is unsubstituted or substituted with one or more groups selected from halogen, hydroxy, unsubstituted or substituted ($C_1$-$C_{12}$)-alkoxy, cyano, nitro, unsubstituted or substituted ($C_3$-$C_{12}$)-cycloalkyl, unsubstituted or substituted aryl, $C(O)R_p$, $C(O)OR_p$, $NR_pR_q$, $SR_p$, $S(O)R_p$ and $SO_2R_p$;

($C_3$-$C_{12}$)-cycloalkyl is unsubstituted or substituted with one or more groups selected from halogen, hydroxy, unsubstituted or substituted ($C_1$-$C_{12}$)-alkoxy cyano, nitro, unsubstituted or substituted aryl, unsubstituted or substituted heterocyclyl, C(O)R, $C(O)OR_p$, $NR_pR_q$, $SR_p$, $S(O)R_p$ and $SO_2R_p$;

aryl is unsubstituted or substituted with one or more groups selected from halogen, hydroxy, unsubstituted or substituted ($C_1$-$C_{12}$)-alkoxy, cyano, nitro, unsubstituted or substituted ($C_1$-$C_{12}$)-alkyl, $CF_3$, $OCF_3$, ($C_2$-$C_{12}$)-alkenyl, ($C_2$-$C_{12}$)-alkynyl, unsubstituted or substituted ($C_3$-$C_{12}$)-cycloalkyl, unsubstituted or substituted aryl, unsubstituted or substituted aryloxy, unsubstituted or substituted heterocyclyl, unsubstituted or substituted O-heterocyclyl, $C(O)R_p$, $C(O)OR_p$, $NR_pR_q$, $SR_p$, $S(O)R_p$ and $SO_2R_p$, or aryl may be fused with an unsubstituted or substituted 5 or 6-membered cycloalkyl ring optionally containing heteroatoms selected from O, N and S;

heterocyclyl is unsubstituted or substituted with one or more groups selected from halogen, hydroxy, unsubstituted or substituted ($C_1$-$C_{12}$)-alkoxy, cyano, nitro, unsubstituted or substituted ($C_1$-$C_{12}$)-alkyl, $CF_3$, $OCF_3$, ($C_2$-$C_{12}$)-alkenyl, ($C_2$-$C_{12}$)-alkynyl, unsubstituted or substituted ($C_3$-$C_{12}$)-cycloalkyl, unsubstituted or substituted aryl, unsubstituted or substituted aryloxy, unsubstituted or substituted heterocyclyl, unsubstituted or substituted O-heterocyclyl, $C(O)R_p$, $C(O)OR_p$, $NR_pR_q$, $SR_p$, $S(O)R_p$ and $SO_2R_p$;

or a stereoisomer, tautomer or a pharmaceutically acceptable salt, prodrug, carboxylic acid isostere or N-oxide thereof.

3. The compound according to claim 2, wherein,
A is selected from ($C_1$-$C_{12}$)-alkyl, ($C_3$-$C_{12}$)-cycloalkyl, aryl and heterocyclyl; wherein the aryl group may be fused with an unsubstituted or substituted 5 or 6-membered cycloalkyl ring optionally containing heteroatoms selected from O, N or S;

n is 0 or 1;

L is selected from NHC(O)NH, NHC(S)NH, *NHSO$_2$, *CONH and *SO$_2$NH; wherein * indicates the point of attachment to A-[CH$_2$]$_n$—;

$X_1$, $X_2$, $X_4$ and $X_5$ are independently selected from N, N-oxide, CH and CR; wherein R is selected from halogen, hydroxy, ($C_1$-$C_{12}$)-alkoxy, cyano, ($C_1$-$C_{12}$)-alkyl, $CF_3$, $OCF_3$, ($C_3$-$C_{12}$)-cycloalkyl, aryl, aryloxy and heterocyclyl;

$Y_1$ and $Y_2$ are independently selected from C=O and CH$_2$;

m is an integer selected from 1 to 4; wherein:
when m is 1, $R_a$ and $R_b$ may be independently selected from $R_1$ and $R_2$;
when m is 2, $R_a$ and $R_b$ may be independently selected from $R_1$, $R_2$, $R_3$ and $R_4$;
when m is 3, $R_a$ and $R_b$ may be independently selected from $R_1$, $R_2$, $R_3$, $R_4$, $R_5$ and $R_6$;
when m is 4, $R_a$ and $R_b$ may be independently selected from $R_1$, $R_2$, $R_3$, $R_4$, $R_5$, $R_6$, $R_7$ and $R_8$;
$R_1$, $R_2$, $R_3$, $R_4$, $R_5$, $R_6$, $R_7$ and $R_8$ are independently selected from hydrogen, $(C_1$-$C_{12})$-alkyl, aryl, aralkyl, and heterocyclyl;
or any two of $R_1$, $R_2$, $R_3$, $R_4$, $R_5$, $R_6$, $R_7$ and $R_8$ form a $(C_3$-$C_{12})$cycloalkyl ring;
$R_9$ is selected from hydrogen or $(C_1$-$C_{12})$-alkyl;
wherein,
$(C_1$-$C_{12})$-alkyl is unsubstituted or substituted with one or more groups selected from halogen, hydroxy, unsubstituted or substituted $(C_1$-$C_{12})$-alkoxy, cyano, unsubstituted or substituted $(C_3$-$C_{12})$-cycloalkyl and unsubstituted or substituted aryl;
$(C_3$-$C_{12})$-cycloalkyl is unsubstituted or substituted with one or more groups selected from halogen, hydroxy, unsubstituted or substituted $(C_1$-$C_{12})$-alkoxy cyano, unsubstituted or substituted aryl and unsubstituted or substituted heterocyclyl;
aryl is unsubstituted or substituted with one or more groups selected from halogen, hydroxy, unsubstituted or substituted $(C_1$-$C_{12})$-alkoxy, cyano, unsubstituted or substituted $(C_1$-$C_{12})$-alkyl, $CF_3$, $OCF_3$, unsubstituted or substituted $(C_3$-$C_{12})$-cycloalkyl, unsubstituted or substituted aryl, unsubstituted or substituted aryloxy, and unsubstituted or substituted heterocyclyl, or aryl may be fused with an unsubstituted or substituted 5 or 6-membered cycloalkyl ring optionally containing heteroatoms selected from O, N and S; and
heterocyclyl is unsubstituted or substituted with one or more groups selected from halogen, hydroxy, unsubstituted or substituted $(C_1$-$C_{12})$-alkoxy, cyano, unsubstituted or substituted $(C_1$-$C_{12})$-alkyl, $CF_3$, $OCF_3$, unsubstituted or substituted $(C_3$-$C_{12})$-cycloalkyl, unsubstituted or substituted aryl, unsubstituted or substituted aryloxy, and unsubstituted or substituted heterocyclyl;

or a stereoisomer, tautomer or a pharmaceutically acceptable salt, prodrug, carboxylic acid isostere or N-oxide thereof.

4. The compound according to claim 2,
wherein,
A is selected from $(C_1$-$C_{12})$-alkyl, $(C_3$-$C_{12})$-cycloalkyl, aryl and heterocyclyl; wherein aryl group may be fused with an unsubstituted or substituted 5 or 6-membered cycloalkyl ring optionally containing heteroatoms selected from O, N or S;
n is 0 or 1;
L is *C(O)NH wherein * indicates the point of attachment to A-[CH$_2$]$_n$—;
$X_2$ is selected from CH and CR, $X_1$, $X_4$ and $X_5$ are independently selected from CH, CR and N; wherein R is selected from halogen, hydroxy, $(C_1$-$C_{12})$-alkoxy, cyano, $(C_1$-$C_{12})$-alkyl, $CF_3$, $OCF_3$ and cycloalkyl;
$Y_1$ and $Y_2$ are independently selected from C=O and CH$_2$;
m is an integer selected from 1 to 4; wherein:
when m is 1, $R_a$ and $R_b$ may be independently selected from $R_1$ and $R_2$;
when m is 2, $R_a$ and $R_b$ may be independently selected from $R_1$, $R_2$, $R_3$ and $R_4$;
when m is 3, $R_a$ and $R_b$ may be independently selected from $R_1$, $R_2$, $R_3$, $R_4$, $R_5$ and $R_6$;
when m is 4, $R_a$ and $R_b$ may be independently selected from $R_1$, $R_2$, $R_3$, $R_4$, $R_5$, $R_6$, $R_7$ and $R_3$; $R_1$, $R_2$, $R_3$, $R_4$, $R_5$, $R_6$, $R_7$ and $R_8$ are independently selected from hydrogen, $(C_1$-$C_{12})$-alkyl, aryl; and aralkyl; or any two of $R_2$, $R_3$, $R_4$, $R_5$, $R_6$, $R_7$ and $R_8$ form a $(C_3$-$C_{12})$ cycloalkyl ring; and
$R_9$ is selected from hydrogen or unsubstituted $(C_1$-$C_6)$-alkyl;
wherein,
$(C_1$-$C_{12})$-alkyl is unsubstituted or substituted with one or more groups selected from halogen, hydroxy, unsubstituted or substituted $(C_1$-$C_{12})$-alkoxy, cyano, unsubstituted or substituted $(C_3$-$C_{12})$-cycloalkyl and unsubstituted or substituted aryl, $(C_3$-$C_{12})$-cycloalkyl is unsubstituted or substituted with one or more groups selected from halogen, hydroxy, unsubstituted or substituted $(C_1$-$C_{12})$-alkoxy cyano, unsubstituted or substituted aryl and unsubstituted or substituted heterocyclyl;
aryl is unsubstituted or substituted with one or more groups selected from halogen, hydroxy, unsubstituted or substituted $(C_1$-$C_{12})$-alkoxy, cyano, unsubstituted or substituted $(C_1$-$C_{12})$-alkyl, $CF_3$, $OCF_3$, unsubstituted or substituted $(C_3$-$C_{12})$-cycloalkyl, unsubstituted or substituted aryl, unsubstituted or substituted aryloxy and unsubstituted or substituted heterocyclyl, or aryl may be fused with an unsubstituted or substituted 5 or 6-membered cycloalkyl ring optionally containing heteroatoms selected from O, N and S; and
heterocyclyl is unsubstituted or substituted with one or more groups selected from halogen, hydroxy, unsubstituted or substituted $(C_1$-$C_{12})$-alkoxy, cyano, unsubstituted or substituted $(C_1$-$C_{12})$-alkyl, $CF_3$, $OCF_3$, unsubstituted or substituted $(C_3$-$C_{12})$-cycloalkyl, unsubstituted or substituted aryl, unsubstituted or substituted aryloxy and unsubstituted or substituted heterocyclyl;

or a stereoisomer, tautomer or a pharmaceutically acceptable salt, prodrug, carboxylic acid isostere or N-oxide thereof.

5. The compound according to claim 4, wherein,
A is selected from aryl or heterocyclyl;
n is 0;
L is *C(O)NH wherein * indicates the point of attachment to A-[CH$_2$]$_n$—,
$X_1$, $X_2$, $X_4$ and $X_5$ are independently selected from CH and CR; wherein R is selected from halogen, hydroxy, $(C_1$-$C_{12})$-alkoxy, cyano, $(C_1$-$C_{12})$-alkyl, $CF_3$ and $OCF_3$;
$Y_1$ is CH$_2$ and $Y_2$ is C=O;
m is 1; wherein $R_a$ and $R_b$ may be independently selected from $R_1$ and $R_2$;
$R_1$ and $R_2$ are independently selected from hydrogen and $(C_1$-$C_{12})$-alkyl; and
$R_9$ is selected from hydrogen or unsubstituted $(C_1$-$C_6)$-alkyl;
wherein,
aryl is unsubstituted or substituted with one or more groups selected from halogen, hydroxy, unsubstituted or substituted $(C_1$-$C_{12})$-alkoxy, unsubstituted or substituted $(C_1$-$C_{12})$-alkyl, $CF_3$, $OCF_3$, unsubstituted or substituted aryl, unsubstituted or substituted aryloxy and unsubstituted or substituted heterocyclyl, or aryl may be fused with an unsubstituted or substituted 5 or 6-membered cycloalkyl ring optionally containing heteroatoms selected from O, N and S; and
heterocyclyl is unsubstituted or substituted with one or more groups selected from halogen, hydroxy, unsubstituted or substituted $(C_1-C_{12})$-alkoxy, unsubstituted or substituted $(C_1-C_{12})$-alkyl, $CF_3$, $OCF_3$, unsubstituted or substituted aryl, unsubstituted or substituted aryloxy and unsubstituted or substituted heterocyclyl;

or a stereoisomer, tautomer or a pharmaceutically acceptable salt, prodrug, carboxylic acid isostere or N-oxide thereof.

6. The compound according to claim 2, wherein,

A is selected from $(C_1-C_{12})$-alkyl, aryl, and heterocyclyl; wherein aryl group may be fused with an unsubstituted or substituted 5 or 6-membered cycloalkyl ring optionally containing heteroatoms selected from O, N or S;

n is 0 or 1;

L is selected from NHC(O)NH or NHC(S)NH;

$X_2$ is selected from CH or CR, $X_1$, $X_4$ and $X_5$ are independently selected from CH, CR and N; wherein R is selected from halogen, hydroxy, $(C_1-C_{12})$-alkoxy, cyano, $(C_1-C_{12})$-alkyl, $CF_3$, $OCF_3$ and cycloalkyl;

$Y_1$ and $Y_2$ are independently selected from C=O and $CH_2$;

m is an integer selected from 1 to 4; wherein:

when m is 1, $R_a$ and $R_b$ may be independently selected from $R_1$ and $R_2$;

when m is 2, $R_a$ and $R_b$ may be independently selected from $R_1$, $R_2$, $R_3$ and $R_4$;

when m is 3, $R_a$ and $R_b$ may be independently selected from $R_1$, $R_2$, $R_3$, $R_4$, $R_5$ and $R_6$;

when m is 4, $R_a$ and $R_b$ may be independently selected from $R_1$, $R_2$, $R_3$, $R_4$, $R_5$, $R_6$, $R_7$ and $R_8$; and $R_1$, $R_2$, $R_3$, $R_4$, $R_5$, $R_6$, $R_7$ and $R_8$ are independently selected from hydrogen, $(C_1-C_{12})$-alkyl, aryl; and aralkyl; or any two of $R_1$, $R_2$, $R_3$, $R_4$, $R_5$, $R_6$, $R_7$ and $R_8$ form a $(C_3-C_{12})$cycloalkyl ring; and $R_9$ is selected from hydrogen or unsubstituted $(C_1-C_6)$-alkyl;

wherein, $(C_1-C_{12})$-alkyl is unsubstituted or substituted with one or more groups selected from halogen, hydroxy, unsubstituted or substituted $(C_1-C_{12})$-alkoxy, cyano, unsubstituted or substituted $(C_3-C_{12})$-cycloalkyl and unsubstituted or substituted aryl, $(C_3-C_{12})$-cycloalkyl is unsubstituted or substituted with one or more groups selected from halogen, hydroxy, unsubstituted or substituted $(C_1-C_{12})$-alkoxy cyano, unsubstituted or substituted aryl and unsubstituted or substituted heterocyclyl;

aryl is unsubstituted or substituted with one or more groups selected from halogen, hydroxy, unsubstituted or substituted $(C_1-C_{12})$-alkoxy, cyano, unsubstituted or substituted $(C_1-C_{12})$-alkyl, $CF_3$, $OCF_3$, unsubstituted or substituted $(C_3-C_{12})$-cycloalkyl, unsubstituted or substituted aryl, unsubstituted or substituted aryloxy and unsubstituted or substituted heterocyclyl, or aryl may be fused with an unsubstituted or substituted 5 or 6-membered cycloalkyl ring optionally containing heteroatoms selected from O, N and S; and heterocyclyl is unsubstituted or substituted with one or more groups selected from halogen, hydroxy, unsubstituted or substituted $(C_1-C_{12})$-alkoxy, cyano, unsubstituted or substituted $(C_1-C_{12})$-alkyl, $CF_3$, $OCF_3$, unsubstituted or substituted $(C_3-C_{12})$-cycloalkyl, unsubstituted or substituted aryl, unsubstituted or substituted aryloxy and unsubstituted or substituted heterocyclyl;

or a stereoisomer, tautomer or a pharmaceutically acceptable salt, prodrug, carboxylic acid isostere or N-oxide thereof.

7. The compound according to claim 2, wherein,

A is selected from $(C_1-C_{12})$-alkyl, aryl and heterocyclyl; wherein aryl group may be fused with an unsubstituted or substituted 5 or 6-membered cycloalkyl ring optionally containing heteroatoms selected from O, N or S;

n is 0 or 1;

L is *$SO_2NH$ wherein * indicates the point of attachment to A-$[CH_2]_n$—;

$X_2$ is selected from CH or CR, $X_1$, $X_4$ and $X_5$ are independently selected from CH, CR and N; wherein R is selected from halogen, hydroxy, $(C_1-C_{12})$-alkoxy, cyano, $(C_1-C_{12})$-alkyl, $CF_3$, $OCF_3$ and cycloalkyl;

$Y_1$ and $Y_2$ are independently selected from C=O and $CH_2$;

m is an integer selected from 1 to 4; wherein:

when m is 1, $R_a$ and $R_b$ may be independently selected from $R_1$ and $R_2$;

when m is 2, $R_a$ and $R_b$ may be independently selected from $R_1$, $R_2$, $R_3$ and $R_4$;

when m is 3, $R_a$ and $R_b$ may be independently selected from $R_1$, $R_2$, $R_3$, $R_4$, $R_5$ and $R_6$;

when m is 4, $R_a$ and $R_b$ may be independently selected from $R_1$, $R_2$, $R_3$, $R_4$, $R_5$, $R_6$, $R_7$ and $R_8$, and $R_1$, $R_2$, $R_3$, $R_4$, $R_5$, $R_6$, $R_7$ and $R_8$ are independently selected from hydrogen, $(C_1-C_{12})$-alkyl, aryl, and aralkyl; or any two of $R_1$, $R_2$, $R_3$, $R_4$, $R_5$, $R_6$, $R_7$ and $R_8$ form a $(C_3-C_{12})$cycloalkyl ring; and $R_9$ is selected from hydrogen or unsubstituted $(C_1-C_6)$-alkyl;

wherein, $(C_1-C_{12})$-alkyl is unsubstituted or substituted with one or more groups selected from halogen, hydroxy, unsubstituted or substituted $(C_1-C_{12})$-alkoxy, cyano, unsubstituted or substituted $(C_3-C_{12})$-cycloalkyl and unsubstituted or substituted aryl, $(C_3-C_{12})$-cycloalkyl is unsubstituted or substituted with one or more groups selected from halogen, hydroxy, unsubstituted or substituted $(C_1-C_{12})$-alkoxy cyano, unsubstituted or substituted aryl and unsubstituted or substituted heterocyclyl;

aryl is unsubstituted or substituted with one or more groups selected from halogen, hydroxy, unsubstituted or substituted $(C_1-C_{12})$-alkoxy, cyano, unsubstituted or substituted $(C_1-C_{12})$-alkyl, $CF_3$, $OCF_3$, unsubstituted or substituted $(C_3-C_{12})$-cycloalkyl, unsubstituted or substituted aryl, unsubstituted or substituted aryloxy and unsubstituted or substituted heterocyclyl, or aryl may be fused with an unsubstituted or substituted 5 or 6-membered cycloalkyl ring optionally containing heteroatoms selected from O, N and S; and heterocyclyl is unsubstituted or substituted with one or more groups selected from halogen, hydroxy, unsubstituted or substituted $(C_1-C_{12})$-alkoxy, cyano, unsubstituted or substituted $(C_1-C_{12})$-alkyl, $CF_3$, $OCF_3$, unsubstituted or substituted $(C_3-C_{12})$-cycloalkyl, unsubstituted or substituted aryl, unsubstituted or substituted aryloxy and unsubstituted or substituted heterocyclyl;

or a stereoisomer, tautomer or a pharmaceutically acceptable salt, prodrug, carboxylic acid isostere or N-oxide thereof.

8. The compound according to claim 2 represented by formula 1b;

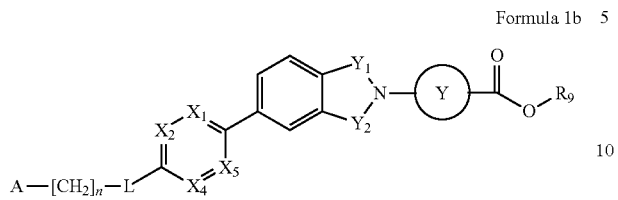

Formula 1b wherein,
A is selected from $(C_1-C_{12})$-alkyl, $(C_3-C_{12})$-cycloalkyl, aryl and heterocyclyl; wherein the aryl group may be fused with an unsubstituted or substituted 5 or 6-membered cycloalkyl ring optionally containing heteroatoms selected from O, N or S;
n is 0 or 1;
L is selected from NHC(O)NH, NHC(S)NH, *NHSO$_2$, *CONH and *SO$_2$NH; wherein * indicates the point of attachment to A-[CH$_2$]$_n$—;
$X_1$, $X_2$, $X_4$ and $X_5$ are independently selected from N,N-oxide, CH and CR; wherein R is selected from halogen, hydroxy, $(C_1-C_{12})$-alkoxy, cyano, $(C_1-C_{12})$-alkyl, CF$_3$, OCF$_3$, $(C_2-C_{12})$-alkenyl, $(C_2-C_{12})$-alkynyl, $(C_3-C_{12})$-cycloalkyl, aryl, aryloxy, heterocyclyl, O-heterocyclyl, C(O)R$_p$, C(O)OR$_p$, NR$_p$R$_q$, SR$_P$, S(O)R$_p$, SO$_2$R$_p$ and C(O)NR$_p$R$_q$;
R$_p$ and R$_q$ are independently selected from hydrogen, $(C_1-C_{12})$-alkyl, aryl, aralkyl and heterocyclyl, or R$_p$ and R$_q$ can optionally form a 3-7 membered ring;
$Y_1$ and $Y_2$ are independently selected from C=O and CH$_2$;
Y is a cycloalkyl ring selected from:

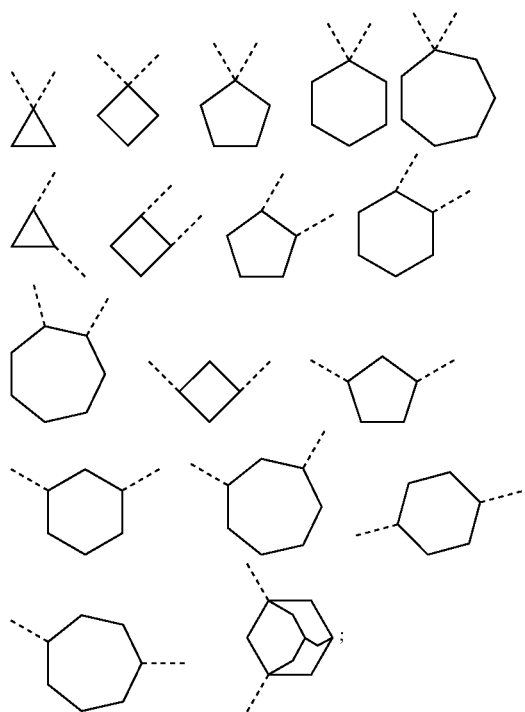

and R$_9$ is selected from hydrogen, $(C_1-C_{12})$-alkyl, aryl, aralkyl and heterocyclyl;

wherein,
$(C_1-C_{12})$-alkyl is unsubstituted or substituted with one or more groups selected from halogen, hydroxy, unsubstituted or substituted $(C_1-C_{12})$-alkoxy, cyano, unsubstituted or substituted $(C_3-C_{12})$-cycloalkyl, and unsubstituted or substituted aryl;
$(C_3-C_{12})$-cycloalkyl is unsubstituted or substituted with one or more groups selected from halogen, hydroxy, unsubstituted or substituted $(C_1-C_{12})$-alkoxy cyano, unsubstituted or substituted aryl, and unsubstituted or substituted heterocyclyl;
aryl is unsubstituted or substituted with one or more groups selected from halogen, hydroxy, unsubstituted or substituted $(C_1-C_{12})$-alkoxy, cyano, unsubstituted or substituted $(C_1-C_{12})$-alkyl, CF$_3$, OCF$_3$, unsubstituted or substituted $(C_3-C_{12})$-cycloalkyl, unsubstituted or substituted aryl, unsubstituted or substituted aryloxy, and unsubstituted or substituted heterocyclyl, or aryl may be fused with an unsubstituted or substituted 5 or 6-membered cycloalkyl ring optionally containing heteroatoms selected from O, N or S; and
heterocyclyl is unsubstituted or substituted with one or more groups selected from halogen, hydroxy, unsubstituted or substituted $(C_1-C_{12})$-alkoxy, cyano, unsubstituted or substituted $(C_1-C_{12})$-alkyl, CF$_3$, OCF$_3$, unsubstituted or substituted $(C_3-C_{12})$-cycloalkyl, unsubstituted or substituted aryl, unsubstituted or substituted aryloxy, and unsubstituted or substituted heterocyclyl;
or a stereoisomer, tautomer or a pharmaceutically acceptable salt, prodrug, carboxylic acid isostere or N-oxide thereof.

9. The compound according to claim 2, wherein,
A is an unsubstituted aryl or an aryl substituted with one or more groups selected from halogen, hydroxy, unsubstituted or substituted $(C_1-C_{12})$-alkoxy, cyano, $(C_1-C_{12})$-alkyl, CF$_3$, OCF$_3$, cycloalkyl, aryl, aryloxy, and heterocyclyl;
wherein,
$(C_1-C_{12})$-alkyl is unsubstituted or substituted with one or more groups selected from halogen, hydroxy, unsubstituted or substituted $(C_1-C_{12})$-alkoxy, cyano, unsubstituted or substituted $(C_3-C_{12})$-cycloalkyl, and unsubstituted or substituted aryl;
$(C_3-C_{12})$-cycloalkyl is unsubstituted or substituted with one or more groups selected from halogen, hydroxy, unsubstituted or substituted $(C_1-C_{12})$-alkoxy cyano, unsubstituted or substituted aryl, and unsubstituted or substituted heterocyclyl;
aryl is unsubstituted or substituted with one or more groups selected from halogen, hydroxy, unsubstituted or substituted $(C_1-C_{12})$-alkoxy, cyano, unsubstituted or substituted $(C_1-C_{12})$-alkyl, CF$_3$, OCF$_3$, unsubstituted or substituted $(C_3-C_{12})$-cycloalkyl, unsubstituted or substituted aryl, unsubstituted or substituted aryloxy, and unsubstituted or substituted heterocyclyl, or aryl may be fused with an unsubstituted or substituted 5 or 6-membered cycloalkyl ring optionally containing heteroatoms selected from O, N or S; and
heterocyclyl is unsubstituted or substituted with one or more groups selected from halogen, hydroxy, unsubstituted or substituted $(C_1-C_{12})$-alkoxy, cyano, unsubstituted or substituted $(C_1-C_{12})$-alkyl, CF$_3$, OCF$_3$, unsubstituted or substituted $(C_3-C_{12})$-cycloalkyl, unsubstituted or substituted aryl, unsubstituted or substituted aryloxy, and unsubstituted or substituted heterocyclyl.

10. The compound according to claim 2,
wherein,
A is an unsubstituted heterocyclyl or a heterocyclyl substituted with one or more groups selected from halogen, hydroxy, unsubstituted or substituted $(C_1-C_{12})$-alkoxy, $CF_3$, $OCF_3$, cyano, $(C_1-C_{12})$-alkyl, cycloalkyl, aryl, aryloxy, and heterocyclyl;
wherein,
- $(C_1-C_{12})$-alkyl is unsubstituted or substituted with one or more groups selected from halogen, hydroxy, unsubstituted or substituted $(C_1-C_{12})$-alkoxy, cyano, unsubstituted or substituted $(C_3-C_{12})$-cycloalkyl, and unsubstituted or substituted aryl;
- $(C_3-C_{12})$-cycloalkyl is unsubstituted or substituted with one or more groups selected from halogen, hydroxy, unsubstituted or substituted $(C_1-C_{12})$-alkoxy cyano, unsubstituted or substituted aryl, and unsubstituted or substituted heterocyclyl;
- aryl is unsubstituted or substituted with one or more groups selected from halogen, hydroxy, unsubstituted or substituted $(C_1-C_{12})$-alkoxy, cyano, unsubstituted or substituted $(C_1-C_{12})$-alkyl, $CF_3$, $OCF_3$, unsubstituted or substituted $(C_3-C_{12})$-cycloalkyl, unsubstituted or substituted aryl, unsubstituted or substituted aryloxy, and unsubstituted or substituted heterocyclyl, or aryl may be fused with an unsubstituted or substituted 5 or 6-membered cycloalkyl ring optionally containing heteroatoms selected from O, N or S; and
- heterocyclyl is unsubstituted or substituted with one or more groups selected from halogen, hydroxy, unsubstituted or substituted $(C_1-C_{12})$-alkoxy, cyano, unsubstituted or substituted $(C_1-C_{12})$-alkyl, $CF_3$, $OCF_3$, unsubstituted or substituted $(C_3-C_{12})$-cycloalkyl, unsubstituted or substituted aryl, unsubstituted or substituted aryloxy, and unsubstituted or substituted heterocyclyl.

11. The compound according to claim 2, wherein n is 0.

12. The compound according to claim 2, wherein L is *CONH.

13. The compound according to claim 2, wherein L is NHC(O)NH.

14. The compound according to claim 2, wherein $X_1$, $X_2$, $X_4$ and $X_5$ are independently selected from CH and CR; wherein R is selected from halogen, hydroxy, $(C_1-C_{12})$-alkoxy, cyano, $(C_1-C_{12})$-alkyl, $CF_3$, $OCF_3$, cycloalkyl, aryl, aryloxy, and heterocyclyl;
wherein,
- $(C_1-C_{12})$-alkyl is unsubstituted or substituted with one or more groups selected from halogen, hydroxy, unsubstituted or substituted $(C_1-C_{12})$-alkoxy, cyano, unsubstituted or substituted $(C_3-C_{12})$-cycloalkyl, and unsubstituted or substituted aryl;
- $(C_3-C_{12})$-cycloalkyl is unsubstituted or substituted with one or more groups selected from halogen, hydroxy, unsubstituted or substituted $(C_1-C_{12})$-alkoxy cyano, unsubstituted or substituted aryl, and unsubstituted or substituted heterocyclyl;
- aryl is unsubstituted or substituted with one or more groups selected from halogen, hydroxy, unsubstituted or substituted $(C_1-C_{12})$-alkoxy, cyano, unsubstituted or substituted $(C_1-C_{12})$-alkyl, $CF_3$, $OCF_3$, unsubstituted or substituted $(C_3-C_{12})$-cycloalkyl, unsubstituted or substituted aryl, unsubstituted or substituted aryloxy, and unsubstituted or substituted heterocyclyl, or aryl may be fused with an unsubstituted or substituted 5 or 6-membered cycloalkyl ring optionally containing heteroatoms selected from O, N or S; and
- heterocyclyl is unsubstituted or substituted with one or more groups selected from halogen, hydroxy, unsubstituted or substituted $(C_1-C_{12})$-alkoxy, cyano, unsubstituted or substituted $(C_1-C_{12})$-alkyl, $CF_3$, $OCF_3$, unsubstituted or substituted $(C_3-C_{12})$-cycloalkyl, unsubstituted or substituted aryl, unsubstituted or substituted aryloxy, and unsubstituted or substituted heterocyclyl.

15. The compound according to claim 2, wherein $X_2$ is selected from CH and CR; $X_1$, $X_4$ and $X_5$ are independently selected from CH, CR and N; wherein R is selected from halogen, hydroxy, $(C_1-C_{12})$-alkoxy, cyano, $(C_1-C_{12})$-alkyl, $CF_3$, $OCF_3$, cycloalkyl, aryl, aryloxy, and heterocyclyl;
wherein,
- $(C_1-C_{12})$-alkyl is unsubstituted or substituted with one or more groups selected from halogen, hydroxy, unsubstituted or substituted $(C_1-C_{12})$-alkoxy, cyano, unsubstituted or substituted $(C_3-C_{12})$-cycloalkyl, and unsubstituted or substituted aryl;
- $(C_3-C_{12})$-cycloalkyl is unsubstituted or substituted with one or more groups selected from halogen, hydroxy, unsubstituted or substituted $(C_1-C_{12})$-alkoxy cyano, unsubstituted or substituted aryl, and unsubstituted or substituted heterocyclyl;
- aryl is unsubstituted or substituted with one or more groups selected from halogen, hydroxy, unsubstituted or substituted $(C_1-C_{12})$-alkoxy, cyano, unsubstituted or substituted $(C_1-C_{12})$-alkyl, $CF_3$, $OCF_3$, unsubstituted or substituted $(C_3-C_{12})$-cycloalkyl, unsubstituted or substituted aryl, unsubstituted or substituted aryloxy, and unsubstituted or substituted heterocyclyl, or aryl may be fused with an unsubstituted or substituted 5 or 6-membered cycloalkyl ring optionally containing heteroatoms selected from O, N or S; and
- heterocyclyl is unsubstituted or substituted with one or more groups selected from halogen, hydroxy, unsubstituted or substituted $(C_1-C_{12})$-alkoxy, cyano, unsubstituted or substituted $(C_1-C_{12})$-alkyl, $CF_3$, $OCF_3$, unsubstituted or substituted $(C_3-C_{12})$-cycloalkyl, unsubstituted or substituted aryl, unsubstituted or substituted aryloxy, and unsubstituted or substituted heterocyclyl.

16. The compound according to claim 2, wherein $Y_1$ is $CH_2$ and $Y_2$ is C=O.

17. The compound according to claim 2, wherein m is 1 and $R_a$ and $R_b$ are independently selected from $R_1$ and $R_2$, wherein $R_1$ and $R_2$ are independently selected from hydrogen, $(C_1-C_{12})$-alkyl, aryl, aralkyl, and heterocyclyl;
wherein,
- $(C_1-C_{12})$-alkyl is unsubstituted or substituted with one or more groups selected from halogen, hydroxy, unsubstituted or substituted $(C_1-C_{12})$-alkoxy, cyano, unsubstituted or substituted $(C_3-C_{12})$-cycloalkyl, and unsubstituted or substituted aryl;
- $(C_3-C_{12})$-cycloalkyl is unsubstituted or substituted with one or more groups selected from halogen, hydroxy, unsubstituted or substituted $(C_1-C_{12})$-alkoxy cyano, unsubstituted or substituted aryl, and unsubstituted or substituted heterocyclyl;
- aryl is unsubstituted or substituted with one or more groups selected from halogen, hydroxy, unsubstituted or substituted $(C_1-C_{12})$-alkoxy, cyano, unsubstituted or substituted $(C_1-C_{12})$-alkyl, $CF_3$, $OCF_3$, unsubstituted or substituted $(C_3-C_{12})$-cycloalkyl, unsubstituted or substituted aryl, unsubstituted or substituted aryloxy, and unsubstituted or substituted heterocyclyl, or aryl may be fused with an unsubstituted or substituted 5 or 6-membered cycloalkyl ring optionally containing heteroatoms selected from O, N or S; and heterocyclyl is unsubstituted or substituted with one or more groups selected from halogen, hydroxy, unsubstituted or substituted $(C_1-C_{12})$-alkoxy, cyano, unsubstituted or substituted $(C_1-C_{12})$-alkyl, $CF_3$, $OCF_3$, unsubstituted or substituted $(C_3-C_{12})$-cycloalkyl, unsubstituted or substituted aryl, unsubstituted or substituted aryloxy, and unsubstituted or substituted heterocyclyl.

18. The compound according to claim 2, wherein $R_9$ is selected from hydrogen or $(C_1-C_{12})$-alkyl, wherein $(C_1-C_{12})$-alkyl is unsubstituted or substituted with one or more groups selected from halogen, hydroxy, $(C_1-C_{12})$-alkoxy, cyano and aryl.

19. The compound according to claim 2, selected from:
(S)-Methyl 2-(6-(4-(3-(4-fluorophenyl)ureido)phenyl)-1-oxoisoindolin-2-yl)-3-methyl butanoate;
(S)-2-(6-(4-(3-(4-Fluorophenyl)ureido)phenyl)-1-oxoisoindolin-2-yl)-3-methyl butanoic acid;
(S)-Methyl 2-(6-(4-(3-(2,4-difluorophenyl)ureido)phenyl)-1-oxoisoindolin-2-yl)-3-methylbutanoate;
(S)-2-(6-(4-(3-(2,4-Difluorophenyl)ureido)phenyl)-1-oxoisoindolin-2-yl)-3-methylbutanoic acid;
(S)-Methyl 2-(6-(4-(3-(2-fluorophenyl)ureido)phenyl)-1-oxoisoindolin-2-yl)-3-methyl butanoate;
(S)-2-(6-(4-(3-(2-Fluorophenyl)ureido)phenyl)-1-oxoisoindolin-2-yl)-3-methyl butanoic acid;
(S)-Methyl 2-(6-(4-(3-(3-fluorophenyl)ureido)phenyl)-1-oxoisoindolin-2-yl)-3-methylbutanoate;
(S)-2-(6-(4-(3-(3-Fluorophenyl)ureido)phenyl)-1-oxoisoindolin-2-yl)-3-methyl butanoic acid;
(S)-Methyl 3-methyl-2-(1-oxo-6-(4-(3-phenylureido)phenyl)isoindolin-2-yl)butanoate;
(S)-3-Methyl-2-(1-oxo-6-(4-(3-phenylureido)phenyl)isoindolin-2-yl)butanoic acid;
(S)-Methyl 2-(6-(4-(3-benzylureido)phenyl)-1-oxoisoindolin-2-yl)-3-methyl butanoate;
(S)-2-(6-(4-(3-Benzylureido)phenyl)-1-oxoisoindolin-2-yl)-3-methylbutanoic acid;
(S)-Methyl 2-(6-(4-(3-(2,6-difluorophenyl)ureido)phenyl)-1-oxoisoindolin-2-yl)-3-methylbutanoate;
(S)-2-(6-(4-(3-(2,6-Difluorophenyl)ureido)phenyl)-1-oxoisoindolin-2-yl)-3-methylbutanoic acid;
(S)-Methyl 3-methyl-2-(1-oxo-6-(4-(3-m-tolylureido)phenyl)isoindolin-2-yl)butanoate;
(S)-3-Methyl-2-(1-oxo-6-(4-(3-m-tolylureido)phenyl)isoindolin-2-yl)butanoic acid;
(S)-Methyl 3-methyl-2-(1-oxo-6-(4-(3-p-tolylureido)phenyl)isoindolin-2-yl)butanoate;
(S)-3-Methyl-2-(1-oxo-6-(4-(3-p-tolylureido)phenyl)isoindolin-2-yl)butanoic acid;
(S)-Methyl 2-(6-(4-(3-(3-methoxyphenyl)ureido)phenyl)-1-oxoisoindolin-2-yl)-3-methylbutanoate;
(S)-2-(6-(4-(3-(3-Methoxyphenyl)ureido)phenyl)-1-oxoisoindolin-2-yl)-3-methyl butanoic acid;
(S)-Methyl-2-(6-(4-(3-(4-methoxyphenyl)ureido)phenyl)-1-oxoisoindolin-2-yl)-3-methylbutanoate;
(S)-2-(6-(4-(3-(4-Methoxyphenyl)ureido)phenyl)-1-oxoisoindolin-2-yl)-3-methylbutanoic acid;
(S)-Methyl-2-(6-(4-(3-(3,5-difluorophenyl)ureido)phenyl)-1-oxoisoindolin-2-yl)-3-methylbutanoate;
(S)-2-(6-(4-(3-(3,5-Difluorophenyl)ureido)phenyl)-1-oxoisoindolin-2-yl)-3-methylbutanoate;
(S)-Methyl 2-(6-(4-(3-(3,4-difluorophenyl)ureido)phenyl)-1-oxoisoindolin-2-yl)-3-methylbutanoate;
(S)-2-(6-(4-(3-(3,4-Difluorophenyl)ureido)phenyl)-1-oxoisoindolin-2-yl)-3-methylbutanoic acid;
(S)-Methyl 2-(6-(4-(3-cyclohexylureido)phenyl)-1-oxoisoindolin-2-yl)-3-methylbutanoate;
(S)-2-(6-(4-(3-Cyclohexylureido)phenyl)-1-oxoisoindolin-2-yl)-3-methylbutanoic acid;
(S)-Methyl 3-methyl-2-(1-oxo-6-(4-(3-(4-(trifluoromethyl)phenyl)ureido)phenyl) isoindolin-2-yl)butanoate;
(S)-3-Methyl-2-(1-oxo-6-(4-(3-(4-(trifluoromethyl)phenyl)ureido)phenyl)isoindolin-2-yl)butanoic acid;
(S)-Methyl 3-methyl-2-(1-oxo-6-(4-(3-(3-(trifluoromethyl)phenyl)ureido)phenyl) isoindolin-2-yl)butanoate;
(S)-3-Methyl-2-(1-oxo-6-(4-(3-(3-(trifluoromethyl)phenyl)ureido)phenyl) isoindolin-2-yl)butanoic acid;
(S)-Methyl 2-(6-(4-(3-(4-cyanophenyl)ureido)phenyl)-1-oxoisoindolin-2-yl)-3-methylbutanoate;
(S)-2-(6-(4-(3-(4-Cyanophenyl)ureido)phenyl)-1-oxoisoindolin-2-yl)-3-methyl butanoic acid;
(S)-Methyl 2-(6-(4-(3-(3-cyanophenyl)ureido)phenyl)-1-oxoisoindolin-2-yl)-3-methylbutanoate;
(S)-2-(6-(4-(3-(3-Cyanophenyl)ureido)phenyl)-1-oxoisoindolin-2-yl)-3-methyl butanoic acid;
(S)-Methyl 2-(6-(4-(3-(4-chloro-2-phenoxyphenyl)ureido)phenyl)-1-oxo isoindolin-2-yl)-3-methylbutanoate;
(S)-2-(6-(4-(3-(4-Chloro-2-phenoxyphenyl)ureido)phenyl)-1-oxoisoindolin-2-yl)-3-methylbutanoic acid;
(S)-Methyl 2-(6-(4-(3-(5-chloro-2-phenoxyphenyl)ureido)phenyl)-1-oxoisoindolin-2-yl)-3-methylbutanoate,
(S)-2-(6-(4-(3-(5-Chloro-2-phenoxyphenyl)ureido)phenyl)-1-oxoisoindolin-2-yl)-3-methylbutanoic acid;
(S)-Methyl 3-methyl-2-(1-oxo-6-(4-(3-(2-phenoxyphenyl)ureido)phenyl)isoindolin-2-yl)butanoate;
(S)-3-Methyl-2-(1-oxo-6-(4-(3-(2-phenoxyphenyl)ureido)phenyl)isoindolin-2-yl)butanoic acid;
(S)-Methyl 3-methyl-2-(1-oxo-6-(4-(3-(4-phenoxyphenyl)ureido)phenyl)isoindolin-2-yl)butanoate;
(S)-3-Methyl-2-(1-oxo-6-(4-(3-(4-phenoxyphenyl)ureido)phenyl)isoindolin-2-yl)butanoic acid;
(S)-Methyl 2-(6-(4-(3-(2-fluorophenyl)thioureido)phenyl)-1-oxoisoindolin-2-yl)-3-methylbutanoate;
(S)-2-(6-(4-(3-(2-Fluorophenyl)thioureido)phenyl)-1-oxoisoindolin-2-yl)-3-methylbutanoic acid;
(S)-Methyl 3-methyl-2-(1-oxo-6-(4-(3-p-tolylthioureido)phenyl)isoindolin-2-yl)butanoate;
(S)-3-Methyl-2-(1-oxo-6-(4-(3-p-tolylthioureido)phenyl)isoindolin-2-yl)butanoic acid;
(S)-Methyl 2-(6-(4-(3-(3-fluorophenyl)thioureido)phenyl)-1-oxoisoindolin-2-yl)-3-methylbutanoate,
(S)-2-(6-(4-(3-(3-Fluorophenyl)thioureido)phenyl)-1-oxoisoindolin-2-yl)-3-methylbutanoic acid;
(S)-Methyl 2-(6-(4-(3-(4-methoxyphenyl)thioureido)phenyl)-1-oxoisoindolin-2-yl)-3-methylbutanoate;
(S)-2-(6-(4-(3-(4-Methoxyphenyl)thioureido)phenyl)-1-oxoisoindolin-2-yl)-3-methylbutanoic acid;
(S)-Methyl 2-(6-(4-(3-(3-methoxyphenyl)thioureido)phenyl)-1-oxoisoindolin-2-yl)-3-methylbutanoate;
(S)-2-(6-(4-(3-(3-Methoxyphenyl)thioureido)phenyl)-1-oxoisoindolin-2-yl)-3-methylbutanoic acid;
(S)-Methyl 2-(6-(4-(3-(4-chlorophenyl)thioureido)phenyl)-1-oxoisoindolin-2-yl)-3-methylbutanoate;
(S)-2-(6-(4-(3-(4-Chlorophenyl)thioureido)phenyl)-1-oxoisoindolin-2-yl)-3-methyl butanoic acid;
(S)-Methyl 2-(6-(4-(3-(4-chlorophenyl)thioureido)phenyl)-1-oxoisoindolin-2-yl)-3-methylbutanoate;
(S)-2-(6-(4-(3-(3-Chlorophenyl)thioureido)phenyl)-1-oxoisoindolin-2-yl)-3-methyl butanoic acid;

(S)-Methyl 3-methyl-2-(1-oxo-6-(4-(3-(2-trifluoromethyl)phenyl)thioureido)phenyl)isoindolin-2-yl)butanoate;
(S)-3-Methyl-2-(1-oxo-6-(4-(3-(2-trifluoromethyl)phenyl)thioureido)phenyl)isoindolin-2-yl)butanoic acid;
(S)-Methyl 2-(6-(4-(3-(4-cyanophenyl)thioureido)phenyl)-1-oxoisoindolin-2-yl)-3-methylbutanoate;
(S)-2-(6-(4-(3-(4-Cyanophenyl)thioureido)phenyl)-1-oxoisoindolin-2-yl)-3-methyl butanoic acid;
(S)-Methyl 2-(6-(4-(3-(4-cyanophenyl)thioureido)phenyl)-1-oxoisoindolin-2-yl)-3-methylbutanoate;
(S)-2-(6-(4-(3-(3-Cyanophenyl)thioureido)phenyl)-1-oxoisoindolin-2-yl)-3-methyl butanoic acid;
(S)-Methyl 3-methyl-2-(1-oxo-6-(4-(3-o-tolylthioureido)phenyl)isoindolin-2-yl)butanoate;
(S)-3-Methyl-2-(1-oxo-6-(4-(3-o-tolylthioureido)phenyl)isoindolin-2-yl)butanoic acid;
(S)-Methyl 2-(6-(4-(3-(2-methoxyphenyl)thioureido)phenyl)-1-oxoisoindolin-2-yl)-3-methylbutanoate;
(S)-2-(6-(4-(3-(2-Methoxyphenyl)thioureido)phenyl)-1-oxoisoindolin-2-yl)-3-methylbutanoic acid;
(S)-Methyl 3-methyl-2-(1-oxo-6-(4-(3-(3-(trifluoromethyl)phenyl)thioureido) phenyl)isoindolin-2-yl)butanoate;
(S)-3-Methyl-2-(1-oxo-6-(4-(3-(3-(trifluoromethyl)phenyl)thioureido)phenyl)isoindolin-2-yl)butanoic acid;
(S)-Methyl 3-methyl-2-(1-oxo-6-(4-(phenylsulfonamido)phenyl)isoindolin-2-yl)butanoate;
(S)-3-Methyl-2-(1-oxo-6-(4-(phenylsulfonamido)phenyl)isoindolin-2-yl)butanoic acid;
(S)-Methyl 2-(6-(4-(4-cyanophenylsulfonamido)phenyl)-1-oxoisoindolin-2-yl)-3-methylbutanoate;
(S)-2-(6-(4-(4-Cyanophenylsulfonamido)phenyl)-1-oxoisoindolin-2-yl)-3-methyl butanoic acid;
(S)-Methyl 2-(6-(4-(3,4-difluorophenylsulfonamido)phenyl)-1-oxoisoindolin-2-yl)-3-methylbutanoate;
(S)-2-(6-(4-(3,4-Difluorophenylsulfonamido)phenyl)-1-oxoisoindolin-2-yl)-3-methylbutanoic acid;
(S)-Methyl 2-(6-(4-(2,4-difluorophenylsulfonamido)phenyl)-1-oxoisoindolin-2-yl)-3-methylbutanoate;
(S)-2-(6-(4-(2,4-Difluorophenylsulfonamido)phenyl)-1-oxoisoindolin-2-yl)-3-methylbutanoic acid;
(S)-Methyl 2-(6-(4-(3,4-dimethoxyphenylsulfonamido)phenyl)-1-oxoisoindolin-2-yl)-3-methylbutanoate;
(S)-2-(6-(4-(3,4-Dimethoxyphenylsulfonamido)phenyl)-1-oxoisoindolin-2-yl)-3-methylbutanoic acid;
(S)-Methyl 2-(6-(4-(3-chlorophenylsulfonamido)phenyl)-1-oxoisoindolin-2-yl)-3-methylbutanoate;
(S)-2-(6-(4-(3-Chlorophenylsulfonamido)phenyl)-1-oxoisoindolin-2-yl)-3-methylbutanoic acid;
(S)-Methyl 2-(6-(4-(4-methoxyphenylsulfonamido)phenyl)-1-oxoisoindolin-2-yl)-3-methylbutanoate;
(S)-2-(6-(4-(4-Methoxyphenylsulfonamido)phenyl)-1-oxoisoindolin-2-yl)-3-methylbutanoic acid;
(S)-Methyl 3-methyl-2-(1-oxo-6-(4-(4-(trifluoromethyl)phenylsulfonamido) phenyl)isoindolin-2-yl)butanoate;
(S)-3-Methyl-2-(1-oxo-6-(4-(4-(trifluoromethyl)phenylsulfonamido)phenyl)isoindolin-2-yl)butanoic acid;
(S)-Methyl 3-methyl-2-(1-oxo-6-(4-(phenylmethylsulfonamido)phenyl)isoindolin-2-yl)butanoate;
(S)-3-Methyl-2-(1-oxo-6-(4-(phenylmethylsulfonamido)phenyl)isoindolin-2-yl)butanoic acid;
(S)-Methyl 3-methyl-2-(6-(4-(1-methylethylsulfonamido)phenyl)-1-oxoisoindolin-2-yl)butanoate;
(S)-3-Methyl-2-(6-(4-(1-methylethylsulfonamido)phenyl)-1-oxoisoindolin-2-yl)butanoic acid;
(S)-Methyl 2-(6-(4-benzamidophenyl)-1-oxoisoindolin-2-yl)-3-methylbutanoate
(S)-2-(6-(4-Benzamidophenyl)-1-oxoisoindolin-2-yl)-3-methylbutanoic acid;
(S)-Methyl 2-(6-(4-(4-fluorobenzamido)phenyl)-1-oxoisoindolin-2-yl)-3-methylbutanoate;
(S)-2-(6-(4-(4-Fluorobenzamido)phenyl)-1-oxoisoindolin-2-yl)-3-methylbutanoic acid;
(S)-Methyl 3-methyl-2-(1-oxo-6-(4-(4-(trifluoromethyl)benzamido)phenyl)isoindolin-2-yl)butanoate;
(S)-3-Methyl-2-(1-oxo-6-(4-(4-(trifluoromethyl)benzamido)phenyl)isoindolin-2-yl)butanoic acid;
(S)-Methyl 2-(6-(4-(4-methoxybenzamido)phenyl)-1-oxoisoindolin-2-yl)-3-methylbutanoate;
(S)-2-(6-(4-(4-Methoxybenzamido)phenyl)-1-oxoisoindolin-2-yl)-3-methyl butanoic acid;
(S)-Methyl 2-(6-(4-(3-fluorobenzamido)phenyl)-1-oxoisoindolin-2-yl)-3-methyl butanoate;
(S)-2-(6-(4-(3-Fluorobenzamido)phenyl)-1-oxoisoindolin-2-yl)-3-methylbutanoic acid;
(S)-Methyl 2-(6-(4-(3-chlorobenzamido)phenyl)-1-oxoisoindolin-2-yl)-3-methylbutanoate;
(S)-2-(6-(4-(3-Chlorobenzamido)phenyl)-1-oxoisoindolin-2-yl)-3-methylbutanoic acid;
(S)-Methyl 2-(6-(4-(2,4-difluorobenzamido)phenyl)-1-oxoisoindolin-2-yl)-3-methylbutanoate;
(S)-2-(6-(4-(2,4-Difluorobenzamido)phenyl)-1-oxoisoindolin-2-yl)-3-methyl butanoic acid;
(S)-Methyl 3-methyl-2-(6-(4-(4-methylbenzamido)phenyl)-1-oxoisoindolin-2-yl)butanoate;
(S)-3-Methyl-2-(6-(4-(4-methylbenzamido)phenyl)-1-oxoisoindolin-2-yl)butanoic acid;
(S)-Methyl 2-(6-(4-(4-chlorobenzamido)phenyl)-1-oxoisoindolin-2-yl)-3-methylbutanoate;
(S)-2-(6-(4-(4-Chlorobenzamido)phenyl)-1-oxoisoindolin-2-yl)-3-methylbutanoic acid;
(S)-Methyl 2-(6-(4-(4-tert-butylbenzamido)phenyl)-1-oxoisoindolin-2-yl)-3-methylbutanoate;
(S)-2-(6-(4-(4-tert-Butylbenzamido)phenyl)-1-oxoisoindolin-2-yl)-3-methyl butanoic acid;
(S)-Methyl 2-(6-(4-(cyclohexanecarboxamido)phenyl)-1-oxoisoindolin-2-yl)-3-methylbutanoate;
(S)-2-(6-(4-(Cyclohexanecarboxamido)phenyl)-1-oxoisoindolin-2-yl)-3-methylbutanoic acid;
(S)-Methyl 2-(6-(4-biphenyl-4-ylcarboxamidophenyl)-1-oxoisoindolin-2-yl)-3-methylbutanoate;
(S)-2-(6-(4-Biphenyl-4-ylcarboxamidophenyl)-1-oxoisoindolin-2-yl)-3-methyl butanoic acid;
(S)-Methyl 2-(6-(4-(2-naphthamido)phenyl)-1-oxoisoindolin-2-yl)-3-methyl butanoate;
(S)-2-(6-(4-(2-Naphthamido)phenyl)-1-oxoisoindolin-2-yl)-3-methylbutanoic acid;
(S)-Methyl 3-methyl-2-(1-oxo-6-(4-(4-pentylbenzamido)phenyl)isoindolin-2-yl) butanoate;
(S)-3-Methyl-2-(1-oxo-6-(4-(4-pentylbenzamido)phenyl)isoindolin-2-yl)butanoic acid;
(S)-Methyl 2-(6-(4-(2-fluoro-6-(trifluoromethyl)benzamido)phenyl)-1-oxoisoindolin-2-yl)-3-methylbutanoate;
(S)-2-(6-(4-(2-Fluoro-6-(trifluoromethyl)benzamido)phenyl)-1-oxoisoindolin-2-yl)-3-methylbutanoic acid;
(S)-Methyl 2-(6-(4-(benzo[d][1,3]dioxole-5-carboxamido)phenyl)-1-oxo isoindolin-2-yl)-3-methylbutanoate;
(S)-2-(6-(4-(Benzo[d][1,3]-dioxole-5-carboxamido)phenyl)-1-oxoisoindolin-2-yl)-3-methylbutanoic acid;

(S)-Methyl 2-(6-(4-(2,6-dichlorobenzamido)phenyl)-1-oxoisoindolin-2-yl)-3-methylbutanoate;
(S)-2-(6-(4-(2,6-Dichlorobenzamido)phenyl)-1-oxoisoindolin-2-yl)-3-methyl butanoic acid;
(S)-Methyl 2-(6-(4-(2-chlorobenzamido)phenyl)-1-oxoisoindolin-2-yl)-3-methyl butanoate;
(S)-2-(6-(4-(2-Chlorobenzamido)phenyl)-1-oxoisoindolin-2-yl)-3-methylbutanoic acid;
(S)-Methyl 2-(6-(4-(2,4-dichlorobenzamido)phenyl)-1-oxoisoindolin-2-yl)-3-methyl butanoate;
(S)-2-(6-(4-(2,4-Dichlorobenzamido)phenyl)-1-oxoisoindolin-2-yl)-3-methyl butanoic acid;
(S)-Methyl 2-(6-(4-(4-butoxybenzamido)phenyl)-1-oxoisoindolin-2-yl)-3-methyl butanoate;
(S)-2-(6-(4-(4-Butoxybenzamido)phenyl)-1-oxoisoindolin-2-yl)-3-methyl butanoic acid;
(S)-Methyl 2-(6-(4-(2,6-difluorobenzamido)phenyl)-1-oxoisoindolin-2-yl)-3-methylbutanoate;
(S)-2-(6-(4-(2,6-Difluorobenzamido)phenyl)-1-oxoisoindolin-2-yl)-3-methyl butanoic acid;
(S)-Methyl 2-(6-(4-(3,4-difluorobenzamido)phenyl)-1-oxoisoindolin-2-yl)-3-methylbutanoate;
(S)-2-(6-(4-(3,4-Difluorobenzamido)phenyl)-1-oxoisoindolin-2-yl)-3-methyl butanoic acid;
(S)-Methyl 2-(6-(4-(3,4-dimethoxybenzamido)phenyl)-1-oxoisoindolin-2-yl)-3-methylbutanoate;
(S)-2-(6-(4-(3,4-Dimethoxybenzamido)phenyl)-1-oxoisoindolin-2-yl)-3-methyl butanoic acid;
(S)-Methyl 3-methyl-2-(1-oxo-6-(4-(3,4,5-trimethoxybenzamido)phenyl) isoindolin-2-yl)butanoate;
(S)-3-Methyl-2-(1-oxo-6-(4-(3,4,5-trimethoxybenzamido)phenyl)isoindolin-2-yl) butanoic acid;
(S)-Methyl 2-(6-(4-(3,5-diethoxybenzamido)phenyl)-1-oxoisoindolin-2-yl)-3-methylbutanoate;
(S)-2-(6-(4-(3,5-Diethoxybenzamido)phenyl)-1-oxoisoindolin-2-yl)-3-methyl butanoic acid;
(S)-Methyl 3-methyl-2-(1-oxo-6-(4-(3-phenoxybenzamido)phenyl)isoindolin-2-yl)butanoate;
(S)-3-Methyl-2-(1-oxo-6-(4-(3-phenoxybenzamido)phenyl)isoindolin-2-yl) butanoic acid;
(S)-Methyl 3-methyl-2-(1-oxo-6-(4-(4-phenoxybenzamido)phenyl)isoindolin-2-yl)butanoate;
(S)-3-Methyl-2-(1-oxo-6-(4-(4-phenoxybenzamido)phenyl)isoindolin-2-yl) butanoic acid;
(S)-Methyl 3-methyl-2-(1-oxo-6-(4-(2-phenoxybenzamido)phenyl)isoindolin-2-yl)butanoate;
(S)-3-Methyl-2-(1-oxo-6-(4-(2-phenoxybenzamido)phenyl)isoindolin-2-yl) butanoic acid;
(S)-Methyl 3-methyl-2-(1-oxo-6-(4-(2,4,6-trimethylbenzamido)phenyl)isoindolin-2-yl)butanoate;
(S)-3-Methyl-2-(1-oxo-6-(4-(2,4,6-trimethylbenzamido)phenyl)isoindolin-2-yl) butanoic acid;
(S)-Methyl 2-(6-(4-(2,4-dimethoxybenzamido)phenyl)-1-oxoisoindolin-2-yl)-3-methylbutanoate;
(S)-2-(6-(4-(2,4-Dimethoxybenzamido)phenyl)-1-oxoisoindolin-2-yl)-3-methyl butanoic acid;
(S)-Methyl 3-methyl-2-(1-oxo-6-(4-(4-(trifluoromethoxy)benzamido)phenyl)isoindolin-2-yl)butanoate;
(S)-3-Methyl-2-(1-oxo-6-(4-(4-(trifluoromethoxy)benzamido)phenyl)isoindolin-2-yl)butanoic acid;
(S)-Methyl 2-(6-(4-(2-methoxybenzamido)phenyl)-1-oxoisoindolin-2-yl)-3-methylbutanoate;
(S)-2-(6-(4-(2-Methoxybenzamido)phenyl)-1-oxoisoindolin-2-yl)-3-methyl butanoic acid;
(S)-Methyl 2-(6-(4-(4-fluoro-3-methylbenzamido)phenyl)-1-oxoisoindolin-2-yl)-3-methylbutanoate;
(S)-2-(6-(4-(4-Fluoro-3-methylbenzamido)phenyl)-1-oxoisoindolin-2-yl)-3-methyl butanoic acid;
(S)-Methyl 2-(6-(4-(4-butylbenzamido)phenyl)-1-oxoisoindolin-2-yl)-3-methyl butanoate;
(S)-2-(6-(4-(4-Butylbenzamido)phenyl)-1-oxoisoindolin-2-yl)-3-methylbutanoic acid;
(S)-Methyl 2-(6-(4-(2,6-difluoro-3-methylbenzamido)phenyl)-1-oxoisoindolin-2-yl)-3-methylbutanoate;
(S)-2-(6-(4-(2,6-Difluoro-3-methylbenzamido)phenyl)-1-oxoisoindolin-2-yl)-3-methylbutanoic acid;
(S)-Methyl 2-(6-(4-(4-ethylbenzamido)phenyl)-1-oxoisoindolin-2-yl)-3-methyl butanoate;
(S)-2-(6-(4-(4-Ethylbenzamido)phenyl)-1-oxoisoindolin-2-yl)-3-methylbutanoic acid;
(S)-Methyl 3-methyl-2-(1-oxo-6-(4-(4-propylbenzamido)phenyl)isoindolin-2-yl) butanoate;
(S)-3-Methyl-2-(1-oxo-6-(4-(4-propylbenzamido)phenyl)isoindolin-2-yl)butanoic acid;
(S)-Methyl 3-methyl-2-(6-(4-(4-octylbenzamido)phenyl)-1-oxoisoindolin-2-yl) butanoate;
(S)-3-Methyl-2-(6-(4-(4-octylbenzamido)phenyl)-1-oxoisoindolin-2-yl)butanoic acid;
(S)-Methyl 2-(6-(4-(4-cyclohexylbenzamido)phenyl)-1-oxoisoindolin-2-yl)-3-methylbutanoate;
(S)-2-(6-(4-(4-Cyclohexylbenzamido)phenyl)-1-oxoisoindolin-2-yl)-3-methyl butanoic acid;
(S)-Methyl 3-methyl-2-(1-oxo-6-(4-(5,5,8,8-tetramethyl-5,6,7,8-tetrahydro naphthalene-2-carboxamido)phenyl)isoindolin-2-yl)butanoate;
(S)-3-Methyl-2-(1-oxo-6-(4-(5,5,8,8-tetramethyl-5,6,7,8-tetrahydro naphthalene-2-carboxamido)phenyl)isoindolin-2-yl)butanoic acid;
(S)-Methyl 2-(6-(4-(1-naphthamido)phenyl)-1-oxoisoindolin-2-yl)-3-methyl butanoate;
(S)-2-(6-(4-(1-Naphthamido)phenyl)-1-oxoisoindolin-2-yl)-3-methylbutanoic acid;
(S)-Methyl 2-(6-(4-(3,5-dimethoxybenzamido)phenyl)-1-oxoisoindolin-2-yl)-3-methylbutanoate;
(S)-2-(6-(4-(3,5-Dimethoxybenzamido)phenyl)-1-oxoisoindolin-2-yl)-3-methyl butanoic acid;
(S)-Methyl 2-(6-(4-(4-hexylbenzamido)phenyl)-1-oxoisoindolin-2-yl)-3-methyl butanoate;
(S)-2-(6-(4-(4-Hexylbenzamido)phenyl)-1-oxoisoindolin-2-yl)-3-methylbutanoic acid;
(S)-Methyl 2-(6-(4-(4-heptylbenzamido)phenyl)-1-oxoisoindolin-2-yl)-3-methyl butanoate;
(S)-2-(6-(4-(4-Heptylbenzamido)phenyl)-1-oxoisoindolin-2-yl)-3-methylbutanoic acid;
(S)-Methyl 3-methyl-2-(6-(4-(4-nonylbenzamido)phenyl)-1-oxoisoindolin-2-yl)butanoate;
(S)-3-Methyl-2-(6-(4-(4-nonylbenzamido)phenyl)-1-oxoisoindolin-2-yl)butanoic acid;
(S)-Methyl 2-(6-(4-(4-decylbenzamido)phenyl)-1-oxoisoindolin-2-yl)-3-methyl butanoate;
(S)-2-(6-(4-(4-Decylbenzamido)phenyl)-1-oxoisoindolin-2-yl)-3-methyl butanoic acid;
(S)-(Methyl 2-(6-(4-(adamentyl-2-carboxamido)phenyl)-1-oxoisoindolin-2-yl)-3-methylbutanoate;
(S)-2-(6-(4-(Adamantyl-2-carboxamido)phenyl)-1-oxoisoindolin-2-yl)-3-methylbutanoic acid;
(S)-Methyl 2-(6-(4-(2-fluoro-4-(trifluoromethyl)benzamido)phenyl)-1-oxoisoindolin-2-yl)-3-methylbutanoate;
(S)-2-(6-(4-(2-Fluoro-4-(trifluoromethyl)benzamido)phenyl)-1-oxoisoindolin-2-yl)-3-methylbutanoic acid;

(S)-Methyl 2-(6-(4-(2-fluoro-3-(trifluoromethyl)benzamido)phenyl)-1-oxoisoindolin-2-yl)-3-methylbutanoate;
(S)-2-(6-(4-(2-Fluoro-3-(trifluoromethyl)benzamido)phenyl)-1-oxoisoindolin-2-yl)-3-methylbutanoic acid;
(S)-Methyl 2-(6-(4-(3-fluoro-4-(trifluoromethyl)benzamido)phenyl)-1-oxoisoindolin-2-yl)-3-methylbutanoate;
(S)-2-(6-(4-(3-Fluoro-4-(trifluoromethyl)benzamido)phenyl)-1-oxoisoindolin-2-yl)-3-methylbutanoic acid;
(S)-Methyl 2-(6-(4-(4-fluoro-2-(trifluoromethyl)benzamido)phenyl)-1-oxoisoindolin-2-yl)-3-methylbutanoate;
(S)-2-(6-(4-(4-Fluoro-2-(trifluoromethyl)benzamido)phenyl)-1-oxoisoindolin-2-yl)-3-methylbutanoic acid;
(S)-Methyl 3-methyl-2-(1-oxo-6-(4-(2-(trifluoromethyl)benzamido)phenyl)iso indolin-2-yl)butanoate;
(S)-3-Methyl-2-(1-oxo-6-(4-(2-(trifluoromethyl)benzamido)phenyl)isoindolin-2-yl)butanoic acid;
(S)-Methyl 2-(6-(4-(2-ethoxybenzamido)phenyl)-1-oxoisoindolin-2-yl)-3-methyl butanoate;
(S)-2-(6-(4-(2-Ethoxybenzamido)phenyl)-1-oxoisoindolin-2-yl)-3-methylbutanoic acid;
(S)-Methyl 2-(6-(4-(4-cyanobenzamido)phenyl)-1-oxoisoindolin-2-yl)-3-methyl butanoate;
(S)-Methyl 2-(6-(4-(3-chloro-2-fluorobenzamido)phenyl)-1-oxoisoindolin-2-yl)-3-methylbutanoate;
(S)-Methyl 2-(6-(4-(4-fluoro-3-(trifluoromethyl)benzamido)phenyl)-1-oxoisoindolin-2-yl)-3-methylbutanoate;
(S)-Methyl 3-methyl-2-(6-(4-(nicotinamido)phenyl)-1-oxoisoindolin-2-yl)butanoate;
(S)-3-Methyl-2-(6-(4-(nicotinamido)phenyl)-1-oxoisoindolin-2-yl)butanoic acid;
(S)-Methyl 2-(6-(4-(2-chloronicotinamido)phenyl)-1-oxoisoindolin-2-yl)-3-methylbutanoate;
(S)-2-(6-(4-(2-Chloronicotinamido)phenyl)-1-oxoisoindolin-2-yl)-3-methyl butanoic acid;
(S)-Methyl 3-methyl-2-(1-oxo-5-(4-(6-(trifluoromethyl)nicotinamido)phenyl)iso indolin-2-yl)butanoate;
(S)-Methyl 2-(6-(4-(6-chloronicotinamido)phenyl)-1-oxoisoindolin-2-yl)-3-methyl butanoate;
(S)-Methyl 3-methyl-2-(6-(4-(6-morpholinonicotinamido)phenyl)-1-oxoisoindolin-2-yl)butanoate;
(S)-3-Methyl-2-(6-(4-(6-morpholinonicotinamido)phenyl)-1-oxoisoindolin-2-yl) butanoic acid;
(S)-Methyl 3-methyl-2-(1-oxo-6-(4-(6-(piperidin-1-yl)nicotinamido)phenyl)iso indolin-2-yl)butanoate;
(S)-3-Methyl-2-(1-oxo-6-(4-(6-(piperidin-1-yl)nicotinamido)phenyl)isoindolin-2-yl)butanoic acid;
(S)-Methyl 3-methyl-2-(1-oxo-6-(4-(6-(pyrrolidin-1-yl)nicotinamido)phenyl)iso indolin-2-yl)butanoate;
(S)-3-Methyl-2-(1-oxo-6-(4-(6-(pyrrolidin-1-yl)nicotinamido)phenyl)isoindolin-2-yl)butanoic acid;
(S)-Methyl 3-methyl-2-(6-(4-(6-(4-methylpiperazin-1-yl)nicotinamido)phenyl)-1-oxoisoindolin-2-yl)butanoate;
(S)-Methyl 2-(5-(4-(3-(4-fluorophenyl)ureido)phenyl)-1-oxoisoindolin-2-yl)-3-methylbutanoate;
(S)-2-(5-(4-(3-(4-Fluorophenyl)ureido)phenyl)-1-oxoisoindolin-2-yl)-3-methylbutanoic acid;
(S)-Methyl 2-(5-(4-(3-(2-fluorophenyl)ureido)phenyl)-1-oxoisoindolin-2-yl)-3-methylbutanoate;
(S)-2-(5-(4-(3-(2-Fluorophenyl)ureido)phenyl)-1-oxoisoindolin-2-yl)-3-methyl butanoic acid;
(S)-Methyl 2-(5-(4-(3-(3-fluorophenyl)ureido)phenyl)-1-oxoisoindolin-2-yl)-3-methylbutanoate;
(S)-2-(5-(4-(3-(3-Fluorophenyl)ureido)phenyl)-1-oxoisoindolin-2-yl)-3-methyl butanoic acid;
(S)-Methyl 3-methyl-2-(1-oxo-5-(4-(3-phenylureido)phenyl)isoindolin-2-yl)butanoate;
(S)-3-Methyl-2-(1-oxo-5-(4-(3-phenylureido)phenyl)isoindolin-2-yl)butanoic acid;
(S)-Methyl 2-(5-(4-(3-benzylureido)phenyl)-1-oxoisoindolin-2-yl)-3-methyl butanoate;
(S)-2-(5-(4-(3-Benzylureido)phenyl)-1-oxoisoindolin-2-yl)-3-methylbutanoic acid;
(S)-Methyl 2-(5-(4-(3-cyclohexylureido)phenyl)-1-oxoisoindolin-2-yl)-3-methyl butanoate;
(S)-2-(5-(4-(3-Cyclohexylureido)phenyl)-1-oxoisoindolin-2-yl)-3-methyl butanoic acid;
(S)-Methyl 2-(5-(4-(3-(2,4-difluorophenyl)ureido)phenyl)-1-oxoisoindolin-2-yl)-3-methylbutanoate;
(S)-2-(5-(4-(3-(2,4-Difluorophenyl)ureido)phenyl)-1-oxoisoindolin-2-yl)-3-methylbutanoic acid;
(S)-Methyl 2-(5-(4-(3-(3,4-difluorophenyl)ureido)phenyl)-1-oxoisoindolin-2-yl)-3-methylbutanoate;
(S)-2-(5-(4-(3-(3,4-Difluorophenyl)ureido)phenyl)-1-oxoisoindolin-2-yl)-3-methylbutanoic acid;
(S)-Methyl 3-methyl-2-(1-oxo-5-(4-(3-p-tolylureido)phenyl)isoindolin-2-yl)butanoate;
(S)-3-Methyl-2-(1-oxo-5-(4-(3-p-tolylureido)phenyl)isoindolin-2-yl)butanoic acid;
(S)-Methyl 3-methyl-2-(1-oxo-5-(4-(3-m-tolylureido)phenyl)isoindolin-2-yl)butanoate;
(S)-3-Methyl-2-(1-oxo-5-(4-(3-m-tolylureido)phenyl)isoindolin-2-yl)butanoic acid;
(S)-Methyl 3-methyl-2-(1-oxo-5-(4-(3-(4-(trifluoromethyl)phenyl)ureido)phenyl) isoindolin-2-yl)butanoate;
(S)-3-Methyl-2-(1-oxo-5-(4-(3-(4-(trifluoromethyl)phenyl)ureido)phenyl)isoindolin-2-yl)butanoic acid;
(S)-Methyl 3-methyl-2-(1-oxo-5-(4-(3-(3-(trifluoromethyl)phenyl)ureido)phenyl) isoindolin-2-yl)butanoate;
(S)-3-Methyl-2-(1-oxo-5-(4-(3-(3-(trifluoromethyl)phenyl)ureido)phenyl)isoindolin-2-yl)butanoic acid;
(S)-Methyl 2-(5-(4-(3-(4-methoxyphenyl)ureido)phenyl)-1-oxoisoindolin-2-yl)-3-methylbutanoate;
(S)-2-(5-(4-(3-(4-Methoxyphenyl)ureido)phenyl)-1-oxoisoindolin-2-yl)-3-methylbutanoic acid;
(S)-Methyl 2-(5-(4-(3-(3-methoxyphenyl)ureido)phenyl)-1-oxoisoindolin-2-yl)-3-methylbutanoate;
(S)-2-(5-(4-(3-(3-Methoxyphenyl)ureido)phenyl)-1-oxoisoindolin-2-yl)-3-methylbutanoic acid;
(S)-Methyl 2-(5-(4-(3-(4-cyanophenyl)ureido)phenyl)-1-oxoisoindolin-2-yl)-3-methylbutanoate;
(S)-2-(5-(4-(3-(4-Cyanophenyl)ureido)phenyl)-1-oxoisoindolin-2-yl)-3-methylbutanoic acid;
(S)-Methyl 2-(5-(4-(3-(3-cyanophenyl)ureido)phenyl)-1-oxoisoindolin-2-yl)-3-methylbutanoate,
(S)-2-(5-(4-(3-(3-Cyanophenyl)ureido)phenyl)-1-oxoisoindolin-2-yl)-3-methylbutanoic acid;
(S)-Methyl 2-(5-(4-(3-(2-fluorophenyl)thioureido)phenyl)-1-oxoisoindolin-2-yl)-3-methylbutanoate;
(S)-2-(5-(4-(3-(2-Fluorophenyl)thioureido)phenyl)-1-oxoisoindolin-2-yl)-3-methylbutanoic acid;
(S)-Methyl 2-(5-(4-(3-(3-fluorophenyl)thioureido)phenyl)-1-oxoisoindolin-2-yl)-3-methylbutanoate;
(S)-2-(5-(4-(3-(3-Fluorophenyl)thioureido)phenyl)-1-oxoisoindolin-2-yl)-3-methyl butanoic acid;
(S)-Methyl 2-(5-(4-(3-(4-methoxyphenyl)thioureido)phenyl)-1-oxoisoindolin-2-yl)-3-methylbutanoate;
(S)-2-(5-(4-(3-(4-Methoxyphenyl)thioureido)phenyl)-1-oxoisoindolin-2-yl)-3-methylbutanoic acid;

(S)-Methyl 2-(5-(4-(3-(3-methoxyphenyl)thioureido)phenyl)-1-oxoisoindolin-2-yl)-3-methylbutanoate;
(S)-2-(5-(4-(3-(3-Methoxyphenyl)thioureido)phenyl)-1-oxoisoindolin-2-yl)-3-methyl butanoic acid;
(S)-Methyl 2-(5-(4-(3-(4-chlorophenyl)thioureido)phenyl)-1-oxoisoindolin-2-yl)-3-methylbutanoate;
(S)-2-(5-(4-(3-(4-Chlorophenyl)thioureido)phenyl)-1-oxoisoindolin-2-yl)-3-methylbutanoic acid;
(S)-Methyl 2-(5-(4-(3-(3-chlorophenyl)thioureido)phenyl)-1-oxoisoindolin-2-yl)-3-methylbutanoate;
(S)-2-(5-(4-(3-(3-Chlorophenyl)thioureido)phenyl)-1-oxoisoindolin-2-yl)-3-methylbutanoic acid;
(S)-Methyl 2-(5-(4-(3-(4-cyanophenyl)thioureido)phenyl)-1-oxoisoindolin-2-yl)-3-methylbutanoate;
(S)-2-(5-(4-(3-(4-Cyanophenyl)thioureido)phenyl)-1-oxoisoindolin-2-yl)-3-methyl butanoic acid;
(S)-Methyl 3-methyl-2-(1-oxo-5-(4-(3-(2-(trifluoromethyl)phenyl)thioureido) phenyl)isoindolin-2-yl)butanoate;
(S)-3-Methyl-2-(1-oxo-5-(4-(3-(2-(trifluoromethyl)phenyl)thioureido)phenyl)isoindolin-2-yl)butanoic acid;
(S)-Methyl 3-methyl-2-(1-oxo-5-(4-(3-o-tolylthioureido)phenyl)isoindolin-2-yl)butanoate;
(S)-3-Methyl-2-(1-oxo-5-(4-(3-o-tolylthioureido)phenyl)isoindolin-2-yl)butanoic acid;
(S)-Methyl 3-methyl-2-(1-oxo-5-(4-(3-p-tolylthioureido)phenyl)isoindolin-2-yl) butanoate;
(S)-3-Methyl-2-(1-oxo-5-(4-(3-p-tolylthioureido)phenyl)isoindolin-2-yl)butanoic acid;
(S)-Methyl 2-(5-(4-(3-(3-fluorophenyl)thioureido)phenyl)-1-oxoisoindolin-2-yl)-3-methylbutanoate;
(S)-2-(5-(4-(3-(3-Fluorophenyl)thioureido)phenyl)-1-oxoisoindolin-2-yl)-3-methyl butanoic acid;
(S)-Methyl 2-(5-(4-(3-(3-methoxyphenyl)thioureido)phenyl)-1-oxoisoindolin-2-yl)-3-methylbutanoate;
(S)-2-(5-(4-(3-(3-Methoxyphenyl)thioureido)phenyl)-1-oxoisoindolin-2-yl)-3-methylbutanoic acid;
(S)-Methyl 2-(5-(4-(3-(2-methoxyphenyl)thioureido)phenyl)-1-oxoisoindolin-2-yl)-3-methylbutanoate;
(S)-2-(5-(4-(3-(2-Methoxyphenyl)thioureido)phenyl)-1-oxoisoindolin-2-yl)-3-methylbutanoic acid;
(S)-Methyl 3-methyl-2-(1-oxo-5-(4-(3-(3-(trifluoromethyl)phenyl)thioureido) phenyl)isoindolin-2-yl)butanoate;
(S)-3-Methyl-2-(1-oxo-5-(4-(3-(3-(trifluoromethyl)phenyl)thioureido)phenyl)isoindolin-2-yl)butanoic acid;
(S)-Methyl 3-methyl-2-(1-oxo-6-(4-(phenylsulfonamido)phenyl)isoindolin-2-yl)butanoate;
(S)-3-Methyl-2-(1-oxo-6-(4-(phenylsulfonamido)phenyl) isoindolin-2-yl)butanoic acid;
(S)-Methyl 2-(5-(4-(4-cyanophenylsulfonamido)phenyl)-1-oxoisoindolin-2-yl)-3-methylbutanoate;
(S)-2-(5-(4-(4-Cyanophenylsulfonamido)phenyl)-1-oxoisoindolin-2-yl)-3-methyl butanoic acid;
(S)-Methyl 2-(5-(4-(3,4-difluorophenylsulfonamido)phenyl)-1-oxoisoindolin-2-yl)-3-methylbutanoate;
(S)-2-(5-(4-(3,4-Difluorophenylsulfonamido)phenyl)-1-oxoisoindolin-2-yl)-3-methylbutanoic acid;
(S)-Methyl 2-(5-(4-(2,4-difluorophenylsulfonamido)phenyl)-1-oxoisoindolin-2-yl)-3-methylbutanoate;
(S)-2-(5-(4-(2,4-Difluorophenylsulfonamido)phenyl)-1-oxoisoindolin-2-yl)-3-methylbutanoic acid;
(S)-Methyl 2-(5-(4-(3,4-dimethoxyphenylsulfonamido)phenyl)-1-oxoisoindolin-2-yl)-3-methylbutanoate;
(S)-2-(5-(4-(3,4-Dimethoxyphenylsulfonamido)phenyl)-1-oxoisoindolin-2-yl)-3-methylbutanoic acid;
(S)-Methyl 2-(5-(4-(3-chlorophenylsulfonamido)phenyl)-1-oxoisoindolin-2-yl)-3-methylbutanoate;
(S)-2-(5-(4-(3-Chlorophenylsulfonamido)phenyl)-1-oxoisoindolin-2-yl)-3-methyl butanoic acid;
(S)-Methyl 2-(5-(4-(4-methoxyphenylsulfonamido)phenyl)-1-oxoisoindolin-2-yl)-3-methylbutanoate;
(S)-2-(5-(4-(4-Methoxyphenylsulfonamido)phenyl)-1-oxoisoindolin-2-yl)-3-methylbutanoic acid;
(S)-Methyl 3-methyl-2-(1-oxo-5-(4-(4-(trifluoromethyl)phenylsulfonamido)phenyl) isoindolin-2-yl)butanoate;
(S)-3-Methyl-2-(1-oxo-5-(4-(4-(trifluoromethyl)phenylsulfonamido)phenyl)isoindolin-2-yl)butanoic acid;
(S)-Methyl 3-methyl-2-(1-oxo-5-(4-(phenylmethylsulfonamido)phenyl)isoindolin-2-yl)butanoate;
(S)-3-Methyl-2-(1-oxo-5-(4-(phenylmethylsulfonamido)phenyl)isoindolin-2-yl)butanoic acid;
(S)-Methyl 2-(5-(4-(cyclohexanesulfonamido)phenyl)-1-oxoisoindolin-2-yl)-3-methylbutanoate;
(S)-2-(5-(4-(Cyclohexanesulfonamido)phenyl)-1-oxoisoindolin-2-yl)-3-methylbutanoic acid;
(S)-Methyl 2-(5-(4-benzamidophenyl)-1-oxoisoindolin-2-yl)-3-methylbutanoate;
(S)-2-(5-(4-Benzamidophenyl)-1-oxoisoindolin-2-yl)-3-methylbutanoic acid;
(S)-Methyl 2-(5-(4-(4-fluorobenzamido)phenyl)-1-oxoisoindolin-2-yl)-3-methyl butanoate;
(S)-2-(5-(4-(4-Fluorobenzamido)phenyl)-1-oxoisoindolin-2-yl)-3-methylbutanoic acid;
(S)-Methyl 3-methyl-2-(1-oxo-5-(4-(4-(trifluoromethyl)benzamido)phenyl)isoindolin-2-yl)butanoate;
(S)-3-Methyl-2-(1-oxo-5-(4-(4-(trifluoromethyl)benzamido)phenyl)isoindolin-2-yl)butanoic acid;
(S)-Methyl 2-(5-(4-(4-methoxybenzamido)phenyl)-1-oxoisoindolin-2-yl)-3-methylbutanoate;
(S)-2-(5-(4-(4-Methoxybenzamido)phenyl)-1-oxoisoindolin-2-yl)-3-methyl butanoic acid;
(S)-Methyl 2-(5-(4-(3-fluorobenzamido)phenyl)-1-oxoisoindolin-2-yl)-3-methyl butanoate;
(S)-2-(5-(4-(3-Fluorobenzamido)phenyl)-1-oxoisoindolin-2-yl)-3-methylbutanoic acid;
(S)-Methyl 2-(5-(4-(3-chlorobenzamido)phenyl)-1-oxoisoindolin-2-yl)-3-methyl butanoate;
(S)-2-(5-(4-(3-Chlorobenzamido)phenyl)-1-oxoisoindolin-2-yl)-3-methylbutanoic acid;
(S)-Methyl 2-(5-(4-(2,4-difluorobenzamido)phenyl)-1-oxoisoindolin-2-yl)-3-methylbutanoate;
(S)-2-(5-(4-(2,4-Difluorobenzamido)phenyl)-1-oxoisoindolin-2-yl)-3-methylbutanoic acid;
(S)-Methyl 3-methyl-2-(5-(4-(4-methylbenzamido)phenyl)-1-oxoisoindolin-2-yl) butanoate;
(S)-3-Methyl-2-(5-(4-(4-methylbenzamido)phenyl)-1-oxoisoindolin-2-yl)butanoic acid;
(S)-Methyl 2-(5-(4-(4-chlorobenzamido)phenyl)-1-oxoisoindolin-2-yl)-3-methyl butanoate;
(S)-2-(5-(4-(4-Chlorobenzamido)phenyl)-1-oxoisoindolin-2-yl)-3-methylbutanoic acid;
(S)-Methyl 2-(5-(4-(4-tert-butylbenzamido)phenyl)-1-oxoisoindolin-2-yl)-3-methylbutanoate;
(S)-2-(5-(4-(4-tert-Butylbenzamido)phenyl)-1-oxoisoindolin-2-yl)-3-methyl butanoic acid;
(S)-Methyl 3-methyl-2-(1-oxo-5-(4-(4-pentylbenzamido)phenyl)isoindolin-2-yl) butanoate;
(S)-3-Methyl-2-(1-oxo-5-(4-(4-pentylbenzamido)phenyl) isoindolin-2-yl)butanoic acid;
(R)-Methyl-3-methyl-2-(1-oxo-6-(4-(3-(3-(trifluoromethyl)phenyl)ureido)phenyl) isoindolin-2-yl)butanoate;

(R)-3-Methyl-2-(1-oxo-6-(4-(3-(3-(trifluoromethyl)phenyl)ureido)phenyl)iso indolin-2-yl)butanoic acid;
Methyl 2-(1-oxo-6-(4-(3-(3-(trifluoromethyl)phenyl)ureido)phenyl)isoindolin-2-yl)acetate;
2-(1-oxo-6-(4-(3-(3-(trifluoromethyl)phenyl)ureido)phenyl)isoindolin-2-yl)acetic acid;
(S)-Methyl 2-(1-oxo-6-(4-(3-(3-(trifluoromethyl)phenyl)ureido)phenyl)isoindolin-2-yl)propanoate;
(S)-2-(1-oxo-6-(4-(3-(3-(trifluoromethyl)phenyl)ureido)phenyl)isoindolin-2-yl) propanoic acid;
Methyl 2-methyl-2-(1-oxo-6-(4-(3-(3-(trifluoromethyl)phenyl)ureido)phenyl)isoindolin-2-yl)propanoate;
2-Methyl-2-(1-oxo-6-(4-(3-(3-(trifluoromethyl)phenyl)ureido)phenyl)isoindolin-2-yl)propanoic acid;
Methyl 1-(1-oxo-6-(4-(3-(3-(trifluoromethyl)phenyl)ureido)phenyl)isoindolin-2-yl)cyclopentanecarboxylate;
1-(1-oxo-6-(4-(3-(3-(trifluoromethyl)phenyl)ureido)phenyl)isoindolin-2-yl)cyclopentanecarboxylic acid;
(S)-Methyl 2-(1-oxo-6-(4-(3-(3-(trifluoromethyl)phenyl)ureido)phenyl)isoindolin-2-yl)-2-phenylacetate;
(S)-2-(1-oxo-6-(4-(3-(3-(trifluoromethyl)phenyl)ureido)phenyl)isoindolin-2-yl)-2-phenylacetic acid;
Methyl 4-(1-oxo-6-(4-(3-(3-(trifluoromethyl)phenyl)ureido)phenyl)isoindolin-2-yl) butanoate;
4-(1-oxo-6-(4-(3-(3-(trifluoromethyl)phenyl)ureido)phenyl)isoindolin-2-yl)butanoic acid;
(S)-Methyl 4-methyl-2-(1-oxo-6-(4-(3-(3-(trifluoromethyl)phenyl)ureido)phenyl) isoindolin-2-yl)pentanoate;
(S)-4-Methyl-2-(1-oxo-6-(4-(3-(3-(trifluoromethyl)phenyl)ureido)phenyl)iso indolin-2-yl)pentanoic acid;
(S)-Methyl 3-methoxy-2-(1-oxo-6-(4-(3-(3-(trifluoromethyl)phenyl)ureido) phenyl)isoindolin-2-yl)propanoate;
(S)-3-Methoxy-2-(1-oxo-6-(4-(3-(3-(trifluoromethyl)phenyl)ureido)phenyl)iso indolin-2-yl)propanoic acid;
(R)-Methyl 3-methyl-2-(1-oxo-5-(4-(3-(3-(trifluoromethyl)phenyl)ureido)phenyl) isoindolin-2-yl)butanoate;
(R)-3-Methyl-2-(1-oxo-5-(4-(3-(3-(trifluoromethyl)phenyl)ureido)phenyl)isoindolin-2-yl)butanoic acid;
Methyl 2-(1-oxo-5-(4-(3-(3-(trifluoromethyl)phenyl)ureido)phenyl)isoindolin-2-yl)acetate;
2-(1-oxo-5-(4-(3-(3-(trifluoromethyl)phenyl)ureido)phenyl)isoindolin-2-yl)acetic acid;
(S)-Methyl 2-(1-oxo-5-(4-(3-(3-(trifluoromethyl)phenyl)ureido)phenyl)isoindolin-2-yl)propanoate;
(S)-2-(1-oxo-5-(4-(3-(3-(trifluoromethyl)phenyl)ureido)phenyl)isoindolin-2-yl) propanoic acid;
Methyl 1-(1-oxo-5-(4-(3-(3-(trifluoromethyl)phenyl)ureido)phenyl)isoindolin-2-yl)cyclopentanecarboxylate;
1-(1-oxo-5-(4-(3-(3-(trifluoromethyl)phenyl)ureido)phenyl)isoindolin-2-yl)cyclopentanecarboxylic acid;
(S)-Methyl 2-(1-oxo-5-(4-(3-(3-(trifluoromethyl)phenyl)ureido)phenyl)isoindolin-2-yl)-2-phenylacetate;
(S)-2-(1-oxo-5-(4-(3-(3-(trifluoromethyl)phenyl)ureido)phenyl)isoindolin-2-yl)-2-phenylacetic acid;
Methyl 4-(1-oxo-5-(4-(3-(3-(trifluoromethyl)phenyl)ureido)phenyl)isoindolin-2-yl) butanoate;
4-(1-oxo-5-(4-(3-(3-(trifluoromethyl)phenyl)ureido)phenyl)isoindolin-2-yl)butanoic acid;
Ethyl 3-(1-oxo-5-(4-(3-(3-(trifluoromethyl)phenyl)ureido)phenyl)isoindolin-2-yl) propanoate;
3-(1-oxo-5-(4-(3-(3-(trifluoromethyl)phenyl)ureido)phenyl)isoindolin-2-yl)propanoic acid;
(S)-Methyl 2-(1-oxo-5-(4-(3-(3-(trifluoromethyl)phenyl)ureido)phenyl)isoindolin-2-yl)-3-phenylpropanoate;
(S)-2-(1-oxo-5-(4-(3-(3-(trifluoromethyl)phenyl)ureido)phenyl)isoindolin-2-yl)-3-phenylpropanoic acid;
(S)-Methyl 3-methoxy-2-(1-oxo-5-(4-(3-(3-(trifluoromethyl)phenyl)ureido)phenyl) isoindolin-2-yl)propanoate;
(S)-3-Methoxy-2-(1-oxo-5-(4-(3-(3-(trifluoromethyl) phenyl)ureido)phenyl)isoindolin-2-yl)propanoic acid;
(S)-Methyl 4-methyl-2-(1-oxo-5-(4-(3-(3-(trifluoromethyl)phenyl)ureido)phenyl) isoindolin-2-yl)pentanoate;
(S)-4-Methyl-2-(1-oxo-5-(4-(3-(3-(trifluoromethyl)phenyl)ureido)phenyl)iso indolin-2-yl)pentanoic acid;
(S)-Methyl 2-(6-(5-(3-(2-chlorophenyl)ureido)pyridin-2-yl)-1-oxoisoindolin-2-yl)-3-methylbutanoate;
(S)-2-(6-(5-(3-(2-Chlorophenyl)ureido)pyridin-2-yl)-1-oxoisoindolin-2-yl)-3-methylbutanoic acid;
(S)-Methyl 2-(6-(5-(3-(4-chloro-2-phenoxyphenyl)ureido)pyridin-2-yl)-1-oxoisoindolin-2-yl)-3-methylbutanoate;
(S)-2-(6-(5-(3-(4-Chloro-2-phenoxyphenyl)ureido)pyridin-2-yl)-1-oxoisoindolin-2-yl)-3-methylbutanoic acid;
(S)-Methyl 2-(6-(5-(3-(3,4-dimethylphenyl)ureido)pyridin-2-yl)-1-oxoisoindolin-2-yl)-3-methylbutanoate;
(S)-2-(6-(5-(3-(3,4-Dimethylphenyl)ureido)pyridin-2-yl)-1-oxoisoindolin-2-yl)-3-methylbutanoic acid;
(S)-Methyl 2-(6-(5-(3-(3,4-difluorophenyl)ureido)pyridin-2-yl)-1-oxoisoindolin-2-yl)-3-methylbutanoate;
(S)-2-(6-(5-(3-(3,4-Difluorophenyl)ureido)pyridin-2-yl)-1-oxoisoindolin-2-yl)-3-methylbutanoic acid;
(S)-Methyl 2-(6-(5-(3-(2,3-dihydro-1H-inden-5-yl)ureido)pyridin-2-yl)-1-oxoisoindolin-2-yl)-3-methylbutanoate;
(S)-2-(6-(5-(3-(2,3-Dihydro-1H-inden-5-yl)ureido)pyridin-2-yl)-1-oxoisoindolin-2-yl)-3-methylbutanoic acid;
(S)-Methyl 2-(6-(5-(4-tert-butylbenzamido)pyridin-2-yl)-1-oxoisoindolin-2-yl)-3-methylbutanoate;
(S)-2-(6-(5-(4-tert-Butylbenzamido)pyridin-2-yl)-1-oxoisoindolin-2-yl)-3-methyl butanoic acid;
(S)-Methyl 3-methyl-2-(1-oxo-6-(5-(4-pentylbenzamido)pyridin-2-yl)isoindolin-2-yl)butanoate;
(S)-3-Methyl-2-(1-oxo-6-(5-(4-pentylbenzamido)pyridin-2-yl)isoindolin-2-yl)butanoic acid;
(S)-Methyl 2-(6-(5-biphenyl-4-ylcarboxamidopyridin-2-yl)-1-oxoisoindolin-2-yl)-3-methylbutanoate;
(S)-2-(6-(5-Biphenyl-4-ylcarboxamidopyridin-2-yl)-1-oxoisoindolin-2-yl)-3-methylbutanoic acid;
(S)-Methyl 2-(6-(5-(2-naphthamido)pyridin-2-yl)-1-oxoisoindolin-2-yl)-3-methyl butanoate;
(S)-2-(6-(5-(2-Naphthamido)pyridin-2-yl)-1-oxoisoindolin-2-yl)-3-methylbutanoic acid;
(S)-Methyl 2-(6-(5-(4-butoxybenzamido)pyridin-2-yl)-1-oxoisoindolin-2-yl)-3-methylbutanoate;
(S)-2-(6-(5-(4-Butoxybenzamido)pyridin-2-yl)-1-oxoisoindolin-2-yl)-3-methylbutanoic acid;
(S)-Methyl 2-(6-(4-(3-(2-chlorophenyl)ureido)-2-(trifluoromethyl)phenyl)-1-oxoisoindolin-2-yl)-3-methylbutanoate;
(S)-2-(6-(4-(3-(2-Chlorophenyl)ureido)-2-(trifluoromethyl)phenyl)-1-oxoisoindolin-2-yl)-3-methylbutanoic acid;
(S)-Methyl 2-(6-(4-(3-(3,4-difluorophenyl)ureido)-2-(trifluoromethyl)phenyl)-1-oxoisoindolin-2-yl)-3-methylbutanoate;
(S)-2-(6-(4-(3-(3,4-Difluorophenyl)ureido)-2-(trifluoromethyl)phenyl)-1-oxoisoindolin-2-yl)-3-methylbutanoic acid;

(S)-Methyl 2-(6-(4-(3-(2,3-dihydro-1H-inden-5-yl)ureido)-2-(trifluoromethyl)phenyl)-1-oxoisoindolin-2-yl)-3-methylbutanoate,
(S)-2-(6-(4-(3-(2,3-Dihydro-1H-inden-5-yl)ureido)-2-(trifluoromethyl)phenyl)-1-oxoisoindolin-2-yl)-3-methylbutanoic acid;
(S)-Methyl 2-(6-(4-(3-(3,4-dimethylphenyl)ureido)-2-(trifluoromethyl)phenyl)-1-oxoisoindolin-2-yl)-3-methylbutanoate;
(S)-2-(6-(4-(3-(3,4-Dimethylphenyl)ureido)-2-(trifluoromethyl)phenyl)-1-oxoiso indolin-2-yl)-3-methylbutanoic acid;
(S)-Methyl 2-(6-(4-(4-tert-butylbenzamido)-2-(trifluoromethyl)phenyl)-1-oxoiso indolin-2-yl)-3-methylbutanoate;
(S)-2-(6-(4-(4-tert-Butylbenzamido)-2-(trifluoromethyl)phenyl)-1-oxoisoindolin-2-yl)-3-methylbutanoic acid;
(S)-Methyl 2-(6-(4-(4-biphenyl-4-ylcarboxamido-2-(trifluoromethyl)phenyl)-1-oxoisoindolin-2-yl)-3-methylbutanoate;
(S)-2-(6-(4-(4-Biphenyl-4-ylcarboxamido-2-(trifluoromethyl)phenyl)-1-oxoisoindolin-2-yl)-3-methylbutanoic acid;
(S)-Methyl 2-(6-(4-(2-naphthamido)-2-(trifluoromethyl)phenyl)-1-oxoisoindolin-2-yl)-3-methylbutanoate;
(S)-2-(6-(4-(2-Naphthamido)-2-(trifluoromethyl)phenyl)-1-oxoisoindolin-2-yl)-3-methylbutanoic acid;
(S)-Methyl 3-methyl-2-(1-oxo-6-(4-(4-pentylbenzamido)-2-(trifluoromethyl)phenyl)isoindolin-2-yl)butanoate;
(S)-3-Methyl-2-(1-oxo-6-(4-(4-pentylbenzamido)-2-(trifluoromethyl)phenyl) isoindolin-2-yl)butanoic acid;
(S)-Methyl 2-(6-(4-(4-butoxybenzamido)-2-(trifluoromethyl)phenyl)-1-oxoisoindolin-2-yl)-3-methylbutanoate;
(S)-2-(6-(4-(4-Butoxybenzamido)-2-(trifluoromethyl)phenyl)-1-oxoisoindolin-2-yl)-3-methylbutanoic acid;
(S)-Methyl 2-(6-(4-(3-(3,4-dimethylphenyl)ureido)-3-fluorophenyl)-1-oxoisoindolin-2-yl)-3-methylbutanoate;
(S)-2-(6-(4-(3-(3,4-Dimethylphenyl)ureido)-3-fluorophenyl)-1-oxoisoindolin-2-yl)-3-methylbutanoic acid;
(S)-Methyl 2-(6-(4-(3-(2,3-dihydro-1H-inden-5-yl)ureido)-3-fluorophenyl)-1-oxoisoindolin-2-yl)-3-methylbutanoate;
(S)-2-(6-(4-(3-(2,3-Dihydro-1H-inden-5-yl)ureido)-3-fluorophenyl)-1-oxoisoindolin-2-yl)-3-methylbutanoic acid;
(S)-Methyl 2-(6-(4-(3-(3,4-difluorophenyl)ureido)-3-fluorophenyl)-1-oxoisoindolin-2-yl)-3-methylbutanoate;
(S)-2-(6-(4-(3-(3,4-Difluorophenyl)ureido)-3-fluorophenyl)-1-oxoisoindolin-2-yl)-3-methylbutanoic acid;
(S)-Methyl 2-(6-(4-(3-(2-chlorophenyl)ureido)-3-fluorophenyl)-1-oxoisoindolin-2-yl)-3-methylbutanoate;
(S)-2-(6-(4-(3-(2-Chlorophenyl)ureido)-3-fluorophenyl)-1-oxoisoindolin-2-yl)-3-methylbutanoic acid;
(S)-Methyl 2-(6-(4-(4-tert-butylbenzamido)-3-fluorophenyl)-1-oxoisoindolin-2-yl)-3-methylbutanoate;
(S)-2-(6-(4-(4-tert-Butylbenzamido)-3-fluorophenyl)-1-oxoisoindolin-2-yl)-3-methylbutanoic acid;
(S)-Methyl 2-(6-(3-fluoro-4-(4-pentylbenzamido)phenyl)-1-oxoisoindolin-2-yl)-3-methylbutanoate;
(S)-2-(6-(3-Fluoro-4-(4-pentylbenzamido)phenyl)-1-oxoisoindolin-2-yl)-3-methylbutanoic acid;
(S)-Methyl 2-(6-(4-biphenyl-4-ylcarboxamido-3-fluorophenyl)-1-oxoisoindolin-2-yl)-3-methylbutanoate;
(S)-2-(6-(4-Biphenyl-4-ylcarboxamido-3-fluorophenyl)-1-oxoisoindolin-2-yl)-3-methylbutanoic acid;
(S)-Methyl 2-(6-(4-(2-naphthamido)-3-fluorophenyl)-1-oxoisoindolin-2-yl)-3-methylbutanoate;
(S)-2-(6-(4-(2-Naphthamido)-3-fluorophenyl)-1-oxoisoindolin-2-yl)-3-methyl butanoic acid;
(S)-Methyl 2-(6-(4-(4-butoxybenzamido)-3-fluorophenyl)-1-oxoisoindolin-2-yl)-3-methylbutanoate;
(S)-2-(6-(4-(4-Butoxybenzamido)-3-fluorophenyl)-1-oxoisoindolin-2-yl)-3-methyl butanoic acid;
(S)-Methyl 2-(6-(4-(4-tert-butylbenzamido)-2-methoxyphenyl)-1-oxoisoindolin-2-yl)-3-methylbutanoate;
(S)-2-(6-(4-(4-tert-Butylbenzamido)-2-methoxyphenyl)-1-oxoisoindolin-2-yl)-3-methylbutanoic acid;
(S)-Methyl 2-(6-(4-biphenyl-4-ylcarboxamido-2-methoxyphenyl)-1-oxoisoindolin-2-yl)-3-methylbutanoate;
(S)-2-(6-(4-Biphenyl-4-ylcarboxamido-2-methoxyphenyl)-1-oxoisoindolin-2-yl)-3-methylbutanoic acid;
(S)-Methyl 2-(6-(4-(4-butoxybenzamido)-2-methoxyphenyl)-1-oxoisoindolin-2-yl)-3-methylbutanoate;
(S)-2-(6-(4-(4-Butoxybenzamido)-2-methoxyphenyl)-1-oxoisoindolin-2-yl)-3-methylbutanoic acid;
(S)-Methyl 2-(6-(2-methoxy-4-(4-pentylbenzamido)phenyl)-1-oxoisoindolin-2-yl)-3-methylbutanoate;
(S)-2-(6-(2-Methoxy-4-(4-pentylbenzamido)phenyl)-1-oxoisoindolin-2-yl)-3-methylbutanoic acid;
(S)-Methyl 2-(6-(2-methoxy-4-(4-(trifluoromethoxy)benzamido)phenyl)-1-oxo isoindolin-2-Y)-3-methylbutanoate;
(S)-2-(6-(2-Methoxy-4-(4-(trifluoromethoxy)benzamido)phenyl)-1-oxoisoindolin-2-yl)-3-methylbutanoic acid;
(S)-Methyl 2-(6-(4-(4-tert-butylbenzamido)-2-methylphenyl)-1-oxoisoindolin-2-yl)-3-methylbutanoate;
(S)-2-(6-(4-(4-tert-Butylbenzamido)-2-methylphenyl)-1-oxoisoindolin-2-yl)-3-methylbutanoic acid;
(S)-Methyl 2-(6-(4-biphenyl-4-ylcarboxamido-2-methylphenyl)-1-oxoisoindolin-2-yl)-3-methylbutanoate;
(S)-2-(6-(4-Biphenyl-4-ylcarboxamido-2-methylphenyl)-1-oxoisoindolin-2-yl)-3-methylbutanoic acid;
(S)-Methyl 2-(6-(4-(4-butoxybenzamido)-2-methylphenyl)-1-oxoisoindolin-2-yl)-3-methylbutanoate;
(S)-2-(6-(4-(4-Butoxybenzamido)-2-methylphenyl)-1-oxoisoindolin-2-yl)-3-methylbutanoic acid;
(S)-Methyl 3-methyl-2-(6-(2-methyl-4-(4-pentylbenzamido)phenyl)-1-oxoisoindolin-2-yl)butanoate;
(S)-3-Methyl-2-(6-(2-methyl-4-(4-pentylbenzamido)phenyl)-1-oxoisoindolin-2-yl)butanoic acid;
(S)-Methyl 3-methyl-2-(6-(2-methyl-4-(4-(trifluoromethoxy)benzamido)phenyl)-1-oxoisoindolin-2-yl)butanoate;
(S)-3-Methyl-2-(6-(2-methyl-4-(4-(trifluoromethoxy)benzamido)phenyl)-1-oxoisoindolin-2-yl)butanoic acid;
(S)-Methyl 2-(6-(4-(4-tert-butylbenzamido)-2-chlorophenyl)-1-oxoisoindolin-2-yl)-3-methylbutanoate;
(S)-2-(6-(4-(4-tert-Butylbenzamido)-2-chlorophenyl)-1-oxoisoindolin-2-yl)-3-methylbutanoic acid;
(S)-Methyl 2-(6-(4-biphenyl-4-ylcarboxamido-2-chlorophenyl)-1-oxoisoindolin-2-yl)-3-methylbutanoate;
(S)-2-(6-(4-Biphenyl-4-ylcarboxamido-2-chlorophenyl)-1-oxoisoindolin-2-yl)-3-methylbutanoic acid;
(S)-Methyl 2-(6-(4-(4-butoxybenzamido)-2-chlorophenyl)-1-oxoisoindolin-2-yl)-3-methylbutanoate;
(S)-2-(6-(4-(4-Butoxybenzamido)-2-chlorophenyl)-1-oxoisoindolin-2-yl)-3-methylbutanoic acid;
(S)-Methyl 2-(6-(2-chloro-4-(4-pentylbenzamido)phenyl)-1-oxoisoindolin-2-yl)-3-methylbutanoate;

(S)-2-(6-(2-Chloro-4-(4-pentylbenzamido)phenyl)-1-oxoisoindolin-2-yl)-3-methylbutanoic acid;
(S)-Methyl 2-(6-(2-chloro-4-(4-(trifluoromethoxy)benzamido)phenyl)-1-oxo isoindolin-2-yl)-3-methylbutanoate;
(S)-2-(6-(2-Chloro-4-(4-(trifluoromethoxy)benzamido)phenyl)-1-oxoisoindolin-2-Vl\-3-methylbutanoic acid;
(S)-Methyl 2-(6-(6-(4-tert-butylbenzamido)pyridin-3-yl)-1-oxoisoindolin-2-yl)-3-methylbutanoate;
(S)-2-(6-(6-(4-tert-Butylbenzamido)pyridin-3-yl)-1-oxoisoindolin-2-yl)-3-methylbutanoic acid;
(S)-Methyl 2-(6-(6-biphenyl-4-ylcarboxamidopyridin-3-yl)-1-oxoisoindolin-2-yl)-3-methylbutanoate;
(S)-Methyl 3-methyl-2-(1-oxo-6-(6-(4-pentylbenzamido)pyridin-3-yl)iso indolin-2-yl)butanoate;
(S)-Methyl 3-methyl-2-(1-oxo-6-(6-(4-(trifluoromethoxy)benzamido)pyridin-3-yl)isoindolin-2-yl)butanoate;
(S)-Methyl 2-(6-(6-(4-tert-butylbenzamido)pyridazin-3-yl)-1-oxoisoindolin-2-yl)-3-methylbutanoate;
(S)-2-(6-(6-(4-tert-Butylbenzamido)pyridazin-3-yl)-1-oxoisoindolin-2-yl)-3-methylbutanoic acid;
(S)-Methyl 3-methyl-2-(1-oxo-6-(6-(4-pentylbenzamido)pyridazin-3-yl)iso indolin-2-yl)butanoate;
(S)-3-Methyl-2-(1-oxo-6-(6-(4-pentylbenzamido)pyridazin-3-yl)isoindolin-2-yl)butanoic acid;
(S)-Methyl 3-methyl-2-(1-oxo-6-(6-(4-(trifluoromethoxy)benzamido)pyridazin-3-yl) isoindolin-2-yl)butanoate;
(S)-3-Methyl-2-(1-oxo-6-(6-(4-(trifluoromethoxy)benzamido)pyridazin-3-yl)isoindolin-2-yl)butanoic acid;
(S)-Methyl 2-(6-(5-(4-tert-butylbenzamido)pyrazin-2-yl)-1-oxoisoindolin-2-yl)-3-methylbutanoate;
(S)-2-(6-(5-(4-tert-Butylbenzamido)pyrazin-2-yl)-1-oxoisoindolin-2-yl)-3-methylbutanoic acid;
(S)-Methyl 2-(6-(5-biphenyl-4-ylcarboxamidopyrazin-2-yl)-1-oxoisoindolin-2-yl)-3-methylbutanoate;
(S)-2-(6-(5-Biphenyl-4-ylcarboxamidopyrazin-2-yl)-1-oxoisoindolin-2-yl)-3-methylbutanoic acid;
(S)-Methyl 2-(6-(5-(4-butoxybenzamido)pyrazin-2-yl)-1-oxoisoindolin-2-yl)-3-methylbutanoate;
(S)-2-(6-(5-(4-Butoxybenzamido)pyrazin-2-yl)-1-oxoisoindolin-2-yl)-3-methylbutanoic acid;
(S)-Methyl 3-methyl-2-(1-oxo-6-(5-(4-pentylbenzamido)pyrazin-2-yl)isoindolin-2-yl)butanoate;
(S)-3-Methyl-2-(1-oxo-6-(5-(4-pentylbenzamido)pyrazin-2-yl)isoindolin-2-yl)butanoic acid;
(S)-Methyl 3-methyl-2-(1-oxo-6-(5-(4-(trifluoromethoxy)benzamido)pyrazin-2-yl)isoindolin-2-yl)butanoate,
(S)-3-Methyl-2-(1-oxo-6-(5-(4-(trifluoromethoxy)benzamido)pyrazin-2-yl)isoindolin-2-yl)butanoic acid;
Methyl 2-(6-(4-([1,1'-biphenyl]-4-ylcarboxamido)phenyl)-1-oxoisoindolin-2-yl)-2-methylpropanoate;
2-(6-(4-([1,1-Biphenyl]-4-ylcarboxamido)phenyl)-1-oxoisoindolin-2-yl)-2-methyl propanoic acid;
Methyl 2-(6-(4-(4-(tert-butyl)benzamido)phenyl)-1-oxoisoindolin-2-yl)-2-methyl propanoate;
2-(6-(4-(4-(tert-Butyl)benzamido)phenyl)-1-oxoisoindolin-2-yl)-2-methylpropanoic acid;
Methyl 2-(6-(4-(4-chlorobenzamido)phenyl)-1-oxoisoindolin-2-yl)-2-methyl propanoate;
2-(6-(4-(4-Chlorobenzamido)phenyl)-1-oxoisoindolin-2-yl)-2-methylpropanoic acid;
Methyl 2-methyl-2-(1-oxo-6-(4-(4-(trifluoromethoxy)benzamido)phenyl)iso indolin-2-yl)propanoate
2-Methyl-2-(1-oxo-6-(4-(4-(trifluoromethoxy)benzamido)phenyl)isoindolin-2-yl)propanoic acid;
Methyl 2-methyl-2-(1-oxo-6-(4-(4-pentylbenzamido)phenyl)isoindolin-2-yl) propanoate;
2-Methyl-2-(1-oxo-6-(4-(4-pentylbenzamido)phenyl)isoindolin-2-yl)propanoic acid;
Methyl 1-(6-(4-([1,1'-biphenyl]-4-ylcarboxamido)phenyl)-1-oxoisoindolin-2-yl)cyclopentanecarboxylate;
1-(6-(4-([1,1-Biphenyl]-4-ylcarboxamido)phenyl)-1-oxoisoindolin-2-yl)cyclopentane carboxylic acid;
Methyl 1-(6-(4-(4-(tert-butyl)benzamido)phenyl)-1-oxoisoindolin-2-yl)cyclopentanecarboxylate;
1-(6-(4-(4-(tert-Butyl)benzamido)phenyl)-1-oxoisoindolin-2-yl)cyclopentane carboxylic acid;
Methyl 1-(6-(4-(4-chlorobenzamido)phenyl)-1-oxoisoindolin-2-yl)cyclopentane carboxylate;
1-(6-(4-(4-Chlorobenzamido)phenyl)-1-oxoisoindolin-2-yl)cyclopentane carboxylic acid;
Methyl 1-(1-oxo-6-(4-(4-(trifluoromethoxy)benzamido)phenyl)isoindolin-2-yl)cyclopentanecarboxylate;
1-(1-oxo-6-(4-(4-(trifluoromethoxy)benzamido)phenyl) isoindolin-2-yl)cyclopentane carboxylic acid;
Methyl 1-(1-oxo-6-(4-(4-pentylbenzamido)phenyl)isoindolin-2-yl)cyclopentane carboxylate;
1-(1-oxo-6-(4-(4-pentylbenzamido)phenyl)isoindolin-2-yl)cyclopentane carboxylic acid;
(R)-Methyl 2-(6-(4-([1,1'-biphenyl]-4-ylcarboxamido)phenyl)-1-oxoisoindolin-2-yl)-3-methylbutanoate;
(R)-2-(6-(4-([1,1'-Biphenyl]-4-ylcarboxamido)phenyl)-1-oxoisoindolin-2-yl)-3-methylbutanoic acid;
Methyl 3-(6-(4-([1,1'-biphenyl]-4-ylcarboxamido)phenyl)-1-oxoisoindolin-2-yl)cyclohexanecarboxylate;
3-(6-(4-([1,1'-Biphenyl]-4-ylcarboxamido)phenyl)-1-oxoisoindolin-2-yl)cyclo hexane carboxylic acid;
Methyl 3-(6-(4-(3-chlorobenzamido)phenyl)-1-oxoisoindolin-2-yl)cyclohexane carboxylate;
3-(6-(4-(3-Chlorobenzamido)phenyl)-1-oxoisoindolin-2-yl)cyclohexane carboxylic acid;
Methyl 3-(6-(4-(4-chlorobenzamido)phenyl)-1-oxoisoindolin-2-yl)cyclohexane carboxylate;
3-(6-(4-(4-Chlorobenzamido)phenyl)-1-oxoisoindolin-2-yl)cyclohexane carboxylic acid;
Methyl 3-(1-oxo-6-(4-(4-(trifluoromethyl)benzamido)phenyl)isoindolin-2-yl)cyclohexanecarboxylate;
3-(1-oxo-6-(4-(4-(trifluoromethyl)benzamido)phenyl) isoindolin-2-yl)cyclohexanecarboxylic acid;
Methyl 3-(6-(4-(5-methyl-2-phenyloxazole-4-carboxamido)phenyl)-1-oxo isoindolin-2-yl)cyclohexanecarboxylate;
3-(6-(4-(5-Methyl-2-phenyloxazole-4-carboxamido)phenyl)-1-oxoisoindolin-2-yl)cyclohexanecarboxylic acid;
(1r,4r)-Methyl 4-(6-(4-([1,1'-biphenyl]-4-ylcarboxamido)phenyl)-1-oxoisoindolin-2-yl)cyclohexanecarboxylate,
(1r,4)-4-(6-(4-([1,1'-Biphenyl]-4-ylcarboxamido)phenyl)-1-oxoisoindolin-2-yl)cyclohexanecarboxylic acid;
(1r,4r)-Methyl 4-(6-(4-(3-chlorobenzamido)phenyl)-1-oxoisoindolin-2-yl)cyclo hexanecarboxylate;
(1r,4r)-4-(6-(4-(3-Chlorobenzamido)phenyl)-1-oxoisoindolin-2-yl)cyclohexane carboxylic acid;
(1r,4r)-Methyl 4-(6-(4-(4-chlorobenzamido)phenyl)-1-oxoisoindolin-2-yl)cyclohexanecarboxylate;
(1r,4r)-4-(6-(4-(4-Chlorobenzamido)phenyl)-1-oxoisoindolin-2-yl)cyclohexane carboxylic acid;
(1r,4r)-Methyl 4-(1-oxo-6-(4-(4-(trifluoromethyl)benzamido)phenyl)isoindolin-2-yl)cyclohexanecarboxylate;
(1r,4r)-4-(1-oxo-6-(4-(4-(trifluoromethyl)benzamido)phenyl)isoindolin-2-yl)cyclohexanecarboxylic acid;

(1r,3s,5R,7S)-Methyl 3-(6-(4-(3-chlorobenzamido)phenyl)-1-oxoisoindolin-2-yl)adamantane-1-carboxylate;
(1r,3s,5R,7S)-3-(6-(4-(3-Chlorobenzamido)phenyl)-1-oxoisoindolin-2-yl) adamantane-1-carboxylic acid;
(1r,3s,5R,7S)-Methyl 3-(6-(4-(4-chlorobenzamido)phenyl)-1-oxoisoindolin-2-yl)adamantane-1-carboxylate;
(1r,3s,5R,7S)-3-(6-(4-(4-Chlorobenzamido)phenyl)-1-oxoisoindolin-2-yl) adamantane-1-carboxylic acid;
(1r,3s,5R,7S)-Methyl 3-(1-oxo-6-(4-(4-(trifluoromethyl)benzamido)phenyl)isoindolin-2-yl)adamantane-1-carboxylate,
(1r,3s,5R,7S)-3-(1-oxo-6-(4-(4-(trifluoromethyl)benzamido)phenyl)isoindolin-2-yl)adamantane-1-carboxylic acid;
(1r,3s,5R,7S)-3-(6-(4-(4-Methylbenzamido)phenyl)-1-oxoisoindolin-2-yl) adamantane-1-carboxylic acid;
Methyl 1-(6-(4-([1,1'-biphenyl]-4-ylcarboxamido)phenyl)-1-oxoisoindolin-2-yl)cyclobutanecarboxylate;
1-(6-(4-([1,1'-Biphenyl]-4-ylcarboxamido)phenyl)-1-oxoisoindolin-2-yl)cyclo butanecarboxylic acid;
Methyl 1-(6-(4-(4-chlorobenzamido)phenyl)-1-oxoisoindolin-2-yl)cyclobutane carboxylate;
1-(6-(4-(4-Chlorobenzamido)phenyl)-1-oxoisoindolin-2-yl)cyclobutane carboxylic acid;
Methyl 1-(1-oxo-6-(4-(4-(trifluoromethyl)benzamido)phenyl)isoindolin-2-yl)cyclobutanecarboxylate;
1-(1-oxo-6-(4-(4-(trifluoromethyl)benzamido)phenyl)isoindolin-2-yl)cyclo butanecarboxylic acid;
Methyl 1-(6-(4-(4-methylbenzamido)phenyl)-1-oxoisoindolin-2-yl)cyclobutane carboxylate;
1-(6-(4-(4-Methylbenzamido)phenyl)-1-oxoisoindolin-2-yl)cyclobutane carboxylic acid;
Methyl 1-(6-(4-biphenyl-4-ylcarboxamidophenyl)-1-oxoisoindolin-2-yl)cyclo propanecarboxylate;
1-(6-(4-([1,1'-Biphenyl]-4-ylcarboxamido)phenyl)-1-oxoisoindolin-2-yl)cyclopropanecarboxylic acid;
Methyl 1-(6-(4-(4-chlorobenzamido)phenyl)-1-oxoisoindolin-2-yl)cyclopropane carboxylate;
1-(6-(4-(4-Chlorobenzamido)phenyl)-1-oxoisoindolin-2-yl)cyclopropane carboxylic acid;
Methyl 1-(1-oxo-6-(4-(4-(trifluoromethyl)benzamido)phenyl)isoindolin-2-yl)cyclopropane carboxylate;
1-(1-oxo-6-(4-(4-(trifluoromethyl)benzamido)phenyl)isoindolin-2-yl)cyclopropane carboxylic acid;
(1S,2R)-Methyl 2-(6-(4-([1,1'-biphenyl]-4-ylcarboxamido)phenyl)-1-oxo isoindolin-2-yl)cyclopentanecarboxylate;
(1S,2R)-2-(6-(4-([1,1'-Biphenyl]-4-ylcarboxamido)phenyl)-1-oxoisoindolin-2-cyclopentanecarboxylic acid;
(1S,2R)-Methyl 2-(6-(4-(4-chlorobenzamido)phenyl)-1-oxoisoindolin-2-yl)cyclopentanecarboxylate;
(1S,2R)-2-(6-(4-(4-Chlorobenzamido)phenyl)-1-oxoisoindolin-2-yl)cyclopentane carboxylic acid;
(1S,2R)-Methyl 2-(1-oxo-6-(4-(4-(trifluoromethyl)benzamido)phenyl)isoindolin-2-yl)cyclopentanecarboxylate;
(1S,2R)-2-(1-oxo-6-(4-(4-(trifluoromethyl)benzamido)phenyl)isoindolin-2-yl)cyclopentane carboxylic acid,
(S)-Methyl 2-(6-(4-([1,1'-biphenyl]-4-ylcarboxamido)-2-fluorophenyl)-1-oxo isoindolin-2-yl)-3-methylbutanoate;
(S)-2-(6-(4-([1,1'-Biphenyl]-4-ylcarboxamido)-2-fluorophenyl)-1-oxoisoindolin-2-yl)-3-methylbutanoic acid;
(S)-Methyl 2-(6-(4-(4-(tert-butyl)benzamido)-2-fluorophenyl)-1-oxoisoindolin-2-yl)-3-methylbutanoate;
(S)-2-(6-(4-(4-(tert-Butyl)benzamido)-2-fluorophenyl)-1-oxoisoindolin-2-yl)-3-methylbutanoic acid;
(S)-Methyl 2-(6-(4-(4-chlorobenzamido)-2-fluorophenyl)-1-oxoisoindolin-2-yl)-3-methylbutanoate;
(S)-2-(6-(4-(4-Chlorobenzamido)-2-fluorophenyl)-1-oxoisoindolin-2-yl)-3-methyl butanoic acid;
(S)-Methyl 2-(6-(2-fluoro-4-(4-(trifluoromethoxy)benzamido)phenyl)-1-oxo isoindolin-2-yl)-3-methylbutanoate;
(S)-2-(6-(2-Fluoro-4-(4-(trifluoromethoxy)benzamido)phenyl)-1-oxoisoindolin-2-yl)-3-methylbutanoic acid;
(S)-Methyl 2-(6-(2-fluoro-4-(4-pentylbenzamido)phenyl)-1-oxoisoindolin-2-yl)-3-methylbutanoate;
(S)-2-(6-(2-Fluoro-4-(4-pentylbenzamido)phenyl)-1-oxoisoindolin-2-yl)-3-methyl butanoic acid;
(S)-Methyl 3-methyl-2-(1-oxo-6-(4-(5-phenylthiazole-2-carboxamido)phenyl) isoindolin-2-yl)butanoate;
(S)-3-Methyl-2-(1-oxo-6-(4-(5-phenylthiazole-2-carboxamido)phenyl)isoindolin-2-yl)butanoic acid;
(S)-Methyl 3-methyl-2-(1-oxo-6-(4-(5-phenyloxazole-2-carboxamido)phenyl) isoindolin-2-yl)butanoate;
(S)-3-Methyl-2-(1-oxo-6-(4-(5-phenyloxazole-2-carboxamido)phenyl)isoindolin-2-yl)butanoic acid;
(S)-Methyl 2-(6-(4-(3-(4-fluorophenyl)isoxazole-5-carboxamido)phenyl)-1-oxoisoindolin-2-yl)-3-methylbutanoate;
(S)-2-(6-(4-(3-(4-Fluorophenyl)isoxazole-5-carboxamido)phenyl)-1-oxo isoindolin-2-yl)-3-methylbutanoic acid;
(S)-Methyl 2-(6-(4-(3-(4-chlorophenyl)isoxazole-5-carboxamido)phenyl)-1-oxoisoindolin-2-yl)-3-methylbutanoate;
(S)-2-(6-(4-(3-(4-Chlorophenyl)isoxazole-5-carboxamido)phenyl)-1-oxo isoindolin-2-yl)-3-methylbutanoic acid;
(S)-Methyl 3-methyl-2-(1-oxo-6-(4-(3-(4-(trifluoromethyl)phenyl)isoxazole-5-carboxamido)phenyl)isoindolin-2-yl)butanoate,
(S)-3-Methyl-2-(1-oxo-6-(4-(3-(4-(trifluoromethyl)phenyl)isoxazole-5-carboxamido)phenyl)isoindolin-2-yl)butanoic acid;
(S)-Methyl 3-methyl-2-(6-(4-(4-(oxazol-5-yl)benzamido)phenyl)-1-oxoisoindolin-2-yl)butanoate;
(S)-3-Methyl-2-(6-(4-(4-(oxazol-5-yl)benzamido)phenyl)-1-oxoisoindolin-2-yl)butanoic acid;
(S)-Methyl 3-methyl-2-(1-oxo-6-(4-(4-phenylthiazole-2-carboxamido)phenyl) isoindolin-2-yl)butanoate,
(S)-3-methyl-2-(1-oxo-6-(4-(4-phenylthiazole-2-carboxamido)phenyl)isoindolin-2-yl)butanoic acid;
(S)-Methyl 3-methyl-2-(1-oxo-6-(4-(5-phenyl-1,3,4-oxadiazole-2-carboxamido) phenyl)isoindolin-2-yl)butanoate;
(S)-Methyl 3-methyl-2-(1-oxo-6-(4-(5-phenyl-1,3,4-thiadiazole-2-carboxamido) phenyl)isoindolin-2-yl)butanoate;
(S)-3-Methyl-2-(1-oxo-6-(4-(5-phenyl-1,3,4-thiadiazole-2-carboxamido) phenyl)isoindolin-2-yl)butanoic acid;
(S)-Methyl 3-methyl-2-(1-oxo-6-(4-(5-phenyl-4H-1,2,4-triazole-3-carboxamido) phenyl)isoindolin-2-yl)butanoate;
(S)-3-Methyl-2-(1-oxo-6-(4-(5-phenyl-4H-1,2,4-triazole-3-carboxamido)phenyl) isoindolin-2-yl)butanoic acid;
(S)-Methyl 2-(6-(4-(4-(2-cyanopropan-2-yl)benzamido)phenyl)-1-oxoisoindolin-2-yl)-3-methylbutanoate;
(S)-2-(6-(4-(4-(2-Cyanopropan-2-yl)benzamido)phenyl)-1-oxoisoindolin-2-yl)-3-methylbutanoic acid;
(S)-Methyl 2-(6-(4-(4-(3-cyanopentan-3-yl)benzamido)phenyl)-1-oxoisoindolin-2-yl)-3-methylbutanoate;

(S)-2-(6-(4-(4-(3-Cyanopentan-3-yl)benzamido)phenyl)-1-oxoisoindolin-2-yl)-3-methylbutanoic acid;
(S)-Methyl 3-methyl-2-(1-oxo-6-(5-(5-phenyloxazole-2-carboxamido)pyridin-2-yl)isoindolin-2-yl)butanoate;
(S)-3-Methyl-2-(1-oxo-6-(5-(5-phenyloxazole-2-carboxamido)pyridin-2-yl)isoindolin-2-yl)butanoic acid;
(S)-Methyl 3-methyl-2-(1-oxo-6-(5-(5-phenylthiazole-2-carboxamido)pyridin-2-yl)isoindolin-2-yl)butanoate;
(S)-3-Methyl-2-(1-oxo-6-(5-(5-phenylthiazole-2-carboxamido)pyridin-2-yl)isoindolin-2-yl)butanoic acid;
(S)-Methyl 2-(6-(5-(3-(4-fluorophenyl)isoxazole-5-carboxamido)pyridin-2-yl)-1-oxo isoindolin-2-yl)-3-methylbutanaote;
(S)-2-(6-(5-(3-(4-Fluorophenyl)isoxazole-5-carboxamido)pyridin-2-yl)-1-oxo isoindolin-2-yl)-3-methylbutanoic acid;
(S)-Methyl 2-(6-(4-(4-(1,3,4-oxadiazol-2-yl)benzamido)phenyl)-1-oxoisoindolin-2-yl)-3-methylbutanoate;
(S)-2-(6-(4-(4-(1,3,4-Oxadiazol-2-yl)benzamido)phenyl)-1-oxoisoindolin-2-yl)-3-methylbutanoic acid;
(S)-Methyl 3-methyl-2-(6-(4-(5-methyl-2-phenyloxazole-4-carboxamido)phenyl)-1-oxoisoindolin-2-yl)butanoate;
(S)-3-Methyl-2-(6-(4-(5-methyl-2-phenyloxazole-4-carboxamido)phenyl)-1-oxoisoindolin-2-yl)butanoic acid;
(S)-Methyl 3-methyl-2-(1-oxo-6-(4-(2-phenyl-5-(trifluoromethyl)oxazole-4-carboxamido)phenyl)isoindolin-2-yl)butanoate;
(S)-3-Methyl-2-(1-oxo-6-(4-(2-phenyl-5-(trifluoromethyl)oxazole-4-carboxamido) phenyl)isoindolin-2-yl) butanoic acid;
(S)-Methyl 3-methyl-2-(6-(2-methyl-4-(4-pentylbenzamido)phenyl)-1-oxoisoindolin-2-yl)butanoate;
(S)-3-Methyl-2-(1-oxo-6-(4-(4-(thiazol-2-yl)benzamido) phenyl)isoindolin-2-yl) butanoic acid;
(S)-Methyl 2-(6-(4-(5-butylpicolinamido)phenyl)-1-oxoisoindolin-2-yl)-3-methylbutanoate;
(S)-2-(6-(4-(5-Butylpicolinamido)phenyl)-1-oxoisoindolin-2-yl)-3-methylbutanoic acid;
(S)-Methyl 3-methyl-2-(1-oxo-6-(4-(quinoline-3-carboxamido)phenyl)isoindolin-2-yl)butanoate;
(S)-3-Methyl-2-(1-oxo-6-(4-(quinoline-3-carboxamido) phenyl)isoindolin-2-yl)butanoic acid;
(S)-Methyl 3-methyl-2-(1-oxo-6-(4-(4-(pyrimidin-5-yl)benzamido)phenyl)isoindolin-2-yl)butanoate;
(S)-3-Methyl-2-(1-oxo-6-(4-(4-(pyrimidin-5-yl)benzamido)phenyl)isoindolin-2-yl)butanoic acid;
(S)-Methyl 3-methyl-2-(6-(5-(5-methyl-2-phenyloxazole-4-carboxamido)pyridin-2-yl)-1-oxoisoindolin-2-yl)butanoate;
(S)-3-Methyl-2-(6-(5-(5-methyl-2-phenyloxazole-4-carboxamido)pyridin-2-yl)-1-oxoisoindolin-2-yl)butanoic acid;
(S)-Methyl 3-methyl-2-(1-oxo-6-(5-(2-phenyl-5-(trifluoromethyl)oxazole-4-carboxamido)pyridin-2-yl)isoindolin-2-yl)butanoate;
(S)-3-Methyl-2-(1-oxo-6-(5-(2-phenyl-5-(trifluoromethyl)oxazole-4-carboxamido) pyridin-2-yl)isoindolin-2-yl)butanoic acid;
(S)-Methyl 3-methyl-2-(1-oxo-6-(4-(2-phenylacetamido) phenyl)isoindolin-2-yl)butanoate,
(S)-3-Methyl-2-(1-oxo-6-(4-(2-phenylacetamido)phenyl) isoindolin-2-yl)butanoic acid;
Methyl 2-(5-(4-biphenyl-4-ylcarboxamidophenyl)-1,3-dioxoisoindolin-2-yl)-3-methyl butanoate;
Methyl 2-(5-(4-(4-tert-butylbenzamido)phenyl)-1,3-dioxoisoindolin-2-yl)-3-methyl butanoate;
Methyl 2-(5-(4-(2,4-dimethoxybenzamido)phenyl)-1,3-dioxoisoindolin-2-yl)-3-methylbutanoate;
Methyl 2-(5-(4-(3-(2-chlorophenyl)ureido)phenyl)-1,3-dioxoisoindolin-2-yl)-3-methylbutanoate;
Methyl 2-(5-(4-(3-(3,4-dimethylphenyl)ureido)phenyl)-1,3-dioxoisoindolin-2-yl)-3-methylbutanoate;
Methyl 2-(5-(4-(4-tert-butylbenzamido)phenyl)isoindolin-2-yl)-3-methyl butanoate;
Methyl 3-methyl-2-(5-(4-(4-pentylbenzamido)phenyl) isoindolin-2-yl)butanoate;
Methyl 2-(5-(4-biphenyl-4-ylcarboxamidophenyl)isoindolin-2-yl)-3-methyl butanoate;
Methyl 2-(5-(4-(2,4-dimethoxyphenylsulfonamido)phenyl)isoindolin-2-yl)-3-methyl butanoate; and
Methyl 3-methyl-2-(5-(4-(3-(2-(trifluoromethyl)phenyl) ureido)phenyl)isoindolin-2-yl)butanoate;

or a stereoisomer, tautomer or a pharmaceutically acceptable salt, prodrug, carboxylic acid isostere or N-oxide thereof.

20. The compound according to claim 19, selected from:
(S)-2-(6-(4-(3-(4-Fluorophenyl)ureido)phenyl)-1-oxoisoindolin-2-yl)-3-methyl butanoic acid;
(S)-2-(6-(4-(3-(2,4-Difluorophenyl)ureido)phenyl)-1-oxoisoindolin-2-yl)-3-methylbutanoic acid;
(S)-2-(6-(4-(3-(2-Fluorophenyl)ureido)phenyl)-1-oxoisoindolin-2-yl)-3-methyl butanoic acid;
(S)-2-(6-(4-(3-(3-Fluorophenyl)ureido)phenyl)-1-oxoisoindolin-2-yl)-3-methyl butanoic acid;
(S)-3-Methyl-2-(1-oxo-6-(4-(3-phenylureido)phenyl) isoindolin-2-yl)butanoic acid;
(S)-2-(6-(4-(3-Benzylureido)phenyl)-1-oxoisoindolin-2-yl)-3-methylbutanoic acid;
(S)-2-(6-(4-(3-(2,6-Difluorophenyl)ureido)phenyl)-1-oxoisoindolin-2-yl)-3-methylbutanoic acid;
(S)-3-Methyl-2-(1-oxo-6-(4-(3-p-tolylureido)phenyl) isoindolin-2-yl)butanoic acid;
(S)-2-(6-(4-(3-(3-Methoxyphenyl)ureido)phenyl)-1-oxoisoindolin-2-yl)-3-methyl butanoic acid;
(S)-2-(6-(4-(3-(4-Methoxyphenyl)ureido)phenyl)-1-oxoisoindolin-2-yl)-3-methylbutanoic acid;
(S)-2-(6-(4-(3-(3,5-Difluorophenyl)ureido)phenyl)-1-oxoisoindolin-2-yl)-3-methylbutanoic acid;
(S)-2-(6-(4-(3-(3,4-Difluorophenyl)ureido)phenyl)-1-oxoisoindolin-2-yl)-3-methylbutanoic acid;
(S)-2-(6-(4-(3-Cyclohexylureido)phenyl)-1-oxoisoindolin-2-yl)-3-methylbutanoic acid;
(S)-3-Methyl-2-(1-oxo-6-(4-(3-(4-(trifluoromethyl)phenyl)ureido)phenyl)isoindolin-2-yl)butanoic acid;
(S)-3-Methyl-2-(1-oxo-6-(4-(3-(3-(trifluoromethyl)phenyl)ureido)phenyl)isoindolin-2-yl)butanoic acid;
(S)-2-(6-(4-(3-(4-Cyanophenyl)ureido)phenyl)-1-oxoisoindolin-2-yl)-3-methyl butanoic acid;
(S)-2-(6-(4-(3-(3-Cyanophenyl)ureido)phenyl)-1-oxoisoindolin-2-yl)-3-methyl butanoic acid;
(S)-2-(6-(4-(3-(4-Chloro-2-phenoxyphenyl)ureido)phenyl)-1-oxoisoindolin-2-yl)-3-methylbutanoic acid;
(S)-2-(6-(4-(3-(5-Chloro-2-phenoxyphenyl)ureido)phenyl)-1-oxoisoindolin-2-yl)-3-methylbutanoic acid;
(S)-3-Methyl-2-(1-oxo-6-(4-(3-(2-phenoxyphenyl)ureido)phenyl)isoindolin-2-yl)butanoic acid;
(S)-3-Methyl-2-(1-oxo-6-(4-(3-(4-phenoxyphenyl)ureido)phenyl)isoindolin-2-yl)butanoic acid;
(S)-2-(6-(4-(3-(2-Fluorophenyl)thioureido)phenyl)-1-oxoisoindolin-2-yl)-3-methylbutanoic acid;
(S)-3-Methyl-2-(1-oxo-6-(4-(3-p-tolylthioureido)phenyl) isoindolin-2-yl)butanoic acid;
(S)-2-(6-(4-(3-(3-Fluorophenyl)thioureido)phenyl)-1-oxoisoindolin-2-yl)-3-methylbutanoic acid;

(S)-2-(6-(4-(3-(4-Methoxyphenyl)thioureido)phenyl)-1-oxoisoindolin-2-yl)-3-methylbutanoic acid;

(S)-2-(6-(4-(3-(3-Methoxyphenyl)thioureido)phenyl)-1-oxoisoindolin-2-yl)-3-methylbutanoic acid;

(S)-2-(6-(4-(3-(4-Chlorophenyl)thioureido)phenyl)-1-oxoisoindolin-2-yl)-3-methyl butanoic acid;

(S)-2-(6-(4-(3-(3-Chlorophenyl)thioureido)phenyl)-1-oxoisoindolin-2-yl)-3-methyl butanoic acid;

(S)-3-Methyl-2-(1-oxo-6-(4-(3-(2-trifluoromethyl)phenyl)thioureido)phenyl)isoindolin-2-yl)butanoic acid;

(S)-2-(6-(4-(3-(4-Cyanophenyl)thioureido)phenyl)-1-oxoisoindolin-2-yl)-3-methyl butanoic acid;

(S)-2-(6-(4-(3-(3-Cyanophenyl)thioureido)phenyl)-1-oxoisoindolin-2-yl)-3-methylbutanoic acid;

(S)-3-Methyl-2-(1-oxo-6-(4-(3-o-tolylthioureido)phenyl)isoindolin-2-yl)butanoic acid;

(S)-2-(6-(4-(3-(2-Methoxyphenyl)thioureido)phenyl)-1-oxoisoindolin-2-yl)-3-methylbutanoic acid;

(S)-3-Methyl-2-(1-oxo-6-(4-(3-(3-(trifluoromethyl)phenyl)thioureido)phenyl)isoindolin-2-yl)butanoic acid;

(S)-3-Methyl-2-(1-oxo-6-(4-(phenylsulfonamido)phenyl)isoindolin-2-yl)butanoic acid;

(S)-2-(6-(4-(4-Cyanophenylsulfonamido)phenyl)-1-oxoisoindolin-2-yl)-3-methyl butanoic acid;

(S)-2-(6-(4-(3,4-Difluorophenylsulfonamido)phenyl)-1-oxoisoindolin-2-yl)-3-methylbutanoic acid;

(S)-2-(6-(4-(2,4-Difluorophenylsulfonamido)phenyl)-1-oxoisoindolin-2-yl)-3-methylbutanoic acid;

(S)-2-(6-(4-(3,4-Dimethoxyphenylsulfonamido)phenyl)-1-oxoisoindolin-2-yl)-3-methylbutanoic acid;

(S)-2-(6-(4-(3-Chlorophenylsulfonamido)phenyl)-1-oxoisoindolin-2-yl)-3-methylbutanoic acid;

(S)-2-(6-(4-(4-Methoxyphenylsulfonamido)phenyl)-1-oxoisoindolin-2-yl)-3-methylbutanoic acid;

(S)-3-Methyl-2-(1-oxo-6-(4-(4-(trifluoromethyl)phenylsulfonamido)phenyl)isoindolin-2-yl)butanoic acid;

(S)-3-Methyl-2-(1-oxo-6-(4-(phenylmethylsulfonamido)phenyl)isoindolin-2-yl)butanoic acid;

(S)-3-Methyl-2-(6-(4-(1-methylethylsulfonamido)phenyl)-1-oxoisoindolin-2-yl)butanoic acid;

(S)-2-(6-(4-Benzamidophenyl)-1-oxoisoindolin-2-yl)-3-methylbutanoic acid;

(S)-2-(6-(4-(4-Fluorobenzamido)phenyl)-1-oxoisoindolin-2-yl)-3-methylbutanoic acid;

(S)-3-Methyl-2-(1-oxo-6-(4-(4-(trifluoromethyl)benzamido)phenyl)isoindolin-2-yl)butanoic acid;

(S)-2-(6-(4-(4-Methoxybenzamido)phenyl)-1-oxoisoindolin-2-yl)-3-methyl butanoic acid;

(S)-2-(6-(4-(3-Fluorobenzamido)phenyl)-1-oxoisoindolin-2-yl)-3-methylbutanoic acid;

(S)-2-(6-(4-(3-Chlorobenzamido)phenyl)-1-oxoisoindolin-2-yl)-3-methylbutanoic acid;

(S)-2-(6-(4-(2,4-Difluorobenzamido)phenyl)-1-oxoisoindolin-2-yl)-3-methyl butanoic acid;

(S)-3-Methyl-2-(6-(4-(4-methylbenzamido)phenyl)-1-oxoisoindolin-2-yl)butanoic acid;

(S)-2-(6-(4-(4-Chlorobenzamido)phenyl)-1-oxoisoindolin-2-yl)-3-methylbutanoic acid;

(S)-2-(6-(4-(4-tert-Butylbenzamido)phenyl)-1-oxoisoindolin-2-yl)-3-methyl butanoic acid;

(S)-2-(6-(4-(Cyclohexanecarboxamido)phenyl)-1-oxoisoindolin-2-yl)-3-methylbutanoic acid;

(S)-2-(6-(4-(Biphenyl-4-ylcarboxamidophenyl)-1-oxoisoindolin-2-yl)-3-methyl butanoic acid;

(S)-2-(6-(4-(2-Naphthamido)phenyl)-1-oxoisoindolin-2-yl)-3-methylbutanoic acid;

(S)-3-Methyl-2-(1-oxo-6-(4-(4-pentylbenzamido)phenyl)isoindolin-2-yl)butanoic acid;

(S)-2-(6-(4-(2-Fluoro-6-(trifluoromethyl)benzamido)phenyl)-1-oxoisoindolin-2-yl)-3-methylbutanoic acid;

(S)-2-(6-(4-(Benzo[d][1,3]dioxole-5-carboxamido)phenyl)-1-oxoisoindolin-2-yl)-3-methylbutanoic acid;

(S)-2-(6-(4-(2,6-Dichlorobenzamido)phenyl)-1-oxoisoindolin-2-yl)-3-methyl butanoic acid;

(S)-2-(6-(4-(2-Chlorobenzamido)phenyl)-1-oxoisoindolin-2-yl)-3-methylbutanoic acid;

(S)-2-(6-(4-(2,4-Dichlorobenzamido)phenyl)-1-oxoisoindolin-2-yl)-3-methyl butanoic acid;

(S)-2-(6-(4-(4-Butoxybenzamido)phenyl)-1-oxoisoindolin-2-yl)-3-methyl butanoic acid;

(S)-2-(6-(4-(2,6-Difluorobenzamido)phenyl)-1-oxoisoindolin-2-yl)-3-methyl butanoic acid;

(S)-2-(6-(4-(3,4-Difluorobenzamido)phenyl)-1-oxoisoindolin-2-yl)-3-methyl butanoic acid;

(S)-2-(6-(4-(3,4-Dimethoxybenzamido)phenyl)-1-oxoisoindolin-2-yl)-3-methyl butanoic acid;

(S)-3-Methyl-2-(1-oxo-6-(4-(3,4,5-trimethoxybenzamido)phenyl)isoindolin-2-yl) butanoic acid;

(S)-2-(6-(4-(3,5-Diethoxybenzamido)phenyl)-1-oxoisoindolin-2-yl)-3-methyl butanoic acid;

(S)-3-Methyl-2-(1-oxo-6-(4-(3-phenoxybenzamido)phenyl)isoindolin-2-yl)butanoic acid;

(S)-3-Methyl-2-(1-oxo-6-(4-(4-phenoxybenzamido)phenyl)isoindolin-2-yl)butanoic acid;

(S)-3-Methyl-2-(1-oxo-6-(4-(2-phenoxybenzamido)phenyl)isoindolin-2-yl)butanoic acid;

(S)-3-Methyl-2-(1-oxo-6-(4-(2,4,6-trimethylbenzamido)phenyl)isoindolin-2-yl) butanoic acid;

(S)-2-(6-(4-(2,4-Dimethoxybenzamido)phenyl)-1-oxoisoindolin-2-yl)-3-methyl butanoic acid;

(S)-3-Methyl-2-(1-oxo-6-(4-(4-(trifluoromethoxy)benzamido)phenyl)isoindolin-2-yl)butanoic acid;

(S)-2-(6-(4-(2-Methoxybenzamido)phenyl)-1-oxoisoindolin-2-yl)-3-methyl butanoic acid;

(S)-2-(6-(4-(4-Fluoro-3-methylbenzamido)phenyl)-1-oxoisoindolin-2-yl)-3-methyl butanoic acid;

(S)-2-(6-(4-(4-Butylbenzamido)phenyl)-1-oxoisoindolin-2-yl)-3-methylbutanoic acid;

(S)-2-(6-(4-(2,6-Difluoro-3-methylbenzamido)phenyl)-1-oxoisoindolin-2-yl)-3-methylbutanoic acid;

(S)-2-(6-(4-(4-Ethylbenzamido)phenyl)-1-oxoisoindolin-2-yl)-3-methylbutanoic acid;

(S)-3-Methyl-2-(1-oxo-6-(4-(4-propylbenzamido)phenyl)isoindolin-2-yl)butanoic acid;

(S)-3-Methyl-2-(6-(4-(4-octylbenzamido)phenyl)-1-oxoisoindolin-2-yl)butanoic acid;

(S)-2-(6-(4-(4-Cyclohexylbenzamido)phenyl)-1-oxoisoindolin-2-yl)-3-methyl butanoic acid;

(S)-3-Methyl-2-(1-oxo-6-(4-(5,5,8,8-tetramethyl-5,6,7,8-tetrahydro naphthalene-2-carboxamido)phenyl)isoindolin-2-yl)butanoic acid;

(S)-2-(6-(4-(1-Naphthamido)phenyl)-1-oxoisoindolin-2-yl)-3-methylbutanoic acid;

(S)-2-(6-(4-(3,5-Dimethoxybenzamido)phenyl)-1-oxoisoindolin-2-yl)-3-methyl butanoic acid;

(S)-2-(6-(4-(4-Hexylbenzamido)phenyl)-1-oxoisoindolin-2-yl)-3-methylbutanoic acid;

(S)-2-(6-(4-(4-Heptylbenzamido)phenyl)-1-oxoisoindolin-2-yl)-3-methylbutanoic acid;

(S)-3-Methyl-2-(6-(4-(4-nonylbenzamido)phenyl)-1-oxoisoindolin-2-yl)butanoic acid;

(S)-2-(6-(4-(4-Decylbenzamido)phenyl)-1-oxoisoindolin-2-yl)-3-methyl butanoic acid;

(S)-2-(6-(4-(Adamantyl-2-carboxamido)phenyl)-1-oxoisoindolin-2-yl)-3-methylbutanoic acid;
(S)-2-(6-(4-(2-Fluoro-4-(trifluoromethyl)benzamido)phenyl)-1-oxoisoindolin-2-yl)-3-methylbutanoic acid;
(S)-2-(6-(4-(2-Fluoro-3-(trifluoromethyl)benzamido)phenyl)-1-oxoisoindolin-2-yl)-3-methylbutanoic acid;
(S)-2-(6-(4-(3-Fluoro-4-(trifluoromethyl)benzamido)phenyl)-1-oxoisoindolin-2-yl)-3-methylbutanoic acid;
(S)-2-(6-(4-(4-Fluoro-2-(trifluoromethyl)benzamido)phenyl)-1-oxoisoindolin-2-yl)-3-methylbutanoic acid;
(S)-3-Methyl-2-(1-oxo-6-(4-(2-(trifluoromethyl)benzamido)phenyl)isoindolin-2-yl)butanoic acid;
(S)-2-(6-(4-(2-Ethoxybenzamido)phenyl)-1-oxoisoindolin-2-yl)-3-methylbutanoic acid;
(S)-3-Methyl-2-(6-(4-(nicotinamido)phenyl)-1-oxoisoindolin-2-yl)butanoic acid;
(S)-2-(6-(4-(2-Chloronicotinamido)phenyl)-1-oxoisoindolin-2-yl)-3-methyl butanoic acid;
(S)-3-Methyl-2-(6-(4-(6-morpholinonicotinamido)phenyl)-1-oxoisoindolin-2-yl) butanoic acid;
(S)-3-Methyl-2-(1-oxo-6-(4-(6-(piperidin-1-yl)nicotinamido)phenyl)isoindolin-2-yl)butanoic acid;
(S)-3-Methyl-2-(1-oxo-6-(4-(6-(pyrrolidin-1-yl)nicotinamido)phenyl)isoindolin-2-yl)butanoic acid;
(S)-2-(5-(4-(3-(4-Fluorophenyl)ureido)phenyl)-1-oxoisoindolin-2-yl)-3-methylbutanoic acid;
(S)-2-(5-(4-(3-(2-Fluorophenyl)ureido)phenyl)-1-oxoisoindolin-2-yl)-3-methyl butanoic acid;
(S)-2-(5-(4-(3-(3-Fluorophenyl)ureido)phenyl)-1-oxoisoindolin-2-yl)-3-methyl butanoic acid;
(S)-3-Methyl-2-(1-oxo-5-(4-(3-phenylureido)phenyl)isoindolin-2-yl)butanoic acid;
(S)-2-(5-(4-(3-Cyclohexylureido)phenyl)-1-oxoisoindolin-2-yl)-3-methyl butanoic acid;
(S)-2-(5-(4-(3-(2,4-Difluorophenyl)ureido)phenyl)-1-oxoisoindolin-2-yl)-3-methylbutanoic acid;
(S)-2-(5-(4-(3-(3,4-Difluorophenyl)ureido)phenyl)-1-oxoisoindolin-2-yl)-3-methylbutanoic acid;
(S)-3-Methyl-2-(1-oxo-5-(4-(3-p-tolylureido)phenyl)isoindolin-2-yl)butanoic acid;
(S)-3-Methyl-2-(1-oxo-5-(4-(3-m-tolylureido)phenyl)isoindolin-2-yl)butanoic acid;
(S)-3-Methyl-2-(1-oxo-5-(4-(3-(4-(trifluoromethyl)phenyl)ureido)phenyl)isoindolin-2-yl)butanoic acid;
(S)-3-Methyl-2-(1-oxo-5-(4-(3-(3-(trifluoromethyl)phenyl)ureido)phenyl)isoindolin-2-yl)butanoic acid;
(S)-2-(5-(4-(3-(4-Methoxyphenyl)ureido)phenyl)-1-oxoisoindolin-2-yl)-3-methylbutanoic acid;
(S)-2-(5-(4-(3-(3-Methoxyphenyl)ureido)phenyl)-1-oxoisoindolin-2-yl)-3-methylbutanoic acid;
(S)-2-(5-(4-(3-(4-Cyanophenyl)ureido)phenyl)-1-oxoisoindolin-2-yl)-3-methylbutanoic acid;
(S)-2-(5-(4-(3-(3-Cyanophenyl)ureido)phenyl)-1-oxoisoindolin-2-yl)-3-methylbutanoic acid;
(S)-2-(5-(4-(3-(2-Fluorophenyl)thioureido)phenyl)-1-oxoisoindolin-2-yl)-3-methylbutanoic acid;
(S)-2-(5-(4-(3-(3-Fluorophenyl)thioureido)phenyl)-1-oxoisoindolin-2-yl)-3-methyl butanoic acid;
(S)-2-(5-(4-(3-(4-Methoxyphenyl)thioureido)phenyl)-1-oxoisoindolin-2-yl)-3-methylbutanoic acid;
(S)-2-(5-(4-(3-(3-Methoxyphenyl)thioureido)phenyl)-1-oxoisoindolin-2-yl)-3-methyl butanoic acid;
(S)-2-(5-(4-(3-(4-Chlorophenyl)thioureido)phenyl)-1-oxoisoindolin-2-yl)-3-methylbutanoic acid;
(S)-2-(5-(4-(3-(3-Chlorophenyl)thioureido)phenyl)-1-oxoisoindolin-2-yl)-3-methylbutanoic acid;
(S)-2-(5-(4-(3-(4-Cyanophenyl)thioureido)phenyl)-1-oxoisoindolin-2-yl)-3-methyl butanoic acid;
(S)-3-Methyl-2-(1-oxo-5-(4-(3-(2-(trifluoromethyl)phenyl)thioureido)phenyl)isoindolin-2-yl)butanoic acid;
(S)-3-Methyl-2-(1-oxo-5-(4-(3-o-tolylthioureido)phenyl)isoindolin-2-yl)butanoic acid;
(S)-3-Methyl-2-(1-oxo-5-(4-(3-p-tolylthioureido)phenyl)isoindolin-2-yl)butanoic acid;
(S)-2-(5-(4-(3-(3-Fluorophenyl)thioureido)phenyl)-1-oxoisoindolin-2-yl)-3-methyl butanoic acid;
(S)-2-(5-(4-(3-(3-Methoxyphenyl)thioureido)phenyl)-1-oxoisoindolin-2-yl)-3-methylbutanoic acid;
(S)-2-(5-(4-(3-(2-Methoxyphenyl)thioureido)phenyl)-1-oxoisoindolin-2-yl)-3-methylbutanoic acid;
(S)-3-Methyl-2-(1-oxo-5-(4-(3-(3-(trifluoromethyl)phenyl)thioureido)phenyl)isoindolin-2-yl)butanoic acid;
(S)-3-Methyl-2-(1-oxo-6-(4-(phenylsulfonamido)phenyl)isoindolin-2-yl)butanoic acid;
(S)-2-(5-(4-(4-Cyanophenylsulfonamido)phenyl)-1-oxoisoindolin-2-yl)-3-methyl butanoic acid;
(S)-2-(5-(4-(3,4-Difluorophenylsulfonamido)phenyl)-1-oxoisoindolin-2-yl)-3-methylbutanoic acid;
(S)-2-(5-(4-(2,4-Difluorophenylsulfonamido)phenyl)-1-oxoisoindolin-2-yl)-3-methylbutanoic acid;
(S)-2-(5-(4-(3,4-Dimethoxyphenylsulfonamido)phenyl)-1-oxoisoindolin-2-yl)-3-methylbutanoic acid;
(S)-2-(5-(4-(3-Chlorophenylsulfonamido)phenyl)-1-oxoisoindolin-2-yl)-3-methyl butanoic acid;
(S)-2-(5-(4-(4-Methoxyphenylsulfonamido)phenyl)-1-oxoisoindolin-2-yl)-3-methylbutanoic acid;
(S)-3-Methyl-2-(1-oxo-5-(4-(4-(trifluoromethyl)phenylsulfonamido)phenyl)isoindolin-2-yl)butanoic acid;
(S)-3-Methyl-2-(1-oxo-5-(4-(phenylmethylsulfonamido)phenyl)isoindolin-2-yl)butanoic acid;
(S)-2-(5-(4-(Cyclohexanesulfonamido)phenyl)-1-oxoisoindolin-2-yl)-3-methylbutanoic acid;
(S)-2-(5-(4-Benzamidophenyl)-1-oxoisoindolin-2-yl)-3-methylbutanoic acid;
(S)-2-(5-(4-(4-Fluorobenzamido)phenyl)-1-oxoisoindolin-2-yl)-3-methylbutanoic acid;
(S)-3-Methyl-2-(1-oxo-5-(4-(4-(trifluoromethyl)benzamido)phenyl)isoindolin-2-yl)butanoic acid;
(S)-2-(5-(4-(4-Methoxybenzamido)phenyl)-1-oxoisoindolin-2-yl)-3-methyl butanoic acid;
(S)-2-(5-(4-(3-Fluorobenzamido)phenyl)-1-oxoisoindolin-2-yl)-3-methylbutanoic acid;
(S)-2-(5-(4-(3-Chlorobenzamido)phenyl)-1-oxoisoindolin-2-yl)-3-methylbutanoic acid;
(S)-2-(5-(4-(2,4-Difluorobenzamido)phenyl)-1-oxoisoindolin-2-yl)-3-methylbutanoic acid;
(S)-3-Methyl-2-(5-(4-(4-methylbenzamido)phenyl)-1-oxoisoindolin-2-yl)butanoic acid;
(S)-2-(5-(4-(4-Chlorobenzamido)phenyl)-1-oxoisoindolin-2-yl)-3-methylbutanoic acid;
(S)-2-(5-(4-(4-tert-Butylbenzamido)phenyl)-1-oxoisoindolin-2-yl)-3-methyl butanoic acid;
(S)-3-Methyl-2-(1-oxo-5-(4-(4-pentylbenzamido)phenyl)isoindolin-2-yl)butanoic acid;
(R)-3-Methyl-2-(1-oxo-6-(4-(3-(3-(trifluoromethyl)phenyl)ureido)phenyl)iso indolin-2-yl)butanoic acid;
2-(1-oxo-6-(4-(3-(trifluoromethyl)phenyl)ureido)phenyl)isoindolin-2-yl)acetic acid;
(S)-2-(1-oxo-6-(4-(3-(3-(trifluoromethyl)phenyl)ureido) phenyl)isoindolin-2-yl) propanoic acid;
2-Methyl-2-(1-oxo-6-(4-(3-(3-(trifluoromethyl)phenyl) ureido)phenyl)isoindolin-2-yl)propanoic acid;

1-(1-oxo-6-(4-(3-(3-(trifluoromethyl)phenyl)ureido)phenyl)isoindolin-2-yl)cyclopentanecarboxylic acid;
(S)-2-(1-oxo-6-(4-(3-(3-(trifluoromethyl)phenyl)ureido)phenyl)isoindolin-2-yl)-2-phenylacetic acid;
4-(1-oxo-6-(4-(3-(3-(trifluoromethyl)phenyl)ureido)phenyl)isoindolin-2-yl)butanoic acid;
(S)-4-Methyl-2-(1-oxo-6-(4-(3-(3-(trifluoromethyl)phenyl)ureido)phenyl)iso indolin-2-yl)pentanoic acid;
(S)-3-Methoxy-2-(1-oxo-6-(4-(3-(3-(trifluoromethyl)phenyl)ureido)phenyl)iso indolin-2-yl)propanoic acid;
(R)-3-Methyl-2-(1-oxo-5-(4-(3-(3-(trifluoromethyl)phenyl)ureido)phenyl)isoindolin-2-yl)butanoic acid;
2-(1-oxo-5-(4-(3-(3-(trifluoromethyl)phenyl)ureido)phenyl)isoindolin-2-yl)acetic acid;
(S)-2-(1-oxo-5-(4-(3-(3-(trifluoromethyl)phenyl)ureido)phenyl)isoindolin-2-yl) propanoic acid;
1-(1-oxo-5-(4-(3-(3-(trifluoromethyl)phenyl)ureido)phenyl)isoindolin-2-yl)cyclopentanecarboxylic acid;
(S)-2-(1-oxo-5-(4-(3-(3-(trifluoromethyl)phenyl)ureido)phenyl)isoindolin-2-yl)-2-phenylacetic acid;
4-(1-oxo-5-(4-(3-(3-(trifluoromethyl)phenyl)ureido)phenyl)isoindolin-2-yl)butanoic acid;
3-(1-oxo-5-(4-(3-(3-(trifluoromethyl)phenyl)ureido)phenyl)isoindolin-2-yl)propanoic acid;
(S)-2-(1-oxo-5-(4-(3-(3-(trifluoromethyl)phenyl)ureido)phenyl)isoindolin-2-yl)-3-phenylpropanoic acid;
(S)-3-Methoxy-2-(1-oxo-5-(4-(3-(3-(trifluoromethyl)phenyl)ureido)phenyl)isoindolin-2-yl)propanoic acid;
(S)-4-Methyl-2-(1-oxo-5-(4-(3-(3-(trifluoromethyl)phenyl)ureido)phenyl)iso indolin-2-yl)pentanoic acid;
(S)-2-(6-(5-(3-(2-Chlorophenyl)ureido)pyridin-2-yl)-1-oxoisoindolin-2-yl)-3-methylbutanoic acid;
(S)-2-(6-(5-(3-(4-Chloro-2-phenoxyphenyl)ureido)pyridin-2-yl)-1-oxoisoindolin-2-yl)-3-methylbutanoic acid;
(S)-2-(6-(5-(3-(3,4-Dimethylphenyl)ureido)pyridin-2-yl)-1-oxoisoindolin-2-yl)-3-methylbutanoic acid;
(S)-2-(6-(5-(3-(3,4-Difluorophenyl)ureido)pyridin-2-yl)-1-oxoisoindolin-2-yl)-3-methylbutanoic acid;
(S)-2-(6-(5-(3-(2,3-Dihydro-1H-inden-5-yl)ureido)pyridin-2-yl)-1-oxoisoindolin-2-yl)-3-methylbutanoic acid;
(S)-2-(6-(5-(4-tert-Butylbenzamido)pyridin-2-yl)-1-oxoisoindolin-2-yl)-3-methyl butanoic acid;
(S)-3-Methyl-2-(1-oxo-6-(5-(4-pentylbenzamido)pyridin-2-yl)isoindolin-2-yl)butanoic acid;
(S)-2-(6-(5-Biphenyl-4-ylcarboxamidopyridin-2-yl)-1-oxoisoindolin-2-yl)-3-methylbutanoic acid; (S)-2-(6-(5-(2-Naphthamido)pyridin-2-yl)-1-oxoisoindolin-2-yl)-3-methylbutanoic acid;
(S)-2-(6-(5-(4-Butoxybenzamido)pyridin-2-yl)-1-oxoisoindolin-2-yl)-3-methylbutanoic acid;
(S)-2-(6-(4-(3-(2-Chlorophenyl)ureido)-2-(trifluoromethyl)phenyl)-1-oxoisoindolin-2-yl)-3-methylbutanoic acid;
(S)-2-(6-(4-(3-(3,4-Difluorophenyl)ureido)-2-(trifluoromethyl)phenyl)-1-oxoisoindolin-2-yl)-3-methylbutanoic acid;
(S)-2-(6-(4-(3-(2,3-Dihydro-1H-inden-5-yl)ureido)-2-(trifluoromethyl)phenyl)-1-oxoisoindolin-2-yl)-3-methylbutanoic acid;
(S)-2-(6-(4-(3-(3,4-Dimethylphenyl)ureido)-2-(trifluoromethyl)phenyl)-1-oxoisoindolin-2-yl)-3-methylbutanoic acid;
(S)-2-(6-(4-(4-tert-Butylbenzamido)-2-(trifluoromethyl)phenyl)-1-oxoisoindolin-2-yl)-3-methylbutanoic acid;
(S)-2-(6-(4-Biphenyl-4-ylcarboxamido-2-(trifluoromethyl)phenyl)-1-oxoisoindolin-2-yl)-3-methylbutanoic acid;

(S)-2-(6-(4-(2-Naphthamido)-2-(trifluoromethyl)phenyl)-1-oxoisoindolin-2-yl)-3-methylbutanoic acid;
(S)-3-Methyl-2-(1-oxo-6-(4-(4-pentylbenzamido)-2-(trifluoromethyl)phenyl) isoindolin-2-yl)butanoic acid;
(S)-2-(6-(4-(4-Butoxybenzamido)-2-(trifluoromethyl)phenyl)-1-oxoisoindolin-2-yl)-3-methylbutanoic acid;
(S)-2-(6-(4-(3-(3,4-Dimethylphenyl)ureido)-3-fluorophenyl)-1-oxoisoindolin-2-yl)-3-methylbutanoic acid;
(S)-2-(6-(4-(3-(2,3-Dihydro-1H-inden-5-yl)ureido)-3-fluorophenyl)-1-oxoisoindolin-2-yl)-3-methylbutanoic acid; (S)-2-(6-(4-(3-(3,4-Difluorophenyl)ureido)-3-fluorophenyl)-1-oxoisoindolin-2-yl)-3-methylbutanoic acid;
(S)-2-(6-(4-(3-(2-Chlorophenyl)ureido)-3-fluorophenyl)-1-oxoisoindolin-2-yl)-3-methylbutanoic acid;
(S)-2-(6-(4-(4-tert-Butylbenzamido)-3-fluorophenyl)-1-oxoisoindolin-2-yl)-3-methylbutanoic acid;
(S)-2-(6-(3-Fluoro-4-(4-pentylbenzamido)phenyl)-1-oxoisoindolin-2-yl)-3-methylbutanoic acid;
(S)-2-(6-(4-Biphenyl-4-ylcarboxamido-3-fluorophenyl)-1-oxoisoindolin-2-yl)-3-methylbutanoic acid;
(S)-2-(6-(4-(2-Naphthamido)-3-fluorophenyl)-1-oxoisoindolin-2-yl)-3-methyl butanoic acid;
(S)-2-(6-(4-(4-Butoxybenzamido)-3-fluorophenyl)-1-oxoisoindolin-2-yl)-3-methyl butanoic acid;
(S)-2-(6-(4-(4-tert-Butylbenzamido)-2-methoxyphenyl)-1-oxoisoindolin-2-yl)-3-methylbutanoic acid;
(S)-2-(6-(4-Biphenyl-4-ylcarboxamido-2-methoxyphenyl)-1-oxoisoindolin-2-yl)-3-methylbutanoic acid;
(S)-2-(6-(4-(4-Butoxybenzamido)-2-methoxyphenyl)-1-oxoisoindolin-2-yl)-3-methylbutanoic acid;
(S)-2-(6-(2-Methoxy-4-(4-pentylbenzamido)phenyl)-1-oxoisoindolin-2-yl)-3-methylbutanoic acid;
(S)-2-(6-(2-Methoxy-4-(4-(trifluoromethoxy)benzamido)phenyl)-1-oxoisoindolin-2-yl)-3-methylbutanoic acid;
(S)-2-(6-(4-(4-tert-Butylbenzamido)-2-methylphenyl)-1-oxoisoindolin-2-yl)-3-methylbutanoic acid;
(S)-2-(6-(4-Biphenyl-4-ylcarboxamido-2-methylphenyl)-1-oxoisoindolin-2-yl)-3-methylbutanoic acid;
(S)-2-(6-(4-(4-Butoxybenzamido)-2-methylphenyl)-1-oxoisoindolin-2-yl)-3-methylbutanoic acid;
(S)-3-Methyl-2-(6-(2-methyl-4-(4-pentylbenzamido)phenyl)-1-oxoisoindolin-2-yl)butanoic acid;
(S)-3-Methyl-2-(6-(2-methyl-4-(4-(trifluoromethoxy)benzamido)phenyl)-1-oxoisoindolin-2-yl)butanoic acid;
(S)-2-(6-(4-(4-tert-Butylbenzamido)-2-chlorophenyl)-1-oxoisoindolin-2-yl)-3-methylbutanoic acid;
(S)-2-(6-(4-Biphenyl-4-ylcarboxamido-2-chlorophenyl)-1-oxoisoindolin-2-yl)-3-methylbutanoic acid;
(S)-2-(6-(4-(4-Butoxybenzamido)-2-chlorophenyl)-1-oxoisoindolin-2-yl)-3-methylbutanoic acid;
(S)-2-(6-(2-Chloro-4-(4-pentylbenzamido)phenyl)-1-oxoisoindolin-2-yl)-3-methylbutanoic acid;
(S)-2-(6-(2-Chloro-4-(4-(trifluoromethoxy)benzamido)phenyl)-1-oxoisoindolin-2-yl)-3-methylbutanoic acid;
(S)-2-(6-(6-(4-tert-Butylbenzamido)pyridin-3-yl)-1-oxoisoindolin-2-yl)-3-methylbutanoic acid;
(S)-2-(6-(6-(4-tert-Butylbenzamido)pyridazin-3-yl)-1-oxoisoindolin-2-yl)-3-methylbutanoic acid;
(S)-3-Methyl-2-(1-oxo-6-(6-(4-pentylbenzamido)pyridazin-3-yl)isoindolin-2-yl)butanoic acid;
(S)-3-Methyl-2-(1-oxo-6-(6-(4-(trifluoromethoxy)benzamido)pyridazin-3-yl)isoindolin-2-yl)butanoic acid;
(S)-2-(6-(5-(4-tert-Butylbenzamido)pyrazin-2-yl)-1-oxoisoindolin-2-yl)-3-methylbutanoic acid;

(S)-2-(6-(5-Biphenyl-4-ylcarboxamidopyrazin-2-yl)-1-oxoisoindolin-2-yl)-3-methylbutanoic acid;
(S)-2-(6-(5-(4-Butoxybenzamido)pyrazin-2-yl)-1-oxoisoindolin-2-yl)-3-methylbutanoic acid;
(S)-3-Methyl-2-(1-oxo-6-(5-(4-pentylbenzamido)pyrazin-2-yl)isoindolin-2-yl)butanoic acid;
(S)-3-Methyl-2-(1-oxo-6-(5-(4-(trifluoromethoxy)benzamido)pyrazin-2-yl)isoindolin-2-yl)butanoic acid;
2-(6-(4-([1,1'-Biphenyl]-4-ylcarboxamido)phenyl)-1-oxoisoindolin-2-yl)-2-methyl propanoic acid;
2-(6-(4-(4-(tert-Butyl)benzamido)phenyl)-1-oxoisoindolin-2-yl)-2-methylpropanoic acid;
2-(6-(4-(4-Chlorobenzamido)phenyl)-1-oxoisoindolin-2-yl)-2-methylpropanoic acid;
2-Methyl-2-(1-oxo-6-(4-(4-(trifluoromethoxy)benzamido)phenyl)isoindolin-2-yl)propanoic acid;
2-Methyl-2-(1-oxo-6-(4-(4-pentylbenzamido)phenyl)isoindolin-2-yl)propanoic acid;
1-(6-(4-([1,1'-Biphenyl]-4-ylcarboxamido)phenyl)-1-oxoisoindolin-2-yl)cyclopentane carboxylic acid;
1-(6-(4-(4-(tert-Butyl)benzamido)phenyl)-1-oxoisoindolin-2-yl)cyclopentane carboxylic acid;
1-(6-(4-(4-Chlorobenzamido)phenyl)-1-oxoisoindolin-2-yl)cyclopentane carboxylic acid;
1-(1-oxo-6-(4-(4-(trifluoromethoxy)benzamido)phenyl)isoindolin-2-yl)cyclopentane carboxylic acid;
1-(1-oxo-6-(4-(4-pentylbenzamido)phenyl)isoindolin-2-yl)cyclopentane carboxylic acid;
(R)-2-(6-(4-([1,1-Biphenyl]-4-ylcarboxamido)phenyl)-1-oxoisoindolin-2-yl)-3-methylbutanoic acid;
3-(6-(4-([1,1-Biphenyl]-4-ylcarboxamido)phenyl)-1-oxoisoindolin-2-yl)cyclohexane carboxylic acid;
3-(6-(4-(3-Chlorobenzamido)phenyl)-1-oxoisoindolin-2-yl)cyclohexane carboxylic acid;
3-(6-(4-(4-Chlorobenzamido)phenyl)-1-oxoisoindolin-2-yl)cyclohexane carboxylic acid;
3-(1-oxo-6-(4-(4-(trifluoromethyl)benzamido)phenyl)isoindolin-2-yl)cyclo hexanecarboxylic acid;
3-(6-(4-(5-Methyl-2-phenyloxazole-4-carboxamido)phenyl)-1-oxoisoindolin-2-yl-cyclohexanecarboxylic acid;
(1r,4r)-4-(6-(4-([1,1'-Biphenyl]-4-ylcarboxamido)phenyl)-1-oxoisoindolin-2-yl)cyclohexanecarboxylic acid;
(1r,4r)-4-(6-(4-(3-Chlorobenzamido)phenyl)-1-oxoisoindolin-2-yl)cyclohexane carboxylic acid;
(1r,4r)-4-(6-(4-(4-Chlorobenzamido)phenyl)-1-oxoisoindolin-2-yl)cyclohexane carboxylic acid;
(1r,4r)-4-(1-oxo-6-(4-(4-(trifluoromethyl)benzamido)phenyl)isoindolin-2-yl)cyclohexanecarboxylic acid;
(1r,3s,5R,7S)-3-(6-(4-(3-Chlorobenzamido)phenyl)-1-oxoisoindolin-2-yl) adamantane-1-carboxylic acid;
(1r,3s,5R,7S)-3-(6-(4-(4-Chlorobenzamido)phenyl)-1-oxoisoindolin-2-yl) adamantane-1-carboxylic acid;
(1r,3s,5R,7S)-3-(1-oxo-6-(4-(4-(trifluoromethyl)benzamido)phenyl)isoindolin-2-yl)adamantane-1-carboxylic acid;
(1r,3s,5R,7S)-3-(6-(4-(4-Methylbenzamido)phenyl)-1-oxoisoindolin-2-yl) adamantane-1-carboxylic acid;
1-(6-(4-([1,1'-Biphenyl]-4-ylcarboxamido)phenyl)-1-oxoisoindolin-2-yl)cyclobutane carboxylic acid;
1-(6-(4-(4-Chlorobenzamido)phenyl)-1-oxoisoindolin-2-yl)cyclobutane carboxylic acid;
1-(1-Oxo-6-(4-(4-(trifluoromethyl)benzamido)phenyl)isoindolin-2-yl)cyclo butanecarboxylic acid;
1-(6-(4-(4-Methylbenzamido)phenyl)-1-oxoisoindolin-2-yl)cyclobutane carboxylic acid;
1-(6-(4-([1,1'-Biphenyl]-4-ylcarboxamido)phenyl)-1-oxoisoindolin-2-yl)cyclopropanecarboxylic acid;
1-(6-(4-(4-Chlorobenzamido)phenyl)-1-oxoisoindolin-2-yl)cyclopropane carboxylic acid;
1-(1-oxo-6-(4-(4-(trifluoromethyl)benzamido)phenyl)isoindolin-2-yl)cyclopropane carboxylic acid;
(1S,2R)-2-(6-(4-(4-Chlorobenzamido)phenyl)-1-oxoisoindolin-2-yl)cyclopentane carboxylic acid;
(1S,2R)-2-(1-oxo-6-(4-(4-(trifluoromethyl)benzamido)phenyl)isoindolin-2-yl)cyclopentanebcarboxylic acid;
(S)-2-(6-(4-([1,1'-Biphenyl]-4-ylcarboxamido)-2-fluorophenyl)-1-oxoisoindolin-2-yl)-3-methylbutanoic acid;
(S)-2-(6-(4-(4-(tert-Butyl)benzamido)-2-fluorophenyl)-1-oxoisoindolin-2-yl)-3-methylbutanoic acid;
(S)-2-(6-(4-(4-Chlorobenzamido)-2-fluorophenyl)-1-oxoisoindolin-2-yl)-3-methyl butanoic acid;
(S)-2-(6-(2-Fluoro-4-(4-(trifluoromethoxy)benzamido)phenyl)-1-oxoisoindolin-2-yl)-3-methylbutanoic acid;
(S)-2-(6-(2-Fluoro-4-(4-pentylbenzamido)phenyl)-1-oxoisoindolin-2-yl)-3-methyl butanoic acid;
(S)-3-Methyl-2-(1-oxo-6-(4-(5-phenylthiazole-2-carboxamido)phenyl)isoindolin-2-yl)butanoic acid;
(S)-3-Methyl-2-(1-oxo-6-(4-(5-phenyloxazole-2-carboxamido)phenyl)isoindolin-2-yl)butanoic acid;
(S)-2-(6-(4-(3-(4-Fluorophenyl)isoxazole-5-carboxamido)phenyl)-1-oxo isoindolin-2-yl)-3-methylbutanoic acid;
(S)-2-(6-(4-(3-(4-Chlorophenyl)isoxazole-5-carboxamido)phenyl)-1-oxo isoindolin-2-yl)-3-methylbutanoic acid;
(S)-3-Methyl-2-(1-oxo-6-(4-(3-(4-(trifluoromethyl)phenyl)isoxazole-5-carboxamido)phenyl)isoindolin-2-yl)butanoic acid;
(S)-3-Methyl-2-(6-(4-(4-(oxazol-5-yl)benzamido)phenyl)-1-oxoisoindolin-2-yl)butanoic acid;
(S)-3-Methyl-2-(1-oxo-6-(4-(4-phenylthiazole-2-carboxamido)phenyl)isoindolin-2-yl)butanoic acid;
(S)-3-Methyl-2-(1-oxo-6-(4-(5-phenyl-1,3,4-thiadiazole-2-carboxamido) phenyl)isoindolin-2-yl)butanoic acid;
(S)-3-Methyl-2-(1-oxo-6-(4-(5-phenyl-4H-1,2,4-triazole-3-carboxamido)phenyl) isoindolin-2-yl)butanoic acid;
(S)-2-(6-(4-(4-(2-Cyanopropan-2-yl)benzamido)phenyl)-1-oxoisoindolin-2-yl)-3-methylbutanoic acid;
(S)-2-(6-(4-(4-(3-Cyanopentan-3-yl)benzamido)phenyl)-1-oxoisoindolin-2-yl)-3-methylbutanoic acid;
(S)-3-Methyl-2-(1-oxo-6-(5-(5-phenyloxazole-2-carboxamido)pyridin-2-yl)isoindolin-2-yl)butanoic acid;
(S)-3-Methyl-2-(1-oxo-6-(5-(5-phenylthiazole-2-carboxamido)pyridin-2-yl)isoindolin-2-yl)butanoic acid;
(S)-2-(6-(5-(3-(4-Fluorophenyl)isoxazole-5-carboxamido)pyridin-2-yl)-1-oxo isoindolin-2-yl)-3-methylbutanoic acid;
(S)-2-(6-(4-(4-(1,3,4-Oxadiazol-2-yl)benzamido)phenyl)-1-oxoisoindolin-2-yl)-3-methylbutanoic acid;
(S)-3-Methyl-2-(6-(4-(5-methyl-2-phenyloxazole-4-carboxamido)phenyl)-1-oxoisoindolin-2-yl)butanoic acid;
(S)-3-Methyl-2-(1-oxo-6-(4-(2-phenyl-5-(trifluoromethyl)oxazole-4-carboxamido) phenyl)isoindolin-2-yl)butanoic acid;
(S)-3-Methyl-2-(1-oxo-6-(4-(4-(thiazol-2-yl)benzamido)phenyl)isoindolin-2-yl) butanoic acid;
(S)-2-(6-(4-(5-Butylpicolinamido)phenyl)-1-oxoisoindolin-2-yl)-3-methylbutanoic acid;
(S)-3-Methyl-2-(1-oxo-6-(4-(quinoline-3-carboxamido) phenyl)isoindolin-2-yl)butanoic acid;
(S)-3-Methyl-2-(1-oxo-6-(4-(pyrimidin-5-yl)benzamido)phenyl)isoindolin-2-yl)butanoic acid;

(S)-3-Methyl-2-(6-(5-(5-methyl-2-phenyloxazole-4-carboxamido)pyridin-2-yl)-1-oxoisoindolin-2-yl)butanoic acid;

(S)-3-Methyl-2-(1-oxo-6-(5-(2-phenyl-5-(trifluoromethyl)oxazole-4-carboxamido) pyridin-2-yl)isoindolin-2-yl)butanoic acid; and (S)-3-Methyl-2-(1-oxo-6-(4-(2-phenylacetamido)phenyl) isoindolin-2-yl)butanoic acid;

or a stereoisomer, tautomer or a pharmaceutically acceptable salt, prodrug, carboxylic acid isostere or N-oxide thereof.

21. A pharmaceutical composition comprising a compound according to claim 2, or a stereoisomer, tautomer or a pharmaceutically acceptable salt, prodrug, carboxylic acid isostere or N-oxide thereof, along with a pharmaceutically acceptable excipient or a carrier.

22. A method of treatment of DGAT1 mediated disease or disorder, comprising administering to a subject in need thereof, a therapeutically effective amount of the compound according to claim 2, or a stereoisomer, tautomer or a pharmaceutically acceptable salt, prodrug, carboxylic acid isostere or N-oxide thereof, wherein the DGAT1 mediated disease or disorder is selected from obesity, type 2 diabetes, impaired glucose tolerance, insulin resistance, hypercholesterolemia, hyperlipidemia, dyslipidemia, mixed dyslipidemia, hypertriglyceridemia, steatosis, nonalcoholic fatty liver disease, atherosclerosis or acne.

23. The method according to claim 22, wherein the DGAT1 mediated disease or disorder is obesity.

24. A process for the preparation of a compound of formula 1a,

Formula 1a

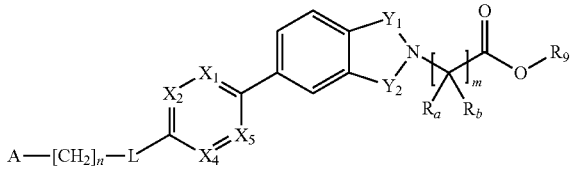

wherein $Y_1=CH_2$, $Y_2=C(O)$; $X_1$, $X_2$, $X_4$ and $X_5$ are independently selected from CH and CR; L=*C(O)NH; * indicates the point of attachment to $A\text{-}(CH_2)_n\text{---}$; m=1; A, n, R, $R_a=R_1$, $R_b=R_2$ and $R_9$ are as defined in formula 1a;
comprising the steps of:

a) reacting a compound of formula 8 ($X_1$, $X_2$, $X_4$ and $X_5$ are independently selected from CH and CR) or a compound of formula 55 ($X_1$, $X_2$, $X_4$ and $X_5$ are independently selected from CH, CR and N);

8 or 55

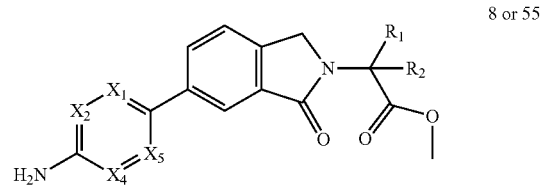

with:
i) A-$(CH_2)_n$—COCl, wherein A and n are as defined in formula 1a;
in presence of pyridine as base in a solvent selected from dichloromethane or tetrahydrofuran (THF) at a temperature ranging from 20-35° C.;

ii) A-$(CH_2)_n$—COOH, wherein A and n are as defined in formula 1a;
in presence of isobutylchloroformate as reagent and N-methylmorpholine as base in THF as solvent at a temperature range of 0° C. to room temperature (20-35° C.) for 2-4 h;

iii) A-$(CH_2)_n$COO—$(C_1\text{-}C_6)$-alkyl, wherein A represents a 5-membered heteroaryl ring containing 1 to 3 heteroatoms selected from N, O and S, and substituted with a phenyl group; wherein both phenyl and heteroaryl rings may be substituted with one or more groups selected from halogen, hydroxy, $(C_1\text{-}C_{12})$-alkoxy, cyano, $(C_1\text{-}C_{12})$-alkyl, $CF_3$ and $OCF_3$; n is as defined in formula 1a; in a solution of 2M trimethylaluminium ($AlMe_3$) in toluene at 60-80° C. in a sealed tube for 2-4 h;

iv) A-$(CH_2)_n$COO—$(C_1\text{-}C_6)$-alkyl, wherein A represents a phenyl group substituted with a 5-membered heteroaryl ring optionally containing 1 to 3 heteroatoms selected from N, O and S, and substituted with a phenyl group; wherein both phenyl and heteroaryl rings may be substituted with one or more groups selected from halogen, hydroxy, $(C_1\text{-}C_{12})$-alkoxy, cyano, $(C_1\text{-}C_{12})$-alkyl, $CF_3$ and $OCF_3$; n is as defined in formula 1a;
in presence of carbonyl chloride in a solvent mixture of dichloromethane and N,N-dimethylformamide (DMF) at 20-35° C. for about 2-4 h; or v) A-$(CH_2)_n$—COOH, wherein A and n are as defined in formula 1a;
in presence of isobutylchloroformate as reagent and N-methylmorpholine as base in THF as solvent at a temperature range of 0° C. to room temperature (20-35° C.) for 2-4 h;
to respectively obtain compound of formula 15 ($X_1$, $X_2$, $X_4$ and $X_5$ are independently selected from CH and CR; representative formula of the compound of formula 1a) or compound of formula 62 ($X_1$, $X_2$, $X_4$ and $X_5$ are independently selected from CH, CR and N; representative formula of the compound of formula 1a):

15 or 62

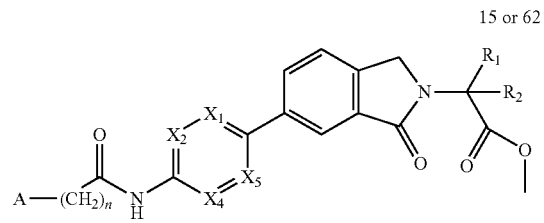

(representative formula of the compound of formula 1a)

b) hydrolysis of the compound of formula 15 ($X_1$, $X_2$, $X_4$ and $X_5$ are independently selected from CH and CR; representative formula of the compound of formula 1a) or compound of formula 62 ($X_1$, $X_2$, $X_4$ and $X_5$ are independently selected from CH, CR and N; representative formula of the compound of formula 1a) obtained in step a) using a reagent selected from 1N Lithium hydroxide (LiOH) or 1N sodium hydroxide (NaOH) in a solvent selected from methanol or THF at a temperature ranging from 20-35° C. to respectively obtain compound of formula 16 ($X_1$, $X_2$, $X_4$ and $X_5$ are independently selected from CH and CR;

representative formula of the compound of formula 1a) or compound of formula 63 ($X_1$, $X_2$, $X_4$ and $X_5$ are independently selected from CH, CR and N;

representative formula of the compound of formula 1a), and

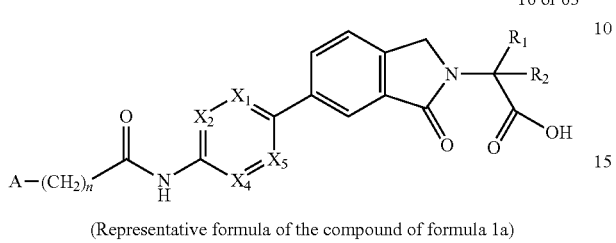

(Representative formula of the compound of formula 1a)

c) optionally converting the compound of formula 16 or 63 obtained in step b) to its corresponding ester prodrugs or pharmaceutically acceptable salts.

25. A process for the preparation of a compound of formula 1a;

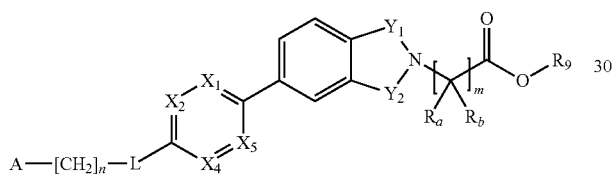

wherein $Y_1$=$CH_2$, $Y_2$=C(O); $X_1$, $X_2$, $X_4$ and $X_5$ are independently selected from CH and CR; L=NHC(O)NH; m=1; A, n, R, $R_a$=$R_1$, $R_b$=$R_2$ and $R_9$ are as defined in formula 1a; comprising the steps of:

a) reacting the compound of formula 8 ($X_1$, $X_2$, $X_4$ and $X_5$ are independently selected from CH and CR) or compound of formula 55 ($X_1$, $X_2$, $X_4$ and $X_5$ are independently selected from CH, CR and N);

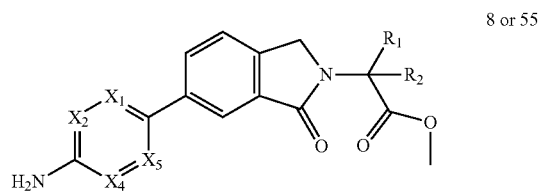

with A-$(CH_2)_n$—NCO; wherein A and n are as defined in formula 1a;

in a solvent selected from dichloromethane or THF at a temperature ranging from 20-35° C., to respectively obtain compound of formula 9 ($X_1$, $X_2$, $X_4$ and $X_5$ are independently selected from CH and CR; representative formula of the compound of formula 1a) or compound of formula 56 ($X_1$, $X_2$, $X_4$ and $X_5$ are independently selected from CH, CR and N; representative formula of the compound of formula 1a):

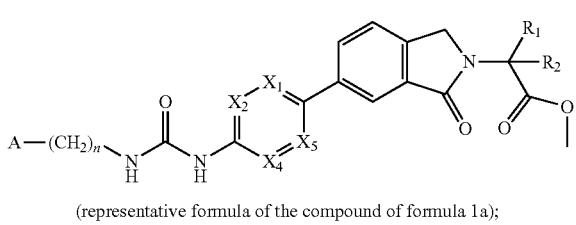

(representative formula of the compound of formula 1a);

b) hydrolysis of compound of formula 9 or 56 obtained in step a) using a reagent selected from 1N LiOH or 1N NaOH in a solvent selected from methanol or THF at a temperature ranging from 20-35° C. to respectively obtain compound of formula 10 ($X_1$, $X_2$, $X_4$ and $X_5$ are independently selected from CH and CR; representative formula of the compound of formula 1a) or compound of formula 57 ($X_1$, $X_2$, $X_4$ and $X_5$ are independently selected from CH, CR and N; (representative formula of the compound of formula 1a);

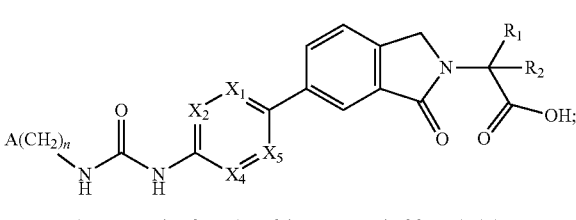

(representative formulae of the compound of formula 1a)

and c) optionally converting the compound of formula 10 ($X_1$, $X_2$, $X_4$ and $X_5$ are independently selected from CH and CR; representative formula of the compound of formula 1a) or compound of formula 57 ($X_1$, $X_2$, $X_4$ and $X_5$ are independently selected from CH, CR and N; (representative formula of the compound of formula 1a) to its corresponding ester prodrugs or pharmaceutically acceptable salts.

26. The process according to claim 24, wherein the compound of formula 8 of step a);

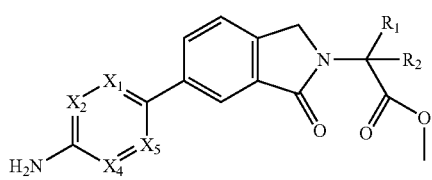

wherein $X_1$, $X_2$, $X_4$, $X_5$, $R_1$ and $R_2$ are as defined in formula 1a; is prepared by a process comprising the steps of:

a) reacting compound of formula 4:

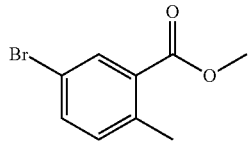

with a compound of formula 4P:

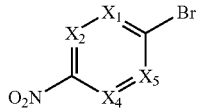
4P wherein $X_1$, $X_2$, $X_4$; and $X_5$, are as defined above;

and bis(pinacolo)diboron, in the presence of a reagent selected from palladium acetate or tetrakis palladium and a base selected from potassium acetate, sodium carbonate or cesium carbonate in a solvent selected from toluene, dioxane, dimethoxyethane, DMF or acetone at a temperature ranging from 70-120° C., to obtain the compound of formula 5;

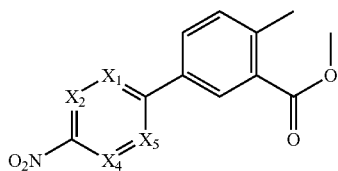
5 b) refluxing the compound of formula 5 with N-bromosuccinimide and a catalytic amount of azobisisobutyronitrile (AIBN) or benzoyl peroxide in carbon tetrachloride ($CCl_4$) as solvent using irradiation (200 watt bulb) at a temperature ranging from 80-100° C. to obtain compound of formula 6;

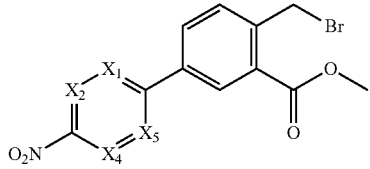
6 c) reacting the compound of formula 6 with compound of formula 6P:

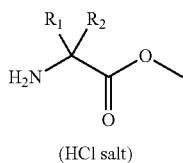
6P
(HCl salt)

wherein $R_1$ and $R_2$ are as defined in formula 1a; with:
  i) triethylamine as a base in a solvent selected from benzene or toluene at a temperature ranging from 70-120° C.; or
  ii) potassium carbonate as a base in a solvent selected from DMF or THF at a temperature ranging from 50-80° C., to obtain compound of formula 7;

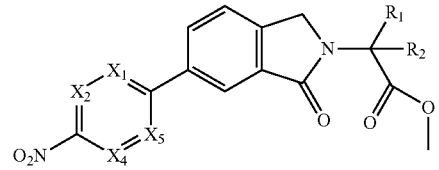
7 d) reducing compound of formula 7; with:
  i) iron (Fe) and ammonium chloride as a reducing agent in a solvent selected from aqueous ethanol or a mixture of ethanol, tetrahydrofuran and water at a temperature ranging from 70-100° C.; or
  ii) Fe and hydrochloric acid (HCl) as a reducing agent in a solvent selected from $H_2O$ or ethanol or combination thereof; or iii) stannous chloride ($SnCl_2$) as a reducing agent in ethyl acetate as solvent; or
  iv) hydrogen over Raney nickel (Ni) palladium over carbon (Pd/C) or platinum over carbon (Pt/C) catalyst as a reducing agent in methanol as solvent at pressure ranging from 50-80 psi and temperature ranging from 20-65° C.; or
  v) cobalt chloride and zinc as a reducing agent in a solvent selected from DMF or water at a temperature ranging from 20-100° C.;
to obtain compound of formula 8.

27. A process for the preparation of a compound of formula 1a,

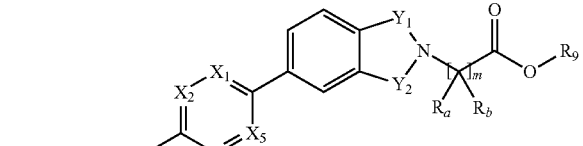

wherein $Y_1$=$CH_2$, $Y_2$=C(O); $X_1$, $X_2$, $X_4$ and $X_5$ are independently selected from CH and CR, L=*C(O)NH; * indicates the point of attachment to A-$(CH_2)_n$—, m=1; A, n, R, $R_a$=$R_1$, $R_b$=$R_2$ and $R_9$ are as defined in formula 1a;

comprising the steps of:
  a) preparing compound of formula 46:

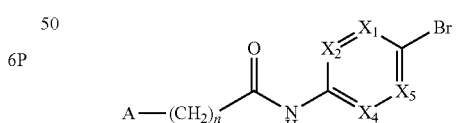
46 by reacting the compound of formula 37:

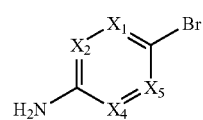
37 wherein, $X_1$, $X_2$, $X_4$ and $X_5$ are independently selected from CH and CR, with A-(CH$_2$)$_n$—COCl, wherein A and n are as defined in formula 1a; in presence of pyridine as base in a solvent selected from dichloromethane or THF at temperature ranging from 20-35° C.;

b) preparing compound of formula 47:

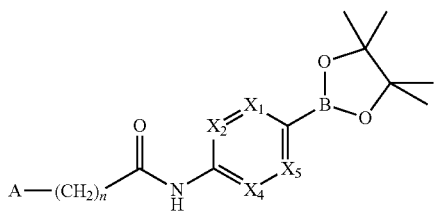

47 by reacting compound of formula 46 with bis(pinacoiato) diboron, [1,1'-bis(diphenylphosphino)ferrocene]dichloropalladium(II) (Pd(dppf)Cl$_2$) and [1,1'-bis(diphenylphosphino)ferrocene]dichloropalladium(II), complex with dichloromethane (Pd(dppf)Cl$_2$:CH$_2$Cl$_2$) in a solvent selected from dioxane, dimethoxyethane, dimethylsulfoxide (DMSO) or DMF at temperature ranging from 50-100° C.;

c) preparing compound of formula 41:

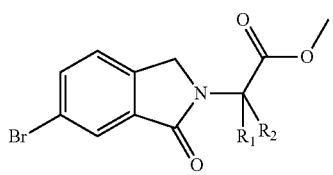

41 by reacting compound of formula 40:

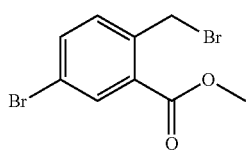

40 with compound of formula 6P:

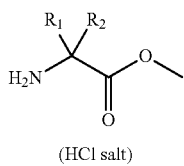

6P (HCl salt)

wherein R$_1$ and R$_2$ are as defined in formula 1a; with:
i) triethylamine as a base in a solvent selected from benzene or toluene at a temperature ranging from 70-120° C.; or
ii) potassium carbonate as a base in a solvent selected from DMF or THF at a temperature ranging from 50-80° C.;

d) reacting compound of formula 47 with compound of formula 41 in presence of Pd(dppf)Cl$_2$:CH$_2$Cl$_2$ and a base selected from potassium carbonate, cesium carbonate or 2M sodium carbonate (Na$_2$CO$_3$) in water, in a solvent selected from DMF, dioxane, dimethoxyethane or acetone under an atmosphere of argon at temperature ranging from 50-100° C. to obtain compound of formula 15 (representative formula of the compound of formula 1a);

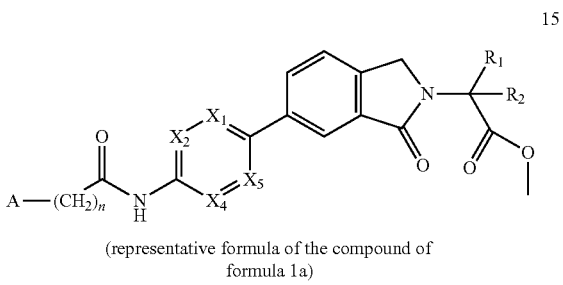

15

(representative formula of the compound of formula 1a)

e) hydrolysis of the compound of formula 15 using a reagent selected from 1N LiOH or 1N NaOH in a solvent selected from methanol or THF at a temperature ranging from 20-35° C. to obtain compound of formula 16 (representative formula of the compound of formula 1a), and

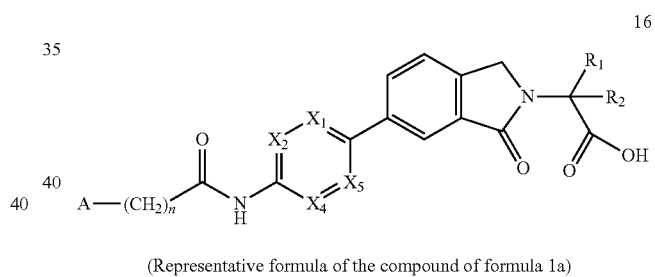

16

(Representative formula of the compound of formula 1a)

f) optionally converting the compound of formula 16 (representative formula of the compound of formula 1a) to its corresponding ester prodrugs or pharmaceutically acceptable salts.

28. A process for the preparation of a compound of formula 1a,

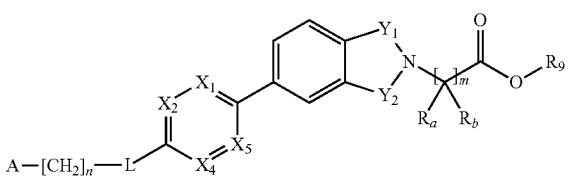

wherein Y$_1$=CH$_2$, Y$_2$=C(O); X$_1$, X$_2$, X$_4$ and X$_5$ are independently selected from CH and CR; L=NHC(O)NH; m=1; A, n, R, R$_a$=R$_1$, R$_b$=R$_2$ and R$_9$ are as defined in formula 1a;

comprising the steps of:

a) preparing compound of formula 38:

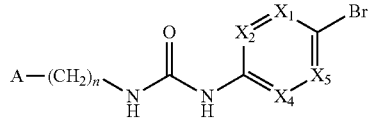

38 by reacting compound of formula 37:

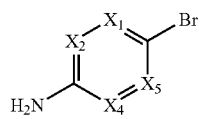

37 wherein, $X_1$, $X_2$, $X_4$ and $X_5$ are independently selected from CH and CR, with A-$(CH_2)_n$—NCO, wherein A and n are as defined in formula 1a; in a solvent selected from dichloromethane or THF at temperature ranging from 20-35° C.;

b) preparing compound of formula 39:

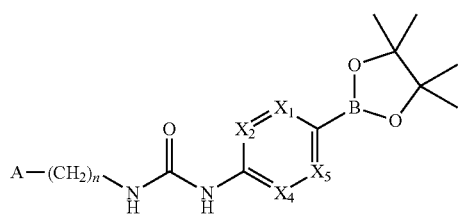

39 by reacting compound of formula 38 with bis(pinacolato) diboron, Pd(dppf)Cl$_2$ and Pd(dppf)Cl$_2$:CH$_2$Cl$_2$ in a solvent selected from dioxane, dimethoxyethane, DMSO or DMF at temperature ranging from 50-100° C.;

c) preparing compound of formula 41:

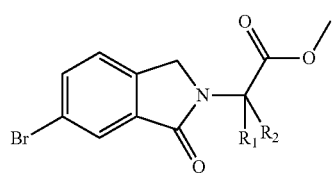

41 by reacting compound of formula 40:

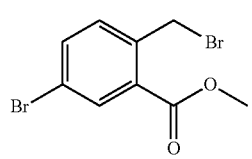

40 with compound of formula 6P:

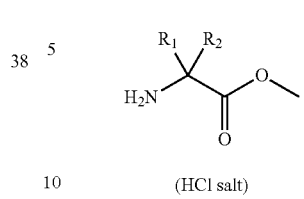

6P (HCl salt)

wherein $R_1$ and $R_2$ are as defined in formula 1a; with:
  i) triethylamine as a base in a solvent selected from benzene or toluene at a temperature ranging from 70-120° C.; or
  ii) potassium carbonate as a base in a solvent selected from DMF or THF at a temperature ranging from 50-80° C.;

d) reacting compound of formula 39 with compound of formula 41 in presence of Pd(dppf)Cl$_2$:CH$_2$Cl$_2$ and a base selected from potassium carbonate, cesium carbonate or 2M Na$_2$CO$_3$ (in water) in a solvent selected from DMF, dioxane, dimethoxyethane or acetone under an atmosphere of argon at temperature ranging from 50-100° C. to obtain compound of formula 9 (representative formula of the compound of formula 1a);

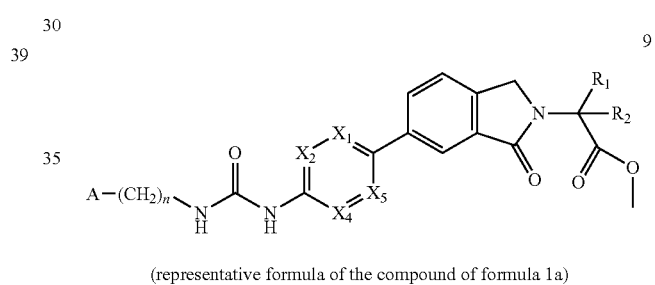

9

(representative formula of the compound of formula 1a)

e) hydrolysis of compound of formula 9 obtained in step d) (representative formula of the compound of formula 1a) using a reagent selected from 1N LiOH or 1N NaOH in a solvent selected from methanol or THF at a temperature ranging from 20-35° C. to obtain compound of formula 10 (representative formula of the compound of formula 1a), and

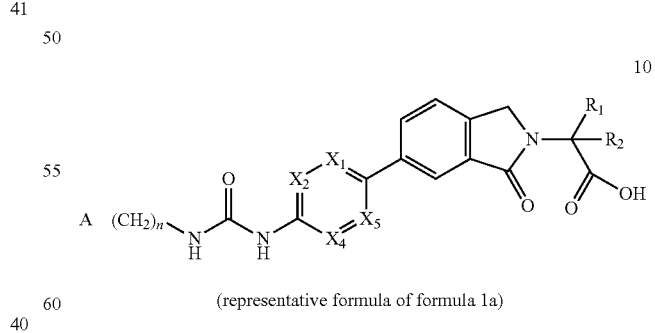

10

(representative formula of formula 1a)

f) optionally converting the compound of formula 10 obtained in step d) (representative formula of the compound of formula 1a) to its corresponding ester prodrugs or pharmaceutically acceptable salts.

29. The process according to claim 24, wherein the compound of formula 55 of step a);

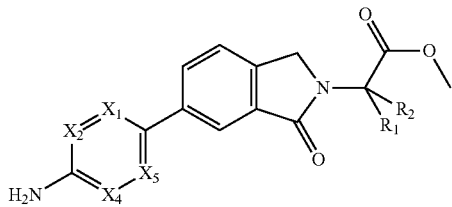

55 wherein $X_1$, $X_2$, $X_4$ and $X_5$ are independently selected from CH, CR and N; wherein R, $R_1$ and $R_2$ are as defined in formula 1a; is prepared by a process comprising the steps of:

a) reacting compound of formula 41,

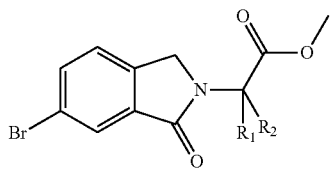

41 with bis(pinacolato)diboron, Pd(dppf)Cl$_2$ and Pd(dppf)Cl$_2$:CH$_2$Cl$_2$ in a solvent selected from dioxane, dimethoxyethane, DMSO or DMF at temperature ranging from 50-100° C. to obtain compound of formula 52;

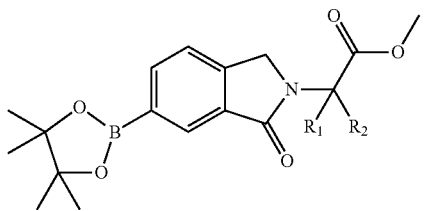

52 b) reacting compound of formula 52 with compound of formula 53:

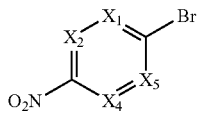

53 wherein $X_1$, $X_2$, $X_4$ and $X_5$ are independently selected from CH, CR and N;
in presence of Pd(dppf)Cl$_2$:CH$_2$Cl$_2$ in a base selected from potassium carbonate, cesium carbonate and 2M Na$_2$CO$_3$ (in water) in a solvent selected from DMF, dioxane, dimethoxyethane or acetone under an atmosphere of argon at temperature ranging from 50-100° C. to obtain compound of formula 54;

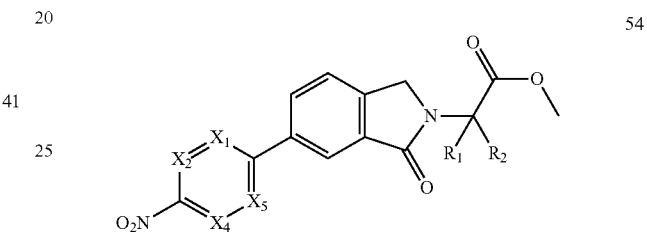

54 c) reducing compound of formula 54; with:
i) Fe and ammonium chloride as a reducing agent in a solvent selected from aqueous ethanol or a mixture of ethanol, tetrahydrofuran and water at a temperature ranging from 70-100° C.; or
ii) Fe and HCl as a reducing agent in a solvent selected from H$_2$O or ethanol or combination thereof; or
iii) SnCl$_2$ as a reducing agent in ethyl acetate as solvent; or
iv) hydrogen over Raney Ni, Pd/C or Pt/C catalyst as a reducing agent in methanol as solvent at pressure ranging from 50-80 psi and temperature ranging from 20-65° C.; or
v) cobalt chloride and zinc as a reducing agent in a solvent selected from DMF or water at a temperature ranging from 20-100° C.

to obtain compound of formula 55.

30. The method according to claim 22, wherein the DGAT1 mediated disease or disorder is hyperlipidemia.

\* \* \* \* \*